(12) United States Patent
Cuevas-Cordobés et al.

(10) Patent No.: US 10,590,140 B2
(45) Date of Patent: Mar. 17, 2020

(54) TETRAHYDROPYRIMIDODIAZEPINE AND DIHYDROPYRIDODIAZEPINE COMPOUNDS FOR TREATING PAIN AND PAIN RELATED CONDITIONS

(71) Applicant: ESTEVE PHARMACEUTICALS, S.A., Barcelona (ES)

(72) Inventors: Félix Cuevas-Cordobés, Valdemoro (ES); Carmen Almansa-Rosales, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/098,244

(22) PCT Filed: May 5, 2017

(86) PCT No.: PCT/EP2017/060780
§ 371 (c)(1),
(2) Date: Nov. 1, 2018

(87) PCT Pub. No.: WO2017/191304
PCT Pub. Date: Nov. 9, 2017

(65) Prior Publication Data
US 2019/0144455 A1 May 16, 2019

(30) Foreign Application Priority Data

May 6, 2016 (EP) .................. 16382199

(51) Int. Cl.
| | |
|---|---|
| *C07D 471/04* | (2006.01) |
| *C07D 487/04* | (2006.01) |
| *C07D 498/10* | (2006.01) |
| *A61K 31/551* | (2006.01) |
| *A61P 25/00* | (2006.01) |
| *A61P 29/00* | (2006.01) |

(52) U.S. Cl.
CPC .......... *C07D 487/04* (2013.01); *A61P 25/00* (2018.01); *A61P 29/00* (2018.01); *C07D 471/04* (2013.01); *C07D 498/10* (2013.01)

(58) Field of Classification Search
CPC ... C07D 471/04; C07D 487/04; C07D 498/10
See application file for complete search history.

(56) References Cited

FOREIGN PATENT DOCUMENTS

| EP | 2163554 | 3/2010 |
| WO | WO 2004/002462 | 1/2004 |

OTHER PUBLICATIONS

Banker et al. "Modern Pharmaceutics", 3rd Ed. p. 596 (1996).*
Burger's Medicinal Chemistry,, edited by Manfred E.Wolf, 5th Ed. Part 1, pp. 975-977 (1995).*
Sharma et al. Future Med. Chem. (2015) 7(17), 2385-2405.*
International Search Report for PCT/EP2017/060780 dated May 29, 2017.
Muneer, J. Pak. Med. Assoc., 2013, 63, 763-769.

* cited by examiner

*Primary Examiner* — Emily A Bernhardt
(74) *Attorney, Agent, or Firm* — Hueschen and Sage

(57) ABSTRACT

The present invention relates to new compounds of general formula (I) that show great affinity and activity towards the subunit α2δ of voltage-gated calcium channels (VGCC), especially α2δ-1 subunit of voltage-gated calcium channels or dual activity towards subunit α2δ of voltage-gated calcium channels (VGCC), especially α2δ-1 subunit of voltage-gated calcium channels, and noradrenaline transporter (NET). The invention is also related to the process for the preparation of said compounds as well as to compositions comprising them, and to their use as medicaments.

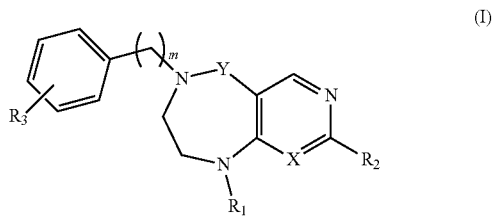

(I)

21 Claims, No Drawings

TETRAHYDROPYRIMIDODIAZEPINE AND DIHYDROPYRIDODIAZEPINE COMPOUNDS FOR TREATING PAIN AND PAIN RELATED CONDITIONS

FIELD OF THE INVENTION

The present invention relates to new compounds that show great affinity and activity towards the subunit α2δ of voltage-gated calcium channels (VGCC), especially α2δ-1 subunit of voltage-gated calcium channels or dual activity towards subunit α2δ of voltage-gated calcium channels (VGCC), especially α2δ-1 subunit of voltage-gated calcium channels, and noradrenaline transporter (NET). The invention is also related to the process for the preparation of said compounds as well as to compositions comprising them, and to their use as medicaments.

BACKGROUND OF THE INVENTION

The adequate management of pain represents an important challenge, since currently available treatments provide in many cases only modest improvements, leaving many patients unrelieved (Turk, D. C., Wilson, H. D., Cahana, A.; 2011; *Lancet;* 377; 2226-2235). Pain affects a big portion of the population with an estimated prevalence of 20% and its incidence, particularly in the case of chronic pain, is increasing due to the population ageing. Additionally, pain is clearly correlated to comorbidities, such as depression, anxiety and insomnia, which leads to important productivity losses and socio-economical burden (Goldberg, D. S., McGee, S. J.; 2011; *BMC Public Health;* 11; 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al.; Pharmacol. Rev.; 2015; 67; 821-870). The VGCC are assembled through interactions of different subunits, namely α1 ($Ca_V\alpha1$), β ($Ca_V\beta$) α2δ ($Ca_V\alpha2\delta$) and γ ($Ca_V\gamma$). The α1 subunits are the key porous forming units of the channel complex, being responsible for $Ca^{2+}$ conduction and generation of $Ca^{2+}$ influx. The α2δ, β, and γ subunits are auxiliary, although they are very important for the regulation of the channel since they increase the expression of α1 subunits in the plasma membrane as well as modulate their function resulting in functional diversity in different cell types. Based on their physiological and pharmacological properties, VGCC can be subdivided into low voltage-activated T-type ($Ca_V3.1$, $Ca_V3.2$, and $Ca_V3.3$), and high voltage-activated L-($Ca_V1.1$ through $Ca_V1.4$), N—($Ca_V2.2$), P/Q-($Ca_V2.1$), and R—($Ca_V2.3$) types, depending on the channel forming $Ca_V\alpha$ subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo; Neurotherapeutics; 2009; 6; 679-692; Zamponi et al., 2015; Neumaier et al.; Prog. Neurobiol.; 2015; 129; 1-36). A large body of data has clearly indicated that VGCC are implicated in mediating various disease states including pain processing. Drugs interacting with the different calcium channel subtypes and subunits have been developed. Current therapeutic agents include drugs targeting L-type $Ca_V1.2$ calcium channels, particularly 1,4-dihydropyridines, which are widely used in the treatment of hypertension. T-type ($Ca_V3$) channels are the target of ethosuximide, widely used in absence epilepsy. Ziconotide, a peptide blocker of N-type ($Ca_V2.2$) calcium channels, has been approved as a treatment of intractable pain.

The $Ca_V1$ and $Ca_V2$ subfamilies contain an auxiliary α2δ subunit which is the therapeutic target of the gabapentinoid drugs of value in certain epilepsies and chronic neuropathic pain (Perret and Luo, 2009; Vink and Alewood; British J. Pharmacol.; 2012; 167; 970-989). To date, there are four known α2δ subunits, each encoded by a unique gene and all possessing splice variants. Each α2δ protein is encoded by a single messenger RNA and is post-translationally cleaved and then linked by disulfide bonds. Four genes encoding α2δ subunits have now been cloned. α2δ-1 was initially cloned from skeletal muscle and shows a fairly ubiquitous distribution. The α2δ-2 and α2δ-3 subunits were subsequently cloned from brain. The most recently identified subunit, α2δ-4, is largely non-neuronal. The human α2δ-4 protein sequence shares 30, 32 and 61% identity with the human α2δ-1, α2δ-2 and α2δ-3 subunits, respectively. The gene structure of all α2δ subunits is similar. All α2δ subunits show several splice variants (Davies et al.; Trends Pharmacol. Sci.; 2007; 28; 220-228; Dolphin, A. C.; Nat. Rev. Neurosci.; 2012; 13; 542-555; Dolphin, A. C.; Biochim. Biophys. Acta; 2013; 1828; 1541-1549).

The $Ca_V\alpha2\delta$-1 subunit may play an important role in neuropathic pain development (Perret and Luo, 2009; Vink and Alewood, 2012). Biochemical data have indicated a significant $Ca_V\alpha2\delta$-1, but not $Ca_V\alpha2\delta$-2, subunit upregulation in the spinal dorsal horn, and DRG (dorsal root ganglia) after nerve injury that correlates with neuropathic pain development. In addition, blocking axonal transport of injury-induced DRG $Ca_V\alpha_2\delta$-1 subunit to the central pre-synaptic terminals diminishes tactile allodynia in nerve injured animals, suggesting that elevated DRG $Ca_V\alpha2\delta$-1 subunit contributes to neuropathic allodynia.

The $Ca_V\alpha2\delta$-1 subunit (and the $Ca_V\alpha2\delta$-2, but not $Ca_V\alpha2\delta$-3 and $Ca_V\alpha2\delta$-4, subunits) is the binding site for gabapentin which has anti-allodynic/hyperalgesic properties in patients and animal models. Because injury-induced $Ca_V\alpha2\delta$-1 expression correlates with neuropathic pain, development and maintenance, and various calcium channels are known to contribute to spinal synaptic neurotransmission and DRG neuron excitability, injury-induced $Ca_V\alpha2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_V\alpha2\delta$-1 subunit can block nerve injury-induced $Ca_V\alpha2\delta$-1 upregulation and prevent the onset of allodynia and reserve established allodynia.

As above mentioned, the α2δ subunits of VGCC form the binding site for gabapentin and pregabalin which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_V\alpha2\delta$-1 subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009; Vink and Alewood, 2012, Zamponi et al., 2015).

Thus, the present invention relates to compounds with inhibitory effect towards α2δ subunits of voltage-gated calcium channels, preferably towards α2δ-1 subunit of voltage-gated calcium channels.

It is also known that Noradrenaline (NA), also called norepinephrine, functions in the human brain and body as a hormone and neurotransmitter. Noradrenaline exerts many effects and mediates a number of functions in living organisms. The effects of noradrenaline are mediated by two distinct super-families of receptors, named alpha- and beta-adrenoceptors. They are further divided into subgroups exhibiting specific roles in modulating behavior and cognition of animals. The release of the neurotransmitter noradrenaline throughout the mammalian brain is important for modulating attention, arousal, and cognition during many behaviors (Mason, S. T.; Prog. Neurobiol.; 1981; 16; 263-303).

The noradrenaline transporter (NET, SLC6A2) is a monoamine transporter mostly expressed in the peripheral and central nervous systems. NET recycles primarily NA, but also serotonin and dopamine, from synaptic spaces into presynaptic neurons. NET is a target of drugs treating a variety of mood and behavioral disorders, such as depression, anxiety, and attention-deficit/hyperactivity disorder (ADHD). Many of these drugs inhibit the uptake of NA into the presynaptic cells through NET. These drugs therefore increase the availability of NA for binding to postsynaptic receptors that regulate adrenergic neurotransmission. NET inhibitors can be specific. For example, the ADHD drug atomoxetine is a NA reuptake inhibitor (NRI) that is highly selective for NET. Reboxetine was the first NRI of a new antidepressant class (Kasper et al.; Expert Opin. Pharmacother.; 2000; 1; 771-782). Some NET inhibitors also bind multiple targets, increasing their efficacy as well as their potential patient population.

Endogenous, descending noradrenergic fibers impose analgesic control over spinal afferent circuitry mediating the transmission of pain signals (Ossipov et al.; J. Clin. Invest.; 2010; 120; 3779-3787). Alterations in multiple aspects of noradrenergic pain processing have been reported, especially in neuropathic pain states (Ossipov et a., 2010; Wang et al.; J. Pain; 2013; 14; 845-853). Numerous studies have demonstrated that activation of spinal α2-adrenergic receptors exerts a strong antinociceptive effect. Spinal clonidine blocked thermal and capsaicin-induced pain in healthy human volunteers (Ossipov et a., 2010). Noradrenergic reuptake inhibitors have been used for the treatment of chronic pain for decades: most notably the tricyclic antidepressants, amitriptyline, and nortriptyline. Once released from the presynaptic neuron, NA typically has a short-lived effect, as much of it is rapidly transported back into the nerve terminal. In blocking the reuptake of NA back into the presynaptic neurons, more neurotransmitter remains for a longer period of time and is therefore available for interaction with pre- and postsynaptic $α_2$-adrenergic receptors (AR). Tricyclic antidepressants and other NA reuptake inhibitors enhance the antinociceptive effect of opioids by increasing the availability of spinal NA. The $α_2$A-AR subtype is necessary for spinal adrenergic analgesia and synergy with opioids for most agonist combinations in both animal and humans (Chabot-Doré et al.; Neuropharmacology; 2015; 99; 285-300).

A selective upregulation of spinal NET in a rat model of neuropathic pain with concurrent downregulation of serotonin transporters has been shown (Fairbanks et al.; Pharmacol. Ther.; 2009; 123; 224-238). Inhibitors of NA reuptake such as nisoxetine, nortriptyline and maprotiline and dual inhibitors of the noradrenaline and serotonin reuptake such as imipramine and milnacipran produce potent anti-nociceptive effects in the formalin model of tonic pain. Neuropathic pain resulting from the chronic constriction injury of the sciatic nerve was prevented by the dual uptake inhibitor, venlafaxine. In the spinal nerve ligation model, amitriptyline, a non-selective serotonin and noradrenaline reuptake blocker, the preferential noradrenaline reuptake inhibitor, desipramine and the selective serotonin and noradrenaline reuptake inhibitors, milnacipran and duloxetine, produce a decrease in pain sensitivity whereas the selective serotonin reuptake inhibitor, fluoxetine, is ineffective (Mochizuki, D.; Psychopharmacol.; 2004; Supplm. 1; S15-S19; Hartrick, C. T.; Expert Opin. Investig. Drugs; 2012; 21; 1827-1834). A number of nonselective investigational agents focused on noradrenergic mechanisms with the potential for additive or even synergistic interaction between multiple mechanisms of action are being developed (Hartrick, 2012).

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al.; Nat. Biotechnol.; 2009; 27; 659-666).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al.; Lancet Neurol.; 2013; 12(11); 1084-1095). In fact, positive synergistic interaction for several compounds, including analgesics, has been described (Schröder et al; J. Pharmacol. Exp. Ther.; 2011; 337; 312-320; Zhang et al.; Cell Death Dis.; 2014; 5; e1138; Gilron et al., 2013).

Given the significant differences in pharmacokinetics, metabolisms and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins, A. L.; Nat. Chem. Biol.; 2008; 4; 682-690).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-dose window of opportunity where a reduced selection pressure can lead to drug resistance. In terms of drug registration, approval of a single compound acting on multiple targets faces significantly lower regulatory barriers than approval of a combination of new drugs (Hopkins, 2008).

Thus, in a preferred embodiment, the compounds of the present invention having affinity for α2δ subunits of voltage-gated calcium channels, preferably towards α2δ-1 subunit of voltage-gated calcium channels, additionally have inhibitory effect towards noradrenaline transporter (NET) and are, thus, more effective to treat chronic pain.

There are two potentially important interactions between NET and α2δ-1 inhibition: 1) synergism in analgesia, thus reducing the risk of specific side effects; and 2) inhibition of pain-related affective comorbidities such as anxiety and/or depressive like behaviors (Nicolson et al.; Harv. Rev. Psychiatry; 2009; 17; 407-420).

1) Preclinical research has demonstrated that gabapentinoids attenuated pain-related behaviors through supraspinal activation of the descending noradrenergic system (Tanabe et al.; J. Neuroosci. Res.; 2008; Hayashida, K.; Eur. J. Pharmacol.; 2008; 598; 21-26). In consequence, the α2δ-1-related analgesia mediated by NA-induced activation of spinal α2-adrenergic receptors can be potentiated by the inhibition of the NET. Some evidence from combination studies in preclinical models of neuropathic pain exist. Oral duloxetine with gabapentin was additive to reduce hypersensitivity induced by nerve injury in rats (Hayashida; 2008). The combination of gabapentin and nortriptyline drugs was synergic in mice submitted to orofacial pain and to peripheral nerve injury model (Miranda, H. F. et al.; J. Orofac. Pain; 2013; 27; 361-366; Pharmacology; 2015; 95; 59-64).

2) Drug modulation of NET and α2δ-1 has been shown to produce antidepressant and anti-anxiety effects respectively (Frampton, J. E.; CNS Drugs; 2014; 28; 835-854; Hajós, M. et al.; CNS Drug Rev.; 2004; 10; 23-44). In consequence, a dual drug that inhibited the NET and α2δ-1 subunit of VGCC may also stabilize pain-related mood impairments by acting directly on both physical pain and the possible mood alterations.

SUMMARY OF THE INVENTION

The present invention discloses novel compounds with great affinity to α2δ subunit of voltage-gated calcium channels, more specifically to the α2δ-1, and which in preferred embodiments also have inhibitory effect towards noradrenaline transporter (NET), thus resulting in a dual activity for treating pain and pain related disorders.

The main object of the present invention is related to compounds of general formula (I):

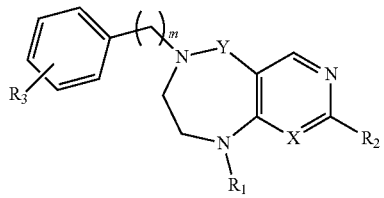

wherein:
X is CRx or N;
Rx is a hydrogen atom; a branched or unbranched $C_{1-6}$ alkyl radical; or a halogen atom;
Y is $CH_2$ or C=O;
m is 0, 1 or 2;
$R_1$ is a hydrogen atom; or a linear or branched $C_{1-6}$ alkyl radical;
$R_2$ is a hydrogen atom; a branched or unbranched $C_{1-6}$ alkyl radical; a halogen atom; haloalkyl; —$SR_{2a}$; —$NR_{2a}R_{2b}$; or —$OR_{2a}$;
$R_{2a}$ and $R_{2b}$ are independently from one another a hydrogen atom; a branched or unbranched $C_{1-6}$ alkyl radical; a $C_{3-6}$ cycloalkyl radical; a —$(CH_2)_r$-aryl radical where the aryl group is 5 or 6-membered ring and r is 0, 1 or 2; a —$(CH_2)_s$-heteroaryl radical where the heteroaryl group is 5 or 6-membered ring with at least one nitrogen atom as heteroatom optionally substituted by at least one halogen atom and s is 0, 1 or 2; or a —$(CH_2)_2$—O—$CH_3$;
$R_3$ is a hydrogen atom; —CN; —OH; halogen; a branched or unbranched $C_{1-6}$ alkyl radical; a —$(CH_2)_p$—O—$R_4$ being p 0, 1 or 2; a —$(CH_2)_q$—$NR_5R_6$ being q 0, 1, 2 or 3; a —$C(CH_3)_2$—$CH_2$—$NR_5R_6$; a —C(=O)$NR_5R_6$; a 5 or 6 membered heteroaryl group having at least one heteroatom selected from N, O or S and being substituted by one or two $R_7$ substituents and that can be attached to the phenyl ring by an $C_{1-3}$ alkylene group; or a 5 or 6 membered heterocycloalkyl ring having one or two nitrogen as heteroatom and being unsubstituted or optionally substituted by one or two $R_8$ substituent and that can be attached to the phenyl ring by an $C_{1-3}$ alkylene group; or —C(=O)$OR_9$;
$R_4$ is a hydrogen atom; a branched or unbranched $C_{1-6}$ alkyl radical; a tert-butyldimethylsilyl radical; a methylbenzenesulfonate radical; a —$CHR_{4a}R_{4b}$; a —$CH_2$—$CHR_{4a}R_{4b}$; or a 5 or 6-membered heterocycloalkyl radical having at least one N atom and being optionally substituted by one or two $R_{4c}$ radical;
$R_{4a}$ is a hydrogen atom; a branched or unbranched $C_{1-6}$ alkyl radical; a 5 or 6-membered aryl group optionally substituted by a at least one halogen atom; or a 5 or 6-membered heteroaryl group having at least one heteroatom selected from N, O or S and optionally substituted by at least a branched or unbranched $C_{1-6}$ alkyl radical;
$R_{4b}$ is a —$(CH_2)_j$—$NR_{4b'}R_{4b''}$ being j 0, 1, 2 or 3;
$R_{4b'}$ and $R_{4b''}$ are independently from one another a hydrogen atom; a branched or unbranched $C_{1-6}$ alkyl radical; a $C_{1-6}$ haloalkyl radical; a benzyl group; a phenethyl group; a tert-butyloxycarbonyl group; or a (trimethylsilyl)ethyloxycarbonyl group; or
$R_{4b'}$ and $R_{4b''}$ together with the bridging nitrogen form a 5 or 6-membered heterocycloalkyl radical optionally containing an additional heteroatom selected from N, O or S;
$R_{4c}$ is a hydrogen atom; a branched or unbranched $C_{1-6}$ alkyl radical; a phenyl group; a benzyl group; or a tert-butyloxycarbonyl group;

R$_5$ and R$_6$ independently from one another represent a hydrogen atom; a branched or unbranched C$_{1-6}$ alkyl radical; a tert-butyloxycarbonyl group; a benzyl group; a phenethyl group; or R$_5$ and R$_6$ together with the bridging nitrogen form a 5 or 6-membered heterocycloalkyl radical which can be mono or bisubstituted by a phenyl group in turn optionally substituted by a branched or unbranched C$_{1-6}$ alkyl radical, a halogen atom, —OH or —CN; or by an —NRR'; R and R' being independently from one another a hydrogen atom or a branched or unbranched C$_{1-6}$ alkyl radical; or R$_5$ and R$_6$ together with the bridging nitrogen form a 5 or 6-membered heterocycloalkyl radical which can be spirofused to another 5 or 6-membered heterocycloalkyl radical having at least one heteroatom selected from N, O or S which can in turn be substituted by one or more substituents selected from a branched or unbranched C$_{1-6}$ alkyl radical; a halogen atom, —OH, —CN or =O;

R$_7$ is a hydrogen atom; a branched or unbranched C$_{1-6}$ alkyl radical; a —C(=O)H group; a —(CH$_2$)$_p$—NR$_{7a}$R$_{7b}$ being p 0, 1, 2 or 3; or a —(CH)R$_{7c}$R$_{7d}$;

R$_{7a}$ and R$_{7b}$ independently from one another represent a hydrogen atom; a branched or unbranched C$_{1-6}$ alkyl radical; a tert-butyloxycarbonyl group; a benzyl group optionally substituted by a halogen; a phenethyl group; a —(CH$_2$)-cyclopropyl group; a hydroxyethoxyethyl group; —OH; —C(=O)H; a pyridinylmethyl group; or R$_{7a}$ and R$_{7b}$ together with the bridging nitrogen form a 5 or 6-membered heterocycloalkyl radical that can additionally contain a second N atom which radical can in turn be substituted by a —NR$_{7a'}$R$_{7b'}$ being R$_{7a'}$ and R$_{7b'}$ a hydrogen atom or a branched or unbranched C$_{1-6}$ alkyl radical; or by a phenyl group in turn optionally substituted by a branched or unbranched C$_{1-6}$ alkyl radical, a halogen atom, —OH or —CN; or R$_{7a}$ and R$_{7b}$ together with the bridging nitrogen form a 5 or 6-membered heterocycloalkyl radical which can be fused to a 5 or 6 membered aromatic ring or can be spirofused to either a single 5 or 6-membered heterocycloalkyl ring having at least one heteroatom selected from N, O or S which in turn can be substituted by one or more substituents selected from a branched or unbranched C$_{1-6}$ alkyl radical, a halogen atom, —OH, —CN or =O; or can be spirofused to a bicyclic ring system formed by a 5 or 6-membered heterocycloalkyl ring having at least one heteroatom selected from N, O or S fused to a 5 or 6-membered aromatic ring;

R$_{7c}$ and R$_{7d}$ independently from one another represent a hydrogen atom; a branched or unbranched C$_{1-6}$ alkyl radical; or C$_{1-6}$alkoxy radical; and R$_8$ is a hydrogen atom; a branched or unbranched C$_{1-6}$ alkyl radical; a tert-butyloxycarbonyl group; a phenyl group; a benzyl group; or a phenethyl group; or a —NR$_{8a}$R$_{8b'}$ being R$_{8a'}$ and R$_{8b'}$ a hydrogen atom or a branched or unbranched C$_{1-6}$ alkyl radical R$_9$ is a hydrogen atom; or a linear or branched C$_{1-6}$ alkyl radical;

or a pharmaceutically acceptable salt, isomer, prodrug or solvate thereof.

It is also an object of the invention different processes for the preparation of compounds of formula (I).

Another object of the invention refers to the use of such compounds of general formula (I) for the treatment and/or prophylaxis of α2δ-1 mediated disorders and more preferably for the treatment and/or prophylaxis of disorders mediated by the α2δ-1 subunit of voltage-gated calcium channels and/or noradrenaline transporter (NET). The compounds of the present invention are particularly suited for the treatment of pain, specially neuropathic pain, and pain related or pain derived conditions.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to compounds of general formula (I)

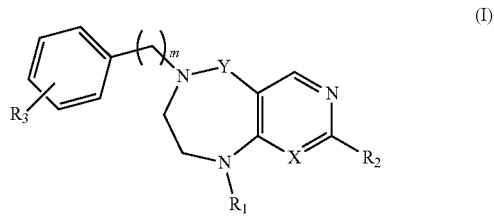

wherein:

X is CRx or N;

Rx is a hydrogen atom; a branched or unbranched C$_{1-6}$ alkyl radical; or a halogen atom;

Y is CH$_2$ or C=O;

m is 0, 1 or 2;

R$_1$ is a hydrogen atom; or a linear or branched C$_{1-6}$ alkyl radical;

R$_2$ is a hydrogen atom; a branched or unbranched C$_{1-6}$ alkyl radical; a halogen atom; haloalkyl; —SR$_{2a}$; —NR$_{2a}$R$_{2b}$; or —OR$_{2a}$;

R$_{2a}$ and R$_{2b}$ are independently from one another a hydrogen atom; a branched or unbranched C$_{1-6}$ alkyl radical; a C$_{3-6}$ cycloalkyl radical; a —(CH$_2$)$_r$-aryl radical where the aryl group is 5 or 6-membered ring and r is 0, 1 or 2; a —(CH$_2$)$_s$-heteroaryl radical where the heteroaryl group is 5 or 6-membered ring with at least one nitrogen atom as heteroatom optionally substituted by at least one halogen atom and s is 0, 1 or 2; or a —(CH$_2$)$_2$—O—CH$_3$;

R$_3$ is a hydrogen atom; —CN; —OH; halogen; a branched or unbranched C$_{1-6}$ alkyl radical; a —(CH$_2$)$_p$—O—R$_4$ being p 0, 1 or 2; a —(CH$_2$)$_q$—NR$_5$R$_6$ being q 0, 1, 2 or 3; a —C(CH$_3$)$_2$—CH$_2$—NR$_5$R$_6$; a —C(=O)NR$_5$R$_6$; a 5 or 6 membered heteroaryl group having at least one heteroatom selected from N, O or S and being substituted by one or two R$_7$ substituents and that can be attached to the phenyl ring by an C$_{1-3}$ alkylene group; or a 5 or 6 membered heterocycloalkyl ring having one or two nitrogen as heteroatom and being unsubstituted or optionally substituted by one or two R$_5$ substituent and that can be attached to the phenyl ring by an C$_{1-3}$ alkylene group; or —C(=O)OR$_9$;

R$_4$ is a hydrogen atom; a branched or unbranched C$_{1-6}$ alkyl radical; a tert-butyldimethylsilyl radical; a methylbenzenesulfonate radical; a —CHR$_{4a}$R$_{4b}$; a —CH$_2$—

$CHR_{4a}R_{4b}$; or a 5 or 6-membered heterocycloalkyl radical having at least one N atom and being optionally substituted by one or two $R_{4c}$ radical;

$R_{4a}$ is a hydrogen atom; a branched or unbranched $C_{1-6}$ alkyl radical; a 5 or 6-membered aryl group optionally substituted by a at least one halogen atom; or a 5 or 6-membered heteroaryl group having at least one heteroatom selected from N, O or S and optionally substituted by at least a branched or unbranched $C_{1-6}$ alkyl radical;

$R_{4b}$ is a —$(CH_2)_j$—$NR_{4b'}R_{4b''}$ being j 0, 1, 2 or 3;

$R_{4b'}$ and $R_{4b''}$ are independently from one another a hydrogen atom; a branched or unbranched $C_{1-6}$ alkyl radical; a $C_{1-6}$ haloalkyl radical; a benzyl group; a phenethyl group; a tert-butyloxycarbonyl group; or a (trimethylsilyl)ethyloxycarbonyl group;

$R_{4b'}$ and $R_{4b''}$ together with the bridging nitrogen form a 5 or 6-membered heterocycloalkyl radical optionally containing an additional heteroatom selected from N, O or S;

$R_{4c}$ is a hydrogen atom; a branched or unbranched $C_{1-6}$ alkyl radical; a phenyl group; a benzyl group; or a tert-butyloxycarbonyl group;

$R_5$ and $R_6$ independently from one another represent a hydrogen atom; a branched or unbranched $C_{1-6}$ alkyl radical; a tert-butyloxycarbonyl group; a benzyl group; a phenethyl group; or $R_5$ and $R_6$ together with the bridging nitrogen form a 5 or 6-membered heterocycloalkyl radical which can be mono or bisubstituted by a phenyl group in turn optionally substituted by a branched or unbranched $C_{1-6}$ alkyl radical, a halogen atom, —OH or —CN; or by an —NRR'; R and R' being independently from one another a hydrogen atom or a branched or unbranched $C_{1-6}$ alkyl radical; or $R_5$ and $R_6$ together with the bridging nitrogen form a 5 or 6-membered heterocycloalkyl radical which can be spirofused to another 5 or 6-membered heterocycloalkyl radical having at least one heteroatom selected from N, O or S which can in turn be substituted by one or more substituents selected from a branched or unbranched $C_{1-6}$ alkyl radical; a halogen atom, —OH, —CN or =O, $R_7$ is a hydrogen atom; a branched or unbranched $C_{1-6}$ alkyl radical; —C(=O)H group; a —$(CH_2)_p$—$NR_{7a}R_{7b}$ being p 0, 1, 2 or 3; or a —$(CH)R_{7c}R_{7d}$;

$R_{7a}$ and $R_{7b}$ independently from one another represent a hydrogen atom; a branched or unbranched $C_{1-6}$ alkyl radical; a tert-butyloxycarbonyl group; a benzyl group optionally substituted by a halogen; a phenethyl group; a —$(CH_2)$-cyclopropyl group; a hydroxyethoxyethyl group; —OH; —C(=O)H; a pyridinylmethyl group; or $R_{7a}$ and $R_{7b}$ together with the bridging nitrogen form a 5 or 6-membered heterocycloalkyl radical that can additionally contain a second N atom which can in turn be substituted by a —$NR_{7a'}R_{7b'}$ being $R_{7a'}$ and $R_{7b'}$ a hydrogen atom or a branched or unbranched $C_{1-6}$ alkyl radical; or by a phenyl group in turn optionally substituted by a branched or unbranched $C_{1-6}$ alkyl radical, a halogen atom, —OH or —CN; or $R_{7a}$ and $R_{7b}$ together with the bridging nitrogen form a 5 or 6-membered heterocycloalkyl radical which can be fused to a 5 or 6 membered aromatic ring or can be spirofused to either a single 5 or 6-membered heterocycloalkyl ring having at least one heteroatom selected from N, O or S which in turn can be substituted by one or more substituents selected from a branched or unbranched $C_{1-6}$ alkyl radical, a halogen atom, —OH, —ON or =O; or can be spirofused to a bicyclic ring system formed by a 5 or 6-membered heterocycloalkyl ring having at least one heteroatom selected from N, O or S fused to a 5 or 6-membered aromatic ring;

$R_{7c}$ and $R_{7d}$ independently from one another represent a hydrogen atom; a branched or unbranched $C_{1-6}$ alkyl radical; or $C_{1-6}$ alkoxy radical; and $R_8$ is a hydrogen atom; a branched or unbranched $C_{1-6}$ alkyl radical; a tert-butyloxycarbonyl group; a phenyl group; a benzyl group; a phenethyl group; or a —$NR8_aR_{8b'}$ being $R_{8a'}$ and $R_{8b'}$ a hydrogen atom or a branched or unbranched $C_{1-6}$ alkyl radical $R_9$ is a hydrogen atom; or a linear or branched $C_{1-6}$ alkyl radical;

or a pharmaceutically acceptable salt, isomer, prodrug or solvate thereof.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

"Halogen" or "halo" as referred in the present invention represent fluorine, chlorine, bromine or iodine. When the term "halo" is combined with other substituents, such as for instance "$C_{1-6}$ haloalkyl" or "$C_{1-6}$ haloalkoxy" it means that the alkyl or alkoxy radical can respectively contain at least one halogen atom.

A leaving group is a group that in a heterolytic bond cleavage keeps the electron pair of the bond. Suitable leaving groups are well known in the art and include Cl, Br, I and —O—$SO_2R^{14}$, wherein $R^{14}$ is F, $C_{1-4}$-alkyl, $C_{1-4}$-haloalkyl, or optionally substituted phenyl. The preferred leaving groups are Cl, Br, I, tosylate, mesylate, triflate, nonaflate and fluorosulphonate.

"$C_{1-6}$ alkyl", as referred to in the present invention, are saturated aliphatic radicals. They may be linear or branched and are optionally substituted. $C_{1-6}$-alkyl as expressed in the present invention means an alkyl radical of 1, 2, 3, 4, 5 or 6 carbon atoms. Preferred alkyl radicals according to the present invention include but are not restricted to methyl, ethyl, propyl, n-propyl, isopropyl, butyl, n-butyl, tert-butyl, isobutyl, sec-butyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl. The most preferred alkyl radical are $C_{1-4}$ alkyl, such as methyl, ethyl, propyl, n-propyl, isopropyl, butyl, n-butyl, tert-butyl, isobutyl, sec-butyl, 1-methylpropyl, 2-methylpropyl or 1,1-dimethylethyl. Alkyl radicals, as defined in the present invention, are optionally mono- or polysubstituted by substitutents independently selected from a halogen, $C_{1-6}$-alkoxy, $C_{1-6}$-alkyl, $C_{1-6}$-haloalkoxy, $C_{1-6}$-haloalkyl, trihaloalkyl or a hydroxyl group.

"$C_{3-6}$ Cycloalkyl" as referred to in the present invention, is understood as meaning saturated and unsaturated (but not aromatic), cyclic hydrocarbons having from 3 to 6 carbon atoms which can optionally be unsubstituted, mono- or polysubstituted. Examples for cycloalkyl radical preferably include but are not restricted to cyclopropyl, cyclobutyl, cyclopentyl, cyclohexyl. Cycloalkyl radicals, as defined in the present invention, are optionally mono- or polysubstituted by substituents independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

A cycloalkylalkyl group/radical $C_{1-6}$, as defined in the present invention, comprises a linear or branched, optionally at least mono-substituted alkyl chain of 1 to 6 atoms which is bonded to a cycloalkyl group, as defined above. The cycloalkylalkyl radical is bonded to the molecule through the alkyl chain. A preferred cycloalkylalkyl group/radical is a cyclopropylmethyl group or a cyclopentylpropyl group, wherein the alkyl chain is optionally branched or substituted. Preferred substituents for cycloalkylalkyl group/radical, according to the present invention, are independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

"Heterocycloalkyl" as referred to in the present invention, are understood as meaning saturated and unsaturated (but not aromatic), generally 5 or 6 membered cyclic hydrocarbons which can optionally be unsubstituted, mono- or polysubstituted and which have at least one heteroatom in their structure selected from N, O or S. Examples for heterocycloalkyl radical preferably include but are not restricted to pyrroline, pyrrolidine, pyrazoline, aziridine, azetidine, tetrahydropyrrole, oxirane, oxetane, dioxetane, tetrahydropyrane, tetrahydrofurane, dioxane, dioxolane, oxazolidine, piperidine, piperazine, morpholine, azepane or diazepane. Heterocycloalkyl radicals, as defined in the present invention, are optionally mono- or polysubstituted by substitutents independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group. More preferably heterocycloalkyl in the context of the present invention are 5 or 6-membered ring systems optionally at least monosubstituted.

A heterocycloalkylalkyl group/radical $C_{1-6}$, as defined in the present invention, comprises a linear or branched, optionally at least mono-substituted alkyl chain of 1 to 6 atoms which is bonded to a cycloalkyl group, as defined above. The heterocycloalkylalkyl radical is bonded to the molecule through the alkyl chain. A preferred heterocycloalkylalkyl group/radical is a piperidinethyl group or a piperazinylmethyl group, wherein the alkyl chain is optionally branched or substituted. Preferred substituents for cycloalkylalkyl group/radical, according to the present invention, are independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

"Aryl" as referred to in the present invention, is understood as meaning ring systems with at least one aromatic ring but without heteroatoms even in only one of the rings. These aryl radicals may optionally be mono- or polysubstituted by substitutents independently selected from a halogen, $C_{1-6}$-alkoxy, $C_{1-6}$-haloalkoxy, $C_{1-6}$-haloalkyl or a hydroxyl group. Preferred examples of aryl radicals include but are not restricted to phenyl, naphthyl, fluoranthenyl, fluorenyl, tetralinyl, indanyl or anthracenyl radicals, which may optionally be mono- or polysubstituted, if not defined otherwise. More preferably aryl in the context of the present invention are 5 or 6-membered ring systems optionally at least monosubstituted.

An arylalkyl radical $C_{1-6}$, as defined in the present invention, comprises a linear or branched, optionally at least mono-substituted alkyl chain of 1 to 6 carbon atoms which is bonded to an aryl group, as defined above. The arylalkyl radical is bonded to the molecule through the alkyl chain. A preferred arylalkyl radical is a benzyl group or a phenetyl group, wherein the alkyl chain is optionally branched or substituted. Preferred substituents for arylalkyl radicals, according to the present invention, are independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

"Heteroaryl" as referred to in the present invention, is understood as meaning heterocyclic ring systems which have at least one aromatic ring and may optionally contain one or more heteroatoms from the group consisting of N, O or S and may optionally be mono- or polysubstituted by substituents independently selected from a halogen, $C_{1-6}$-alkyl, $C_{1-6}$-alkoxy, $C_{1-6}$-haloalkoxy, $C_{1-6}$-haloalkyl trihaloalkyl or a hydroxyl group. Preferred examples of heteroaryls include but are not restricted to furan, benzofuran, pyrrole, pyridine, pyrimidine, pyridazine, pyrazine, quinoline, isoquinoline, phthalazine, triazole, pyrazole, isoxazole, indole, benzotriazole, benzodioxolane, benzodioxane, benzimidazole, carbazole and quinazoline. More preferably heteroaryl in the context of the present invention are 5 or 6-membered ring systems optionally at least monosubstituted.

Heteroarylalkyl group/radical $C_{1-6}$ as defined in the present invention, comprises a linear or branched, optionally at least mono-substituted alkyl chain of 1 to 6 carbon atoms which is bonded to an heteroaryl group, as defined above. The heteroarylalkyl radical is bonded to the molecule through the alkyl chain. A preferred heteroarylalkyl radical is a piridinylmethyl group, wherein the alkyl chain is optionally branched or substituted. Preferred substituents for heteroarylalkyl radicals, according to the present invention, are independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

"Heterocyclic ring" or "heterocyclic system", as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

The term "$C_{1-3}$ alkylene" is understood as meaning a divalent alkyl group like —$CH_2$— or —$CH_2$—$CH_2$— or —$CH_2$—$CH_2$—$CH_2$—. An "alkylene" may also be unsaturated The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, heteroaryl groups, cycloalkyl groups, etc.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition particularly includes physiologically acceptable salts, this term must be understood as equivalent to "pharmacologically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These physiologically acceptable salts may be formed with cations or bases and, in the context of this invention, are understood to be salts formed by at least one compound used in accordance with the invention— normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention— normally protonated, for example in nitrogen—such as a cation and at least one physiologically tolerated anion, particularly when used on humans and/or mammals This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention, $R_1$ is a $C_{1-6}$ alkyl radical, more preferably a $C_{1-4}$ alkyl radical and even more preferably a methyl or ethyl group.

In another particular and preferred embodiment of the invention, $R_2$ is a hydrogen atom; a branched or unbranched $C_{1-6}$ alkyl radical, preferably methyl; a halogen atom, preferably chloro; haloalkyl, preferably trifluoromethyl; a —$SR_{2a}$; a —$NR_{2a}R_{2b}$; or a —$OR_{2a}$; where $R_{2a}$ and $R_{2b}$ are independently selected from a hydrogen atom; a branched or unbranched $C_{1-6}$ alkyl radical, preferably methyl, ethyl, isopropyl or isobutyl; —$(CH_2)_2$—O—$CH_3$; or a group selected from:

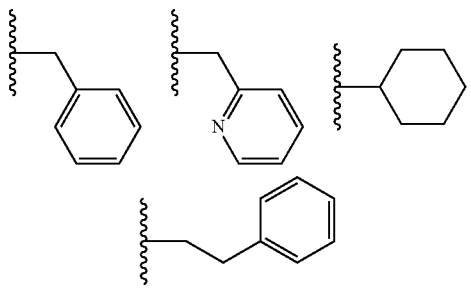

In a still particular embodiment of the invention $R_3$ represents a —$(CH_2)_p$—O—$R_4$ wherein p is 0, 1 or 2 and wherein $R_4$ is:

a hydrogen atom;

a branched or unbranched $C_{1-6}$ alkyl radical, preferably methyl or ethyl;

a tert-butyldimethylsilyl radical;

a methylbenzenesulfonate radical;

a —$CHR_{4a}R_{4b}$ or a —$CH_2$—$CHR_{4a}R_{4b}$ a wherein $R_{4a}$ is a hydrogen atom; a branched or unbranched $C_{1-6}$ alkyl radical, preferably methyl or isopropyl; or a group selected from:

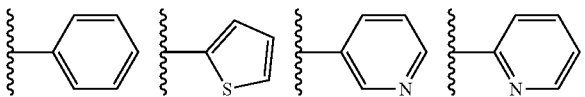

and wherein $R_{4b}$ is a —$(CH_2)_j$—$NR_{4b'}R_{4b''}$ being j 0, 1, 2 or 3 and $R_{4b'}$ and $R_{4b''}$ are independently from one another a hydrogen atom; a branched or unbranched $C_{1-6}$ alkyl radical, preferably methyl; a $C_{1-6}$ haloalkyl radical; a benzyl group; a phenethyl group; a tert-butyloxycarbonyl group; a (trimethylsilyl)ethyloxycarbonyl group; or $R_{4b'}$ and $R_{4b''}$ together with the bridging nitrogen form a group selected from:

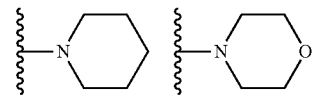

a group selected from:

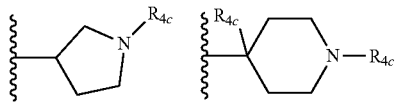

wherein $R_{4c}$ is a hydrogen atom; a branched or unbranched $C_{1-6}$ alkyl radical, preferably methyl; a phenyl group; a benzyl group; or a tert-butyloxycarbonyl group.

Another particular embodiment of the invention is that where $R_3$ represents a —$(CH_2)_q$—$NR_5R_6$; —$C(CH_3)_2$—$CH_2$—$NR_5R_6$; or —$C(=O)NR_5R_6$ wherein q is 0, 1, 2 or 3 and wherein $R_5$ and $R_6$ independently from one another is:
a hydrogen atom;
a branched or unbranched $C_{1-6}$ alkyl radical, preferably methyl;
a tert-butyloxycarbonyl group;
a group selected from:

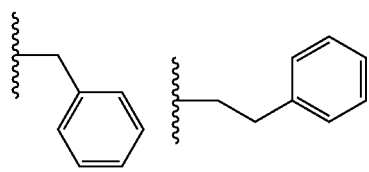

or wherein $R_5$ and $R_6$ together with the bridging nitrogen form the following structures:

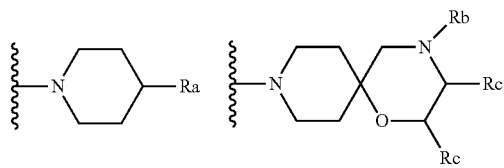

wherein $R_a$ is a phenyl group in turn optionally substituted by a branched or unbranched $C_{1-6}$ alkyl radical, a halogen atom, —OH or —CN; or a —NRR' where R and R' are independently from one another a hydrogen atom or a branched or unbranched $C_{1-6}$ alkyl radical;

$R_b$ is a branched or unbranched $C_{1-6}$ alkyl radical, preferably methyl or isopropyl; a halogen atom; —OH; or —CN; and $R_c$ is a branched or unbranched $C_{1-6}$ alkyl radical, preferably methyl or isopropyl; a halogen atom; —OH; —CN; or =O.

Yet another particular embodiment is that in which $R_3$ represents group selected from:

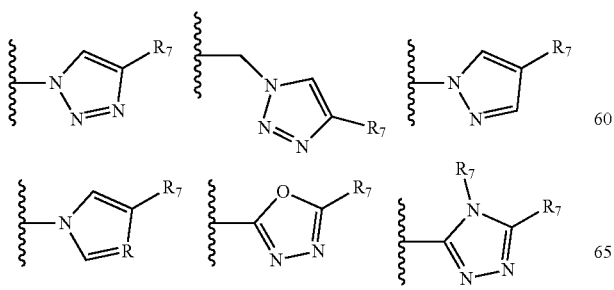

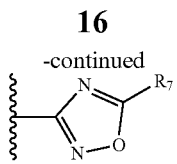

wherein $R_7$ is:
a hydrogen atom;
a branched or unbranched $C_{1-6}$ alkyl radical, preferably methyl or ethyl;
a —C(=O)H group;
a —$(CH_2)_p$—$NR_{7a}R_{7b}$ being p 0, 1, 2 or 3 or a —(CH)$R_{7c}R_{7d}$;
wherein $R_{7a}$ and $R_{7b}$ independently from one another represent a hydrogen atom; a branched or unbranched $C_{1-6}$ alkyl radical, preferably methyl or ethyl; a tert-butyloxycarbonyl group; a benzyl group optionally substituted by a halogen; a phenethyl group; a —$(CH_2)$-cyclopropyl; a hydroxyethoxyethyl group; —OH; a —C(=O)H group; a pyridinylmethyl group; or $R_{7a}$ and $R_{7b}$ together with the bridging nitrogen represents one of the following structures:

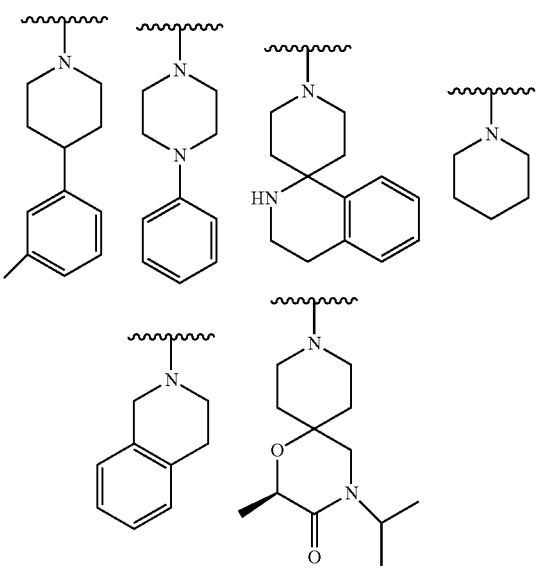

where R" is a hydrogen or an —OH group;
and wherein $R_{7c}$ and $R_{7d}$ independently from one another represent a hydrogen atom; a branched or unbranched $C_{1-6}$ alkyl radical; or $C_{1-6}$ alkoxy radical, preferably ethoxy.

Another particular embodiment of the invention contemplates that $R_3$ represents a group selected from:

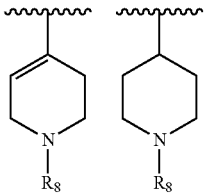

wherein $R_8$ is a hydrogen atom; a branched or unbranched $C_{1-6}$ alkyl radical; a tert-butyloxycarbonyl group; a benzyl group or a phenethyl group.

In a still particular embodiment $R_3$ is a —C(=O)OR$_9$ wherein is $R_9$ a hydrogen atom or a linear or branched $C_{1-6}$ alkyl radical, preferably methyl.

A particularly preferred embodiment of the invention is represented by compounds of general formula (I) where $R_1$ is a $C_{1-6}$ alkyl radical, more preferably $C_{1-4}$ alkyl radical and even more preferably methyl or ethyl;

$R_2$ is a hydrogen atom; a branched or unbranched $C_{1-6}$ alkyl radical, preferably methyl; a halogen atom, preferably chloro; haloalkyl, preferably trifluoromethyl; a —SR$_{2a}$; a —NR$_{2a}$R$_{2b}$; or a —OR$_{2a}$; where $R_{2a}$ and $R_{2b}$ are independently selected from a hydrogen atom; a branched or unbranched $C_{1-4}$ alkyl radical, preferably methyl, ethyl, isopropyl or isobutyl; —(CH$_2$)$_2$—O—CH$_3$; or a group selected from:

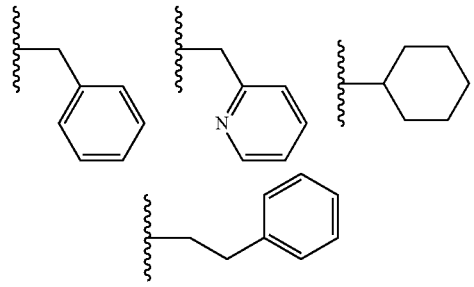

and $R_3$ represents a —(CH$_2$)$_p$—O—R$_4$ wherein p is 0, 1 or 2 and wherein $R_4$ is:

a hydrogen atom;

a branched or unbranched $C_{1-6}$ alkyl radical, preferably methyl or ethyl;

a tert-butyldimethylsilyl radical;

a methylbenzenesulfonate radical;

a —CHR$_{4a}$R$_{4b}$ or a —CH$_2$—CHR$_{4a}$R$_{4b}$ wherein $R_{4a}$ is a hydrogen atom; a branched or unbranched $C_{1-6}$ alkyl radical, preferably methyl or isopropyl; or a group selected from:

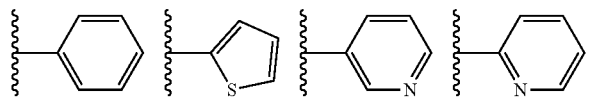

and wherein $R_{4b}$ is a —(CH$_2$)$_j$—NR$_{4b'}$R$_{4b''}$ being j 0, 1, 2 or 3 and $R_{4b'}$ and $R_{4b''}$ are independently from one another a hydrogen atom; a branched or unbranched $C_{1-6}$ alkyl radical, preferably methyl; a $C_{1-6}$ haloalkyl radical; a benzyl group; a phenethyl group; a tert-butyloxycarbonyl group; a (trimethylsilyl)ethyloxycarbonyl group; or $R_{4b'}$ and $R_{4b''}$ together with the bridging nitrogen form a group selected from:

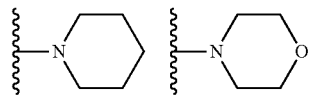

a group selected from:

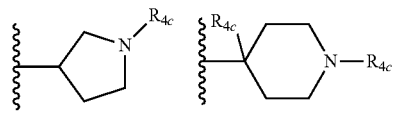

wherein $R_{4c}$ is a hydrogen atom; a branched or unbranched $C_{1-6}$ alkyl radical, preferably methyl; a phenyl group; a benzyl group; or a tert-butyloxycarbonyl group.

Another particularly preferred embodiment of the invention is represented by compounds of formula (I) where $R_1$ is a $C_{1-6}$ alkyl radical, more preferably $C_{1-4}$ alkyl radical and even more preferably methyl or ethyl;

$R_2$ is a hydrogen atom; a branched or unbranched $C_{1-6}$ alkyl radical, preferably methyl; a halogen atom, preferably chloro; haloalkyl, preferably trifluoromethyl; a —SR$_{2a}$; a —NR$_{2a}$R$_{2b}$; or a —OR$_{2a}$; where $R_{2a}$ and $R_{2b}$ are independently selected from a hydrogen atom; a branched or unbranched $C_{1-4}$ alkyl radical, preferably methyl, ethyl, isopropyl or isobutyl; —(CH$_2$)$_2$—O—CH$_3$; or a group selected from:

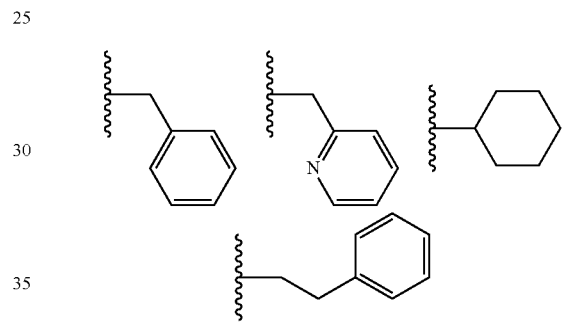

and $R_3$ represents a —(CH$_2$)$_q$—NR$_5$R$_6$; —C(CH$_3$)$_2$—CH$_2$—NR$_5$R$_6$; or —C(=O)NR$_5$R$_6$ wherein q is 0, 1, 2 or 3 and wherein $R_5$ and $R_6$ independently from one another is:

a hydrogen atom;

a branched or unbranched $C_{1-6}$ alkyl radical, preferably methyl;

a tert-butyloxycarbonyl group;

a group selected from:

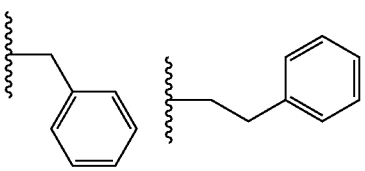

or wherein $R_5$ and $R_6$ together with the bridging nitrogen form the following structures:

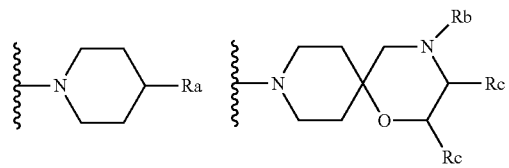

wherein $R_a$ is a phenyl group in turn optionally substituted by a branched or unbranched $C_{1-6}$ alkyl radical, a halogen atom, —OH or —CN; or a —NRR' where R and R' are independently from one another a hydrogen atom or a branched or unbranched $C_{1-6}$ alkyl radical;

$R_b$ is a branched or unbranched $C_{1-6}$ alkyl radical, preferably methyl or isopropyl; a halogen atom; —OH; or —CN; and $R_c$ is a branched or unbranched $C_{1-6}$ alkyl radical, preferably methyl or isopropyl; a halogen atom; —OH; —CN; or =O.

A further particularly preferred embodiment is represented by compounds of general formula (I) where $R_1$ is a $C_{1-6}$ alkyl radical, more preferably $C_{1-4}$ alkyl radical and even more preferably methyl or ethyl;

$R_2$ is a hydrogen atom; a branched or unbranched $C_{1-6}$ alkyl radical, preferably methyl; a halogen atom, preferably chloro; haloalkyl, preferably trifluoromethyl; a —$SR_{2a}$; a —$NR_{2a}R_{2b}$; or a —$OR_{2a}$; where $R_{2a}$ and $R_{2b}$ are independently selected from a hydrogen atom; a branched or unbranched $C_{1-4}$ alkyl radical, preferably methyl, ethyl, isopropyl or isobutyl; —$(CH_2)_2$—O—$CH_3$; or a group selected from:

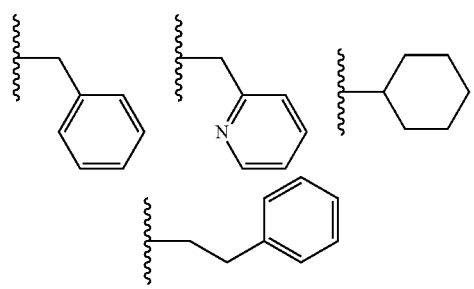

and $R_3$ represents a group selected from:

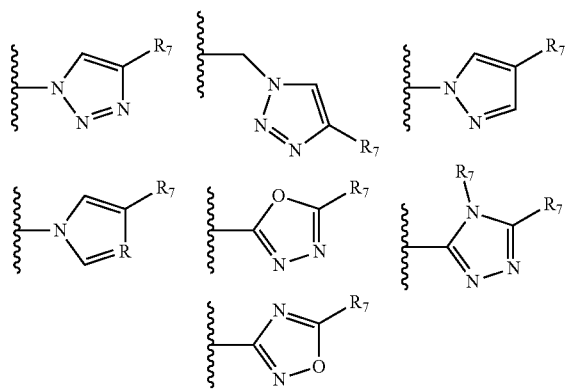

wherein $R_7$ is:
a hydrogen atom;
a branched or unbranched $C_{1-6}$ alkyl radical, preferably methyl or ethyl;
a —C(=O)H group;
a —$(CH_2)_p$—$NR_{7a}R_{7b}$ being p 0, 1, 2 or 3 or a —(CH)$R_{7c}R_{7d}$;
wherein $R_{7a}$ and $R_{7b}$ independently from one another represent a hydrogen atom; a branched or unbranched $C_{1-6}$ alkyl radical, preferably methyl or ethyl; a tert-butyloxycarbonyl group; a benzyl group optionally substituted by a halogen; a phenethyl group; a —$(CH_2)$-cyclopropyl; a hydroxyethoxyethyl group; —OH; C(=O)H group; a pyridinylmethyl group; or $R_{7a}$ and $R_{7b}$ together with the bridging nitrogen represents one of the following structures:

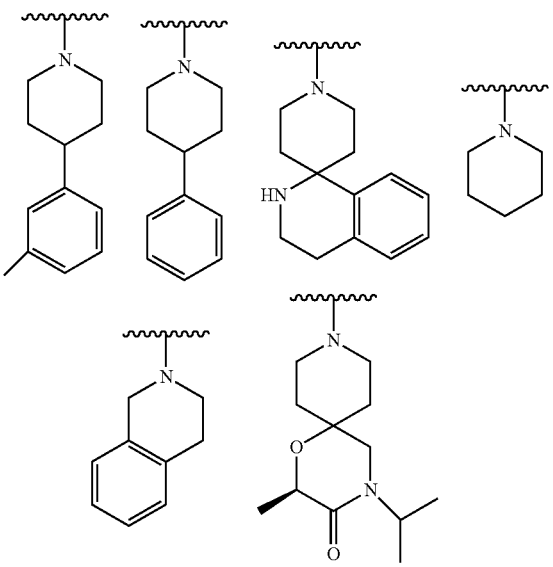

where R" is a hydrogen or an —OH group;
and wherein $R_{7c}$ and $R_{7d}$ independently from one another represent a hydrogen atom; a branched or unbranched $C_{1-6}$ alkyl radical; or $C_{1-6}$ alkoxy radical, preferably ethoxy.

The compounds of the present invention represented by the above described formula (I) may include enantiomers depending on the presence of chiral centers or isomers depending on the presence of double bonds (e.g. Z, E). The single isomers, enantiomers or diastereoisomers and mixtures thereof fall within the scope of the present invention.

Among all the compounds described in the general formula (I), the following compounds are preferred for showing and intense inhibitory effect towards subunit α2δ-1 of voltage-gated calcium channels (VGCC):

[1] tert-Butyl methyl(3-(3-(9-methyl-2-(methylthio)-5-oxo-5,7,8,9-tetrahydro-6H-pyrimido [4,5-e][1,4]diazepin-6-yl)phenoxy)-3-phenylpropyl)carbamate;

[2] tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

[3] tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

[4] tert-butyl methyl(2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate;

[5] tert-butyl (2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate;

[6] tert-butyl methyl(2-(3-(9-methyl-2-(methylthio)-5-oxo-5,7,8,9-tetrahydro-6H-pyrimido[4,5-e][1,4]diazepin-6-yl)phenoxy)propyl)carbamate;

[7] tert-butyl methyl(3-methyl-2-(3-(9-methyl-2-(methylthio)-5-oxo-5,7,8,9-tetrahydro-6H-pyrimido[4,5-e][1,4]diazepin-6-yl)phenoxy)butyl)carbamate;

[8] tert-butyl methyl(2-(4-(9-methyl-2-(methylthio)-5-oxo-5,7,8,9-tetrahydro-6H-pyrimido[4,5-e][1,4]diazepin-6-yl)phenoxy)-2-phenylethyl)carbamate;

[9] tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

[10] tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

[11] tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

[12] tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[13] tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[14] tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[15] tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

[16] tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

[17] tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

[18] tert-butyl methyl(2-((3-(9-methyl-2-(methylthio)-5-oxo-5,7,8,9-tetrahydro-6H-pyrimido[4,5-e][1,4]diazepin-6-yl)benzyl)oxy)-1-phenylethyl)carbamate;

[19] 2-(trimethylsilyl)ethyl methyl(2-((3-(9-methyl-2-(methylthio)-5-oxo-5,7,8,9-tetrahydro-6H-pyrimido[4,5-e][1,4]diazepin-6-yl)benzyl)oxy)-2-phenylethyl)carbamate;

[20] tert-butyl methyl(3-(3-(9-methyl-2-(methylthio)-5-oxo-5,7,8,9-tetrahydro-6H-pyrimido[4,5-e][1,4]diazepin-6-yl)phenoxy)propyl)carbamate;

[21] tert-butyl benzyl(3-(3-(9-methyl-2-(methylthio)-5-oxo-5,7,8,9-tetrahydro-6H-pyrimido[4,5-e][1,4]diazepin-6-yl)phenoxy)propyl)carbamate;

[22] tert-butyl methyl(2-(3-(9-methyl-2-(methylthio)-5-oxo-5,7,8,9-tetrahydro-6H-pyrimido[4,5-e][1,4]diazepin-6-yl)phenoxy)ethyl)carbamate;

[23] tert-butyl methyl(3-(3-(9-methyl-2-(methylthio)-5-oxo-5,7,8,9-tetrahydro-6H-pyrimido[4,5-e][1,4]diazepin-6-yl)phenyl)propyl)carbamate;

[24] tert-butyl methyl(3-(9-methyl-2-(methylthio)-5-oxo-5,7,8,9-tetrahydro-6H-pyrimido[4,5-e][1,4]diazepin-6-yl)phenethyl)carbamate;

[25] tert-butyl methyl(2-methyl-2-(3-(9-methyl-2-(methylthio)-5-oxo-5,7,8,9-tetrahydro-6H-pyrimido[4,5-e][1,4]diazepin-6-yl)phenyl)propyl)carbamate;

[26] tert-butyl methyl(3-(9-methyl-2-(methylthio)-5-oxo-5,7,8,9-tetrahydro-6H-pyrimido[4,5-e][1,4]diazepin-6-yl)benzyl)carbamate;

[27] tert-butyl 3-(3-(9-methyl-2-(methylthio)-5-oxo-5,7,8,9-tetrahydro-6H-pyrimido[4,5-e][1,4]diazepin-6-yl)phenoxy)pyrrolidine-1-carboxylate;

[28] tert-butyl 4-((3-(9-methyl-2-(methylthio)-5-oxo-5,7,8,9-tetrahydro-6H-pyrimido[4,5-e][1,4]diazepin-6-yl)benzyl)oxy)-4-phenylpiperidine-1-carboxylate;

[29] 9-methyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one;

[30] 9-ethyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one;

[31] 9-methyl-6-(3-(5-methyl-1,2,4-oxadiazol-3-yl)phenyl)-2-(methylthio)-6,7,8,9-tetrahydro-5H-pyrimido[4,5-e][1,4]diazepin-5-one;

[32] 6-(3-methoxyphenyl)-9-methyl-2-(methylthio)-6,7,8,9-tetrahydro-5H-pyrimido[4,5-e][1,4]diazepin-5-one;

[33] 3-(9-methyl-2-(methylthio)-5-oxo-5,7,8,9-tetrahydro-6H-pyrimido[4,5-e][1,4]diazepin-6-yl)benzonitrile;

[34] 6-(3-((tert-butyldimethylsilyl)oxy)phenyl)-9-methyl-2-(methylthio)-6,7,8,9-tetrahydro-5H-pyrimido[4,5-e][1,4]diazepin-5-one;

[35] 6-(3-bromophenyl)-9-methyl-2-(methylthio)-6,7,8,9-tetrahydro-5H-pyrimido[4,5-e][1,4]diazepin-5-one;

[36] 6-(3-(2-hydroxyethyl)phenyl)-9-methyl-2-(methylthio)-6,7,8,9-tetrahydro-5H-pyrimido[4,5-e][1,4]diazepin-5-one;

[37] 6-(4-methoxyphenyl)-9-methyl-2-(methylthio)-6,7,8,9-tetrahydro-5H-pyrimido[4,5-e][1,4]diazepin-5-one;

[38] 6-(4-((tert-butyldimethylsilyl)oxy)phenyl)-9-methyl-2-(methylthio)-6,7,8,9-tetrahydro-5H-pyrimido[4,5-e][1,4]diazepin-5-one;

[39] tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

[40] tert-butyl ((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

[41] tert-butyl benzyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

[42] 6-(3-(4-(diethoxymethyl)-1H-1,2,3-triazol-1-yl)phenyl)-9-methyl-2-(methylthio)-6,7,8,9-tetrahydro-5H-pyrimido[4,5-e][1,4]diazepin-5-one;

[43] tert-butyl methyl(2-(1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)ethyl)carbamate;

[44] tert-butyl methyl((1-(3-(9-methyl-2-(methylthio)-5-oxo-5,7,8,9-tetrahydro-6H-pyrimido[4,5-e][1,4]diazepin-6-yl)benzyl)-1H-1,2,3-triazol-4-yl)methyl)carbamate;

[45] tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-pyrazol-4-yl)methyl)carbamate;

[46] tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-imidazol-4-yl)methyl)carbamate;

[47] tert-butyl methyl((5-(3-(9-methyl-2-(methylthio)-5-oxo-5,7,8,9-tetrahydro-6H-pyrimido[4,5-e][1,4]diazepin-6-yl)phenyl)-1,3,4-oxadiazol-2-yl)methyl)carbamate;

[48] tert-butyl methyl(3-(2-(9-methyl-2-(methylthio)-5-oxo-5,7,8,9-tetrahydro-6H-pyrimido[4,5-e][1,4]diazepin-6-yl) phenoxy)-3-phenylpropyl)carbamate;

[49] tert-butyl methyl(4-methyl-3-((3-(9-methyl-2-(methylthio)-5-oxo-5,7,8,9-tetrahydro-6H-pyrimido[4,5-e][1,4]diazepin-6-yl)benzyl)oxy)pentyl)carbamate;

[50] tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)butyl)carbamate;

[51] 2-(trimethylsilyl)ethyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[52] tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-2-yl)propyl)carbamate;

[53] tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-3-yl)propyl)carbamate;

[54] 8-(ethylamino)-1-methyl-4-(3-(5-methyl-1,3,4-oxadiazol-2-yl)phenyl)-1,2,3,4-tetrahydro-5H-pyrido[4,3-e][1,4]diazepin-5-one;

[55] 4-(3-(4-ethyl-5-methyl-4H-1,2,4-triazol-3-yl)phenyl)-8-(ethylamino)-1-methyl-1,2,3,4-tetrahydro-5H-pyrido[4,3-e][1,4]diazepin-5-one;

[56] tert-butyl (3-(3-(8-(ethylamino)-1-methyl-5-oxo-1,2,3,5-tetrahydro-4H-pyrido[4,3-e][1,4]diazepin-4-yl)phenoxy)-3-phenylpropyl)(methyl)carbamate;

[57] tert-butyl (3-((3-(8-(ethylamino)-1-methyl-5-oxo-1,2,3,5-tetrahydro-4H-pyrido[4,3-e][1,4]diazepin-4-yl)benzyl)oxy)-3-phenylpropyl)(methyl)carbamate;

[58] 2-(trimethylsilyl)ethyl (3-(3-(8-(ethylamino)-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[59] 2-(trimethylsilyl)ethyl (3-(3-(8-(dimethylamino)-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[60] 2-(trimethylsilyl)ethyl (3-((3-(8-(ethylamino)-1-methyl-5-oxo-1,2,3,5-tetrahydro-4H-pyrido[4,3-e][1,4]diazepin-4-yl)benzyl)oxy)-3-(thiophen-2-yl)propyl)(methyl)carbamate;

[61] tert-butyl (2-fluoroethyl)(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[62] tert-Butyl methyl(2-(3-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate;

[63] tert-butyl methyl(2-(4-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate;

[64] tert-butyl methyl(4-((9-methyl-2-(methylthio)-5-oxo-5,7,8,9-tetrahydro-6H-pyrimido[4,5-e][1,4]diazepin-6-yl)methyl)benzyl)carbamate;

[65] tert-Butyl (R)-(3-((3-(2-(ethylamino)-9-methyl-5,7,8,9-tetrahydro-6H-pyrimido[4,5-e][1,4]diazepin-6-yl)benzyl)oxy)-3-phenylpropyl)(methyl)carbamate;

[66] N-ethyl-9-methyl-6-(3-(5-methyl-1,3,4-oxadiazol-2-yl)phenyl)-6,7,8,9-tetrahydro-5H-pyrimido[4,5-e][1,4]diazepin-2-amine;

[67] N-ethyl-6-(3-methoxybenzyl)-9-methyl-6,7,8,9-tetrahydro-5H-pyrimido[4,5-e][1,4]diazepin-2-amine;

[68] N-ethyl-6-(4-methoxybenzyl)-9-methyl-6,7,8,9-tetrahydro-5H-pyrimido[4,5-e][1,4]diazepin-2-amine;

[69] tert-Butyl (3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[70] tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[71] tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[72] tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate;

[73] tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)carbamate;

[74] tert-butyl (2-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate;

[75] tert-butyl (2-(3-(2-(ethylamino)-9-methyl-5-oxo-5,7,8,9-tetrahydro-6H-pyrimido[4,5-e][1,4]diazepin-6-yl)phenoxy)-3-methylbutyl)(methyl)carbamate;

[76] tert-butyl (2-(4-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate;

[77] tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[78] tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[79] tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[80] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[81] tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[82] tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[83] tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[84] tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[85] tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[86] tert-butyl (2-((3-(2-(ethylamino)-9-methyl-5-oxo-5,7,8,9-tetrahydro-6H-pyrimido[4,5-e][1,4]diazepin-6-yl)benzyl)oxy)-1-phenylethyl)(methyl)carbamate;

[87] 2-(trimethylsilyl)ethyl (2-((3-(2-(ethylamino)-9-methyl-5-oxo-5,7,8,9-tetrahydro-6H-pyrimido[4,5-e][1,4]diazepin-6-yl)benzyl)oxy)-2-phenylethyl)(methyl)carbamate;

[88] tert-butyl (3-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate;

[89] tert-butyl benzyl(3-(3-(2-(ethylamino)-9-methyl-5-oxo-5,7,8,9-tetrahydro-6H-pyrimido[4,5-e][1,4]diazepin-6-yl)phenoxy)propyl)carbamate;

[90] tert-butyl (2-(3-(2-(ethylamino)-9-methyl-5-oxo-5,7,8,9-tetrahydro-6H-pyrimido[4,5-e][1,4]diazepin-6-yl)phenoxy)ethyl)(methyl)carbamate;

[91] tert-butyl (3-(3-(2-(ethylamino)-9-methyl-5-oxo-5,7,8,9-tetrahydro-6H-pyrimido[4,5-e][1,4]diazepin-6-yl)phenyl)propyl)(methyl)carbamate;

[92] tert-butyl (3-(2-(ethylamino)-9-methyl-5-oxo-5,7,8,9-tetrahydro-6H-pyrimido[4,5-e][1,4]diazepin-6-yl)phenethyl)(methyl)carbamate;

[93] tert-butyl (2-(3-(2-(ethylamino)-9-methyl-5-oxo-5,7,8,9-tetrahydro-6H-pyrimido[4,5-e][1,4]diazepin-6-yl)phenyl)-2-methylpropyl)(methyl)carbamate;

[94] tert-butyl (3-(2-(ethylamino)-9-methyl-5-oxo-5,7,8,9-tetrahydro-6H-pyrimido[4,5-e][1,4]diazepin-6-yl)benzyl)(methyl)carbamate;

[95] tert-butyl 3-(3-(2-(ethylamino)-9-methyl-5-oxo-5,7,8,9-tetrahydro-6H-pyrimido[4,5-e][1,4]diazepin-6-yl)phenoxy)pyrrolidine-1-carboxylate;

[96] tert-butyl 4-((3-(2-(ethylamino)-9-methyl-5-oxo-5,7,8,9-tetrahydro-6H-pyrimido[4,5-e][1,4]diazepin-6-yl)benzyl)oxy)-4-phenylpiperidine-1-carboxylate;

[97] 2-(ethylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[98] 2-(isobutylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[99] 2-((2-methoxyethyl)amino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[100] 9-methyl-6-(3-(5-methyl-1,3,4-oxadiazol-2-yl)phenyl)-2-(methylamino)-6,7,8,9-tetrahydro-5H-pyrimido[4,5-e][1,4]diazepin-5-one;

[101] 2-amino-9-methyl-6-(3-(5-methyl-1,3,4-oxadiazol-2-yl)phenyl)-6,7,8,9-tetrahydro-5H-pyrimido[4,5-e][1,4]di2-(benzylamino)-9-methyl-6-(3-(5-methyl-1,3,4-oxadiazol-2-yl)phenyl)-6,7,8,9-tetrahydro-5H-pyrimido[4,5-e][1,4]diazepin-5-one azepin-5-one;

[102] 2-(benzylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[103] 2-(cyclohexylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[104] 2-(benzyl(methyl)amino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[105] 9-methyl-6-(3-(5-methyl-1,3,4-oxadiazol-2-yl)phenyl)-2-(phenethylamino)-6,7,8,9-tetrahydro-5H-pyrimido[4,5-e][1,4]diazepin-5-one;

[106] 9-methyl-2-(methyl (pyridin-2-ylmethyl)amino)-6-(3-(5-methyl-1,3,4-oxadiazol-2-yl)phenyl)-6,7,8,9-tetrahydro-5H-pyrimido[4,5-e][1,4]diazepin-5-one;

[107] 9-ethyl-2-(ethylamino)-6-(3-(5-methyl-1,3,4-oxadiazol-2-yl)phenyl)-6,7,8,9-tetrahydro-5H-pyrimido[4,5-e][1,4]diazepin-5-one;

[108] 2-(ethylamino)-9-methyl-6-(3-(5-methyl-1,2,4-oxadiazol-3-yl)phenyl)-6,7,8,9-tetrahydro-5H-pyrimido[4,5-e][1,4]diazepin-5-one;

[109] 2-(ethylamino)-6-(3-methoxyphenyl)-9-methyl-6,7,8,9-tetrahydro-5H-pyrimido[4,5-e][1,4]diazepin-5-one;

[110] 3-(2-(ethylamino)-9-methyl-5-oxo-5,7,8,9-tetrahydro-6H-pyrimido[4,5-e][1,4]diazepin-6-yl)benzonitrile;

[111] 6-(3-((tert-butyldimethylsilyl)oxy)phenyl)-2-(ethylamino)-9-methyl-6,7,8,9-tetrahydro-5H-pyrimido[4,5-e][1,4]diazepin-5-one;

[112] 2-(ethylamino)-6-(3-(2-hydroxyethyl)phenyl)-9-methyl-6,7,8,9-tetrahydro-5H-pyrimido[4,5-e][1,4]diazepin-5-one;

[113] 2-(ethylamino)-6-(3-(2-hydroxyethyl)phenyl)-9-methyl-6,7,8,9-tetrahydro-5H-pyrimido[4,5-e][1,4]diazepin-5-one;

[114] 2-(ethylamino)-6-(4-methoxyphenyl)-9-methyl-6,7,8,9-tetrahydro-5H-pyrimido[4,5-e][1,4]diazepin-5-one;

[115] 6-(4-((tert-butyldimethylsilyl)oxy)phenyl)-2-(ethylamino)-9-methyl-6,7,8,9-tetrahydro-5H-pyrimido[4,5-e][1,4]diazepin-5-one;

[116] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)(methyl)carbamate;

[117] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate;

[118] tert-butyl benzyl((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate;

[119] 6-(3-(4-(diethoxymethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[120] tert-butyl (2-(1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)ethyl)(methyl)carbamate;

[121] tert-butyl ((1-(3-(2-(ethylamino)-9-methyl-5-oxo-5,7,8,9-tetrahydro-6H-pyrimido[4,5-e][1,4]diazepin-6-yl)benzyl)-1H-1,2,3-triazol-4-yl)methyl)(methyl)carbamate;

[122] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-pyrazol-4-yl)methyl)(methyl)carbamate;

[123] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-imidazol-4-yl)methyl)(methyl)carbamate;

[124] tert-butyl ((5-(3-(2-(ethylamino)-9-methyl-5-oxo-5,7,8,9-tetrahydro-6H-pyrimido[4,5-e][1,4]diazepin-6-yl)phenyl)-1,3,4-oxadiazol-2-yl)methyl)(methyl)carbamate;

[125] tert-butyl (3-(2-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[126] tert-butyl (3-((3-(2-(ethylamino)-9-methyl-5-oxo-5,7,8,9-tetrahydro-6H-pyrimido[4,5-e][1,4]diazepin-6-yl)benzyl)oxy)-4-methylpentyl)(methyl)carbamate;

[127] tert-butyl (3-((3-(2-(ethylamino)-9-methyl-5-oxo-5,7,8,9-tetrahydro-6H-pyrimido[4,5-e][1,4]diazepin-6-yl)benzyl)oxy)butyl)(methyl)carbamate;

[128] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-2-yl)propyl)(methyl)carbamate;

[129] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-3-yl)propyl)(methyl)carbamate;

[130] tert-butyl (R)-(3-((3-(2-amino-9-methyl-5-oxo-5,7,8,9-tetrahydro-6H-pyrimido[4,5-e][1,4]diazepin-6-yl)benzyl)oxy)-3-phenylpropyl)(methyl)carbamate;

[131] tert-butyl (R)-(3-((3-(2-(dimethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[132] tert-butyl (R)-methyl(3-((3-(9-methyl-2-(methylamino)-5-oxo-5,7,8,9-tetrahydro-6H-pyrimido[4,5-e][1,4]diazepin-6-yl)benzyl)oxy)-3-phenylpropyl)carbamate;

[133] 2-(trimethylsilyl)ethyl (3-(3-(2-(dimethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[134] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(2-fluoroethyl)carbamate;

[135] tert-butyl (2-(3-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate;

[136] tert-butyl (2-(4-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate;

[137] tert-butyl (4-((2-(ethylamino)-9-methyl-5-oxo-5,7,8,9-tetrahydro-6H-pyrimido[4,5-e][1,4]diazepin-6-yl)methyl)benzyl)(methyl)carbamate;

[138] tert-Butyl (R)-(3-((3-(2-methoxy-9-methyl-5-oxo-5,7,8,9-tetrahydro-6H-pyrimido[4,5-e][1,4]diazepin-6-yl)benzyl)oxy)-3-phenylpropyl)(methyl)carbamate;

[139] tert-butyl (3-((3-(2-methoxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[140] tert-Butyl (R)-(3-((3-(2-hydroxy-9-methyl-5-oxo-5,7,8,9-tetrahydro-6H-pyrimido[4,5-e][1,4]diazepin-6-yl)benzyl)oxy)-3-phenylpropyl)(methyl)carbamate;

[141] tert-butyl (3-((3-(2-hydroxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[142] tert-Butyl (R)-(3-((3-(2,9-dimethyl-5-oxo-5,7,8,9-tetrahydro-6H-pyrimido[4,5-e][1,4]diazepin-6-yl)benzyl)oxy)-3-phenylpropyl)(methyl)carbamate;

[143] tert-butyl (3-((3-(2,9-dimethyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[144] 2-(trimethylsilyl)ethyl (3-(3-(2,9-dimethyl-5-oxo-5,7,8,9-tetrahydro-6H-pyrimido[4,5-e][1,4]diazepin-6-yl)phenoxy)-3-(thiophen-2-yl)propyl)(methyl)carbamate;

[145] tert-Butyl (R)-methyl(3-((3-(9-methyl-5-oxo-5,7,8,9-tetrahydro-6H-pyrimido[4,5-e][1,4]diazepin-6-yl)benzyl)oxy)-3-phenylpropyl)carbamate;

[146] tert-butyl methyl(3-((3-(9-methyl-5-oxo-5,7,8,9-tetrahydro-6H-pyrimido[4,5-e][1,4]diazepin-6-yl)benzyl)oxy)-3-(thiophen-2-yl)propyl)carbamate;

[147] 2-(trimethylsilyl)ethyl methyl(3-(3-(9-methyl-5-oxo-5,7,8,9-tetrahydro-6H-pyrimido[4,5-e][1,4]diazepin-6-yl)phenoxy)-3-(thiophen-2-yl)propyl)carbamate;

[148] 2-(Ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[149] (R)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[150] (S)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[151] 9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[152] (R)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[153] (S)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[154] 2-(ethylamino)-9-methyl-6-(3-(2-(methylamino)-1-phenylethoxy)phenyl)-6,7,8,9-tetrahydro-5H-pyrimido[4,5-e][1,4]diazepin-5-one;

[155] 9-methyl-6-(3-(2-(methylamino)-1-phenylethoxy)phenyl)-2-(methylthio)-6,7,8,9-tetrahydro-5H-pyrimido[4,5-e][1,4]diazepin-5-one;

[156] 6-(3-(2-amino-1-phenylethoxy)phenyl)-2-(ethylamino)-9-methyl-6,7,8,9-tetrahydro-5H-pyrimido[4,5-e][1,4]diazepin-5-one;

[157] 2-(ethylamino)-9-methyl-6-(3-((1-(methylamino)propan-2-yl)oxy)phenyl)-6,7,8,9-tetrahydro-5H-pyrimido[4,5-e][1,4]diazepin-5-one;

[158] 2-(ethylamino)-9-methyl-6-(3-((3-methyl-1-(methylamino)butan-2-yl)oxy)phenyl)-6,7,8,9-tetrahydro-5H-pyrimido[4,5-e][1,4]diazepin-5-one;

[159] 2-(ethylamino)-9-methyl-6-(4-(2-(methylamino)-1-phenylethoxy)phenyl)-6,7,8,9-tetrahydro-5H-pyrimido[4,5-e][1,4]diazepin-5-one;

[160] 2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[161] (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[162] (S)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[163] 9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[164] (R)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[165] (S)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[166] 2-(ethylamino)-9-methyl-6-(3-((2-(methylamino)-2-phenylethoxy)methyl)phenyl)-6,7,8,9-tetrahydro-5H-pyrimido[4,5-e][1,4]diazepin-5-one;

[167] 9-methyl-6-(3-((2-(methylamino)-2-phenylethoxy)methyl)phenyl)-2-(methylthio)-6,7,8,9-tetrahydro-5H-pyrimido[4,5-e][1,4]diazepin-5-one;

[168] 2-(ethylamino)-9-methyl-6-(3-(3-(methylamino)propoxy)phenyl)-6,7,8,9-tetrahydro-5H-pyrimido[4,5-e][1,4]diazepin-5-one;

[169] 6-(3-(3-(benzylamino)propoxy)phenyl)-2-(ethylamino)-9-methyl-6,7,8,9-tetrahydro-5H-pyrimido[4,5-e][1,4]diazepin-5-one;

[170] 2-(ethylamino)-9-methyl-6-(3-(2-(methylamino)ethoxy)phenyl)-6,7,8,9-tetrahydro-5H-pyrimido[4,5-e][1,4]diazepin-5-one;

[171] 2-(ethylamino)-9-methyl-6-(3-(3-(methylamino)propyl)phenyl)-6,7,8,9-tetrahydro-5H-pyrimido[4,5-e][1,4]diazepin-5-one;

[172] 2-(ethylamino)-9-methyl-6-(3-(2-(methylamino)ethyl)phenyl)-6,7,8,9-tetrahydro-5H-pyrimido[4,5-e][1,4]diazepin-5-one;

[173] 2-(ethylamino)-9-methyl-6-(3-(2-methyl-1-(methylamino)propan-2-yl)phenyl)-6,7,8,9-tetrahydro-5H-pyrimido[4,5-e][1,4]diazepin-5-one;

[174] 2-(ethylamino)-9-methyl-6-(3-((methylamino)methyl)phenyl)-6,7,8,9-tetrahydro-5H-pyrimido[4,5-e][1,4]diazepin-5-one;

[175] 2-(ethylamino)-9-methyl-6-(3-(pyrrolidin-3-yloxy)phenyl)-6,7,8,9-tetrahydro-5H-pyrimido[4,5-e][1,4]diazepin-5-one;

[176] 2-(ethylamino)-9-methyl-6-(3-(((4-phenylpiperidin-4-yl)oxy)methyl)phenyl)-6,7,8,9-tetrahydro-5H-pyrimido[4,5-e][1,4]diazepin-5-one;

[177] 2-(ethylamino)-6-(3-hydroxyphenyl)-9-methyl-6,7,8,9-tetrahydro-5H-pyrimido[4,5-e][1,4]diazepin-5-one;

[178] 2-(ethylamino)-6-(4-hydroxyphenyl)-9-methyl-6,7,8,9-tetrahydro-5H-pyrimido[4,5-e][1,4]diazepin-5-one;

[179] 9-methyl-2-(methylthio)-6-(3-(((4-phenylpiperidin-4-yl)oxy)methyl)phenyl)-6,7,8,9-tetrahydro-5H-pyrimido[4,5-e][1,4]diazepin-5-one;

[180] 2-(ethylamino)-9-methyl-6-(3-(4-((methylamino)methyl)-1H-1,2,3-triazol-1-yl)phenyl)-6,7,8,9-tetrahydro-5H-pyrimido[4,5-e][1,4]diazepin-5-one;

[181] 6-(3-(4-(aminomethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[182] 6-(3-(4-((benzylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[183] 2-(ethylamino)-9-methyl-6-(3-(4-(2-(methylamino)ethyl)-1H-1,2,3-triazol-1-yl)phenyl)-6,7,8,9-tetrahydro-5H-pyrimido[4,5-e][1,4]diazepin-5-one;

[184] 2-(ethylamino)-9-methyl-6-(3-((4-((methylamino)methyl)-1H-1,2,3-triazol-1-yl)methyl)phenyl)-6,7,8,9-tetrahydro-5H-pyrimido[4,5-e][1,4]diazepin-5-one;

[185] 2-(ethylamino)-9-methyl-6-(3-(4-((methylamino)methyl)-1H-pyrazol-1-yl)phenyl)-6,7,8,9-tetrahydro-5H-pyrimido[4,5-e][1,4]diazepin-5-one;

[186] 2-(ethylamino)-9-methyl-6-(3-(4-((methylamino)methyl)-1H-imidazol-1-yl)phenyl)-6,7,8,9-tetrahydro-5H-pyrimido[4,5-e][1,4]diazepin-5-one;

[187] 2-(ethylamino)-9-methyl-6-(3-(5-((methylamino)methyl)-1,3,4-oxadiazol-2-yl)phenyl)-6,7,8,9-tetrahydro-5H-pyrimido[4,5-e][1,4]diazepin-5-one;

[188] 2-(ethylamino)-9-methyl-6-(2-(3-(methylamino)-1-phenylpropoxy)phenyl)-6,7,8,9-tetrahydro-5H-pyrimido[4,5-e][1,4]diazepin-5-one;

[189] 2-(ethylamino)-9-methyl-6-(3-(((4-methyl-1-(methylamino)pentan-3-yl)oxy)methyl)phenyl)-6,7,8,9-tetrahydro-5H-pyrimido[4,5-e][1,4]diazepin-5-one;

[190] 9-methyl-6-(3-(((4-methyl-1-(methylamino)pentan-3-yl)oxy)methyl)phenyl)-2-(methylthio)-6,7,8,9-tetrahydro-5H-pyrimido[4,5-e][1,4]diazepin-5-one;

[191] 2-(ethylamino)-9-methyl-6-(3-(((4-(methylamino)butan-2-yl)oxy)methyl)phenyl)-6,7,8,9-tetrahydro-5H-pyrimido[4,5-e][1,4]diazepin-5-one;

[192] 9-methyl-6-(3-(((4-(methylamino)butan-2-yl)oxy)methyl)phenyl)-2-(methylthio)-6,7,8,9-tetrahydro-5H-pyrimido[4,5-e][1,4]diazepin-5-one;

[193] 2-(ethylamino)-9-methyl-6-(3-(3-(methylamino)-1-(pyridin-2-yl)propoxy)phenyl)-6,7,8,9-tetrahydro-5H-pyrimido[4,5-e][1,4]diazepin-5-one;

[194] 2-(ethylamino)-9-methyl-6-(3-(3-(methylamino)-1-(pyridin-3-yl)propoxy)phenyl)-6,7,8,9-tetrahydro-5H-pyrimido[4,5-e][1,4]diazepin-5-one;

[195] (R)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one;

[196] (R)-2-(dimethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[197] (R)-9-methyl-2-(methylamino)-6-(3-((3-(methylamino)-1-phenylpropoxy)methyl)phenyl)-6,7,8,9-tetrahydro-5H-pyrimido[4,5-e][1,4]diazepin-5-one;

[198] 8-(ethylamino)-1-methyl-4-(3-(3-(methylamino)-1-phenylpropoxy)phenyl)-1,2,3,4-tetrahydro-5H-pyrido[4,3-e][1,4]diazepin-5-one;

[199] 8-(ethylamino)-1-methyl-4-(3-((3-(methylamino)-1-phenylpropoxy)methyl)phenyl)-1,2,3,4-tetrahydro-5H-pyrido[4,3-e][1,4]diazepin-5-one;

[200] 2-(ethylamino)-9-methyl-6-(3-(2-(methylamino)-1-phenylethoxy)benzyl)-6,7,8,9-tetrahydro-5H-pyrimido[4,5-e][1,4]diazepin-5-one;

[201] 2-(ethylamino)-9-methyl-6-(4-(2-(methylamino)-1-phenylethoxy)benzyl)-6,7,8,9-tetrahydro-5H-pyrimido[4,5-e][1,4]diazepin-5-one;

[202] 2-(ethylamino)-9-methyl-6-(4-((methylamino)methyl)benzyl)-6,7,8,9-tetrahydro-5H-pyrimido[4,5-e][1,4]diazepin-5-one;

[203] (R)—N-ethyl-9-methyl-6-(3-((3-(methylamino)-1-phenylpropoxy)methyl)phenyl)-6,7,8,9-tetrahydro-5H-pyrimido[4,5-e][1,4]diazepin-2-amine;

[204] (R)-2-methoxy-9-methyl-6-(3-((3-(methylamino)-1-phenylpropoxy)methyl)phenyl)-6,7,8,9-tetrahydro-5H-pyrimido[4,5-e][1,4]diazepin-5-one;

[205] (R)-2-hydroxy-9-methyl-6-(3-((3-(methylamino)-1-phenylpropoxy)methyl)phenyl)-6,7,8,9-tetrahydro-5H-pyrimido[4,5-e][1,4]diazepin-5-one;

[206] (R)-2,9-dimethyl-6-(3-((3-(methylamino)-1-phenylpropoxy)methyl)phenyl)-6,7,8,9-tetrahydro-5H-pyrimido[4,5-e][1,4]diazepin-5-one;

[207] (R)-9-methyl-6-(3-((3-(methylamino)-1-phenylpropoxy)methyl)phenyl)-6,7,8,9-tetrahydro-5H-pyrimido[4,5-e][1,4]diazepin-5-one;

[208] 9-Methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[209] (R)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[210] (S)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[211] 2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[212] (R)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[213] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[214] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[215] (R)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[216] (S)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[217] 9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[218] (R)-9-methyl-6-(3-(3-(methylamino)-1-(thiophen-2H)propoxy)phenyl)-2-(methylthio)-6,7,8,9-tetrahydro-5H-pyrimido[4,5-e][1,4]diazepin-5-one;

[219] (S)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[220] 2-(ethylamino)-6-(3-(3-((2-fluoroethyl)amino)-1-(thiophen-2-yl)propoxy)phenyl)-9-methyl-6,7,8,9-tetrahydro-5H-pyrimido[4,5-e][1,4]diazepin-5-one;

[221] 2-methoxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[222] 2-hydroxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[223] 2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[224] 9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[225] 2-(Ethylamino)-9-methyl-6-(3-((2-(methylamino)-1-phenylethoxy)methyl)phenyl)-6,7,8,9-tetrahydro-5H-pyrimido[4,5-e][1,4]diazepin-5-one;

[226] 9-methyl-6-(3-((2-(methylamino)-1-phenylethoxy) methyl)phenyl)-2-(methylthio)-6,7,8,9-tetrahydro-5H-pyrimido[4,5-e][1,4]diazepin-5-one;

[227] 8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[228] 8-(ethylamino)-1-methyl-4-(3-((3-(methylamino)-1-(thiophen-2-yl)propoxy)methyl)phenyl)-1,2,3,4-tetrahydro-5H-pyrido[4,3-e][1,4]diazepin-5-one;

[229] 8-(dimethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[230] 2-(dimethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[231] 2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[232] 9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[233] tert-Butyl 4-(3-(2-(ethylamino)-9-methyl-5-oxo-5,7,8,9-tetrahydro-6H-pyrimido[4,5-e][1,4]diazepin-6-yl)phenyl)-3,6-dihydropyridine-1(2H)-carboxylate;

[234] tert-Butyl 4-(3-(2-(ethylamino)-9-methyl-5-oxo-5,7,8,9-tetrahydro-6H-pyrimido[4,5-e][1,4]diazepin-6-yl)phenyl)piperidine-1-carboxylate;

[235] 2-(Ethylamino)-9-methyl-6-(3-(piperidin-4-yl)phenyl)-6,7,8,9-tetrahydro-5H-pyrimido[4,5-e][1,4]diazepin-5-one;

[236] (R)-6-(3-((3-(Dimethylamino)-1-phenylpropoxy) methyl)phenyl)-2-(ethylamino)-9-methyl-6,7,8,9-tetrahydro-5H-pyrimido[4,5-e][1,4]diazepin-5-one;

[237] (S)-6-(3-((3-(dimethylamino)-1-phenylpropoxy) methyl)phenyl)-2-(ethylamino)-9-methyl-6,7,8,9-tetrahydro-5H-pyrimido[4,5-e][1,4]diazepin-5-one;

[238] 6-(3-(3-(dimethylamino)-1-phenylpropoxy)phenyl)-2-(ethylamino)-9-methyl-6,7,8,9-tetrahydro-5H-pyrimido[4,5-e][1,4]diazepin-5-one;

[239] 6-(3-(2-(dimethylamino)-1-phenylethoxy)phenyl)-2-(ethylamino)-9-methyl-6,7,8,9-tetrahydro-5H-pyrimido[4,5-e][1,4]diazepin-5-one;

[240] 6-(3-(3-(benzyl(methyl)amino)propyl)phenyl)-2-(ethylamino)-9-methyl-6,7,8,9-tetrahydro-5H-pyrimido[4,5-e][1,4]diazepin-5-one;

[241] 6-(3-(3-(dimethylamino)propyl)phenyl)-2-(ethylamino)-9-methyl-6,7,8,9-tetrahydro-5H-pyrimido[4,5-e][1,4]diazepin-5-one;

[242] 6-(3-(4-((dimethylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[243] 6-(3-(4-((benzyl(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[244] 2-(ethylamino)-9-methyl-6-(3-(4-((methyl(phenethyl) amino)methyl)-1H-1,2,3-triazol-1-yl)phenyl)-6,7,8,9-tetrahydro-5H-pyrimido[4,5-e][1,4]diazepin-5-one;

[245] 6-(3-(4-((bis(cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[246] 6-(3-(4-(((cyclopropylmethyl)(methyl)amino) methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[247] 6-(3-(4-(2-(benzyl(methyl)amino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[248] 6-(3-(4-(2-(dimethylamino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[249] 2-(ethylamino)-9-methyl-6-(3-(4-(2-(methyl(phenethyl)amino)ethyl)-1H-1,2,3-triazol-1-yl)phenyl)-6,7,8,9-tetrahydro-5H-pyrimido[4,5-e][1,4]diazepin-5-one;

[250] 6-(3-((4-((benzyl(methyl)amino)methyl)-1H-1,2,3-triazol-1-yl)methyl)phenyl)-2-(ethylamino)-9-methyl-6,7,8,9-tetrahydro-5H-pyrimido[4,5-e][1,4]diazepin-5-one;

[251] 6-(3-(4-((benzyl(methyl)amino)methyl)-1H-pyrazol-1-yl)phenyl)-2-(ethylamino)-9-methyl-6,7,8,9-tetrahydro-5H-pyrimido[4,5-e][1,4]diazepin-5-one;

[252] 2-(ethylamino)-9-methyl-6-(3-(4-((methyl(phenethyl) amino)methyl)-1H-pyrazol-1-yl)phenyl)-6,7,8,9-tetrahydro-5H-pyrimido[4,5-e][1,4]diazepin-5-one;

[253] 6-(3-(4-((benzyl(methyl)amino)methyl)-1H-imidazol-1-yl)phenyl)-2-(ethylamino)-9-methyl-6,7,8,9-tetrahydro-5H-pyrimido[4,5-e][1,4]diazepin-5-one;

[254] 2-(ethylamino)-9-methyl-6-(3-(4-((methyl(phenethyl) amino)methyl)-1H-imidazol-1-yl)phenyl)-6,7,8,9-tetrahydro-5H-pyrimido[4,5-e][1,4]diazepin-5-one;

[255] 6-(3-(5-((benzyl(methyl)amino)methyl)-1,3,4-oxadiazol-2-yl)phenyl)-2-(ethylamino)-9-methyl-6,7,8,9-tetrahydro-5H-pyrimido[4,5-e][1,4]diazepin-5-one;

[256] 6-(3-(3-(benzyl(methyl)amino)propoxy)phenyl)-2-(ethylamino)-9-methyl-6,7,8,9-tetrahydro-5H-pyrimido[4,5-e][1,4]diazepin-5-one;

[257] 6-(3-(3-(dimethylamino)propoxy)phenyl)-2-(ethylamino)-9-methyl-6,7,8,9-tetrahydro-5H-pyrimido[4,5-e][1,4]diazepin-5-one;

[258] 2-(ethylamino)-9-methyl-6-(3-(3-(methyl(phenethyl) amino)propoxy)phenyl)-6,7,8,9-tetrahydro-5H-pyrimido[4,5-e][1,4]diazepin-5-one;

[259] 6-(3-(1-benzylpiperidin-4-yl)phenyl)-2-(ethylamino)-9-methyl-6,7,8,9-tetrahydro-5H-pyrimido[4,5-e][1,4]diazepin-5-one;

[260] 2-(ethylamino)-9-methyl-6-(3-(1-methylpiperidin-4-yl)phenyl)-6,7,8,9-tetrahydro-5H-pyrimido[4,5-e][1,4]diazepin-5-one;

[261] 2-(ethylamino)-9-methyl-6-(3-(1-phenethylpiperidin-4-yl)phenyl)-6,7,8,9-tetrahydro-5H-pyrimido[4,5-e][1,4]diazepin-5-one;

[262] 6-(3-((1-(benzyl(methyl)amino)propan-2-yl)oxy)phenyl)-2-(ethylamino)-9-methyl-6,7,8,9-tetrahydro-5H-pyrimido[4,5-e][1,4]diazepin-5-one;

[263] 2-(ethylamino)-9-methyl-6-(3-((1-(methyl(phenethyl) amino)propan-2-yl)oxy)phenyl)-6,7,8,9-tetrahydro-5H-pyrimido[4,5-e][1,4]diazepin-5-one;

[264] 6-(3-(2-(benzyl(methyl)amino)ethoxy)phenyl)-2-(ethylamino)-9-methyl-6,7,8,9-tetrahydro-5H-pyrimido[4,5-e][1,4]diazepin-5-one;

[265] 2-(ethylamino)-9-methyl-6-(3-(2-(methyl(phenethyl) amino)ethoxy)phenyl)-6,7,8,9-tetrahydro-5H-pyrimido[4,5-e][1,4]diazepin-5-one;

[266] 6-(3-((1-benzylpyrrolidin-3-yl)oxy)phenyl)-2-(ethylamino)-9-methyl-6,7,8,9-tetrahydro-5H-pyrimido[4,5-e][1,4]diazepin-5-one;

[267] 6-(3-((1-(benzyl(methyl)amino)-3-methylbutan-2-yl) oxy)phenyl)-2-(ethylamino)-9-methyl-6,7,8,9-tetrahydro-5H-pyrimido[4,5-e][1,4]diazepin-5-one;

[268] 2-(ethylamino)-9-methyl-6-(3-((3-methyl-1-(methyl (phenethyl)amino)butan-2-yl)oxy)phenyl)-6,7,8,9-tetrahydro-5H-pyrimido[4,5-e][1,4]diazepin-5-one;

[269] 6-(3-(2-(benzyl(methyl)amino)ethyl)phenyl)-2-(ethylamino)-9-methyl-6,7,8,9-tetrahydro-5H-pyrimido[4,5-e][1,4]diazepin-5-one;

[270] 2-(ethylamino)-9-methyl-6-(3-(2-(methyl(phenethyl)amino)ethyl)phenyl)-6,7,8,9-tetrahydro-5H-pyrimido[4,5-e][1,4]diazepin-5-one;

[271] 9-methyl-6-(3-(((1-methyl-4-phenylpiperidin-4-yl)oxy)methyl)phenyl)-2-(methylthio)-6,7,8,9-tetrahydro-5H-pyrimido[4,5-e][1,4]diazepin-5-one;

[272] 2-(ethylamino)-9-methyl-6-(3-(((1-methyl-4-phenylpiperidin-4-yl)oxy)methyl)phenyl)-6,7,8,9-tetrahydro-5H-pyrimido[4,5-e][1,4]diazepin-5-one;

[273] 2-(ethylamino)-6-(3-(4-(((2-(2-hydroxyethoxy)ethyl)(methyl)amino)methyl)-1H-1,2,3-triazol-1-yl)phenyl)-9-methyl-6,7,8,9-tetrahydro-5H-pyrimido[4,5-e][1,4]diazepin-5-one;

[274] 3-(2-(Ethylamino)-9-methyl-5-oxo-5,7,8,9-tetrahydro-6H-pyrimido[4,5-e][1,4]diazepin-6-yl)phenethyl 4-methylbenzenesulfonate;

[275] 2-(Ethylamino)-6-(3-(2-(4-(3-hydroxyphenyl)piperidin-1-yl)ethyl)phenyl)-9-methyl-6,7,8,9-tetrahydro-5H-pyrimido[4,5-e][1,4]diazepin-5-one;

[276] (R)-9-(3-(2-(ethylamino)-9-methyl-5-oxo-5,7,8,9-tetrahydro-6H-pyrimido[4,5-e][1,4]diazepin-6-yl)phenethyl)-4-isopropyl-2-methyl-1-oxa-4,9-diazaspiro[5.5]undecan-3-one;

[277] 1-(3-(2-(Ethylamino)-9-methyl-5-oxo-5,7,8,9-tetrahydro-6H-pyrimido[4,5-e][1,4]diazepin-6-yl)phenyl)-1H-1,2,3-triazole-4-carbaldehyde;

[278] 2-(Ethylamino)-9-methyl-6-(3-(4-((4-phenylpiperidin-1-yl)methyl)-1H-1,2,3-triazol-1-yl)phenyl)-6,7,8,9-tetrahydro-5H-pyrimido[4,5-e][1,4]diazepin-5-one;

[279] 2-(ethylamino)-6-(3-(4-((4-(3-hydroxyphenyl)piperidin-1-yl)methyl)-1H-1,2,3-triazol-1-yl)phenyl)-9-methyl-6,7,8,9-tetrahydro-5H-pyrimido[4,5-e][1,4]diazepin-5-one;

[280] 2-(ethylamino)-9-methyl-6-(3-(4-((4-phenylpiperazin-1-yl)methyl)-1H-1,2,3-triazol-1-yl)phenyl)-6,7,8,9-tetrahydro-5H-pyrimido[4,5-e][1,4]diazepin-5-one;

[281] 2-(ethylamino)-9-methyl-6-(3-(4-(piperidin-1-ylmethyl)-1H-1,2,3-triazol-1-yl)phenyl)-6,7,8,9-tetrahydro-5H-pyrimido[4,5-e][1,4]diazepin-5-one;

[282] 6-(3-(4-((3,4-dihydroisoquinolin-2(1H)-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[283] 6-(3-(4-((3,4-dihydro-2H-spiro[isoquinoline-1,4'-piperidin]-1'-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[284] (R)-9-((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)-4-isopropyl-2-methyl-1-oxa-4,9-diazaspiro[5.5]undecan-3-one;

[285] 6-(3-(4-(((cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[286] 2-(ethylamino)-6-(3-(4-((ethylamino)methyl)-1H-1,2,3-triazol-1-yl)phenyl)-9-methyl-6,7,8,9-tetrahydro-5H-pyrimido[4,5-e][1,4]diazepin-5-one;

[287] 2-(ethylamino)-6-(3-(4-(((4-fluorobenzyl)(methyl)amino)methyl)-1H-1,2,3-triazol-1-yl)phenyl)-9-methyl-6,7,8,9-tetrahydro-5H-pyrimido[4,5-e][1,4]diazepin-5-one;

[288] 2-(ethylamino)-9-methyl-6-(3-(4-((methyl(pyridin-2-ylmethyl)amino)methyl)-1H-1,2,3-triazol-1-yl)phenyl)-6,7,8,9-tetrahydro-5H-pyrimido[4,5-e][1,4]diazepin-5-one;

[289] 2-(ethylamino)-9-methyl-6-(3-(4-((methyl(pyridin-3-ylmethyl)amino)methyl)-1H-1,2,3-triazol-1-yl)phenyl)-6,7,8,9-tetrahydro-5H-pyrimido[4,5-e][1,4]diazepin-5-one;

[290] 2-(ethylamino)-6-(3-(4-(((2-(2-hydroxyethoxy)ethyl)amino)methyl)-1H-1,2,3-triazol-1-yl)phenyl)-9-methyl-6,7,8,9-tetrahydro-5H-pyrimido[4,5-e][1,4]diazepin-5-one;

[291] 6-(3-(4-((4-(dimethylamino)-4-phenylpiperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[292] 6-(3-((4-(dimethylamino)-4-phenylpiperidin-1-yl)methyl)phenyl)-2-(ethylamino)-9-methyl-6,7,8,9-tetrahydro-5H-pyrimido[4,5-e][1,4]diazepin-5-one;

[293] 6-(3-(4-((4-(dimethylamino)-4-(3-hydroxyphenyl)piperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[294] 6-(3-(4-((4-(dimethylamino)-4-phenylpiperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one;

[295] 6-(3-(4-((4-(dimethylamino)-4-(3-hydroxyphenyl)piperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one;

[296] 6-(3-(4-((4-(dimethylamino)-4-(3-hydroxyphenyl)piperidin-1-yl)methyl)-1H-imidazol-1-yl)phenyl)-2-(ethylamino)-9-methyl-6,7,8,9-tetrahydro-5H-pyrimido[4,5-e][1,4]diazepin-5-one;

[297] 2-(trimethylsilyl)ethyl (3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[298] 2-(trimethylsilyl)ethyl (S)-(3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[299] 2-(trimethylsilyl)ethyl (S)-(3-(4-((8-chloro-1-methyl-5-oxo-1,2,3,5-tetrahydro-4H-pyrido[4,3-e][1,4]diazepin-4-yl)methyl)phenoxy)-3-(thiophen-2-yl)propyl)(methyl)carbamate;

[300] tert-butyl (3-((3-(8-chloro-1-methyl-5-oxo-1,2,3,5-tetrahydro-4H-pyrido[4,3-e][1,4]diazepin-4-yl)benzyl)oxy)-3-phenylpropyl)(methyl)carbamate;

[301] 2-(Trimethylsilyl)ethyl (S)-(3-(4-((1,8-dimethyl-5-oxo-1,2,3,5-tetrahydro-4H-pyrido[4,3-e][1,4]diazepin-4-yl)methyl)phenoxy)-3-(thiophen-2-yl)propyl)(methyl)carbamate;

[302] 2-(trimethylsilyl)ethyl (3-(3-(1,8-dimethyl-5-oxo-1,2,3,5-tetrahydro-4H-pyrido[4,3-e][1,4]diazepin-4-yl)phenoxy)-3-(thiophen-2-yl)propyl)(methyl)carbamate;

[303] tert-butyl (3-((3-(1,8-dimethyl-5-oxo-1,2,3,5-tetrahydro-4H-pyrido[4,3-e][1,4]diazepin-4-yl)benzyl)oxy)-3-phenylpropyl)(methyl)carbamate;

[304] (S)-8-Amino-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[305] (S)-8-amino-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[306] 1,8-dimethyl-4-(3-((3-(methylamino)-1-phenylpropoxy)methyl)phenyl)-1,2,3,4-tetrahydro-5H-pyrido[4,3-e][1,4]diazepin-5-one;

[307] 1,8-dimethyl-4-(3-(3-(methylamino)-1-(thiophen-2-yl)propoxy)phenyl)-1,2,3,4-tetrahydro-5H-pyrido[4,3-e][1,4]diazepin-5-one;

[308] (S)-1,8-dimethyl-4-(4-(3-(methylamino)-1-(thiophen-2-yl)propoxy)benzyl)-1,2,3,4-tetrahydro-5H-pyrido[4,3-e][1,4]diazepin-5-one;
[309] methyl 3-(2-(ethylamino)-9-methyl-5-oxo-5,7,8,9-tetrahydro-6H-pyrimido[4,5-e][1,4]diazepin-6-yl)benzoate;
[310] 2-(ethylamino)-6-(3-(2-hydroxyethyl)phenyl)-9-methyl-6,7,8,9-tetrahydro-5H-pyrimido[4,5-e][1,4]diazepin-5-one;
[311] 6-(3-bromophenyl)-2-(ethylamino)-9-methyl-6,7,8,9-tetrahydro-5H-pyrimido[4,5-e][1,4]diazepin-5-one;
[312] 6-(3-(4-(Dimethylamino)-4-phenylpiperidin-1-yl)phenyl)-2-(ethylamino)-9-methyl-6,7,8,9-tetrahydro-5H-pyrimido[4,5-e][1,4]diazepin-5-one;
[313] 3-(2-(Ethylamino-9-methyl-5-oxo-5,7,8,9-tetrahydro-6H-pyrimido[4,5-e][1,4]diazepin-6-yl)benzoic acid;
[314] 6-(3-(4-(Dimethylamino)-4-phenylpiperidine-1-carbonyl)-phenyl)-2-(ethylamino)-9-methyl-6,7,8,9-tetrahydro-5H-pyrimido[4,5-e][1,4]-diazepin-5-one;
[315] 9-methyl-6-(4-((3-(methylamino)-1-phenylpropoxy)methyl)phenyl)-2-(methylthio)-6,7,8,9-tetrahydro-5H-pyrimido[4,5-e][1,4]diazepin-5-one;
[316] 9-methyl-6-(4-(3-(methylamino)-1-phenylpropoxy)phenyl)-2-(methylthio)-6,7,8,9-tetrahydro-5H-pyrimido[4,5-e][1,4]diazepin-5-one;
[317] 1-methyl-4-(3-((3-(methylamino)-1-phenylpropoxy)methyl)phenyl)-1,2,3,4-tetrahydro-5H-pyrido[4,3-e][1,4]diazepin-5-one;
[318] 9-methyl-6-(2-((3-(methylamino)-1-phenylpropoxy)methyl)phenyl)-2-(methylthio)-6,7,8,9-tetrahydro-5H-pyrimido[4,5-e][1,4]diazepin-5-one;
[319] 9-methyl-6-(2-(2-(methylamino)-1-phenylethoxy)phenyl)-2-(methylthio)-6,7,8,9-tetrahydro-5H-pyrimido[4,5-e][1,4]diazepin-5-one;
[320] 9-methyl-6-(2-((2-(methylamino)-1-phenylethoxy)methyl)phenyl)-2-(methylthio)-6,7,8,9-tetrahydro-5H-pyrimido[4,5-e][1,4]diazepin-5-one;
[321] 9-methyl-6-(4-((2-(methylamino)-1-phenylethoxy)methyl)phenyl)-2-(methylthio)-6,7,8,9-tetrahydro-5H-pyrimido[4,5-e][1,4]diazepin-5-one;
[322] 9-methyl-6-(3-((3-(methylamino)-1-phenylpropoxy)methyl)phenyl)-2-(trifluoromethyl)-6,7,8,9-tetrahydro-5H-pyrimido[4,5-e][1,4]diazepin-5-one;
[323] 1-methyl-4-(3-(3-(methylamino)-1-(thiophen-2-yl)propoxy)phenyl)-1,2,3,4-tetrahydro-5H-pyrido[4,3-e][1,4]diazepin-5-one;
[324] (R)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[325] (S)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[326] (S)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[327] (R)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[328] 9-methyl-6-(4-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;
[329] 9-methyl-6-(3-(3-(methylamino)-1-(thiophen-2-yl)propoxy)phenyl)-2-(trifluoromethyl)-6,7,8,9-tetrahydro-5H-pyrimido[4,5-e][1,4]diazepin-5-one;
[330] 9-methyl-6-(3-((3-(methylamino)-1-(thiophen-2-yl)propoxy)methyl)phenyl)-2-(trifluoromethyl)-6,7,8,9-tetrahydro-5H-pyrimido[4,5-e][1,4]diazepin-5-one;
[331] (S)-8-methoxy-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[332] (S)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one;
[333] 2-(ethylamino)-9-methyl-6-(4-(3-(methylamino)-1-phenylpropoxy)phenyl)-6,7,8,9-tetrahydro-5H-pyrimido[4,5-e][1,4]diazepin-5-one;
[334] 2-(ethylamino)-9-methyl-6-(4-((3-(methylamino)-1-phenylpropoxy)methyl)phenyl)-6,7,8,9-tetrahydro-5H-pyrimido[4,5-e][1,4]diazepin-5-one;
[335] 2-(benzylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;
[336] 9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;
[337] 2-(ethylamino)-9-methyl-6-(2-((3-(methylamino)-1-phenylpropoxy)methyl)phenyl)-6,7,8,9-tetrahydro-5H-pyrimido[4,5-e][1,4]diazepin-5-one;
[338] 2-(ethylamino)-9-methyl-6-(2-(2-(methylamino)-1-phenylethoxy)phenyl)-6,7,8,9-tetrahydro-5H-pyrimido[4,5-e][1,4]diazepin-5-one;
[339] 2-(ethylamino)-9-methyl-6-(2-((2-(methylamino)-1-phenylethoxy)methyl)phenyl)-6,7,8,9-tetrahydro-5H-pyrimido[4,5-e][1,4]diazepin-5-one;
[340] 2-(ethylamino)-9-methyl-6-(4-((2-(methylamino)-1-phenylethoxy)methyl)phenyl)-6,7,8,9-tetrahydro-5H-pyrimido[4,5-e][1,4]diazepin-5-one;
[341] (R)-9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;
[342] (R)-9-methyl-2-(methyl(pyridin-3-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;
[343] (R)-9-methyl-6-(3-((3-(methylamino)-1-phenylpropoxy)methyl)phenyl)-2-((pyridin-2-ylmethyl)amino)-6,7,8,9-tetrahydro-5H-pyrimido[4,5-e][1,4]diazepin-5-one;
[344] (R)-2-(((5-fluoropyridin-2-yl)methyl)(methyl)amino)-9-methyl-6-(3-((3-(methylamino)-1-phenylpropoxy)methyl)phenyl)-6,7,8,9-tetrahydro-5H-pyrimido[4,5-e][1,4]diazepin-5-one;
[345] 2-(ethylamino)-6-(3-((3-((2-fluoroethyl)amino)-1-(thiophen-2-yl)propoxy)methyl)phenyl)-9-methyl-6,7,8,9-tetrahydro-5H-pyrimido[4,5-e][1,4]diazepin-5-one;
[346] (S)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[347] (R)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[348] 2-(ethylamino)-9-methyl-6-(4-((3-(methylamino)-1-(thiophen-2-yl)propoxy)methyl)phenyl)-6,7,8,9-tetrahydro-5H-pyrimido[4,5-e][1,4]diazepin-5-one;
[349] 2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;
[350] (S)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one
[351] (R)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;

[352] (S)-2-amino-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[353] 2,9-dimethyl-6-(4-((3-(methylamino)-1-phenylpropoxy)methyl)phenyl)-6,7,8,9-tetrahydro-5H-pyrimido[4,5-e][1,4]diazepin-5-one;

[354] 2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;

[355] 2,9-dimethyl-6-(4-((2-(methylamino)-1-phenylethoxy)methyl)phenyl)-6,7,8,9-tetrahydro-5H-pyrimido[4,5-e][1,4]diazepin-5-one;

[356] (R)-2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;

[357] (R)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[358] (S)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[359] (S)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[360] (R)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[361] 9-methyl-6-(4-(3-(methylamino)-1-phenylpropoxy)phenyl)-6,7,8,9-tetrahydro-5H-pyrimido[4,5-e][1,4]diazepin-5-one;

[362] 9-methyl-6-(2-(2-(methylamino)-1-phenylethoxy)phenyl)-6,7,8,9-tetrahydro-5H-pyrimido[4,5-e][1,4]diazepin-5-one;

[363] (R)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[364] (S)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[365] 9-methyl-6-(2-((3-(methylamino)-1-phenylpropoxy)methyl)benzyl)-2-(methylthio)-6,7,8,9-tetrahydro-5H-pyrimido[4,5-e][1,4]diazepin-5-one;

[366] 9-methyl-6-(3-((3-(methylamino)-1-phenylpropoxy)benzyl)-2-(methylthio)-6,7,8,9-tetrahydro-5H-pyrimido[4,5-e][1,4]diazepin-5-one;

[367] 9-methyl-6-(3-((3-(methylamino)-1-phenylpropoxy)methyl)benzyl)-2-(methylthio)-6,7,8,9-tetrahydro-5H-pyrimido[4,5-e][1,4]diazepin-5-one;

[368] 9-methyl-6-(4-((3-(methylamino)-1-phenylpropoxy)methyl)benzyl)-2-(methylthio)-6,7,8,9-tetrahydro-5H-pyrimido[4,5-e][1,4]diazepin-5-one;

[369] 9-methyl-6-(4-(3-(methylamino)-1-phenylpropoxy)benzyl)-2-(methylthio)-6,7,8,9-tetrahydro-5H-pyrimido[4,5-e][1,4]diazepin-5-one;

[370] 9-methyl-6-(2-(3-(methylamino)-1-phenylpropoxy)benzyl)-2-(methylthio)-6,7,8,9-tetrahydro-5H-pyrimido[4,5-e][1,4]diazepin-5-one;

[371] 9-methyl-6-(2-(2-(methylamino)-1-phenylethoxy)benzyl)-2-(methylthio)-6,7,8,9-tetrahydro-5H-pyrimido[4,5-e][1,4]diazepin-5-one;

[372] 9-methyl-6-(3-((2-(methylamino)-1-phenylethoxy)methyl)benzyl)-2-(methylthio)-6,7,8,9-tetrahydro-5H-pyrimido[4,5-e][1,4]diazepin-5-one;

[373] 9-methyl-6-(2-((2-(methylamino)-1-phenylethoxy)methyl)benzyl)-2-(methylthio)-6,7,8,9-tetrahydro-5H-pyrimido[4,5-e][1,4]diazepin-5-one;

[374] 9-methyl-6-(4-((2-(methylamino)-1-phenylethoxy)methyl)benzyl)-2-(methylthio)-6,7,8,9-tetrahydro-5H-pyrimido[4,5-e][1,4]diazepin-5-one;

[375] (S)-2-methoxy-9-methyl-6-(4-(3-(methylamino)-1-phenylpropoxy)benzyl)-6,7,8,9-tetrahydro-5H-pyrimido[4,5-e][1,4]diazepin-5-one;

[376] 6-(4-(1-(2-fluorophenyl)-3-(methylamino)propoxy)benzyl)-2-methoxy-9-methyl-6,7,8,9-tetrahydro-5H-pyrimido[4,5-e][1,4]diazepin-5-one;

[377] (S)-1-methyl-4-(4-(3-(methylamino)-1-phenylpropoxy)benzyl)-1,2,3,4-tetrahydro-5H-pyrido[4,3-e][1,4]diazepin-5-one;

[378] 9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[379] (S)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[380] (R)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[381] 1-methyl-4-(4-(3-(methylamino)-1-(thiophen-2-yl)propoxy)benzyl)-1,2,3,4-tetrahydro-5H-pyrido[4,3-e][1,4]diazepin-5-one;

[382] (S)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[383] (S)-8-(ethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[384] (S)-8-(dimethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[385] (S)-8-methoxy-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[386] (S)-9-methyl-6-(4-(3-(methylamino)-1-(thiophen-2-yl)propoxy)benzyl)-2-(trifluoromethyl)-6,7,8,9-tetrahydro-5H-pyrimido[4,5-e][1,4]diazepin-5-one;

[387] 2-methoxy-9-methyl-6-(4-(3-(methylamino)-1-(thiophen-3-yl)propoxy)benzyl)-6,7,8,9-tetrahydro-5H-pyrimido[4,5-e][1,4]diazepin-5-one;

[388] 2-methoxy-9-methyl-6-(4-(3-(methylamino)-1-(3-methylthiophen-2-yl)propoxy)benzyl)-6,7,8,9-tetrahydro-5H-pyrimido[4,5-e][1,4]diazepin-5-one;

[389] (S)-1-ethyl-8-methoxy-4-(4-(3-(methylamino)-1-(thiophen-2-yl)propoxy)benzyl)-1,2,3,4-tetrahydro-5H-pyrido[4,3-e][1,4]diazepin-5-one;

[390] 2-methoxy-9-methyl-6-(4-(3-(methylamino)-1-(thiazol-2H)propoxy)benzyl)-6,7,8,9-tetrahydro-5H-pyrimido[4,5-e][1,4]diazepin-5-one;

[391] (S)-1-ethyl-4-(4-(3-(methylamino)-1-(thiophen-2-yl)propoxy)benzyl)-1,2,3,4-tetrahydro-5H-pyrido[4,3-e][1,4]diazepin-5-one;

[392] 2-methoxy-9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one;

[393] (S)-2-methoxy-9-methyl-6-(3-methyl-4-(3-(methylamino)-1-(thiophen-2-yl)propoxy)benzyl)-6,7,8,9-tetrahydro-5H-pyrimido[4,5-e][1,4]diazepin-5-one;

[394] (S)-6-(3-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[395] (S)-9-ethyl-2-methoxy-6-(4-(3-(methylamino)-1-(thiophen-2-yl)propoxy)benzyl)-6,7,8,9-tetrahydro-5H-pyrimido[4,5-e][1,4]diazepin-5-one;

[396] 2-methoxy-9-methyl-6-(4-(3-(methylamino)-1-(4-methylthiophen-2-yl)propoxy)benzyl)-6,7,8,9-tetrahydro-5H-pyrimido[4,5-e][1,4]diazepin-5-one;

[397] (S)-2-methoxy-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one;

[398] (S)-9-ethyl-6-(4-(3-(methylamino)-1-(thiophen-2-yl)propoxy)benzyl)-6,7,8,9-tetrahydro-5H-pyrimido[4,5-e][1,4]diazepin-5-one;

[399] (S)-9-fluoro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[400] (S)-9-chloro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[401] (S)-6-(2-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[402] (S)-2-methoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[403] (S)-6-(4-fluoro-2-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[404] 2-(ethylamino)-9-methyl-6-(2-((3-(methylamino)-1-phenylpropoxy)methyl)benzyl)-6,7,8,9-tetrahydro-5H-pyrimido[4,5-e][1,4]diazepin-5-one;

[405] 2-(ethylamino)-9-methyl-6-(4-((3-(methylamino)-1-phenylpropoxy)methyl)benzyl)-6,7,8,9-tetrahydro-5H-pyrimido[4,5-e][1,4]diazepin-5-one;

[406] 2-(ethylamino)-9-methyl-6-(3-((3-(methylamino)-1-phenylpropoxy)methyl)benzyl)-6,7,8,9-tetrahydro-5H-pyrimido[4,5-e][1,4]diazepin-5-one;

[407] 2-(ethylamino)-9-methyl-6-(3-(3-(methylamino)-1-phenylpropoxy)benzyl)-6,7,8,9-tetrahydro-5H-pyrimido[4,5-e][1,4]diazepin-5-one;

[408] 2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[409] 2-(ethylamino)-9-methyl-6-(2-(3-(methylamino)-1-phenylpropoxy)benzyl)-6,7,8,9-tetrahydro-5H-pyrimido[4,5-e][1,4]diazepin-5-one;

[410] 2-(ethylamino)-9-methyl-6-(2-(2-(methylamino)-1-phenylethoxy)benzyl)-6,7,8,9-tetrahydro-5H-pyrimido[4,5-e][1,4]diazepin-5-one;

[411] 2-(ethylamino)-9-methyl-6-(3-((2-(methylamino)-1-phenylethoxy)methyl)benzyl)-6,7,8,9-tetrahydro-5H-pyrimido[4,5-e][1,4]diazepin-5-one;

[412] 2-(ethylamino)-9-methyl-6-(2-((2-(methylamino)-1-phenylethoxy)methyl)benzyl)-6,7,8,9-tetrahydro-5H-pyrimido[4,5-e][1,4]diazepin-5-one;

[413] 2-(ethylamino)-9-methyl-6-(4-((2-(methylamino)-1-phenylethoxy)methyl)benzyl)-6,7,8,9-tetrahydro-5H-pyrimido[4,5-e][1,4]diazepin-5-one;

[414] (S)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[415] (R)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[416] 2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[417] (S)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[418] (R)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[419] (S)-2-(dimethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[420] (S)-2-amino-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[421] 2,9-dimethyl-6-(2-((3-(methylamino)-1-phenylpropoxy)methyl)benzyl)-6,7,8,9-tetrahydro-5H-pyrimido[4,5-e][1,4]diazepin-5-one;

[422] 2,9-dimethyl-6-(4-((3-(methylamino)-1-phenylpropoxy)methyl)benzyl)-6,7,8,9-tetrahydro-5H-pyrimido[4,5-e][1,4]diazepin-5-one;

[423] 2,9-dimethyl-6-(3-((3-(methylamino)-1-phenylpropoxy)methyl)benzyl)-6,7,8,9-tetrahydro-5H-pyrimido[4,5-e][1,4]diazepin-5-one;

[424] 2,9-dimethyl-6-(2-((2-(methylamino)-1-phenylethoxy)methyl)benzyl)-6,7,8,9-tetrahydro-5H-pyrimido[4,5-e][1,4]diazepin-5-one;

[425] 2,9-dimethyl-6-(4-(3-(methylamino)-1-phenylpropoxy)benzyl)-6,7,8,9-tetrahydro-5H-pyrimido[4,5-e][1,4]diazepin-5-one;

[426] 2-ethyl-9-methyl-6-(4-(3-(methylamino)-1-phenylpropoxy)benzyl)-6,7,8,9-tetrahydro-5H-pyrimido[4,5-e][1,4]diazepin-5-one;

[427] (R)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[428] (S)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[429] 9-methyl-6-(3-(3-(methylamino)-1-phenylpropoxy)benzyl)-6,7,8,9-tetrahydro-5H-pyrimido[4,5-e][1,4]diazepin-5-one;

[430] 9-methyl-6-(4-(3-(methylamino)-1-phenylpropoxy)benzyl)-6,7,8,9-tetrahydro-5H-pyrimido[4,5-e][1,4]diazepin-5-one;

[431] 9-methyl-6-(2-(3-(methylamino)-1-phenylpropoxy)benzyl)-6,7,8,9-tetrahydro-5H-pyrimido[4,5-e][1,4]diazepin-5-one;

[432] 9-methyl-6-(2-(2-(methylamino)-1-phenylethoxy)benzyl)-6,7,8,9-tetrahydro-5H-pyrimido[4,5-e][1,4]diazepin-5-one;

[433] (S)-9-methyl-6-(4-(3-(methylamino)-1-phenylpropoxy)benzyl)-6,7,8,9-tetrahydro-5H-pyrimido[4,5-e][1,4]diazepin-5-one;

[434] (R)-9-methyl-6-(4-(3-(methylamino)-1-phenylpropoxy)benzyl)-6,7,8,9-tetrahydro-5H-pyrimido[4,5-e][1,4]diazepin-5-one;

[435] 9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[436] (S)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[437] (R)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[438] 6-(3-(2-(4-(dimethylamino)-4-phenylpiperidin-1-yl)ethyl)phenyl)-2-(ethylamino)-9-methyl-6,7,8,9-tetrahydro-5H-pyrimido[4,5-e][1,4]diazepin-5-one;

[439] 2-(ethylamino)-9-methyl-6-(3-(2-(piperidin-1-yl)ethoxy)phenyl)-6,7,8,9-tetrahydro-5H-pyrimido[4,5-e][1,4]diazepin-5-one;

[440] 2-(ethylamino)-9-methyl-6-(3-(2-morpholinoethoxy)phenyl)-6,7,8,9-tetrahydro-5H-pyrimido[4,5-e][1,4]diazepin-5-one;

[441] 6-(3-(5-((4-(dimethylamino)-4-phenylpiperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one;

[442] 6-(3-(5-((4-(dimethylamino)-4-(3-hydroxyphenyl)piperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one;

[443] 6-(4-(1-(2-fluorophenyl)-3-(methylamino)propoxy)benzyl)-9-methyl-6,7,8,9-tetrahydro-5H-pyrimido[4,5-e][1,4]diazepin-5-one;

[444] 4-(4-(1-(2-fluorophenyl)-3-(methylamino)propoxy)benzyl)-8-methoxy-1-methyl-1,2,3,4-tetrahydro-5H-pyrido[4,3-e][1,4]diazepin-5-one;

[445] 4-(4-(1-(2-fluorophenyl)-3-(methylamino)propoxy)benzyl)-1-methyl-1,2,3,4-tetrahydro-5H-pyrido[4,3-e][1,4]diazepin-5-one;

[446] 6-(4-(1-(3-fluorophenyl)-3-(methylamino)propoxy)benzyl)-2-methoxy-9-methyl-6,7,8,9-tetrahydro-5H-pyrimido[4,5-e][1,4]diazepin-5-one;

[447] 6-(4-(1-(3-fluorophenyl)-3-(methylamino)propoxy)benzyl)-9-methyl-6,7,8,9-tetrahydro-5H-pyrimido[4,5-e][1,4]diazepin-5-one;

[448] 4-(4-(1-(3-fluorophenyl)-3-(methylamino)propoxy)benzyl)-8-methoxy-1-methyl-1,2,3,4-tetrahydro-5H-pyrido[4,3-e][1,4]diazepin-5-one;

[449] 4-(4-(1-(3-fluorophenyl)-3-(methylamino)propoxy)benzyl)-1-methyl-1,2,3,4-tetrahydro-5H-pyrido[4,3-e][1,4]diazepin-5-one;

[450] 6-(4-(1-(4-fluorophenyl)-3-(methylamino)propoxy)benzyl)-2-methoxy-9-methyl-6,7,8,9-tetrahydro-5H-pyrimido[4,5-e][1,4]diazepin-5-one;

[451] 6-(4-(1-(4-fluorophenyl)-3-(methylamino)propoxy)benzyl)-9-methyl-6,7,8,9-tetrahydro-5H-pyrimido[4,5-e][1,4]diazepin-5-one;

[452] 4-(4-(1-(4-fluorophenyl)-3-(methylamino)propoxy)benzyl)-8-methoxy-1-methyl-1,2,3,4-tetrahydro-5H-pyrido[4,3-e][1,4]diazepin-5-one;

[453] 4-(4-(1-(4-fluorophenyl)-3-(methylamino)propoxy)benzyl)-1-methyl-1,2,3,4-tetrahydro-5H-pyrido[4,3-e][1,4]diazepin-5-one;

[454] 6-(4-(1-(2-chlorophenyl)-3-(methylamino)propoxy)benzyl)-2-methoxy-9-methyl-6,7,8,9-tetrahydro-5H-pyrimido[4,5-e][1,4]diazepin-5-one;

[455] 6-(4-(1-(2-chlorophenyl)-3-(methylamino)propoxy)benzyl)-9-methyl-6,7,8,9-tetrahydro-5H-pyrimido[4,5-e][1,4]diazepin-5-one;

[456] 4-(4-(1-(2-chlorophenyl)-3-(methylamino)propoxy)benzyl)-1-methyl-1,2,3,4-tetrahydro-5H-pyrido[4,3-e][1,4]diazepin-5-one;

[457] 6-(4-(1-(3-chlorophenyl)-3-(methylamino)propoxy)benzyl)-2-methoxy-9-methyl-6,7,8,9-tetrahydro-5H-pyrimido[4,5-e][1,4]diazepin-5-one;

[458] 6-(4-(1-(3-chlorophenyl)-3-(methylamino)propoxy)benzyl)-9-methyl-6,7,8,9-tetrahydro-5H-pyrimido[4,5-e][1,4]diazepin-5-one;

[459] 4-(4-(1-(3-chlorophenyl)-3-(methylamino)propoxy)benzyl)-1-methyl-1,2,3,4-tetrahydro-5H-pyrido[4,3-e][1,4]diazepin-5-one;

[460] 6-(4-(1-(4-chlorophenyl)-3-(methylamino)propoxy)benzyl)-2-methoxy-9-methyl-6,7,8,9-tetrahydro-5H-pyrimido[4,5-e][1,4]diazepin-5-one;

[461] 6-(4-(1-(4-chlorophenyl)-3-(methylamino)propoxy)benzyl)-9-methyl-6,7,8,9-tetrahydro-5H-pyrimido[4,5-e][1,4]diazepin-5-one;

[462] 4-(4-(1-(4-chlorophenyl)-3-(methylamino)propoxy)benzyl)-1-methyl-1,2,3,4-tetrahydro-5H-pyrido[4,3-e][1,4]diazepin-5-one;

[463] (S)-8-methoxy-1-methyl-4-(4-(3-(methylamino)-1-phenylpropoxy)benzyl)-1,2,3,4-tetrahydro-5H-pyrido[4,3-e][1,4]diazepin-5-one;

[464] 1-methyl-4-(4-(3-(methylamino)-1-(5-methylthiophen-2-yl)propoxy)benzyl)-1,2,3,4-tetrahydro-5H-pyrido[4,3-e][1,4]diazepin-5-one;

[465] 9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one;

[466] 8-methoxy-1-methyl-4-(4-(3-(methylamino)-1-(5-methylthiophen-2-yl)propoxy)benzyl)-1,2,3,4-tetrahydro-5H-pyrido[4,3-e][1,4]diazepin-5-one;

[467] 8-methoxy-1-methyl-4-(4-(3-(methylamino)-1-(thiophen-3-yl)propoxy)benzyl)-1,2,3,4-tetrahydro-5H-pyrido[4,3-e][1,4]diazepin-5-one;

[468] 1-methyl-4-(4-(3-(methylamino)-1-(thiophen-3-yl)propoxy)benzyl)-1,2,3,4-tetrahydro-5H-pyrido[4,3-e][1,4]diazepin-5-one;

[469] 9-methyl-6-(4-(3-(methylamino)-1-(thiophen-3-yl)propoxy)benzyl)-6,7,8,9-tetrahydro-5H-pyrimido[4,5-e][1,4]diazepin-5-one;

[470] (S)-4-(3-fluoro-4-(3-(methylamino)-1-(thiophen-2-yl)propoxy)benzyl)-1-methyl-1,2,3,4-tetrahydro-5H-pyrido[4,3-e][1,4]diazepin-5-one;

[471] (S)-4-(3-fluoro-4-(3-(methylamino)-1-(thiophen-2-yl)propoxy)benzyl)-8-methoxy-1-methyl-1,2,3,4-tetrahydro-5H-pyrido[4,3-e][1,4]diazepin-5-one;

[472] (S)-6-(3-fluoro-4-(3-(methylamino)-1-(thiophen-2-yl)propoxy)benzyl)-9-methyl-6,7,8,9-tetrahydro-5H-pyrimido[4,5-e][1,4]diazepin-5-one;

[473] (S)-6-(2-fluoro-4-(3-(methylamino)-1-(thiophen-2-yl)propoxy)benzyl)-9-methyl-6,7,8,9-tetrahydro-5H-pyrimido[4,5-e][1,4]diazepin-5-one;

[474] (S)-4-(2-fluoro-4-(3-(methylamino)-1-(thiophen-2-yl)propoxy)benzyl)-8-methoxy-1-methyl-1,2,3,4-tetrahydro-5H-pyrido[4,3-e][1,4]diazepin-5-one;

[475] (S)-4-(2-fluoro-4-(3-(methylamino)-1-(thiophen-2-yl)propoxy)benzyl)-1-methyl-1,2,3,4-tetrahydro-5H-pyrido[4,3-e][1,4]diazepin-5-one;

[476] (S)-8-methoxy-1-methyl-4-(2-methyl-4-(3-(methylamino)-1-(thiophen-2-yl)propoxy)benzyl)-1,2,3,4-tetrahydro-5H-pyrido[4,3-e][1,4]diazepin-5-one;

[477] (S)-1-methyl-4-(2-methyl-4-(3-(methylamino)-1-(thiophen-2-yl)propoxy)benzyl)-1,2,3,4-tetrahydro-5H-pyrido[4,3-e][1,4]diazepin-5-one;

[478] (S)-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one;

[479] (S)-6-(3-chloro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[480] (S)-6-(3-chloro-4-(3-(methylamino)-1-(thiophen-2-yl)propoxy)benzyl)-9-methyl-6,7,8,9-tetrahydro-5H-pyrimido[4,5-e][1,4]diazepin-5-one;

[481] (S)-4-(3-chloro-4-(3-(methylamino)-1-(thiophen-2-yl)propoxy)benzyl)-1-methyl-1,2,3,4-tetrahydro-5H-pyrido[4,3-e][1,4]diazepin-5-one;

[482] (S)-6-(2-chloro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[483] (S)-6-(2-chloro-4-(3-(methylamino)-1-(thiophen-2-yl)propoxy)benzyl)-9-methyl-6,7,8,9-tetrahydro-5H-pyrimido[4,5-e][1,4]diazepin-5-one;

[484] (S)-4-(2-chloro-4-(3-(methylamino)-1-(thiophen-2-yl)propoxy)benzyl)-1-methyl-1,2,3,4-tetrahydro-5H-pyrido[4,3-e][1,4]diazepin-5-one;

[485] (S)-2-ethoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[486] (S)-8-methoxy-4-(4-(3-(methylamino)-1-(thiophen-2-yl)propoxy)benzyl)-1,2,3,4-tetrahydro-5H-pyrido[4,3-e][1,4]diazepin-5-one;

[487] (S)-1-isopropyl-4-(4-(3-(methylamino)-1-(thiophen-2-yl)propoxy)benzyl)-1,2,3,4-tetrahydro-5H-pyrido[4,3-e][1,4]diazepin-5-one; and

[488] (S)-9-isopropyl-6-(4-(3-(methylamino)-1-(thiophen-2-yl)propoxy)benzyl)-6,7,8,9-tetrahydro-5H-pyrimido[4,5-e][1,4]diazepin-5-one.

Among compounds of general formula (I) some subgroups of compounds have shown in addition a dual affinity towards subunit α2δ-1 of voltage-gated calcium channels (VGCC) and noradrenaline transporter (NET). These compounds having dual affinity represent the preferred embodiments of the invention and are represented among one of the following of formula (Ia), (Ib), (Ic), (Id), (Ie), (If) or (Ig):

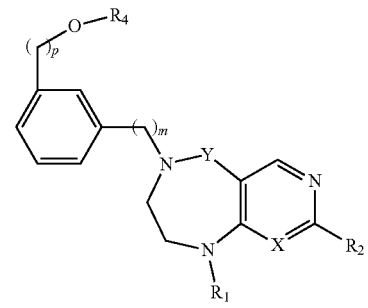
(Ia)

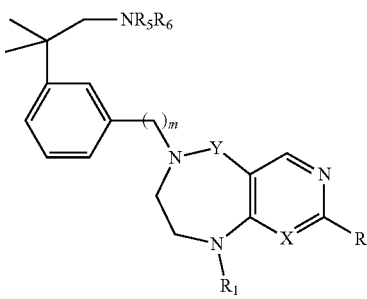
(Ib)

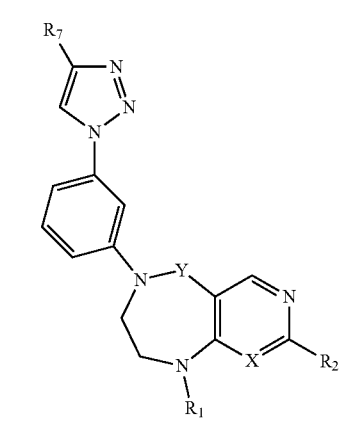
(Ic)

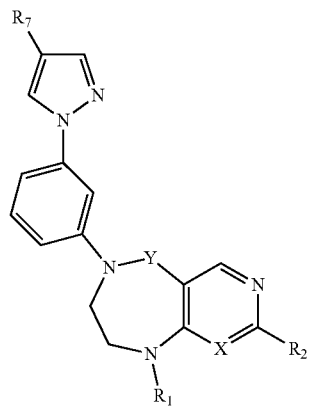
(Id)

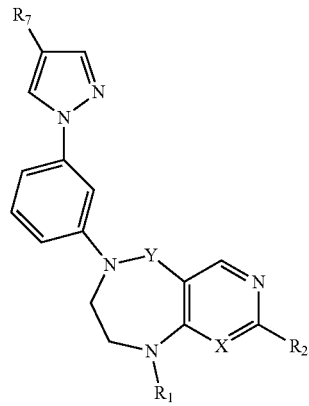
(Ie)

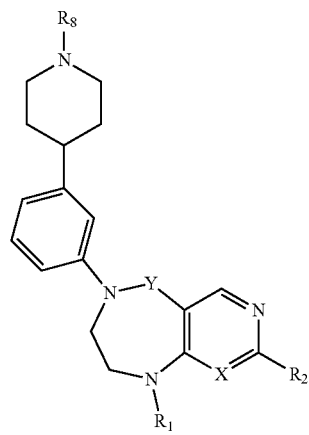
(If)

-continued

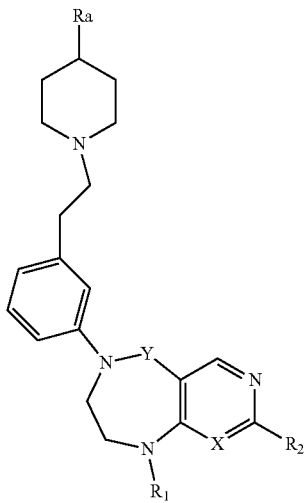

(Ig)

wherein X, Y, R₁, R₂, m and p are as defined before for general formula (I), and R₄ represents a —CHR₄ₐR₄ᵦ or a —CH₂—CHR₄ₐR₄ᵦ moiety where R₄ₐ is a group selected from:

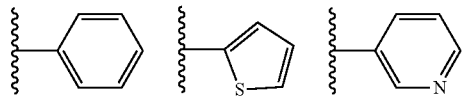

and R₄ᵦ represents a —(CH₂)ⱼ—NR₄ᵦ'R₄ᵦ'' moiety being j 0, 1, 2 or 3 and R₄ᵦ' and R₄ᵦ'' are independently from one another a hydrogen atom; a branched or unbranched C₁₋₆ alkyl radical, preferably methyl; a benzyl group; or a phenethyl group;

R₅ and R₆ are independently a hydrogen atom or a branched or unbranched C₁₋₆ alkyl radical, preferably methyl;

R₇ is a —(CH₂)ₚ—NR₇ₐR₇ᵦ moiety being p 0, 1, 2 or 3 and where

R₇ₐ and R₇ᵦ independently from one another represent a hydrogen atom; a branched or unbranched C₁₋₆ alkyl radical, preferably methyl; a benzyl group optionally substituted by a halogen; a phenethyl group; a —(CH₂)-cyclopropyl; a pyridinylmethyl group; or R₇ₐ and R₇ᵦ together with the bridging nitrogen form one of the following structures:

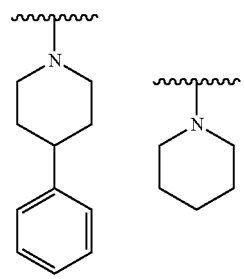 [SMILES: *N1CCC(c2ccccc2)CC1 ; *N1CCCCC1]

R₈ is a phenethyl group; and

Rₐ is phenyl group optionally substituted with and —OH group.

The preferred compounds of the invention showing dual inhibitory effect towards subunit α2δ-1 of voltage-gated calcium channels (VGCC) and noradrenaline transporter (NET) are selected from the following group:

[148] 2-(Ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[149] (R)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[150] (S)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[151] 9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[152] (R)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[153] (S)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[154] 2-(ethylamino)-9-methyl-6-(3-(2-(methylamino)-1-phenylethoxy)phenyl)-6,7,8,9-tetrahydro-5H-pyrimido[4,5-e][1,4]diazepin-5-one;

[156] 6-(3-(2-amino-1-phenylethoxy)phenyl)-2-(ethylamino)-9-methyl-6,7,8,9-tetrahydro-5H-pyrimido[4,5-e][1,4]diazepin-5-one;

[159] 2-(ethylamino)-9-methyl-6-(4-(2-(methylamino)-1-phenylethoxy)phenyl)-6,7,8,9-tetrahydro-5H-pyrimido[4,5-e][1,4]diazepin-5-one;

[160] 2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[161] (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[162] (S)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[163] 9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[164] (R)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[165] (S)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[166] 2-(ethylamino)-9-methyl-6-(3-((2-(methylamino)-2-phenylethoxy)methyl)phenyl)-6,7,8,9-tetrahydro-5H-pyrimido[4,5-e][1,4]diazepin-5-one;

[167] 9-methyl-6-(3-((2-(methylamino)-2-phenylethoxy)methyl)phenyl)-2-(methylthio)-6,7,8,9-tetrahydro-5H-pyrimido[4,5-e][1,4]diazepin-5-one;

[169] 6-(3-(3-(benzylamino)propoxy)phenyl)-2-(ethylamino)-9-methyl-6,7,8,9-tetrahydro-5H-pyrimido[4,5-e][1,4]diazepin-5-one;

[173] 2-(ethylamino)-9-methyl-6-(3-(2-methyl-1-(methylamino)propan-2-yl)phenyl)-6,7,8,9-tetrahydro-5H-pyrimido[4,5-e][1,4]diazepin-5-one;

[176] 2-(ethylamino)-9-methyl-6-(3-(((4-phenylpiperidin-4-yl)oxy)methyl)phenyl)-6,7,8,9-tetrahydro-5H-pyrimido[4,5-e][1,4]diazepin-5-one;

[179] 9-methyl-2-(methylthio)-6-(3-(((4-phenylpiperidin-4-yl)oxy)methyl)phenyl)-6,7,8,9-tetrahydro-5H-pyrimido[4,5-e][1,4]diazepin-5-one;

[182] 6-(3-(4-((benzylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[183] 2-(ethylamino)-9-methyl-6-(3-(4-(2-(methylamino)ethyl)-1H-1,2,3-triazol-1-yl)phenyl)-6,7,8,9-tetrahydro-5H-pyrimido[4,5-e][1,4]diazepin-5-one;

[193] 2-(ethylamino)-9-methyl-6-(3-(3-(methylamino)-1-(pyridin-2-yl)propoxy)phenyl)-6,7,8,9-tetrahydro-5H-pyrimido[4,5-e][1,4]diazepin-5-one;

[194] 2-(ethylamino)-9-methyl-6-(3-(3-(methylamino)-1-(pyridin-3-yl)propoxy)phenyl)-6,7,8,9-tetrahydro-5H-pyrimido[4,5-e][1,4]diazepin-5-one;

[195] (R)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one;

[196] (R)-2-(dimethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[197] (R)-9-methyl-2-(methylamino)-6-(3-((3-(methylamino)-1-phenylpropoxy)methyl)phenyl)-6,7,8,9-tetrahydro-5H-pyrimido[4,5-e][1,4]diazepin-5-one;

[198] 8-(ethylamino)-1-methyl-4-(3-(3-(methylamino)-1-phenylpropoxy)phenyl)-1,2,3,4-tetrahydro-5H-pyrido[4,3-e][1,4]diazepin-5-one;

[199] 8-(ethylamino)-1-methyl-4-(3-((3-(methylamino)-1-phenylpropoxy)methyl)phenyl)-1,2,3,4-tetrahydro-5H-pyrido[4,3-e][1,4]diazepin-5-one;

[201] 2-(ethylamino)-9-methyl-6-(4-(2-(methylamino)-1-phenylethoxy)benzyl)-6,7,8,9-tetrahydro-5H-pyrimido[4,5-e][1,4]diazepin-5-one;

[203] (R)—N-ethyl-9-methyl-6-(3-((3-(methylamino)-1-phenylpropoxy)methyl)phenyl)-6,7,8,9-tetrahydro-5H-pyrimido[4,5-e][1,4]diazepin-2-amine;

[204] (R)-2-methoxy-9-methyl-6-(3-((3-(methylamino)-1-phenylpropoxy)methyl)phenyl)-6,7,8,9-tetrahydro-5H-pyrimido[4,5-e][1,4]diazepin-5-one;

[205] (R)-2-hydroxy-9-methyl-6-(3-((3-(methylamino)-1-phenylpropoxy)methyl)phenyl)-6,7,8,9-tetrahydro-5H-pyrimido[4,5-e][1,4]diazepin-5-one;

[206] (R)-2,9-dimethyl-6-(3-((3-(methylamino)-1-phenylpropoxy)methyl)phenyl)-6,7,8,9-tetrahydro-5H-pyrimido[4,5-e][1,4]diazepin-5-one;

[207] (R)-9-methyl-6-(3-((3-(methylamino)-1-phenylpropoxy)methyl)phenyl)-6,7,8,9-tetrahydro-5H-pyrimido[4,5-e][1,4]diazepin-5-one;

[208] 9-Methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[209] (R)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[210] (S)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[211] 2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[212] (R)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[213] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[214] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[215] (R)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[216] (S)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[217] 9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[218] (R)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[219] (S)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[220] 2-(ethylamino)-6-(3-(3-((2-fluoroethyl)amino)-1-(thiophen-2-yl)propoxy)phenyl)-9-methyl-6,7,8,9-tetrahydro-5H-pyrimido[4,5-e][1,4]diazepin-5-one;

[221] 2-methoxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[222] 2-hydroxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[223] 2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[224] 9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[225] 2-(Ethylamino)-9-methyl-6-(3-((2-(methylamino)-1-phenylethoxy)methyl)phenyl)-6,7,8,9-tetrahydro-5H-pyrimido[4,5-e][1,4]diazepin-5-one;

[226] 9-methyl-6-(3-((2-(methylamino)-1-phenylethoxy)methyl)phenyl)-2-(methylthio)-6,7,8,9-tetrahydro-5H-pyrimido[4,5-e][1,4]diazepin-5-one;

[227] 8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[229] 8-(dimethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[230] 2-(dimethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[231] 2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[232] 9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[236] (R)-6-(3-((3-(Dimethylamino)-1-phenylpropoxy)methyl)phenyl)-2-(ethylamino)-9-methyl-6,7,8,9-tetrahydro-5H-pyrimido[4,5-e][1,4]diazepin-5-one;

[237] (S)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one;

[238] 6-(3-(3-(dimethylamino)-1-phenylpropoxy)phenyl)-2-(ethylamino)-9-methyl-6,7,8,9-tetrahydro-5H-pyrimido[4,5-e][1,4]diazepin-5-one;

[239] 6-(3-(2-(dimethylamino)-1-phenylethoxy)phenyl)-2-(ethylamino)-9-methyl-6,7,8,9-tetrahydro-5H-pyrimido[4,5-e][1,4]diazepin-5-one;

[240] 6-(3-(3-(benzyl(methyl)amino)propyl)phenyl)-2-(ethylamino)-9-methyl-6,7,8,9-tetrahydro-5H-pyrimido[4,5-e][1,4]diazepin-5-one;

[241] 6-(3-(3-(dimethylamino)propyl)phenyl)-2-(ethylamino)-9-methyl-6,7,8,9-tetrahydro-5H-pyrimido[4,5-e][1,4]diazepin-5-one;

[242] 6-(3-(4-((dimethylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[243] 6-(3-(4-((benzyl(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[244] 2-(ethylamino)-9-methyl-6-(3-(4-((methyl(phenethyl)amino)methyl)-1H-1,2,3-triazol-1-yl)phenyl)-6,7,8,9-tetrahydro-5H-pyrimido[4,5-e][1,4]diazepin-5-one;

[246] 6-(3-(4-(((cyclopropylmethyl)(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[251] 6-(3-(4-((benzyl(methyl)amino)methyl)-1H-pyrazol-1-yl)phenyl)-2-(ethylamino)-9-methyl-6,7,8,9-tetrahydro-5H-pyrimido[4,5-e][1,4]diazepin-5-one;

[252] 2-(ethylamino)-9-methyl-6-(3-(4-((methyl(phenethyl)amino)methyl)-1H-pyrazol-1-yl)phenyl)-6,7,8,9-tetrahydro-5H-pyrimido[4,5-e][1,4]diazepin-5-one;

[253] 6-(3-(4-((benzyl(methyl)amino)methyl)-1H-imidazol-1-yl)phenyl)-2-(ethylamino)-9-methyl-6,7,8,9-tetrahydro-5H-pyrimido[4,5-e][1,4]diazepin-5-one;

[254] 2-(ethylamino)-9-methyl-6-(3-(4-((methyl(phenethyl)amino)methyl)-1H-imidazol-1-yl)phenyl)-6,7,8,9-tetrahydro-5H-pyrimido[4,5-e][1,4]diazepin-5-one;

[256] 6-(3-(3-(benzyl(methyl)amino)propoxy)phenyl)-2-(ethylamino)-9-methyl-6,7,8,9-tetrahydro-5H-pyrimido[4,5-e][1,4]diazepin-5-one;

[261] 2-(ethylamino)-9-methyl-6-(3-(1-phenethylpiperidin-4-yl)phenyl)-6,7,8,9-tetrahydro-5H-pyrimido[4,5-e][1,4]diazepin-5-one;

[264] 6-(3-(2-(benzyl(methyl)amino)ethoxy)phenyl)-2-(ethylamino)-9-methyl-6,7,8,9-tetrahydro-5H-pyrimido[4,5-e][1,4]diazepin-5-one;

[265] 2-(ethylamino)-9-methyl-6-(3-(2-(methyl(phenethyl)amino)ethoxy)phenyl)-6,7,8,9-tetrahydro-5H-pyrimido[4,5-e][1,4]diazepin-5-one;

[271] 9-methyl-6-(3-(((1-methyl-4-phenylpiperidin-4-yl)oxy)methyl)phenyl)-2-(methylthio)-6,7,8,9-tetrahydro-5H-pyrimido[4,5-e][1,4]diazepin-5-one;

[272] 2-(ethylamino)-9-methyl-6-(3-(((1-methyl-4-phenylpiperidin-4-yl)oxy)methyl)phenyl)-6,7,8,9-tetrahydro-5H-pyrimido[4,5-e][1,4]diazepin-5-one;

[275] 2-(Ethylamino)-6-(3-(2-(4-(3-hydroxyphenyl)piperidin-1-yl)ethyl)phenyl)-9-methyl-6,7,8,9-tetrahydro-5H-pyrimido[4,5-e][1,4]diazepin-5-one;

[278] 2-(Ethylamino)-9-methyl-6-(3-(4-((4-phenylpiperidin-1-yl)methyl)-1H-1,2,3-triazol-1-yl)phenyl)-6,7,8,9-tetrahydro-5H-pyrimido[4,5-e][1,4]diazepin-5-one;

[279] 2-(ethylamino)-6-(3-(4-((4-(3-hydroxyphenyl)piperidin-1-yl)methyl)-1H-1,2,3-triazol-1-yl)phenyl)-9-methyl-6,7,8,9-tetrahydro-5H-pyrimido[4,5-e][1,4]diazepin-5-one;

[281] 2-(ethylamino)-9-methyl-6-(3-(4-(piperidin-1-ylmethyl)-1H-1,2,3-triazol-1-yl)phenyl)-6,7,8,9-tetrahydro-5H-pyrimido[4,5-e][1,4]diazepin-5-one;

[285] 6-(3-(4-(((cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[287] 2-(ethylamino)-6-(3-(4-(((4-fluorobenzyl)(methyl)amino)methyl)-1H-1,2,3-triazol-1-yl)phenyl)-9-methyl-6,7,8,9-tetrahydro-5H-pyrimido[4,5-e][1,4]diazepin-5-one;

[288] 2-(ethylamino)-9-methyl-6-(3-(4-((methyl(pyridin-2-ylmethyl)amino)methyl)-1H-1,2,3-triazol-1-yl)phenyl)-6,7,8,9-tetrahydro-5H-pyrimido[4,5-e][1,4]diazepin-5-one; and

[289] 2-(ethylamino)-9-methyl-6-(3-(4-((methyl(pyridin-3-ylmethyl)amino)methyl)-1H-1,2,3-triazol-1-yl)phenyl)-6,7,8,9-tetrahydro-5H-pyrimido[4,5-e][1,4]diazepin-5-one.

[304] (S)-8-amino-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[305] (S)-8-amino-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[307] 1,8-dimethyl-4-(3-(3-(methylamino)-1-(thiophen-2-yl)propoxy)phenyl)-1,2,3,4-tetrahydro-5H-pyrido[4,3-e][1,4]diazepin-5-one;

[308] (S)-1,8-dimethyl-4-(4-(3-(methylamino)-1-(thiophen-2-yl)propoxy)benzyl)-1,2,3,4-tetrahydro-5H-pyrido[4,3-e][1,4]diazepin-5-one;

[315] 9-methyl-6-(4-((3-(methylamino)-1-phenylpropoxy)methyl)phenyl)-2-(methylthio)-6,7,8,9-tetrahydro-5H-pyrimido[4,5-e][1,4]diazepin-5-one;

[316] 9-methyl-6-(4-(3-(methylamino)-1-phenylpropoxy)phenyl)-2-(methylthio)-6,7,8,9-tetrahydro-5H-pyrimido[4,5-e][1,4]diazepin-5-one;

[321] 9-methyl-6-(4-((2-(methylamino)-1-phenylethoxy)methyl)phenyl)-2-(methylthio)-6,7,8,9-tetrahydro-5H-pyrimido[4,5-e][1,4]diazepin-5-one;

[322] 9-methyl-6-(3-((3-(methylamino)-1-phenylpropoxy)methyl)phenyl)-2-(trifluoromethyl)-6,7,8,9-tetrahydro-5H-pyrimido[4,5-e][1,4]diazepin-5-one;

[323] 1-methyl-4-(3-(3-(methylamino)-1-(thiophen-2-yl)propoxy)phenyl)-1,2,3,4-tetrahydro-5H-pyrido[4,3-e][1,4]diazepin-5-one;

[325] (S)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[326] (S)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[327] (R)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[328] 9-methyl-6-(4-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[329] 9-methyl-6-(3-(3-(methylamino)-1-(thiophen-2-yl)propoxy)phenyl)-2-(trifluoromethyl)-6,7,8,9-tetrahydro-5H-pyrimido[4,5-e][1,4]diazepin-5-one;

[330] 9-methyl-6-(3-((3-(methylamino)-1-(thiophen-2-yl)propoxy)methyl)phenyl)-2-(trifluoromethyl)-6,7,8,9-tetrahydro-5H-pyrimido[4,5-e][1,4]diazepin-5-one;

[331] (S)-8-methoxy-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[333] 2-(ethylamino)-9-methyl-6-(4-(3-(methylamino)-1-phenylpropoxy)phenyl)-6,7,8,9-tetrahydro-5H-pyrimido[4,5-e][1,4]diazepin-5-one;

[334] 2-(ethylamino)-9-methyl-6-(4-((3-(methylamino)-1-phenylpropoxy)methyl)phenyl)-6,7,8,9-tetrahydro-5H-pyrimido[4,5-e][1,4]diazepin-5-one;

[335] 2-(benzylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[336] 9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;

[340] 2-(ethylamino)-9-methyl-6-(4-((2-(methylamino)-1-phenylethoxy)methyl)phenyl)-6,7,8,9-tetrahydro-5H-pyrimido[4,5-e][1,4]diazepin-5-one;

[341] (R)-9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;

[342] (R)-9-methyl-2-(methyl(pyridin-3-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;

[343] (R)-9-methyl-6-(3-((3-(methylamino)-1-phenylpropoxy)methyl)phenyl)-2-((pyridin-2-ylmethyl)amino)-6,7,8,9-tetrahydro-5H-pyrimido[4,5-e][1,4]diazepin-5-one;

[344] (R)-2-(((5-fluoropyridin-2-yl)methyl)(methyl)amino)-9-methyl-6-(3-((3-(methylamino)-1-phenylpropoxy)methyl)phenyl)-6,7,8,9-tetrahydro-5H-pyrimido[4,5-e][1,4]diazepin-5-one

[347] (R)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[348] 2-(ethylamino)-9-methyl-6-(4-((3-(methylamino)-1-(thiophen-2-yl)propoxy)methyl)phenyl)-6,7,8,9-tetrahydro-5H-pyrimido[4,5-e][1,4]diazepin-5-one;

[349] 2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;

[350] (R)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;

[351] (S)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;

[352] (S)-2-amino-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[353] 2,9-dimethyl-6-(4-((3-(methylamino)-1-phenylpropoxy)methyl)phenyl)-6,7,8,9-tetrahydro-5H-pyrimido[4,5-e][1,4]diazepin-5-one;

[354] 2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;

[355] 2,9-dimethyl-6-(4-((2-(methylamino)-1-phenylethoxy)methyl)phenyl)-6,7,8,9-tetrahydro-5H-pyrimido[4,5-e][1,4]diazepin-5-one;

[356] (R)-2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;

[357] (R)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[358] (S)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[360] (R)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[364] (S)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[366] 9-methyl-6-(3-(3-(methylamino)-1-phenylpropoxy)benzyl)-2-(methylthio)-6,7,8,9-tetrahydro-5H-pyrimido[4,5-e][1,4]diazepin-5-one;

[367] 9-methyl-6-(3-((3-(methylamino)-1-phenylpropoxy)methyl)benzyl)-2-(methylthio)-6,7,8,9-tetrahydro-5H-pyrimido[4,5-e][1,4]diazepin-5-one;

[368] 9-methyl-6-(4-((3-(methylamino)-1-phenylpropoxy)methyl)benzyl)-2-(methylthio)-6,7,8,9-tetrahydro-5H-pyrimido[4,5-e][1,4]diazepin-5-one;

[369] 9-methyl-6-(4-(3-(methylamino)-1-phenylpropoxy)benzyl)-2-(methylthio)-6,7,8,9-tetrahydro-5H-pyrimido[4,5-e][1,4]diazepin-5-one;

[372] 9-methyl-6-(3-((2-(methylamino)-1-phenylethoxy)methyl)benzyl)-2-(methylthio)-6,7,8,9-tetrahydro-5H-pyrimido[4,5-e][1,4]diazepin-5-one;

[374] 9-methyl-6-(4-((2-(methylamino)-1-phenylethoxy)methyl)benzyl)-2-(methylthio)-6,7,8,9-tetrahydro-5H-pyrimido[4,5-e][1,4]diazepin-5-one;

[375] (S)-2-methoxy-9-methyl-6-(4-(3-(methylamino)-1-phenylpropoxy)benzyl)-6,7,8,9-tetrahydro-5H-pyrimido[4,5-e][1,4]diazepin-5-one;

[378] 9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[379] (S)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[380] (R)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[381] 1-methyl-4-(4-(3-(methylamino)-1-(thiophen-2-yl)propoxy)benzyl)-1,2,3,4-tetrahydro-5H-pyrido[4,3-e][1,4]diazepin-5-one;

[382] (S)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[383] (S)-8-(ethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[384] (S)-8-(dimethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[385] (S)-8-methoxy-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[386] (S)-9-methyl-6-(4-(3-(methylamino)-1-(thiophen-2-yl)propoxy)benzyl)-2-(trifluoromethyl)-6,7,8,9-tetrahydro-5H-pyrimido[4,5-e][1,4]diazepin-5-one;

[387] 2-methoxy-9-methyl-6-(4-(3-(methylamino)-1-(thiophen-3-yl)propoxy)benzyl)-6,7,8,9-tetrahydro-5H-pyrimido[4,5-e][1,4]diazepin-5-one;

[388] 2-methoxy-9-methyl-6-(4-(3-(methylamino)-1-(3-methylthiophen-2-yl)propoxy)benzyl)-6,7,8,9-tetrahydro-5H-pyrimido[4,5-e][1,4]diazepin-5-one;

[389] (S)-1-ethyl-8-methoxy-4-(4-(3-(methylamino)-1-(thiophen-2-yl)propoxy)benzyl)-1,2,3,4-tetrahydro-5H-pyrido[4,3-e][1,4]diazepin-5-one;

[391] (S)-1-ethyl-4-(4-(3-(methylamino)-1-(thiophen-2-yl)propoxy)benzyl)-1,2,3,4-tetrahydro-5H-pyrido[4,3-e][1,4]diazepin-5-one;

[392] 2-methoxy-9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one;

[394] (S)-6-(3-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[395] S)-9-ethyl-2-methoxy-6-(4-(3-(methylamino)-1-(thiophen-2-yl)propoxy)benzyl)-6,7,8,9-tetrahydro-5H-pyrimido[4,5-e][1,4]diazepin-5-one;

[396] 2-methoxy-9-methyl-6-(4-(3-(methylamino)-1-(4-methylthiophen-2-yl)propoxy)benzyl)-6,7,8,9-tetrahydro-5H-pyrimido[4,5-e][1,4]diazepin-5-one;

[397] (S)-2-methoxy-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one;

[398] (S)-9-ethyl-6-(4-(3-(methylamino)-1-(thiophen-2-yl)propoxy)benzyl)-6,7,8,9-tetrahydro-5H-pyrimido[4,5-e][1,4]diazepin-5-one;

[399] (S)-9-fluoro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[400] (S)-9-chloro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[401] (S)-6-(2-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[402] (S)-2-methoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[405] 2-(ethylamino)-9-methyl-6-(4-((3-(methylamino)-1-phenylpropoxy)methyl)benzyl)-6,7,8,9-tetrahydro-5H-pyrimido[4,5-e][1,4]diazepin-5-one;

[406] 2-(ethylamino)-9-methyl-6-(3-((3-(methylamino)-1-phenylpropoxy)methyl)benzyl)-6,7,8,9-tetrahydro-5H-pyrimido[4,5-e][1,4]diazepin-5-one;

[408] 2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[411] 2-(ethylamino)-9-methyl-6-(3-((2-(methylamino)-1-phenylethoxy)methyl)benzyl)-6,7,8,9-tetrahydro-5H-pyrimido[4,5-e][1,4]diazepin-5-one;

[413] 2-(ethylamino)-9-methyl-6-(4-((2-(methylamino)-1-phenylethoxy)methyl)benzyl)-6,7,8,9-tetrahydro-5H-pyrimido[4,5-e][1,4]diazepin-5-one;

[414] (S)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[415] (R)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[416] 2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[417] (S)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[418] (R)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[419] (S)-2-(dimethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[420] (S)-2-amino-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[422] 2,9-dimethyl-6-(4-((3-(methylamino)-1-phenylpropoxy)methyl)benzyl)-6,7,8,9-tetrahydro-5H-pyrimido[4,5-e][1,4]diazepin-5-one;

[423] 2,9-dimethyl-6-(3-((3-(methylamino)-1-phenylpropoxy)methyl)benzyl)-6,7,8,9-tetrahydro-5H-pyrimido[4,5-e][1,4]diazepin-5-one;

[425] 2,9-dimethyl-6-(4-(3-(methylamino)-1-phenylpropoxy)benzyl)-6,7,8,9-tetrahydro-5H-pyrimido[4,5-e][1,4]diazepin-5-one;

[426] 2-ethyl-9-methyl-6-(4-(3-(methylamino)-1-phenylpropoxy)benzyl)-6,7,8,9-tetrahydro-5H-pyrimido[4,5-e][1,4]diazepin-5-one;

[427] (R)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[428] (S)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[430] 9-methyl-6-(4-(3-(methylamino)-1-phenylpropoxy)benzyl)-6,7,8,9-tetrahydro-5H-pyrimido[4,5-e][1,4]diazepin-5-one;

[433] (S)-9-methyl-6-(4-(3-(methylamino)-1-phenylpropoxy)benzyl)-6,7,8,9-tetrahydro-5H-pyrimido[4,5-e][1,4]diazepin-5-one;

[434] (R)-9-methyl-6-(4-(3-(methylamino)-1-phenylpropoxy)benzyl)-6,7,8,9-tetrahydro-5H-pyrimido[4,5-e][1,4]diazepin-5-one;

[435] 9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[436] (S)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[437] (R)-9-methyl-6-(4-(3-(methylamino)-1-(thiophen-2-yl)propoxy)benzyl)-6,7,8,9-tetrahydro-5H-pyrimido[4,5-e][1,4]diazepin-5-one; and

[442] 6-(3-(5-((4-(dimethylamino)-4-(3-hydroxyphenyl)piperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one.

In another aspect, the invention refers to the processes for obtaining the compounds of general formula (I). Several procedures have been developed for obtaining all the compounds of the invention, and the procedures will be explained below in methods A, B and C.

The obtained reaction products may, if desired, be purified by conventional methods, such as crystallization and chromatography. Where the processes described below for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

Method A

Method A represents a first process for synthesizing compounds according to general formula (I). Method A allows for the preparation of compounds of general formula (I') that is compounds of formula (I) where m is 0 and Y represents either a C=O or a CH$_2$. In this sense, a process is described for the preparation of a compound of general formula (I'):

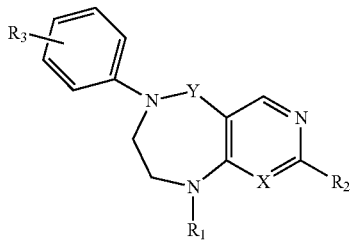

comprising the reaction between a compound of formula (VII) or formula (IV):

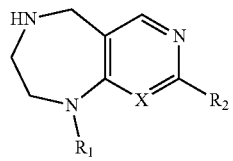

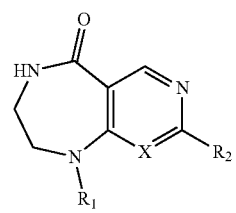

and a compound of formula (VIII):

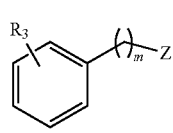

wherein R$_1$, R$_2$, R$_3$ and X and Y are as defined for general formula (I) along the present description, m is 0 and Z is a suitable leaving group such as a halogen.

The reaction when Y—CH$_2$— is preferably carried out in the presence of a Pd catalyst, preferably Pd$_2$(dba)$_3$ and a suitable ligand, preferably 2-dicyclohexylphosphino-2',4',6'-triisopropylbiphenyl (Xphos) or 4,5-Bis(diphenylphosphino)-9,9-dimethylxanthene (tBu-Xantphos), in the presence of a base, preferably KOtBu or Cs$_2$CO$_3$ and in an organic solvent, preferably toluene or 1,4-dioxane, at a temperature range of preferably 50-140° C.

In the case where Y is C=O preferably the coupling reaction of the intermediate of general formula (VII) with a compound of general formula (VIII), is carried out in the presence of a copper salt as catalyst, preferably CuI, also an appropriate ligand, preferably N1,N2-dimethylethane-1,2-diamine, and an inorganic base, preferably K$_3$PO$_4$ or K$_2$CO$_3$ in an organic solvent, preferably 1,4-dioxane or N,N-dimethylformamide (DMF) at a temperature range of preferably 80-130° C.

Method B

Method B represents a process for synthesizing compounds according to general formula (I"), namely compounds of general formula (I) where m is 1 or 2 and Y represents a C=O.

In this sense, a process is described for the preparation of a compound of general formula (I"):

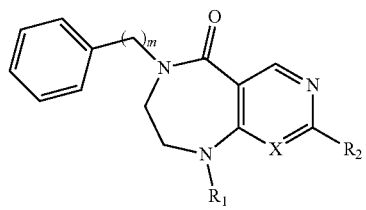

comprising the reaction between a compound of formula (IV):

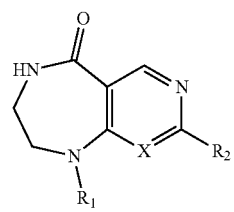

and a compound of formula (VIII):

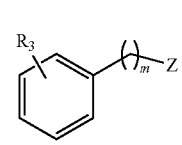

wherein R$_1$, R$_2$, R$_3$ and X are as defined for general formula (I) along the present description, m represents 1 or 2 and Z represents a suitable leaving group such as a for instance a halogen.

The reaction between (IV) and (VIII) is preferably carried out in the presence of a base, preferably NaH, in an organic solvent, preferably THF or DMF, at a temperature range of preferably 0-60° C.

Method C

Method C represents the third process for synthesizing compounds according to general formula (I). Method C allows for the preparation of compounds of general formula (I''') that is compounds of formula (I) where m is 1 or 2 and Y represents a —CH$_2$—.

In this sense, a process is described for the preparation of a compound of general formula (I'''):

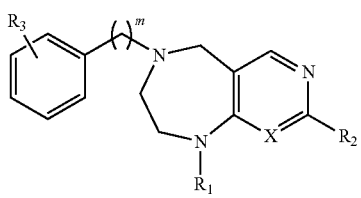

(I''')

comprising the reaction between a compound of formula (VII):

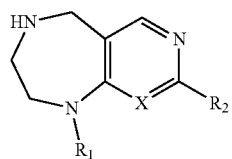

(VII)

and either:
a) a compound of formula (IX):

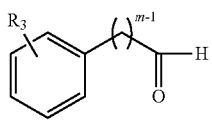

(IX)

b) a compound of formula (VIII):

(VIII)

wherein $R_1$, $R_2$, $R_3$ and X are as defined for general formula (I) along the present description, m is 1 or 2 and Z is a suitable leaving group such as a halogen.

The reductive amination reaction of an intermediate of formula (VII) and an aldehyde of formula (IX), is preferably carried out in the presence of a reductive reagent, preferably sodium triacetoxyborohydride, and in the presence of a base, preferably diisopropylethylamine (DIPEA) or triethylamine (TEA), in an organic solvent, preferably 1,2-dichloroethane (DCE).

The reaction between (VII) and (VIII) is preferably carried out in the presence of a base, preferably NaH, in an organic solvent, preferably THF or DMF, at a temperature range of preferably 0-60° C.

The different reactions of methods A, B and C as well as reactions for preparing the intermediate compounds for such reactions are depicted in scheme 1:

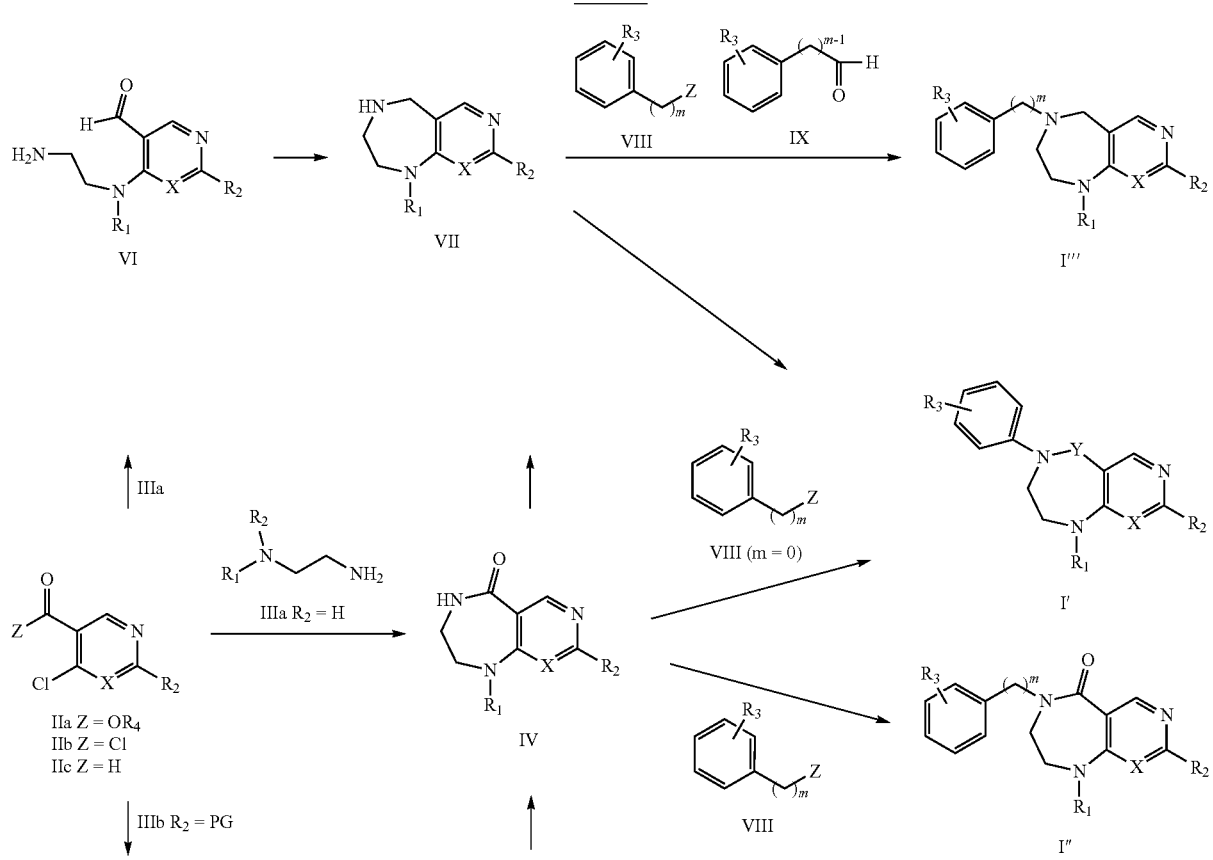

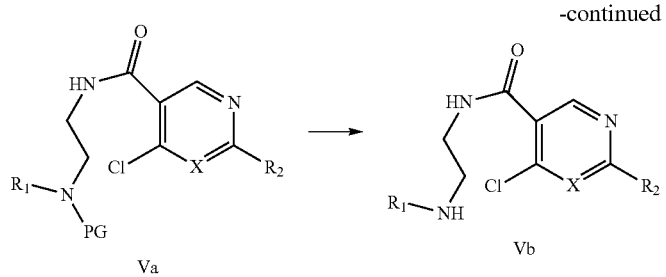

The intermediate compounds VII and IV which are the basic reagents for producing compounds of formula (I) according to methods A, B and C can be prepared by different routes as shown in scheme 1 above.

Compound (IV) can be prepared for instance by a reaction of a compound of formula (IIa) where $R_4$ is and alkyl, preferably ethyl or methyl, with a diamine of general formula (IIIa) ideally in the presence of a base, preferably KOtBu and in an organic solvent, preferably tetrahydrofuran (THF) or a mixture of organic solvent and water, preferably THF/water, at a suitable temperature, preferably in the range of 0-60° C.

Alternatively, intermediates of general formula IV can be prepared by the following sequence of reactions (Scheme 1):

a) The reaction of a compound of formula (IIb) with an amine of formula (IIIb), where PG (Protecting Group) is an amine protecting group such as a carbamate, preferably tert-butoxy carbonyl, in the presence of a base, preferably DIPEA or TEA, in an organic solvent, preferably THF or DCM, at a temperature range of 0-60° C.

b) The deprotection reaction of a compound of general formula (Va) by any suitable method, such as treatment with an acid, preferably HCl or trifluoroacetic acid in an appropriate solvent such as 1,4-dioxane, DCM, ethyl acetate or a mixture of an organic solvent and water.

c) The intramolecular reaction of an intermediate of general formula Vb in the presence of a base, preferably $Cs_2CO_3$ in an organic solvent, preferably DMF at a temperature range of 20-130° C.

In turn, intermediate of formula (VII) can also be prepared by different routes. The first synthetic route involves the following sequence of reactions (see scheme 1):

a) The reaction of a compound of general formula (IIc) with a diamine of general formula (IIIa), in the presence of a base, preferably DIPEA or TEA, in an organic solvent, preferably acetonitrile, at a temperature range of 0-60° C.

b) The intramolecular reductive amination reaction of a compound of formula VI, in the presence of a reductive reagent, preferably sodium triacetoxyborohydride, in an organic solvent, preferably DCE.

Alternatively, intermediates of general formula (VII) can be prepared by reduction of an intermediate of general formula IV by any suitable reductive reagent.

On the other hand, in order to get the high variability of compounds of general formula (I), the functional groups of the compounds of formula (I), (IV) and (VII) can be interconverted using different methods such as:

The reduction, in the case of $R_2$ is a thioether functional group or an halogen, using suitable reductive reagent, preferably triethylsilane or hydrogen in the presence of Pd/C as catalyst, in an organic solvent, preferably THF.

The oxidation of the thioether to sulfoxide or sulfone, using an appropriate oxidant, preferably m-chloroperbenzoic acid in an organic solvent, preferably dichloromethane (DCM), and the subsequent reaction of these intermediates with different reagents:

a) the reaction with an amine of formula $HNR_{2a}R_{2b}$ in an aqueous solvent such as mixtures of ethanol and water, to provide a compound where $R_2$ is $NR_{2a}R_{2b}$, b) the reaction with an alkoxide, such as a sodium alkoxide of formula $NaOR_{2a}$, in an alcoholic solvent such as $HOR_{2a}$, to provide a compound where $R_2$ is $OR_{2a}$, c) the reaction with sodium hydroxide in an aqueous solvent such as mixtures of THF and water, to provide a compound where $R_2$ is OH, d) the reaction with a Grignard reagent of formula AlkylMgBr, in an organic solvent such as mixtures of THF and diethylether, to provide a compound where $R_2$ is Alkyl, e) the reaction with a reducing reagent such as Pd/C and triethylsilane, in an organic solvent such as THF, to provide a compound where $R_2$ is H.

Additionally these groups can also be introduced at any step from the halogen substituted analogues, ie from compounds of formula I, IV and VII where $R_2$ is halogen, using the same reactions conditions.

Alternatively the functional groups of the compounds of formula I can be interconverted in the position corresponding to $R_3$ using different methods, such as those depicted in Scheme 2 and described below. In said Scheme, Q represent the transition moiety of the molecule between the amine group present in several compounds according of the invention and the phenyl ring of formula (I) that attaches to the rest of the molecule. Q can be, for instance, the following moiety as defined for formula (I): the —$(CH_2)_p$—O— moiety, the —$(CH_2)_q$— moiety; the —$C(CH_3)_2$—$CH_2$— moiety; —C(=O)—; or the 5 or 6 membered heteroaryl group having at least one heteroatom selected from N, O or S; n seeks to represent an alkylene group and R in each position represents any of the possible substituents defined in the corresponding amine group along the description in said position.

Scheme 2:

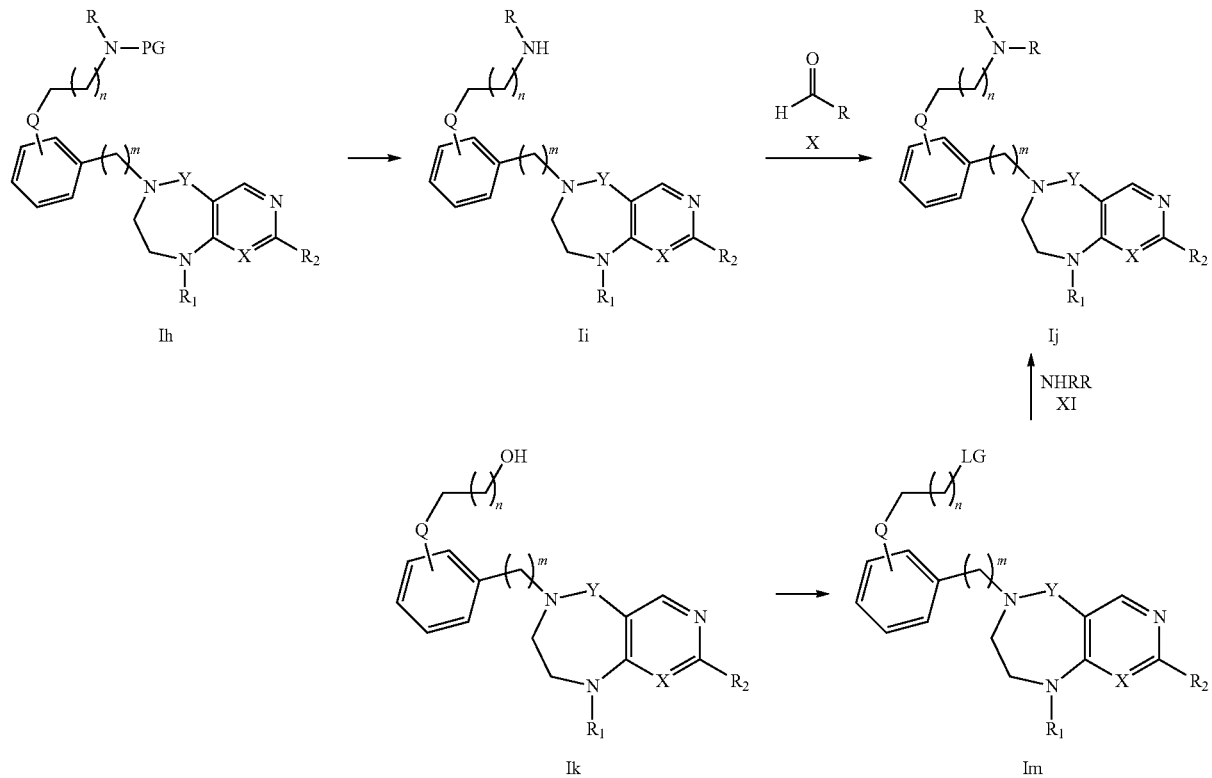

The deprotection reaction of a compound of general formula (Ih) where PG is an amine protecting group such as a carbamate, preferably tert-butoxy carbonyl or 2-trimethylsililethoxy carbonyl (Teoc), is carried out by any suitable method, such as treatment with an acid, preferably HCl or trifluoroacetic acid in an appropriate solvent such as 1,4-dioxane, DCM, ethyl acetate or a mixture of an organic solvent and water. Alternatively, the deprotection can be made by treatment with $ZnBr_2$ in an organic solvent, preferably DCM. Also alternatively the Teoc deprotection can be performed by reaction with CsF in an organic solvent, preferably DMF at a temperature range of 20-130° C., or alternatively under microwave irradiation.

The reductive amination reaction of compounds of formula (Ii) with an aldehyde of formula X to give compounds of formula (Ij) is preferably carried out with a reductive reagent, preferably sodium triacetoxyborohydride, in an aprotic solvent, preferably DCE, in the presence of an organic base, preferably DIPEA or TEA. Alternatively, the reaction can be carried out in the presence of an acid, preferably acetic acid.

Alternatively, compounds of formula (Ij) can be obtained by reaction of a compound of general formula (Im), wherein LG is a leaving group such as an halogen or sulfonate, with an amine of general formula XI, in an organic solvent or a mixture of organic solvent and water, preferably ethanol or ethanol/water, at suitable temperature, such as in the range of 0-150° C.; alternatively in the presence of a base, preferably TEA.

Compounds of general formula (Im) can be obtained by the derivatization of an alcohol of general formula (Ik) by any suitable method, preferably with methylsulfonyl chloride in the presence of a base, preferably TEA, in an organic solvent, preferably DCM, at a suitable temperature, such as in the range of −5-40° C.

Other different interconversion methods can be used to prepare compounds of general formula I. One of such methods involves the coupling reaction of an halogenated intermediate with a boronic acid or boronic ester using a palladium catalyst, preferably tetrakis triphenylphosphine palladium, an inorganic base, preferably $NaHCO_3$, in an organic solvent or a mixture of organic solvent and water, preferably 1,4-dioxane or 1-4-dioxane/water at a suitable temperature, such as in the range of 60-150° C., optionally using microwave radiation. Another of such reactions involves the reductive amination reaction of an aldehyde intermediate with an amine, preferably carried out with a reductive reagent, preferably sodium triacetoxyborohydride, in an aprotic solvent, preferably DCE, in the presence of an organic base, preferably DIPEA.

These and other interconversions are suitably described in experimental part of the present specification.

Compounds of formula (IIa), (IIb), (IIc), (IIIa), (IIIb), (VIII) and (IX) as shown in scheme 1 and compounds (X) and (XI) from scheme 2 are commercially available or can be prepared from commercially available reagents using methods described in the literature.

Compounds of general formula (I) for which $R_3$ contains a Protecting Group (PG), such as Boc or 2-(trimethylsilyl) ethylcarbamate), can be used as intermediates useful for the preparation of other compounds of general formula (I) as defined above.

In a particular embodiments, these intermediate compounds of general formula (I) are selected from:

tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

tert-butyl methyl(2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate;

tert-butyl (2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate;

tert-butyl methyl(2-(3-(9-methyl-2-(methylthio)-5-oxo-5,7,8,9-tetrahydro-6H-pyrimido[4,5-e][1,4]diazepin-6-yl)phenoxy)propyl)carbamate;

tert-butyl methyl(3-methyl-2-(3-(9-methyl-2-(methylthio)-5-oxo-5,7,8,9-tetrahydro-6H-pyrimido[4,5-e][1,4]diazepin-6-yl)phenoxy)butyl)carbamate;

tert-butyl methyl(2-(4-(9-methyl-2-(methylthio)-5-oxo-5,7,8,9-tetrahydro-6H-pyrimido[4,5-e][1,4]diazepin-6-yl)phenoxy)-2-phenylethyl)carbamate;

tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

tert-butyl methyl(2-((3-(9-methyl-2-(methylthio)-5-oxo-5,7,8,9-tetrahydro-6H-pyrimido[4,5-e][1,4]diazepin-6-yl)benzyl)oxy)-1-phenylethyl)carbamate;

2-(trimethylsilyl)ethyl methyl(2-((3-(9-methyl-2-(methylthio)-5-oxo-5,7,8,9-tetrahydro-6H-pyrimido[4,5-e][1,4]diazepin-6-yl)benzyl)oxy)-2-phenylethyl)carbamate;

tert-butyl methyl(3-(3-(9-methyl-2-(methylthio)-5-oxo-5,7,8,9-tetrahydro-6H-pyrimido[4,5-e][1,4]diazepin-6-yl)phenoxy)propyl)carbamate;

tert-butyl benzyl(3-(3-(9-methyl-2-(methylthio)-5-oxo-5,7,8,9-tetrahydro-6H-pyrimido[4,5-e][1,4]diazepin-6-yl)phenoxy)propyl)carbamate;

tert-butyl methyl(2-(3-(9-methyl-2-(methylthio)-5-oxo-5,7,8,9-tetrahydro-6H-pyrimido[4,5-e][1,4]diazepin-6-yl)phenoxy)ethyl)carbamate;

tert-butyl methyl(3-(3-(9-methyl-2-(methylthio)-5-oxo-5,7,8,9-tetrahydro-6H-pyrimido[4,5-e][1,4]diazepin-6-yl)phenyl)propyl)carbamate;

tert-butyl methyl(3-(9-methyl-2-(methylthio)-5-oxo-5,7,8,9-tetrahydro-6H-pyrimido[4,5-e][1,4]diazepin-6-yl)phenethyl)carbamate;

tert-butyl methyl(2-methyl-2-(3-(9-methyl-2-(methylthio)-5-oxo-5,7,8,9-tetrahydro-6H-pyrimido[4,5-e][1,4]diazepin-6-yl)phenyl)propyl)carbamate;

tert-butyl methyl(3-(9-methyl-2-(methylthio)-5-oxo-5,7,8,9-tetrahydro-6H-pyrimido[4,5-e][1,4]diazepin-6-yl)benzyl)carbamate;

tert-butyl 3-(3-(9-methyl-2-(methylthio)-5-oxo-5,7,8,9-tetrahydro-6H-pyrimido[4,5-e][1,4]diazepin-6-yl)phenoxy)pyrrolidine-1-carboxylate;

tert-butyl 4-((3-(9-methyl-2-(methylthio)-5-oxo-5,7,8,9-tetrahydro-6H-pyrimido[4,5-e][1,4]diazepin-6-yl)benzyl)oxy)-4-phenylpiperidine-1-carboxylate;

9-methyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one;

9-ethyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one;

9-methyl-6-(3-(5-methyl-1,2,4-oxadiazol-3-yl)phenyl)-2-(methylthio)-6,7,8,9-tetrahydro-5H-pyrimido[4,5-e][1,4]diazepin-5-one;

6-(3-methoxyphenyl)-9-methyl-2-(methylthio)-6,7,8,9-tetrahydro-5H-pyrimido[4,5-e][1,4]diazepin-5-one;

3-(9-methyl-2-(methylthio)-5-oxo-5,7,8,9-tetrahydro-6H-pyrimido[4,5-e][1,4]diazepin-6-yl)benzonitrile;

6-(3-((tert-butyldimethylsilyl)oxy)phenyl)-9-methyl-2-(methylthio)-6,7,8,9-tetrahydro-5H-pyrimido[4,5-e][1,4]diazepin-5-one;

6-(3-bromophenyl)-9-methyl-2-(methylthio)-6,7,8,9-tetrahydro-5H-pyrimido[4,5-e][1,4]diazepin-5-one;

6-(3-(2-hydroxyethyl)phenyl)-9-methyl-2-(methylthio)-6,7,8,9-tetrahydro-5H-pyrimido[4,5-e][1,4]diazepin-5-one;

6-(4-methoxyphenyl)-9-methyl-2-(methylthio)-6,7,8,9-tetrahydro-5H-pyrimido[4,5-e][1,4]diazepin-5-one;

6-(4-((tert-butyldimethylsilyl)oxy)phenyl)-9-methyl-2-(methylthio)-6,7,8,9-tetrahydro-5H-pyrimido[4,5-e][1,4]diazepin-5-one;

tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

tert-butyl ((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

tert-butyl benzyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

6-(3-(4-(diethoxymethyl)-1H-1,2,3-triazol-1-yl)phenyl)-9-methyl-2-(methylthio)-6,7,8,9-tetrahydro-5H-pyrimido[4,5-e][1,4]diazepin-5-one;

tert-butyl methyl(2-(1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)ethyl)carbamate;

tert-butyl methyl((1-(3-(9-methyl-2-(methylthio)-5-oxo-5,7,8,9-tetrahydro-6H-pyrimido[4,5-e][1,4]diazepin-6-yl)benzyl)-1H-1,2,3-triazol-4-yl)methyl)carbamate;

tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-pyrazol-4-yl)methyl)carbamate;

tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-imidazol-4-yl)methyl)carbamate;

tert-butyl methyl((5-(3-(9-methyl-2-(methylthio)-5-oxo-5,7,8,9-tetrahydro-6H-pyrimido[4,5-e][1,4]diazepin-6-yl)phenyl)-1,3,4-oxadiazol-2-yl)methyl)carbamate;

tert-butyl methyl(3-(2-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

tert-butyl methyl(4-methyl-3-((3-(9-methyl-2-(methylthio)-5-oxo-5,7,8,9-tetrahydro-6H-pyrimido[4,5-e][1,4]diazepin-6-yl)benzyl)oxy)pentyl)carbamate;

tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)butyl)carbamate;

2-(trimethylsilyl)ethyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-2-yl)propyl)carbamate;

tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-3-yl)propyl)carbamate;

tert-butyl (3-(3-(8-(ethylamino)-1-methyl-5-oxo-1,2,3,5-tetrahydro-4H-pyrido[4,3-e][1,4]diazepin-4-yl)phenoxy)-3-phenylpropyl)(methyl)carbamate;

tert-butyl (3-((3-(8-(ethylamino)-1-methyl-5-oxo-1,2,3,5-tetrahydro-4H-pyrido[4,3-e][1,4]diazepin-4-yl)benzyl)oxy)-3-phenylpropyl)(methyl)carbamate;

2-(trimethylsilyl)ethyl (3-(3-(8-(ethylamino)-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

2-(trimethylsilyl)ethyl (3-(3-(8-(dimethylamino)-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

2-(trimethylsilyl)ethyl (3-((3-(8-(ethylamino)-1-methyl-5-oxo-1,2,3,5-tetrahydro-4H-pyrido[4,3-e][1,4]diazepin-4-yl)benzyl)oxy)-3-(thiophen-2-yl)propyl)(methyl)carbamate;

tert-butyl (2-fluoroethyl)(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

tert-butyl methyl(2-(3-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate;

tert-butyl methyl(2-(4-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate;

tert-butyl methyl(4-((9-methyl-2-(methylthio)-5-oxo-5,7,8,9-tetrahydro-6H-pyrimido[4,5-e][1,4]diazepin-6-yl)methyl)benzyl)carbamate;

tert-butyl (R)-(3-((3-(2-(ethylamino)-9-methyl-5,7,8,9-tetrahydro-6H-pyrimido[4,5-e][1,4]diazepin-6-yl)benzyl)oxy)-3-phenylpropyl)(methyl)carbamate;

tert-butyl (3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate;

tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)carbamate;

tert-butyl (2-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate;

tert-butyl (2-(3-(2-(ethylamino)-9-methyl-5-oxo-5,7,8,9-tetrahydro-6H-pyrimido[4,5-e][1,4]diazepin-6-yl)phenoxy)-3-methylbutyl)(methyl)carbamate;

tert-butyl (2-(4-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate;

tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

tert-butyl (2-((3-(2-(ethylamino)-9-methyl-5-oxo-5,7,8,9-tetrahydro-6H-pyrimido[4,5-e][1,4]diazepin-6-yl)benzyl)oxy)-1-phenylethyl)(methyl)carbamate;

2-(trimethylsilyl)ethyl (2-((3-(2-(ethylamino)-9-methyl-5-oxo-5,7,8,9-tetrahydro-6H-pyrimido[4,5-e][1,4]diazepin-6-yl)benzyl)oxy)-2-phenylethyl)(methyl)carbamate;

tert-butyl (3-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate;

tert-butyl benzyl(3-(3-(2-(ethylamino)-9-methyl-5-oxo-5,7,8,9-tetrahydro-6H-pyrimido[4,5-e][1,4]diazepin-6-yl)phenoxy)propyl)carbamate;

tert-butyl (2-(3-(2-(ethylamino)-9-methyl-5-oxo-5,7,8,9-tetrahydro-6H-pyrimido[4,5-e][1,4]diazepin-6-yl)phenoxy)ethyl)(methyl)carbamate;

tert-butyl (3-(3-(2-(ethylamino)-9-methyl-5-oxo-5,7,8,9-tetrahydro-6H-pyrimido[4,5-e][1,4]diazepin-6-yl)phenyl)propyl)(methyl)carbamate;

tert-butyl (3-(2-(ethylamino)-9-methyl-5-oxo-5,7,8,9-tetrahydro-6H-pyrimido[4,5-e][1,4]diazepin-6-yl)phenethyl)(methyl)carbamate;

tert-butyl (2-(3-(2-(ethylamino)-9-methyl-5-oxo-5,7,8,9-tetrahydro-6H-pyrimido[4,5-e][1,4]diazepin-6-yl)phenyl)-2-methylpropyl)(methyl)carbamate;

tert-butyl (3-(2-(ethylamino)-9-methyl-5-oxo-5,7,8,9-tetrahydro-6H-pyrimido[4,5-e][1,4]diazepin-6-yl)benzyl)(methyl)carbamate;

tert-butyl 3-(3-(2-(ethylamino)-9-methyl-5-oxo-5,7,8,9-tetrahydro-6H-pyrimido[4,5-e][1,4]diazepin-6-yl)phenoxy)pyrrolidine-1-carboxylate;

tert-butyl 4-((3-(2-(ethylamino)-9-methyl-5-oxo-5,7,8,9-tetrahydro-6H-pyrimido[4,5-e][1,4]diazepin-6-yl)benzyl)oxy)-4-phenylpiperidine-1-carboxylate;

6-(3-((tert-butyldimethylsilyl)oxy)phenyl)-2-(ethylamino)-9-methyl-6,7,8,9-tetrahydro-5H-pyrimido[4,5-e][1,4]diazepin-5-one;

6-(3-bromophenyl)-2-(ethylamino)-9-methyl-6,7,8,9-tetrahydro-5H-pyrimido[4,5-e][1,4]diazepin-5-one;

2-(ethylamino)-6-(3-(2-hydroxyethyl)phenyl)-9-methyl-6,7,8,9-tetrahydro-5H-pyrimido[4,5-e][1,4]diazepin-5-one;

6-(4-((tert-butyldimethylsilyl)oxy)phenyl)-2-(ethylamino)-9-methyl-6,7,8,9-tetrahydro-5H-pyrimido[4,5-e][1,4]diazepin-5-one;

tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)(methyl)carbamate;

tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate;

tert-butyl benzyl((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate;

6-(3-(4-(diethoxymethyl)-1H-1,2,3-triazol-1-yl)phenyl)-2-(ethylamino)-9-methyl-6,7,8,9-tetrahydro-5H-pyrimido[4,5-e][1,4]diazepin-5-one;

tert-butyl (2-(1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)ethyl)(methyl)carbamate;

tert-butyl ((1-(3-(2-(ethylamino)-9-methyl-5-oxo-5,7,8,9-tetrahydro-6H-pyrimido[4,5-e][1,4]diazepin-6-yl)benzyl)-1H-1,2,3-triazol-4-yl)methyl)(methyl) carbamate;

tert-butyl ((1-(3-(2-(ethylamino)-9-methyl-5-oxo-5,7,8,9-tetrahydro-6H-pyrimido[4,5-e][1,4]diazepin-6-yl)phenyl)-1H-pyrazol-4-yl)methyl)(methyl)carbamate;

tert-butyl ((1-(3-(2-(ethylamino)-9-methyl-5-oxo-5,7,8,9-tetrahydro-6H-pyrimido[4,5-e][1,4]diazepin-6-yl)phenyl)-1H-imidazol-4-yl)methyl)(methyl)carbamate;

tert-butyl ((5-(3-(2-(ethylamino)-9-methyl-5-oxo-5,7,8,9-tetrahydro-6H-pyrimido[4,5-e][1,4]diazepin-6-yl)phenyl)-1,3,4-oxadiazol-2-yl)methyl)(methyl) carbamate;

tert-butyl (3-(2-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

tert-butyl (3-((3-(2-(ethylamino)-9-methyl-5-oxo-5,7,8,9-tetrahydro-6H-pyrimido[4,5-e][1,4]diazepin-6-yl)benzyl)oxy)-4-methylpentyl)(methyl)carbamate;

tert-butyl (3-((3-(2-(ethylamino)-9-methyl-5-oxo-5,7,8,9-tetrahydro-6H-pyrimido[4,5-e][1,4]diazepin-6-yl)benzyl)oxy)butyl)(methyl)carbamate;

tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-2-yl)propyl)(methyl)carbamate;

tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-3-yl)propyl)(methyl)carbamate;

tert-butyl (R)-(3-((3-(2-amino-9-methyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (R)-3-((3-(2-(dimethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (R)-methyl(3-((3-(9-methyl-2-(methylamino)-5-oxo-5,7,8,9-tetrahydro-6H-pyrimido[4,5-e][1,4]diazepin-6-yl)benzyl)oxy)-3-phenylpropyl)carbamate;

2-(trimethylsilyl)ethyl (3-(3-(2-(dimethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(2-fluoroethyl)carbamate;

tert-butyl (2-(3-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate;

tert-butyl (2-(4-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate;

tert-butyl (4-((2-(ethylamino)-9-methyl-5-oxo-5,7,8,9-tetrahydro-6H-pyrimido[4,5-e][1,4]diazepin-6-yl)methyl)benzyl)(methyl)carbamate;

tert-butyl (R)-(3-((3-(2-methoxy-9-methyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (3-((3-(2-methoxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

tert-butyl (R)-(3-((3-(2-hydroxy-9-methyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (3-((3-(2-hydroxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

tert-butyl (R)-(3-((3-(2,9-dimethyl-5-oxo-5,7,8,9-tetrahydro-6H-pyrimido[4,5-e][1,4]diazepin-6-yl)benzyl)oxy)-3-phenylpropyl)(methyl)carbamate;

tert-butyl (3-((3-(2,9-dimethyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

2-(trimethylsilyl)ethyl (3-(3-(2,9-dimethyl-5-oxo-5,7,8,9-tetrahydro-6H-pyrimido[4,5-e][1,4]diazepin-6-yl)phenoxy)-3-(thiophen-2-yl)propyl)(methyl)carbamate;

tert-butyl (R)-methyl(3-((3-(9-methyl-5-oxo-5,7,8,9-tetrahydro-6H-pyrimido[4,5-e][1,4]diazepin-6-yl)benzyl)oxy)-3-phenylpropyl)carbamate;

tert-butyl methyl(3-((3-(9-methyl-5-oxo-5,7,8,9-tetrahydro-6H-pyrimido[4,5-e][1,4]diazepin-6-yl)benzyl)oxy)-3-(thiophen-2-yl)propyl)carbamate;

2-(trimethylsilyl)ethyl methyl(3-(3-(9-methyl-5-oxo-5,7,8,9-tetrahydro-6H-pyrimido[4,5-e][1,4]diazepin-6-yl)phenoxy)-3-(thiophen-2-yl)propyl)carbamate;

2-(ethylamino)-9-methyl-6-(3-(5-((methylamino)methyl)-1,3,4-oxadiazol-2-yl)phenyl)-6,7,8,9-tetrahydro-5H-pyrimido[4,5-e][1,4]diazepin-5-one;

tert-butyl 4-3-(2-(ethylamino)-9-methyl-5-oxo-5,7,8,9-tetrahydro-6H-pyrimido[4,5-e][1,4]diazepin-6-yl)phenyl)-3,6-dihydropyridine-1(2H)-carboxylate;

tert-butyl 4-(3-(2-(ethylamino)-9-methyl-5-oxo-5,7,8,9-tetrahydro-6H-pyrimido[4,5-e][1,4]diazepin-6-yl)phenyl)piperidine-1-carboxylate;

3-(2-(ethylamino)-9-methyl-5-oxo-5,7,8,9-tetrahydro-6H-pyrimido[4,5-e][1,4]diazepin-6-yl)phenethyl 4-methylbenzenesulfonate; and 1-(3-(2-(ethylamino)-9-methyl-5-oxo-5,7,8,9-tetrahydro-6H-pyrimido[4,5-e][1,4]diazepin-6-yl)phenyl)-1H-1,2,3-triazole-4-carbaldehyde.

Turning to another aspect, the invention also relates to the therapeutic use of the compounds of general formula (I). As mentioned above, compounds of general formula (I) show a strong affinity to subunit α2δ and more preferably to α2δ-1 subunit of voltage-gated calcium channels. In a more preferred embodiment of the invention compounds of general formula (I) show a strong affinity both to subunit α2δ and more preferably to α2δ-1 subunit of voltage-gated calcium channels as well as to noradrenaline transporter (NET) and can behave as agonists, antagonists, inverse agonists, partial antagonists or partial agonists thereof. Therefore, compounds of general formula (I) are useful as medicaments.

They are suitable for the treatment and/or prophylaxis of diseases and/or disorders mediated by the subunit α2δ, especially α2δ-1 subunit of voltage-gated calcium channels and/or noradrenaline transporter (NET). In this sense, compounds of formula (I) are suitable for the treatment and/or prophylaxis of pain, especially neuropathic pain, inflammatory pain, and chronic pain or other pain conditions involving allodynia and/or hyperalgesia, depression anxiety and attention-deficit-/hyperactivity disorder (ADHD).

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and/or prophylaxis of allodynia and more specifically mechanical or thermal allodynia.

In another preferred embodiment compounds of the invention are used for the treatment and/or prophylaxis of hyperalgesia.

In yet another preferred embodiment compounds of the invention are used for the treatment and/or prophylaxis of neuropathic pain and more specifically for the treatment and/or prophylaxis of hyperpathia.

A related aspect of the invention refers to the use of compounds of formula (I) for the manufacture of a medicament for the treatment and/or prophylaxis of disorders and diseases mediated by the subunit α2δ, especially α2δ-1 subunit of voltage-gated calcium channels and/or noradrenaline transporter (NET), as explained before.

Another related aspect of the invention refers to a method for the treatment and/or prophylaxis of disorders and diseases mediated by the subunit α2δ, especially α2δ-1 subunit of voltage-gated calcium channels and/or noradrenaline transporter (NET), as explained before comprising the administration of a therapeutically effective amount of a compound of general formula (I) to a subject in need thereof.

Another aspect of the invention is a pharmaceutical composition, which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the subunit α2δ, especially α2δ-1 subunit of voltage-gated calcium channels and/or noradrenaline transporter (NET) and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathecal, rectal, transdermal, transmucosal or nasal administration.

The composition of the invention can be formulated for oral administration in any form preferably selected from the group consisting of tablets, dragées, capsules, pills, chewing gums, powders, drops, gels, juices, syrups, solutions and suspensions. The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

In a preferred embodiment, the pharmaceutical compositions are in oral form, either solid or liquid. Suitable dose forms for oral administration may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

In the next preparation examples the preparation of both intermediates compounds as well as compounds according to the invention are disclosed.

The following abbreviations are used in the examples:
ACN: Acetonitrile
Anh: Anhydrous
Aq: Aqueous
BINAP: 2,2'-bis(diphenylphosphino)-1,1'-binaphthalene
Conc: Concentrated
CH: Cyclohexane
DCM: Dichloromethane
DCE: 1,2-Dichloroethane
DIAD: Diisopropyl azodicarboxylate
DIBAL: Diisobutylaluminium hydride
DIPEA: N,N-Diisopropylethylamine
DMA: N,N-Dimethylacetamide
DMSO: Dimethylsulfoxide
EtOAc: Ethyl acetate
EtOH: Ethanol
Ex: Example
h: Hour/s
HPLC: High-performance liquid chromatography
HRMS: High-resolution mass spectrometry
INT: Intermediate
MeOH: Methanol
MS: Mass spectrometry
Min: Minutes
Quant: Quantitative
Ret: Retention
rt: Room temperature
Sat: Saturated
TBAF: Tetrabutylammonium fluoride
TEA: Et$_3$N, Triethylamine
TFA: Trifluoroacetic acid
THF: Tetrahydrofuran
XPhos: 2-Dicyclohexylphosphino-2',4',6'-triisopropylbiphenyl
Wt: Weight The following methods were used to generate the HPLC or HPLC-MS data:

Method A: Column Eclipse XDB-C18 4.6×150 mm, 5 μm; flow rate 1 mL/min; A: H$_2$O (0.05% TFA); B: ACN; Gradient: 5% to 95% B in 7 min, isocratic 95% B 5 min.

Method B: Column Zorbax SB-C18 2.1×50 mm, 1.8 μm; flow rate 0.5 mL/min; A: H$_2$O (0.1% formic acid); B: ACN (0.1% formic acid); Gradient: 5% to 95% B in 4 min, isocratic 95% B 4 min.

Preparation Examples

INT 1. tert-Butyl (3-(3-iodophenoxy)propyl)(methyl)carbamate

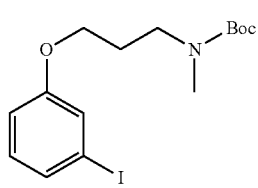 [SMILES: CN(CCCOc1cccc(I)c1)C(=O)OC(C)(C)C]

To a solution of tert-butyl (3-hydroxypropyl)(methyl) carbamate (210 mg, 1.11 mmol) in THF (7 mL), 3-iodophenol (269 mg, 1.22 mmol) and PPh$_3$ (320 mg, 1.22 mmol) were added. The mixture was cooled to 0° C. and then DIAD (247 mg, 1.22 mmol) was added dropwise. The reaction mixture was warmed slowly at rt and stirred for 16 h. The solvent was removed under vacuum and the residue was purified by flash chromatography, silica gel, gradient CH to 70% EtOAc to afford the title product (390 mg, 90% yield). ESI$^+$-MS m/z, 414.0 (M+Na).

INT 2. tert-Butyl (R)-(3-((3-bromobenzyl)oxy)-3-phenylpropyl)(methyl) carbamate

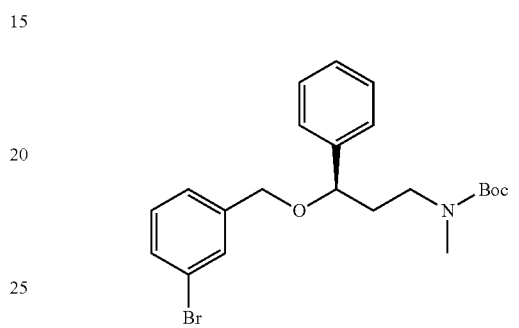

To a solution of tert-butyl (R)-(3-hydroxy-3-phenylpropyl)(methyl)carbamate (2.25 g, 8.48 mmol) in DMF (30 mL) cooled at 0° C., NaH (509 mg, 60% suspension in mineral oil, 12.72 mmol) was added and the solution was stirred at rt for 30 min. Then, the reaction mixture was cooled again at 0° C. and a solution of 1-bromo-3-(bromomethyl)benzene (3.18 g, 12.72 mmol) in DMF (5 mL) was added. The reaction mixture was stirred at rt for 3 h, water was added carefully and extracted with EtOAc; the organic phase was dried with Na$_2$SO$_4$ and the solvent was removed under vacuum. Purification by flash chromatography, silica gel, gradient from CH to 100% acetone afforded the title product (3.3 g, 90% yield). HPLC (Method B): Ret, 6.78; ESI$^+$-MS m/z, 456.1 (M+Na).

INT 3. tert-Butyl (3-(3-iodophenoxy)-3-(thiophen-2-yl)propyl)(methyl) carbamate

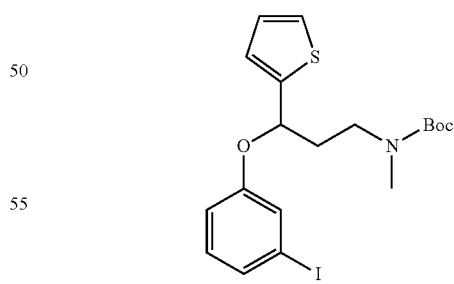

a) 2-(3-Chloro-1-(3-iodophenoxy)propyl)thiophene

3-Chloro-1-(thiophen-2-yl) propan-1-ol was treated with the conditions used in INT 1 to afford the title compound (40% yield). $^1$H-NMR, (CDCl$_3$, 300 MHz), δ (ppm): 2.31 (m, 1H), 2.57 (m, 1H), 3.60 (m, 1H), 3.79 (m, 1H), 5.66 (m, 1H), 6.94 (m, 3H), 7.06 (m, 1H), 7.28 (m, 2H), 7.32 (m, 1H).

b) 3-(3-Iodophenoxy)-N-methyl-3-(thiophen-2-yl) propan-1-amine

To a solution of the compound obtained in step a (416 mg, 1.09 mmol) in EtOH (1.2 mL), methylamine (40% water solution, 2.9 mL, 33 mmol) was added, and the mixture was heated in a sealed tube at 130° C. for 1.5 h. Water was added, extracted with DCM and the solvent was removed under vacuum to afford the desired product that was used in the next step without further purification. HPLC (Method B): Ret, 4.01; ESI$^+$-MS m/z, 374.0 (M+H).

c) Title Compound

The compound obtained in step b, was dissolved in DCM (8 mL) cooled at 0° C., di-tert-butyldicarbonate (262 mg, 1.2 mmol) was added and the reaction mixture was stirred at rt for 15 h. Water was added, the mixture was extracted with DCM and washed with NaHCO$_3$ sat solution and brine. The solvent was removed under vacuum. Purification by flash chromatography, silica gel, gradient CH to 50% EtOAc, afforded the title compound (370 mg, 71% global yield 2 steps). ESI$^+$-MS m/z, 496.1 (M+Na).

INT 4. tert-Butyl (3-(3-iodophenoxy)-3-phenylpropyl)(methyl)carbamate

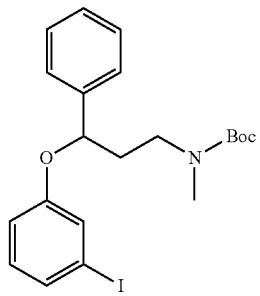 [SMILES: CN(CCC(Oc1cccc(I)c1)c1ccccc1)C(=O)OC(C)(C)C]

3-(3-Iodophenoxy)-N-methyl-3-phenylpropan-1-amine was treated with the conditions used in INT 3 step c to afford the title compound (88% yield). HPLC (Method B): Ret, 6.47 min; ESI$^+$-MS m/z, 490.1 (M+Na).

INT 5. tert-Butyl (2-(3-(chloromethyl)phenoxy)-2-phenylethyl)(methyl) carbamate

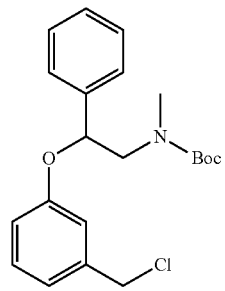 [SMILES: CN(CC(Oc1cccc(CCl)c1)c1ccccc1)C(=O)OC(C)(C)C]

a) tert-Butyl (2-(3-(((tert-butyldimethylsilyl)oxy) methyl)phenoxy)-2-phenylethyl)(methyl)carbamate tert-Butyl (2-hydroxy-2-phenylethyl)(methyl)carbamate was treated with 3-(((tert-butyldimethylsilyl)oxy)methyl) phenol with the conditions used in INT 1 to afford the title compound (55% yield). ESI$^+$-MS m/z, 494.3 (M+Na).

b) tert-Butyl (2-(3-(hydroxymethyl)phenoxy)-2-phenylethyl)(methyl)carbamate

To a solution of the compound obtained in step a (470 mg, 0.99 mmol) in THF (6 mL), tetrabutylammonium fluoride (1M solution in THF, 1.49 mL, 1.49 mmol) was added and the mixture was stirred at rt for 3 h. NH$_4$Cl sat solution was added, extracted with EtOAc and the organic layer was concentrated under vacuum. Purification by flash chromatography, silica gel, gradient CH to 100% EtOAc, afforded the title compound (300 mg, 84% yield). $^1$H-NMR, (CDCl$_3$, 400 MHz), δ (ppm): 1.47 (s, 9H), 2.96 (m, 3H), 3.47 (m, 1H), 3.72 (m, 1H), 4.61 (d, J=5.6 Hz, 2H), 5.39 (m, 1H), 6.75 (m, 1H), 6.90 (m, 2H), 7.18 (t, J=7.8 Hz, 1H), 7.36 (m, 5H).

c) Title Compound

To a solution of the compound obtained in step b (300 mg, 0.84 mmol) and TEA (0.23 mL, 1.68 mmol) in DCM (6 mL) at 0° C., methanesulfonyl chloride (0.072 mL, 0.92 mmol) was added dropwise, the reaction was warmed at rt and stirred for 20 h. Brine was added, extracted with DCM and the organic layer dried with Na$_2$SO$_4$ and concentrated under vacuum. Purification by flash chromatography, silica gel, gradient CH to 100% EtOAc afforded the title compound (255 mg, 81% yield). $^1$H-NMR, (CDCl$_3$, 300 MHz), δ (ppm): 1.46 (s, 9H), 2.96 (m, 3H), 3.47 (m, 1H), 3.72 (m, 1H), 4.49 (s, 2H), 5.39 (m, 1H), 6.77 (m, 1H), 6.91 (m, 2H), 7.17 (t, J=8 Hz, 1H), 7.36 (m, 5H).

INT 6. 2-(1-(3-Iodophenyl)-1H-1,2,3-triazol-4-yl) ethyl 4-methylbenzene Sulfonate

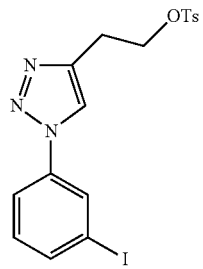 [SMILES: Cc1ccc(S(=O)(=O)OCCc2cn(-c3cccc(I)c3)nn2)cc1]

To a solution of but-3-yn-1-yl 4-methylbenzenesulfonate (1.3 g, 5.80 mmol) in a mixture of t-BuOH:H$_2$O (1:1, 50 mL) at rt, 1-azido-3-iodobenzene (1.7 g, 6.96 mmol), CuSO$_4$.5H$_2$O (148 mg, 0.58 mmol) and sodium ascorbate (230 mg, 1.16 mmol) were added and the mixture was stirred at rt for 16 h. A solution of NH$_4$Cl/NH$_3$ (prepared with 10 mL of 30% NH$_3$ aq solution in 1 L NH$_4$Cl aq sat solution) was added and the mixture was extracted with EtOAc. The organic phase was dried with Na$_2$SO$_4$ and the solvent was removed under vacuum. Purification by flash chromatography, silica gel, gradient CH to 100% EtOAc, afforded the

INT 7.
1-(3-Bromophenyl)-1H-imidazole-4-carbaldehyde

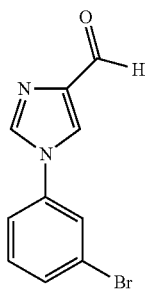 [SMILES: O=Cc1cn(-c2cccc(Br)c2)cn1]

To a mixture of (S)-Proline (24 mg, 0.20 mmol) and CuI (40 mg, 0.21 mmol) under Ar atmosphere in a sealed tube, anh DMSO (4 mL) was added and the mixture was stirred for 5 min at rt. Imidazole-4-carbaldehyde (100 mg, 1.04 mmol), 1-bromo-3-iodobenzene (324 mg, 1.14 mmol) and anh $K_2CO_3$ (431 mg, 3.12 mmol) were added and the mixture was heated at 90° C. for 16 h. The reaction mixture was cooled at rt, DCM was added and it was washed with $NH_4Cl$ sat solution and brine. The organic phase was dried with $Na_2SO_4$, filtered and concentrated under vacuum to give a residue that was purified by flash chromatography, silica gel, gradient DCM to 20% MeOH, to afford the title compound (150 mg, 57% yield). ESI$^+$-MS m/z, 273.0 (M+Na).

INT 8. tert-Butyl ((1-(3-bromophenyl)-1H-imidazol-4-yl)methyl)(methyl)carbamate

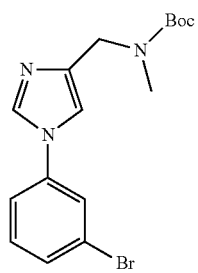 [SMILES: CN(Cc1cn(-c2cccc(Br)c2)cn1)C(=O)OC(C)(C)C]

a) 1-(1-(3-Bromophenyl)-1H-imidazol-4-yl)-N-methylmethanamine

To a solution of 1-(3-bromophenyl)-1H-imidazole-4-carbaldehyde (INT 7, 50 mg, 0.2 mmol) in EtOH (1 mL), a solution of methylamine (33% in EtOH, 37 μL, 0.3 mmol) was added and the mixture was heated at 70° C. in a sealed tube for 16 h. The reaction mixture was cooled to rt and the solvent was removed under vacuum. The crude product was dissolved in MeOH (2 mL), cooled at 0° C. and $NaBH_4$ (11 mg, 0.3 mmol) was added. The mixture was stirred at rt for 1 h. The solvent was removed under vacuum, the residue was dissolved in DCM, washed with $NaHCO_3$ sat solution and the aq phase extracted with DCM. The combined organic phases were concentrated under vacuum to afford the title compound that was used in the next step without further purification.

b) Title Compound

The compound obtained in step a was treated with the conditions used in INT 3 step c to afford the title compound (55% global yield, 2 steps). ESI$^+$-MS m/z, 366.1 (M+H).

INT 9. 2-(Chloromethyl)-5-(3-iodophenyl)-1,3,4-oxadiazole

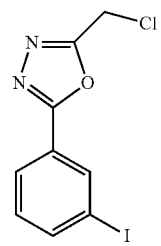 [SMILES: ClCc1nnc(-c2cccc(I)c2)o1]

a) Ethyl 5-(3-iodophenyl)-1,3,4-oxadiazole-2-carboxylate

To a solution of 5-(3-iodophenyl)-1,3,4-oxadiazole-2-carbohydrazide (1.25 g, 4.77 mmol) and TEA (1.45 g, 14.31 mmol) in DCM (20 mL) cooled at 0° C., ethyl 2-chloro-2-oxoacetate (651 mg, 4.77 mmol) was added dropwise. The reaction mixture was slowly warmed to rt and stirred for 6 h; then, 4-methylbenzenesulfonyl chloride (910 mg, 4.77 mmol) was added and the mixture was stirred for 16 h. The reaction mixture was diluted with EtOAc, washed with water, $NaHCO_3$ sat solution and brine. The organic layer was concentrated under vacuum and the residue was purified by flash chromatography, silica gel, gradient CH to 100% EtOAc to afford the desired product (1.22 g, 74% yield). ESI$^+$-MS m/z, 367.0 (M+Na).

b) (5-(3-Iodophenyl)-1,3,4-oxadiazol-2-yl)methanol

To a solution of the compound obtained in step a (800 mg, 2.32 mmol) in a mixture of MeOH/THF (1:1) (16 mL) cooled at 0° C., $NaBH_4$ (220 mg, 5.81 mmol) was added and the mixture was heated at 50° C. for 5 h. The reaction mixture was cooled to rt, some drops of water were added and the solvent was removed under vacuum. The residue was dissolved in EtOAc and washed with water and brine. The organic layer was dried with $Na_2SO_4$, filtered and the solvent was removed under vacuum to afford the desired product that was used in the next step without further purification (650 mg, 93% yield). ESI$^+$-MS m/z, 303.0 (M+H).

c) Title Compound

To a solution of the compound obtained in step b (600 mg, 1.98 mmol) and TEA (0.55 mL, 3.97 mmol) in DCM (12 mL) at 0° C., methylsulfonyl chloride (273 mg, 2.38 mmol) was added dropwise and the reaction mixture was allowed to warm to rt and stirred for 2 h. Brine was added and the mixture was extracted with DCM, dried with $Na_2SO_4$ and the solvent was removed under vacuum to afford the desired product that was used in the next step without further purification (630 mg, quant yield). HPLC-MS (Method B): Ret, 5.14 min; ESI$^+$-MS m/z, 321.0 (M+H).

INT 10. 9-Methyl-2-(methylthio)-6,7,8,9-tetrahydro-5H-pyrimido[4,5-e][1,4]diazepin-5-one A solution of potassium tert-butoxyde (1.0 g, 8.42 mmol) in THF (with 0.2% content in water, 25 mL) was stirred under air at rt for 10 min. Then, a solution of ethyl 4-chloro-2-(methylthio)pyrimidine-5-carboxylate (1.0 g, 4.21 mmol) and N1-methylethane-1,2-diamine (329 mg, 4.21 mmol) in THF (with 0.2% water content, 18 mL) was added dropwise and the mixture was stirred at rt for 24 h. Additional amounts of potassium tert-butoxyde were added after 4 h (4.21 mmol) and 16 h (6.31 mmol) to complete the reaction. The reaction mixture was concentrated under vacuum, DCM was added and the solution was washed successively with water, NH$_4$Cl sat solution and brine. The organic phase was concentrated under vacuum to afford the titled product as white solid (388 mg, 41% yield). ESI$^+$-HRMS m/z, 225.0813 (M+H).

INT 11. 8-(Ethylamino)-1-methyl-1,2,3,4-tetrahydro-5H-pyrido[4,3-e][1,4]diazepin-5-one

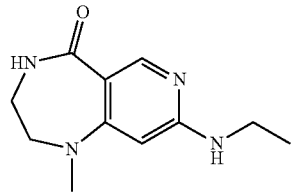 [SMILES: CCNc1cc2c(cn1)C(=O)NCCN2C]

a) tert-Butyl (2-(4,6-dichloronicotinamido)ethyl)(methyl)carbamate

To a solution of 4,6-dichloronicotinoyl chloride (1 g, 4.88 mmol) in THF (8 mL) at 0° C., a solution of tert-butyl (2-aminoethyl)(methyl)carbamate (850 mg, 4.88 mmol) and TEA (2.52 mL, 18.10 mmol) in THF (12 mL) was added. The mixture was stirred at 0° C. for 10 min and then at rt for 2.5 h. Water was added and extracted with DCM, dried with Na$_2$SO$_4$, the solvent was removed under vacuum and the residue was purified by flash chromatography, silica gel, gradient CH to 100% EtOAc to afford the title compound (1.5 g, 88% yield). HPLC-MS (Method B): Ret, 4.63 min; ESI$^+$-MS m/z, 370.0 (M+Na).

b) 4,6-Dichloro-N-(2-(methylamino)ethyl)nicotinamide

To a solution of the compound obtained in step a (280 mg, 0.80 mmol) in dioxane (1.46 mL), HCl (4M solution in dioxane, 3.02 mL, 12.06 mmol) was added and the mixture was stirred at rt for 2.5 h. The reaction mixture was concentrated to dryness under vacuum to afford the title compound as dihydrochloride (240 mg, 93% yield). HPLC-MS (Method A): Ret, 3.95 min; ESI$^+$-MS m/z, 248.1 (M+H).

c) 8-Chloro-1-methyl-1,2,3,4-tetrahydro-5H-pyrido[4,3-e][1,4]diazepin-5-one

A mixture of the compound obtained in step b (300 mg, 1.20 mmol) and Cs$_2$CO$_3$ (1.57 g, 4.84 mmol) in DMF (34.5 mL) was heated at 100° C. for 16 h. The reaction mixture was cooled at rt, water was added and the mixture was concentrated. Water was added, extracted with EtOAc, dried with Na$_2$SO$_4$, the solvent was removed under vacuum and the residue was purified by flash chromatography, silica gel, gradient DCM to 40% MeOH, to afford the title compound (95 mg, 37% yield). HPLC-MS (Method B): Ret, 2.31 min; ESI$^+$-MS m/z, 212.1 (M+H).

d) Title Compound

A mixture of the compound obtained in step c (88 mg, 0.41 mmol) and ethylamine (70% solution in water, 2.68 mL, 33.3 mmol) was irradiated with microwaves at 135° C. for 2 h. The solvent was removed under vacuum and the residue was purified by flash chromatography, silica gel, gradient DCM to 40% MeOH, to afford the title compound (59 mg, 64% yield). ESI$^+$-MS m/z, 221.1 (M+H).

INT 12. N-ethyl-9-methyl-6,7,8,9-tetrahydro-5H-pyrimido[4,5-e][1,4]diazepin-2-amine

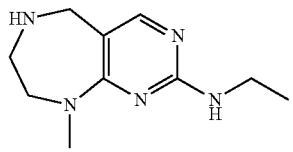

a) 4-((2-Aminoethyl)(methyl)amino)-2-(methylthio)pyrimidine-5-carbaldehyde

To a solution of 4-chloro-2-(methylthio)pyrimidine-5-carbaldehyde (712 mg, 3.77 mmol) in ACN (40 mL) at 0° C., TEA (2.47 mL, 17.74 mmol) and N1-methylethane-1,2-diamine (0.42 mL, 4.91 mmol) were added and the mixture was stirred at rt for 20 h. NaHCO$_3$ sat. solution was added and extracted with EtOAc. The organic phase was concentrated under vacuum and the residue was purified by flash chromatography, silica gel, gradient DCM to 30% MeOH, to afford the title compound (627 mg, 73% yield). $^1$H-NMR, (CDCl$_3$, 300 MHz), δ (ppm): 2.56 (s, 3H), 3.34 (s, 3H), 3.51 (m, 2H), 4.04 (m, 2H), 8.06 (m, 1H), 8.16 (s, 1H).

b) 9-Methyl-2-(methylthio)-6,7,8,9-tetrahydro-5H-pyrimido[4,5-e][1,4]diazepine

To a solution of the compound obtained in step a (210 mg, 0.92 mmol) in DCE (38 mL), NaBH(OAc)$_3$ (393 mg, 1.85 mmol) was added and the reaction mixture was stirred at rt for 1.5 h. NaHCO$_3$ sat. solution was added and extracted with DCM. The organic phase was concentrated under vacuum and the residue was purified by flash chromatography, silica gel, gradient DCM to 20% MeOH, to afford the title compound (152 mg, 78% yield). ESI$^+$-HRMS m/z, 211.1006 (M+H).

c) tert-Butyl 9-methyl-2-(methylthio)-5,7,8,9-tetrahydro-6H-pyrimido[4,5-e][1,4]diazepine-6-carboxylate The compound obtained in step b was treated with the conditions used in INT 3 step c to afford the title compound (90% yield). ESI$^+$-MS m/z, 311.1 (M+H).

d) tert-Butyl 2-(ethylamino)-9-methyl-5,7,8,9-tetrahydro-6H-pyrimido[4,5-e][1,4]diazepine-6-carboxylate To a solution of the compound obtained in step c (227 mg, 0.73 mmol) in DCM (4 mL), m-chloroperbenzoic acid (252 mg, 1.46 mmol) was added and the mixture was stirred at rt for 3.5 h. NaHCO₃ sat solution was added and the mixture was extracted with DCM. The organic layer was dried with MgSO₄ and the solvent removed under vacuum. The crude was treated with ethylamine (70% solution in water, 2.1 mL, 26.10 mmol) and the mixture was stirred at rt for 72 h. The reaction mixture was concentrated under vacuum and purified by flash chromatography, silica gel, gradient DCM to 20% MeOH, to afford the desired product (94 mg, 47% yield). ¹H-NMR, (CDCl₃, 300 MHz), δ (ppm): 1.20 (t, J=7.2 Hz, 3H), 1.43 (s, 9H), 3.10 (s, 3H), 3.40 (m, 2H), 3.57 (m, 2H), 3.73 (m, 2H), 4.29 and 4.41 (s, 2H), 5.06 (bs, 1H), 7.59 and 7.69 (s, 1H).

e) Title Compound

To a solution of the compound obtained in step d (94 mg, 0.30 mmol) in dioxane (0.3 mL) HCl (4M solution in dioxane, 1.0 mL, 4.28 mmol) was added and the mixture was stirred at rt for 16 h. The reaction mixture was concentrated under vacuum, 10% Na₂CO₃ aq solution was added, extracted with DCM and the organic phase was concentrated to dryness to afford the title compound (61 mg, 96% yield). ESI⁺-HRMS m/z, 208.1560 (M+H).

INT 13. 2-(Trimethylsilyl)ethyl (S)-(3-(4-(chloromethyl)phenoxy)-3-(thiophen-2-yl)propyl)(methyl) carbamate

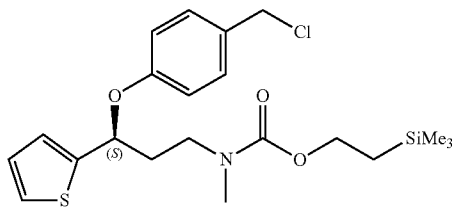

a) (S)-4-(3-(Methylamino)-1-(thiophen-2-yl) propoxy)benzonitrile

To a solution of (S)-3-(methylamino)-1-(thiophen-2-yl) propan-1-ol (1.6 g, 9.34 mmol) in DMA (20 mL), NaH (561 mg, 60% suspension in mineral oil, 14.01 mmol) was added and the solution was stirred at rt for 30 min. A solution of 4-fluorobenzonitrile (2.26 g, 18.69 mmol) in DMA (10 mL) was added and the mixture was heated at 90° C. for 2 h. Water was added and extracted with EtOAc. The organic layer was dried with Na₂SO₄ and the solvent was removed under vacuum to afford the title compound, that was used in the next step without further purification. HPLC-MS (Method B): Ret, 3.64 min; ESI⁺-MS m/z, 273.1 (M+H).

b) 2-(Trimethylsilyl)ethyl (S)-(3-(4-cyanophenoxy)-3-(thiophen-2-yl)propyl)(methyl)carbamate To a solution of the compound obtained in step a (3.0 g, 11.01 mmol) in DCM (25 mL), DIPEA (1.92 mL, 11.01 mmol) and a solution of 4-nitrophenyl (2-(trimethylsilyl) ethyl)carbonate (3.12 g, 11.01 mmol) in DCM (10 mL) were added and the reaction mixture was stirred at rt for 16 h. The reaction mixture was washed with NaHCO₃ sat solution and then with 2 M NaOH aq solution (three times). The organic layer was dried with Na₂SO₄, the solvent was removed under vacuum and the residue was purified by flash chromatography, silica gel, gradient CH to 100% EtOAc, to afford the title compound (3.1 g, 66% global yield, 2 steps). HPLC-MS (Method B): Ret, 6.24 min; ESI⁺-MS m/z, 439.1 (M+Na).

c) 2-(Trimethylsilyl)ethyl (S)-(3-(4-(hydroxymethyl) phenoxy)-3-(thiophen-2-yl)-propyl)(methyl)carbamate To a solution of the compound obtained in step b (3.0 g, 7.20 mmol) in toluene (25 mL) at 0° C. under Ar atmosphere, DIBAL (1 M solution in toluene, 10.08 mL, 10.08 mmol) was dropwise added and the mixture was stirred at 0° C. for additional 2 h. HCl 10% aq solution (60 mL) was added at 0° C. and the mixture was stirred at rt for 1 h. The aq layer was extracted with DCM, the organic layer was washed with water and brine and the solvent was removed under vacuum. The residue was dissolved in MeOH (25 mL), NaBH₄ (409 mg, 10.80 mmol) was added at 0° C. in portions and the mixture was stirred at rt for 2 h. The reaction mixture was concentrated under vacuum, the residue was diluted with EtOAc and washed with water and brine. The organic layer was dried with Na₂SO₄, concentrated under vacuum and the residue was purified by flash chromatography, silica gel, gradient CH to 100% EtOAc, to afford the title compound (750 mg, 25% yield). HPLC-MS (Method B): Ret, 5.77 min; ESI⁺-MS m/z, 444.1 (M+Na).

d) Title Compound

To a solution of the compound obtained in step c (500 mg, 1.18 mmol) in DCM (12 mL), TEA (240 mg, 2.37 mmol) was added. The mixture was cooled at 0° C. and methanesulfonyl chloride (163 mg, 1.42 mmol) was added dropwise. The mixture was warmed at rt and stirred for 3 h. Water was added and extracted with DCM. The organic layer was washed with brine, dried with Na₂SO₄ and the solvent was removed under vacuum to afford the title compound, that was used in the next step without further purification (515 mg, quant). HPLC-MS (Method B): Ret, 6.63 min; ESI⁺-MS m/z, 462.1 (M+Na).

INT 14: 2-Methoxy-9-methyl-6,7,8,9-tetrahydro-5H-pyrimido[4,5-e][1,4]diazepin-5-one

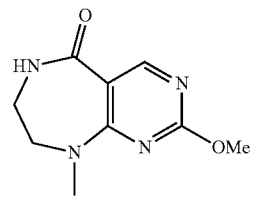

To a solution of 9-methyl-2-(methylthio)-6,7,8,9-tetrahydro-5H-pyrimido[4,5-e][1,4]diazepin-5-one (INT 10, 550 mg, 2.45 mmol) in MeOH (14 mL), NaOMe (795 mg, 14.71 mmol) was added and the mixture was irradiated with microwaves at 110° C. for 3 h. The solvent was removed under vacuum and the residue was purified by flash chromatography, silica gel, gradient DCM to 30% MeOH, to afford the title compound (450 mg, 88% yield). HPLC-MS (Method A): Ret, 3.49 min; ESI⁺-MS m/z, 209.1 (M+H).

Example 1: tert-Butyl methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate

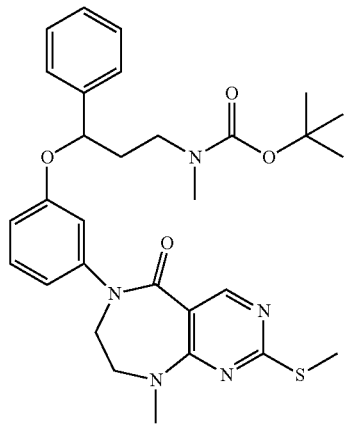 [SMILES: CSc1ncc2c(n1)N(C)CCN(c1cccc(OC(CCN(C)C(=O)OC(C)(C)C)c3ccccc3)c1)C2=O]

To a solution of 9-methyl-2-(methylthio)-6,7,8,9-tetrahydro-5H-pyrimido[4,5-e][1,4]diazepin-5-one (INT 10, 120 mg, 0.53 mmol) and tert-butyl (3-(3-iodophenoxy)-3-phenylpropyl)(methyl)carbamate (INT 4, 375 mg, 0.80 mmol) in dioxane (8 mL), CuI (31 mg, 0.16 mmol), $K_3PO_4$ (227 mg, 1.07 mmol) and N1,N2-dimethylethane-1,2-diamine (14 mg, 0.16 mmol) were added and the mixture was heated at 100° C. under Ar atmosphere for 16 h. The reaction mixture was cooled to rt and the solvent was removed under vacuum to give a crude product that was purified by flash chromatography, silica gel, gradient CH to 100% EtOAc, to afford the title compound (270 mg, 90% yield). $ESI^+$-MS m/z, 586.2 (M+Na).

This method was used for the preparation of Ex 2-61 using suitable starting materials:

| EX | Structure | Chemical name | 1H-NMR (ppm) | Method/Ret (min) | MS |
|---|---|---|---|---|---|
| 2 | 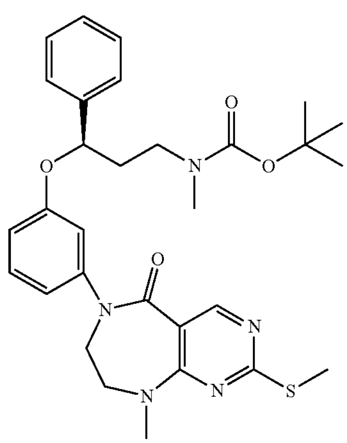 [SMILES: CSc1ncc2c(n1)N(C)CCN(c1cccc(O[C@H](CCN(C)C(=O)OC(C)(C)C)c3ccccc3)c1)C2=O] | tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate | (500 MHz, $CDCl_3$):1.41(s, 9H), 2.12(m, 2H), 2.56(s, 3H), 2.85(s, 3H), 3.28(s, 3H), 3.40(m, 2H), 3.69(m, 2H), 3.88(m, 2H), 5.12(m, 1H), 6.71(m, 1H), 6.82(m, 2H), 7.18(m, 1H), 7.28(m, 1H), 7.35(m, 4H), 8.77(s, 1H). | | 564.3 (M + H) |
| 3 | 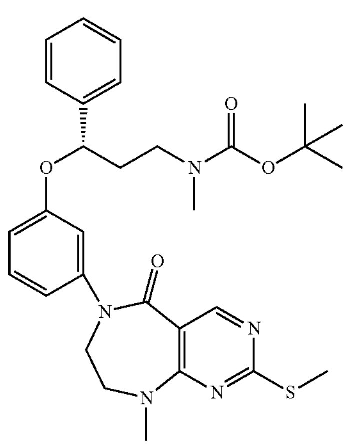 [SMILES: CSc1ncc2c(n1)N(C)CCN(c1cccc(O[C@@H](CCN(C)C(=O)OC(C)(C)C)c3ccccc3)c1)C2=O] | tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate | (400 MHz, $CDCl_3$):1.42(s, 9H), 2.14(m, 2H), 2.57(s, 3H), 2.86(s, 3H), 3.28(s, 3H), 3.41(m, 2H), 3.71(m, 2H), 3.90(m, 2H), 5.13(m, 1H), 6.72(m, 1H), 6.82(m, 2H), 7.20(m, 1H), 7.28(m, 1H), 7.35(m, 4H), 8.78(s, 1H). | | 564.3 (M + H) |

| EX | Structure | Chemical name | 1H-NMR (ppm) | Method/Ret (min) | MS |
|---|---|---|---|---|---|
| 4 | 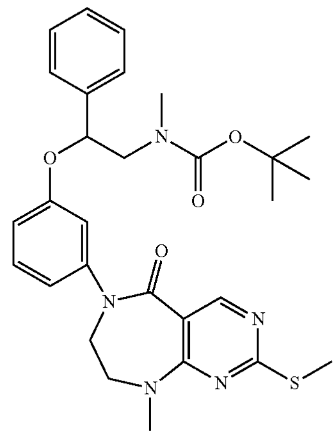 [SMILES: CSc1ncc2c(n1)N(C)CCN(c1cccc(OC(CN(C)C(=O)OC(C)(C)C)c3ccccc3)c1)C2=O] | tert-butyl methyl(2-(3-(9-methyl-2-(methylthio)-5-oxo-5,7,8,9-tetrahydro-6H-pyrimido[4,5-e][1,4]diazepin-6-yl)phenoxy)-2-phenylethyl) carbamate | (300 MHz, CDCl$_3$):1.45(bs, 9H), 2.55(s, 3H), 2.94(m, 3H), 3.28(s, 3H), 3.49(m, 1H), 3.68(m, 1H), 3.72(m, 2H), 3.90(m, 2H), 5.37(m, 1H), 6.72(m, 1H), 6.82(m, 2H), 7.20(m, 1H), 7.35(m, 5H), 8.77(s, 1H). | | 572.3 (M + Na) |
| 5 | 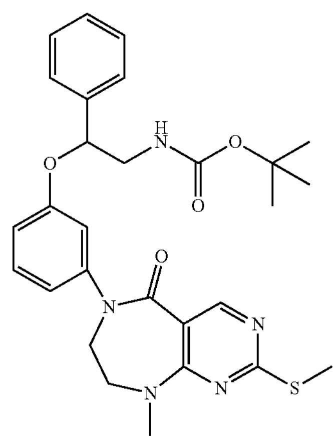 [SMILES: CSc1ncc2c(n1)N(C)CCN(c1cccc(OC(CNC(=O)OC(C)(C)C)c3ccccc3)c1)C2=O] | tert-butyl (2-(3-(9-methyl-2-(methylthio)-5-oxo-5,7,8,9-tetrahydro-6H-pyrimido[4,5-e][1,4]diazepin-6-yl)phenoxy)-2-phenylethyl) carbamate | (400 MHz, CDCl$_3$):1.45(s, 9H), 2.55(s, 3H), 3.27(s, 3H), 3.41 (m, 1H), 3.66(m, 1 H), 3.71(m, 2H), 3.89(m, 2 H), 5.06(bs, 1H), 5.25(m, 1 H), 6.73(m, 1H), 6.84(m, 2 H), 7.20(m, 1H), 7.35(m, 5 H), 8.77(s, 1H). | | 534.3 (M − H) |
| 6 | 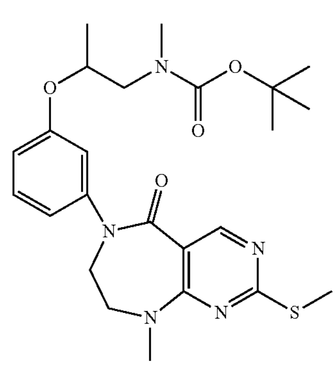 [SMILES: CSc1ncc2c(n1)N(C)CCN(c1cccc(OC(C)CN(C)C(=O)OC(C)(C)C)c1)C2=O] | tert-butyl methyl(2-(3-(9-methyl-2-(methylthio)-5-oxo-5,7,8,9-tetrahydro-6H-pyrimido[4,5-e][1,4]diazepin-6-yl)phenoxy)propyl) carbamate | (400 MHz, CDCl$_3$):1.28(d. J = 6 Hz, 3H), 1.45(s, 9H), 2.55(s, 3H), 2.94(s, 3H), 3.28(s, 3H), 3.35(m, 1H), 3.45 (m, 1H), 3.79 (m, 2H), 3.98 (m, 2H), 4.62 (m, 1H), 6.85 (m, 3H), 7.28 (m, 1H), 8.77 (s, 1H). | | 510.2 (M + Na) |

| EX | Structure | Chemical name | 1H-NMR (ppm) | Method/Ret (min) | MS |
|---|---|---|---|---|---|
| 7 | 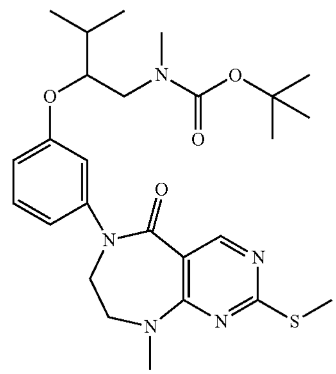 [SMILES: CSc1ncc2c(n1)N(C)CCN(c1cccc(OC(CN(C)C(=O)OC(C)(C)C)C(C)C)c1)C2=O] | tert-butyl methyl(3-methyl-2-(3-(9-methyl-2-(methylthio)-5-oxo-5,7,8,9-tetrahydro-6H-pyrimido[4,5-e][1,4]diazepin-6-yl)phenoxy)butyl) carbamate | (300 MHz, CDCl$_3$):0.98(m, 6H), 1.42(m, 9H), 1.93(m, 2H), 2.52(s, 3H), 2.84(s, 3H), 3.14(m, 1H), 3.27(s, 3H), 3.63(m, 1H), 3.77(m, 2H), 3.94(m, 2H), 4.34(m, 1H), 6.79(m, 3H), 7.26(m, 1H), 8.74(s, 1H). | | 538.3 (M + Na) |
| 8 | 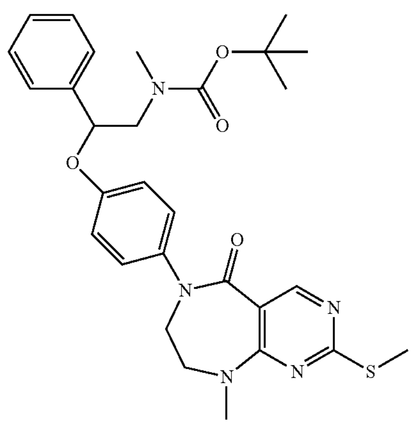 [SMILES: CSc1ncc2c(n1)N(C)CCN(c1ccc(OC(CN(C)C(=O)OC(C)(C)C)c3ccccc3)cc1)C2=O] | tert-butyl methyl(2-(4-(9-methyl-2-(methylthio)-5-oxo-5,7,8,9-tetrahydro-6H-pyrimido[4,5-e][1,4]diazepin-6-yl)phenoxy)-2-phenylethyl) carbamate | | A/7.52 | 572.2 (M + Na) |
| 9 | 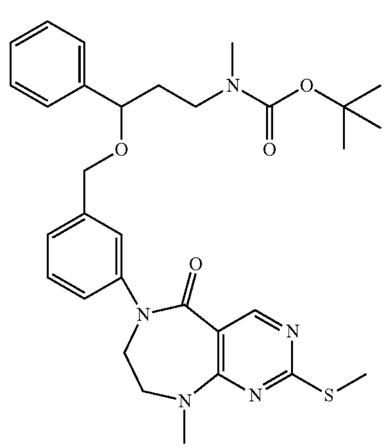 [SMILES: CSc1ncc2c(n1)N(C)CCN(c1cccc(COC(CCN(C)C(=O)OC(C)(C)C)c3ccccc3)c1)C2=O] | tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl) carbamate | | B/5.65 | 578.3 (M + H) |

| EX | Structure | Chemical name | 1H-NMR (ppm) | Method/ Ret (min) | MS |
|---|---|---|---|---|---|
| 10 | 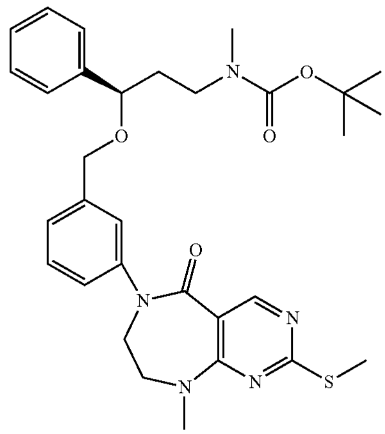 [SMILES: CSc1ncc2c(n1)N(C)CCN(c1cccc(CO[C@H](CCN(C)C(=O)OC(C)(C)C)c3ccccc3)c1)C2=O] | tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl) carbamate | (400 MHz, CDCl$_3$):1.43(s, 9H), 1.92(m, 1H), 2.06(m, 1H), 2.56(s, 3H), 2.82(s, 3H), 3.29(s, 3H), 3.35(m, 2H), 3.80(m, 2H), 4.00(m, 2H), 4.29(m, 1H), 4.35(m, 1H), 4.42(m, 1H), 7.22(m, 3H), 7.36(m, 6H), 8.79(s, 1H). | | |
| 11 | 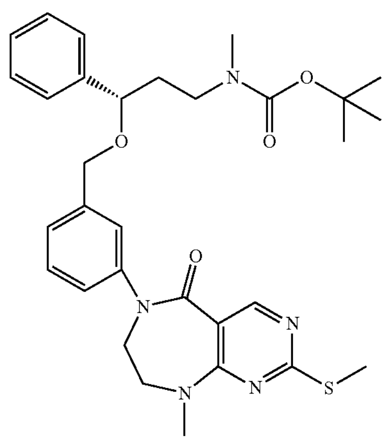 [SMILES: CSc1ncc2c(n1)N(C)CCN(c1cccc(CO[C@@H](CCN(C)C(=O)OC(C)(C)C)c3ccccc3)c1)C2=O] | tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl) carbamate | (400 MHz, CDCl$_3$):1.43(s, 9H), 1.92(m, 1H), 2.06(m, 1H), 2.56(s, 3H), 2.82(s, 3H), 3.29(s, 3H), 3.35(m, 2H), 3.80(m, 2H), 4.00(m, 2H), 4.29(m, 1H), 4.35(m, 1H), 4.42(m, 1H), 7.22(m, 3H), 7.36(m, 6H), 8.79(s, 1H). | | |
| 12 | 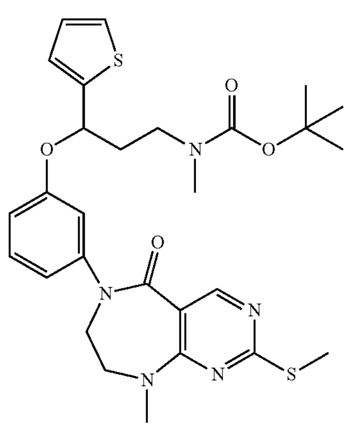 [SMILES: CSc1ncc2c(n1)N(C)CCN(c1cccc(OC(CCN(C)C(=O)OC(C)(C)C)c3cccs3)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl) carbamate | (300 MHz, CDCl$_3$):1.42(s, 9H), 2.25(m, 2H), 2.56(s, 3H), 2.86(s, 3H), 3.29(s, 3H), 3.39(m, 2H), 3.75(m, 2H), 3.93(m, 2H), 5.43(m, 1H), 6.82(m, 1H), 6.87(m, 2H), 6.95(m, 1H), 7.03(m, 1H), 7.25(m, 2H), 8.78(s, 1H). | | 592.2 (M + Na) |

| EX | Structure | Chemical name | 1H-NMR (ppm) | Method/Ret (min) | MS |
|---|---|---|---|---|---|
| 13 | 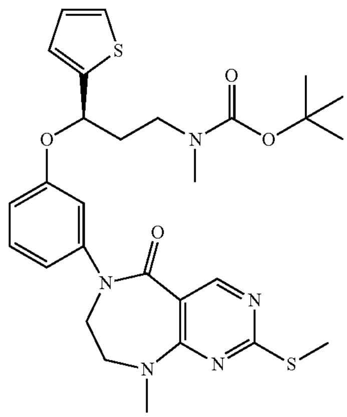 [SMILES: CSc1ncc2c(n1)N(C)CCN(c1cccc(O[C@H](CCN(C)C(=O)OC(C)(C)C)c3cccs3)c1)C2=O] | tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl) carbamate | (300 MHz, CDCl$_3$):1.42(s, 9H), 2.25(m, 2H), 2.56(s, 3H), 2.86(s, 3H), 3.29(s,3H), 3.39(m, 2H), 3.75(m, 2H), 3.93(m, 2H), 5.43(m, 1H), 6.82(m, 1H), 6.87(m, 2H), 6.95(m, 1H), 7.03(m, 1H), 7.25(m, 2H), 8.78(s, 1H). | | |
| 14 | 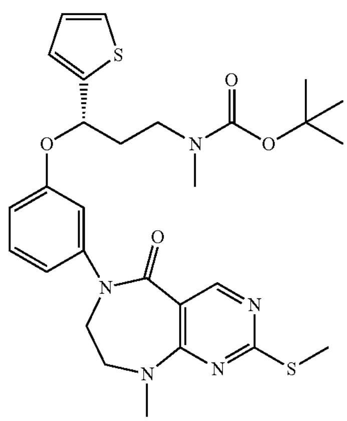 [SMILES: CSc1ncc2c(n1)N(C)CCN(c1cccc(O[C@@H](CCN(C)C(=O)OC(C)(C)C)c3cccs3)c1)C2=O] | tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl) carbamate | (300 MHz, CDCl$_3$):1.42(s, 9H), 2.25(m, 2H), 2.56(s, 3H), 2.86(s, 3H), 3.29(s, 3H), 3.39(m, 2H), 3.75(m, 2H), 3.93(m, 2H), 5.43(m, 1H), 6.82(m, 1H), 6.87(m, 2H), 6.95(m, 1H), 7.03(m, 1H), 7.25(m, 2H), 8.78(s, 1H). | | |
| 15 | 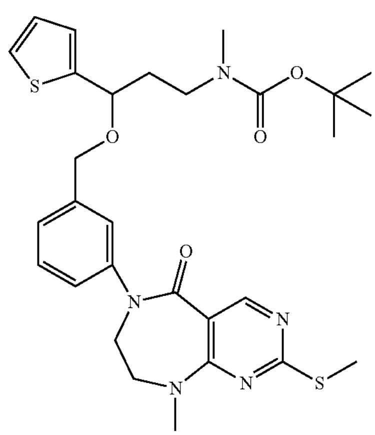 [SMILES: CSc1ncc2c(n1)N(C)CCN(c1cccc(COC(CCN(C)C(=O)OC(C)(C)C)c3cccs3)c1)C2=O] | tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl) carbamate | | B/5.73 | 584.3 (M + H) |

| EX | Structure | Chemical name | 1H-NMR (ppm) | Method/Ret (min) | MS |
|---|---|---|---|---|---|
| 16 | 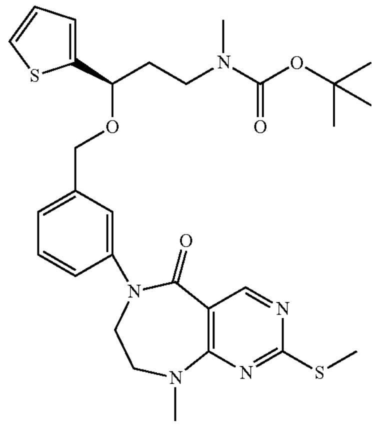 [SMILES: CSc1ncc2c(n1)N(C)CCN(c1cccc(CO[C@H](CCN(C)C(=O)OC(C)(C)C)c3cccs3)c1)C2=O] | tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl) carbamate | (400 MHz, CDCl$_3$):1.44(s, 9H), 2.03(, 1H), 2.19(m, 1H), 2.56(s, 3H), 2.84(s, 3H), 3.30(s, 3H), 3.35(m, 2H), 3.80(m, 2H), 4.01(m, 2H), 4.34(m, 1H), 4.51(m, 1H), 4.63(m, 1H), 7.00(m, 2H), 7.23(m, 3H), 7.31(m, 1H), 7.39(m, 1H), 8.80(s, 1H). | | |
| 17 | 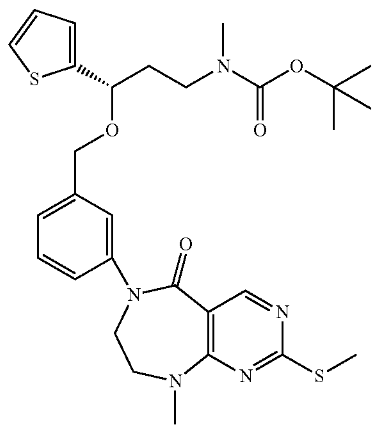 | tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl) carbamate | (400 MHz, CDCl$_3$):1.44(s, 9H), 2.03(, 1H), 2.19(m, 1H), 2.56(s, 3H), 2.84(s, 3H), 3.30(s, 3H), 3.35(m, 2H), 3.80(m, 2H), 4.01(m, 2H), 4.34(m, 1H), 4.51(m, 1H), 4.63(m, 1H), 7.00(m, 2H), 7.23(m, 3H), 7.31(m, 1H), 7.39(m, 1H), 8.80(s, 1H). | | |
| 18 | 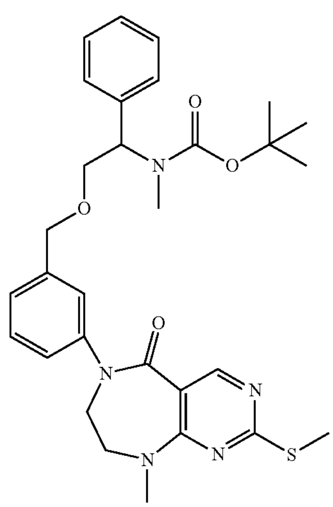 [SMILES: CSc1ncc2c(n1)N(C)CCN(c1cccc(COCC(c3ccccc3)N(C)C(=O)OC(C)(C)C)c1)C2=O] | tert-butyl methyl(2-((3-(9-methyl-2-(methylthio)-5-oxo-5,7,8,9-tetrahydro-6H-pyrimido[4,5-e][1,4]diazepin-6-yl)benzyl)oxy)-1-phenylethyl) carbamate | (400 MHz, CDCl$_3$):1.47(s, 9H), 2.57(s, 3H), 2.71(bs, 3H), 3.31(s, 3H), 3.80(m, 2H), 3.96(m, 2H), 4.00(m, 2H), 4.63(m, 2H), 5.54(m, 1H), 7.27(m, 6H), 7.34(m, 2H), 7.40(m, 1H), 8.81 (s, 1H). | | 564.3 (M + H) |

| EX | Structure | Chemical name | 1H-NMR (ppm) | Method/Ret (min) | MS |
|---|---|---|---|---|---|
| 19 | 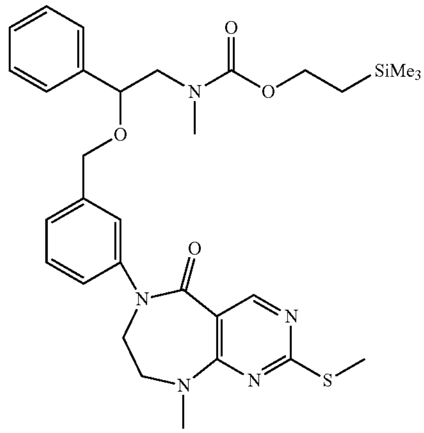 [SMILES: CSc1ncc2c(n1)N(C)CCN(c1cccc(COC(CN(C)C(=O)OCC[Si](C)(C)C)c3ccccc3)c1)C2=O] | 2-(trimethylsilyl)ethyl methyl(2-((3-(9-methyl-2-(methylthio)-5-oxo-5,7,8,9-tetrahydro-6H-pyrimido[4,5-e][1,4]diazepin-6-yl)benzyl)oxy)-2-phenylethyl) carbamate | (400 MHz, CDCl₃):0.05(s, 9H), 0.97(m, 2H)2.56(s, 3H), 2.90(m, 3H), 3.30(s, 3H), 3.48(m, 2H)3.80(m, 2H), 4.00(m, 2H), 4.06(m, 1H), 4.18(m, 1H), 4.33(m, 1H), 4.54(m, 1H), 4.65(m, 1H), 7.21(m, 3H), 7.36(m, 6H), 8.80(s, 1H). | | 608.3 |
| 20 | 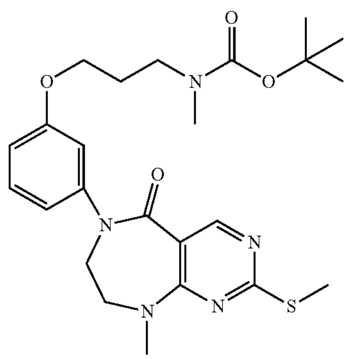 [SMILES: CSc1ncc2c(n1)N(C)CCN(c1cccc(OCCCN(C)C(=O)OC(C)(C)C)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)propyl) carbamate | (400 MHz, CDCl₃):1.45(s, 9H), 2.01 (m, 2H), 2.57(s, 3H), 2.89(s, 3H), 3.30(s, 3H), 3.40(m, 2H), 3.80(m, 2H), 3.98(m, 2H), 3.99(m, 2H), 6.85(m, 3H), 7.32(m, 1H), 8.79(s, 1H). | | 510.2 (M + Na) |
| 21 | 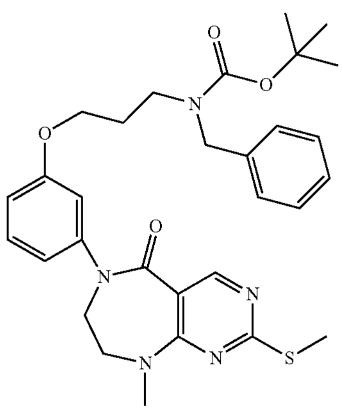 [SMILES: CSc1ncc2c(n1)N(C)CCN(c1cccc(OCCCN(Cc3ccccc3)C(=O)OC(C)(C)C)c1)C2=O] | tert-butyl benzyl(3-(3-(9-methyl-2-(methylthio)-5-oxo-5,7,8,9-tetrahydro-6H-pyrimido[4,5-e][1,4]diazepin-6-yl)phenoxy)propyl) carbamate | (300 MHz, CDCl₃):1.47(s, 9H), 2.00(m, 2H), 2.56(s, 3H), 3.29(s, 3H), 3.37(m, 2H), 3.78(m, 2H), 3.94(m, 2H), 3.99(m, 2H), 4.46(bs, 2H), 6.82(m, 3H), 7.29(m, 6H), 8.78(s, 1H). | | 586.3 (M + Na) |
| 22 | 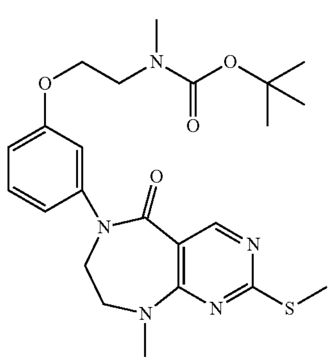 [SMILES: CSc1ncc2c(n1)N(C)CCN(c1cccc(OCCN(C)C(=O)OC(C)(C)C)c1)C2=O] | tert-butyl methyl(2-(3-(9-methyl-2-(methylthio)-5-oxo-5,7,8,9-tetrahydro-6H-pyrimido[4,5-e][1,4]diazepin-6-yl)phenoxy)ethyl) carbamate | (400 MHz, CDCl₃):1.47(s, 9H), 2.57(s, 3H), 2.99(s, 3H), 3.30(s, 3H), 3.61(m, 2H), 3.80(m, 2H), 3.99(m, 2H), 4.10(m, 2H), 6.86(m, 3H), 7.32(m, 1H), 8.79(s, 1H). | | 496.2 (M + Na) |

| EX | Structure | Chemical name | 1H-NMR (ppm) | Method/Ret (min) | MS |
|---|---|---|---|---|---|
| 23 | 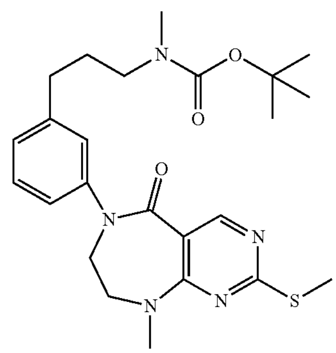 [SMILES: CSc1ncc2c(n1)N(C)CCN(c1cccc(CCCN(C)C(=O)OC(C)(C)C)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenyl)propyl) carbamate | (400 MHz, CDCl$_3$):1.46(s, 9H), 1.86(m, 2H), 2.56(s, 3H), 2.63(m, 2H), 2.85(s, 3H), 3.27(m, 2H), 3.30(s, 3H), 3.81(m, 2H), 4.00(m, 2H), 7.11(m, 3H), 7.34(m, 1H), 8.79(s, 1H). | | 494.2 (M + Na) |
| 24 | 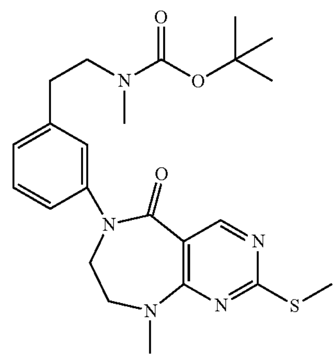 [SMILES: CSc1ncc2c(n1)N(C)CCN(c1cccc(CCN(C)C(=O)OC(C)(C)C)c1)C2=O] | tert-butyl methyl(3-(9-methyl-2-(methylthio)-5-oxo-5,7,8,9-tetrahydro-6H-pyrimido[4,5-e][1,4]diazepin-6-yl)phenethyl) carbamate | (400 MHz, CDCl$_3$):1.41 (bs, 9H), 2.57 (s, 3H), 2.82(m, 2H), 2.83(s, 3H), 3.30(s, 3H), 3.45(m, 2H), 3.79(m, 2H), 3.99(m, 2H), 7.14(m, 3H), 7.35(m, 1H), 8.79(s, 1H). | | 480.2 (M + Na) |
| 25 | 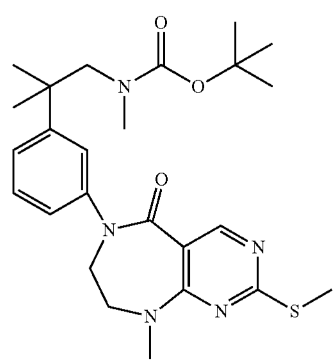 [SMILES: CSc1ncc2c(n1)N(C)CCN(c1cccc(C(C)(C)CN(C)C(=O)OC(C)(C)C)c1)C2=O] | tert-butyl methyl(2-methyl-2-(3-(9-methyl-2-(methylthio)-5-oxo-5,7,8,9-tetrahydro-6H-pyrimido[4,5-e][1,4]diazepin-6-yl)phenyl)propyl) carbamate | (300 MHz, CDCl$_3$):1.36(s, 6H), 1.43(s, 9H), 2.55(s, 3H), 2.56(s, 3H), 3.30(s, 3H), 3.41(m, 2H), 3.79(m, 2H), 4.00(m, 2H), 7.13(m, 3H), 7.32(m, 1H), 8.78(s, 1H). | | |
| 26 | 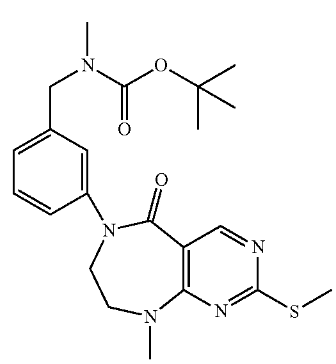 [SMILES: CSc1ncc2c(n1)N(C)CCN(c1cccc(CN(C)C(=O)OC(C)(C)C)c1)C2=O] | tert-butyl methyl(3-(9-methyl-2-(methylthio)-5-oxo-5,7,8,9-tetrahydro-6H-pyrimido[4,5-e][1,4]diazepin-6-yl)benzyl) carbamate | (400 MHz, CDCl$_3$):1.49(bs, 9H), 2.56 (s, 3H), 2.85(bs, 3H), 3.30 (s, 3H), 3.80(m, 2H), 4.00(m, 2H), 4.45(m, 2H), 7.15(m, 2H), 7.20(m, 1H), 7.39(m, 1H), 8.79(s, 1H). | | 466.1 (M + Na) |

| EX | Structure | Chemical name | 1H-NMR (ppm) | Method/Ret (min) | MS |
|---|---|---|---|---|---|
| 27 | 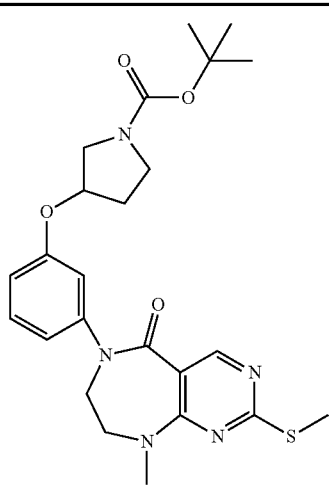 | tert-butyl 3-(3-(9-methyl-2-(methylthio)-5-oxo-5,7,8,9-tetrahydro-6H-pyrimido[4,5-e][1,4]diazepin-6-yl)phenoxy)pyrrolidine-1-carboxylate | (300 MHz, CDCl$_3$):1.48(s, 9H), 2.13(s, 3H), 2.57(s, 3H), 3.31(s, 3H), 3.58(m, 4H), 3.81(m, 2H), 4.01(m, 2H), 4.90(m, 1H), 6.85(m, 3H), 7.34(m, 1H), 8.79(s, 1H). | | 508.2 (M + Na) |
| 28 | 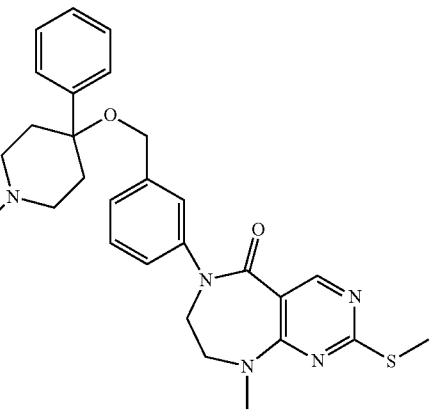 | tert-butyl 4-((3-(9-methyl-2-(methylthio)-5-oxo-5,7,8,9-tetrahydro-6H-pyrimido[4,5-e][1,4]diazepin-6-yl)benzyl)oxy)-4-phenylpiperidine-1-carboxylate | (400 MHz, CDCl$_3$):1.49(s, 9H), 1.95(m, 2H), 2.17(m, 2H), 2.56(s, 3H), 3.27(m, 2H), 3.31(s, 3H), 3.80(m, 2H), 4.00(m, 2H), 4.04(m, 2H), 4.14(s, 2H), 7.20(m, 2H), 7.25(m, 1H), 7.31(m, 1H), 7.39(m, 3H), 7.45(m, 2H), 8.79(s, 1H). | | 612.3 (M + Na) |
| 29 | 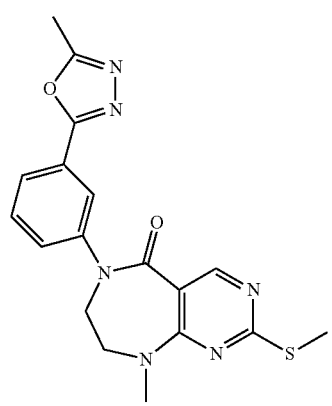 [SMILES: CSc1ncc2c(n1)N(C)CCN(c1cccc(-c3nnc(C)o3)c1)C2=O] | 9-methyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one | (500 MHz, CDCl$_3$):2.58(s, 3H), 2.64(s, 3H), 3.33(s, 3H), 3.86(m, 2H), 4.08(m, 2H), 7.52(m, 1H), 7.58(m, 1H), 7.96(m, 1H), 7.99(m, 3H), 8.82(s, 1H). | | 383.1 (M + H) |

-continued

| EX | Structure | Chemical name | 1H-NMR (ppm) | Method/Ret (min) | MS |
|---|---|---|---|---|---|
| 30 | 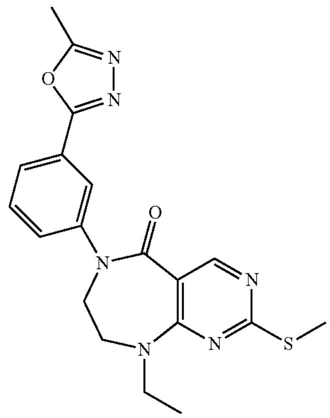 [SMILES: CCN1CCN(c2cccc(-c3nnc(C)o3)c2)C(=O)c2cnc(SC)nc21] | 9-ethyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one | (400 MHz, CDCl$_3$):1.25(t, J = 7 Hz, 3H), 2.53(s, 3H), 2.60(s, 3H), 3.80(q, J = 7 Hz, 2H), 3.83(m, 2H), 4.03(m, 2H), 7.46(m, 1H), 7.53(m, 1H), 7.90(m, 1H), 7.93(m, 1H), 8.80(s, 1H). | | 397.1 (M + H) |
| 31 | 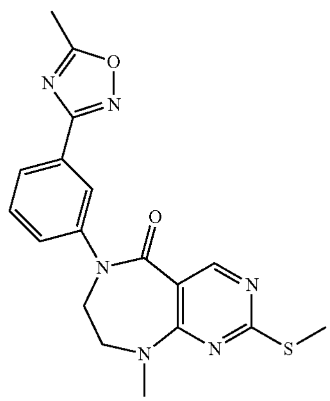 [SMILES: CSc1ncc2c(n1)N(C)CCN(c1cccc(-c3noc(C)n3)c1)C2=O] | 9-methyl-6-(3-(5-methyl-1,2,4-oxadiazol-3-yl)phenyl)-2-(methylthio)-6,7,8,9-tetrahydro-5H-pyrimido[4,5-e][1,4]diazepin-5-one | (500 MHz, CDCl$_3$):2.55(s, 3H), 2.64(s, 3H), 3.29(s, 3H), 3.82(m, 2H), 4.04(m, 2H), 7.46(m, 1H), 7.52(m, 1H), 7.97(m, 2H), 8.77(s, 1H). | | 383.1 (M + H) |
| 32 | 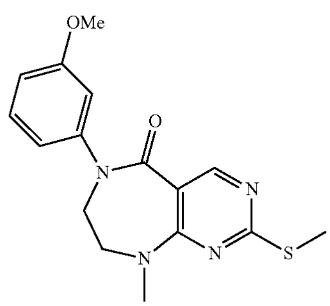 [SMILES: COc1cccc(N2CCN(C)c3nc(SC)ncc3C2=O)c1] | 6-(3-methoxyphenyl)-9-methyl-2-(methylthio)-6,7,8,9-tetrahydro-5H-pyrimido[4,5-e][1,4]diazepin-5-one | | B/4.20 | 331.1 (M + H) |
| 33 | 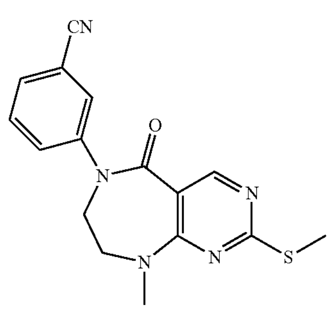 [SMILES: CSc1ncc2c(n1)N(C)CCN(c1cccc(C#N)c1)C2=O] | 3-(9-methyl-2-(methylthio)-5-oxo-5,7,8,9-tetrahydro-6H-pyrimido[4,5-e][1,4]diazepin-6-yl)benzonitrile | (500 MHz, CDCl$_3$):2.58(s, 3H), 3.35(s, 3H), 3.84(m, 2H), 4.04(m, 2H), 7.56(m, 1H), 7.59(m, 2H), 7.63(m, 1H), 8.80(s, 1H). | | 326.1 (M + H) |

| EX | Structure | Chemical name | 1H-NMR (ppm) | Method/ Ret (min) | MS |
|----|-----------|---------------|--------------|-------------------|----|
| 34 | OTBDMS structure | 6-(3-((tert-butyldimethyl-silyl)oxy)phenyl)-9-methyl-2-(methylthio)-6,7,8,9-tetrahydro-5H-pyrimido[4,5-e][1,4]diazepin-5-one | (500 MHz CDCl$_3$):0.22(s, 6H), 0.99(s, 9H), 2.55(s, 3H), 3.28(s, 3H), 3.77(m, 2H), 3.97(m, 2H), 6.76(m, 1H), 6.79(m, 1H), 6.87(m, 1H), 7.25(m, 1H), 8.77(s, 1H). | | 431.2 (M + H) |
| 35 | Br structure | 6-(3-bromophenyl)-9-methyl-2-(methylthio)-6,7,8,9-tetrahydro-5H-pyrimido[4,5-e][1,4]diazepin-5-one | (300 MHz, CDCl$_3$):2.58(s, 3H), 3.32(s, 3H), 3.82(m, 2H), 4.01(m, 2H), 7.26(m, 1H), 7.31(m, 1H), 7.44(m, 1H), 7.27(m, 1H), 8.80(s, 1H). | | |
| 36 | OH structure | 6-(3-(2-hydroxyethyl)phenyl)-9-methyl-2-(methylthio)-6,7,8,9-tetrahydro-5H-pyrimido[4,5-e][1,4]diazepin-5-one | (500 MHz, CDCl$_3$):2.52(s, 3H), 2.78(t, J = 6.5 Hz, 2H), 3.26(s, 3H), 3.73(t, J = 6.5 Hz, 2H), 3.76(m, 2H), 3.93(m, 2H), 7.09(m, 3H), 7.29(m, 1H), 8.69(s, 1H). | | 367.1 (M + Na) |
| 37 | MeO structure | 6-(4-methoxyphenyl)-9-methyl-2-(methylthio)-6,7,8,9-tetrahydro-5H-pyrimido[4,5-e][1,4]diazepin-5-one | (300 MHz, CDCl$_3$):2.56(s, 3H), 3.29(s, 3H)3.79(m, 2H), 3.83(s, 3H), 3.96(m, 2H), 6.94(dAB, 2H), 7.20(dAB, 2H), 8.80 (s, 1H) | | 331.1 (M + H) |
| 38 | TBDMSO structure | 6-(4-((tert-butyldimethyl-silyl)oxy)phenyl)-9-methyl-2-(methylthio)-6,7,8,9-tetrahydro-5H-pyrimido[4,5-e][1,4]diazepin-5-one | (400 MHz, CDCl$_3$):0.21(s, 6H), 0.99(s, 9H), 2.55(s, 3H), 3.38(s, 3H), 3.78(m, 2H), 3.95(m, 2H), 6.86(dAB, 2H), 7.12(dAB, 2H), 8.78 (s, 1H) | | 431.2 (M + H) |

-continued

| EX | Structure | Chemical name | 1H-NMR (ppm) | Method/Ret (min) | MS |
|---|---|---|---|---|---|
| 39 | 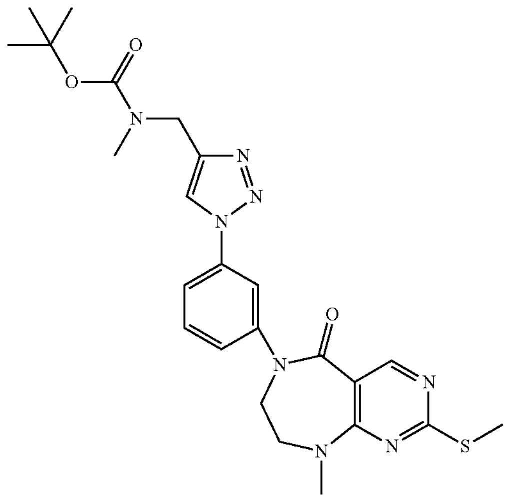 [SMILES: CSc1ncc2c(n1)N(C)CCN(c1cccc(-n3cc(CN(C)C(=O)OC(C)(C)C)nn3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl) carbamate | (300 MHz, CDCl$_3$):1.46(s, 9H), 2.54(s, 3H), 2.94(m, 3H), 3.29(s, 3H), 3.83(m, 2H), 4.05(m, 2H), 4.55(s, 2H), 7.35(m, 1H), 7.56(m, 2H), 7.74(m, 1H), 7.90(bs, 1H), 8.75(s, 1H). | | 533.2 (M + Na) |
| 40 | 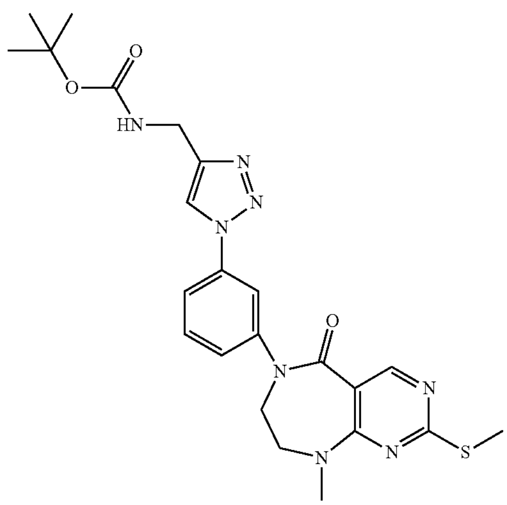 [SMILES: CSc1ncc2c(n1)N(C)CCN(c1cccc(-n3cc(CNC(=O)OC(C)(C)C)nn3)c1)C2=O] | tert-butyl ((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl) carbamate | (300 MHz, CDCl$_3$):1.43(s, 9H), 2.54(m, 3H), 3.28(s, 3H), 3.82(m, 2H), 4.03(m, 2H), 4.43(d, J = 6 Hz, 2H), 5.34(bs, 1H), 7.34(m, 1H), 7.51(m, 1H), 7.58(m, 1H), 7.73(m, 1H), 7.98(s, 1H), 8.74 (s, 1H). | | 519.2 (M + Na) |
| 41 | 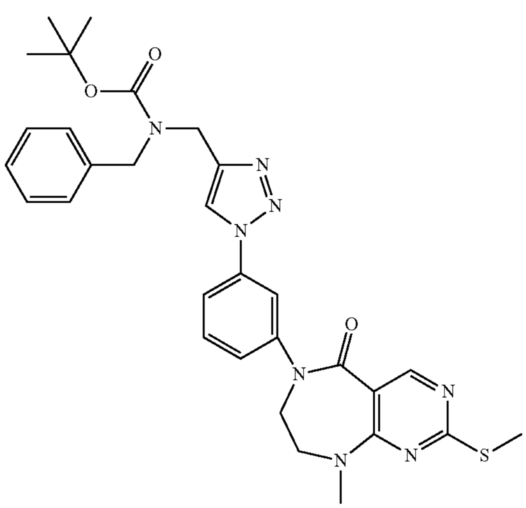 [SMILES: CSc1ncc2c(n1)N(C)CCN(c1cccc(-n3cc(CN(Cc4ccccc4)C(=O)OC(C)(C)C)nn3)c1)C2=O] | tert-butyl benzyl((1-(3-(9-methyl-2-(methylthio)-5-oxo-5,7,8,9-tetrahydro-6H pyrimido[4,5-e][1,4]diazepin-6-yl)phenyl)-1H-1,2,3-triazol-4-yl)methyl) carbamate | (300 MHz, CDCl$_3$):1.47(s, 9H), 2.54(m, 3H), 3.29(s, 3H), 3.83(m, 2H), 4.04(m, 2H), 4.52(s, 2H), 7.31(m, 6H), 7.52(m, 2H), 7.72(m, 1H), 7.96(bs, 1H), 8.76(s, 1H). | | 609.2 (M + Na) |

| EX | Structure | Chemical name | 1H-NMR (ppm) | Method/Ret (min) | MS |
|---|---|---|---|---|---|
| 42 | 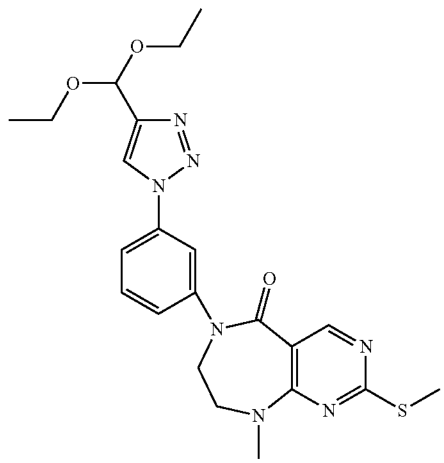 [SMILES: CCOC(OCC)c1cn(-c2cccc(N3CCN(C)c4nc(SC)ncc4C3=O)c2)nn1] | 6-(3-(4-(diethoxymethyl)-1H-1,2,3-triazol-1-yl)phenyl)-9-methyl-2-(methylthio)-6,7,8,9-tetrahydro-5H-pyrimido[4,5-e][1,4]diazepin-5-one | (400 MHz, CDCl$_3$):1.21(t, J = 7 Hz, 6H), 2.50(m, 3H), 3.25(s, 3H), 3.64(m, 4H), 3.81(m, 2H), 4.02(m, 2H), 5.73(s, 1H), 7.31(m, 1H), 7.49(m, 1H), 7.59(m, 1H), 7.73(m, 1H), 8.04(s, 1H), 8.70 (s, 1H). | | 470.2 (M + H) |
| 43 | 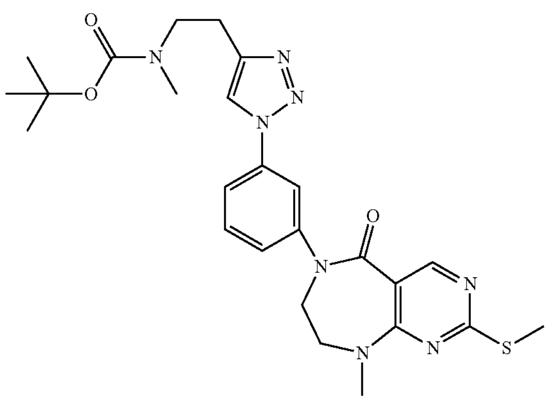 [SMILES: CSc1ncc2c(n1)N(C)CCN(c1cccc(-n3cc(CCN(C)C(=O)OC(C)(C)C)nn3)c1)C2=O] | tert-butyl methyl(2-(1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)ethyl) carbamate | (400 MHz, CDCl$_3$):1.43(s, 9H), 2.57(s, 3H), 2.88(s, 3H), 3.03(bs, 2H), 3.32(s, 3H), 3.61(bs, 2H), 3.84(m, 2H), 4.07(m, 2H), 7.37(m, 1H), 7.55(m, 1H), 7.61(m, 1H), 7.75(m, 1H), 7.86(s, 1H), 8.80(s, 1H). | | 547.2 (M + Na) |
| 44 | 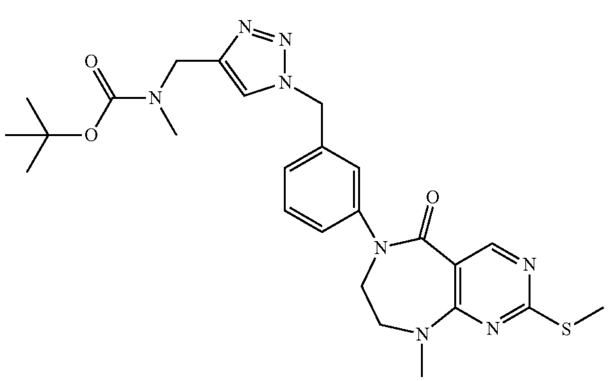 [SMILES: CSc1ncc2c(n1)N(C)CCN(c1cccc(Cn3cc(CN(C)C(=O)OC(C)(C)C)nn3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)benzyl)-1H-1,2,3-triazol-4-yl)methyl) carbamate | (500 MHz, CDCl$_3$):1.43(s, 9H), 2.54(s, 3H), 2.89(s, 3H), 3.28(s, 3H), 3.78(m, 2H), 3.97(m, 2H), 4.47(s, 2H), 5.51 (s, 2H), 7.14(m, 1H), 7.25(m, 2H), 7.41 (m, 1H), 7.52(bs, 1H), 8.75(s, 1H). | | 547.2 (M + Na) |

| EX | Structure | Chemical name | 1H-NMR (ppm) | Method/Ret (min) | MS |
|---|---|---|---|---|---|
| 45 | 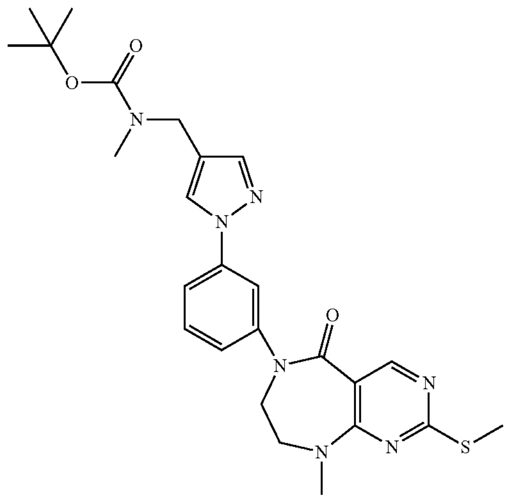 [SMILES: CSc1ncc2c(n1)N(C)CCN(c1cccc(-n3cc(CN(C)C(=O)OC(C)(C)C)cn3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-pyrazol-4-yl)methyl) carbamate | (300 MHz, CDCl$_3$):1.49(s, 9H), 2.54(s, 3H), 2.84(s, 3H), 3.29(s, 3H), 3.82(m, 2H), 4.03(m, 2H), 4.31(s, 2H), 7.20(m, 1H), 7.46(m, 1H), 7.54(m, 1H), 7.63(s, 1H), 7.67(m, 1H), 7.85(bs, 1H), 8.77(s, 1H). | | 532.2 (M + Na) |
| 46 | 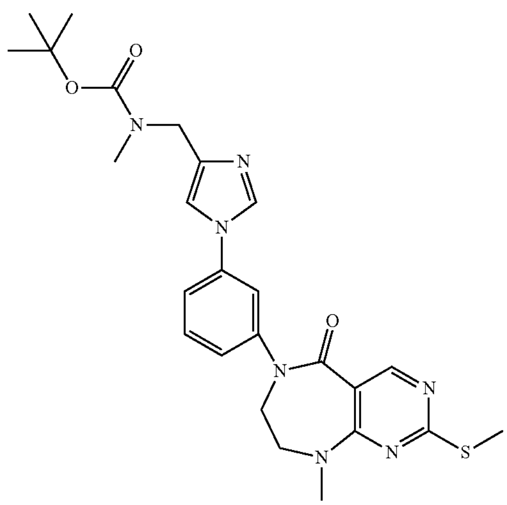 [SMILES: CSc1ncc2c(n1)N(C)CCN(c1cccc(-n3cnc(CN(C)C(=O)OC(C)(C)C)c3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-imidazol-4-yl)methyl) carbamate | (300 MHz, CDCl$_3$):1.46(s, 9H), 2.54(s, 3H), 2.94(s, 3H), 3.29(s, 3H), 3.82(m, 2H), 4.03(m, 2H), 4.40(s, 2H), 7.15(bs, 1H), 7.26(m, 2H), 7.38(m, 1H), 7.51(s, 1H), 7.78(m, 1H), 8.76(s, 1H). | | 510.2 (M + H) |
| 47 | 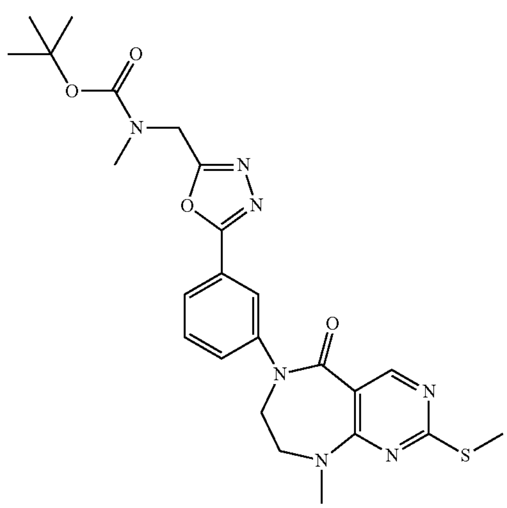 [SMILES: CSc1ncc2c(n1)N(C)CCN(c1cccc(-c3nnc(CN(C)C(=O)OC(C)(C)C)o3)c1)C2=O] | tert-butyl methyl((5-(3-(9-methyl-2-(methylthio)-5-oxo-5,7,8,9-tetrahydro-6H-pyrimido[4,5-e][1,4]diazepin-6-yl)phenyl)-1,3,4-oxadiazol-2-yl)methyl) carbamate | (400 MHz, CDCl$_3$):1.49(s, 9H), 2.5(s, 3H), 3.00(bs, 3H), 3.32(s, 3H), 3.85(m, 2H), 4.06(m, 2H), 4.72(m, 2H), 7.55(m, 2H), 7.96(m, 2H), 8.79(s, 1H). | | 512.2 (M + H) |

-continued

| EX | Structure | Chemical name | 1H-NMR (ppm) | Method/ Ret (min) | MS |
|---|---|---|---|---|---|
| 48 | 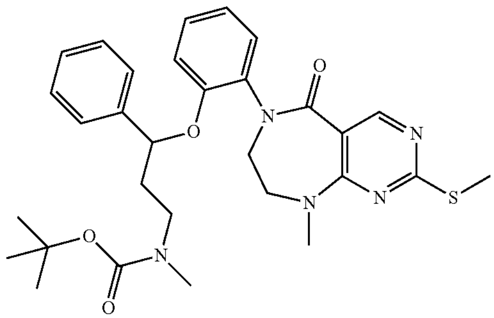 [SMILES: CSc1ncc2c(n1)N(C)CCN(c1ccccc1OC(CCN(C)C(=O)OC(C)(C)C)c1ccccc1)C2=O] | tert-butyl methyl(3-(2-(9-methyl-2-(methylthio)-5-oxo-5,7,8,9-tetrahydro-6H-pyrimido[4,5-e][1,4]diazepin-6-yl)phenoxy)-3-phenylpropyl) carbamate | (400 MHz, CDCl$_3$):1.39(b s, 9H), 2, 10 (m, 2H), 2.58(s, 3H), 2.74(s, 3H)3.26(m, 2H), 3.33(s, 3H)3.87(m, 2H), 3.95(m, 2H), 5.19(m, 1H), 6.76(d, J = 7.9 Hz, 1H), 6.94(t, J = 7.9 Hz, 1H), 7.11 (t, J = 7.9 Hz, 1H), 7.21 (dd, J1 = 7.9, J2 = 1.6 Hz, 1H), 7.33 (m, 5H), 8.80 (s, 1H). | | |
| 49 | 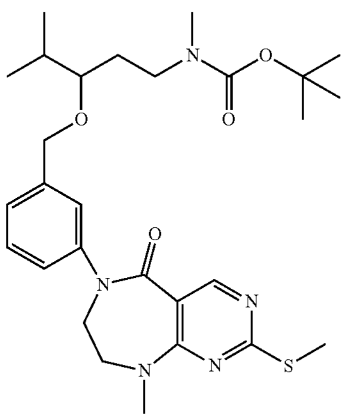 [SMILES: CSc1ncc2c(n1)N(C)CCN(c1cccc(COC(CCN(C)C(=O)OC(C)(C)C)C(C)C)c1)C2=O] | tert-butyl methyl (4-methyl-3-((3-(9-methyl-2-(methylthio)-5-oxo-5,7,8,9-tetrahydro-6H-pyrimido[4,5-e][1,4]diazepin-6-yl)benzyl)oxy)pentyl) carbamate | | B/5.82 | 544.3 (M + H) |
| 50 | 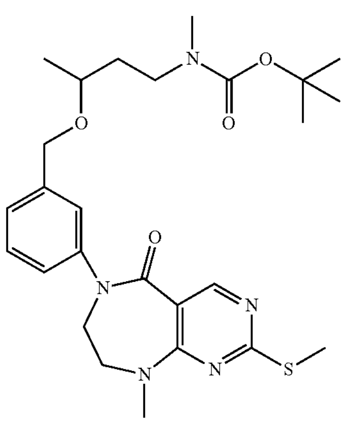 [SMILES: CSc1ncc2c(n1)N(C)CCN(c1cccc(COC(C)CCN(C)C(=O)OC(C)(C)C)c1)C2=O] | tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)butyl) carbamate | | B/5.30 | 516.3 (M + H) |

-continued

| EX | Structure | Chemical name | 1H-NMR (ppm) | Method/Ret (min) | MS |
|---|---|---|---|---|---|
| 51 | 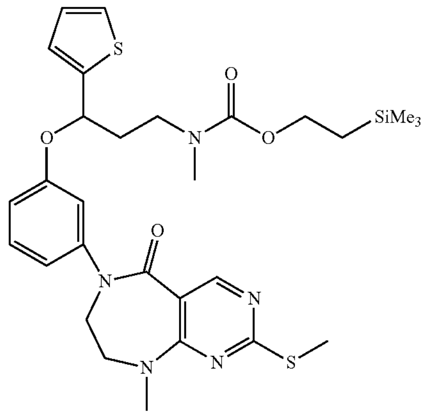 [SMILES: CSc1ncc2c(n1)N(C)CCN(c1cccc(OC(CCN(C)C(=O)OCC[Si](C)(C)C)c3cccs3)c1)C2=O] | 2-(trimethyl-silyl)ethyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl) carbamate | | B/6.13 | 614.2 (M + H) |
| 52 | 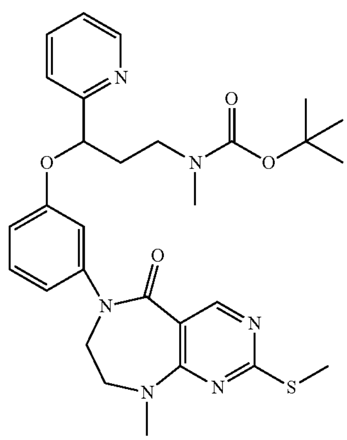 [SMILES: CSc1ncc2c(n1)N(C)CCN(c1cccc(OC(CCN(C)C(=O)OC(C)(C)C)c3ccccn3)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-2-yl)propyl) carbamate | | B/4.98 | 565.3 (M + H) |
| 53 | 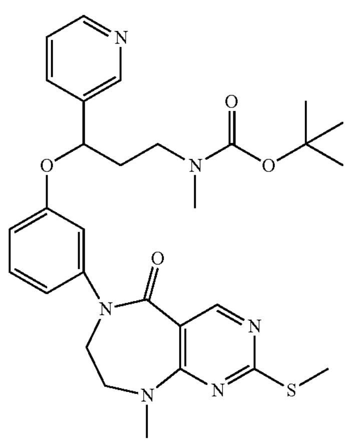 [SMILES: CSc1ncc2c(n1)N(C)CCN(c1cccc(OC(CCN(C)C(=O)OC(C)(C)C)c3cccnc3)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-3-yl)propyl) carbamate | | B/4.51 | 565.3 (M + H) |

| EX | Structure | Chemical name | 1H-NMR (ppm) | Method/Ret (min) | MS |
|---|---|---|---|---|---|
| 54 | 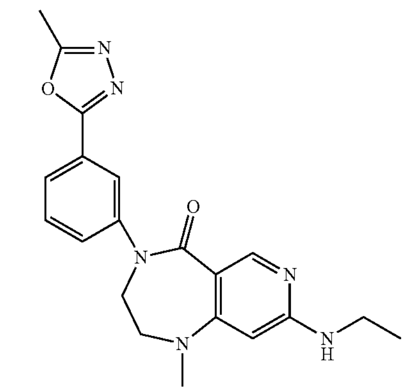 [SMILES: CCNc1cc2c(cn1)C(=O)N(c1cccc(-c3nnc(C)o3)c1)CCN2C] | 8-(ethylamino)-1-methyl-4-(3-(5-methyl-1,3,4-oxadiazol-2-yl)phenyl)-1,2,3,4-tetrahydro-5H-pyrido[4,3-e][1,4]diazepin-5-one | | B/4.82 | 379.2 (M + H) |
| 55 | 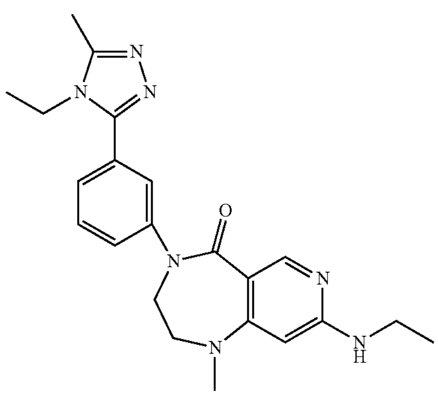 [SMILES: CCNc1cc2c(cn1)C(=O)N(c1cccc(-c3nnc(C)n3CC)c1)CCN2C] | 4-(3-(4-ethyl-5-methyl-4H-1,2,4-triazol-3-yl)phenyl)-8-(ethylamino)-1-methyl-1,2,3,4-tetrahydro-5H-pyrido[4,3-e][1,4]diazepin-5-one | | B/4.34 | 406.3 (M + H) |
| 56 | 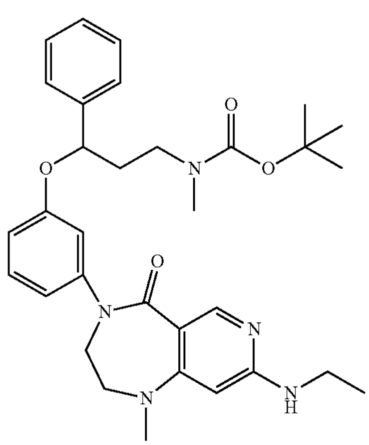 [SMILES: CCNc1cc2c(cn1)C(=O)N(c1cccc(OC(CCN(C)C(=O)OC(C)(C)C)c3ccccc3)c1)CCN2C] | tert-butyl (3-(3-(8-(ethylamino)-1-methyl-5-oxo-1,2,3,5-tetrahydro-4H-pyrido[4,3-e][1,4]diazepin-4-yl)phenoxy)-3-phenylpropyl)(methyl)carbamate | (500 MHz, CDCl$_3$):1.30(t, J = 7 Hz, 3H), 1.42(s, 9H), 2.09(m, 1H), 2.17(m, 1H), 2.86(s, 3H), 2.93(s, 3H), 3.32(m, 2H), 3.40(m, 2H), 3.46(m, 2H), 3.84(m, 2H), 4.78(bs, 1H), 5.14(m, 1H), 6.69(m, 1H), 6.88(m, 2H), 7.18(t, J = 8.2 Hz, 1H), 7.27 (m, 2H), 7.35 (m, 4H), 8.45 (s, 1H). | | 560.3 (M + H) |

-continued

| EX | Structure | Chemical name | 1H-NMR (ppm) | Method/ Ret (min) | MS |
|----|-----------|---------------|--------------|-------------------|-----|
| 57 | 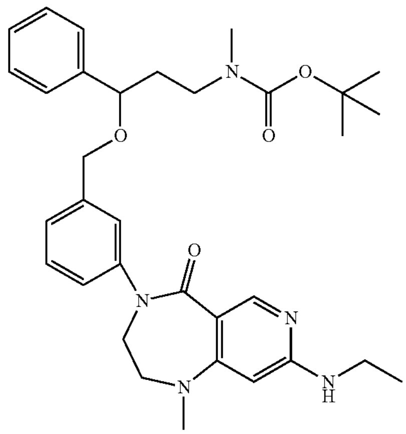 [SMILES: CCNc1cc2c(cn1)C(=O)N(c1cccc(COC(CCN(C)C(=O)OC(C)(C)C)c3ccccc3)c1)CCN2C] | tert-butyl (3-((3-(8-(ethylamino)-1-methyl-5-oxo-1,2,3,5-tetrahydro-4H-pyrido[4,3-e][1,4]diazepin-4-yl)benzyl)oxy)-3-phenylpropyl)(methyl) carbamate | | A/7.15 | 574.3 (M + H) |
| 58 | 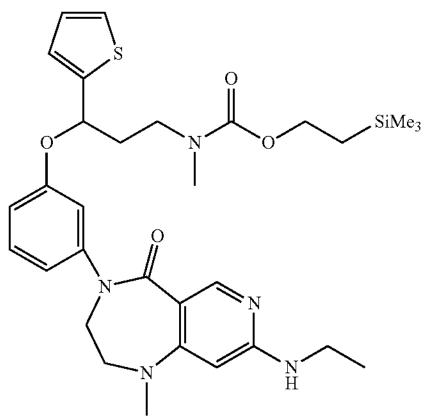 [SMILES: CCNc1cc2c(cn1)C(=O)N(c1cccc(OC(CCN(C)C(=O)OCC[Si](C)(C)C)c3cccs3)c1)CCN2C] | 2-(trimethylsilyl)ethyl (3-(3-(8-(ethylamino)-1-methyl-5-oxo-1,2,3,5-tetrahydro-4H-pyrido[4,3-e][1,4]diazepin-4-yl)phenoxy)-3-(thiophen-2-yl)propyl)(methyl) carbamate | | A/7.67 | 610.3 (M + H) |
| 59 | 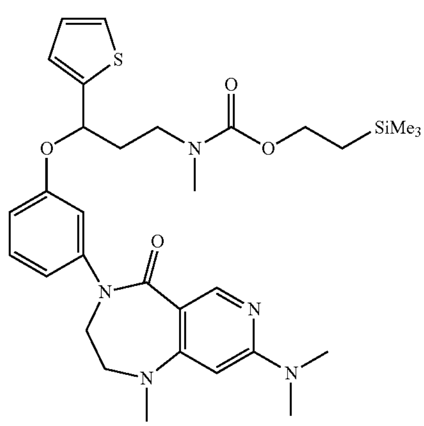 [SMILES: CN(CCC(Oc1cccc(N2CCN(C)c3cc(N(C)C)ncc3C2=O)c1)c1cccs1)C(=O)OCC[Si](C)(C)C] | 2-(trimethylsilyl)ethyl (3-(3-(8-(dimethylamino)-1-methyl-5-oxo-1,2,3,5-tetrahydro-4H-pyrido[4,3-e][1,4]diazepin-4-yl)phenoxy)-3-(thiophen-2-yl)propyl)(methyl) carbamate | | A/7.60 | 610.3 (M + H) |

| EX | Structure | Chemical name | 1H-NMR (ppm) | Method/Ret (min) | MS |
|---|---|---|---|---|---|
| 60 | 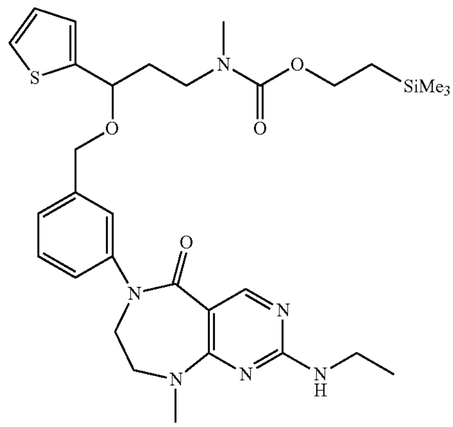 [SMILES: CCNc1ncc2c(n1)N(C)CCN(c1cccc(COC(CCN(C)C(=O)OCC[Si](C)(C)C)c3cccs3)c1)C2=O] | 2-(trimethylsilyl)ethyl (3-((3-(8-(ethylamino)-1-methyl-5-oxo-1,2,3,5-tetrahydro-4H-pyrido[4,3-e][1,4]diazepin-4-yl)benzyl)oxy)-3-(thiophen-2-yl)propyl)(methyl) carbamate | | A/7.78 | 624.3 (M + H) |
| 61 | 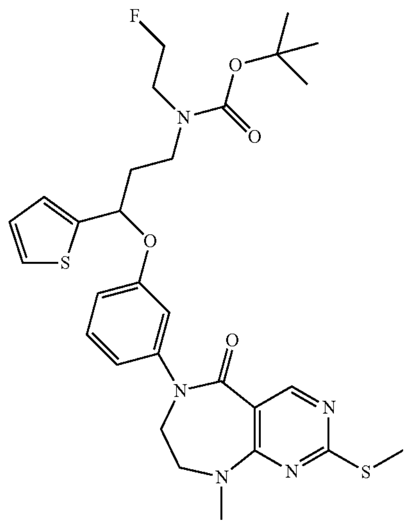 [SMILES: CSc1ncc2c(n1)N(C)CCN(c1cccc(OC(CCN(CCF)C(=O)OC(C)(C)C)c3cccs3)c1)C2=O] | tert-butyl (2-fluoroethyl) (3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl) carbamate | | B/5.65 | 602.2 (M + H) |

Example 62: tert-Butyl methyl(2-(3-((9-methyl-2-(methylthio)-5-oxo-5,7,8,9-tetrahydro-6H-pyrimido [4,5-e][1,4]diazepin-6-yl)methyl)phenoxy)-2-phenylethyl) carbamate

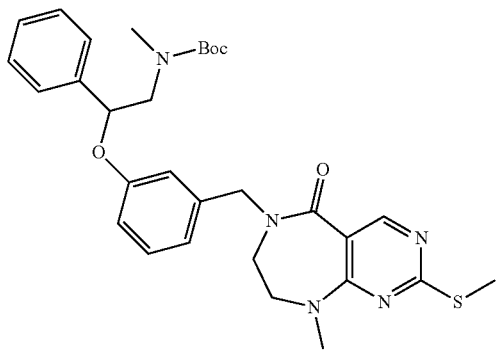 [SMILES: CSc1ncc2c(n1)N(C)CCN(Cc1cccc(OC(CN(C)C(=O)OC(C)(C)C)c3ccccc3)c1)C2=O]

To a solution of 9-methyl-2-(methylthio)-6,7,8,9-tetrahydro-5H-pyrimido[4,5-e][1,4]diazepin-5-one (INT 10, 70 mg, 0.31 mmol) in DMF (3 mL) cooled at 0° C., NaH (60% suspension in mineral oil, 19 mg, 0.46 mmol) was added and the mixture was stirred at rt for 30 min. The reaction mixture was cooled again at 0° C. and a solution of tert-butyl (2-(3-(chloromethyl)phenoxy)-2-phenylethyl)(methyl)carbamate (INT 5, 204 mg, 0.46 mmol) in DMF (2 mL) was added. The reaction mixture was stirred at rt for 16 h, water was added and extracted with EtOAc. The organic layer was dried with Na$_2$SO$_4$, filtered and concentrated under vacuum. Purification by flash chromatography, silica gel, gradient CH to 100% EtOAc afforded the title compound (155 mg, 88% yield). $^1$H-NMR, (CDCl$_3$, 300 MHz), δ (ppm): 1.44 (s, 9H), 2.56 (s, 3H), 2.93 (m, 3H), 3.10 (m, 1H), 3.16 (s, 3H), 3.31 (m, 3H), 3.49 (m, 1H), 3.67 (m, 1H), 4.42 (m, 1H), 4.83 (m, 1H), 5.34 (m, 1H), 7.77 (m, 3H), 7.22 (m, 6H), 8.83 (s, 1H).

This method was used for the preparation of Ex 63-64 using suitable starting materials:

| EX | Structure | Chemical name | 1H-NMR (ppm) | Method/Ret (min) | MS |
|---|---|---|---|---|---|
| 63 | 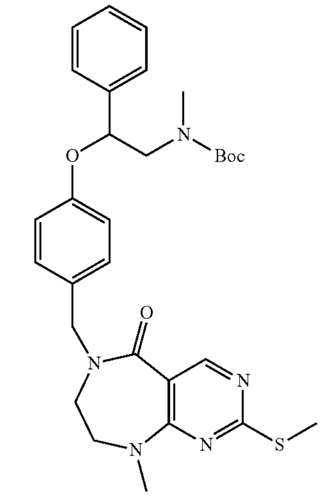 [SMILES: CSc1ncc2c(n1)N(C)CCN(Cc1ccc(OC(CN(C)C(=O)OC(C)(C)C)c3ccccc3)cc1)C2=O] | tert-butyl methyl(2-(4-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate | (300 MHz, CDCl$_3$):1.45(s, 9H), 2.51 (s, 3H), 2.92(m, 3 H), 3.17(s, 3H), 3.44(m, 5H), 3.68(m, 1H), 4.61(m, 2H), 5.34(m, 1H), 6.80(m, 2H), 7.12(m, 2H), 7.33(m, 5H), 8.78(s, 1H) | | 586.2 (M + Na) |
| 64 | 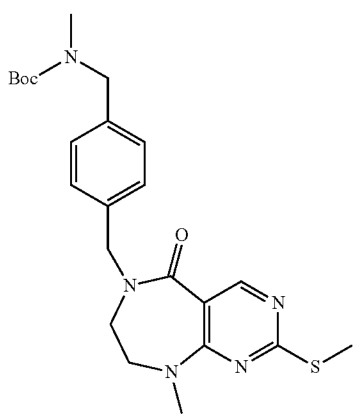 [SMILES: CSc1ncc2c(n1)N(C)CCN(Cc1ccc(CN(C)C(=O)OC(C)(C)C)cc1)C2=O] | tert-butyl methyl(4-((9-methyl-2-(methylthio)-5-oxo-5,7,8,9-tetrahydro-6H-pyrimido[4,5-e][1,4]diazepin-6-yl)methyl)benzyl)carbamate | (300 MHz, CDCl$_3$):1.48(s, 9H), 2.53(s, 3H), 2.81(bs, 3 H), 3.19(s, 3H), 3.49(m, 4H), 4.39(m, 2H), 4.73(s, 2H), 7.24(m, 4H), 8.82(s, 1H) | | 480.2 (M + Na) |

Example 65: tert-Butyl (R)-(3-((3-(2-(ethylamino)-9-methyl-5,7,8,9-tetrahydro-6H-pyrimido[4,5-e][1,4]diazepin-6-yl)benzyl)oxy)-3-phenylpropyl)(methyl)carbamate

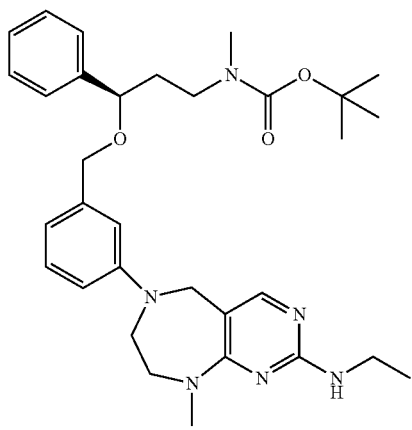 [SMILES: CCNc1ncc2c(n1)N(C)CCN(c1cccc(CO[C@H](CCN(C)C(=O)OC(C)(C)C)c3ccccc3)c1)C2]

A sealed tube was charged with Pd$_2$(dba)$_3$ (26 mg, 0.028 mmol), XPhos (27 mg, 0.056 mmol) and potassium tert-butoxide (31 mg, 0.28 mmol) under Ar atmosphere. A solution of tert-butyl (R)-(3-((3-bromobenzyl)oxy)-3-phenylpropyl)(methyl)carbamate (INT 2, 73 mg, 0.17 mmol) in deoxygenated anh toluene (0.5 mL) and a solution of N-ethyl-9-methyl-6,7,8,9-tetrahydro-5H-pyrimido[4,5-e][1,4]diazepin-2-amine (INT 12, 29 mg, 0.14 mmol) in deoxygenated anh toluene (0.5 mL) were added and the mixture was heated at 130° C. for 40 h. The reaction mixture was concentrated under vacuum and purified by flash chromatography, silica gel, gradient hexane to 15% acetone, to afford the title compound (12 mg, 15% yield). HPLC (Method B): Ret, 4.89 min; ESI$^+$-MS m/z, 561.4 (M+Na).

This method was used for the preparation of Ex 66 using suitable starting materials:

| EX | Structure | Chemical name | 1H-NMR (ppm) | Method/Ret (min) | MS |
|----|-----------|---------------|--------------|------------------|-----|
| 66 | 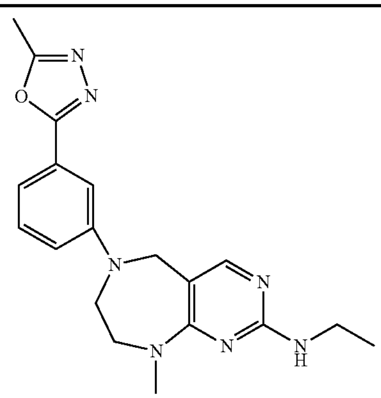 | N-ethyl-9-methyl-6-(3-(5-methyl-1,3,4-oxadiazol-2-yl)phenyl)-6,7,8,9-tetrahydro-5H-pyrimido[4,5-e][1,4]diazepin-2-amine | | A/5.51 | 366.2 (M + H) |

Example 67: N-ethyl-6-(3-methoxybenzyl)-9-methyl-6,7,8,9-tetrahydro-5H-pyrimido[4,5-e][1,4]diazepin-2-amine

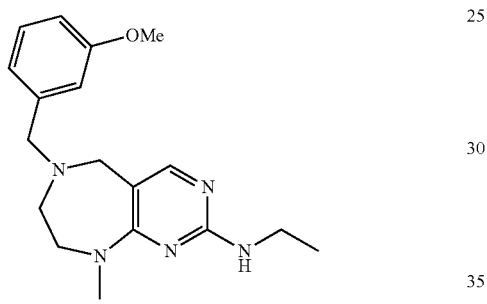

To a solution of N-ethyl-9-methyl-6,7,8,9-tetrahydro-5H-pyrimido[4,5-e][1,4]diazepin-2-amine (INT 12, 30 mg, 0.144 mmol) and DIPEA (0.076 mL, 0.436 mmol) in DCM (3.6 mL), 3-methoxybenzaldehyde (0.022 mL, 0.180 mmol) and NaBH(OAc)$_3$ (62 mg, 0.293 mmol) were added and the mixture was stirred at rt for 16 h. NaHCO$_3$ sat solution was added, extracted with DCM and the organic layer was concentrated under vacuum. Purification by flash chromatography, silica gel, gradient DCM to 10% MeOH afforded the desired product (25 mg, 58% yield). HPLC (Method A): Ret, 4.29 min; ESI$^+$-HRMS m/z, 328.2121 (M+H).

This method was used for the preparation of Ex 68 using suitable starting materials:

| EX | Structure | Chemical name | 1H-NMR (ppm) | Method/Ret (min) | MS |
|----|-----------|---------------|--------------|------------------|-----|
| 68 | 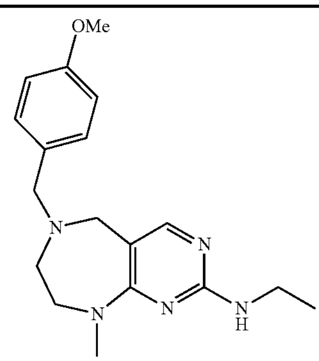 | N-ethyl-6-(4-methoxybenzyl)-9-methyl-6,7,8,9-tetrahydro-5H-pyrimido[4,5-e][1,4]diazepin-2-amine | | A/4.26 | 328.2 (M + H) |

Example 69: tert-Butyl (3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate

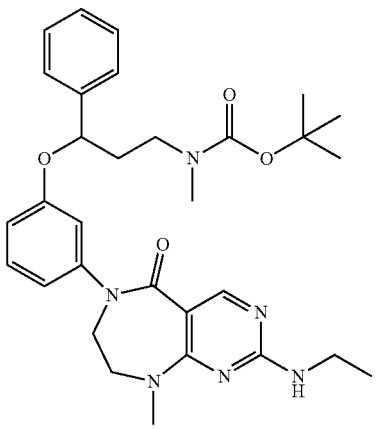 [SMILES: CCNc1ncc2c(n1)N(C)CCN(c1cccc(OC(CCN(C)C(=O)OC(C)(C)C)c3ccccc3)c1)C2=O]

To a solution of tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate (Obtained in Ex 1, 270 mg, 0.48 mmol) in DCM (6 mL), m-chloroperbenzoic acid (143 mg, 0.62 mmol) was added and the mixture was stirred at rt for 1 h. NaHCO$_3$ sat solution was added and the mixture was extracted with DCM. The organic layer was washed with brine, dried with Na$_2$SO$_4$ and the solvent removed under vacuum. The crude was dissolved in THF (6 mL), ethylamine (1.20 mL of a 2M solution in THF, 2.39 mmol) was added and the mixture was stirred at rt for 16 h. The crude residue was concentrated under vacuum and purified by flash chromatography, silica gel, gradient CH to 100% EtOAc, to afford the desired product (200 mg, 74% yield). HPLC (Method A): Ret, 7.13 min; ESI$^+$-MS m/z, 583.3 (M+Na).

This method was used for the preparation of Ex 70-137 using suitable starting materials:

| EX | Structure | Chemical name | 1H-NMR (ppm) | Method/Ret (min) | MS |
|---|---|---|---|---|---|
| 70 | 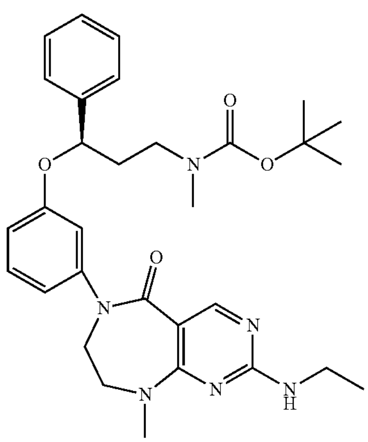 [SMILES: CCNc1ncc2c(n1)N(C)CCN(c1cccc(O[C@H](CCN(C)C(=O)OC(C)(C)C)c3ccccc3)c1)C2=O] | tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl) carbamate | (500 MHz, CDCl$_3$):1.24(t, J = 7 Hz, 3H), 1.43(s, 9H), 2.08(m, 1H), 2.16(m, 1H), 2.85(s, 3H), 3.20(s, 3H), 3.39 (m, 2H), 3.47 (m, 2H), 3.63 (m, 2H), 3.86 (m, 2H), 5.13 (m, 1H), 6.67 (m, 1H), 6.82 (m, 2H), 7.16 (m, 1H), 7.26 (m, 1H), 7.34 (m, 4H), 8.71 (s, 1H). | | 561.3 |
| 71 | 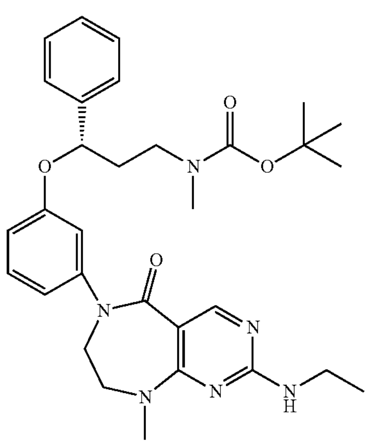 [SMILES: CCNc1ncc2c(n1)N(C)CCN(c1cccc(O[C@@H](CCN(C)C(=O)OC(C)(C)C)c3ccccc3)c1)C2=O] | tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl) carbamate | (300 MHz, CDCl$_3$):1.25(t, J = 7 Hz, 3H), 1.42(s, 9H), 2.11(m, 2H), 2.85(s, 3H), 3.20(s, 3H), 3.40(m, 2H), 3.48(m, 2H), 3.63(m, 2H), 3.87(m, 2H), 5.11 (m, 1H), 6.68(m, 1H), 6.83(m, 2H), 7.17(m, 1H), 7.26(m, 1H), 7.35(m, 4H), 8.71(s, 1H). | | |

-continued

| EX | Structure | Chemical name | 1H-NMR (ppm) | Method/ Ret (min) | MS |
|---|---|---|---|---|---|
| 72 | 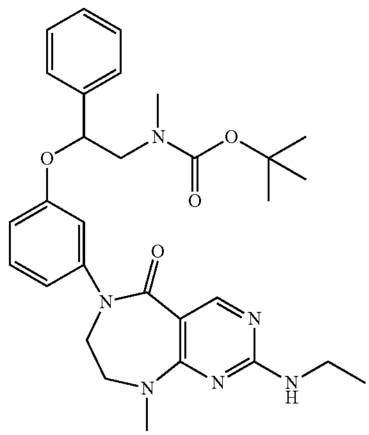 [SMILES: CCNc1ncc2c(n1)N(C)CCN(c1cccc(OC(CN(C)C(=O)OC(C)(C)C)c3ccccc3)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate | | A/ 6.96 | 547.3 |
| 73 | 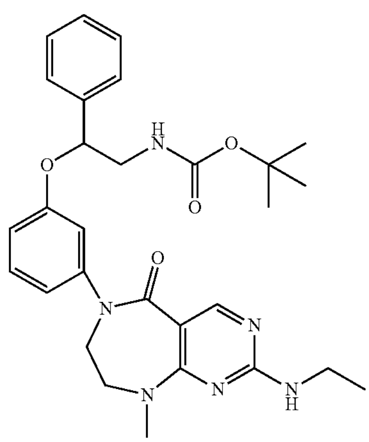 [SMILES: CCNc1ncc2c(n1)N(C)CCN(c1cccc(OC(CNC(=O)OC(C)(C)C)c3ccccc3)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)carbamate | | A/ 6.66 | 555.2 (M + Na) |
| 74 | 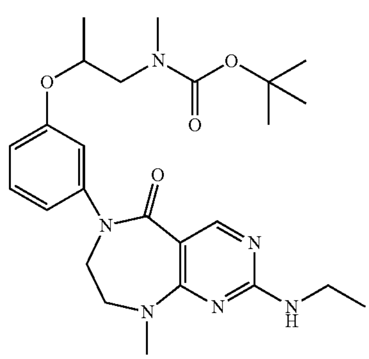 [SMILES: CCNc1ncc2c(n1)N(C)CCN(c1cccc(OC(C)CN(C)C(=O)OC(C)(C)C)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate | | A/ 6.47 | 507.3 (M + Na) |

-continued

| EX | Structure | Chemical name | 1H-NMR (ppm) | Method/ Ret (min) | MS |
|---|---|---|---|---|---|
| 75 | 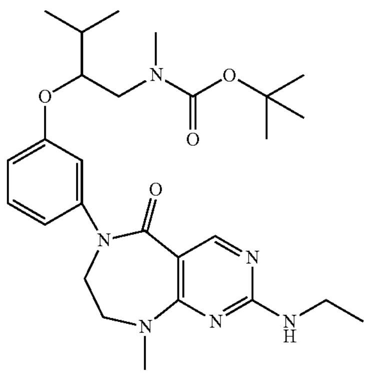 [SMILES: CCNc1ncc2c(n1)N(C)CCN(c1cccc(OC(CN(C)C(=O)OC(C)(C)C)C(C)C)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)-3-methylbutyl)(methyl)carbamate | | A/ 6.98 | 535.2 (M + Na) |
| 76 | 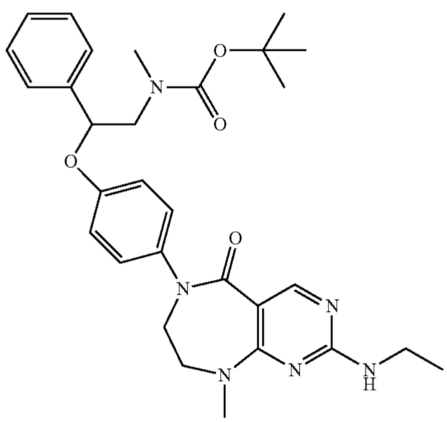 [SMILES: CCNc1ncc2c(n1)N(C)CCN(c1ccc(OC(CN(C)C(=O)OC(C)(C)C)c3ccccc3)cc1)C2=O] | tert-butyl (2-(4-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate | | A/ 7.00 | 547.3 (M + H) |
| 77 | 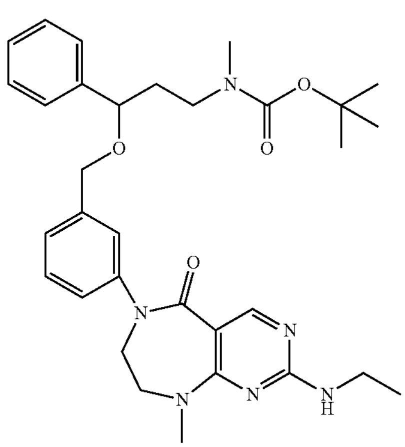 [SMILES: CCNc1ncc2c(n1)N(C)CCN(c1cccc(COC(CCN(C)C(=O)OC(C)(C)C)c3ccccc3)c1)C2=O] | tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate | | B/ 4.78 | 575.3 (M + H) |

-continued

| EX | Structure | Chemical name | 1H-NMR (ppm) | Method/Ret (min) | MS |
|---|---|---|---|---|---|
| 78 | 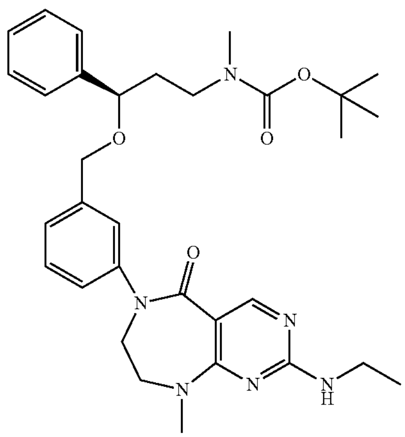 [SMILES: CCNc1ncc2c(n1)N(C)CCN(c1cccc(CO[C@H](CCN(C)C(=O)OC(C)(C)C)c3ccccc3)c1)C2=O] | tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl) carbamate | (300 MHz, CDCl$_3$):1.25(t, J = 7 Hz, 3H), 1.43(s, 9H), 1.92(m, 1H), 2.05(m, 1H), 2.82(s, 3H), 3.23(s, 3H), 3.33 (m, 2H), 3.48 (m, 2H), 3.73 (m, 2H), 3.98 (m, 2H), 4.35 (m, 3H), 5.26 (bs, 1H), 7.21 (m, 3H), 7.35 (m, 6H), 8.73 (s, 1H). | | |
| 79 | 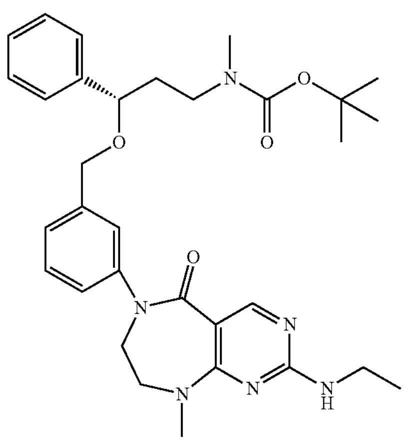 [SMILES: CCNc1ncc2c(n1)N(C)CCN(c1cccc(CO[C@@H](CCN(C)C(=O)OC(C)(C)C)c3ccccc3)c1)C2=O] | tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl) carbamate | (400 MHz, CDCl$_3$):1.27(t, J = 7 Hz, 3H), 1.44(s, 9H), 1.92(m, 1H), 2.07(m, 1H), 2.83(s, 3H), 3.24 (s, 3H), 3.35 (m, 2H), 3.49 (m, 2H), 3.74 (m, 2H), 3.98 (m, 2H), 4.35 (m, 3H), 5.16 (bs, 1H), 7.22 (m, 3H), 7.36 (m, 6H), 8.74 (s, 1H). | | 575.3 (M + H) |
| 80 | 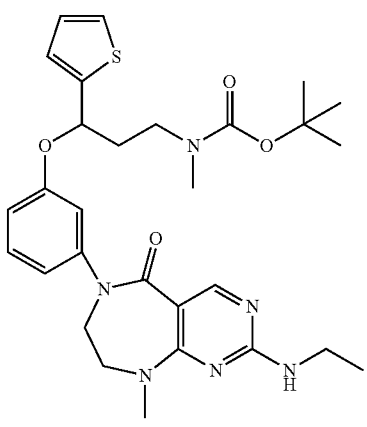 [SMILES: CCNc1ncc2c(n1)N(C)CCN(c1cccc(OC(CCN(C)C(=O)OC(C)(C)C)c3cccs3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl) carbamate | (300 MHz, CDCl$_3$):1.26(t, J = 7 Hz, 3H), 1.43(s, 9H), 2.19(m, 1H), 2.30(m, 1H), 2.86(s, 3H), 3.22 (s, 3H), 3.40 (m, 2H), 3.48 (m, 2H), 3.68 (m, 2H), 3.91 (m, 2H), 5.12 (m, 2H), 5.42 (bs, 1H), 6.79 (m, 1H), 6.88 (m, 1H), 6.96 (m, 2H), 7.03 (m, 1H), 7.24 (m, 2H), 8.72 (s, 1H). | | 567.3 (M + H) |

-continued

| EX | Structure | Chemical name | 1H-NMR (ppm) | Method/ Ret (min) | MS |
|---|---|---|---|---|---|
| 81 | 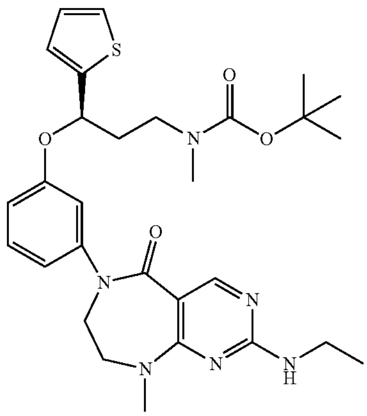 [SMILES: CCNc1ncc2c(n1)N(C)CCN(c1cccc(O[C@H](CCN(C)C(=O)OC(C)(C)C)c3cccs3)c1)C2=O] | tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl) carbamate | (400 MHz, CDCl₃):1.26(t, J = 7 Hz, 3H), 1.43(s, 9H), 2.19(m, 1H), 2.30(m, 1H), 2.86(s, 3H), 3.22 (s, 3H), 3.39 (m, 2H), 3.49 (m, 2H), 3.69 (m, 2H), 3.91 (m, 2H), 5.21 (bs, 1H), 5.43 (m, 1H), 6.80 (m, 1H), 6.88 (m, 2H), 6.95 (m, 1H), 7.04 (m, 1H), 7.23 (m, 2H), 8.72 (s, 1H). | | |
| 82 | 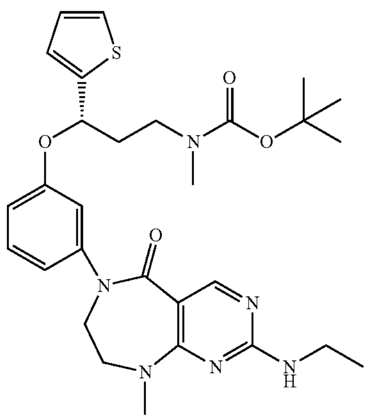 [SMILES: CCNc1ncc2c(n1)N(C)CCN(c1cccc(O[C@@H](CCN(C)C(=O)OC(C)(C)C)c3cccs3)c1)C2=O] | tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl) carbamate | (400 MHz, CDCl₃):1.26(t, J = 7 Hz, 3H), 1.43(s, 9H), 2.19(m, 1H), 2.30(m, 1H), 2.86(s, 3H), 3.22 (s, 3H), 3.39 (m, 2H), 3.49 (m, 2H), 3.69 (m, 2H), 3.91 (m, 2H), 5.21 (bs, 1H), 5.43 (m, 1H), 6.80 (m, 1H), 6.88 (m, 1H), 6.95 (m, 2H), 7.04 (m, 1H), 7.23 (m, 1H), 8.72 (m, 2H), (s, 1H). | | |
| 83 | 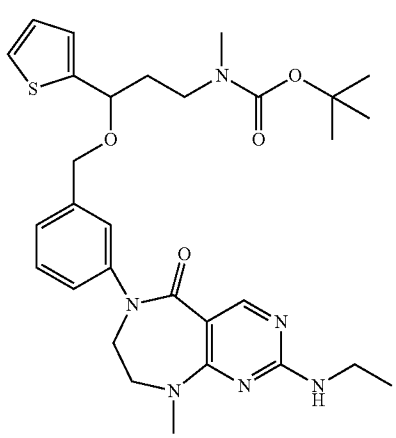 | tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | | A/ 7.07 | 581.3 (M + H) |

-continued

| EX | Structure | Chemical name | 1H-NMR (ppm) | Method/Ret (min) | MS |
|---|---|---|---|---|---|
| 84 | 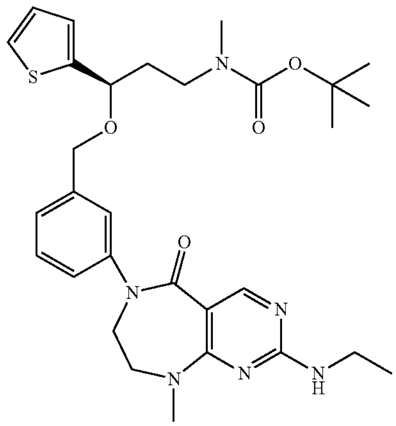 [SMILES: CCNc1ncc2c(n1)N(C)CCN(c1cccc(CO[C@H](CCN(C)C(=O)OC(C)(C)C)c3cccs3)c1)C2=O] | tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | (400 MHz, CDCl₃):1.26(t, J = 7 Hz, 3H), 1.45(s, 9H), 2.03(m, 1H), 2.18(m, 1H), 2.84(s, 3H), 3.24 (s, 3H), 3.34 (m, 2H), 3.50 (m, 2H), 3.74 (m, 2H), 3.99 (m, 2H), 4.35 (m, 1H), 4.51 (m, 1H), 4.63 (m, 1H), 5.11 (bs, 1H), 7.01 (m, 2H), 7.22 (m, 3H), 7.31 (m, 1H), 7.38 (m, 1H), 8.74(s, 1H). | | |
| 85 | 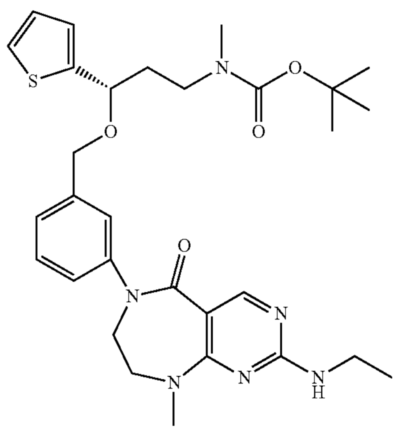 [SMILES: CCNc1ncc2c(n1)N(C)CCN(c1cccc(CO[C@@H](CCN(C)C(=O)OC(C)(C)C)c3cccs3)c1)C2=O] | tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | (400 MHz, CDCl₃):1.26(t, J = 7 Hz, 3H), 1.45(s, 9H), 2.03(m, 1H), 2.18(m, 1H), 2.84(s, 3H), 3.24 (s, 3H), 3.34 (m, 2H), 3.50 (m, 2H), 3.74 (m, 2H), 3.99 (m, 2H), 4.35 (m, 1H), 4.51 (m, 1H), 4.63 (m, 1H), 5.11 (bs, 1H), 7.01 (m, 2H), 7.22 (m, 3H), 7.31 (m, 1H), 7.38(m, 1H), 8.74(s, 1H). | | |
| 86 | 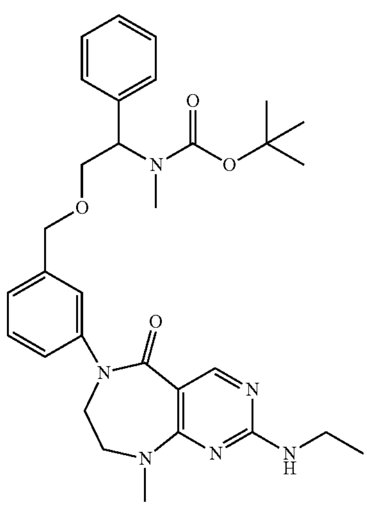 [SMILES: CCNc1ncc2c(n1)N(C)CCN(c1cccc(COCC(c3ccccc3)N(C)C(=O)OC(C)(C)C)c1)C2=O] | tert-butyl (2-((3-(2-(ethylamino)-9-methyl-5-oxo-5,7,8,9-tetrahydro-6H-pyrimido[4,5-e][1,4]diazepin-6-yl)benzyl)oxy)-1-phenylethyl)(methyl) carbamate | (400 MHz, CDCl₃):1.26(t, J = 7 Hz, 3H), 1.46(s, 9H), 2.71(s, 3H), 3.23(s, 3H), 3.48 (m, 2H), 3.73(m, 2H), 3.96(m, 4H), 4.62(m, 2H), 5.54(m, 1H), 7.25(m, 6H), 7.35(m, 3H), 8.74(s, 1H). | | 561.3 (M + H) |

| EX | Structure | Chemical name | 1H-NMR (ppm) | Method/Ret (min) | MS |
|---|---|---|---|---|---|
| 87 | 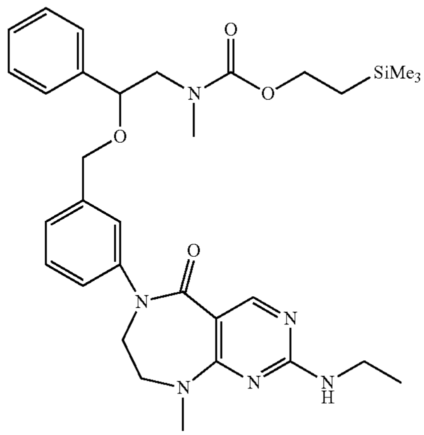 [SMILES: CCNc1ncc2c(n1)N(C)CCN(c1cccc(COC(CN(C)C(=O)OCC[Si](C)(C)C)c3ccccc3)c1)C2=O] | 2-(trimethylsilyl)ethyl (2-((3-(2-(ethylamino)-9-methyl-5-oxo-5,7,8,9-tetrahydro-6H-pyrimido[4,5-e][1,4]diazepin-6-yl)benzyl)oxy)-2-phenylethyl)(methyl)carbamate | (300 MHz CDCl$_3$):0.04(s, 9H), 0.95(m, 2H), 1.25(t, J = 7 Hz, 3H), 2.90 (m, 3H), 3.23 (s, 3H), 3.47 (m, 4H), 3.73 (m, 2H), 3.96 (m, 2H), 4.06 (m, 1H), 4.18 (m, 1H), 4.31 (m, 1H), 4.51 (m, 1H), 4.64 (m, 1H), 7.20 (m, 3H), 7.36 (m, 6H), 8.73 (s, 1H). | | 605.3 (M + H) |
| 88 | 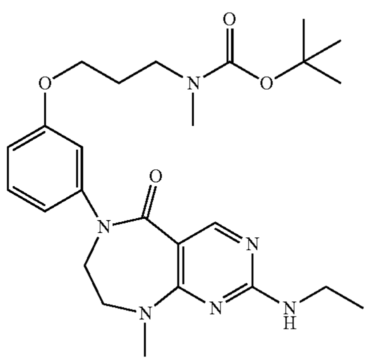 [SMILES: CCNc1ncc2c(n1)N(C)CCN(c1cccc(OCCCN(C)C(=O)OC(C)(C)C)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate | | A/ 6.37 | 507.3 (M + Na) |
| 89 | 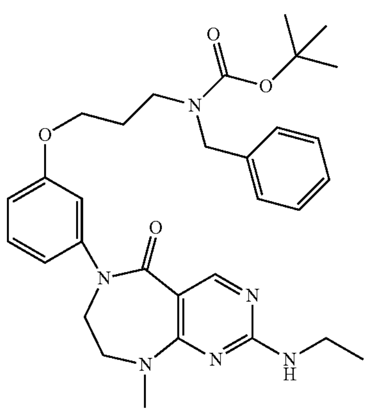 [SMILES: CCNc1ncc2c(n1)N(C)CCN(c1cccc(OCCCN(Cc3ccccc3)C(=O)OC(C)(C)C)c1)C2=O] | tert-butyl benzyl (3-(3-(2-(ethylamino)-9-methyl-5-oxo-5,7,8,9-tetrahydro-6H-pyrimido[4,5-e][1,4]diazepin-6-yl)phenoxy)propyl)carbamate | | A/ 7.19 | 583.2 (M + Na) |
| 90 | 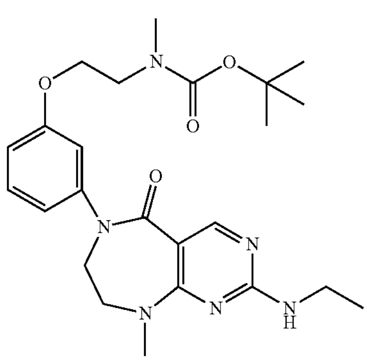 [SMILES: CCNc1ncc2c(n1)N(C)CCN(c1cccc(CCCN(C)C(=O)OC(C)(C)C)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)ethyl)(methyl)carbamate | | B/ 4.22 | 471.3 |

| EX | Chemical name | 1H-NMR (ppm) | Method/Ret (min) | MS |
|---|---|---|---|---|
| 91 | tert-butyl (3-(3-(2-(ethylamino)-9-methyl-5-oxo-5,7,8,9-tetrahydro-6H-pyrimido[4,5-e][1,4]diazepin-6-yl)phenyl)propyl)(methyl)carbamate | (300 MHz, CDCl₃):1.24(t, J = 7 Hz, 3H), 1.46(s ,9H), 1.85(m, 2H), 2.61(m, 2H), 2.86(s, 3H), 3.24 (s, 3H), 3.29 (m, 2H), 3.47 (m, 2H), 3.74 (m, 2H), 3.96 (m, 2H), 7.10 (m, 3H), 7.32 (m, 1H), 8.73(s, 1H). | | 469.3 (M + H) |
| 92 | tert-butyl (3-(2-(ethylamino)-9-methyl-5-oxo-5,7,8,9-tetrahydro-6H-pyrimido[4,5-e][1,4]diazepin-6-yl)phenethyl)(methyl)carbamate | | A/ 6.21 | 477.3 (M + Na) |
| 93 | tert-butyl (2-(3-(2-(ethylamino)-9-methyl-5-oxo-5,7,8,9-tetrahydro-6H-pyrimido[4,5-e][1,4]diazepin-6-yl)phenyl)-2-methylpropyl)(methyl)carbamate | (400 MHz, CDCl₃):1.25(t, J = 7 Hz, 3H), 1.36(s, 6H), 1.44(s, 9H), 2.53(m, 3H), 3.24(s, 3H), 3.43(m, 2H), 3.48 (m, 2H), 3.73(m, 2H), 3.98(m, 2H), 7.12(m, 1H), 7.27(m, 2H), 7.35(m, 1H), 8.72(s, 1H). | | |
| 94 | tert-butyl (3-(2-(ethylamino)-9-methyl-5-oxo-5,7,8,9-tetrahydro-6H-pyrimido[4,5-e][1,4]diazepin-6-yl)benzyl)(methyl)carbamate | (400 MHz, CDCl₃):1.24(t, J = 7 Hz, 3H), 1.48(s, 9H), 2.84(m, 3H), 3.22(s, 3H), 3.46(m, 2H), 3.71(m, 2H), 3.97(m, 2H), 4.43(m, 2H), 7.12(m, 2H), 7.19(m, 1H), 7.36(m, 1H), 8.71 (s, 1H). | | 463.2 (M + Na) |

| EX | Structure | Chemical name | 1H-NMR (ppm) | Method/Ret (min) | MS |
|---|---|---|---|---|---|
| 95 | 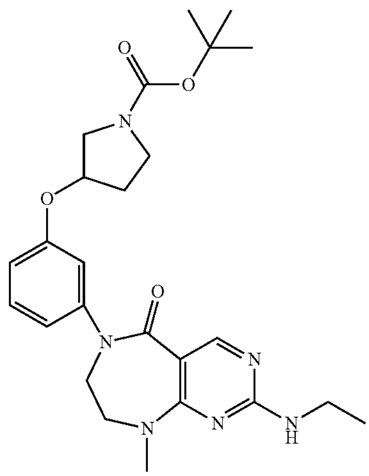 [SMILES: CCNc1ncc2c(n1)N(C)CCN(c1cccc(OC3CCN(C(=O)OC(C)(C)C)C3)c1)C2=O] | tert-butyl 3-(3-(2-(ethylamino)-9-methyl-5-oxo-5,7,8,9-tetrahydro-6H-pyrimido[4,5-e][1,4]diazepin-6-yl)phenoxy)pyrrolidine-1-carboxylate | (500 MHz, CDCl₃):1.25(t, J = 7 Hz, 3H), 1.48(s, 9H), 2.16(m, 2H), 3.23(s, 3H), 3.48(m, 2H), 3.57(m, 4H), 3.73(m, 2H), 3.97(m, 2H), 4.90(m, 1H), 6.77(m, 1H), 6.86(m, 1H), 6.89(m, 1H), 7.31(m, 1H), 8.73(s, 1H). | | 505.2 (M + Na) |
| 96 | 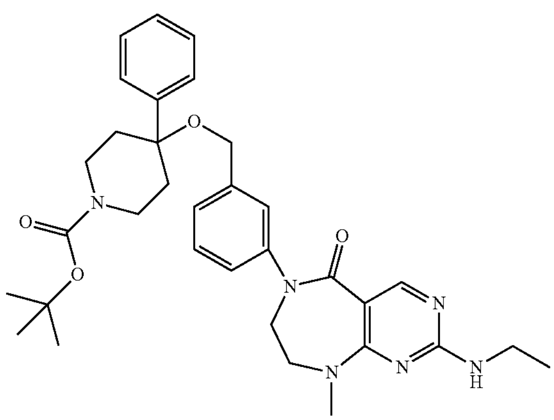 [SMILES: CCNc1ncc2c(n1)N(C)CCN(c1cccc(COC3(c4ccccc4)CCN(C(=O)OC(C)(C)C)CC3)c1)C2=O] | tert-butyl 4-((3-(2-(ethylamino)-9-methyl-5-oxo-5,7,8,9-tetrahydro-6H-pyrimido[4,5-e][1,4]diazepin-6-yl)benzyl)oxy)-4-phenylpiperidine-1-carboxylate | (400 MHz, CDCl₃):1.23(t, J = 7 Hz, 3H), 1.47(s, 9H), 1.92(m, 2H), 2.15(m, 2H), 3.22(s, 3H), 3.27(m, 2H), 3.45(m, 2H), 3.71(m, 2H), 3.96(m, 2H), 4.01(m, 2H), 4.12(m, 2H), 7.19(m, 3H), 7.28(m, 1H), 7.36(m, 3H), 7.44(m, 2H), 8.73(s, 1H). | | 587.3 (M + H) |
| 97 | 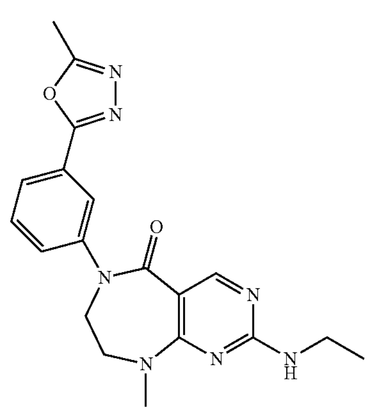 [SMILES: CCNc1ncc2c(n1)N(C)CCN(c1cccc(-c3nnc(C)o3)c1)C2=O] | 2-(ethylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | | A/ 4.88 | 380.2 (M + H) |

| EX | Structure | Chemical name | 1H-NMR (ppm) | Method/ Ret (min) | MS |
|---|---|---|---|---|---|
| 98 | 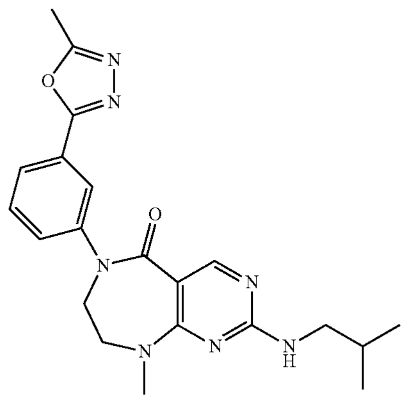 [SMILES: Cc1nnc(-c2cccc(N3CCN(C)c4nc(NCC(C)C)ncc4C3=O)c2)o1] | 2-(isobutylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | | A/ 5.55 | 408.2 (M + H) |
| 99 | 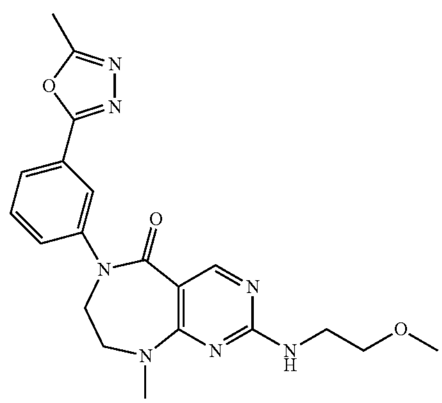 [SMILES: COCCNc1ncc2c(n1)N(C)CCN(c1cccc(-c3nnc(C)o3)c1)C2=O] | 2-((2-methoxyethyl)amino)-9-methyl-6-(3-(5-methyl-1,3,4-oxadiazol-2-yl)phenyl)-6,7,8,9-tetrahydro-5H-pyrimido[4,5-e][1,4]diazepin-5-one | | A/ 4.74 | 410.2 (M + H) |
| 100 | 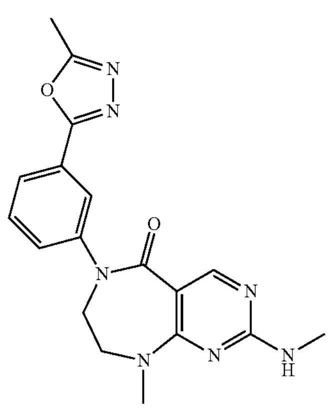 [SMILES: CNc1ncc2c(n1)N(C)CCN(c1cccc(-c3nnc(C)o3)c1)C2=O] | 9-methyl-6-(3-(5-methyl-1,3,4-oxadiazol-2-yl)phenyl)-2-(methylamino)-6,7,8,9-tetrahydro-5H-pyrimido[4,5-e][1,4]diazepin-5-one | | A/ 4.65 | 366.2 (M + H) |

-continued

| EX | Structure | Chemical name | 1H-NMR (ppm) | Method/ Ret (min) | MS |
|---|---|---|---|---|---|
| 101 | 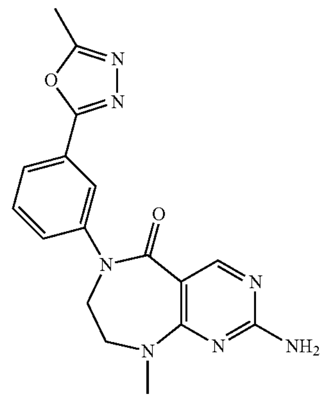 [SMILES: Cc1nnc(-c2cccc(N3CCN(C)c4nc(N)ncc4C3=O)c2)o1] | 2-amino-9-methyl-6-(3-(5-methyl-1,3,4-oxadiazol-2-yl)phenyl)-6,7,8,9-tetrahydro-5H-pyrimido[4,5-e][1,4]diazepin-5-one | | A/ 4.40 | 352.2 (M + H) |
| 102 | 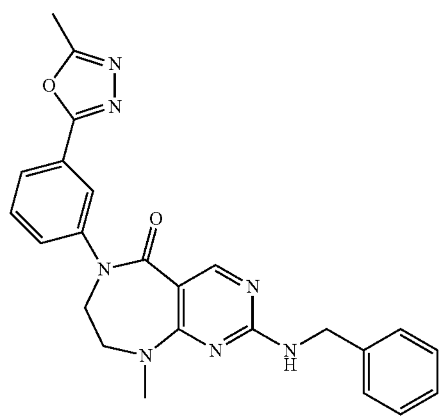 [SMILES: Cc1nnc(-c2cccc(N3CCN(C)c4nc(NCc5ccccc5)ncc4C3=O)c2)o1] | 2-(benzylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | | A/ 5.61 | 442.2 (M + H) |
| 103 | 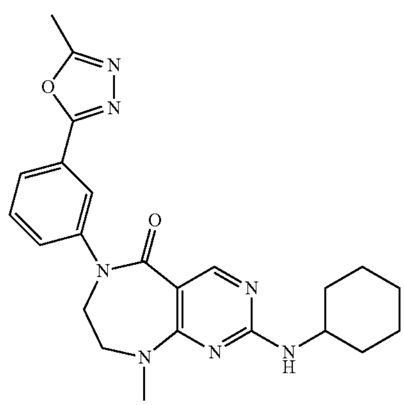 [SMILES: Cc1nnc(-c2cccc(N3CCN(C)c4nc(NC5CCCCC5)ncc4C3=O)c2)o1] | 2-(cyclohexylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | | A/ 5.81 | 434.2 (M + H) |

-continued

| EX | Structure | Chemical name | 1H-NMR (ppm) | Method/ Ret (min) | MS |
|---|---|---|---|---|---|
| 104 | 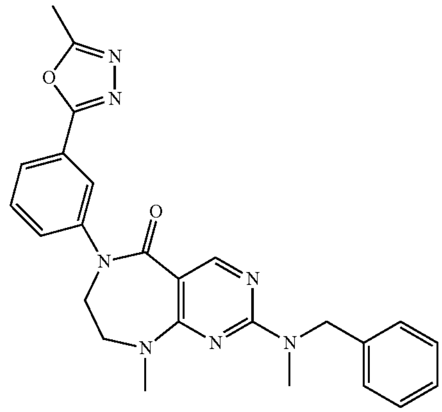 [SMILES: Cc1nnc(-c2cccc(N3CCN(C)c4nc(N(C)Cc5ccccc5)ncc4C3=O)c2)o1] | 2-(benzyl(methyl)amino)-9-methyl-6-(3-(5-methyl-1,3,4-oxadiazol-2-yl)phenyl)-6,7,8,9-tetrahydro-5H-pyrimido[4,5-e][1,4]diazepin-5-one | | A/ 5.71 | 456.2 (M + H) |
| 105 | 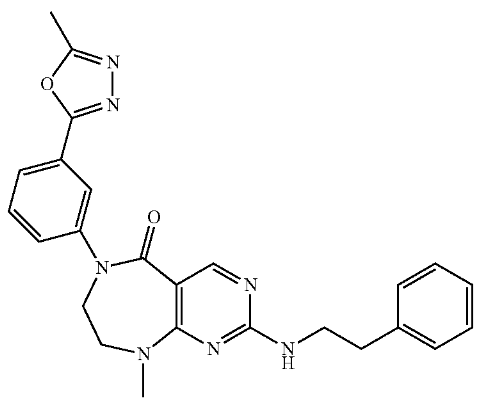 [SMILES: Cc1nnc(-c2cccc(N3CCN(C)c4nc(NCCc5ccccc5)ncc4C3=O)c2)o1] | 9-methyl-6-(3-(5-methyl-1,3,4-oxadiazol-2-yl)phenyl)-2-(phenethylamino)-6,7,8,9-tetrahydro-5H-pyrimido[4,5-e][1,4]diazepin-5-one | | A/ 5.77 | 456.2 (M + H) |
| 106 | 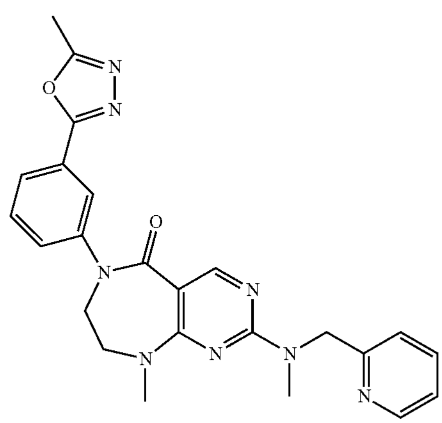 [SMILES: Cc1nnc(-c2cccc(N3CCN(C)c4nc(N(C)Cc5ccccn5)ncc4C3=O)c2)o1] | 9-methyl-2-(methyl(pyridin-2-ylmethyl)amino)-6-(3-(5-methyl-1,3,4-oxadiazol-2-yl)phenyl)-6,7,8,9-tetrahydro-5H-pyrimido[4,5-e][1,4]diazepin-5-one | | A/ 4.42 | 457.2 (M + H) |

-continued

| EX | Structure | Chemical name | 1H-NMR (ppm) | Method/Ret (min) | MS |
|---|---|---|---|---|---|
| 107 | 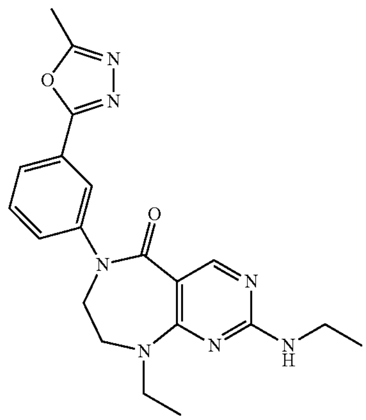 [SMILES: CCNc1ncc2c(n1)N(CC)CCN(c1cccc(-c3nnc(C)o3)c1)C2=O] | 9-ethyl-2-(ethylamino)-6-(3-(5-methyl-1,3,4-oxadiazol-2-yl)phenyl)-6,7,8,9-tetrahydro-5H-pyrimido[4,5-e][1,4]diazepin-5-one | | A/ 5.25 | 394.2 (M + H) |
| 108 | 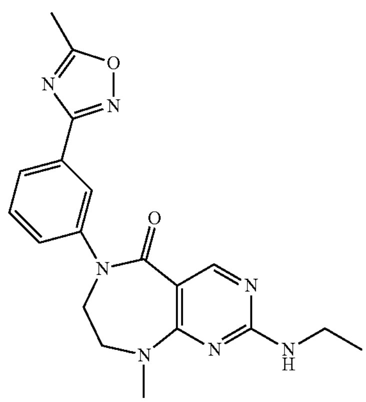 [SMILES: CCNc1ncc2c(n1)N(C)CCN(c1cccc(-c3noc(C)n3)c1)C2=O] | 2-(ethylamino)-9-methyl-6-(3-(5-methyl-1,2,4-oxadiazol-3-yl)phenyl)-6,7,8,9-tetrahydro-5H-pyrimido[4,5-e][1,4]diazepin-5-one | | A/ 5.36 | 380.2 (M + H) |
| 109 | 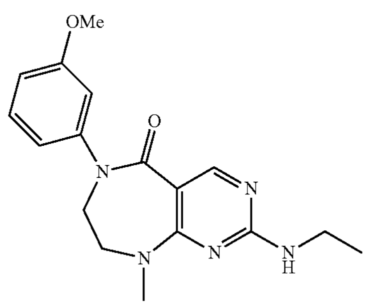 [SMILES: CCNc1ncc2c(n1)N(C)CCN(c1cccc(OC)c1)C2=O] | 2-(ethylamino)-6-(3-methoxyphenyl)-9-methyl-6,7,8,9-tetrahydro-5H-pyrimido[4,5-e][1,4]diazepin-5-one | | A/ 5.21 | 328.2 (M + H) |
| 110 | 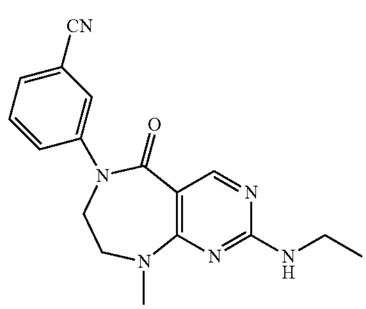 [SMILES: CCNc1ncc2c(n1)N(C)CCN(c1cccc(C#N)c1)C2=O] | 3-(2-(ethylamino)-9-methyl-5-oxo-5,7,8,9-tetrahydro-6H-pyrimido[4,5-e][1,4]diazepin-6-yl)benzonitrile | | A/ 5.03 | 323.2 (M + H) |

-continued

| EX | Structure | Chemical name | 1H-NMR (ppm) | Method/Ret (min) | MS |
|----|-----------|---------------|--------------|------------------|-----|
| 111 | 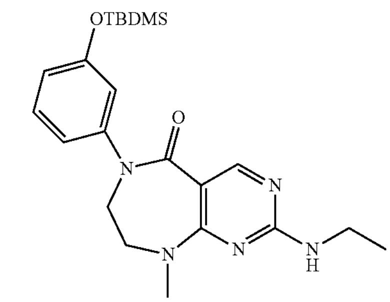 [SMILES: CCNc1ncc2c(n1)N(C)CCN(c1cccc(O[Si](C)(C)C(C)(C)C)c1)C2=O] | 6-(3-((tert-butyldimethylsilyl)oxy)phenyl)-2-(ethylamino)-9-methyl-6,7,8,9-tetrahydro-5H-pyrimido[4,5-e][1,4]diazepin-5-one | (500 MHz, CDCl$_3$):0.23(s, 6H), 0.99(s, 9H), 1.25(t, J = 7 Hz, 3H), 3.23 (m, 3H), 3.47 (m, 2H), 3.71 (m, 2H), 3.96 (m, 2H), 6.74 (m, 1H), 6.79 (t, J = 2 Hz, 1H), 6.89(m, 1H), 7.24(t, J = 8 Hz, 1H), 8.73(s, 1H). | | 428.2 (M + H) |
| 112 | 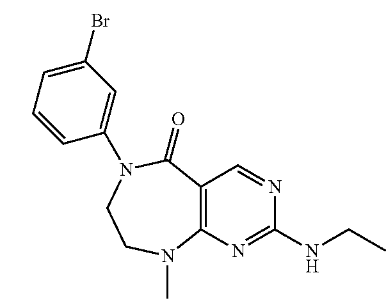 | 6-(3-bromophenyl)-2-(ethylamino)-9-methyl-6,7,8,9-tetrahydro-5H-pyrimido[4,5-e][1,4]diazepin-5-one | (400 MHz, CDCl$_3$):1.26(t, J = 7 Hz, 3H), 3.22(m, 3H), 3.47(m, 2H), 3.73(m, 2H), 3.96(m, 2H), 7.25(m, 2H), 7.39(m, 1H), 7.46(m, 1H), 8.72(s, 1H). | | 376.0 (M + H) |
| 113 | 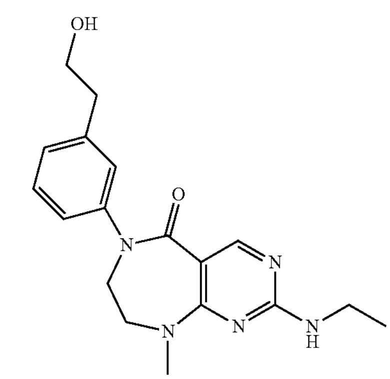 [SMILES: CCNc1ncc2c(n1)N(C)CCN(c1cccc(CCO)c1)C2=O] | 2-(ethylamino)-6-(3-(2-hydroxyethyl)phenyl)-9-methyl-6,7,8,9-tetrahydro-5H-pyrimido[4,5-e][1,4]diazepin-5-one | (300 MHz, CD$_3$OD):1.23(t, J = 7 Hz, 3H), 2.85(t, J = 6.7 Hz, 2H), 3.26 (m, 3H), 3.44 (q, J = 7 Hz, 2H), 3.77(m, 4H), 3.99(m, 2H), 7.16(m, 3H), 7.36(m, 1H), 8.54(s, 1H). | | 342.2 (M + H) |
| 114 | 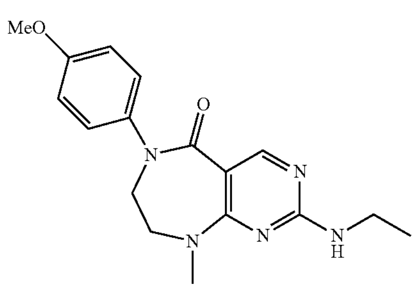 [SMILES: CCNc1ncc2c(n1)N(C)CCN(c1ccc(OC)cc1)C2=O] | 2-(ethylamino)-6-(4-methoxyphenyl)-9-methyl-6,7,8,9-tetrahydro-5H-pyrimido[4,5-e][1,4]diazepin-5-one | | A/ 5.18 | 328.2 (M + H) |

| EX | Structure | Chemical name | 1H-NMR (ppm) | Method/ Ret (min) | MS |
|---|---|---|---|---|---|
| 115 | 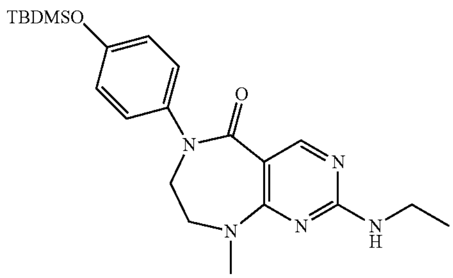 [SMILES: CCNc1ncc2c(n1)N(C)CCN(c1ccc(O[Si](C)(C)C(C)(C)C)cc1)C2=O] | 6-(4-((tert-butyldimethylsilyl)oxy) phenyl)-2-(ethylamino)-9-methyl-6,7,8,9-tetrahydro-5H-pyrimido[4,5-e][1,4]diazepin-5-one | (500 MHz, CDCl$_3$):0.22(s, 6H), 1.00(s, 9H), 1.25(t, J = 7.3 Hz, 3H), 3.22(s, 3H), 3.47(m, 2H), 3.72(m, 2H), 3.93(m, 2H), 6.85(dAB, 2H), 7.13(dAB, 2H), 8.73(s, 1H) | | 428.2 (M + H) |
| 116 | 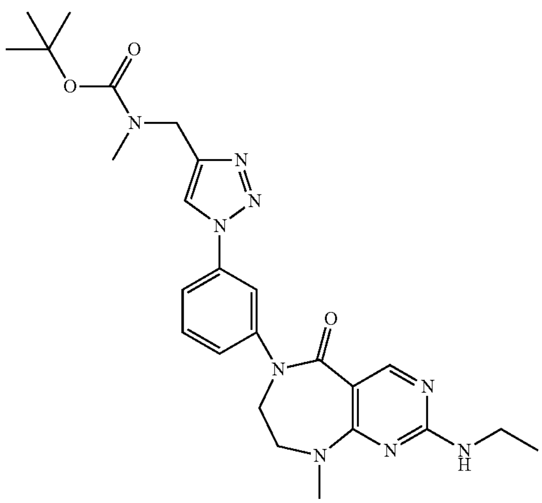 [SMILES: CCNc1ncc2c(n1)N(C)CCN(c1cccc(-n3cc(CN(C)C(=O)OC(C)(C)C)nn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)(methyl) carbamate | | A/ 5.92 | 508.2 (M + H) |
| 117 | 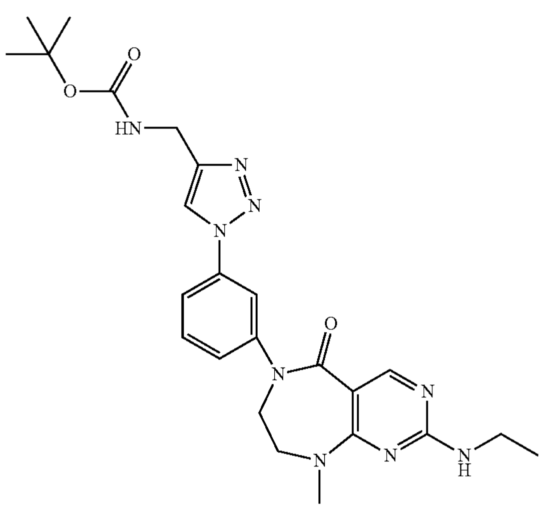 [SMILES: CCNc1ncc2c(n1)N(C)CCN(c1cccc(-n3cc(CNC(=O)OC(C)(C)C)nn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate | (500 MHz, CDCl$_3$):1.24(t, J = 7, 2 Hz, 3H), 1.45(s, 9H), 3.23(s, 3H), 3.47(m, 2H),3.76 (m, 2H), 4.02 (m, 2H),4.45 (d, H = 6 Hz, 2H), 5.40(m, 1H), 7.36(m, 1H), 7.51(m, 1H), 7.57(m, 1H), 7.72(m, 1H), 7.99(s, 1H), 8.70(s, 1 H) | A/ 5.62 | |

| EX | Structure | Chemical name | 1H-NMR (ppm) | Method/Ret (min) | MS |
|---|---|---|---|---|---|
| 118 | 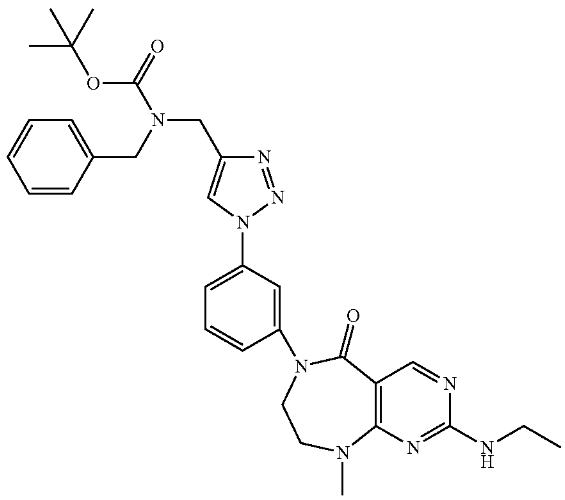 [SMILES: CCNc1ncc2c(n1)N(C)CCN(c1cccc(-n3cc(CN(Cc4ccccc4)C(=O)OC(C)(C)C)nn3)c1)C2=O] | tert-butyl benzyl((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate | | A/ 6.78 | 606.3 (M + Na) |
| 119 | 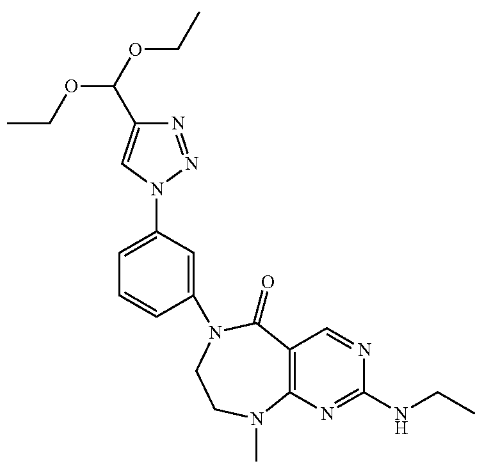 [SMILES: CCNc1ncc2c(n1)N(C)CCN(c1cccc(-n3cc(C(OCC)OCC)nn3)c1)C2=O] | 6-(3-(4-(diethoxymethyl)-1H-1,2,3-triazol-1-yl)phenyl)-2-(ethylamino)-9-methyl-6,7,8,9-tetrahydro-5H-pyrimido[4,5-e][1,4]diazepin-5-one | (400 MHz, CDCl$_3$):1.28(m, 9H), 3.27(m, 3H), 3.49(m, 2H), 3.70(m, 4H), 3.80(m, 2H), 4.07(m, 2H), 5.80(s, 1H), 7.39(m, 1H), 7.56(t, J = 7.8 Hz, 1H), 7.64(m, 1H), 7.76(m, 1H), 8.07s, 1H), 8.72 (s, 1H). | | |
| 120 | 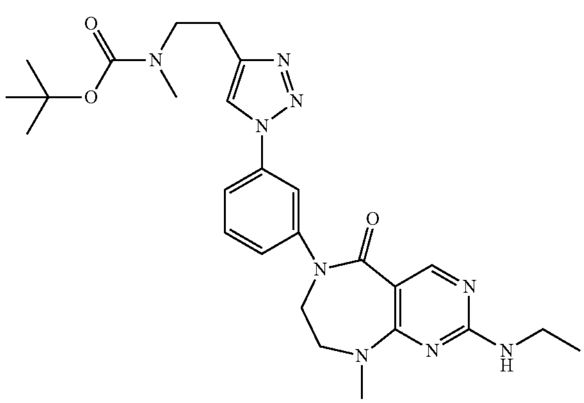 [SMILES: CCNc1ncc2c(n1)N(C)CCN(c1cccc(-n3cc(CCN(C)C(=O)OC(C)(C)C)nn3)c1)C2=O] | tert-butyl (2-(1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)ethyl)(methyl) carbamate | (500 MHz, CDCl$_3$):1.26(t, J = 7, 2 Hz, 3H), 1.43(s, 9H), 2.87(s, 3H), 3.03(m, 2H), 3.25(s, 3H), 3.48(m, 2H), 3.60(m, 2H), 3.78(m, 2H), 4.05(m, 2H), 7.37(m, 1H), 7.53(m, 1H), 7.58(m, 1H), 7.72(m, 1H), 7.83(bs, 1H), 8.73(s, 1H) | A/ 5.85 | |

| EX | Structure | Chemical name | 1H-NMR (ppm) | Method/Ret (min) | MS |
|---|---|---|---|---|---|
| 121 | 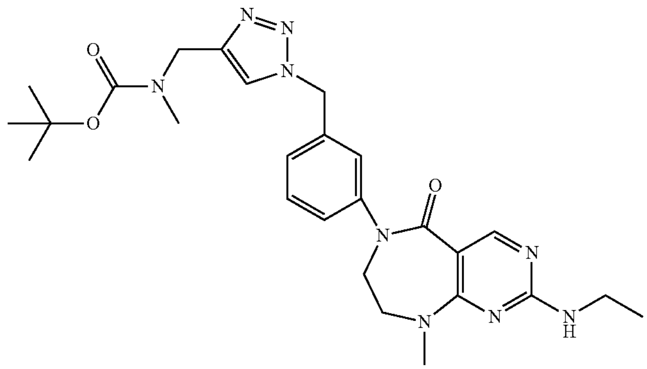 [SMILES: CCNc1ncc2c(n1)N(C)CCN(c1cccc(Cn3cc(CN(C)C(=O)OC(C)(C)C)nn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)benzyl)-1H-1,2,3-triazol-4-yl)methyl)(methyl) carbamate | | A/ 5.69 | 522.3 (M + H) |
| 122 | 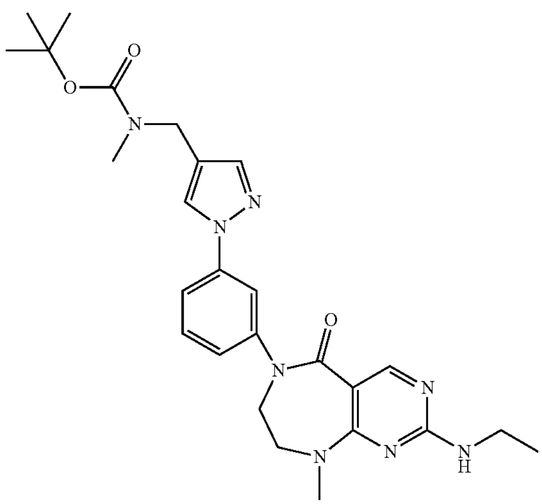 [SMILES: CCNc1ncc2c(n1)N(C)CCN(c1cccc(-n3cc(CN(C)C(=O)OC(C)(C)C)cn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-pyrazol-4-yl)methyl)(methyl) carbamate | | A/ 6.21 | 529.3 (M + Na) |
| 123 | 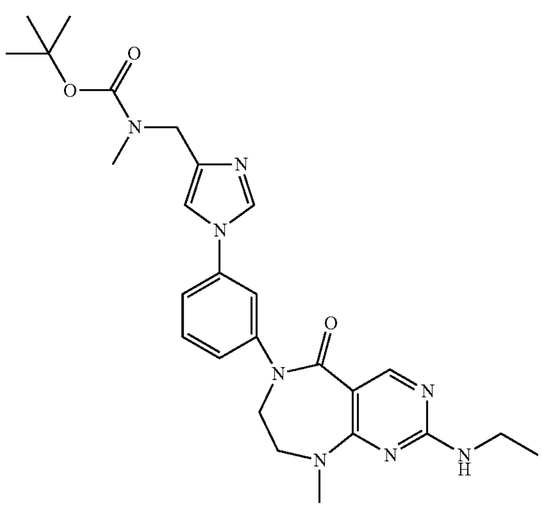 [SMILES: CCNc1ncc2c(n1)N(C)CCN(c1cccc(-n3cnc(CN(C)C(=O)OC(C)(C)C)c3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-imidazol-4-yl)methyl)(methyl) carbamate | | A/ 4.99 | 507.3 (M + H) |

-continued

| EX | Structure | Chemical name | 1H-NMR (ppm) | Method/ Ret (min) | MS |
|---|---|---|---|---|---|
| 124 | 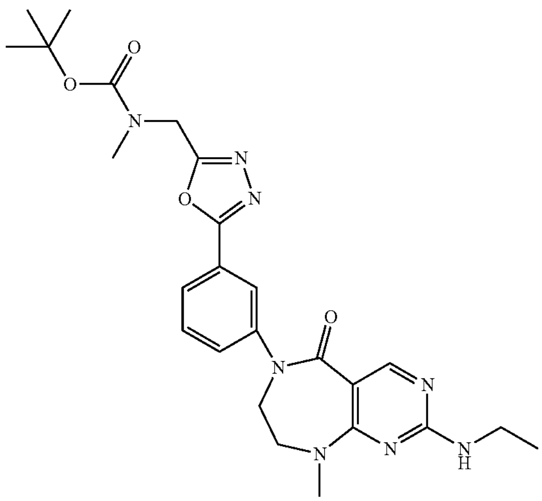 [SMILES: CCNc1ncc2c(n1)N(C)CCN(c1cccc(-c3nnc(CN(C)C(=O)OC(C)(C)C)o3)c1)C2=O] | tert-butyl ((5-(3-(2-(ethylamino)-9-methyl-5-oxo-5,7,8,9-tetrahydro-6H-pyrimido[4,5-e][1,4]diazepin-6-yl)phenyl)-1,3,4-oxadiazol-2-yl)methyl)(methyl) carbamate | | A/ 5.86 | 509.3 (M + H) |
| 125 | 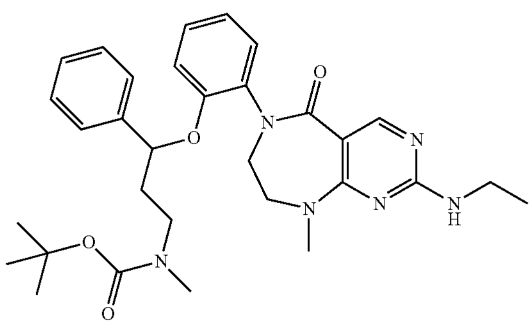 [SMILES: CCNc1ncc2c(n1)N(C)CCN(c1ccccc1OC(CCN(C)C(=O)OC(C)(C)C)c1ccccc1)C2=O] | tert-butyl (3-(2-(2-(ethylamino)-9-methyl-5-oxo-5,7,8,9-tetrahydro-6H-pyrimido[4,5-e][1,4]diazepin-6-yl)phenoxy)-3-phenylpropyl)(methyl) carbamate | | A/ 7.07 | 561.4 (M + H) |
| 126 | 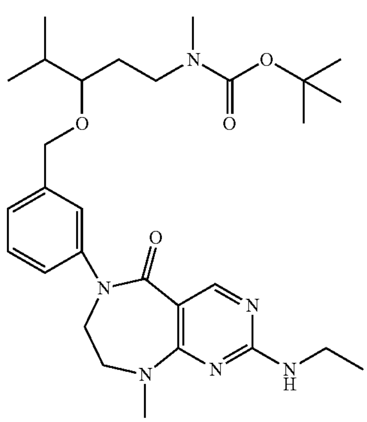 [SMILES: CCNc1ncc2c(n1)N(C)CCN(c1cccc(COC(CCN(C)C(=O)OC(C)(C)C)C(C)C)c1)C2=O] | tert-butyl (3-((3-(2-(ethylamino)-9-methyl-5-oxo-5,7,8,9-tetrahydro-6H-pyrimido[4,5-e][1,4]diazepin-6-yl)benzyl)oxy)-4-methylpentyl)(methyl) carbamate | (400 MHz, CDCl$_3$):0.94(m, 6H), 1.24(t, J = 7.2 Hz, 3H), 1.45(s, 9H), 1.70(m, 2H), 1.96(m, 1H), 2.84(s, 3H), 3.19(m, 1H), 3.22(m, 3H), 3.28(m, 2H), 3.46(m, 2H), 3.73(m, 2H), 3.98(m, 2H), 4.51(qAB, 2H), 5.60(bs, 1H), 7.20(m, 1H), 7.27(m, 2H), 7.37(m, 1H), 8.73(s, 1H). | | |

| EX | Structure | Chemical name | 1H-NMR (ppm) | Method/Ret (min) | MS |
|----|-----------|---------------|--------------|------------------|-----|
| 127 | 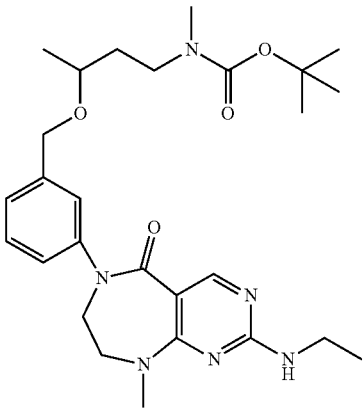 [SMILES: CCNc1ncc2c(n1)N(C)CCN(c1cccc(COC(C)CCN(C)C(=O)OC(C)(C)C)c1)C2=O] | tert-butyl (3-((3-(2-(ethylamino)-9-methyl-5-oxo-5,7,8,9-tetrahydro-6H-pyrimido[4,5-e][1,4]diazepin-6-yl)benzyl)oxy)butyl)(methyl)carbamate | | B/ 6.55 | 513.3 (M + H) |
| 128 | 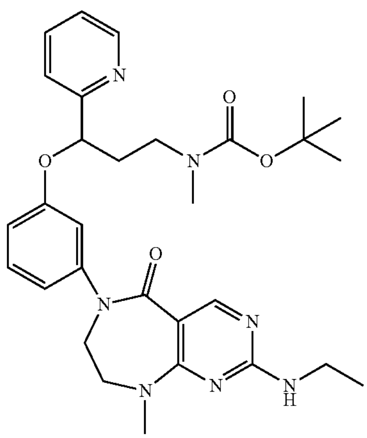 [SMILES: CCNc1ncc2c(n1)N(C)CCN(c1cccc(OC(CCN(C)C(=O)OC(C)(C)C)c3ccccn3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-2-yl)propyl)(methyl)carbamate | | B/ 4.20 | 562.3 (M + H) |
| 129 | 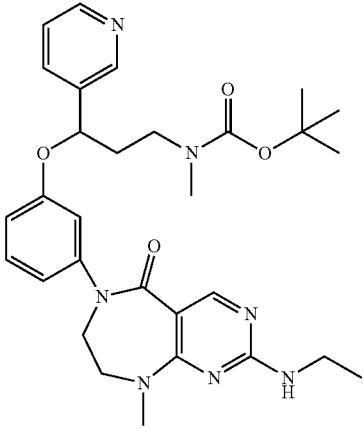 [SMILES: CCNc1ncc2c(n1)N(C)CCN(c1cccc(OC(CCN(C)C(=O)OC(C)(C)C)c3cccnc3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-3-yl)propyl)(methyl)carbamate | | B/ 4.16 | 562.3 (M + H) |

-continued

| EX | Structure | Chemical name | 1H-NMR (ppm) | Method/ Ret (min) | MS |
|---|---|---|---|---|---|
| 130 | 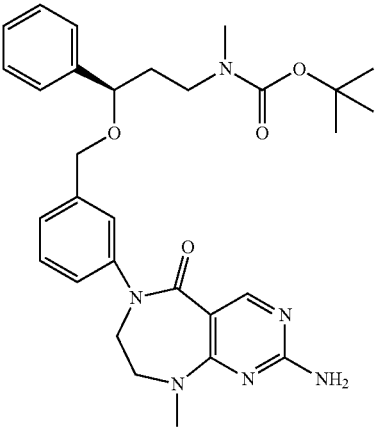 [SMILES: CN(CC[C@@H](OCc1cccc(N2CCN(C)c3nc(N)ncc3C2=O)c1)c1ccccc1)C(=O)OC(C)(C)C] | tert-butyl (R)-(3-((3-(2-amino-9-methyl-5-oxo-5,7,8,9-tetrahydro-6H-pyrimido[4,5-e][1,4]diazepin-6-yl)benzyl)oxy)-3-phenylpropyl)(methyl)carbamate | | B/ 4.55 | 547.3 (M + H) |
| 131 | 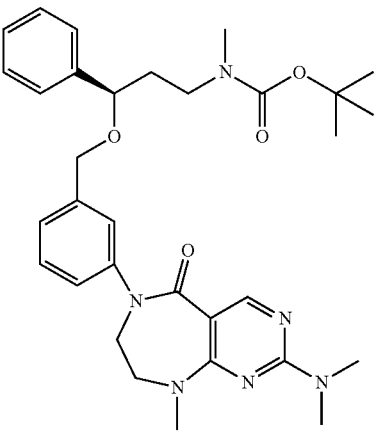 [SMILES: CN(CC[C@@H](OCc1cccc(N2CCN(C)c3nc(N(C)C)ncc3C2=O)c1)c1ccccc1)C(=O)OC(C)(C)C] | tert-butyl (R)-(3-((3-(2-(dimethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate | | B/ 5.10 | 575.3 (M + H) |
| 132 | 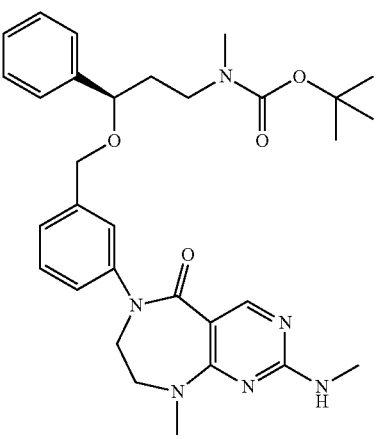 [SMILES: CNc1ncc2c(n1)N(C)CCN(c1cccc(CO[C@H](CCN(C)C(=O)OC(C)(C)C)c3ccccc3)c1)C2=O] | tert-butyl (R)-methyl(3-((3-(9-methyl-2-(methylamino)-5-oxo-5,7,8,9-tetrahydro-6H-pyrimido[4,5-e][1,4]diazepin-6-yl)benzyl)oxy)-3-phenylpropyl)carbamate | | B/ 5.20 | 561.3 (M + H) |

| EX | Structure | Chemical name | 1H-NMR (ppm) | Method/Ret (min) | MS |
|---|---|---|---|---|---|
| 133 | 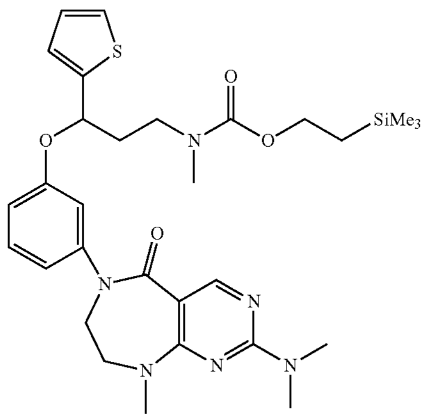 [SMILES: CN(CCC(Oc1cccc(N2CCN(C)c3nc(N(C)C)ncc3C2=O)c1)c1cccs1)C(=O)OCC[Si](C)(C)C] | 2-(trimethylsilyl)ethyl (3-(3-(2-(dimethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate | | B/ 5.14 | 611.3 (M + H) |
| 134 | 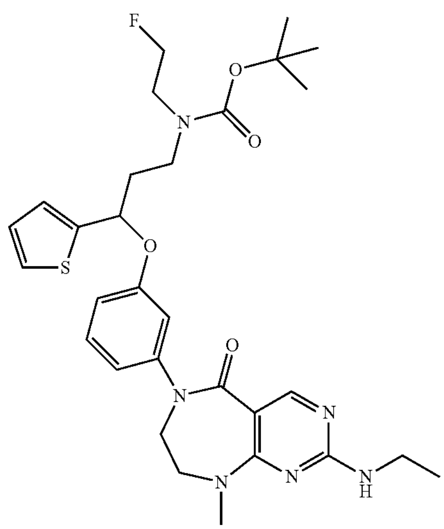 [SMILES: CCNc1ncc2c(n1)N(C)CCN(c1cccc(OC(CCN(CCF)C(=O)OC(C)(C)C)c3cccs3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(2-fluoroethyl)carbamate | | B/ 4.52 | 599.3 (M + H) |
| 135 | 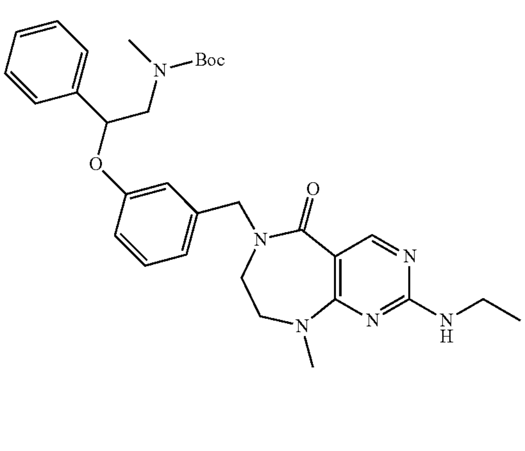 [SMILES: CCNc1ncc2c(n1)N(C)CCN(Cc1cccc(OC(CN(C)C(=O)OC(C)(C)C)c3ccccc3)c1)C2=O] | tert-butyl (2-(3-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate | (400 MHz, CDCl$_3$):1.25 (t, J = 7.3 Hz, 3H), 1.44(bs, 9H), 2.94(m, 3H), 3.11(s, 3H), 3.13(m, 1H), 3.28(m, 3H), 3.48(m, 3H), 3.67(m, 1H), 4.44(m, 1H), 4.81(m, 1H), 5.15(bs, 1H), 5.34(m, 1H), 6.77(m, 3H), 7.14(m, 1H), 7.27(m, 5H), 8.78(s, 1H) | | |

| EX | Structure | Chemical name | 1H-NMR (ppm) | Method/Ret (min) | MS |
|---|---|---|---|---|---|
| 136 | 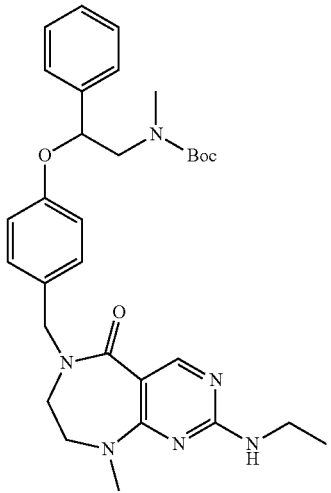 [SMILES: CCNc1ncc2c(n1)N(C)CCN(Cc1ccc(OC(CN(C)C(=O)OC(C)(C)C)c3ccccc3)cc1)C2=O] | tert-butyl (2-(4-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate | | A/ 7.14 | 583.3 (M + Na) |
| 137 | 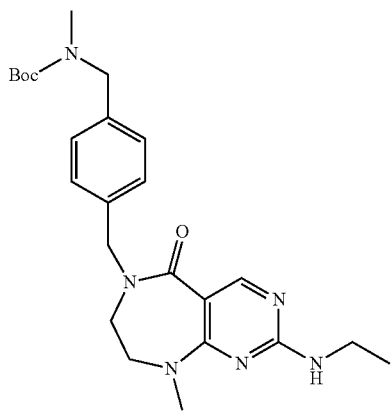 [SMILES: CCNc1ncc2c(n1)N(C)CCN(Cc1ccc(CN(C)C(=O)OC(C)(C)C)cc1)C2=O] | tert-butyl (4-((2-(ethylamino)-9-methyl-5-oxo-5,7,8,9-tetrahydro-6H-pyrimido[4,5-e][1,4]diazepin-6-yl)methyl)benzyl)(methyl)carbamate | (400 MHz, CDCl$_3$):1.23(t, J = 7.3 Hz, 3H), 1.48(bs, 9H), 2.81(bs, 3H), 3.13(s, 3H) 3.46(m, 6H), 4.41(bs(2H), 4.73(s, 2H), 7.19 (d, J = 8 Hz, 2H), 7.27(d, J = 8 Hz, 2H), 8.77(s, 1H). | | 455.2 (M + H) |

Example 138: tert-Butyl (R)-(3-((3-(2-methoxy-9-methyl-5-oxo-5,7,8,9-tetrahydro-6H-pyrimido[4,5-e][1,4]diazepin-6-yl)benzyl)oxy)-3-phenylpropyl)(methyl)carbamate

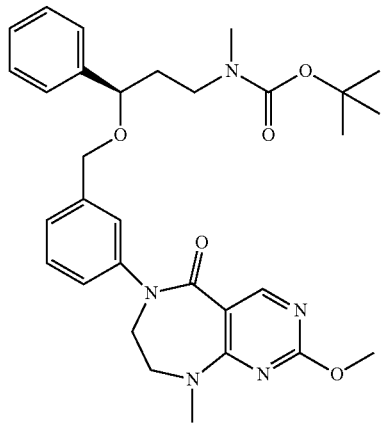 [SMILES: COc1ncc2c(n1)N(C)CCN(c1cccc(CO[C@H](CCN(C)C(=O)OC(C)(C)C)c3ccccc3)c1)C2=O]

To a solution of tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate (obtained in Ex 10, 72 mg, 0.124 mmol) in DCM (2 mL), m-chloroperbenzoic acid (37 mg, 0.162 mmol) was added and the mixture was stirred at rt for 1 h. NaHCO$_3$ sat solution was added and the mixture was extracted with DCM. The organic layer was washed with brine, dried with Na$_2$SO$_4$ and the solvent removed under vacuum. The crude residue was dissolved in MeOH (3 mL), sodium methoxide (40 mg, 0.74 mmol) was added and the mixture was heated at 50° C. for 20 h. The reaction mixture was cooled at rt, filtered and the solvent removed under vacuum. Purification by flash chromatography, silica gel, gradient CH to 100% EtOAc, afforded the title product (55 mg, 80% yield). HPLC (Method B): Ret, 5.87 min; ESI$^+$-MS m/z, 562.3 (M+H).

This method was used for the preparation of Ex 139 using suitable starting materials:

Example 140: tert-Butyl (R)-(3-((3-(2-hydroxy-9-methyl-5-oxo-5,7,8,9-tetrahydro-6H-pyrimido[4,5-e][1,4]diazepin-6-yl)benzyl)oxy)-3-phenylpropyl)(methyl)carbamate

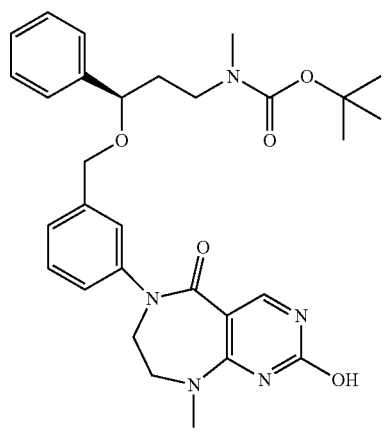 [SMILES: CN(CC[C@@H](OCc1cccc(N2CCN(C)c3nc(O)ncc3C2=O)c1)c1ccccc1)C(=O)OC(C)(C)C]

To a solution of tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate (obtained in Ex 10, 47 mg, 0.082 mmol) in DCM (1.3 mL), m-chloroperbenzoic acid (25 mg, 0.108 mmol) was added and the mixture was stirred at rt for 1 h. NaHCO$_3$ sat solution was added and the mixture was extracted with DCM. The organic layer was washed with brine, dried with Na$_2$SO$_4$ and the solvent removed under vacuum. The crude residue was dissolved in THF (1 mL), NaOH (30% aq solution, 2 mL) was added and the mixture was stirred at rt for 20 h. The reaction mixture was concentrated under vacuum and purified by flash chromatography, silica gel, gradient DCM to 35% MeOH, to afford the title product (35 mg, 78% yield). HPLC (Method B): Ret, 5.82 min; ESI$^+$-MS m/z, 548.3 (M+H).

This method was used for the preparation of Ex 141 using suitable starting materials:

| EX | Structure | Chemical name | 1H-NMR (ppm) | Method/ Ret (min) | MS |
|---|---|---|---|---|---|
| 139 | 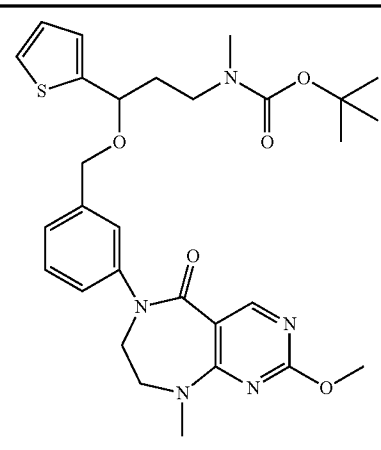 | tert-butyl (3-((3-(2-methoxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate | | B/5.23 | 568.3 (M + H) |

| EX | Structure | Chemical name | 1H-NMR (ppm) | Method/ Ret (min) | MS |
|---|---|---|---|---|---|
| 141 | 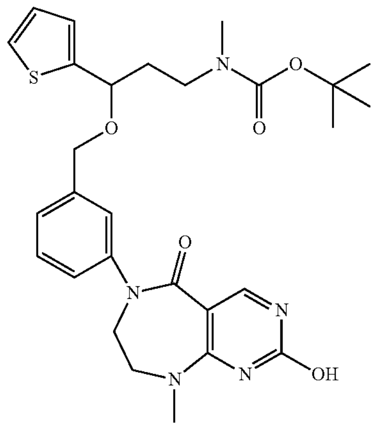 [SMILES: CN(CCC(OCc1cccc(N2CCN(C)c3nc(O)ncc3C2=O)c1)c1cccs1)C(=O)OC(C)(C)C] | tert-butyl (3-((3-(2-hydroxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | | B/4.80 | 554.2 (M + H) |

Example 142: tert-Butyl (R)-(3-((3-(2,9-dimethyl-5-oxo-5,7,8,9-tetrahydro-6H-pyrimido[4,5-e][1,4]diazepin-6-yl)benzyl)oxy)-3-phenylpropyl)(methyl)carbamate

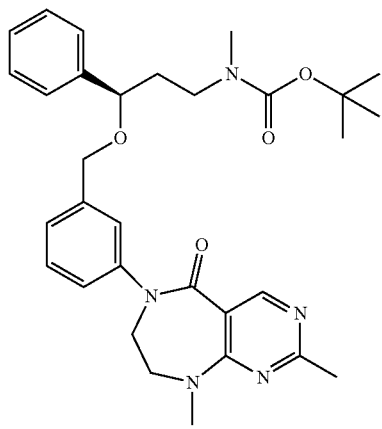 [SMILES: Cc1ncc2c(n1)N(C)CCN(c1cccc(CO[C@H](CCN(C)C(=O)OC(C)(C)C)c3ccccc3)c1)C2=O]

To a solution of tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate (obtained in Ex 10, 104 mg, 0.180 mmol) in DCM (2.5 mL), m-chloroperbenzoic acid (50 mg, 0.234 mmol) was added and the mixture was stirred at rt for 1 h. NaHCO$_3$ sat solution was added and the mixture was extracted with DCM. The organic layer was washed with brine, dried with Na$_2$SO$_4$ and the solvent removed under vacuum. The crude residue was dissolved in THF (4 mL), cooled at 0° C. and methylmagnesium bromide (3M solution in diethylether, 0.066 mL, 0.198 mmol) was added. The mixture was stirred at 0° C. for 30 min. NH$_4$Cl aq sat solution was added and extracted with DCM. The organic layer was washed with brine, dried with Na$_2$SO$_4$, filtered and concentrated under vacuum. Purification by flash chromatography, silica gel, gradient CH to 75% EtOAc afforded the title product (60 mg, 61% yield). HPLC (Method B): Ret, 4.56 min; ESI$^+$-MS m/z, 546.3 (M+H).

This method was used for the preparation of Ex 143-144 using suitable starting materials:

| EX | Structure | Chemical name | 1H-NMR (ppm) | Method/ Ret (min) | MS |
|---|---|---|---|---|---|
| 143 | 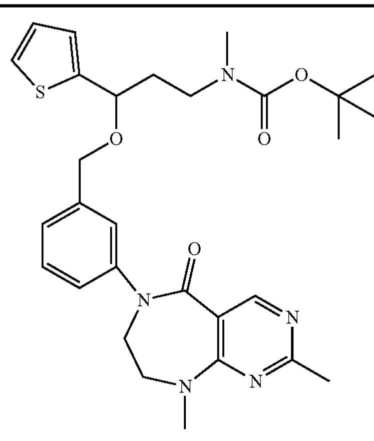 | tert-butyl (3-((3-(2,9-dimethyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | | B/4.90 | 552.3 (M + H) |

| EX | Structure | Chemical name | 1H-NMR (ppm) | Method/Ret (min) | MS |
|---|---|---|---|---|---|
| 144 | 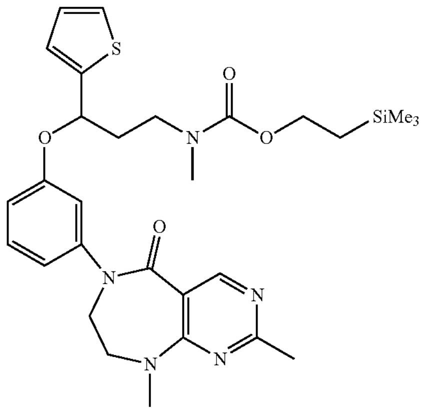 | 2-(trimethylsilyl)ethyl (3-(3-(2,9-dimethyl-5-oxo-5,7,8,9-tetrahydro-6H-pyrimido[4,5-e][1,4]diazepin-6-yl)phenoxy)-3-(thiophen-2-yl)propyl)(methyl)carbamate | | B/4.95 | 582.2 (M + H) |

Example 145: tert-Butyl (R)-methyl(3-((3-(9-methyl-5-oxo-5,7,8,9-tetrahydro-6H-pyrimido[4,5-e][1,4]diazepin-6-yl)benzyl)oxy)-3-phenylpropyl)carbamate

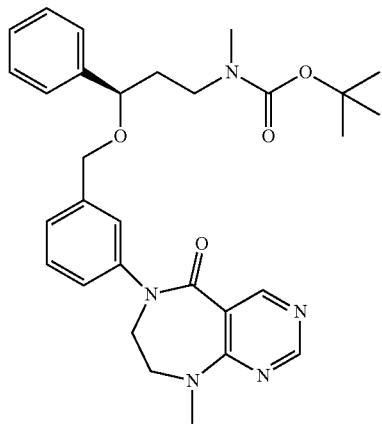 [SMILES: CN(CC[C@@H](OCc1cccc(N2CCN(C)c3ncncc3C2=O)c1)c1ccccc1)C(=O)OC(C)(C)C]

To a solution of tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate (obtained in Ex 10, 160 mg, 0.277 mmol) in THF (2 mL), 5% Pd/C (16 mg, 10% wt) was added, cooled at 0° C. and triethylsilane (0.221 ml, 1.38 mmol) was added. The mixture was stirred at 0° C. for 15 min and then at rt for 4.5 h, filtered through a pad of Celite and the filtrate was concentrated under vacuum. Purification by flash chromatography, silica gel, gradient CH to 100% EtOAc afforded the title product (120 mg, 82% yield). HPLC (Method B): Ret, 4.73 min; ESI$^+$-MS m/z, 532.3 (M+H).

This method was used for the preparation of Ex 146-147 using suitable starting materials:

| EX | Structure | Chemical name | 1H-NMR (ppm) | Method/Ret (min) | MS |
|---|---|---|---|---|---|
| 146 | 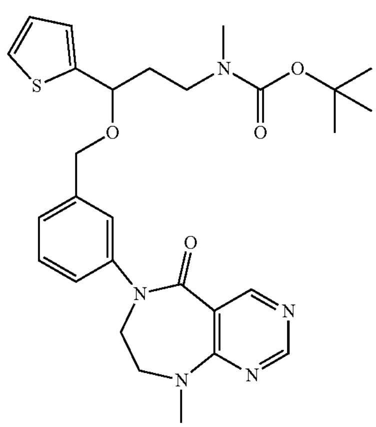 [SMILES: CN(CCC(OCc1cccc(N2CCN(C)c3ncncc3C2=O)c1)c1cccs1)C(=O)OC(C)(C)C] | tert-butyl methyl(3-((3-(9-methyl-5-oxo-5,7,8,9-tetrahydro-6H-pyrimido[4,5-e][1,4]diazepin-6-yl)benzyl)oxy)-3-(thiophen-2-yl)propyl)carbamate | | B/4.75 | 538.3 (M + H) |

| EX | Structure | Chemical name | 1H-NMR (ppm) | Method/Ret (min) | MS |
|---|---|---|---|---|---|
| 147 | 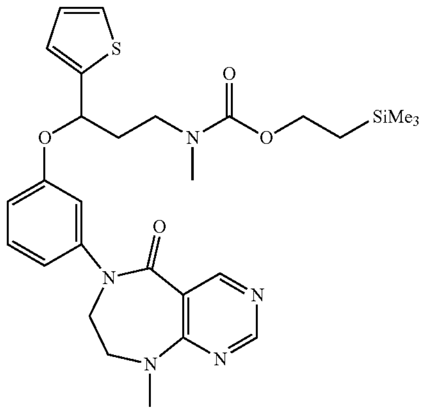 [SMILES: CN(CCC(Oc1cccc(N2CCN(C)c3ncncc3C2=O)c1)c1cccs1)C(=O)OCC[Si](C)(C)C] | 2-(trimethylsilyl)ethyl methyl(3-(3-(9-methyl-5-oxo-5,7,8,9-tetrahydro-6H-pyrimido[4,5-e][1,4]diazepin-6-yl)phenoxy)-3-(thiophen-2-yl)propyl)carbamate | | B/5.18 | 568.2 (M + H) |

Ex 148: 2-(Ethylamino)-9-methyl-6-(3-(3-(methylamino)-1-phenylpropoxy)phenyl)-6,7,8,9-tetrahydro-5H-pyrimido[4,5-e][1,4]diazepin-5-one

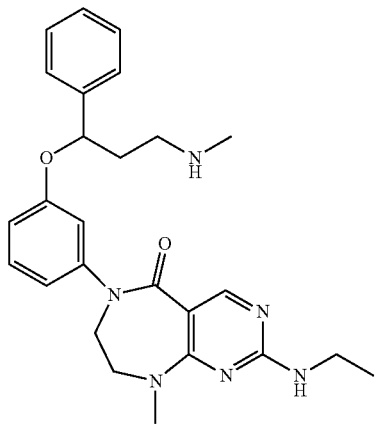 [SMILES: CCNc1ncc2c(n1)N(C)CCN(c1cccc(OC(CCNC)c3ccccc3)c1)C2=O]

To a solution of tert-butyl (3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate (obtained in Ex 69, 51 mg, 0.091 mmol) in dioxane (0.3 mL), HCl (4M solution in dioxane, 0.318 mL, 1.27 mmol) was added and the mixture was stirred at rt for 45 min. The reaction mixture was concentrated to dryness under vacuum. To obtain the free base, DCM was added, washed with Na$_2$CO$_3$ (10% solution), and the aqueous phase was extracted with DCM. The combined organic layers were concentrated under vacuum to afford the title compound (40 mg, 95% yield). HPLC (Method A): Ret, 4.92 min; ESI$^+$-HRMS m/z, 461.2646 (M+H).

This method was used for the preparation of Ex 149-207 using suitable starting materials:

| EX | Structure | Chemical name | Method | Ret (min) | MS |
|---|---|---|---|---|---|
| 149 | 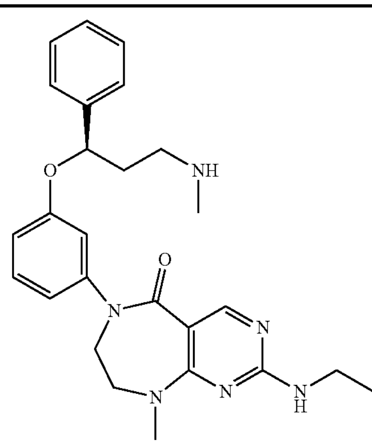 | (R)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | A | 4.95 | 461.3 (M + H) |

-continued

| EX | Structure | Chemical name | Method | Ret (min) | MS |
|---|---|---|---|---|---|
| 150 | 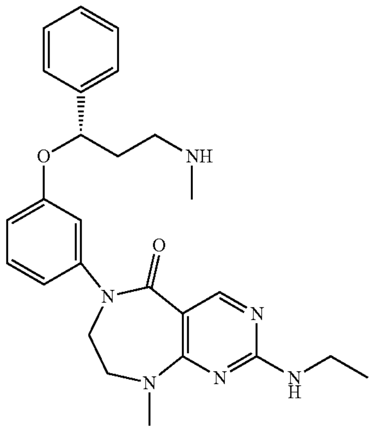 [SMILES: CCNc1ncc2c(n1)N(C)CCN(c1cccc(O[C@@H](CCNC)c3ccccc3)c1)C2=O] | (S)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | A | 4.95 | 461.3 (M + H) |
| 151 | 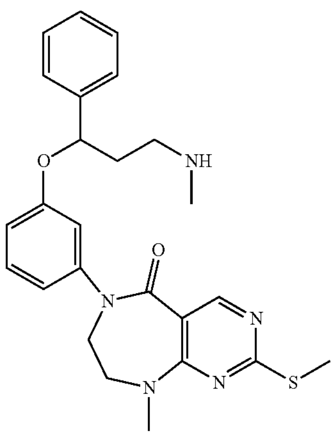 | 9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | A | 5.23 | 464.2 (M + H) |
| 152 | 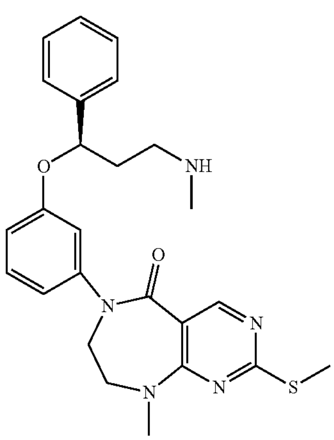 [SMILES: CNCC[C@@H](Oc1cccc(N2CCN(C)c3nc(SC)ncc3C2=O)c1)c1ccccc1] | (R)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | A | 5.23 | 464.2 (M + H) |

-continued

| EX | Structure | Chemical name | Method | Ret (min) | MS |
|---|---|---|---|---|---|
| 153 | 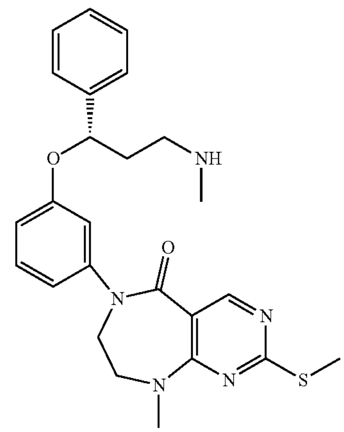 | (S)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | A | 5.23 | 464.2 (M + H) |
| 154 | 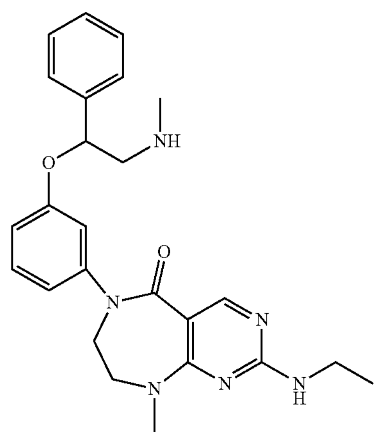 [SMILES: CCNc1ncc2c(n1)N(C)CCN(c1cccc(OC(CNC)c3ccccc3)c1)C2=O] | 2-(ethylamino)-9-methyl-6-(3-(2-(methylamino)-1-phenylethoxy)phenyl)-6,7,8,9-tetrahydro-5H-pyrimido[4,5-e][1,4]diazepin-5-one | A | 4.84 | 447.2 (M + H) |
| 155 | 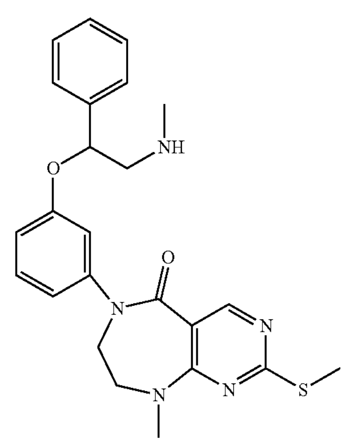 [SMILES: CNCC(Oc1cccc(N2CCN(C)c3nc(SC)ncc3C2=O)c1)c1ccccc1] | 9-methyl-6-(3-(2-(methylamino)-1-phenylethoxy)phenyl)-2-(methylthio)-6,7,8,9-tetrahydro-5H-pyrimido[4,5-e][1,4]diazepin-5-one | A | 5.11 | 450.2 (M + H) |

| EX | Structure | Chemical name | Method | Ret (min) | MS |
|---|---|---|---|---|---|
| 156 | 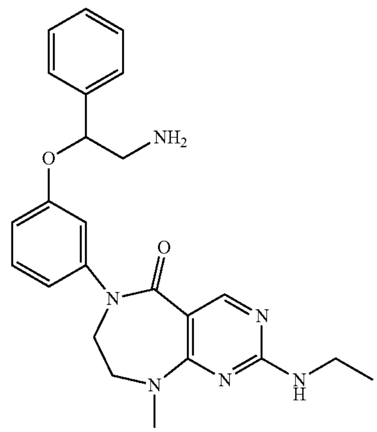 [SMILES: CCNc1ncc2c(n1)N(C)CCN(c1cccc(OC(CN)c3ccccc3)c1)C2=O] | 6-(3-(2-amino-1-phenylethoxy)phenyl)-2-(ethylamino)-9-methyl-6,7,8,9-tetrahydro-5H-pyrimido[4,5-e][1,4]diazepin-5-one | A | 4.77 | 433.2 (M + H) |
| 157 | 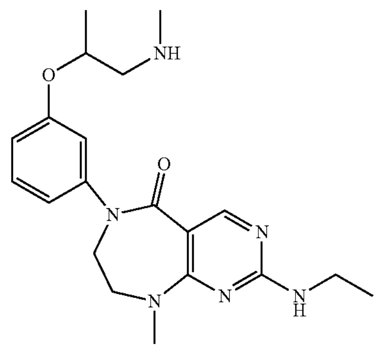 [SMILES: CCNc1ncc2c(n1)N(C)CCN(c1cccc(OC(C)CNC)c1)C2=O] | 2-(ethylamino)-9-methyl-6-(3-((1-(methylamino)propan-2-yl)oxy)phenyl)-6,7,8,9-tetrahydro-5H-pyrimido[4,5-e][1,4]diazepin-5-one | A | 4.35 | 385.2 (M + H) |
| 158 | 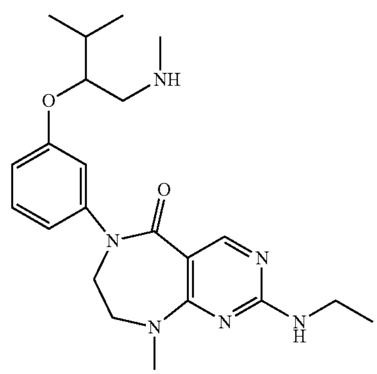 [SMILES: CCNc1ncc2c(n1)N(C)CCN(c1cccc(OC(CNC)C(C)C)c1)C2=O] | 2-(ethylamino)-9-methyl-6-(3-((3-methyl-1-(methylamino)butan-2-yl)oxy)phenyl)-6,7,8,9-tetrahydro-5H-pyrimido[4,5-e][1,4]diazepin-5-one | A | 4.71 | 413.3 (M + H) |
| 159 | 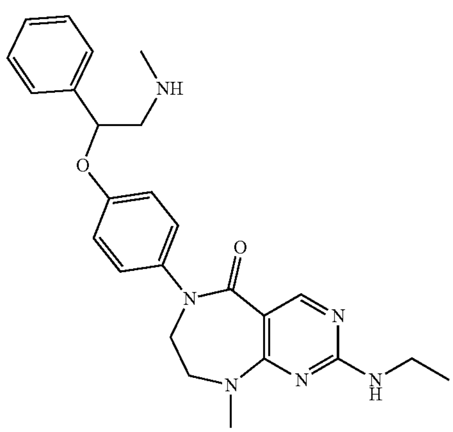 [SMILES: CCNc1ncc2c(n1)N(C)CCN(c1ccc(OC(CNC)c3ccccc3)cc1)C2=O] | 2-(ethylamino)-9-methyl-6-(4-(2-(methylamino)-1-phenylethoxy)phenyl)-6,7,8,9-tetrahydro-5H-pyrimido[4,5-e][1,4]diazepin-5-one | A | 4.81 | 447.3 (M + H) |

-continued

| EX | Structure | Chemical name | Method | Ret (min) | MS |
|---|---|---|---|---|---|
| 160 | 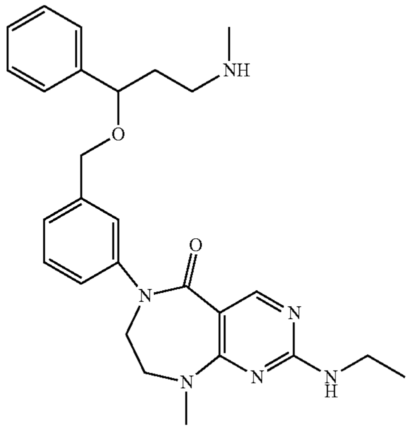 [SMILES: CCNc1ncc2c(n1)N(C)CCN(c1cccc(COC(CCNC)c3ccccc3)c1)C2=O] | 2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | A | 5.04 | 475.3 (M + H) |
| 161 | 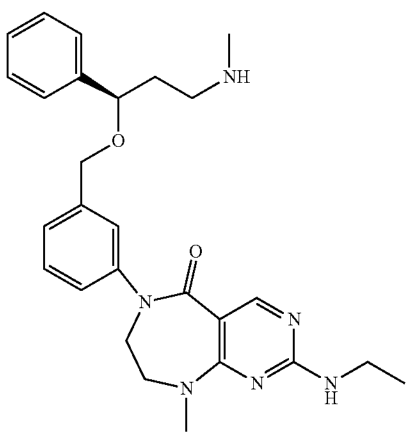 [SMILES: CCNc1ncc2c(n1)N(C)CCN(c1cccc(CO[C@H](CCNC)c3ccccc3)c1)C2=O] | (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | A | 5.06 | 475.3 (M + H) |
| 162 | 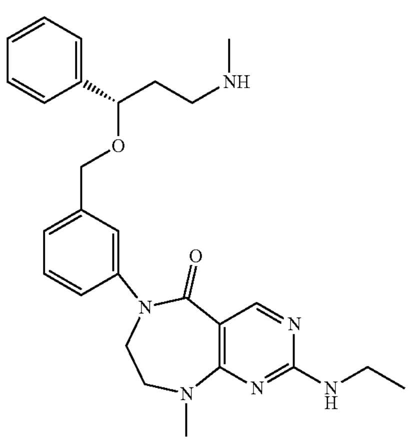 [SMILES: CCNc1ncc2c(n1)N(C)CCN(c1cccc(CO[C@@H](CCNC)c3ccccc3)c1)C2=O] | (S)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | A | 5.06 | 475.3 (M + H) |

| EX | Structure | Chemical name | Method | Ret (min) | MS |
|---|---|---|---|---|---|
| 163 | 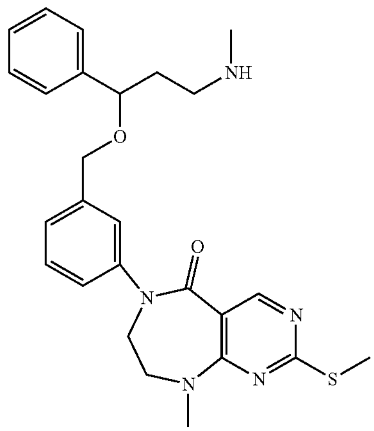 | 9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | A | 5.37 | 478.2 (M + H) |
| 164 | 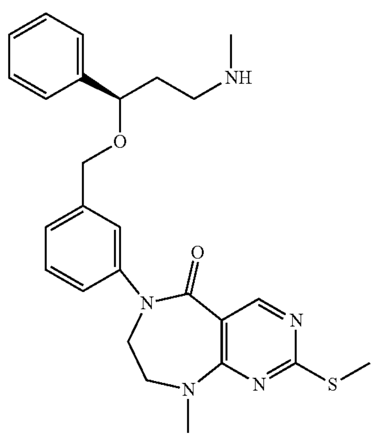 [SMILES: CNCC[C@@H](OCc1cccc(N2CCN(C)c3nc(SC)ncc3C2=O)c1)c1ccccc1] | (R)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | A | 5.37 | 478.2 |
| 165 | 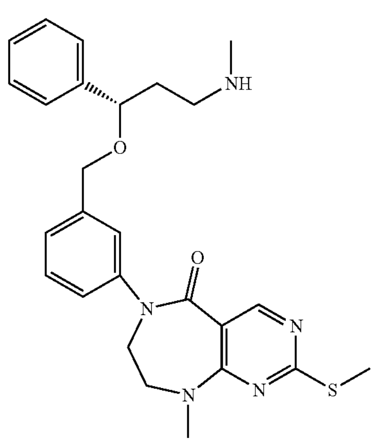 | (S)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | A | 5.39 | 478.2 (M + H) |

-continued
| EX | Structure | Chemical name | Method | Ret (min) | MS |
|---|---|---|---|---|---|
| 166 | 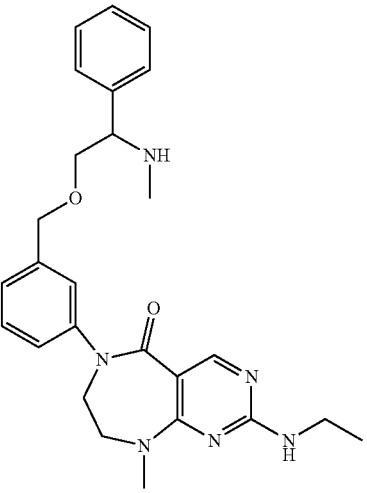 [SMILES: CCNc1ncc2c(n1)N(C)CCN(c1cccc(COCC(NC)c3ccccc3)c1)C2=O] | 2-(ethylamino)-9-methyl-6-(3-((2-(methylamino)-2-phenylethoxy)methyl)phenyl)-6,7,8,9-tetrahydro-5H-pyrimido[4,5-e][1,4]diazepin-5-one | A | 4.85 | 461.3 (M + H) |
| 167 | 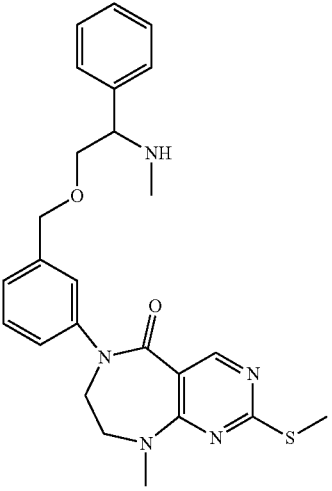 [SMILES: CNC(COCc1cccc(N2CCN(C)c3nc(SC)ncc3C2=O)c1)c1ccccc1] | 9-methyl-6-(3-((2-(methylamino)-2-phenylethoxy)methyl)phenyl)-2-(methylthio)-6,7,8,9-tetrahydro-5H-pyrimido[4,5-e][1,4]diazepin-5-one | A | 5.14 | 464.2 (M + H) |
| 168 | 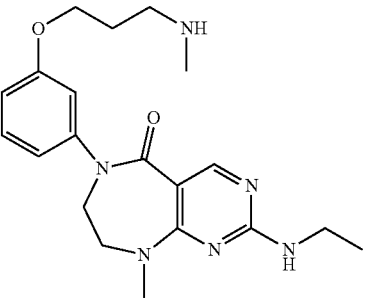 [SMILES: CCNc1ncc2c(n1)N(C)CCN(c1cccc(OCCCNC)c1)C2=O] | 2-(ethylamino)-9-methyl-6-(3-(3-(methylamino)propoxy)phenyl)-6,7,8,9-tetrahydro-5H-pyrimido[4,5-e][1,4]diazepin-5-one | A | 4.32 | 385.2 (M + H) |

-continued

| EX | Structure | Chemical name | Method | Ret (min) | MS |
|---|---|---|---|---|---|
| 169 | 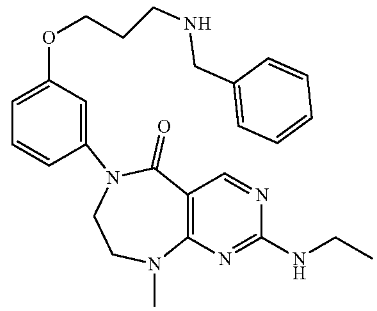 [SMILES: CCNc1ncc2c(n1)N(C)CCN(c1cccc(OCCCNCc3ccccc3)c1)C2=O] | 6-(3-(3-(benzylamino)propoxy)phenyl)-2-(ethylamino)-9-methyl-6,7,8,9-tetrahydro-5H-pyrimido[4,5-e][1,4]diazepin-5-one | A | 4.87 | 461.3 (M + H) |
| 170 | 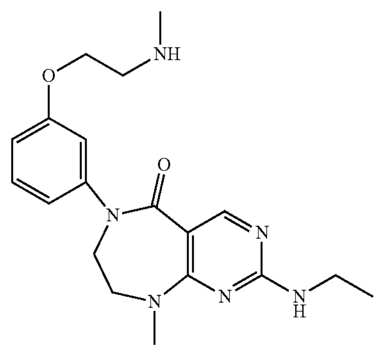 [SMILES: CCNc1ncc2c(n1)N(C)CCN(c1cccc(OCCNC)c1)C2=O] | 2-(ethylamino)-9-methyl-6-(3-(2-(methylamino)ethoxy)phenyl)-6,7,8,9-tetrahydro-5H-pyrimido[4,5-e][1,4]diazepin-5-one | A | 4.21 | 371.2 (M + H) |
| 171 | 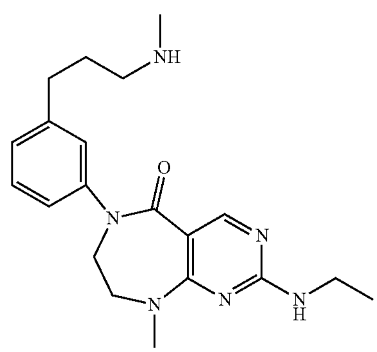 [SMILES: CCNc1ncc2c(n1)N(C)CCN(c1cccc(CCCNC)c1)C2=O] | 2-(ethylamino)-9-methyl-6-(3-(3-(methylamino)propyl)phenyl)-6,7,8,9-tetrahydro-5H-pyrimido[4,5-e][1,4]diazepin-5-one | A | 4.32 | 369.2 (M + H) |
| 172 | 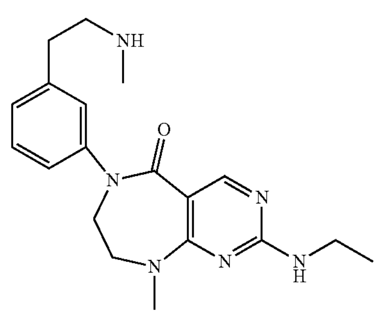 [SMILES: CCNc1ncc2c(n1)N(C)CCN(c1cccc(CCNC)c1)C2=O] | 2-(ethylamino)-9-methyl-6-(3-(2-(methylamino)ethyl)phenyl)-6,7,8,9-tetrahydro-5H-pyrimido[4,5-e][1,4]diazepin-5-one | A | 4.19 | 355.2 (M + H) |

| EX | Structure | Chemical name | Method | Ret (min) | MS |
|---|---|---|---|---|---|
| 173 | 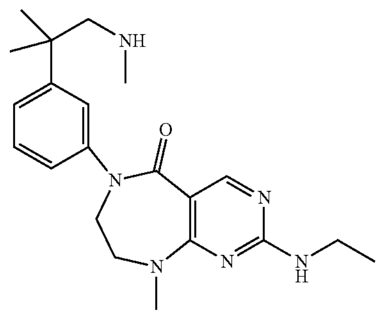 [SMILES: CCNc1ncc2c(n1)N(C)CCN(c1cccc(C(C)(C)CNC)c1)C2=O] | 2-(ethylamino)-9-methyl-6-(3-(2-methyl-1-(methylamino)propan-2-yl)phenyl)-6,7,8,9-tetrahydro-5H-pyrimido[4,5-e][1,4]diazepin-5-one | A | 4.45 | 383.3 (M + H) |
| 174 | 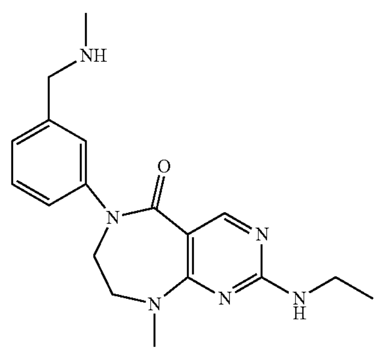 [SMILES: CCNc1ncc2c(n1)N(C)CCN(c1cccc(CNC)c1)C2=O] | 2-(ethylamino)-9-methyl-6-(3-((methylamino)methyl)phenyl)-6,7,8,9-tetrahydro-5H-pyrimido[4,5-e][1,4]diazepin-5-one | A | 3.94 | 341.2 (M + H) |
| 175 | 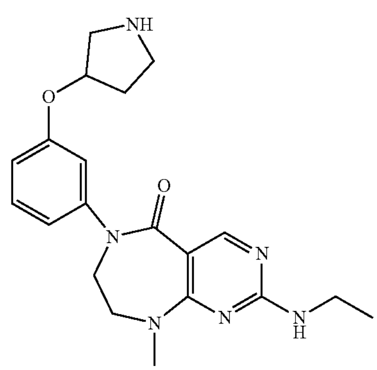 [SMILES: CCNc1ncc2c(n1)N(C)CCN(c1cccc(OC3CCNC3)c1)C2=O] | 2-(ethylamino)-9-methyl-6-(3-(pyrrolidin-3-yloxy)phenyl)-6,7,8,9-tetrahydro-5H-pyrimido[4,5-e][1,4]diazepin-5-one | A | 4.25 | 383.2 (M + H) |
| 176 | 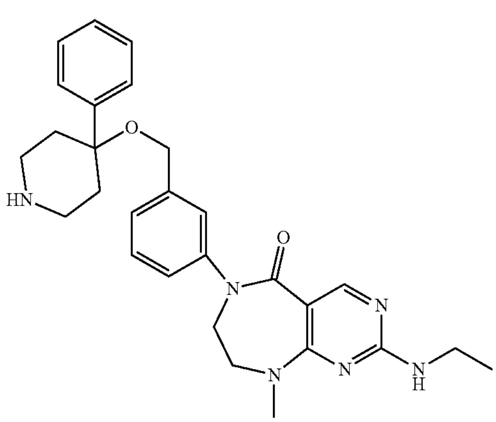 [SMILES: CCNc1ncc2c(n1)N(C)CCN(c1cccc(COC3(c4ccccc4)CCNCC3)c1)C2=O] | 2-(ethylamino)-9-methyl-6-(3-(((4-phenylpiperidin-4-yl)oxy)methyl)phenyl)-6,7,8,9-tetrahydro-5H-pyrimido[4,5-e][1,4]diazepin-5-one | A | 5.05 | 487.3 (M + H) |

| EX | Structure | Chemical name | Method | Ret (min) | MS |
|---|---|---|---|---|---|
| 177 | 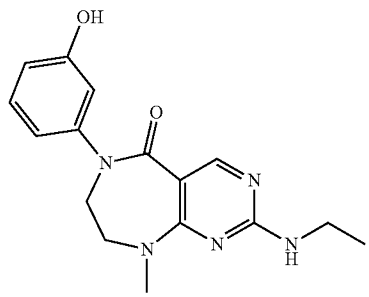 [SMILES: CCNc1ncc2c(n1)N(C)CCN(c1cccc(O)c1)C2=O] | 2-(ethylamino)-6-(3-hydroxyphenyl)-9-methyl-6,7,8,9-tetrahydro-5H-pyrimido[4,5-e][1,4]diazepin-5-one | A | 4.71 | 314.2 (M + H) |
| 178 | 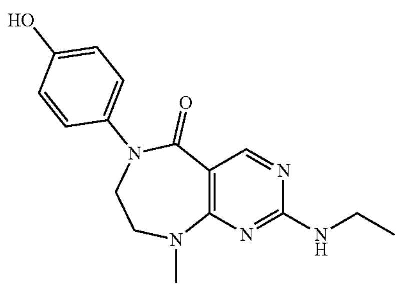 [SMILES: CCNc1ncc2c(n1)N(C)CCN(c1ccc(O)cc1)C2=O] | 2-(ethylamino)-6-(4-hydroxyphenyl)-9-methyl-6,7,8,9-tetrahydro-5H-pyrimido[4,5-e][1,4]diazepin-5-one | A | 4.61 | 314.2 (M + H) |
| 179 | 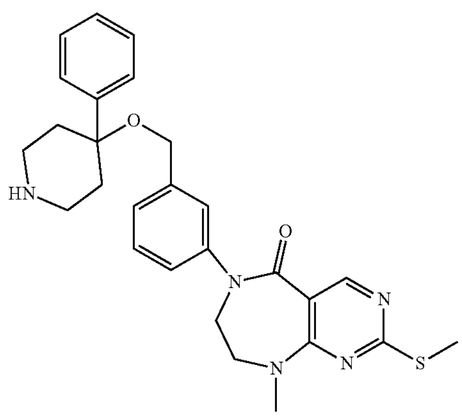 [SMILES: CSc1ncc2c(n1)N(C)CCN(c1cccc(COC3(c4ccccc4)CCNCC3)c1)C2=O] | 9-methyl-2-(methylthio)-6-(3-(((4-phenylpiperidin-4-yl)oxy)methyl)phenyl)-6,7,8,9-tetrahydro-5H-pyrimido[4,5-e][1,4]diazepin-5-one | A | 5.39 | 490.2 (M + H) |
| 180 | 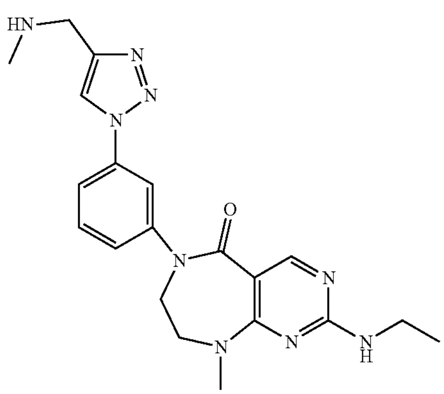 [SMILES: CCNc1ncc2c(n1)N(C)CCN(c1cccc(-n3cc(CNC)nn3)c1)C2=O] | 2-(ethylamino)-9-methyl-6-(3-(4-((methylamino)methyl)-1H-1,2,3-triazol-1-yl)phenyl)-6,7,8,9-tetrahydro-5H-pyrimido[4,5-e][1,4]diazepin-5-one | A | 4.22 | 408.2 (M + H) |

-continued

| EX | Structure | Chemical name | Method | Ret (min) | MS |
|---|---|---|---|---|---|
| 181 | 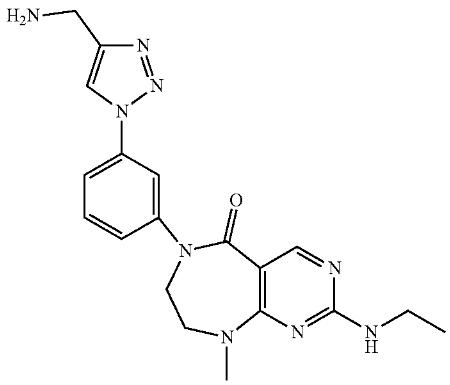 [SMILES: CCNc1ncc2c(n1)N(C)CCN(c1cccc(-n3cc(CN)nn3)c1)C2=O] | 6-(3-(4-(aminomethyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.17 | 394.2 (M + H) |
| 182 | 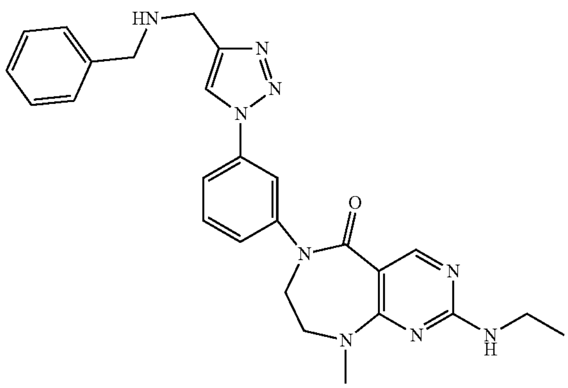 [SMILES: CCNc1ncc2c(n1)N(C)CCN(c1cccc(-n3cc(CNCc4ccccc4)nn3)c1)C2=O] | 6-(3-(4-((benzylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.73 | 484.3 (M + H) |
| 183 | 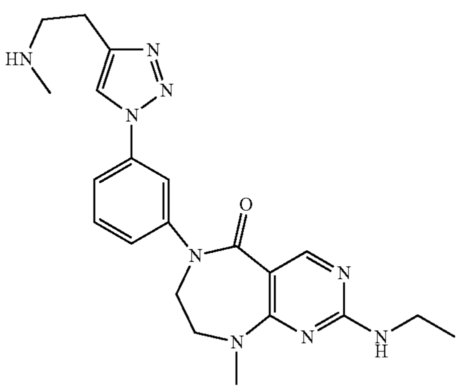 [SMILES: CCNc1ncc2c(n1)N(C)CCN(c1cccc(-n3cc(CCNC)nn3)c1)C2=O] | 2-(ethylamino)-9-methyl-6-(3-(4-(2-(methylamino)ethyl)-1H-1,2,3-triazol-1-yl)phenyl)-6,7,8,9-tetrahydro-5H-pyrimido[4,5-e][1,4]diazepin-5-one | A | 4.25 | 422.2 (M + H) |
| 184 | 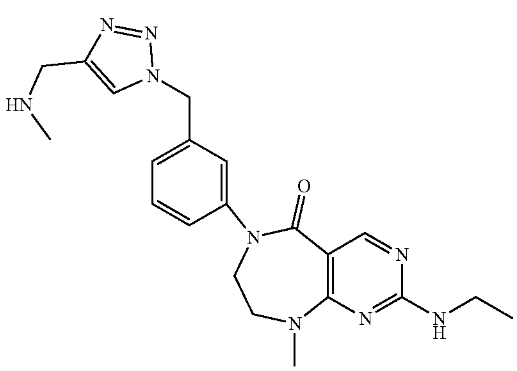 [SMILES: CCNc1ncc2c(n1)N(C)CCN(c1cccc(Cn3cc(CNC)nn3)c1)C2=O] | 2-(ethylamino)-9-methyl-6-(3-((4-((methylamino)methyl)-1H-1,2,3-triazol-1-yl)methyl)phenyl)-6,7,8,9-tetrahydro-5H-pyrimido[4,5-e][1,4]diazepin-5-one | A | 4.22 | 422.2 (M + H) |

-continued

| EX | Structure | Chemical name | Method | Ret (min) | MS |
|---|---|---|---|---|---|
| 185 | 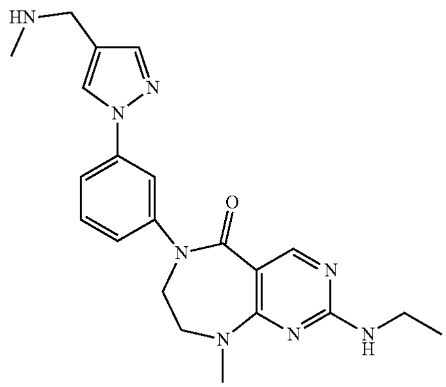 [SMILES: CCNc1ncc2c(n1)N(C)CCN(c1cccc(-n3cc(CNC)cn3)c1)C2=O] | 2-(ethylamino)-9-methyl-6-(3-(4-((methylamino)methyl)-1H-pyrazol-1-yl)phenyl)-6,7,8,9-tetrahydro-5H-pyrimido[4,5-e][1,4]diazepin-5-one | A | 4.28 | 407.2 (M + H) |
| 186 | 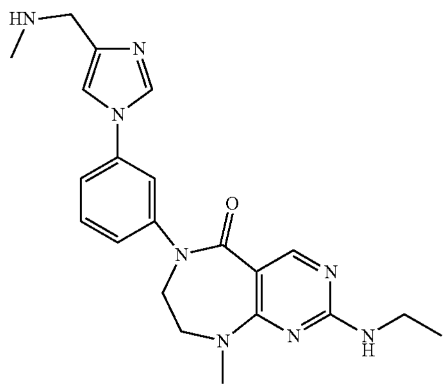 [SMILES: CCNc1ncc2c(n1)N(C)CCN(c1cccc(-n3cnc(CNC)c3)c1)C2=O] | 2-(ethylamino)-9-methyl-6-(3-(4-((methylamino)methyl)-1H-imidazol-1-yl)phenyl)-6,7,8,9-tetrahydro-5H-pyrimido[4,5-e][1,4]diazepin-5-one | A | 4.12 | 407.2 (M + H) |
| 187 | 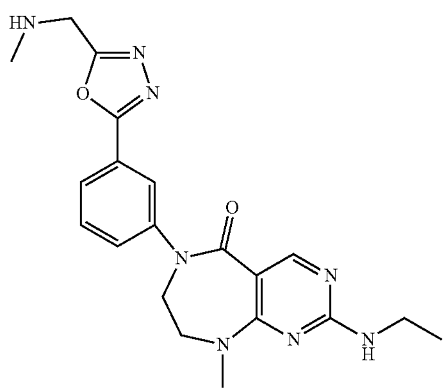 [SMILES: CCNc1ncc2c(n1)N(C)CCN(c1cccc(-c3nnc(CNC)o3)c1)C2=O] | 2-(ethylamino)-9-methyl-6-(3-(5-((methylamino)methyl)-1,3,4-oxadiazol-2-yl)phenyl)-6,7,8,9-tetrahydro-5H-pyrimido[4,5-e][1,4]diazepin-5-one | A | 4.16 | 409.2 (M + H) |
| 188 | 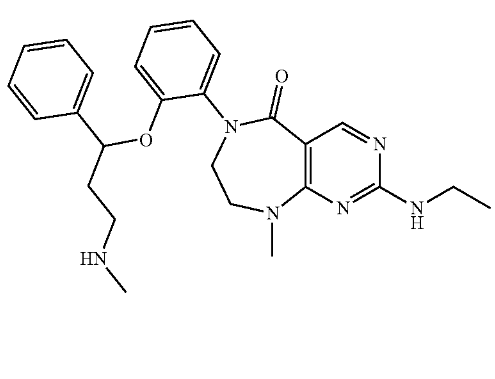 [SMILES: CCNc1ncc2c(n1)N(C)CCN(c1ccccc1OC(CCNC)c1ccccc1)C2=O] | 2-(ethylamino)-9-methyl-6-(2-(3-(methylamino)-1-phenylpropoxy)phenyl)-6,7,8,9-tetrahydro-5H-pyrimido[4,5-e][1,4]diazepin-5-one | A | 5.01 | 461.3 (M + H) |

| EX | Structure | Chemical name | Method | Ret (min) | MS |
|---|---|---|---|---|---|
| 189 | 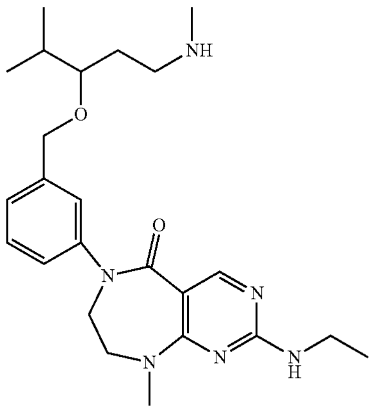 [SMILES: CCNc1ncc2c(n1)N(C)CCN(c1cccc(COC(CCNC)C(C)C)c1)C2=O] | 2-(ethylamino)-9-methyl-6-(3-(((4-methyl-1-(methylamino)pentan-3-yl)oxy)methyl)phenyl)-6,7,8,9-tetrahydro-5H-pyrimido[4,5-e][1,4]diazepin-5-one | A | 4.86 | 441.3 (M + H) |
| 190 | 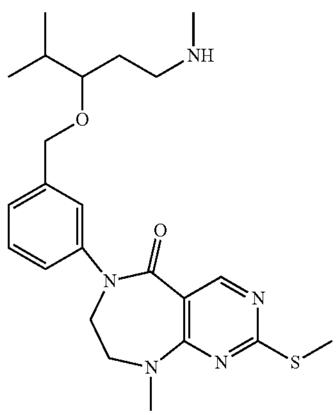 [SMILES: CNCCC(OCc1cccc(N2CCN(C)c3nc(SC)ncc3C2=O)c1)C(C)C] | 9-methyl-6-(3-(((4-methyl-1-(methylamino)pentan-3-yl)oxy)methyl)phenyl)-2-(methylthio)-6,7,8,9-tetrahydro-5H-pyrimido[4,5-e][1,4]diazepin-5-one | A | 5.14 | 444.2 (M + H) |
| 191 | 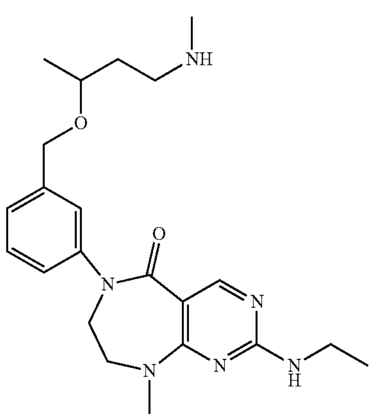 [SMILES: CCNc1ncc2c(n1)N(C)CCN(c1cccc(COC(C)CCNC)c1)C2=O] | 2-(ethylamino)-9-methyl-6-(3-(((4-(methylamino)butan-2-yl)oxy)methyl)phenyl)-6,7,8,9-tetrahydro-5H-pyrimido[4,5-e][1,4]diazepin-5-one | A | 4.45 | 413.3 (M + H) |

-continued
| EX | Structure | Chemical name | Method | Ret (min) | MS |
|---|---|---|---|---|---|
| 192 | 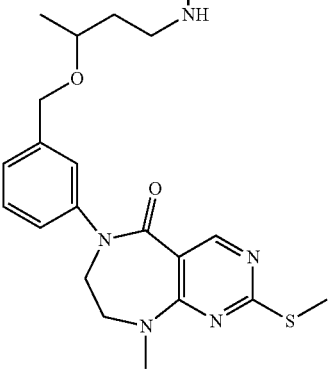 | 9-methyl-6-(3-(((4-(methylamino)butan-2-yl)oxy)methyl)phenyl)-2-(methylthio)-6,7,8,9-tetrahydro-5H-pyrimido[4,5-e][1,4]diazepin-5-one | A | 4.66 | 416.2 (M + H) |
| 193 | 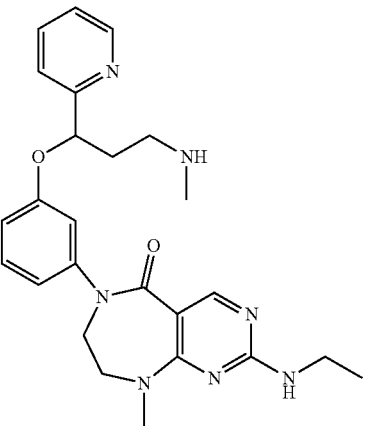 [SMILES: CCNc1ncc2c(n1)N(C)CCN(c1cccc(OC(CCNC)c3ccccn3)c1)C2=O] | 2-(ethylamino)-9-methyl-6-(3-(3-(methylamino)-1-(pyridin-2-yl)propoxy)phenyl)-6,7,8,9-tetrahydro-5H-pyrimido[4,5-e][1,4]diazepin-5-one | A | 4.38 | 462.3 (M + H) |
| 194 | 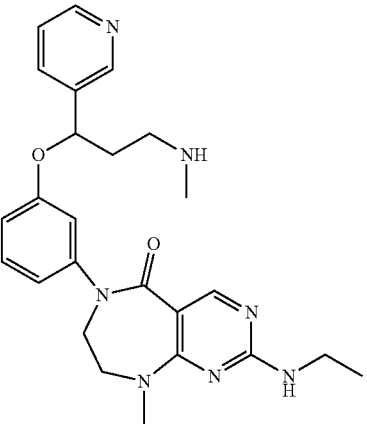 [SMILES: CCNc1ncc2c(n1)N(C)CCN(c1cccc(OC(CCNC)c3cccnc3)c1)C2=O] | 2-(ethylamino)-9-methyl-6-(3-(3-(methylamino)-1-(pyridin-3-yl)propoxy)phenyl)-6,7,8,9-tetrahydro-5H-pyrimido[4,5-e][1,4]diazepin-5-one | A | 4.00 | 462.3 (M + H) |

-continued

| EX | Structure | Chemical name | Method | Ret (min) | MS |
|---|---|---|---|---|---|
| 195 | 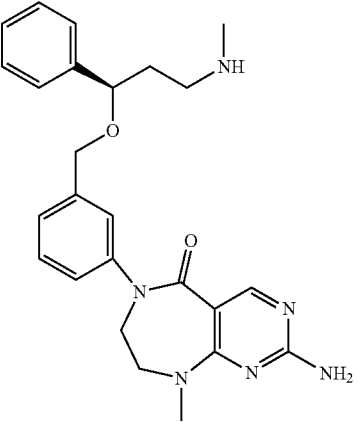 [SMILES: CNCC[C@@H](OCc1cccc(N2CCN(C)c3nc(N)ncc3C2=O)c1)c1ccccc1] | (R)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one | A | 4.69 | 447.2 (M + H) |
| 196 | 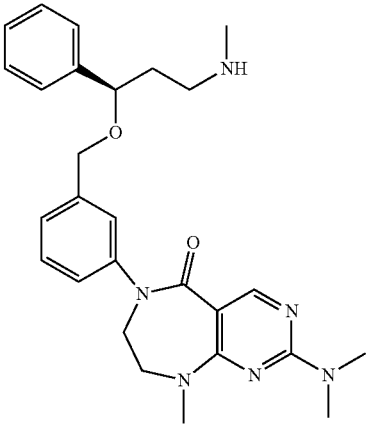 [SMILES: CNCC[C@@H](OCc1cccc(N2CCN(C)c3nc(N(C)C)ncc3C2=O)c1)c1ccccc1] | (R)-2-(dimethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | A | 4.96 | 475.3 (M + H) |
| 197 | 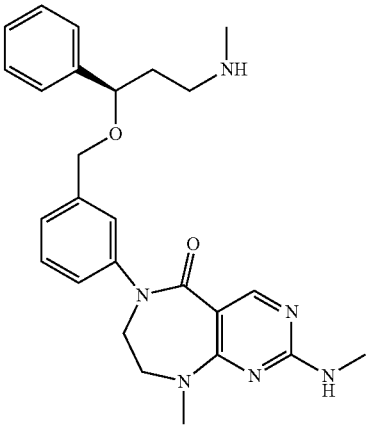 [SMILES: CNCC[C@@H](OCc1cccc(N2CCN(C)c3nc(NC)ncc3C2=O)c1)c1ccccc1] | (R)-9-methyl-2-(methylamino)-6-(3-((3-(methylamino)-1-phenylpropoxy)methyl)phenyl)-6,7,8,9-tetrahydro-5H-pyrimido[4,5-e][1,4]diazepin-5-one | A | 4.88 | 461.3 (M + H) |

-continued

| EX | Structure | Chemical name | Method | Ret (min) | MS |
|---|---|---|---|---|---|
| 198 | 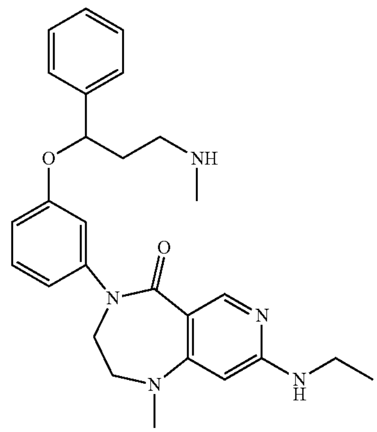 [SMILES: CCNc1cc2c(cn1)C(=O)N(c1cccc(OC(CCNC)c3ccccc3)c1)CCN2C] | 8-(ethylamino)-1-methyl-4-(3-(3-(methylamino)-1-phenylpropoxy)phenyl)-1,2,3,4-tetrahydro-5H-pyrido[4,3-e][1,4]diazepin-5-one | A | 4.85 | 460.3 (M + H) |
| 199 | 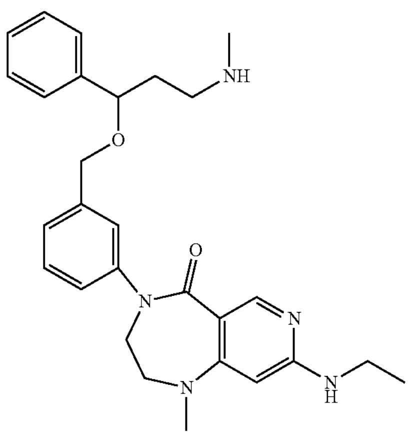 [SMILES: CCNc1cc2c(cn1)C(=O)N(c1cccc(COC(CCNC)c3ccccc3)c1)CCN2C] | 8-(ethylamino)-1-methyl-4-(3-((3-(methylamino)-1-phenylpropoxy)methyl)phenyl)-1,2,3,4-tetrahydro-5H-pyrido[4,3-e][1,4]diazepin-5-one | A | 4.98 | 474.3 (M + H) |
| 200 | 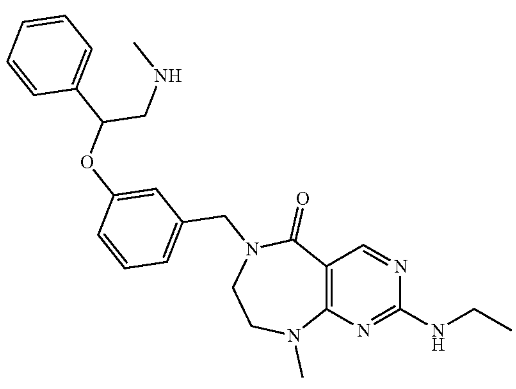 [SMILES: CCNc1ncc2c(n1)N(C)CCN(Cc1cccc(OC(CNC)c3ccccc3)c1)C2=O] | 2-(ethylamino)-9-methyl-6-(3-(2-(methylamino)-1-phenylethoxy)benzyl)-6,7,8,9-tetrahydro-5H-pyrimido[4,5-e][1,4]diazepin-5-one | A | 4.79 | 461.3 (M + H) |

-continued

| EX | Structure | Chemical name | Method | Ret (min) | MS |
|---|---|---|---|---|---|
| 201 | 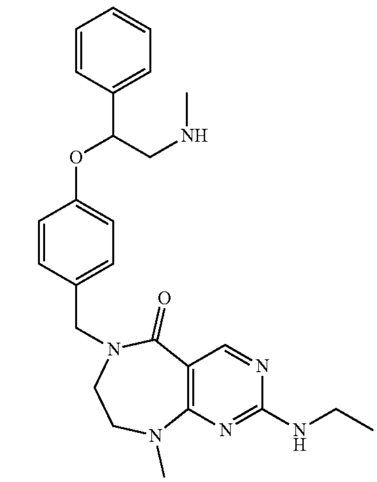 [SMILES: CCNc1ncc2c(n1)N(C)CCN(Cc1ccc(OC(CNC)c3ccccc3)cc1)C2=O] | 2-(ethylamino)-9-methyl-6-(4-(2-(methylamino)-1-phenylethoxy)benzyl)-6,7,8,9-tetrahydro-5H-pyrimido[4,5-e][1,4]diazepin-5-one | A | 4.83 | 461.3 (M + H) |
| 202 | 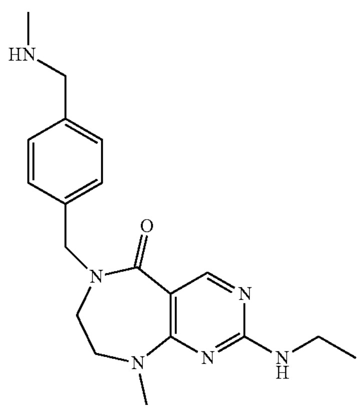 [SMILES: CCNc1ncc2c(n1)N(C)CCN(Cc1ccc(CNC)cc1)C2=O] | 2-(ethylamino)-9-methyl-6-(4-((methylamino)methyl)benzyl)-6,7,8,9-tetrahydro-5H-pyrimido[4,5-e][1,4]diazepin-5-one | A | 4.11 | 355.2 (M + H) |
| 203 | 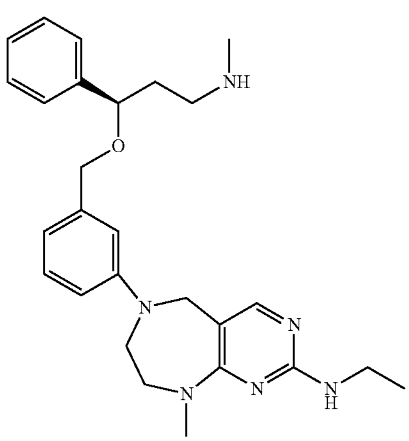 [SMILES: CCNc1ncc2c(n1)N(C)CCN(c1cccc(CO[C@H](CCNC)c3ccccc3)c1)C2] | (R)-N-ethyl-9-methyl-6-(3-((3-(methylamino)-1-phenylpropoxy)methyl)phenyl)-6,7,8,9-tetrahydro-5H-pyrimido[4,5-e][1,4]diazepin-2-amine | A | 5.35 | 461.3 (M + H) |

| EX | Structure | Chemical name | Method | Ret (min) | MS |
|---|---|---|---|---|---|
| 204 | 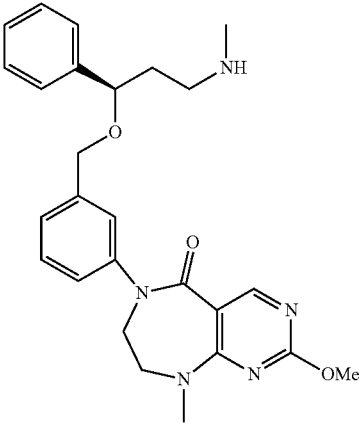 [SMILES: CNCC[C@@H](OCc1cccc(N2CCN(C)c3nc(OC)ncc3C2=O)c1)c1ccccc1] | (R)-2-methoxy-9-methyl-6-(3-((3-(methylamino)-1-phenylpropoxy)methyl)phenyl)-6,7,8,9-tetrahydro-5H-pyrimido[4,5-e][1,4]diazepin-5-one | A | 4.93 | 462.2 (M + H) |
| 205 | 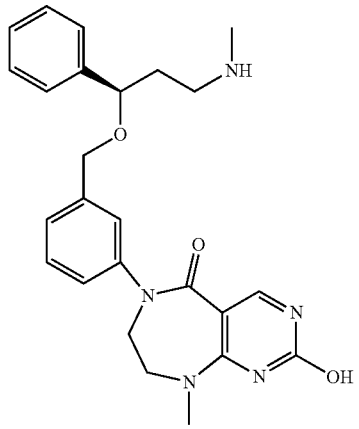 [SMILES: CNCC[C@@H](OCc1cccc(N2CCN(C)c3nc(O)ncc3C2=O)c1)c1ccccc1] | (R)-2-hydroxy-9-methyl-6-(3-((3-(methylamino)-1-phenylpropoxy)methyl)phenyl)-6,7,8,9-tetrahydro-5H-pyrimido[4,5-e][1,4]diazepin-5-one | A | 4.79 | 448.2 (M + H) |
| 206 | 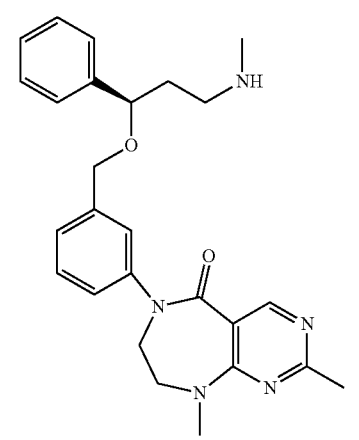 [SMILES: CNCC[C@@H](OCc1cccc(N2CCN(C)c3nc(C)ncc3C2=O)c1)c1ccccc1] | (R)-2,9-dimethyl-6-(3-((3-(methylamino)-1-phenylpropoxy)methyl)phenyl)-6,7,8,9-tetrahydro-5H-pyrimido[4,5-e][1,4]diazepin-5-one | A | 4.71 | 446.2 (M + H) |

| EX | Structure | Chemical name | Method | Ret (min) | MS |
|---|---|---|---|---|---|
| 207 | 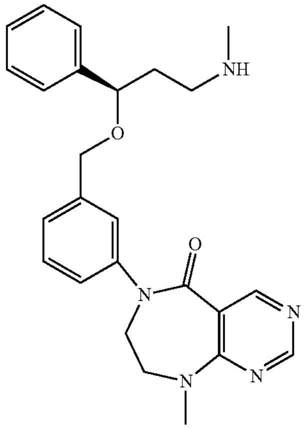 [SMILES: CNCC[C@@H](OCc1cccc(N2CCN(C)c3ncncc3C2=O)c1)c1ccccc1] | (R)-9-methyl-6-(3-((3-(methylamino)-1-phenylpropoxy)methyl)phenyl)-6,7,8,9-tetrahydro-5H-pyrimido[4,5-e][1,4]diazepin-5-one | A | 4.64 | 432.2 (M + H) |

Example 208: 9-Methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one

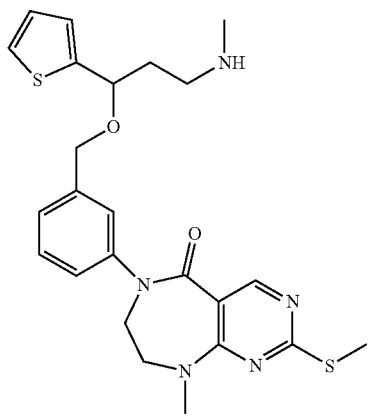 [SMILES: CNCCC(OCc1cccc(N2CCN(C)c3nc(SC)ncc3C2=O)c1)c1cccs1]

In a round bottomed flask, ZnBr$_2$ (243 mg, 1.079 mmol) was dried under vacuum at 250° C. for 3 h. Once the solid reached rt, a solution of tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate (Ex 15, 105 mg, 0.18 mmol) in DCM (6 ml) was added and the mixture was stirred at rt under Ar atmosphere for 20 h. Water was added and the mixture was stirred for 1 h. The phases were separated and the aqueous phase was extracted with DCM. The organic phase was concentrated under vacuum and purified by flash chromatography, silica gel, gradient DCM to 25% MeOH, to afford the title compound (45 mg, 51% yield). HPLC (Method A): Ret, 5.24 min; ESI$^+$-HRMS m/z, 484.1829 (M+H).

This method was used for the preparation of Ex 209-224 using suitable starting materials:

| EX | Structure | Chemical name | Method | Ret (min) | MS |
|---|---|---|---|---|---|
| 209 | 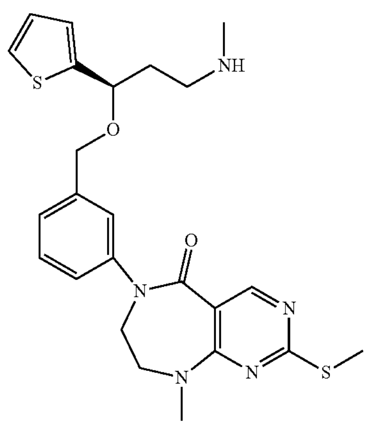 [SMILES: CNCC[C@@H](OCc1cccc(N2CCN(C)c3nc(SC)ncc3C2=O)c1)c1cccs1] | (R)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | A | 5.25 | 484.2 (M + H) |

-continued

| EX | Structure | Chemical name | Method | Ret (min) | MS |
|---|---|---|---|---|---|
| 210 | 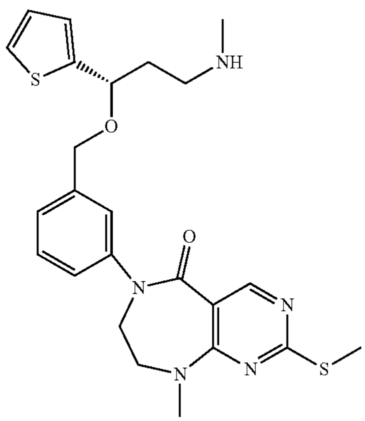 [SMILES: CNCC[C@H](OCc1cccc(N2CCN(C)c3nc(SC)ncc3C2=O)c1)c1cccs1] | (S)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | A | 5.26 | 484.2 (M + H) |
| 211 | 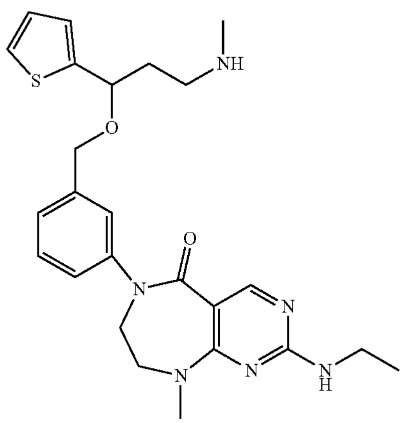 | 2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.97 | 481.2 (M + H) |
| 212 | 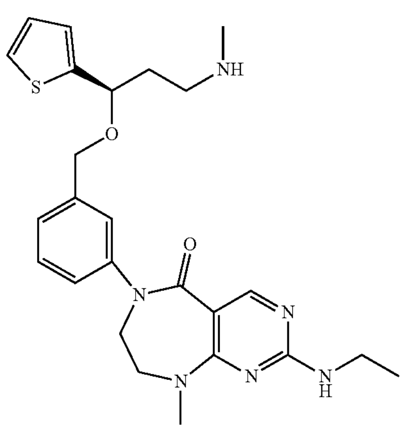 [SMILES: CCNc1ncc2c(n1)N(C)CCN(c1cccc(CO[C@H](CCNC)c3cccs3)c1)C2=O] | (R)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.95 | 481.2 (M + H) |

| EX | Structure | Chemical name | Method | Ret (min) | MS |
|---|---|---|---|---|---|
| 213 | 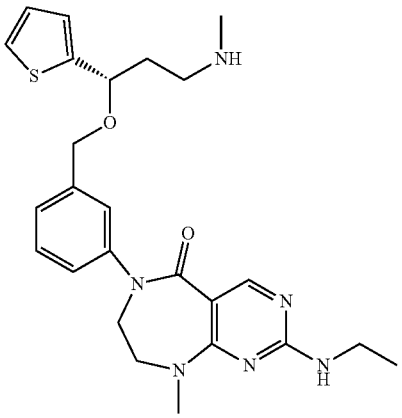 | (S)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.95 | 481.3 (M + H) |
| 214 | 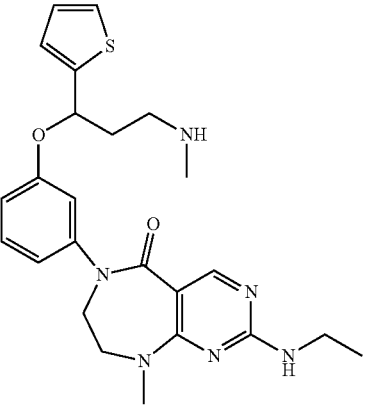 | 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.87 | 467.2 (M + H) |
| 215 | 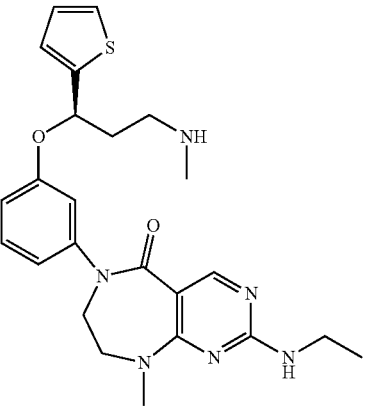 [SMILES: CCNc1ncc2c(n1)N(C)CCN(c1cccc(O[C@H](CCNC)c3cccs3)c1)C2=O] | (R)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.86 | 467.2 (M + H) |

-continued

| EX | Structure | Chemical name | Method | Ret (min) | MS |
|---|---|---|---|---|---|
| 216 | 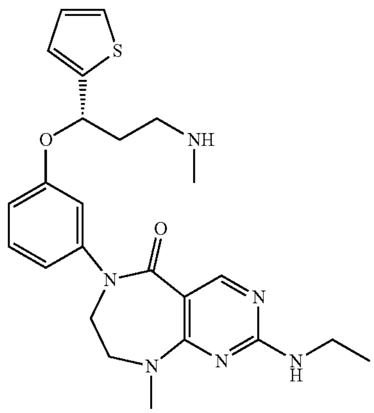 [SMILES: CCNc1ncc2c(n1)N(C)CCN(c1cccc(O[C@@H](CCNC)c3cccs3)c1)C2=O] | (S)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.83 | 467.2 (M + H) |
| 217 | 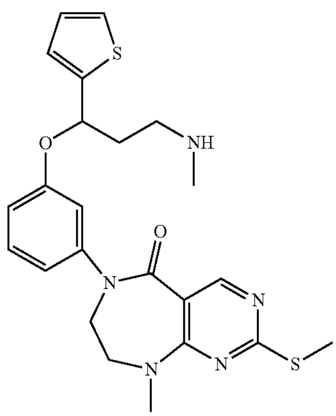 [SMILES: CNCCC(Oc1cccc(N2CCN(C)c3nc(SC)ncc3C2=O)c1)c1cccs1] | 9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | A | 5.12 | 470.2 (M + H) |
| 218 | 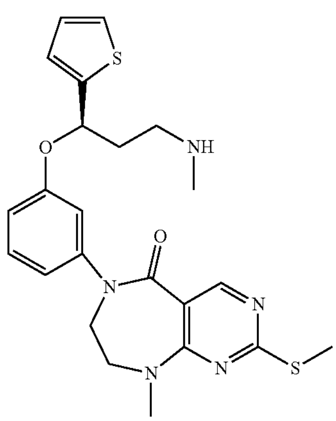 [SMILES: CNCC[C@@H](Oc1cccc(N2CCN(C)c3nc(SC)ncc3C2=O)c1)c1cccs1] | (R)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | A | 5.12 | 470.1 (M + H) |

-continued

| EX | Structure | Chemical name | Method | Ret (min) | MS |
|---|---|---|---|---|---|
| 219 | 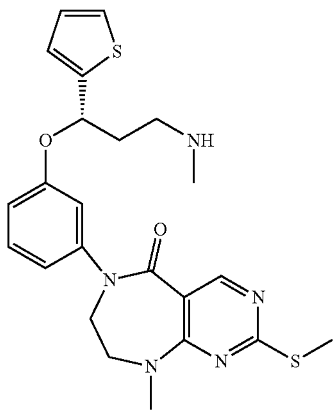 [SMILES: CNCC[C@H](Oc1cccc(N2CCN(C)c3nc(SC)ncc3C2=O)c1)c1cccs1] | (S)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | A | 5.12 | 470.2 (M + H) |
| 220 | 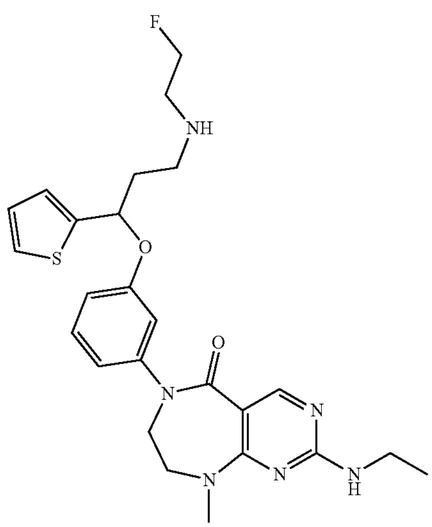 [SMILES: CCNc1ncc2c(n1)N(C)CCN(c1cccc(OC(CCNCCF)c3cccs3)c1)C2=O] | 2-(ethylamino)-6-(3-(3-((2-fluoroethyl)amino)-1-(thiophen-2-yl)propoxy)phenyl)-9-methyl-6,7,8,9-tetrahydro-5H-pyrimido[4,5-e][1,4]diazepin-5-one | A | 4.89 | 499.2 (M + H) |
| 221 | 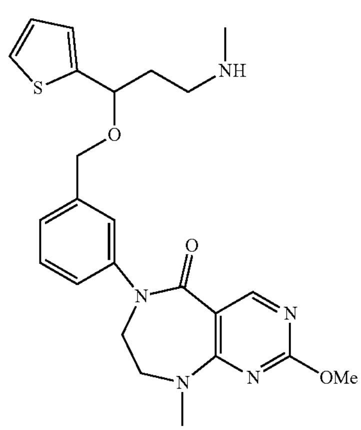 [SMILES: CNCCC(OCc1cccc(N2CCN(C)c3nc(OC)ncc3C2=O)c1)c1cccs1] | 2-methoxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.75 | 468.2 (M + H) |

| EX | Structure | Chemical name | Method | Ret (min) | MS |
|---|---|---|---|---|---|
| 222 | 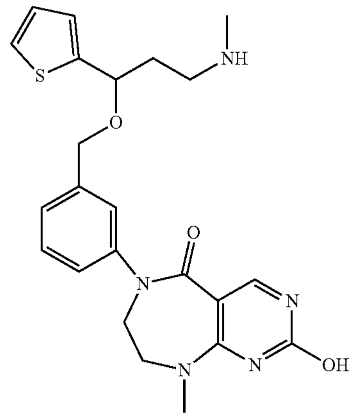 [SMILES: CNCCC(OCc1cccc(N2CCN(C)c3nc(O)ncc3C2=O)c1)c1cccs1] | 2-hydroxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.64 | 454.2 (M + H) |
| 223 | 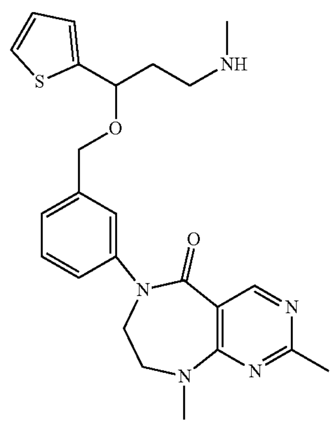 [SMILES: CNCCC(OCc1cccc(N2CCN(C)c3nc(C)ncc3C2=O)c1)c1cccs1] | 2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.59 | 452.2 (M + H) |
| 224 | 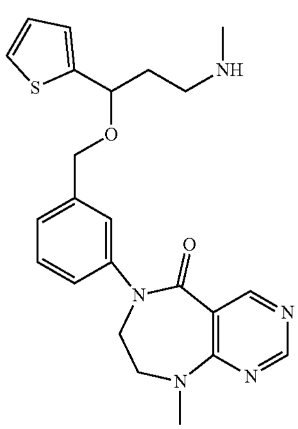 [SMILES: CNCCC(OCc1cccc(N2CCN(C)c3ncncc3C2=O)c1)c1cccs1] | 9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.54 | 438.2 (M + H) |

Ex 225: 2-(Ethylamino)-9-methyl-6-(3-((2-(methyl-amino)-1-phenylethoxy)methyl)phenyl)-6,7,8,9-tetrahydro-5H-pyrimido[4,5-e][1,4]diazepin-5-one

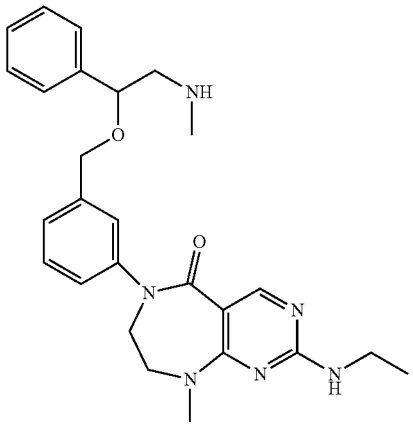 [SMILES: CCNc1ncc2c(n1)N(C)CCN(c1cccc(COC(CNC)c3ccccc3)c1)C2=O]

To a solution of 2-(trimethylsilyl)ethyl-(2-((3-(2-(ethyl-amino)-9-methyl-5-oxo-5,7,8,9-tetrahydro-6H-pyrimido[4,5-e][1,4]diazepin-6-yl)benzyl)oxy)-2-phenylethyl)(methyl)-carbamate (Ex 87, 90 mg, 0.15 mmol) in DMF (3 mL), CsF (113 mg, 0.74 mmol) was added and the mixture was heated at 90° C. for 1 h. The reaction mixture was cooled to rt and the solvent was removed under vacuum. Purification by flash chromatography, silica gel, gradient DCM to 30% MeOH, afforded the desired product (47 mg, 68% yield). HPLC (Method A): Ret, 5.01 min; ESI$^+$-HRMS m/z, 461.2368 (M+1).

This method was used for the preparation of Ex 226-232 using suitable starting materials:

| EX | Structure | Chemical name | Method | Ret (min) | MS |
|---|---|---|---|---|---|
| 226 | 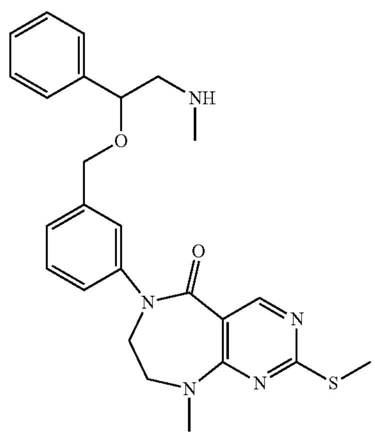 [SMILES: CNCC(OCc1cccc(N2CCN(C)c3nc(SC)ncc3C2=O)c1)c1ccccc1] | 9-methyl-6-(3-((2-(methylamino)-1-phenylethoxy)methyl)phenyl)-2-(methylthio)-6,7,8,9-tetrahydro-5H-pyrimido[4,5-e][1,4]diazepin-5-one | A | 5.32 | 464.2 (M + H) |
| 227 | 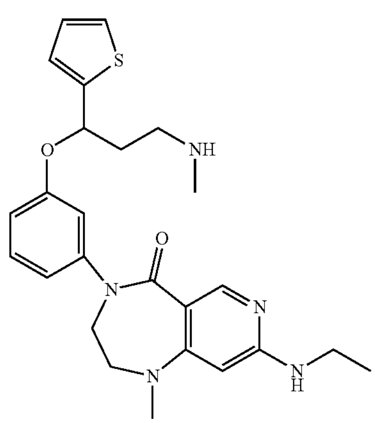 [SMILES: CCNc1cc2c(cn1)C(=O)N(c1cccc(OC(CCNC)c3cccs3)c1)CCN2C] | 8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.81 | 466.2 (M + H) |

-continued

| EX | Structure | Chemical name | Method | Ret (min) | MS |
|---|---|---|---|---|---|
| 228 | 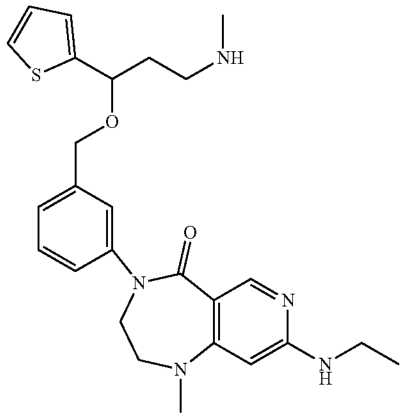 [SMILES: CCNc1cc2c(cn1)C(=O)N(c1cccc(COC(CCNC)c3cccs3)c1)CCN2C] | 8-(ethylamino)-1-methyl-4-(3-((3-(methylamino)-1-(thiophen-2-yl)propoxy)methyl)phenyl)-1,2,3,4-tetrahydro-5H-pyrido[4,3-e][1,4]diazepin-5-one | A | 4.93 | 480.2 (M + H) |
| 229 | 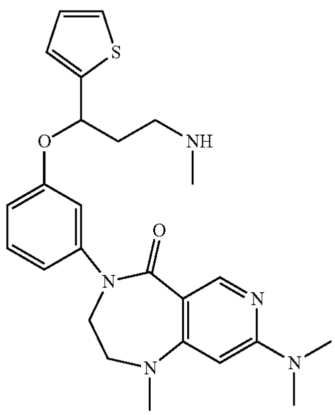 [SMILES: CNCCC(Oc1cccc(N2CCN(C)c3cc(N(C)C)ncc3C2=O)c1)c1cccs1] | 8-(dimethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.70 | 466.2 (M + H) |
| 230 | 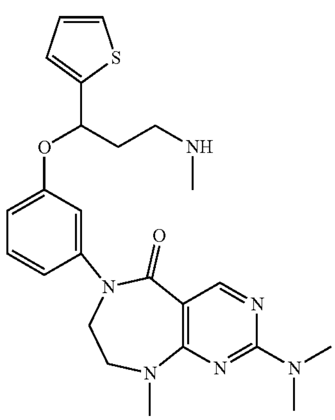 [SMILES: CNCCC(Oc1cccc(N2CCN(C)c3nc(N(C)C)ncc3C2=O)c1)c1cccs1] | 2-(dimethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.72 | 467.2 (M + H) |

| EX | Structure | Chemical name | Method | Ret (min) | MS |
|---|---|---|---|---|---|
| 231 | 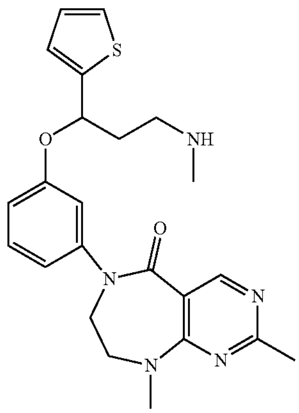 [SMILES: CNCCC(Oc1cccc(N2CCN(C)c3nc(C)ncc3C2=O)c1)c1cccs1] | 2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.46 | 438.2 (M + H) |
| 232 | 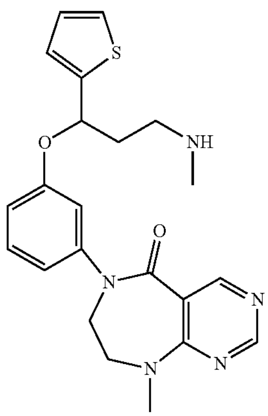 [SMILES: CNCCC(Oc1cccc(N2CCN(C)c3ncncc3C2=O)c1)c1cccs1] | 9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.35 | 424.2 (M + H) |

Example 233: tert-Butyl 4-(3-(2-(ethylamino)-9-methyl-5-oxo-5,7,8,9-tetrahydro-6H-pyrimido[4,5-e][1,4]diazepin-6-yl)phenyl)-3,6-dihydropyridine-1(2H)-carboxylate

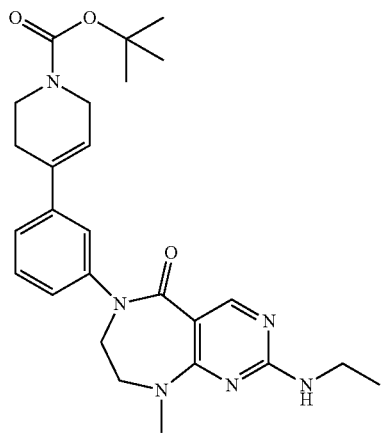 [SMILES: CCNc1ncc2c(n1)N(C)CCN(c1cccc(C3=CCN(C(=O)OC(C)(C)C)CC3)c1)C2=O]

A mixture of 6-(3-bromophenyl)-2-(ethylamino)-9-methyl-6,7,8,9-tetrahydro-5H-pyrimido[4,5-e][1,4]-diazepin-5-one (Ex 112, 311 mg, 0.82 mmol), tert-butyl 4-(4,4,5,5-tetramethyl-1,3,2-dioxaborolan-2-yl)-3,6-dihydropyridine-1(2H)-carboxylate (256 mg, 0.82 mmol), Pd(PPh$_3$)$_4$ (57 mg, 0.05 mmol), NaHCO$_3$ sat solution (2.1 mL) in dioxane (2.1 mL), was irradiated with microwaves at 120° C. for 10 min. Water was added, and the aq layer was extracted with DCM. The combined organic layers were washed with brine, dried with Na$_2$SO$_4$ and concentrated under vacuum. Purification by flash chromatography, silica gel, gradient CH to 100% EtOAc, afforded the title compound (342 mg, 86% yield). ESI$^+$-MS m/z, 479.2 (M+H).

Example 234: tert-Butyl 4-(3-(2-(ethylamino)-9-methyl-5-oxo-5,7,8,9-tetrahydro-6H-pyrimido[4,5-e][1,4]diazepin-6-yl)phenyl)piperidine-1-carboxylate

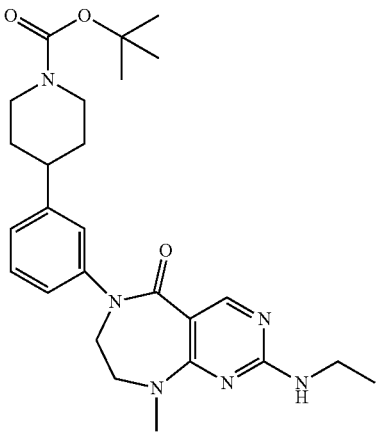 [SMILES: CCNc1ncc2c(n1)N(C)CCN(c1cccc(C3CCN(C(=O)OC(C)(C)C)CC3)c1)C2=O]

tert-Butyl 4-(3-(2-(ethylamino)-9-methyl-5-oxo-5,7,8,9-tetrahydro-6H-pyrimido[4,5-e][1,4]diazepin-6-yl)phenyl)-3,6-dihydro-pyridine-1(2H)-carboxylate (obtained in Ex 233, 328 mg, 0.68 mmol) was dissolved in EtOH (33 mL) and purged several times with argon and vacuum, then 5% Pd/C (102 mg, 0.048 mmol) was added and the reaction mixture was stirred under H₂ atmosphere at rt for 3 days. The reaction mixture was filtered through a plug of Celite, the solvent was removed under vacuum to afford the desired product (286 mg, 87% yield). ESI⁺-MS m/z, 481.2 (M+H).

Example 235: 2-(Ethylamino)-9-methyl-6-(3-(piperidin-4-yl)phenyl)-6,7,8,9-tetrahydro-5H-pyrimido[4,5-e][1,4]diazepin-5-one

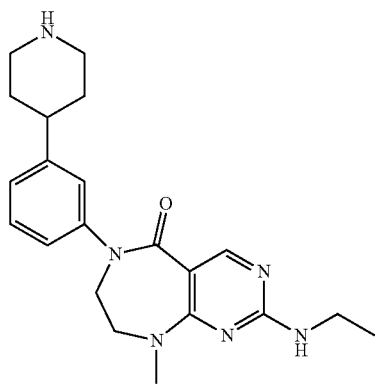 [SMILES: CCNc1ncc2c(n1)N(C)CCN(c1cccc(C3CCNCC3)c1)C2=O]

tert-Butyl 4-(3-(2-(ethylamino)-9-methyl-5-oxo-5,7,8,9-tetrahydro-6H-pyrimido[4,5-e][1,4]diazepin-6-yl)phenyl)piperidine-1-carboxylate (obtained in Ex 234) was treated with the conditions used in Ex 148 to afford the title compound (87% yield). HPLC (Method A): Ret, 4.29 min; ESI⁺-HRMS m/z, 381.2397 (M+H).

Example 236: (R)-6-(3-((3-(Dimethylamino)-1-phenylpropoxy)methyl)phenyl)-2-(ethylamino)-9-methyl-6,7,8,9-tetrahydro-5H-pyrimido[4,5-e][1,4]diazepin-5-one

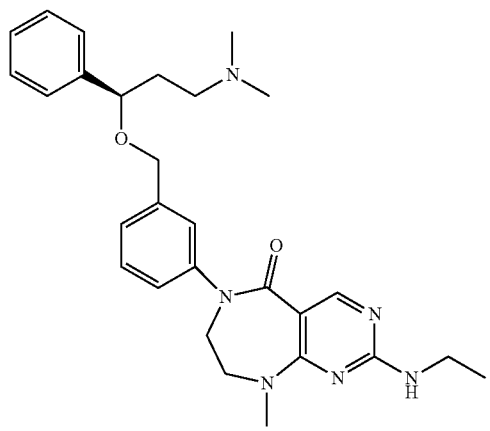 [SMILES: CCNc1ncc2c(n1)N(C)CCN(c1cccc(CO[C@H](CCN(C)C)c3ccccc3)c1)C2=O]

To a solution of (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one (Ex 161, 50 mg, 0.105 mmol), paraformaldehyde (13 mg, 0.421 mmol) and DIPEA (92 μL, 0.527 mmol) in DCE (4 mL), NaBH(OAc)₃ (89 mg, 0.421 mmol) and acetic acid (6 μL, 0.105 mmol) were added and the reaction mixture was stirred at rt for 3 days. NaHCO₃ sat solution was added to the reaction mixture and extracted with DCM. The organic layer was washed with brine, dried with Na₂SO₄ and concentrated under vacuum. Purification by flash chromatography, silica gel, gradient DCM to 30% MeOH, afforded the title compound (25 mg, 48% yield). HPLC (Method A): Ret, 5.08 min; ESI⁺-HRMS m/z, 489.2964 (M+1).

This method was used for the preparation of Ex 237-273 using suitable starting materials:

| EX | Structure | Chemical name | Method | Ret (min) | MS (M + H) |
|---|---|---|---|---|---|
| 237 | 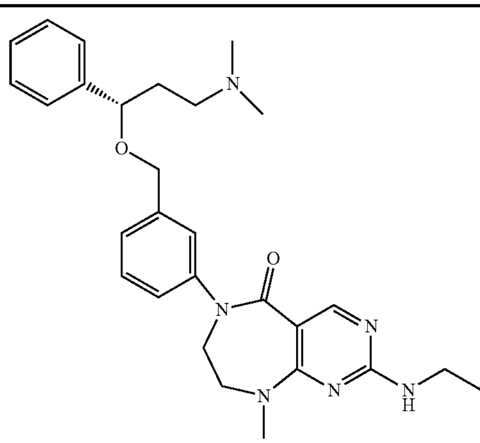 | (S)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one | A | 5.10 | 489.3 (M + H) |

| EX | Chemical name | Method | Ret (min) | MS (M + H) |
|---|---|---|---|---|
| 238 | 6-(3-(3-(dimethylamino)-1-phenylpropoxy)phenyl)-2-(ethylamino)-9-methyl-6,7,8,9-tetrahydro-5H-pyrimido[4,5-e][1,4]diazepin-5-one | A | 4.97 | 475.3 (M + H) |
| 239 | 6-(3-(2-(dimethylamino)-1-phenylethoxy)phenyl)-2-(ethylamino)-9-methyl-6,7,8,9-tetrahydro-5H-pyrimido[4,5-e][1,4]diazepin-5-one | A | 4.86 | 461.3 (M + H) |
| 240 | 6-(3-(3-(benzyl(methyl)amino)propyl)phenyl)-2-(ethylamino)-9-methyl-6,7,8,9-tetrahydro-5H-pyrimido[4,5-e][1,4]diazepin-5-one | A | 4.89 | 459.3 (M + H) |
| 241 | 6-(3-(3-(dimethylamino)propyl)phenyl)-2-(ethylamino)-9-methyl-6,7,8,9-tetrahydro-5H-pyrimido[4,5-e][1,4]diazepin-5-one | A | 4.36 | 383.3 (M + H) |

| EX | Structure | Chemical name | Method | Ret (min) | MS (M + H) |
|---|---|---|---|---|---|
| 242 | 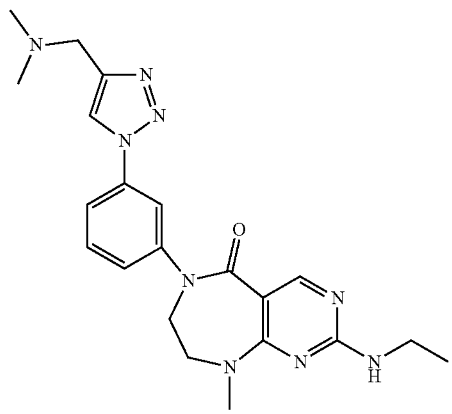 [SMILES: CCNc1ncc2c(n1)N(C)CCN(c1cccc(-n3cc(CN(C)C)nn3)c1)C2=O] | 6-(3-(4-((dimethylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.24 | 422.2 (M + H) |
| 243 | 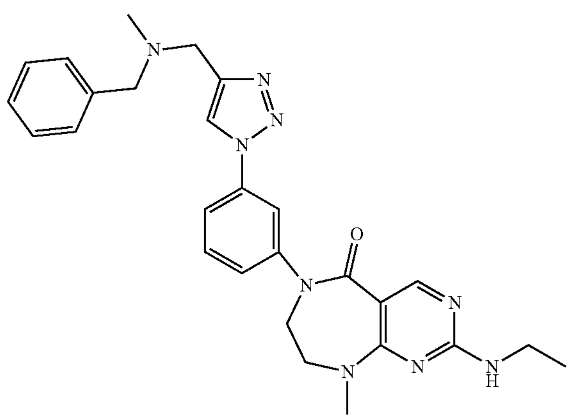 [SMILES: CCNc1ncc2c(n1)N(C)CCN(c1cccc(-n3cc(CN(C)Cc4ccccc4)nn3)c1)C2=O] | 6-(3-(4-((benzyl(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.79 | 498.3 (M + H) |
| 244 | 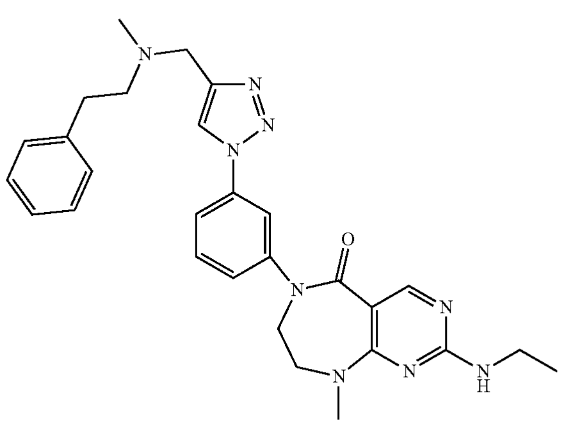 | 2-(ethylamino)-9-methyl-6-(3-(4-((methyl(phenethyl)amino)methyl)-1H-1,2,3-triazol-1-yl)phenyl)-6,7,8,9-tetrahydro-5H-pyrimido[4,5-e][1,4]diazepin-5-one | A | 4.98 | 512.3 (M + H) |

-continued

| EX | Structure | Chemical name | Method | Ret (min) | MS (M + H) |
|---|---|---|---|---|---|
| 245 | 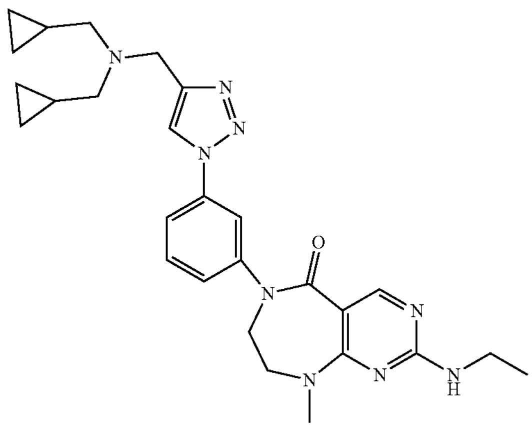 [SMILES: CCNc1ncc2c(n1)N(C)CCN(c1cccc(-n3cc(CN(CC4CC4)CC4CC4)nn3)c1)C2=O] | 6-(3-(4-((bis(cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.80 | 502.3 (M + H) |
| 246 | 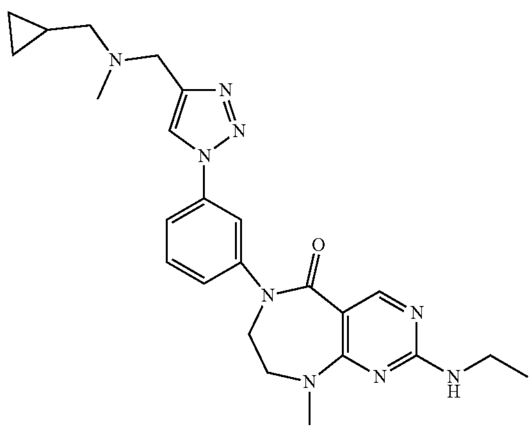 [SMILES: CCNc1ncc2c(n1)N(C)CCN(c1cccc(-n3cc(CN(C)CC4CC4)nn3)c1)C2=O] | 6-(3-(4-(((cyclopropylmethyl)(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.52 | 462.3 (M + H) |
| 247 | 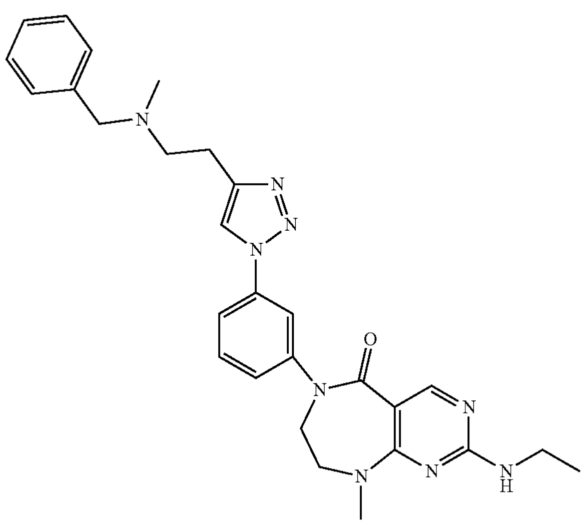 [SMILES: CCNc1ncc2c(n1)N(C)CCN(c1cccc(-n3cc(CCN(C)Cc4ccccc4)nn3)c1)C2=O] | 6-(3-(4-(2-(benzyl(methyl)amino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.82 | 512.3 (M + H) |

-continued

| EX | Structure | Chemical name | Method | Ret (min) | MS (M + H) |
|---|---|---|---|---|---|
| 248 | 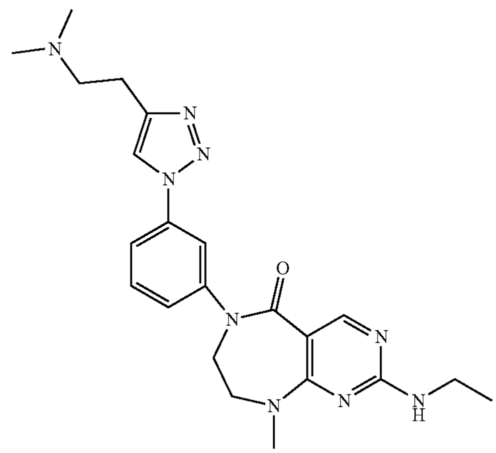 [SMILES: CCNc1ncc2c(n1)N(C)CCN(c1cccc(-n3cc(CCN(C)C)nn3)c1)C2=O] | 6-(3-(4-(2-(dimethylamino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.31 | 436.3 (M + H) |
| 249 | 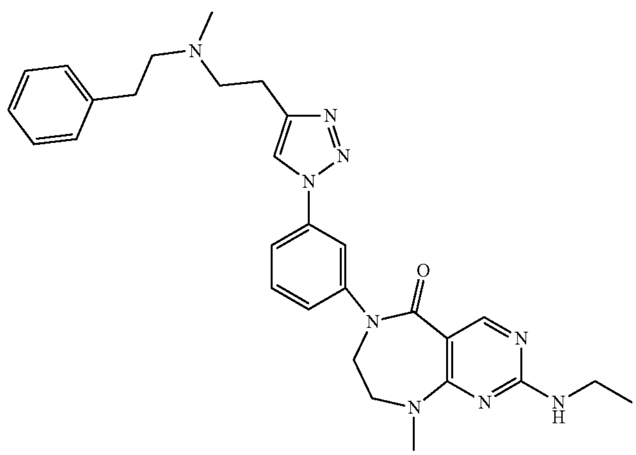 [SMILES: CCNc1ncc2c(n1)N(C)CCN(c1cccc(-n3cc(CCN(C)CCc4ccccc4)nn3)c1)C2=O] | 2-(ethylamino)-9-methyl-6-(3-(4-(2-(methyl(phenethyl)amino)ethyl)-1H-1,2,3-triazol-1-yl)phenyl)-6,7,8,9-tetrahydro-5H-pyrimido[4,5-e][1,4]diazepin-5-one | A | 4.99 | 526.3 (M + H) |
| 250 | 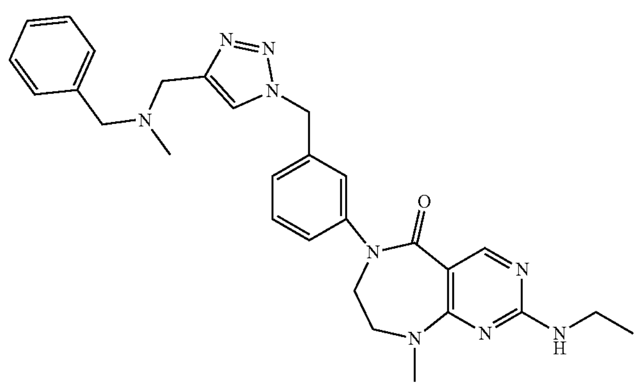 [SMILES: CCNc1ncc2c(n1)N(C)CCN(c1cccc(Cn3cc(CN(C)Cc4ccccc4)nn3)c1)C2=O] | 6-(3-((4-((benzyl(methyl)amino)methyl)-1H-1,2,3-triazol-1-yl)methyl)phenyl)-2-(ethylamino)-9-methyl-6,7,8,9-tetrahydro-5H-pyrimido[4,5-e][1,4]diazepin-5-one | A | 4.73 | 512.3 (M + H) |

-continued

| EX | Structure | Chemical name | Method | Ret (min) | MS (M + H) |
|---|---|---|---|---|---|
| 251 | 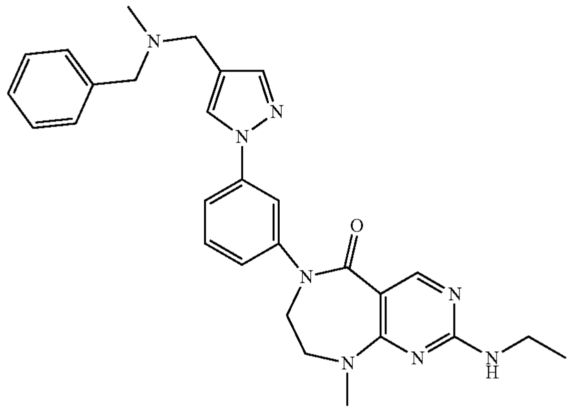 [SMILES: CCNc1ncc2c(n1)N(C)CCN(c1cccc(-n3cc(CN(C)Cc4ccccc4)cn3)c1)C2=O] | 6-(3-(4-((benzyl(methyl)amino)methyl)-1H-pyrazol-1-yl)phenyl)-2-(ethylamino)-9-methyl-6,7,8,9-tetrahydro-5H-pyrimido[4,5-e][1,4]diazepin-5-one | A | 4.86 | 497.3 (M + H) |
| 252 | 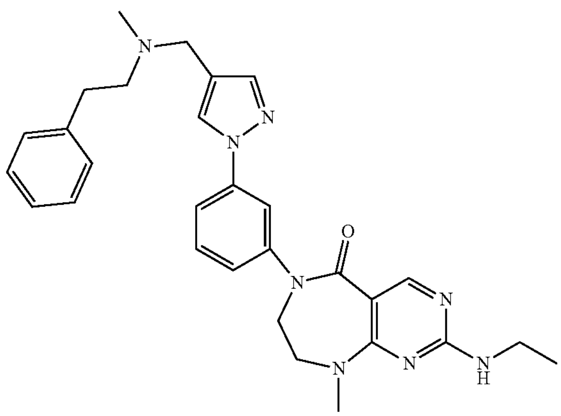 [SMILES: CCNc1ncc2c(n1)N(C)CCN(c1cccc(-n3cc(CN(C)CCc4ccccc4)cn3)c1)C2=O] | 2-(ethylamino)-9-methyl-6-(3-(4-((methyl(phenethyl)amino)methyl)-1H-pyrazol-1-yl)phenyl)-6,7,8,9-tetrahydro-5H-pyrimido[4,5-e][1,4]diazepin-5-one | A | 5.03 | 511.3 (M + H) |
| 253 | 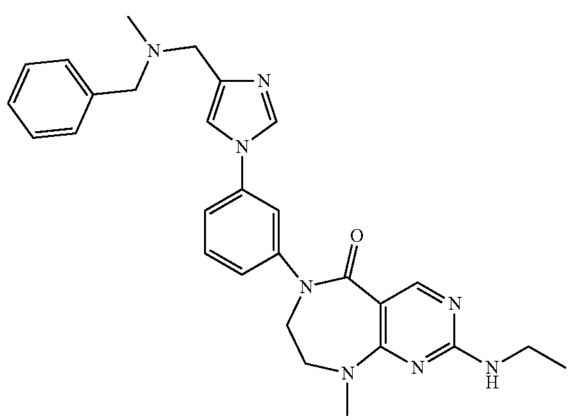 [SMILES: CCNc1ncc2c(n1)N(C)CCN(c1cccc(-n3cnc(CN(C)Cc4ccccc4)c3)c1)C2=O] | 6-(3-(4-((benzyl(methyl)amino)methyl)-1H-imidazol-1-yl)phenyl)-2-(ethylamino)-9-methyl-6,7,8,9-tetrahydro-5H-pyrimido[4,5-e][1,4]diazepin-5-one | A | 4.74 | 497.3 (M + H) |

| EX | Structure | Chemical name | Method | Ret (min) | MS (M + H) |
|---|---|---|---|---|---|
| 254 | 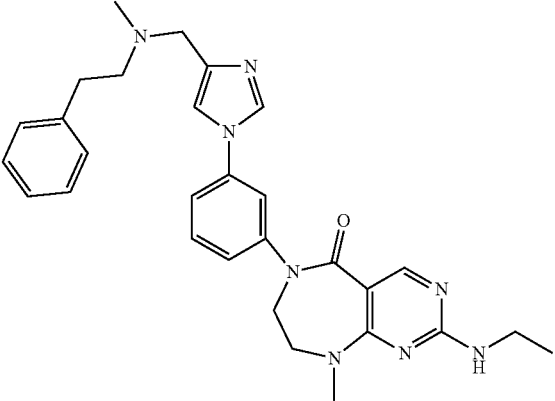 | 2-(ethylamino)-9-methyl-6-(3-(4-((methyl(phenethyl)amino)methyl)-1H-imidazol-1-yl)phenyl)-6,7,8,9-tetrahydro-5H-pyrimido[4,5-e][1,4]diazepin-5-one | A | 4.90 | 511.3 (M + H) |
| 255 | 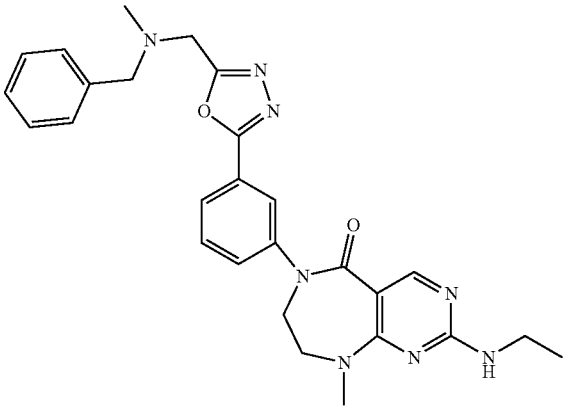 [SMILES: CCNc1ncc2c(n1)N(C)CCN(c1cccc(-c3nnc(CN(C)Cc4ccccc4)o3)c1)C2=O] | 6-(3-(5-((benzyl(methyl)amino)methyl)-1,3,4-oxadiazol-2-yl)phenyl)-2-(ethylamino)-9-methyl-6,7,8,9-tetrahydro-5H-pyrimido[4,5-e][1,4]diazepin-5-one | A | 4.81 | 499.3 (M + H) |
| 256 | 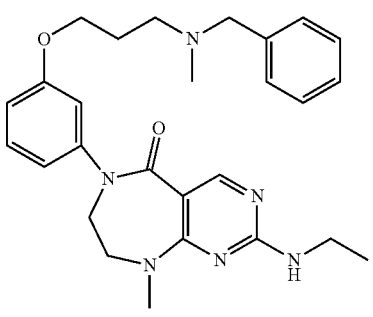 [SMILES: CCNc1ncc2c(n1)N(C)CCN(c1cccc(OCCCN(C)Cc3ccccc3)c1)C2=O] | 6-(3-(3-(benzyl(methyl)amino)propoxy)phenyl)-2-(ethylamino)-9-methyl-6,7,8,9-tetrahydro-5H-pyrimido[4,5-e][1,4]diazepin-5-one | A | 4.91 | 475.3 (M + H) |
| 257 | 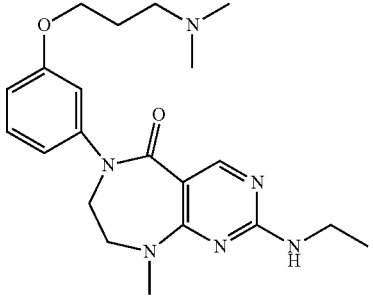 [SMILES: CCNc1ncc2c(n1)N(C)CCN(c1cccc(OCCCN(C)C)c1)C2=O] | 6-(3-(3-(dimethylamino)propoxy)phenyl)-2-(ethylamino)-9-methyl-6,7,8,9-tetrahydro-5H-pyrimido[4,5-e][1,4]diazepin-5-one | A | 4.36 | 399.2 (M + H) |

| EX | Structure | Chemical name | Method | Ret (min) | MS (M + H) |
|---|---|---|---|---|---|
| 258 | 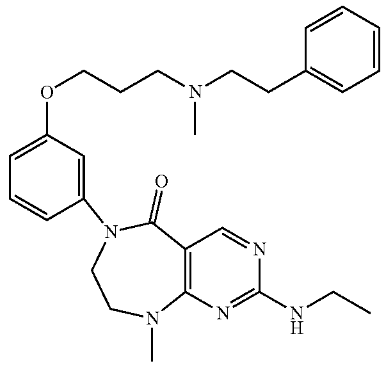 [SMILES: CCNc1ncc2c(n1)N(C)CCN(c1cccc(OCCCN(C)CCc3ccccc3)c1)C2=O] | 2-(ethylamino)-9-methyl-6-(3-(3-(methyl(phenethyl)amino)propoxy)phenyl)-6,7,8,9-tetrahydro-5H-pyrimido[4,5-e][1,4]diazepin-5-one | A | 5.11 | 489.3 (M + H) |
| 259 | 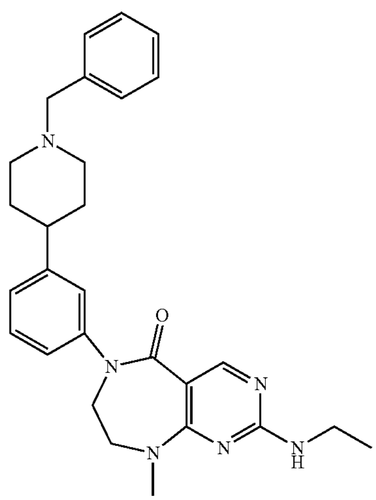 [SMILES: CCNc1ncc2c(n1)N(C)CCN(c1cccc(C3CCN(Cc4ccccc4)CC3)c1)C2=O] | 6-(3-(1-benzylpiperidin-4-yl)phenyl)-2-(ethylamino)-9-methyl-6,7,8,9-tetrahydro-5H-pyrimido[4,5-e][1,4]diazepin-5-one | A | 4.93 | 471.3 (M + H) |
| 260 | 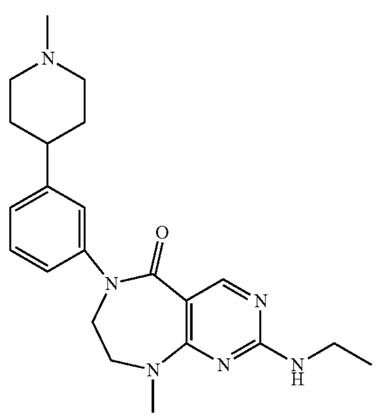 [SMILES: CCNc1ncc2c(n1)N(C)CCN(c1cccc(C3CCN(C)CC3)c1)C2=O] | 2-(ethylamino)-9-methyl-6-(3-(1-methylpiperidin-4-yl)phenyl)-6,7,8,9-tetrahydro-5H-pyrimido[4,5-e][1,4]diazepin-5-one | A | 4.33 | 395.2 (M + H) |

| EX | Structure | Chemical name | Method | Ret (min) | MS (M + H) |
|---|---|---|---|---|---|
| 261 | 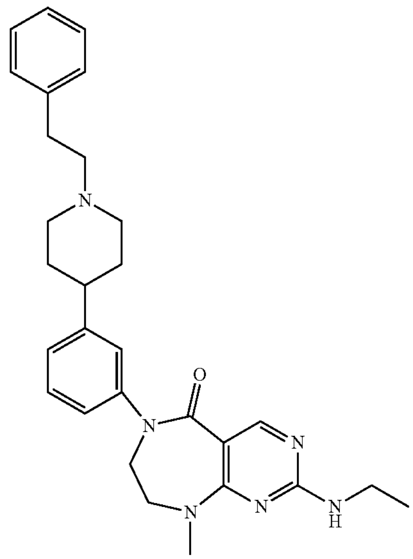 [SMILES: CCNc1ncc2c(n1)N(C)CCN(c1cccc(C3CCN(CCc4ccccc4)CC3)c1)C2=O] | 2-(ethylamino)-9-methyl-6-(3-(1-phenethylpiperidin-4-yl)phenyl)-6,7,8,9-tetrahydro-5H-pyrimido[4,5-e][1,4]diazepin-5-one | A | 5.09 | 485.3 (M + H) |
| 262 | 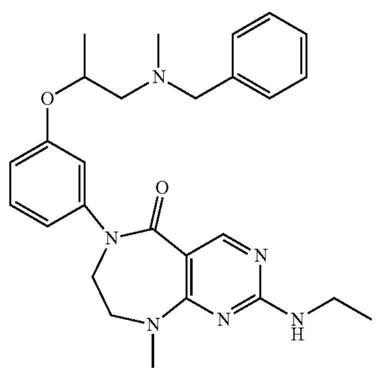 | 6-(3-((1-(benzyl(methyl)amino)propan-2-yl)oxy)phenyl)-2-(ethylamino)-9-methyl-6,7,8,9-tetrahydro-5H-pyrimido[4,5-e][1,4]diazepin-5-one | A | 4.92 | 475.3 (M + H) |
| 263 | 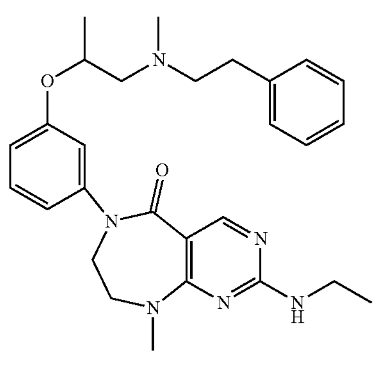 [SMILES: CCNc1ncc2c(n1)N(C)CCN(c1cccc(OC(C)CN(C)CCc3ccccc3)c1)C2=O] | 2-(ethylamino)-9-methyl-6-(3-((1-(methyl(phenethyl)amino)propan-2-yl)oxy)phenyl)-6,7,8,9-tetrahydro-5H-pyrimido[4,5-e][1,4]diazepin-5-one | A | 5.09 | 489.3 (M + H) |

| EX | Structure | Chemical name | Method | Ret (min) | MS (M + H) |
|---|---|---|---|---|---|
| 264 | 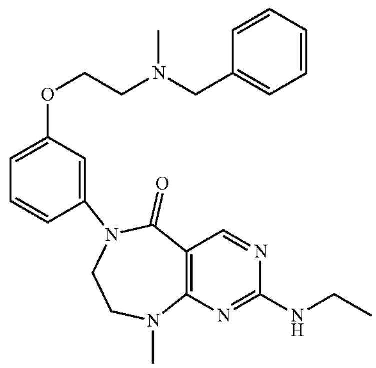 | 6-(3-(2-(benzyl(methyl)amino)ethoxy)phenyl)-2-(ethylamino)-9-methyl-6,7,8,9-tetrahydro-5H-pyrimido[4,5-e][1,4]diazepin-5-one | A | 4.79 | 461.3 (M + H) |
| 265 | 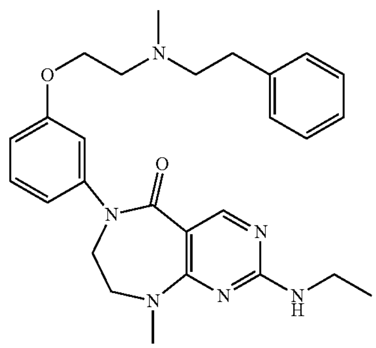 [SMILES: CCNc1ncc2c(n1)N(C)CCN(c1cccc(OCCN(C)CCc3ccccc3)c1)C2=O] | 2-(ethylamino)-9-methyl-6-(3-(2-(methyl(phenethyl)amino)ethoxy)phenyl)-6,7,8,9-tetrahydro-5H-pyrimido[4,5-e][1,4]diazepin-5-one | A | 4.98 | 475.3 (M + H) |
| 266 | 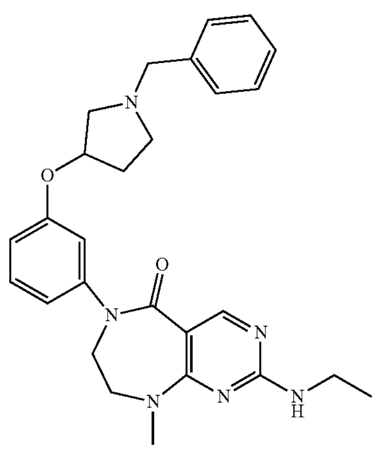 [SMILES: CCNc1ncc2c(n1)N(C)CCN(c1cccc(OC3CCN(Cc4ccccc4)C3)c1)C2=O] | 6-(3-((1-benzylpyrrolidin-3-yl)oxy)phenyl)-2-(ethylamino)-9-methyl-6,7,8,9-tetrahydro-5H-pyrimido[4,5-e][1,4]diazepin-5-one | A | 4.86 | 473.3 (M + H) |
| 267 | 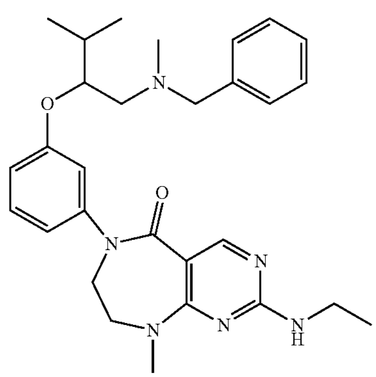 [SMILES: CCNc1ncc2c(n1)N(C)CCN(c1cccc(OC(CN(C)Cc3ccccc3)C(C)C)c1)C2=O] | 6-(3-((1-(benzyl(methyl)amino)-3-methylbutan-2-yl)oxy)phenyl)-2-(ethylamino)-9-methyl-6,7,8,9-tetrahydro-5H-pyrimido[4,5-e][1,4]diazepin-5-one | A | 5.30 | 503.3 (M + H) |

-continued

| EX | Structure | Chemical name | Method | Ret (min) | MS (M + H) |
|---|---|---|---|---|---|
| 268 | 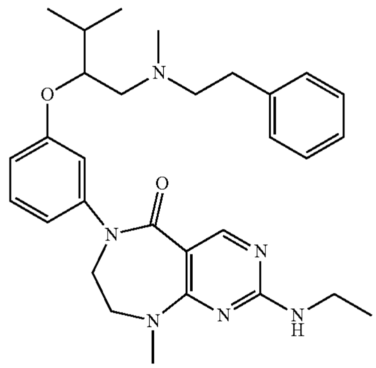 [SMILES: CCNc1ncc2c(n1)N(C)CCN(c1cccc(OC(CN(C)CCc3ccccc3)C(C)C)c1)C2=O] | 2-(ethylamino)-9-methyl-6-(3-((3-methyl-1-(methyl(phenethyl)amino)butan-2-yl)oxy)phenyl)-6,7,8,9-tetrahydro-5H-pyrimido[4,5-e][1,4]diazepin-5-one | A | 5.44 | 517.3 (M + H) |
| 269 | 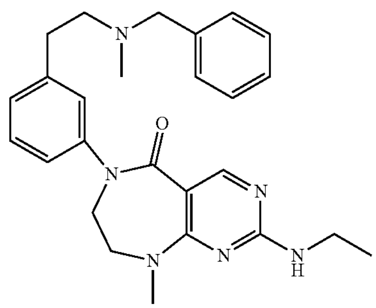 [SMILES: CCNc1ncc2c(n1)N(C)CCN(c1cccc(CCN(C)Cc3ccccc3)c1)C2=O] | 6-(3-(2-(benzyl(methyl)amino)ethyl)phenyl)-2-(ethylamino)-9-methyl-6,7,8,9-tetrahydro-5H-pyrimido[4,5-e][1,4]diazepin-5-one | A | 4.79 | 445.3 (M + H) |
| 270 | 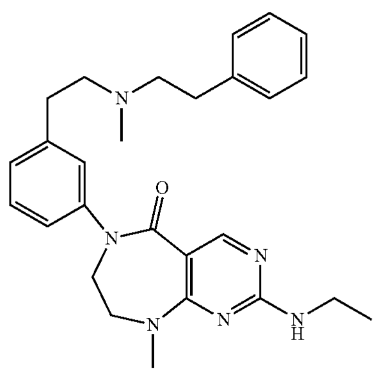 [SMILES: CCNc1ncc2c(n1)N(C)CCN(c1cccc(CCN(C)CCc3ccccc3)c1)C2=O] | 2-(ethylamino)-9-methyl-6-(3-(2-(methyl(phenethyl)amino)ethyl)phenyl)-6,7,8,9-tetrahydro-5H-pyrimido[4,5-e][1,4]diazepin-5-one | A | 5.01 | 459.3 (M + H) |
| 271 | 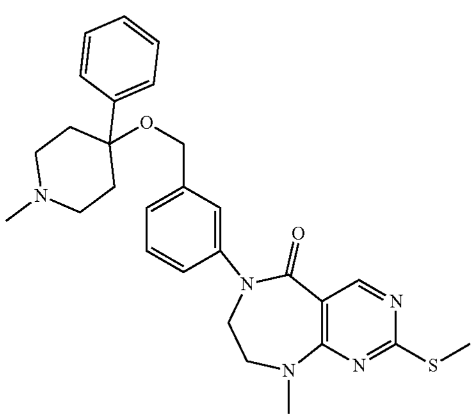 | 9-methyl-6-(3-(((1-methyl-4-phenylpiperidin-4-yl)oxy)methyl)phenyl)-2-(methylthio)-6,7,8,9-tetrahydro-5H-pyrimido[4,5-e][1,4]diazepin-5-one | A | 5.43 | 504.2 (M + H) |

| EX | Structure | Chemical name | Method | Ret (min) | MS (M + H) |
|---|---|---|---|---|---|
| 272 | 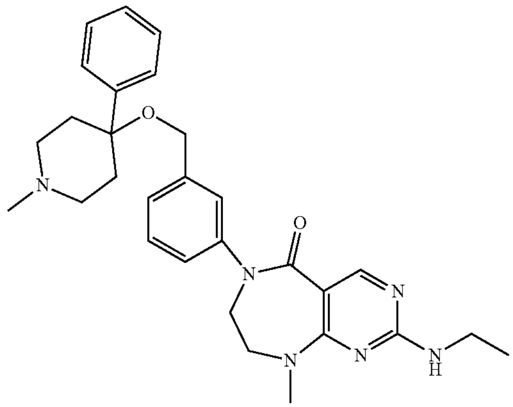 [SMILES: CCNc1ncc2c(n1)N(C)CCN(c1cccc(COC3(c4ccccc4)CCN(C)CC3)c1)C2=O] | 2-(ethylamino)-9-methyl-6-(3-(((1-methyl-4-phenylpiperidin-4-yl)oxy)methyl)phenyl)-6,7,8,9-tetrahydro-5H-pyrimido[4,5-e][1,4]diazepin-5-one | A | 5.06 | 501.3 (M + H) |
| 273 | 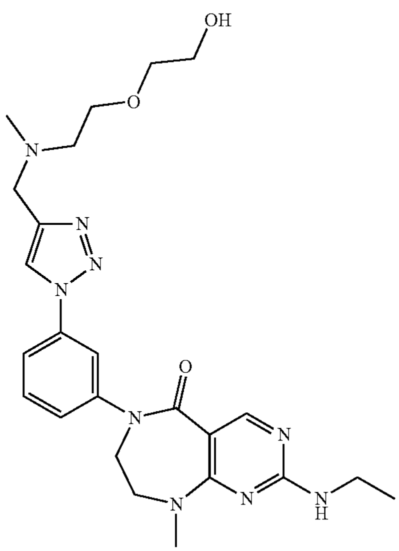 [SMILES: CCNc1ncc2c(n1)N(C)CCN(c1cccc(-n3cc(CN(C)CCOCCO)nn3)c1)C2=O] | 2-(ethylamino)-6-(3-(4-(((2-(2-hydroxyethoxy)ethyl)(methyl)amino)methyl)-1H-1,2,3-triazol-1-yl)phenyl)-9-methyl-6,7,8,9-tetrahydro-5H-pyrimido[4,5-e][1,4]diazepin-5-one | A | 4.28 | 518.3 (M + Na) |

Example 274: 3-(2-(Ethylamino)-9-methyl-5-oxo-5,7,8,9-tetrahydro-6H-pyrimido[4,5-e][1,4]diazepin-6-yl)phenethyl 4-methylbenzenesulfonate

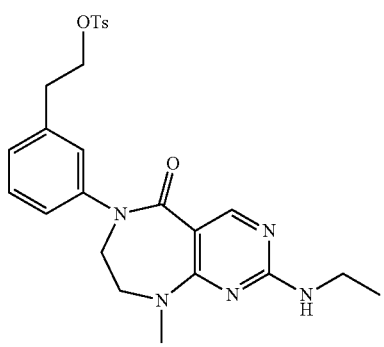 [SMILES: CCNc1ncc2c(n1)N(C)CCN(c1cccc(CCOS(=O)(=O)c3ccc(C)cc3)c1)C2=O]

To a mixture of 2-(ethylamino)-6-(3-(2-hydroxyethyl)phenyl)-9-methyl-6,7,8,9-tetrahydro-5H-pyrimido[4,5-e][1,4]diazepin-5-one (Ex 113, 57 mg, 0.167 mmol) and TEA (47 µL, 0.334 mmol) in DCM (5 mL) cooled at 0° C., tosyl chloride (32 mg, 0.167 mmol) and 4-dimethylaminopyridine (4 mg, 0.033 mmol) were added and the reaction was allowed to warm at rt and stirred for 16 h. The reaction mixture was cooled at 0° C. and additional amounts of TEA (47 µL, 0.334 mmol), tosyl chloride (32 mg, 0.167 mmol) and 4-dimethylaminopyridine (4 mg, 0.033 mmol) were added to complete the reaction and the mixture was stirred at rt for 16 h. The reaction mixture was diluted with DCM, washed with water and the organic phase was concentrated under vacuum. Purification by flash chromatography, silica gel, gradient DCM to 20% MeOH afforded the title compound (73 mg, 88% yield). HPLC (Method B): Ret, 4.21 min; ESI⁺-MS m/z, 496.2 (M+H).

Example 275: 2-(Ethylamino)-6-(3-(2-(4-(3-hydroxyphenyl)piperidin-1-yl)ethyl)phenyl)-9-methyl-6,7,8,9-tetrahydro-5H-pyrimido[4,5-e][1,4]diazepin-5-one

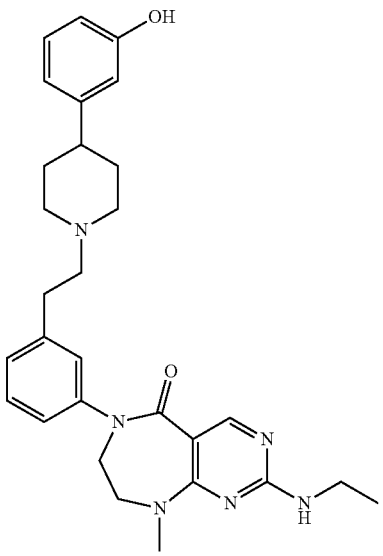 [SMILES: CCNc1ncc2c(n1)N(C)CCN(c1cccc(CCN3CCC(c4cccc(O)c4)CC3)c1)C2=O]

A solution of 3-(2-(ethylamino)-9-methyl-5-oxo-5,7,8,9-tetrahydro-6H-pyrimido[4,5-e][1,4]diazepin-6-yl)phenethyl 4-methylbenzenesulfonate (Ex 274, 36 mg, 0.073 mmol), 4-(3-hydroxyphenyl)piperidine (15.5 mg, 0.087 mmol), diisopropylethylamine (25 µL, 0.145 mmol), and tetrabutylammonium iodide (14 mg, 0.036 mmol) in THF (2 mL) was heated at 100° C. in a sealed tube for 16 h. The reaction mixture was cooled to rt, diluted with EtOAc, washed with water and the organic phase was concentrated under vacuum. Purification by flash chromatography, silica gel, gradient DCM to 15% MeOH afforded the title compound as white solid (21 mg, 54% yield). HPLC (Method A): Ret, 4.79 min; ESI⁺-HRMS m/z, 501.2975 (M+H).

This method was used for the preparation of Ex 276 using suitable starting materials:

Example 277: 1-(3-(2-(Ethylamino)-9-methyl-5-oxo-5,7,8,9-tetrahydro-6H-pyrimido[4,5-e][1,4]diazepin-6-yl)phenyl)-1H-1,2,3-triazole-4-carbaldehyde

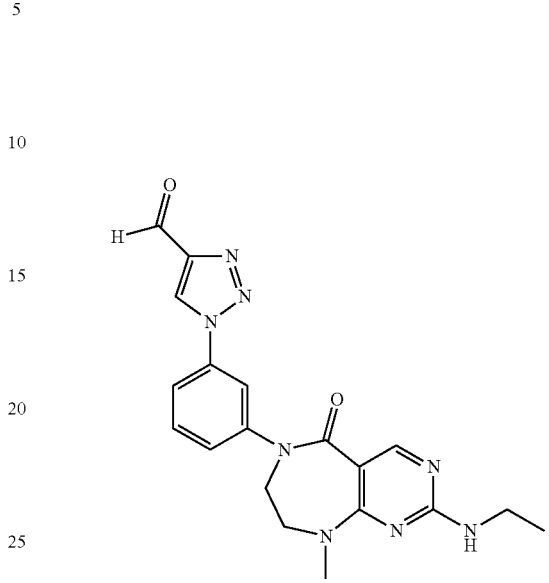

To a solution of 6-(3-(4-(diethoxymethyl)-1H-1,2,3-triazol-1-yl)phenyl)-2-(ethylamino)-9-methyl-6,7,8,9-tetrahydro-5H-pyrimido[4,5-e][1,4]diazepin-5-one (Ex 119, 160 mg, 0.343 mmol) in dioxane (2 mL), HCl (4M solution in dioxane, 3.4 mL, 13.72 mmol) was added and the mixture was stirred at rt for 1.5 h. The reaction mixture was concentrated under vacuum to afford the title compound (135 mg, quant yield). HPLC (Method B): Ret, 3.41 min; ESI⁺-MS m/z, 393.2 (M+H).

| EX | Structure | Chemical name | Method | Ret (min) | MS (M + H) |
|---|---|---|---|---|---|
| 276 | 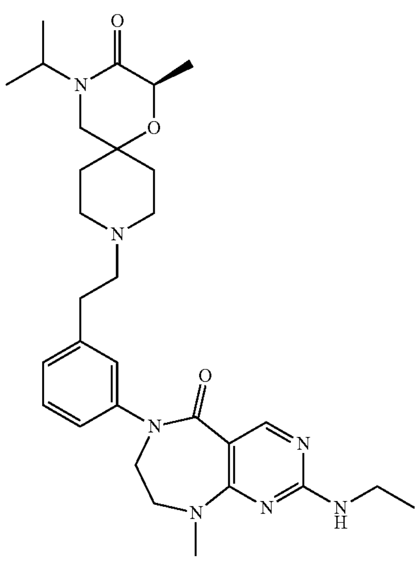 [SMILES: CCNc1ncc2c(n1)N(C)CCN(c1cccc(CCN3CCC4(CC3)CN(C(C)C)C(=O)[C@@H](C)O4)c1)C2=O] | (R)-9-(3-(2-(ethylamino)-9-methyl-5-oxo-5,7,8,9-tetrahydro-6H-pyrimido[4,5-e][1,4]diazepin-6-yl)phenethyl)-4-isopropyl-2-methyl-1-oxa-4,9-diazaspiro[5.5]undecan-3-one | A | 4.65 | 550.3 (M + H) |

Example 278: 2-(Ethylamino)-9-methyl-6-(3-(4-((4-phenylpiperidin-1-yl)methyl)-1H-1,2,3-triazol-1-yl)phenyl)-6,7,8,9-tetrahydro-5H-pyrimido[4,5-e][1,4]diazepin-5-one

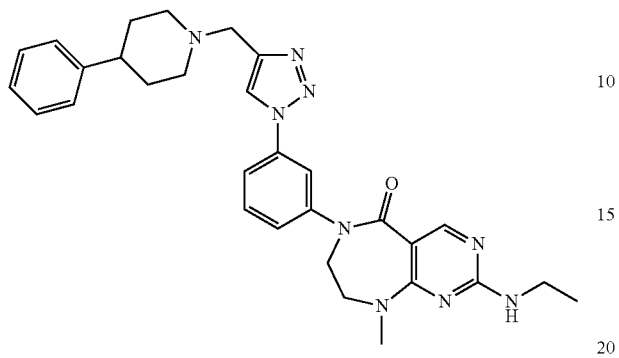

To a mixture of 1-(3-(2-(ethylamino)-9-methyl-5-oxo-5,7,8,9-tetrahydro-6H-pyrimido[4,5-e][1,4]diazepin-6-yl)phenyl)-1H-1,2,3-triazole-4-carbaldehyde (Ex 277, 50 mg, 0.127 mmol), 4-phenylpiperidine (31 mg, 0.191 mmol) and DIPEA (67 μL, 0.382 mmol) in DCE (4 mL), NaBH(OAc)$_3$ (54 mg, 0.255 mmol) was added and the reaction mixture was stirred at rt for 20 h. NaHCO$_3$ sat solution was added, the mixture was extracted with DCM and the organic phase was concentrated under vacuum. Purification by flash chromatography, silica gel, gradient DCM to 10% MeOH, afforded the title compound as white solid (34 mg, 49% yield). HPLC (Method A): Ret, 5.13 min; ESI$^+$-HRMS m/z, 538.3023 (M+H).

This method was used for the preparation of Ex 279-290 using suitable starting materials:

| EX | Structure | Chemical name | Method | Ret (min) | MS (M +H) |
|---|---|---|---|---|---|
| 279 | 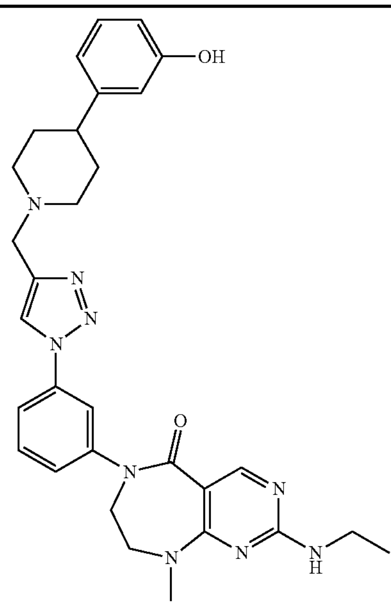 | 2-(ethylamino)-6-(3-(4-((4-(3-hydroxyphenyl)piperidin-1-yl)methyl)-1H-1,2,3-triazol-1-yl)phenyl)-9-methyl-6,7,8,9-tetrahydro-5H-pyrimido[4,5-e][1,4]diazepin-5-one | A | 4.76 | 554.3 (M + H) |

-continued

| EX | Structure | Chemical name | Method | Ret (min) | MS (M +H) |
|---|---|---|---|---|---|
| 280 | 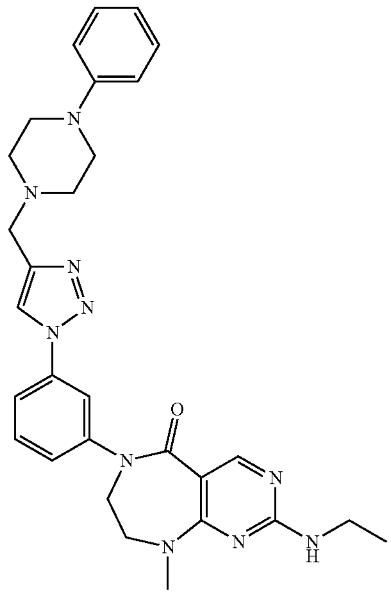 [SMILES: CCNc1ncc2c(n1)N(C)CCN(c1cccc(-n3cc(CN4CCN(c5ccccc5)CC4)nn3)c1)C2=O] | 2-(ethylamino)-9-methyl-6-(3-(4-((4-phenylpiperazin-1-yl)methyl)-1H-1,2,3-triazol-1-yl)phenyl)-6,7,8,9-tetrahydro-5H-pyrimido[4,5-e][1,4]diazepin-5-one | A | 5.00 | 539.3 (M + H) |
| 281 | 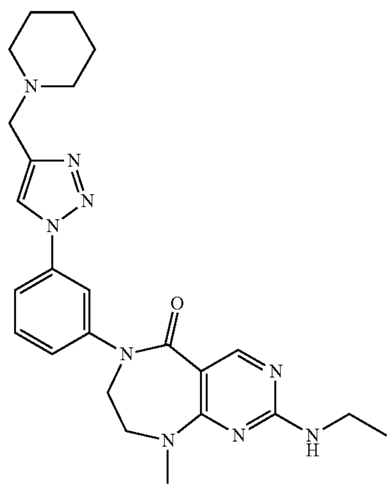 [SMILES: CCNc1ncc2c(n1)N(C)CCN(c1cccc(-n3cc(CN4CCCCC4)nn3)c1)C2=O] | 2-(ethylamino)-9-methyl-6-(3-(4-(piperidin-1-ylmethyl)-1H-1,2,3-triazol-1-yl)phenyl)-6,7,8,9-tetrahydro-5H-pyrimido[4,5-e][1,4]diazepin-5-one | A | 4.44 | 462.3 (M + H) |
| 282 | 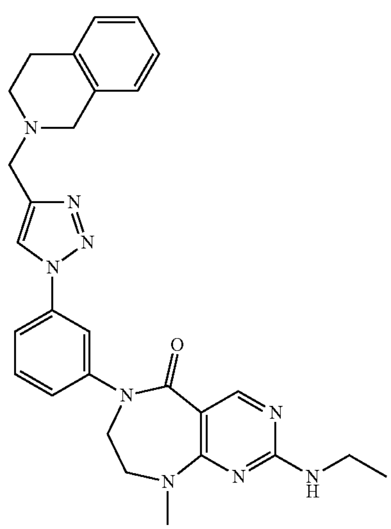 [SMILES: CCNc1ncc2c(n1)N(C)CCN(c1cccc(-n3cc(CN4CCc5ccccc5C4)nn3)c1)C2=O] | 6-(3-(4-((3,4-dihydroisoquinolin-2(1H)-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.81 | 510.3 (M + H) |

| EX | Structure | Chemical name | Method | Ret (min) | MS (M +H) |
|---|---|---|---|---|---|
| 283 | 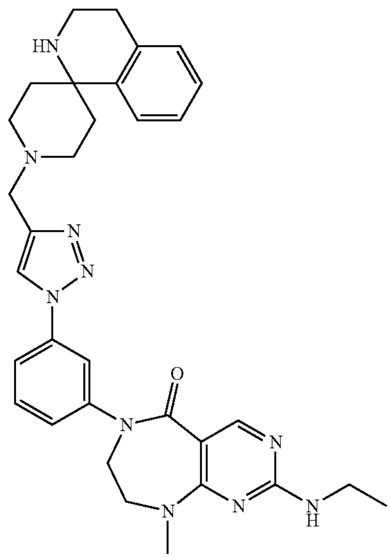 [SMILES: CCNc1ncc2c(n1)N(C)CCN(c1cccc(-n3cc(CN4CCC5(CC4)NCCc4ccccc45)nn3)c1)C2=O] | 6-(3-(4-((3,4-dihydro-2H-spiro[isoquinoline-1,4'-piperidin]-1'-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 6.91 | 579.3 (M + H) |
| 284 | 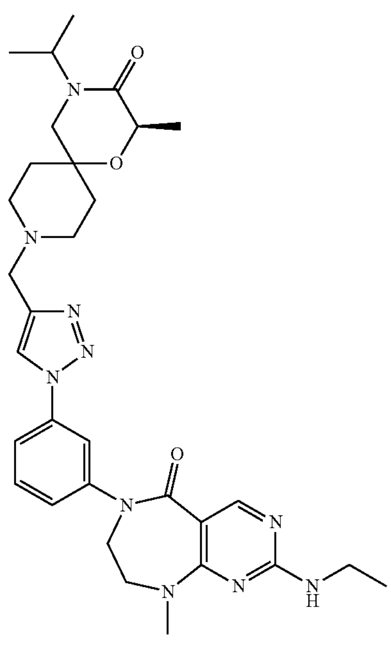 [SMILES: CCNc1ncc2c(n1)N(C)CCN(c1cccc(-n3cc(CN4CCC5(CC4)CN(C(C)C)C(=O)[C@@H](C)O5)nn3)c1)C2=O] | (R)-9-((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)-4-isopropyl-2-methyl-1-oxa-4,9-diazaspiro[5.5]undecan-3-one | A | 4.67 | 603.4 (M + H) |

| EX | Structure | Chemical name | Method | Ret (min) | MS (M +H) |
|---|---|---|---|---|---|
| 285 | 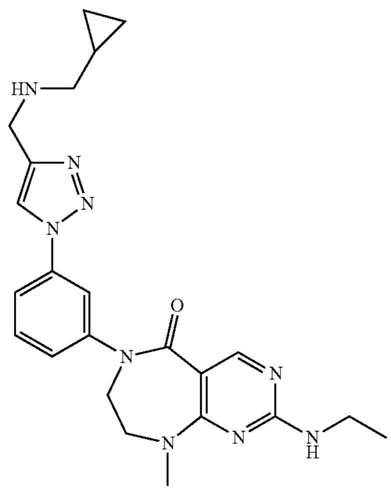 [SMILES: CCNc1ncc2c(n1)N(C)CCN(c1cccc(-n3cc(CNCC4CC4)nn3)c1)C2=O] | 6-(3-(4-(((cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.45 | 448.3 (M + H) |
| 286 | 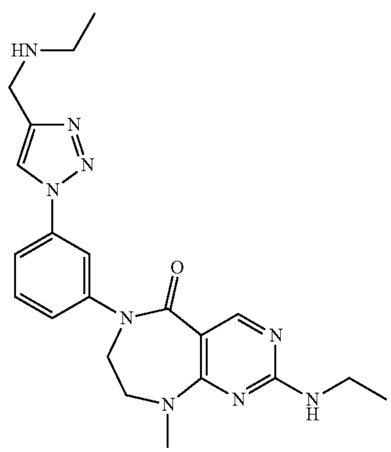 [SMILES: CCNCc1cn(-c2cccc(N3CCN(C)c4nc(NCC)ncc4C3=O)c2)nn1] | 2-(ethylamino)-6-(3-(4-((ethylamino)methyl)-1H-1,2,3-triazol-1-yl)phenyl)-9-methyl-6,7,8,9-tetrahydro-5H-pyrimido[4,5-e][1,4]diazepin-5-one | A | 4.27 | 422.2 (M + H) |
| 287 | 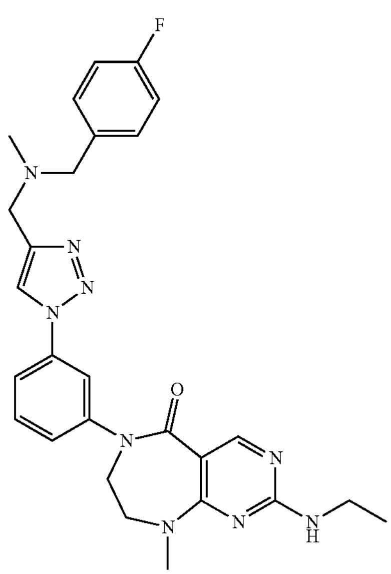 [SMILES: CCNc1ncc2c(n1)N(C)CCN(c1cccc(-n3cc(CN(C)Cc4ccc(F)cc4)nn3)c1)C2=O] | 2-(ethylamino)-6-(3-(4-(((4-fluorobenzyl)(methyl)amino)methyl)-1H-1,2,3-triazol-1-yl)phenyl)-9-methyl-6,7,8,9-tetrahydro-5H-pyrimido[4,5-e][1,4]diazepin-5-one | A | 4.89 | 516.3 (M + H) |

| EX | Structure | Chemical name | Method | Ret (min) | MS (M +H) |
|---|---|---|---|---|---|
| 288 | 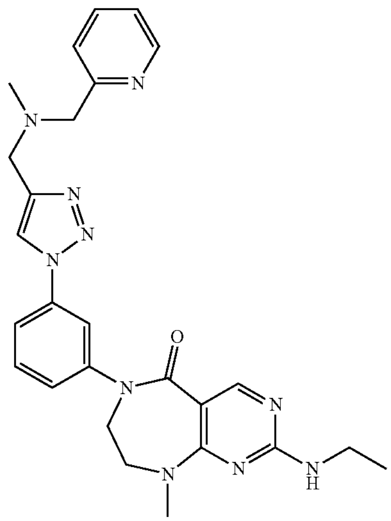 [SMILES: CCNc1ncc2c(n1)N(C)CCN(c1cccc(-n3cc(CN(C)Cc4ccccn4)nn3)c1)C2=O] | 2-(ethylamino)-9-methyl-6-(3-(4-((methyl(pyridin-2-ylmethyl)amino)methyl)-1H-1,2,3-triazol-1-yl)phenyl)-6,7,8,9-tetrahydro-5H-pyrimido[4,5-e][1,4]diazepin-5-one | A | 4.50 | 499.3 (M + H) |
| 289 | 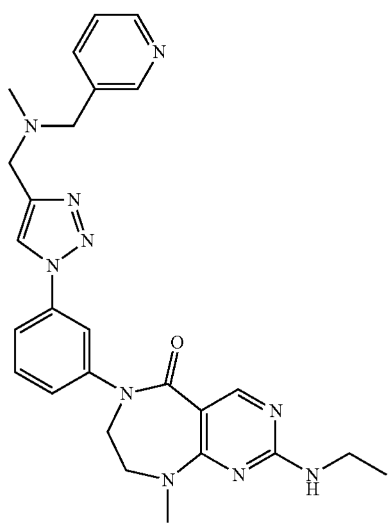 [SMILES: CCNc1ncc2c(n1)N(C)CCN(c1cccc(-n3cc(CN(C)Cc4cccnc4)nn3)c1)C2=O] | 2-(ethylamino)-9-methyl-6-(3-(4-((methyl(pyridin-3-ylmethyl)amino)methyl)-1H-1,2,3-triazol-1-yl)phenyl)-6,7,8,9-tetrahydro-5H-pyrimido[4,5-e][1,4]diazepin-5-one | A | 4.24 | 499.3 (M + H) |
| 290 | 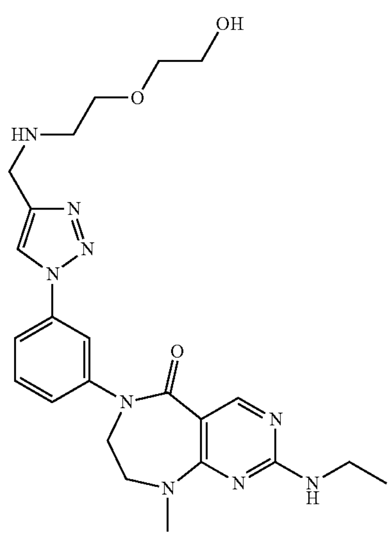 [SMILES: CCNc1ncc2c(n1)N(C)CCN(c1cccc(-n3cc(CNCCOCCO)nn3)c1)C2=O] | 2-(ethylamino)-6-(3-(4-(((2-(2-hydroxyethoxy)ethyl)amino)methyl)-1H-1,2,3-triazol-1-yl)phenyl)-9-methyl-6,7,8,9-tetrahydro-5H-pyrimido[4,5-e][1,4]diazepin-5-one | A | 4.22 | 482.3 (M + H) |

| EX | Structure | Chemical name | Method | Ret (min) | MS (M +H) |
|---|---|---|---|---|---|
| 291 | 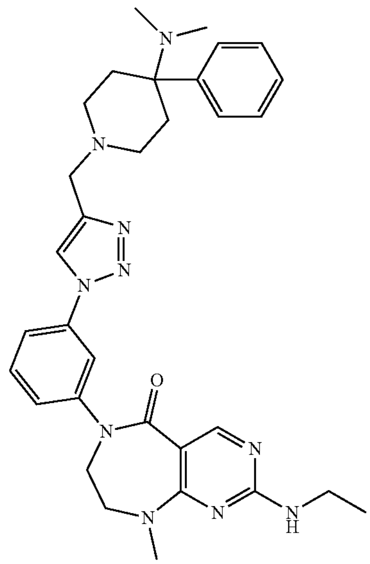 [SMILES: CCNc1ncc2c(n1)N(C)CCN(c1cccc(-n3cc(CN4CCC(c5ccccc5)(N(C)C)CC4)nn3)c1)C2=O] | 6-(3-(4-((4-(dimethylamino)-4-phenylpiperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.28 | 581.3 (M + H) |
| 292 | 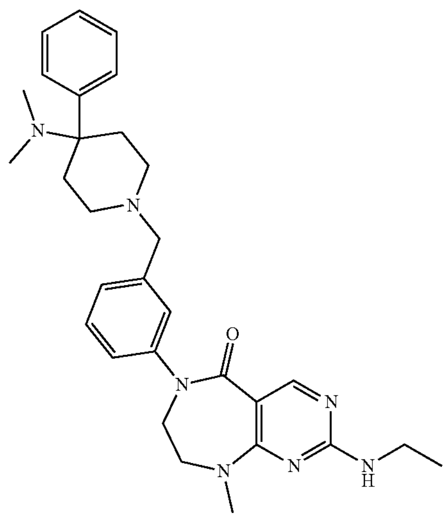 [SMILES: CCNc1ncc2c(n1)N(C)CCN(c1cccc(CN3CCC(c4ccccc4)(N(C)C)CC3)c1)C2=O] | 6-(3-((4-(dimethylamino)-4-phenylpiperidin-1-yl)methyl)phenyl)-2-(ethylamino)-9-methyl-6,7,8,9-tetrahydro-5H-pyrimido[4,5-e][1,4]diazepin-5-one | A | 4.14 | 514.3 (M + H) |
| 293 | 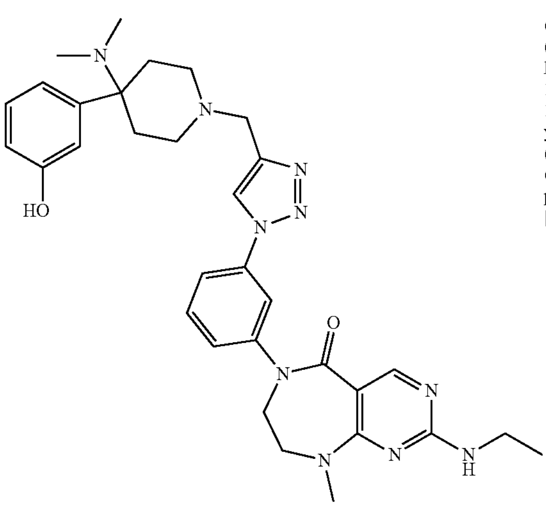 [SMILES: CCNc1ncc2c(n1)N(C)CCN(c1cccc(-n3cc(CN4CCC(c5cccc(O)c5)(N(C)C)CC4)nn3)c1)C2=O] | 6-(3-(4-((4-(dimethylamino)-4-(3-hydroxyphenyl)piperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | A | 4.21 | 597.3 (M + H) |

| EX | Structure | Chemical name | Method | Ret (min) | MS (M +H) |
|---|---|---|---|---|---|
| 294 | 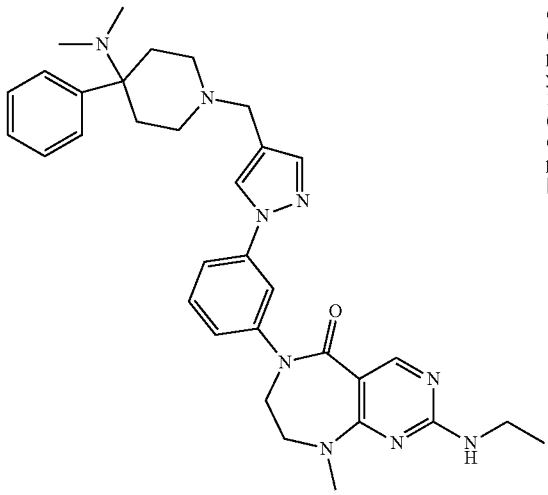 [SMILES: CCNc1ncc2c(n1)N(C)CCN(c1cccc(-n3cc(CN4CCC(c5ccccc5)(N(C)C)CC4)cn3)c1)C2=O] | 6-(3-(4-((4-(dimethylamino)-4-phenylpiperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one | A | 4.32 | 580.4 (M + H) |
| 295 | 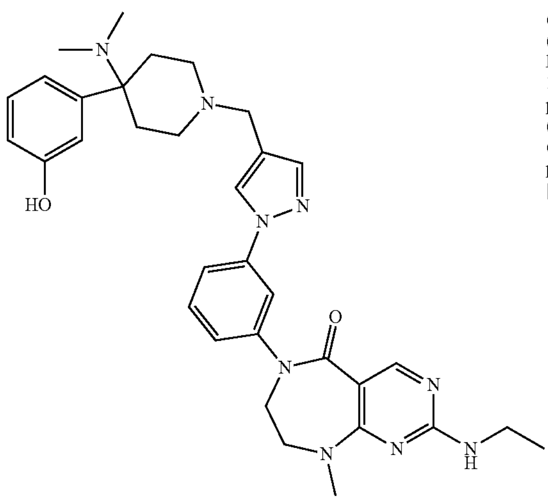 [SMILES: CCNc1ncc2c(n1)N(C)CCN(c1cccc(-n3cc(CN4CCC(c5cccc(O)c5)(N(C)C)CC4)cn3)c1)C2=O] | 6-(3-(4-((4-(dimethylamino)-4-(3-hydroxyphenyl)piperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one | A | 4.25 | 596.3 (M + H) |
| 296 | 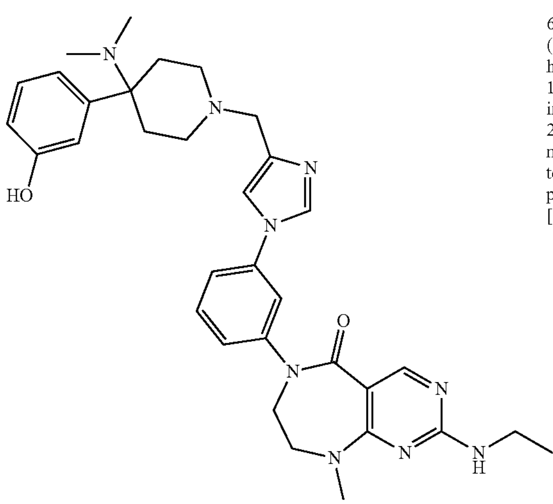 [SMILES: CCNc1ncc2c(n1)N(C)CCN(c1cccc(-n3cnc(CN4CCC(c5cccc(O)c5)(N(C)C)CC4)c3)c1)C2=O] | 6-(3-(4-((4-(dimethylamino)-4-(3-hydroxyphenyl)piperidin-1-yl)methyl)-1H-imidazol-1-yl)phenyl)-2-(ethylamino)-9-methyl-6,7,8,9-tetrahydro-5H-pyrimido[4,5-e][1,4]diazepin-5-one | A | 4.15 | 596.3 (M + H) |

Ex 297-300 were prepared by the method described in Ex 1 using suitable starting materials:

| EX | Structure | Chemical name | Method | RET (min) | MS |
|---|---|---|---|---|---|
| 297 | 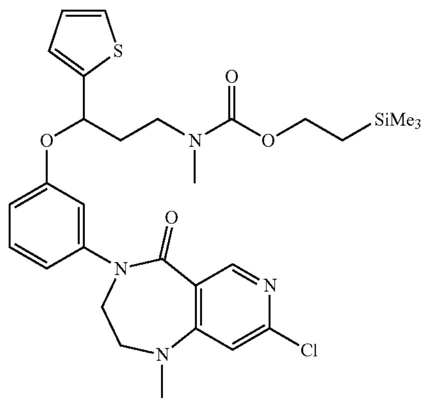 [SMILES: CN(CCC(Oc1cccc(N2CCN(C)c3cc(Cl)ncc3C2=O)c1)c1cccs1)C(=O)OCC[Si](C)(C)C] | 2-(trimethylsilyl)ethyl (3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate | B | 6.12 | 601.2 (M + H) |
| 298 | 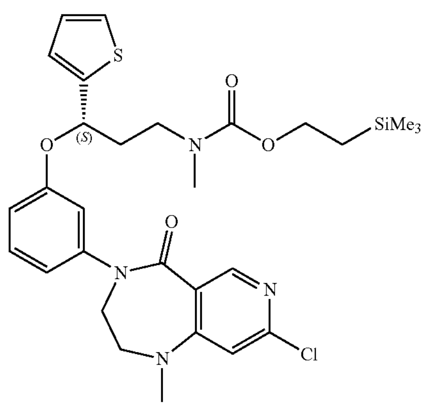 | 2-(trimethylsilyl)ethyl (S)-(3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate | B | 6.12 | 601.2 (M + H) |
| 299 | 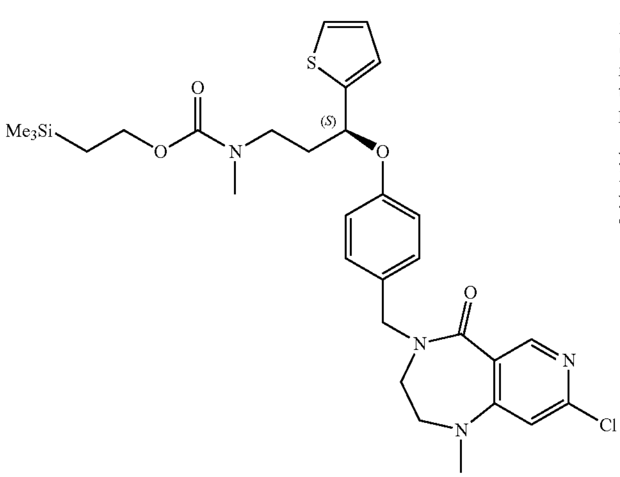 | 2-(trimethylsilyl)ethyl (S)-(3-(4-((8-chloro-1-methyl-5-oxo-1,2,3,5-tetrahydro-4H-pyrido[4,3-e][1,4]diazepin-4-yl)methyl)phenoxy)-3-(thiophen-2-yl)propyl)(methyl)carbamate | B | 6.15 | 615.2 (M + H) |

| EX | Structure | Chemical name | Method | RET (min) | MS |
|---|---|---|---|---|---|
| 300 | 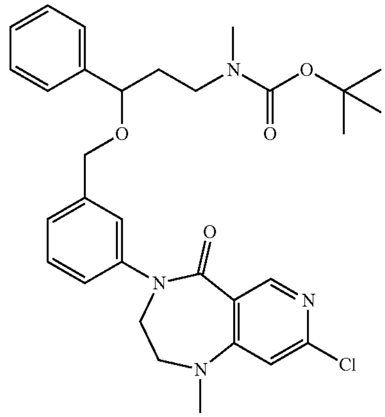 [SMILES: CN(CCC(OCc1cccc(N2CCN(C)c3cc(Cl)ncc3C2=O)c1)c1ccccc1)C(=O)OC(C)(C)C] | tert-butyl (3-((3-(8-chloro-1-methyl-5-oxo-1,2,3,5-tetrahydro-4H-pyrido[4,3-e][1,4]diazepin-4-yl)benzyl)oxy)-3-phenylpropyl)(methyl)carbamate | B | 5.77 | 565.3 (M + H) |

Example 301: 2-(Trimethylsilyl)ethyl (S)-(3-(4-((1,8-dimethyl-5-oxo-1,2,3,5-tetrahydro-4H-pyrido[4,3-e][1,4]diazepin-4-yl)methyl)phenoxy)-3-(thiophen-2-yl)propyl)(methyl)carbamate

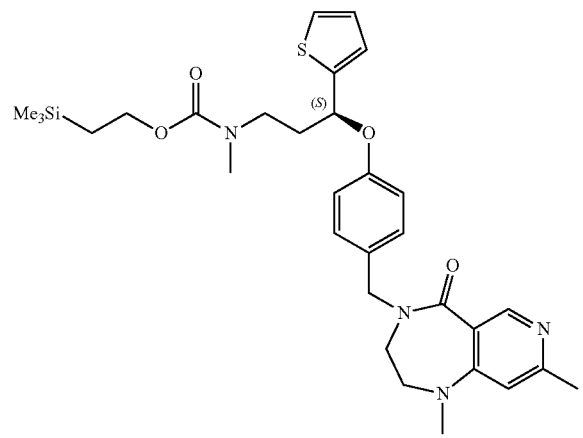

To a mixture of 2-(trimethylsilyl)ethyl (S)-(3-(4-((8-chloro-1-methyl-5-oxo-1,2,3,5-tetrahydro-4H-pyrido[4,3-e][1,4]diazepin-4-yl)methyl)phenoxy)-3-(thiophen-2-yl)propyl)-(methyl)carbamate (Ex 299, 70 mg, 0.114 mmol) and Pd(PPh$_3$)$_4$ (14 mg, 0.011 mmol) in dry and degassed toluene (2 mL), Me$_4$Sn (40 mg, 0.225 mmol) was added and the mixture was heated at 120° C. in a sealed tube under Ar atmosphere for 16 h. The reaction mixture was cooled at rt and concentrated under vacuum. Purification by flash chromatography, silica gel, gradient DCM to 30% MeOH, afforded the title compound as white solid (31 mg, 45% yield). HPLC (Method B): Ret, 4.93 min; ESI$^+$-MS m/z, 595.3 (M+H).

This method was used for the preparation of Ex 302-303 using suitable starting materials:

| EX | Structure | Chemical name | Method | Ret (min) | MS |
|---|---|---|---|---|---|
| 302 | 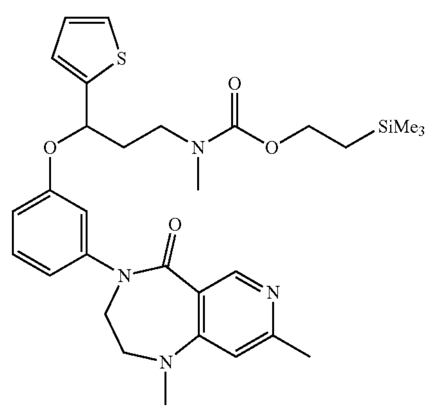 [SMILES: Cc1cc2c(cn1)C(=O)N(c1cccc(OC(CCN(C)C(=O)OCC[Si](C)(C)C)c3cccs3)c1)CCN2C] | 2-(trimethylsilyl)ethyl (3-(3-(1,8-dimethyl-5-oxo-1,2,3,5-tetrahydro-4H-pyrido[4,3-e][1,4]diazepin-4-yl)phenoxy)-3-(thiophen-2-yl)propyl)(methyl)carbamate | B | 4.81 | 581.3 (M + H) |

| EX | Structure | Chemical name | Method | Ret (min) | MS |
|---|---|---|---|---|---|
| 303 | 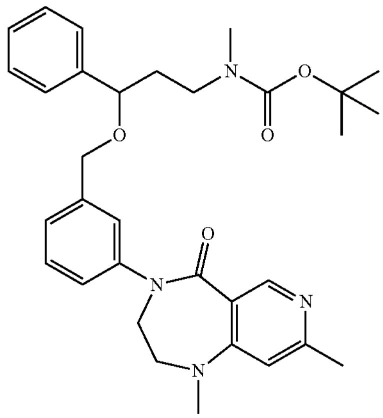 [SMILES: Cc1cc2c(cn1)C(=O)N(c1cccc(COC(CCN(C)C(=O)OC(C)(C)C)c3ccccc3)c1)CCN2C] | tert-butyl (3-((3-(1,8-dimethyl-5-oxo-1,2,3,5-tetrahydro-4H-pyrido[4,3-e][1,4]diazepin-4-yl)benzyl)oxy)-3-phenylpropyl)(methyl)carbamate | B | 4.65 | 545.3 (M + H) |

Example 304: (S)-8-Amino-1-methyl-4-(3-(3-(methylamino)-1-(thiophen-2-yl)propoxy)phenyl)-1,2,3,4-tetrahydro-5H-pyrido[4,3-e][1,4]diazepin-5-one

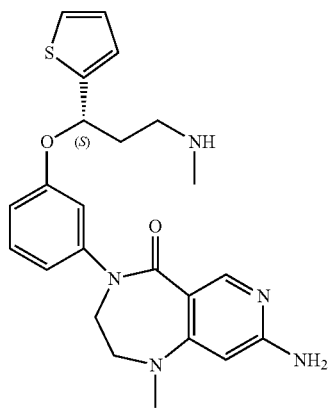

An oven-dried Schlenk tube was charged with Pd$_2$(dba)$_3$ (9 mg, 0.009 mmol) and [1,1'-biphenyl]-2-yldicyclohexylphosphane (8 mg, 0.022 mmol), evacuated and back-filled with argon. A solution of 2-(trimethylsilyl)ethyl (S)-(3-(3-(8-chloro-1-methyl-5-oxo-1,2,3,5-tetrahydro-4H-pyrido[4,3-e][1,4]diazepin-4-yl)phenoxy)-3-(thiophen-2H)propyl)-(methyl)carbamate (Ex 298, 110 mg, 0.183 mmol) in THF (0.5 mL) and lithium bis(trimethylsilyl)amide (0.366 mL, 1 M solution in THF, 0.366 mmol) were added. The mixture was heated at 70° C. for 16 h. The reaction mixture was cooled at rt, TBAF (0.55 mL, 1 M solution in THF, 0.55 mmol) was added and the reaction mixture was stirred at rt for 45 min. NH$_4$Cl sat solution was added, extracted with EtOAc and the organic phase was concentrated under vacuum. Purification by flash chromatography, silica gel, gradient DCM to 40% MeOH/NH$_3$ aq (1:0.01), afforded the title compound as white solid (55 mg, 68% yield). HPLC (Method A): Ret, 4.52 min; ESI$^+$-MS m/z, 438.2 (M+H).

This method was used for the preparation of Ex 305 using suitable starting materials:

| EX | Structure | Chemical name | Method | Ret (min) | MS |
|---|---|---|---|---|---|
| 305 | 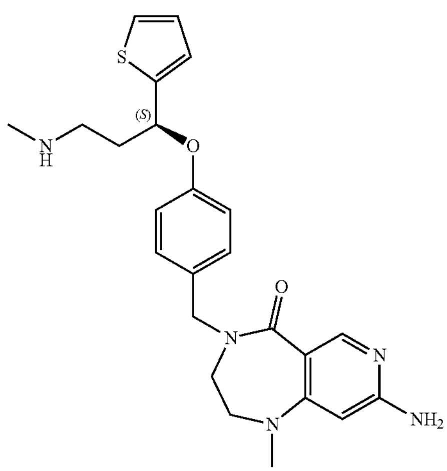 | (S)-8-amino-1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.54 | 452.2 (M + H) |

Ex 306 was prepared by the method described in Ex 148 using suitable starting materials:

| EX | Structure | Chemical name | Method | Ret (min) | MS |
|---|---|---|---|---|---|
| 306 | 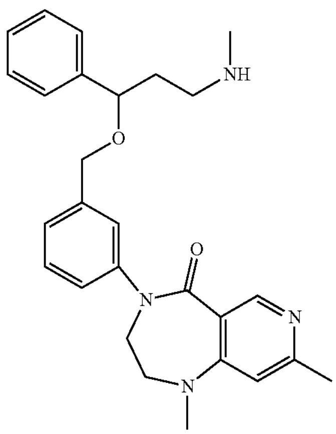 [SMILES: CNCCC(OCc1cccc(N2CCN(C)c3cc(C)ncc3C2=O)c1)c1ccccc1] | 1,8-dimethyl-4-(3-((3-(methylamino)-1-phenylpropoxy)methyl)phenyl)-1,2,3,4-tetrahydro-5H-pyrido[4,3-e][1,4]diazepin-5-one | A | 4.77 | 445.2 (M + H) |

Ex 307-308 were prepared by the method described in Ex 225 using suitable starting materials:

| EX | Structure | Chemical name | Method | Ret (min) | MS |
|---|---|---|---|---|---|
| 307 | 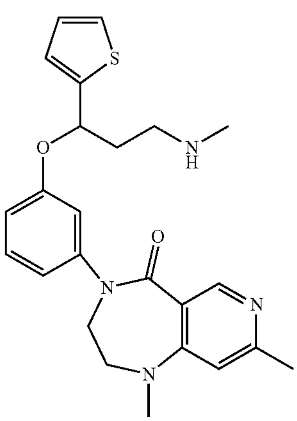 [SMILES: CNCCC(Oc1cccc(N2CCN(C)c3cc(C)ncc3C2=O)c1)c1cccs1] | 1,8-dimethyl-4-(3-(3-(methylamino)-1-(thiophen-2-yl)propoxy)phenyl)-1,2,3,4-tetrahydro-5H-pyrido[4,3-e][1,4]diazepin-5-one | A | 4.48 | 437.2 (M + H) |
| 308 | 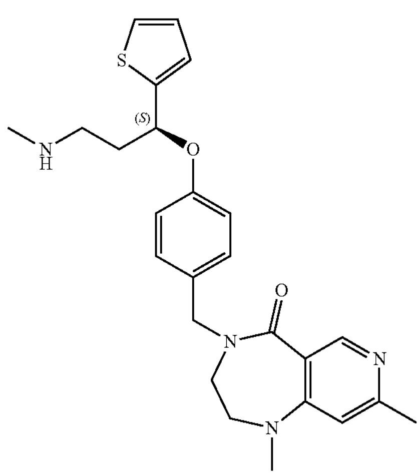 | (S)-1,8-dimethyl-4-(4-(3-(methylamino)-1-(thiophen-2-yl)propoxy)benzyl)-1,2,3,4-tetrahydro-5H-pyrido[4,3-e][1,4]diazepin-5-one | A | 4.50 | 451.2 (M + H) |

Ex 309-311 were prepared by a sequence of reactions according to the methods described in Ex 1 and 69, and using suitable starting materials:

| EX | Structure | Chemical name | Method | Ret (min) | MS |
|---|---|---|---|---|---|
| 309 | 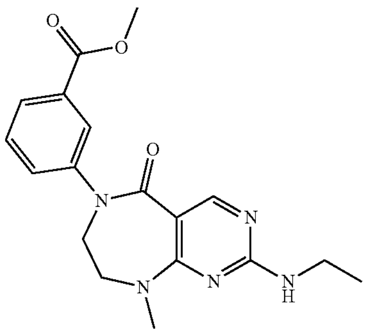 [SMILES: CCNc1ncc2c(n1)N(C)CCN(c1cccc(C(=O)OC)c1)C2=O] | methyl 3-(2-(ethylamino)-9-methyl-5-oxo-5,7,8,9-tetrahydro-6H-pyrimido[4,5-e][1,4]diazepin-6-yl)benzoate | A | 5.22 | 356.1 (M + H) |
| 310 | 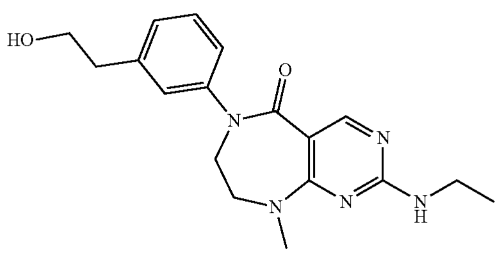 [SMILES: CCNc1ncc2c(n1)N(C)CCN(c1cccc(CCO)c1)C2=O] | 2-(ethylamino)-6-(3-(2-hydroxyethyl)phenyl)-9-methyl-6,7,8,9-tetrahydro-5H-pyrimido[4,5-e][1,4]diazepin-5-one | A | 4.74 | 342.1 (M + H) |
| 311 | 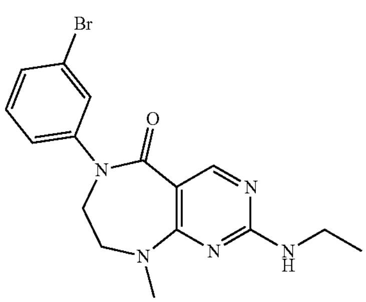 [SMILES: CCNc1ncc2c(n1)N(C)CCN(c1cccc(Br)c1)C2=O] | 6-(3-bromophenyl)-2-(ethylamino)-9-methyl-6,7,8,9-tetrahydro-5H-pyrimido[4,5-e][1,4]diazepin-5-one | A | 5.60 | 376.0 (M + H) |

Example 312: 6-(3-(4-(Dimethylamino)-4-phenylpiperidin-1-yl)phenyl)-2-(ethylamino)-9-methyl-6,7,8,9-tetrahydro-5H-pyrimido[4,5-e][1,4]diazepin-5-one

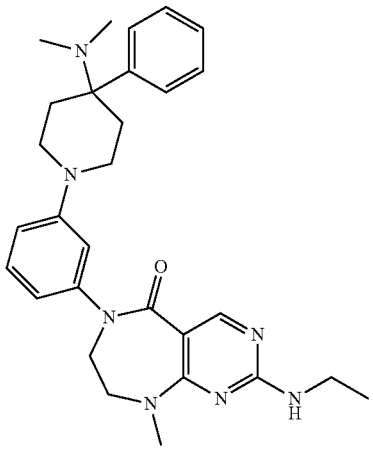 [SMILES: CCNc1ncc2c(n1)N(C)CCN(c1cccc(N3CCC(c4ccccc4)(N(C)C)CC3)c1)C2=O]

A mixture of Pd$_2$(dba)$_3$ (9.4 mg, 0.010 mmol), BINAP (26 mg, 0.041 mmol), NaO$^t$Bu (67 mg, 0.696 mmol), N,N-dimethyl-4-phenylpiperidin-4-amine dihydrochloride (65 mg, 0.235 mmol) and 6-(3-bromophenyl)-2-(ethylamino)-9-methyl-6,7,8,9-tetrahydro-5H-pyrimido[4,5-e][1,4]diazepin-5-one (Ex 311, 77 mg, 0.205 mmol) in dry dioxane (2 mL) was heated at 110° C. in a sealed tube for 20 h. The reaction mixture was cooled at rt, filtered through a pad of celite, washed with DCM and the filtrate was concentrated under vacuum. Purification by flash chromatography, silica gel, gradient from DCM to 20% MeOH afforded the title compound (11 mg, 11% yield). HPLC (Method A): Ret, 4.93 min; ESI$^+$-MS m/z, 500.3 (M+H).

Example 313: 3-(2-(Ethylamino)-9-methyl-5-oxo-5,7,8,9-tetrahydro-6H-pyrimido[4,5-e][1,4]diazepin-6-yl)benzoic Acid

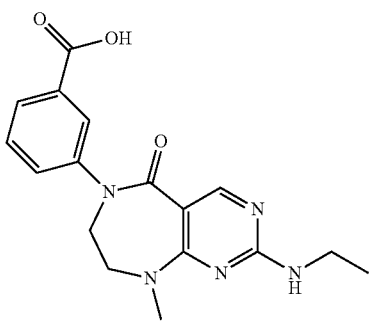 [SMILES: CCNc1ncc2c(n1)N(C)CCN(c1cccc(C(=O)O)c1)C2=O]

To a solution of methyl 3-(2-(ethylamino)-9-methyl-5-oxo-5,7,8,9-tetrahydro-6H-pyrimido[4,5-e][1,4]-diazepin-6-yl)benzoate (Ex 309, 133 mg, 0.374 mmol) in a 1:1 mixture of THF:H$_2$O (3 mL), lithium hydroxide hydrate (94 mg, 2.245 mmol) was added and the mixture was stirred at rt for 20 h. NH$_4$Cl aq sat solution was added and it was extracted with EtOAc and DCM. The combined organic layers were concentrated under vacuum to afford the title compound (128 mg, quant yield). HPLC (Method B): Ret, 3.35 min; ESI$^+$-MS m/z, 342.2 (M+H).

Example 314: 6-(3-(4-(Dimethylamino)-4-phenylpiperidine-1-carbonyl)-phenyl)-2-(ethylamino)-9-methyl-6,7,8,9-tetrahydro-5H-pyrimido[4,5-e][1,4]-diazepin-5-one

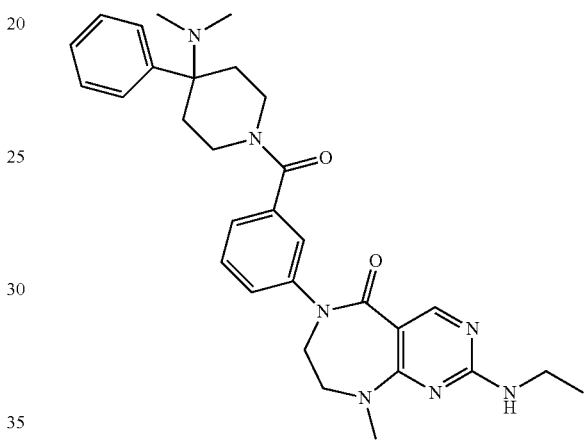

To a suspension of 3-(2-(ethylamino)-9-methyl-5-oxo-5,7,8,9-tetrahydro-6H-pyrimido[4,5-e][1,4]diazepin-6-yl)benzoic acid (Ex 313, 126 mg, 0.368 mmol) in DCM (2 mL) DIPEA (80 mg, 0.613 mmol) and 1-[bis(dimethylamino)methylene]-1H-1,2,3-triazolo[4,5-b]pyridinium 3-oxid hexafluorophosphate (163 mg, 0.429 mmol) and the mixture was stirred at rt for 30 min. A suspension of N,N-dimethyl-4-phenylpiperidin-4-amine dihydrochloride (85 mg, 0.307 mmol) and DIPEA (80 mg, 0.613 mmol) in DCM (1 mL) was added and the mixture was stirred at rt for 20 h. DCM was added, washed with water and NaHCO$_3$ sat solution and the organic layer was concentrated under vacuum. Purification by flash chromatography, silica gel, gradient from DCM to 10% MeOH afforded the title compound (39 mg, 24% yield). HPLC (Method A): Ret, 4.60 min; ESI$^+$-MS m/z, 528.3 (M+H).

Ex 315-322 were prepared by a sequence of reactions according to the methods described in Ex 1 and 148, and using suitable starting materials:

| EX | Structure | Chemical name | Method | Ret (min) | MS |
|---|---|---|---|---|---|
| 315 | 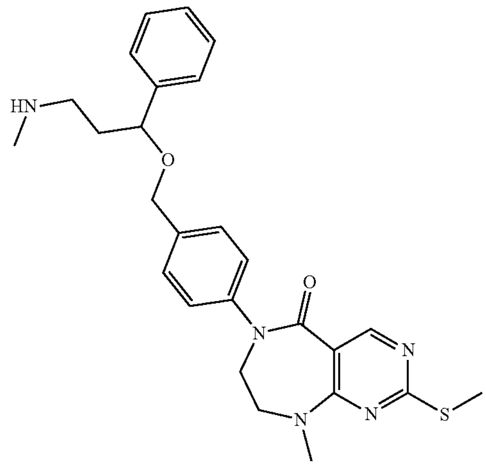 | 9-methyl-6-(4-((3-(methylamino)-1-phenylpropoxy)methyl)phenyl)-2-(methylthio)-6,7,8,9-tetrahydro-5H-pyrimido[4,5-e][1,4]diazepin-5-one | A | 5.31 | 478.2 (M + H) |
| 316 | 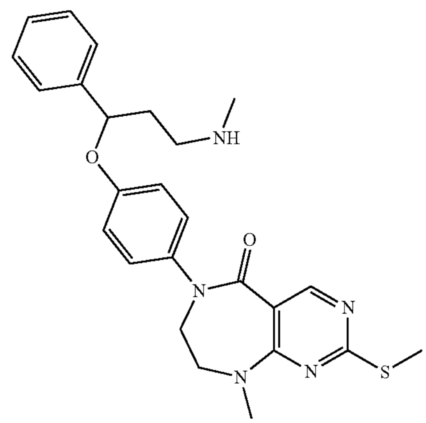 [SMILES: CNCCC(Oc1ccc(N2CCN(C)c3nc(SC)ncc3C2=O)cc1)c1ccccc1] | 9-methyl-6-(4-(3-(methylamino)-1-phenylpropoxy)phenyl)-2-(methylthio)-6,7,8,9-tetrahydro-5H-pyrimido[4,5-e][1,4]diazepin-5-one | A | 5.13 | 464.2 (M + H) |
| 317 | 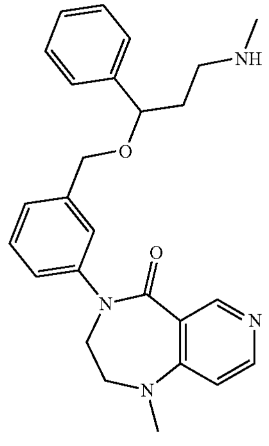 [SMILES: CNCCC(OCc1cccc(N2CCN(C)c3ccncc3C2=O)c1)c1ccccc1] | 1-methyl-4-(3-((3-(methylamino)-1-phenylpropoxy)methyl)phenyl)-1,2,3,4-tetrahydro-5H-pyrido[4,3-e][1,4]diazepin-5-one | A | 4.63 | 431.2 (M + H) |

-continued

| EX | Structure | Chemical name | Method | Ret (min) | MS |
|---|---|---|---|---|---|
| 318 | 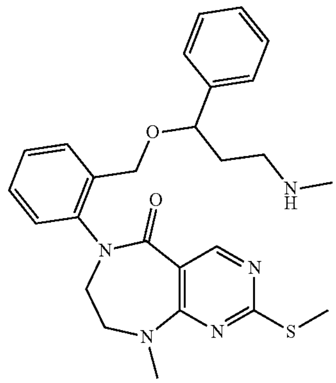 [SMILES: CNCCC(OCc1ccccc1N1CCN(C)c2nc(SC)ncc2C1=O)c1ccccc1] | 9-methyl-6-(2-((3-(methylamino)-1-phenylpropoxy)methyl)phenyl)-2-(methylthio)-6,7,8,9-tetrahydro-5H-pyrimido[4,5-e][1,4]diazepin-5-one | A | 5.27 | 478.2 (M + H) |
| 319 | 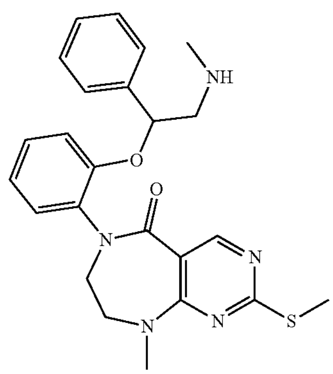 [SMILES: CNCC(Oc1ccccc1N1CCN(C)c2nc(SC)ncc2C1=O)c1ccccc1] | 9-methyl-6-(2-(2-(methylamino)-1-phenylethoxy)phenyl)-2-(methylthio)-6,7,8,9-tetrahydro-5H-pyrimido[4,5-e][1,4]diazepin-5-one | A | 5.40 | 450.2 (M + H) |
| 320 | 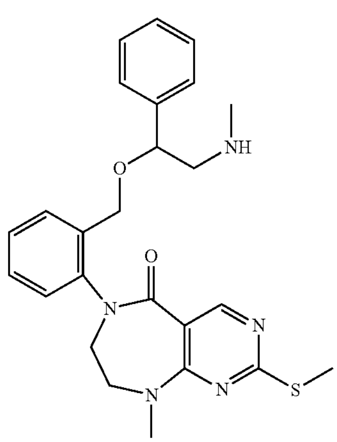 [SMILES: CNCC(OCc1ccccc1N1CCN(C)c2nc(SC)ncc2C1=O)c1ccccc1] | 9-methyl-6-(2-((2-(methylamino)-1-phenylethoxy)methyl)phenyl)-2-(methylthio)-6,7,8,9-tetrahydro-5H-pyrimido[4,5-e][1,4]diazepin-5-one | A | 5.22 | 464.2 (M + H) |

-continued

| EX | Structure | Chemical name | Method | Ret (min) | MS |
|---|---|---|---|---|---|
| 321 | 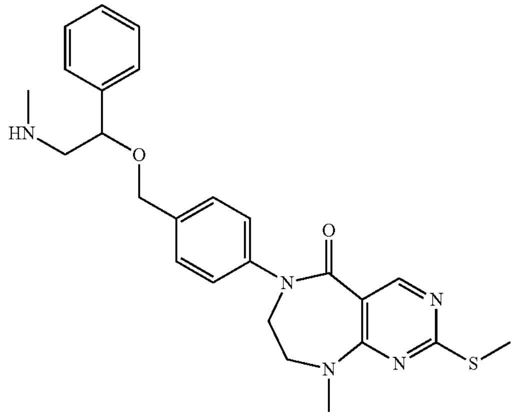 [SMILES: CNCC(OCc1ccc(N2CCN(C)c3nc(SC)ncc3C2=O)cc1)c1ccccc1] | 9-methyl-6-(4-((2-(methylamino)-1-phenylethoxy)methyl)phenyl)-2-(methylthio)-6,7,8,9-tetrahydro-5H-pyrimido[4,5-e][1,4]diazepin-5-one | A | 5.25 | 464.2 (M + H) |
| 322 | 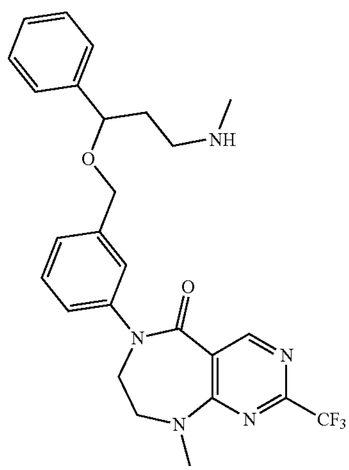 [SMILES: CNCCC(OCc1cccc(N2CCN(C)c3nc(C(F)(F)F)ncc3C2=O)c1)c1ccccc1] | 9-methyl-6-(3-((3-(methylamino)-1-phenylpropoxy)methyl)phenyl)-2-(trifluoromethyl)-6,7,8,9-tetrahydro-5H-pyrimido[4,5-e][1,4]diazepin-5-one | A | 6.23 | 500.2 (M + H) |

Ex 323-331 were prepared by a sequence of reactions according to the methods described in Ex 1 and 225, and using suitable starting materials:

| EX | Structure | Chemical name | Method | Ret (min) | MS |
|---|---|---|---|---|---|
| 323 | 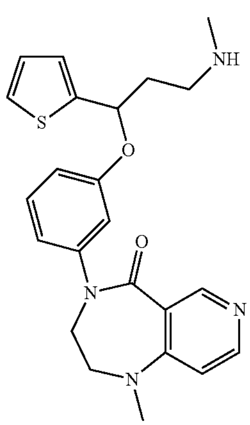 [SMILES: CNCCC(Oc1cccc(N2CCN(C)c3ccncc3C2=O)c1)c1cccs1] | 1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.36 | 423.2 (M + H) |

-continued

| EX | Structure | Chemical name | Method | Ret (min) | MS |
|---|---|---|---|---|---|
| 324 | 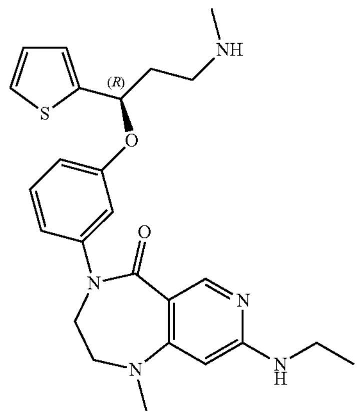 | (R)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.74 | 466.2 (M + H) |
| 325 | 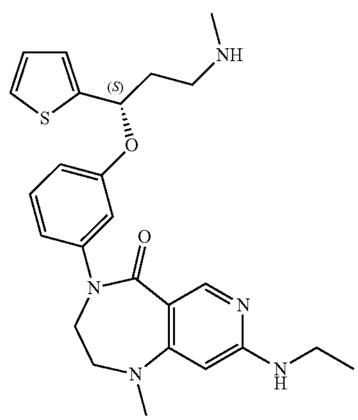 | (S)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.77 | 466.2 (M + H) |
| 326 | 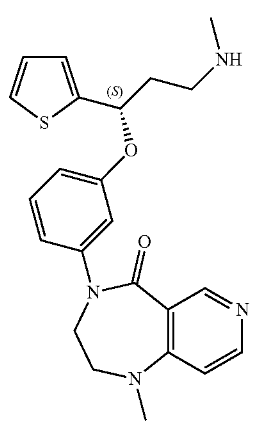 | (S)-1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.39 | 423.2 (M + H) |

-continued

| EX | Structure | Chemical name | Method | Ret (min) | MS |
|---|---|---|---|---|---|
| 327 | 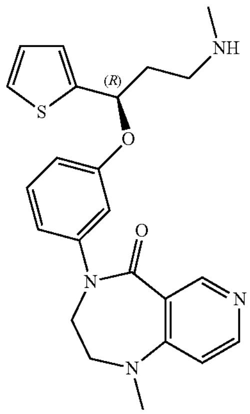 | (R)-1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.39 | 423.2 (M + H) |
| 328 | 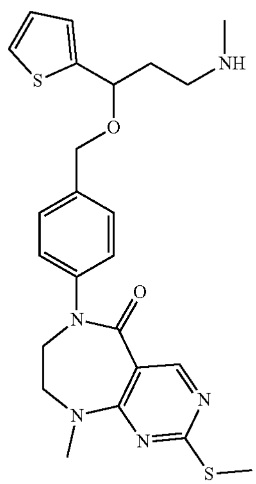 [SMILES: CNCCC(OCc1ccc(N2CCN(C)c3nc(SC)ncc3C2=O)cc1)c1cccs1] | 9-methyl-6-(4-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | A | 5.22 | 484.2 (M + H) |
| 329 | 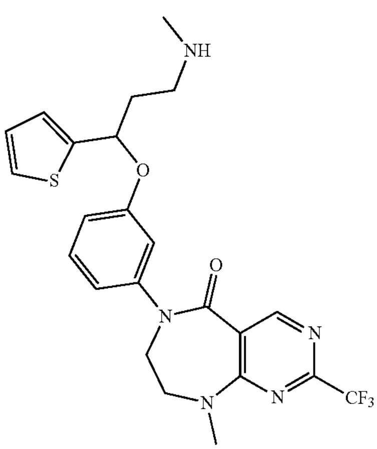 [SMILES: CNCCC(Oc1cccc(N2CCN(C)c3nc(C(F)(F)F)ncc3C2=O)c1)c1cccs1] | 9-methyl-6-(3-(3-(methylamino)-1-(thiophen-2-yl)propoxy)phenyl)-2-(trifluoromethyl)-6,7,8,9-tetrahydro-5H-pyrimido[4,5-e][1,4]diazepin-5-one | A | 6.02 | 492.1 (M + H) |

-continued

| EX | Structure | Chemical name | Method | Ret (min) | MS |
|---|---|---|---|---|---|
| 330 | 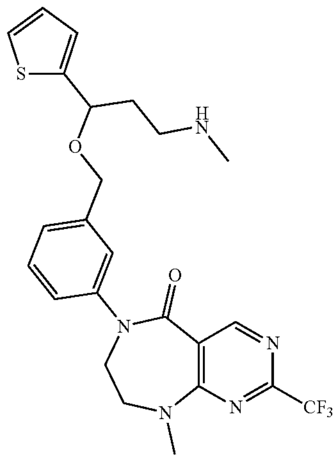 [SMILES: CNCCC(OCc1cccc(N2CCN(C)c3nc(C(F)(F)F)ncc3C2=O)c1)c1cccs1] | 9-methyl-6-(3-((3-(methylamino)-1-(thiophen-2-yl)propoxy)methyl)phenyl)-2-(trifluoromethyl)-6,7,8,9-tetrahydro-5H-pyrimido[4,5-e][1,4]diazepin-5-one | A | 6.16 | 506.2 (M + H) |
| 331 | 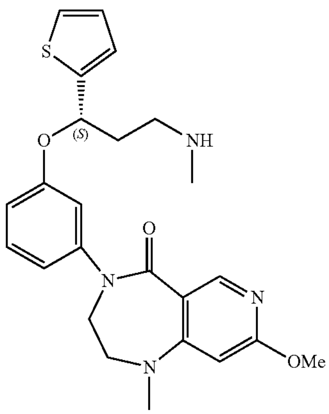 | (S)-8-methoxy-1-methyl-4-(3-(3-(methylamino)-1-(thiophen-2-yl)propoxy)phenyl)-1,2,3,4-tetrahydro-5H-pyrido[4,3-e][1,4]diazepin-5-one | A | 4.59 | 453.2 (M + H) |

Ex 332-344 were prepared by a sequence of reactions according to the methods described in Ex 1, 69 and 148, and using suitable starting materials:

| EX | Structure | Chemical name | Method | Ret (min) | MS |
|---|---|---|---|---|---|
| 332 | 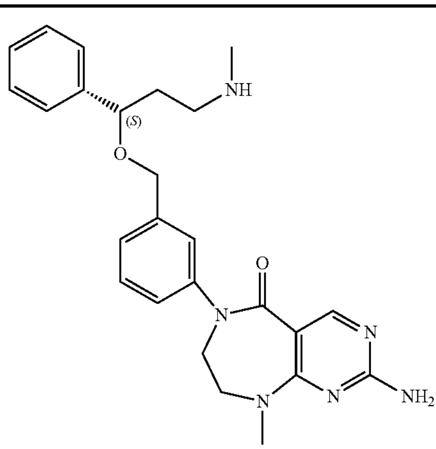 | (S)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one | A | 4.74 | 447.2 (M + H) |

-continued

| EX | Structure | Chemical name | Method | Ret (min) | MS |
|---|---|---|---|---|---|
| 333 | 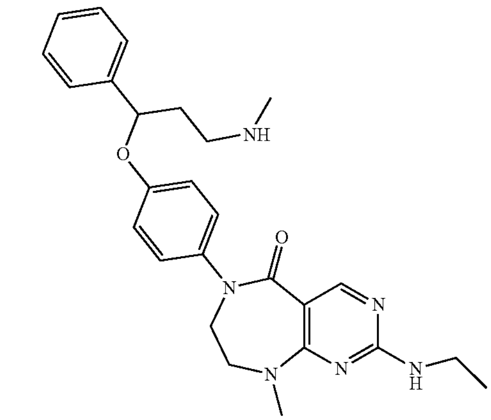 [SMILES: CCNc1ncc2c(n1)N(C)CCN(c1ccc(OC(CCNC)c3ccccc3)cc1)C2=O] | 2-(ethylamino)-9-methyl-6-(4-(3-(methylamino)-1-phenylpropoxy)phenyl)-6,7,8,9-tetrahydro-5H-pyrimido[4,5-e][1,4]diazepin-5-one | A | 4.90 | 461.3 (M + H) |
| 334 | 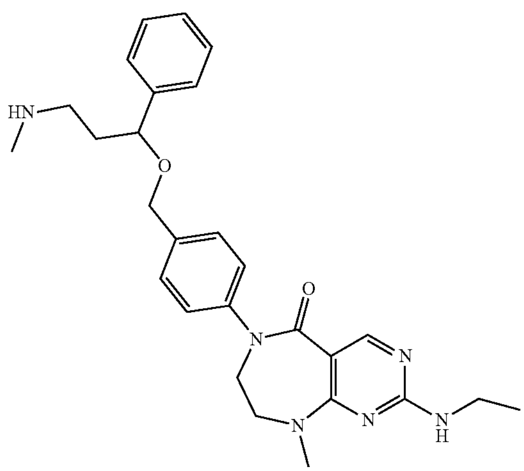 [SMILES: CCNc1ncc2c(n1)N(C)CCN(c1ccc(COC(CCNC)c3ccccc3)cc1)C2=O] | 2-(ethylamino)-9-methyl-6-(4-((3-(methylamino)-1-phenylpropoxy)methyl)phenyl)-6,7,8,9-tetrahydro-5H-pyrimido[4,5-e][1,4]diazepin-5-one | A | 5.05 | 475.3 (M + H) |
| 335 | 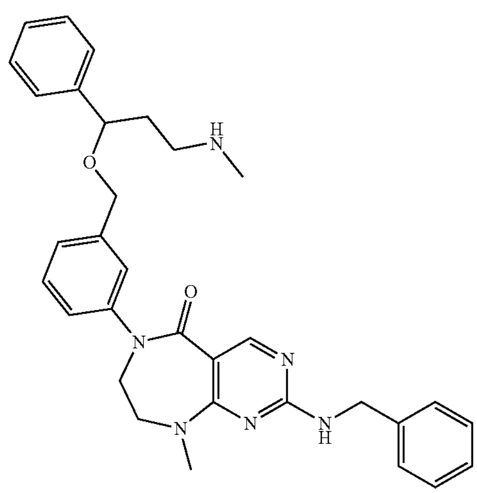 [SMILES: CNCCC(OCc1cccc(N2CCN(C)c3nc(NCc4ccccc4)ncc3C2=O)c1)c1ccccc1] | 2-(benzylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | A | 5.50 | 537.2 (M + H) |

-continued

| EX | Structure | Chemical name | Method | Ret (min) | MS |
|---|---|---|---|---|---|
| 336 | 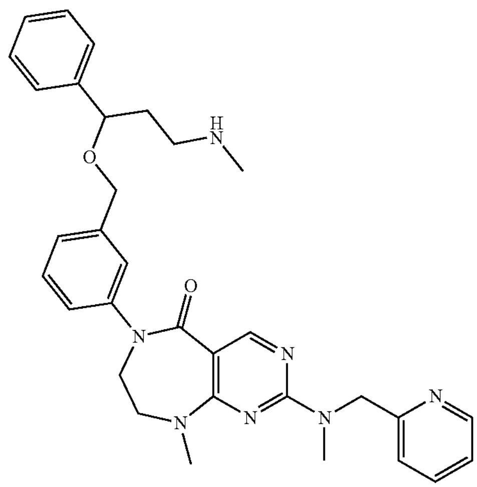 [SMILES: CNCCC(OCc1cccc(N2CCN(C)c3nc(N(C)Cc4ccccn4)ncc3C2=O)c1)c1ccccc1] | 9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | A | 4.67 | 552.3 (M + H) |
| 337 | 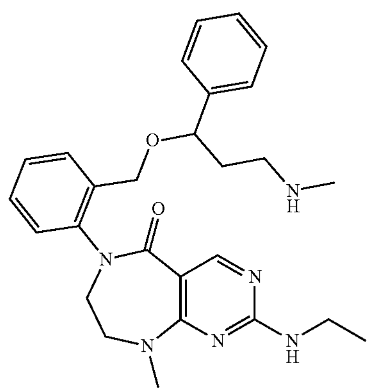 [SMILES: CCNc1ncc2c(n1)N(C)CCN(c1ccccc1COC(CCNC)c1ccccc1)C2=O] | 2-(ethylamino)-9-methyl-6-(2-((3-(methylamino)-1-phenylpropoxy)methyl)phenyl)-6,7,8,9-tetrahydro-5H-pyrimido[4,5-e][1,4]diazepin-5-one | A | 4.80 | 475.3 (M + H) |
| 338 | 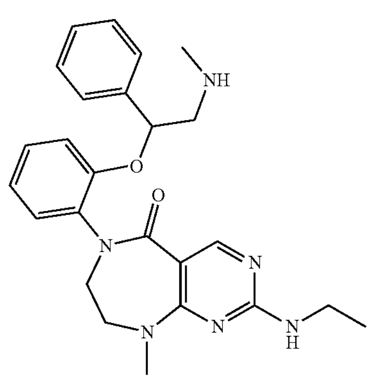 [SMILES: CCNc1ncc2c(n1)N(C)CCN(c1ccccc1OC(CNC)c1ccccc1)C2=O] | 2-(ethylamino)-9-methyl-6-(2-(2-(methylamino)-1-phenylethoxy)phenyl)-6,7,8,9-tetrahydro-5H-pyrimido[4,5-e][1,4]diazepin-5-one | A | 4.95 | 447.3 (M + H) |

| EX | Structure | Chemical name | Method | Ret (min) | MS |
|---|---|---|---|---|---|
| 339 | 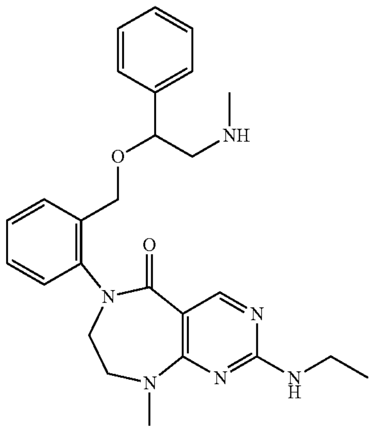 [SMILES: CCNc1ncc2c(n1)N(C)CCN(c1ccccc1COC(CNC)c1ccccc1)C2=O] | 2-(ethylamino)-9-methyl-6-(2-((2-(methylamino)-1-phenylethoxy)methyl)phenyl)-6,7,8,9-tetrahydro-5H-pyrimido[4,5-e][1,4]diazepin-5-one | A | 4.75 | 461.3 (M + H) |
| 340 | 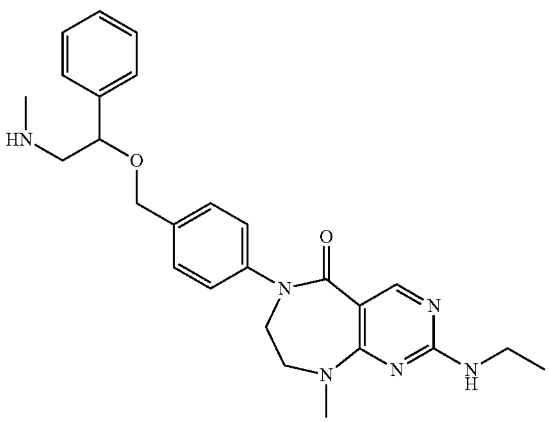 [SMILES: CCNc1ncc2c(n1)N(C)CCN(c1ccc(COC(CNC)c3ccccc3)cc1)C2=O] | 2-(ethylamino)-9-methyl-6-(4-((2-(methylamino)-1-phenylethoxy)methyl)phenyl)-6,7,8,9-tetrahydro-5H-pyrimido[4,5-e][1,4]diazepin-5-one | A | 4.95 | 461.3 (M + H) |
| 341 | 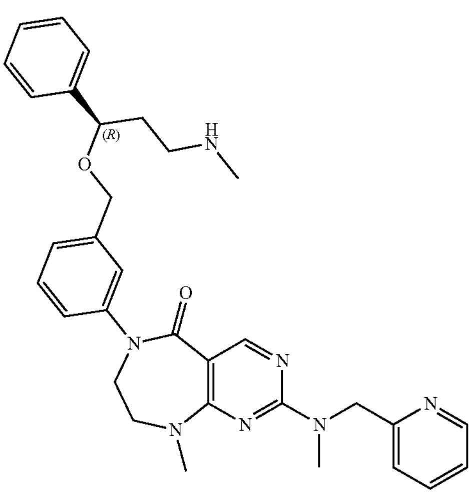 | (R)-9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | A | 4.77 | 552.3 (M + H) |

| EX | Structure | Chemical name | Method | Ret (min) | MS |
|---|---|---|---|---|---|
| 342 | 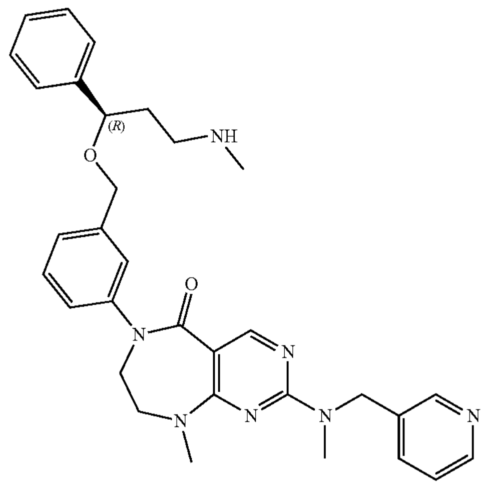 | (R)-9-methyl-2-(methyl(pyridin-3-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | A | 4.53 | 552.3 (M + H) |
| 343 | 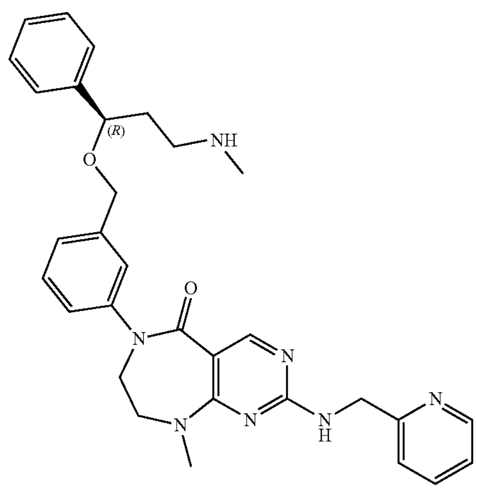 | (R)-9-methyl-6-(3-((3-(methylamino)-1-phenylpropoxy)methyl)phenyl)-2-((pyridin-2-ylmethyl)amino)-6,7,8,9-tetrahydro-5H-pyrimido[4,5-e][1,4]diazepin-5-one | A | 4.56 | 538.3 (M + H) |
| 344 | 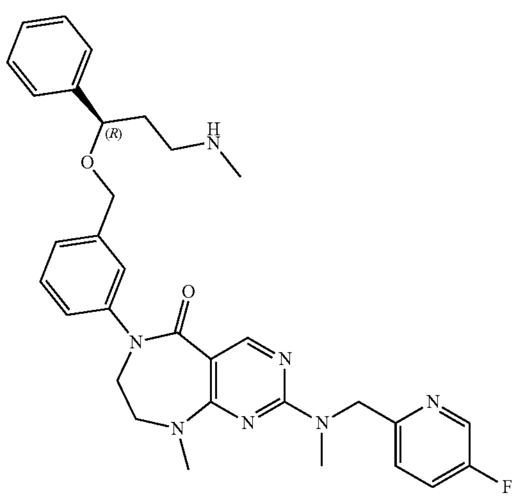 | (R)-2-(((5-fluoropyridin-2-yl)methyl)(methyl)amino)-9-methyl-6-(3-((3-(methylamino)-1-phenylpropoxy)methyl)phenyl)-6,7,8,9-tetrahydro-5H-pyrimido[4,5-e][1,4]diazepin-5-one | A | 5.26 | 570.3 (M + H) |

Ex 345-347 were prepared by a sequence of reactions according to the methods described in Ex 1, 69 and 208, and using suitable starting materials:

Ex 348-352 were prepared by a sequence of reactions according to the methods described in Ex 1, 69 and 225, and using suitable starting materials:

| EX | Structure | Chemical name | Method | Ret (min) | MS |
|---|---|---|---|---|---|
| 345 | 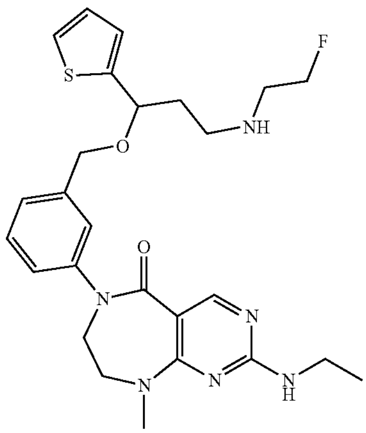 [SMILES: CCNc1ncc2c(n1)N(C)CCN(c1cccc(COC(CCNCCF)c3cccs3)c1)C2=O] | 2-(ethylamino)-6-(3-((3-((2-fluoroethyl)amino)-1-(thiophen-2-yl)propoxy)methyl)phenyl)-9-methyl-6,7,8,9-tetrahydro-5H-pyrimido[4,5-e][1,4]diazepin-5-one | A | 5.01 | 513.3 (M + H) |
| 346 | 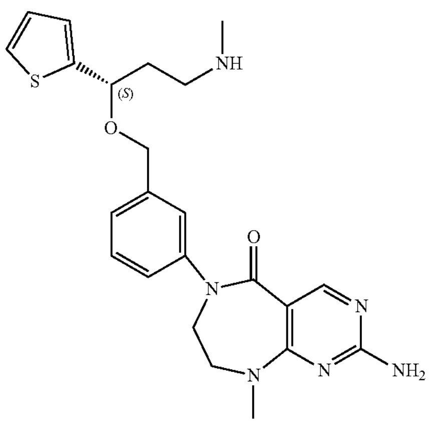 | (S)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.63 | 453.2 (M + H) |
| 347 | 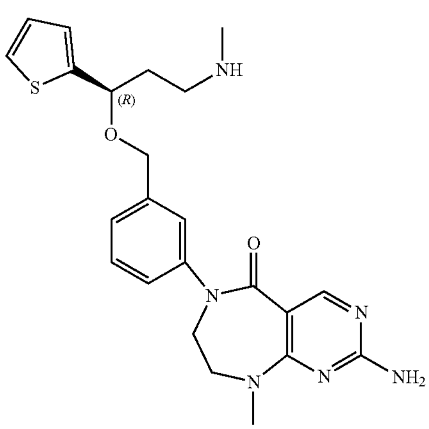 | (R)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.60 | 453.2 (M + H) |

| EX | Structure | Chemical name | Method | Ret (min) | MS |
|---|---|---|---|---|---|
| 348 | 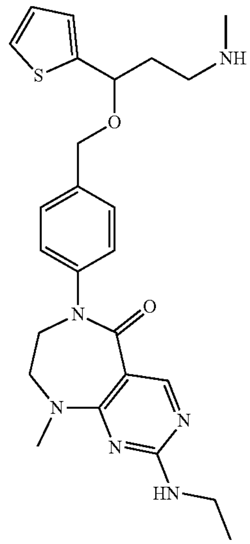 [SMILES: CCNc1ncc2c(n1)N(C)CCN(c1ccc(COC(CCNC)c3cccs3)cc1)C2=O] | 2-(ethylamino)-9-methyl-6-(4-((3-(methylamino)-1-(thiophen-2-yl)propoxy)methyl)phenyl)-6,7,8,9-tetrahydro-5H-pyrimido[4,5-e][1,4]diazepin-5-one | A | 4.93 | 481.2 (M + H) |
| 349 | 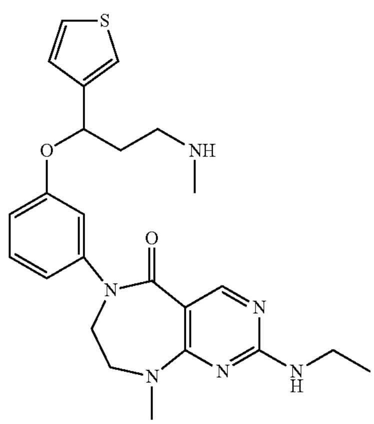 [SMILES: CCNc1ncc2c(n1)N(C)CCN(c1cccc(OC(CCNC)c3ccsc3)c1)C2=O] | 2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | A | 4.86 | 467.2 (M + H) |
| 350 | 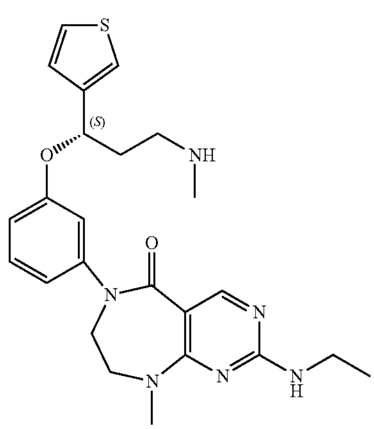 | (S)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | A | 4.86 | 467.2 (M + H) |

-continued

| EX | Structure | Chemical name | Method | Ret (min) | MS |
|---|---|---|---|---|---|
| 351 | 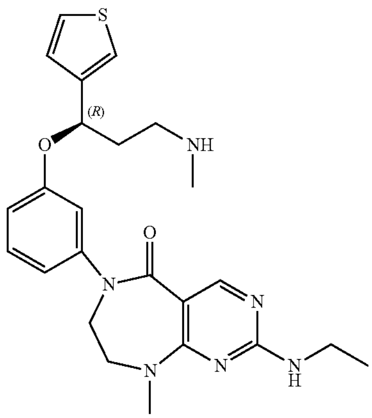 | (R)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | A | 4.86 | 467.2 (M + H) |
| 352 | 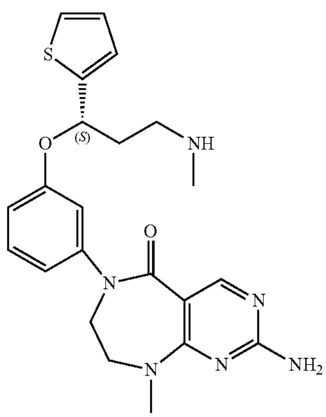 | (S)-2-amino-9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.44 | 439.2 (M + H) |

Ex 353-356 were prepared by a sequence of reactions according to the methods described in Ex 1, 142 and 148, and using suitable starting materials:

| EX | Structure | Chemical name | Method | Ret (min) | MS |
|---|---|---|---|---|---|
| 353 | 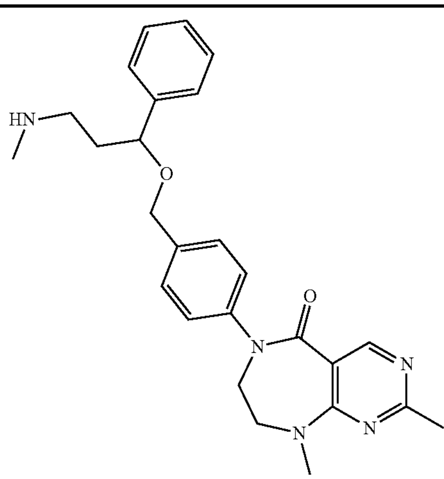 | 2,9-dimethyl-6-(4-((3-(methylamino)-1-phenylpropoxy)methyl)phenyl)-6,7,8,9-tetrahydro-5H-pyrimido[4,5-e][1,4]diazepin-5-one | A | 4.70 | 446.2 (M + H) |

-continued

| EX | Structure | Chemical name | Method | Ret (min) | MS |
|---|---|---|---|---|---|
| 354 | 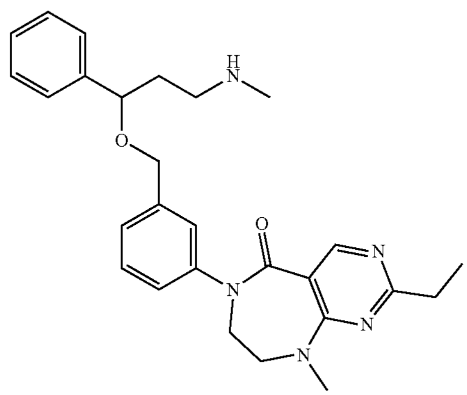 [SMILES: CCc1ncc2c(n1)N(C)CCN(c1cccc(COC(CCNC)c3ccccc3)c1)C2=O] | 2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one | A | 4.90 | 460.3 (M + H) |
| 355 | 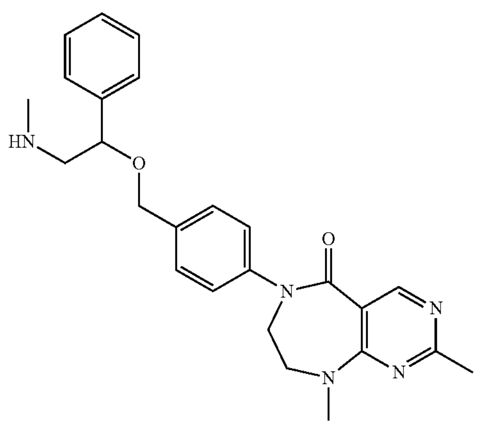 [SMILES: CNCC(OCc1ccc(N2CCN(C)c3nc(C)ncc3C2=O)cc1)c1ccccc1] | 2,9-dimethyl-6-(4-((2-(methylamino)-1-phenylethoxy)methyl)phenyl)-6,7,8,9-tetrahydro-5H-pyrimido[4,5-e][1,4]diazepin-5-one | A | 4.63 | 432.2 (M + H) |
| 356 | 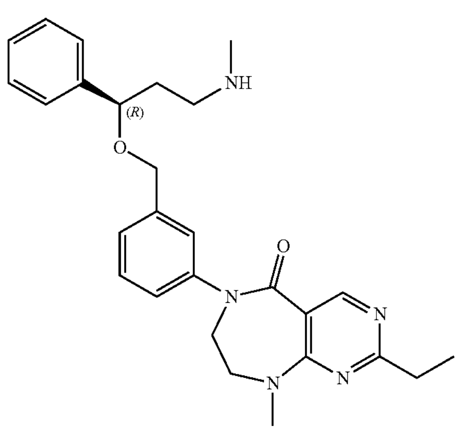 | (R)-2-ethyl-9-methyl-6-(3-((3-(methylamino)-1-phenylpropoxy)methyl)phenyl(-6,7,8,9-tetrahydro-5H-pyrimido[4,5-e][1,4]diazepin-5-one | A | 4.87 | 460.2 (M + H) |

Ex 357-360 were prepared by a sequence of reactions according to the methods described in Ex 1, 142 and 225, and using suitable starting materials:

| EX | Structure | Chemical name | Method | Ret (min) | MS |
|---|---|---|---|---|---|
| 357 | 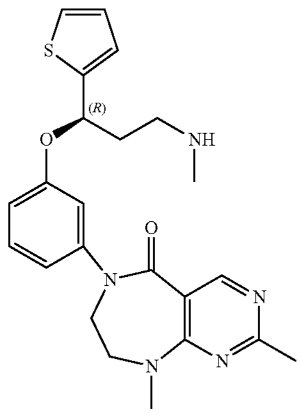 | (R)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.50 | 438.2 (M + H) |
| 358 | 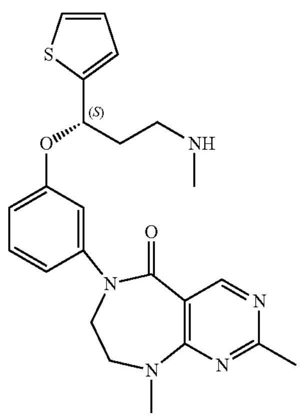 | (S)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.50 | 438.2 (M + H) |
| 359 | 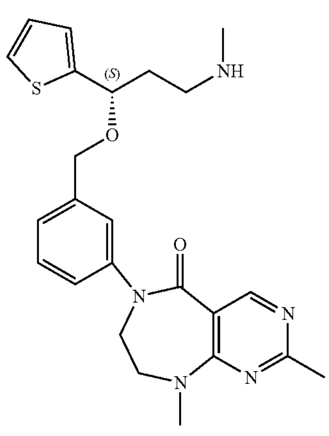 | (S)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.59 | 452.2 (M + H) |

-continued

| EX | Structure | Chemical name | Method | Ret (min) | MS |
|---|---|---|---|---|---|
| 360 | 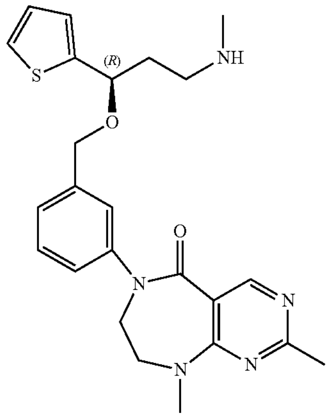 | (R)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | A | 4.59 | 452.2 (M + H) |

Ex 361-362 were prepared by a sequence of reactions according to the methods described in Ex 1, 145 and 148, and using suitable starting materials:

Ex 363-364 were prepared by a sequence of reactions according to the methods described in Ex 1, 145 and 225, and using suitable starting materials:

| EX | Structure | Chemical name | Method | Ret (min) | MS |
|---|---|---|---|---|---|
| 361 | 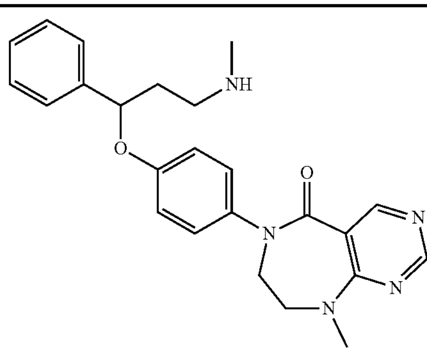 | 9-methyl-6-(4-(3-(methylamino)-1-phenylpropoxy)phenyl)-6,7,8,9-tetrahydro-5H-pyrimido[4,5-e][1,4]diazepin-5-one | A | 4.41 | 418.3 (M + H) |
| 362 | 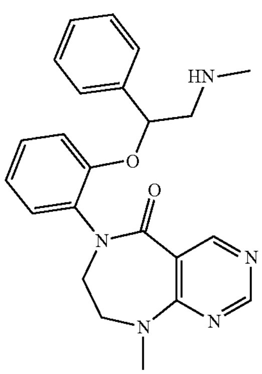 [SMILES: CNCC(Oc1ccccc1N1CCN(C)c2ncncc2C1=O)c1ccccc1] | 9-methyl-6-(2-(2-(methylamino)-1-phenylethoxy)phenyl)-6,7,8,9-tetrahydro-5H-pyrimido[4,5-e][1,4]diazepin-5-one | A | 4.51 | 404.2 (M + H) |

| EX | Structure | Chemical name | Method | Ret (min) | MS |
|---|---|---|---|---|---|
| 363 | 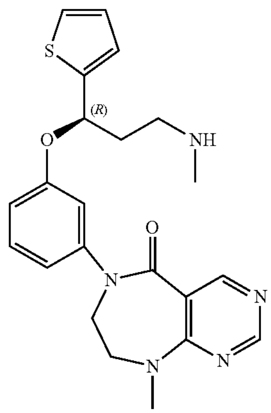 | (R)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.39 | 424.2 (M + H) |
| 364 | 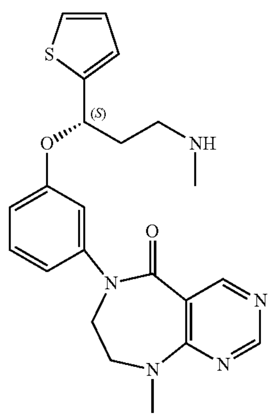 | (S)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | A | 4.40 | 424.2 (M + H) |

Ex 365-377 were prepared by a sequence of reactions according to the methods described in Ex 62 and 148, and using suitable starting materials:

| EX | Structure | Chemical name | Method | Ret (min) | MS |
|---|---|---|---|---|---|
| 365 | 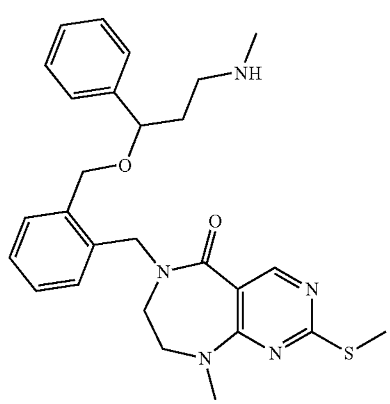 [SMILES: CNCCC(OCc1ccccc1CN1CCN(C)c2nc(SC)ncc2C1=O)c1ccccc1] | 9-methyl-6-(2-((3-(methylamino)-1-phenylpropoxy)methyl)benzyl)-2-(methylthio)-6,7,8,9-tetrahydro-5H-pyrimido[4,5-e][1,4]diazepin-5-one | A | 5.46 | 492.2 (M + H) |

| EX | Structure | Chemical name | Method | Ret (min) | MS |
|---|---|---|---|---|---|
| 366 | 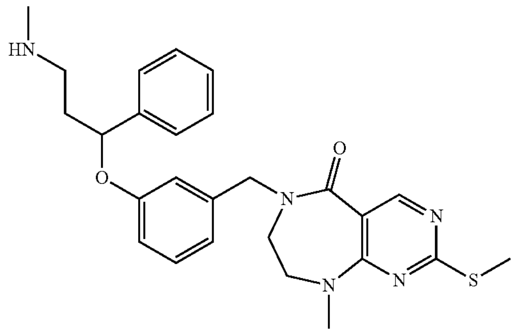 [SMILES: CNCCC(Oc1cccc(CN2CCN(C)c3nc(SC)ncc3C2=O)c1)c1ccccc1] | 9-methyl-6-(3-(3-(methylamino)-1-phenylpropoxy)benzyl)-2-(methylthio)-6,7,8,9-tetrahydro-5H-pyrimido[4,5-e][1,4]diazepin-5-one | A | 5.20 | 478.2 (M + H) |
| 367 | 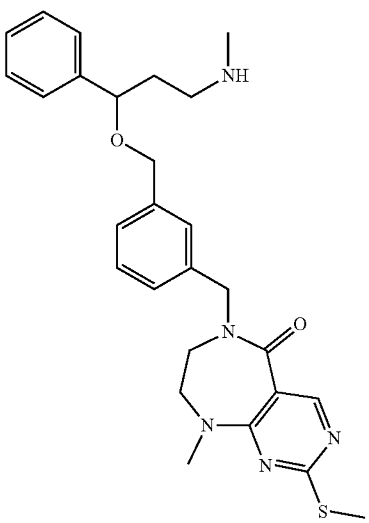 [SMILES: CNCCC(OCc1cccc(CN2CCN(C)c3nc(SC)ncc3C2=O)c1)c1ccccc1] | 9-methyl-6-(3-((3-(methylamino)-1-phenylpropoxy)methyl)benzyl)-2-(methylthio)-6,7,8,9-tetrahydro-5H-pyrimido[4,5-e][1,4]diazepin-5-one | A | 5.43 | 492.3 (M + H) |
| 368 | 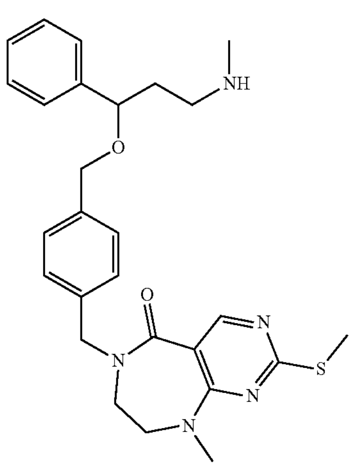 [SMILES: CNCCC(OCc1ccc(CN2CCN(C)c3nc(SC)ncc3C2=O)cc1)c1ccccc1] | 9-methyl-6-(4-((3-(methylamino)-1-phenylpropoxy)methyl)benzyl)-2-(methylthio)-6,7,8,9-tetrahydro-5H-pyrimido[4,5-e][1,4]diazepin-5-one | A | 5.38 | 492.3 (M + H) |

-continued

| EX | Structure | Chemical name | Method | Ret (min) | MS |
|---|---|---|---|---|---|
| 369 | 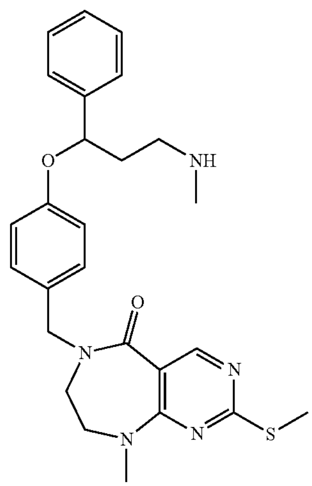 [SMILES: CNCCC(Oc1ccc(CN2CCN(C)c3nc(SC)ncc3C2=O)cc1)c1ccccc1] | 9-methyl-6-(4-(3-(methylamino)-1-phenylpropoxy)benzyl)-2-(methylthio)-6,7,8,9-tetrahydro-5H-pyrimido[4,5-e][1,4]diazepin-5-one | A | 5.12 | 478.2 (M + H) |
| 370 | 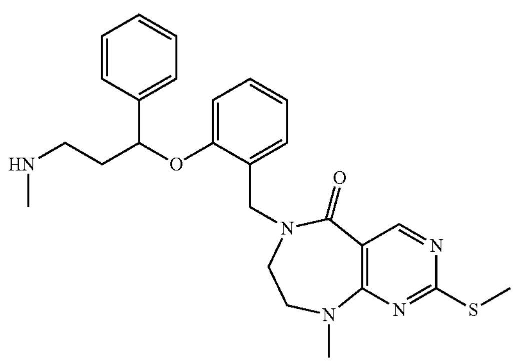 [SMILES: CNCCC(Oc1ccccc1CN1CCN(C)c2nc(SC)ncc2C1=O)c1ccccc1] | 9-methyl-6-(2-(3-(methylamino)-1-phenylpropoxy)benzyl)-2-(methylthio)-6,7,8,9-tetrahydro-5H-pyrimido[4,5-e][1,4]diazepin-5-one | A | 5.55 | 478.2 (M + H) |
| 371 | 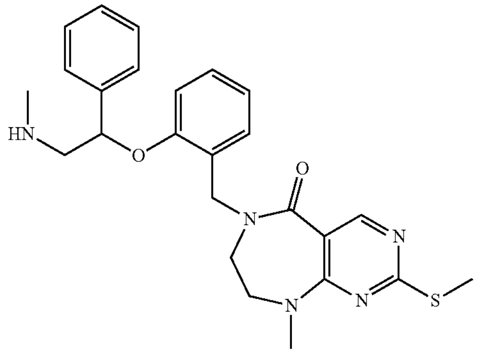 [SMILES: CNCC(Oc1ccccc1CN1CCN(C)c2nc(SC)ncc2C1=O)c1ccccc1] | 9-methyl-6-(2-(2-(methylamino)-1-phenylethoxy)benzyl)-2-(methylthio)-6,7,8,9-tetrahydro-5H-pyrimido[4,5-e][1,4]diazepin-5-one | A | 5.54 | 464.2 (M + H) |

| EX | Structure | Chemical name | Method | Ret (min) | MS |
|---|---|---|---|---|---|
| 372 | 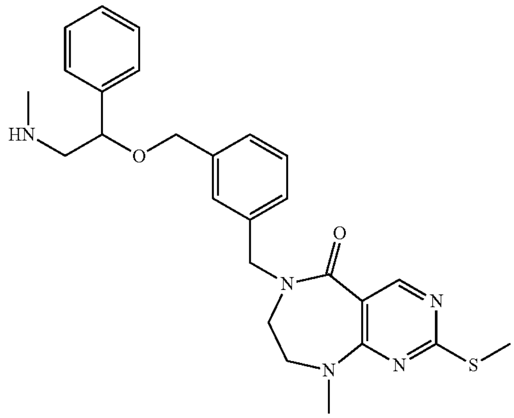 [SMILES: CNCC(OCc1cccc(CN2CCN(C)c3nc(SC)ncc3C2=O)c1)c1ccccc1] | 9-methyl-6-(3-((2-(methylamino)-1-phenylethoxy)methyl)benzyl)-2-(methylthio)-6,7,8,9-tetrahydro-5H-pyrimido[4,5-e][1,4]diazepin-5-one | A | 5.35 | 478.2 (M + H) |
| 373 | 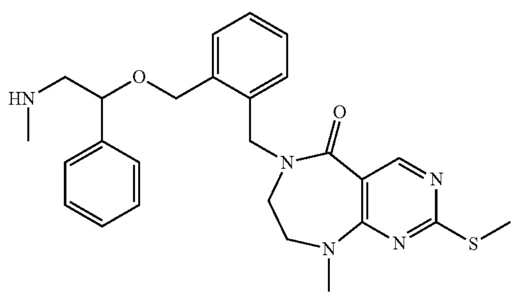 [SMILES: CNCC(OCc1ccccc1CN1CCN(C)c2nc(SC)ncc2C1=O)c1ccccc1] | 9-methyl-6-(2-((2-(methylamino)-1-phenylethoxy)methyl)benzyl)-2-(methylthio)-6,7,8,9-tetrahydro-5H-pyrimido[4,5-e][1,4]diazepin-5-one | A | 5.44 | 478.2 (M + H) |
| 374 | 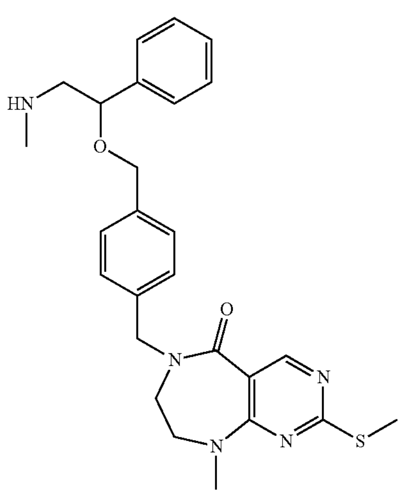 [SMILES: CNCC(OCc1ccc(CN2CCN(C)c3nc(SC)ncc3C2=O)cc1)c1ccccc1] | 9-methyl-6-(4-((2-(methylamino)-1-phenylethoxy)methyl)benzyl)-2-(methylthio)-6,7,8,9-tetrahydro-5H-pyrimido[4,5-e][1,4]diazepin-5-one | A | 5.27 | 478.2 (M + H) |

| EX | Structure | Chemical name | Method | Ret (min) | MS |
|---|---|---|---|---|---|
| 375 | 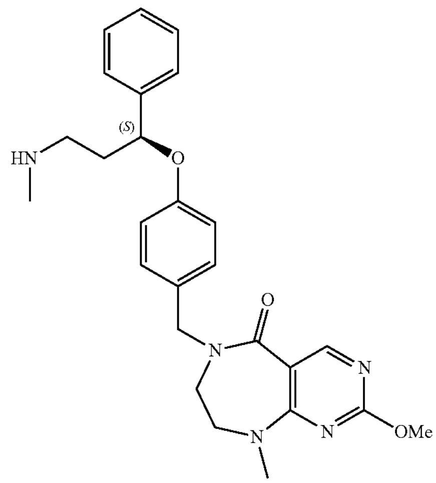 | (S)-2-methoxy-9-methyl-6-(4-(3-(methylamino)-1-phenylpropoxy)benzyl)-6,7,8,9-tetrahydro-5H-pyrimido[4,5-e][1,4]diazepin-5-one | A | 4.78 | 462.3 (M + H) |
| 376 | 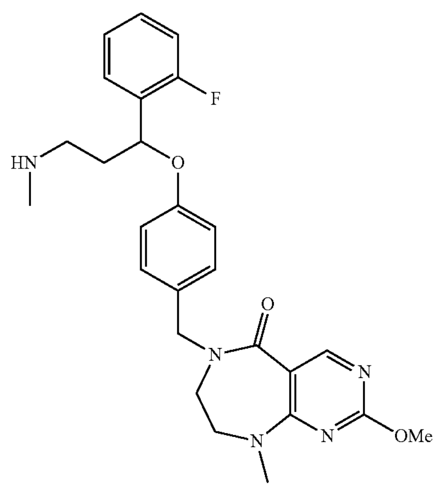 | 6-(4-(1-(2-fluorophenyl)-3-(methylamino)propoxy)benzyl)-2-methoxy-9-methyl-6,7,8,9-tetrahydro-5H-pyrimido[4,5-e][1,4]diazepin-5-one | A | 4.77 | 480.2 (M + H) |
| 377 | 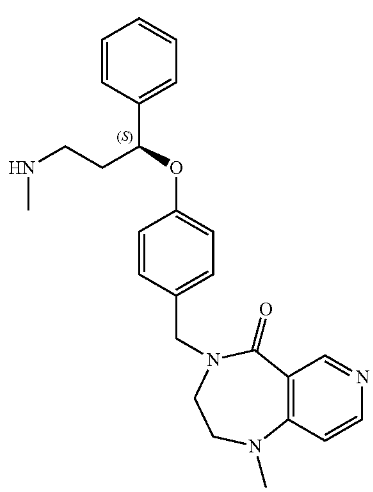 | (S)-1-methyl-4-(4-(3-(methylamino)-1-phenylpropoxy)benzyl)-1,2,3,4-tetrahydro-5H-pyrido[4,3-e][1,4]diazepin-5-one | A | 4.54 | 431.3 (M + H) |

Ex 378-403 were prepared by a sequence of reactions according to the methods described in Ex 62 and 225, and using suitable starting materials:

| EX | Structure | Chemical name | Method | Ret (min) | MS |
|---|---|---|---|---|---|
| 378 | 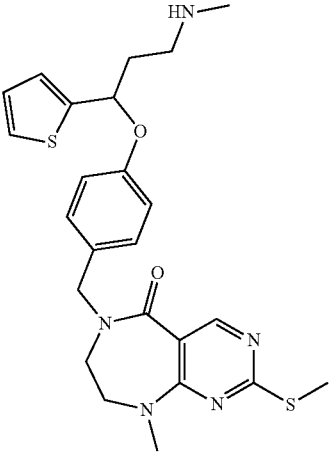 [SMILES: CNCCC(Oc1ccc(CN2CCN(C)c3nc(SC)ncc3C2=O)cc1)c1cccs1] | 9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | A | 5.04 | 484.2 (M + H) |
| 379 | 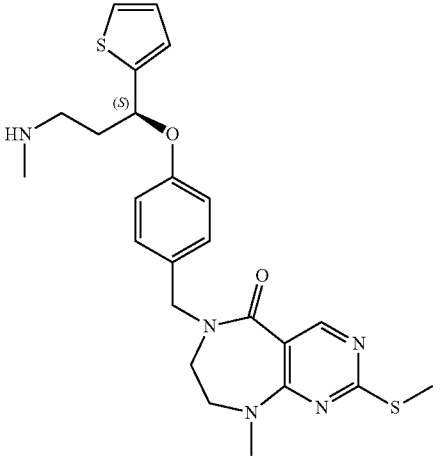 | (S)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | A | 5.03 | 484.2 (M + H) |
| 380 | 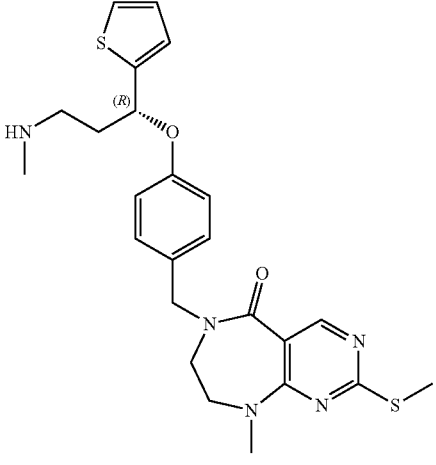 | (R)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | A | 5.01 | 484.1 (M + H) |

-continued

| EX | Structure | Chemical name | Method | Ret (min) | MS |
|---|---|---|---|---|---|
| 381 | 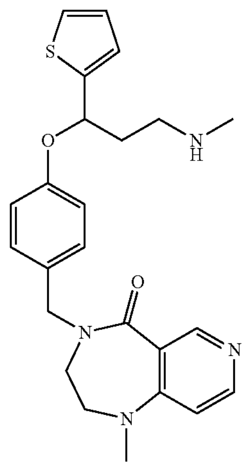 [SMILES: CNCCC(Oc1ccc(CN2CCN(C)c3ccncc3C2=O)cc1)c1cccs1] | 1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.43 | 437.1 (M + H) |
| 382 | 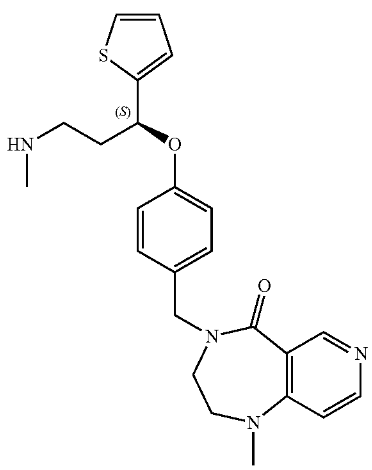 | (S)-1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.42 | 437.2 (M + H) |
| 383 | 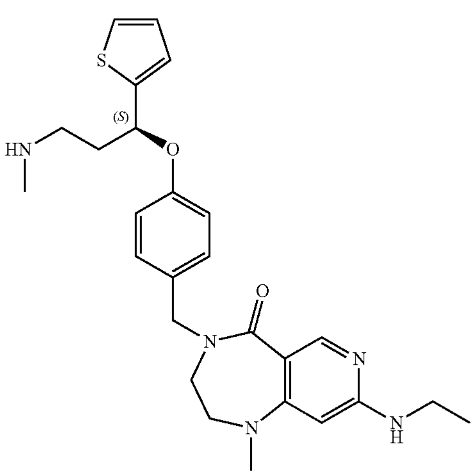 | (S)-8-(ethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.79 | 480.2 (M + H) |

-continued

| EX | Structure | Chemical name | Method | Ret (min) | MS |
|---|---|---|---|---|---|
| 384 | 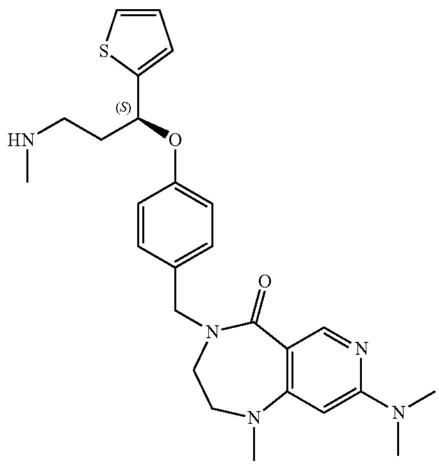 | (S)-8-(dimethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.72 | 480.2 (M + H) |
| 385 | 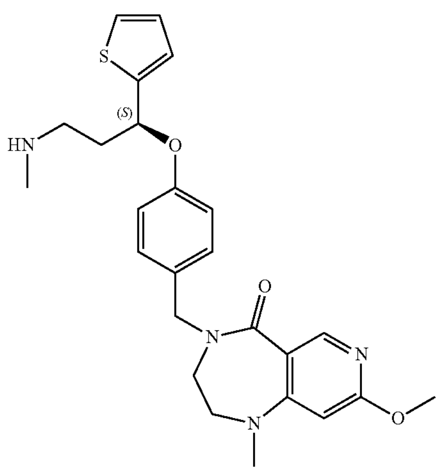 | (S)-8-methoxy-1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.54 | 467.2 (M + H) |
| 386 | 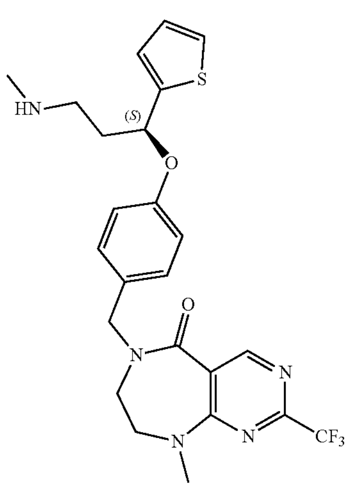 | (S)-9-methyl-6-(4-(3-(methylamino)-1-(thiophen-2-yl)propoxy)benzyl)-2-(trifluoromethyl)-6,7,8,9-tetrahydro-5H-pyrimido[4,5-e][1,4]diazepin-5-one | A | 6.04 | 506.1 (M + H) |

| EX | Structure | Chemical name | Method | Ret (min) | MS |
|---|---|---|---|---|---|
| 387 | 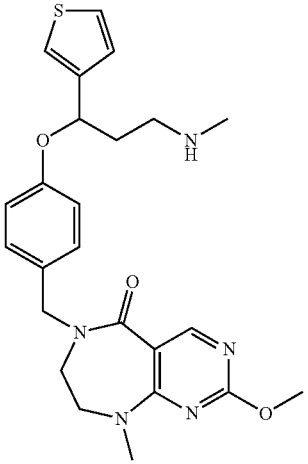 [SMILES: CNCCC(Oc1ccc(CN2CCN(C)c3nc(OC)ncc3C2=O)cc1)c1ccsc1] | 2-methoxy-9-methyl-6-(4-(3-(methylamino)-1-(thiophen-3-yl)propoxy)benzyl)-6,7,8,9-tetrahydro-5H-pyrimido[4,5-e][1,4]diazepin-5-one | A | 4.66 | 468.1 (M + H) |
| 388 | 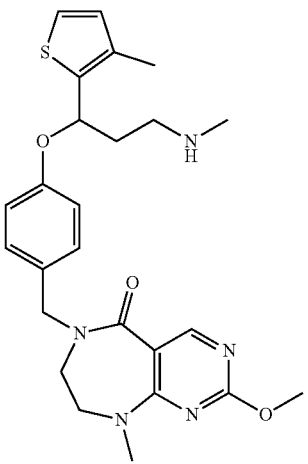 [SMILES: CNCCC(Oc1ccc(CN2CCN(C)c3nc(OC)ncc3C2=O)cc1)c1sccc1C] | 2-methoxy-9-methyl-6-(4-(3-(methylamino)-1-(3-methylthiophen-2-yl)propoxy)benzyl)-6,7,8,9-tetrahydro-5H-pyrimido[4,5-e][1,4]diazepin-5-one | A | 4.78 | 482.3 (M + H) |
| 389 | 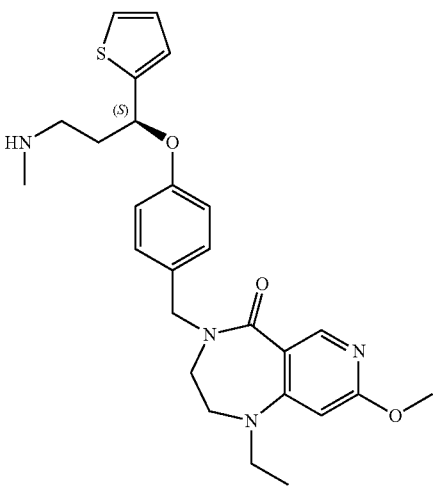 | (S)-1-ethyl-8-methoxy-4-(4-(3-(methylamino)-1-(thiophen-2-yl)propoxy)benzyl)-1,2,3,4-tetrahydro-5H-pyrido[4,3-e][1,4]diazepin-5-one | A | 4.68 | 481.3 (M + H) |

| EX | Structure | Chemical name | Method | Ret (min) | MS |
|---|---|---|---|---|---|
| 390 | 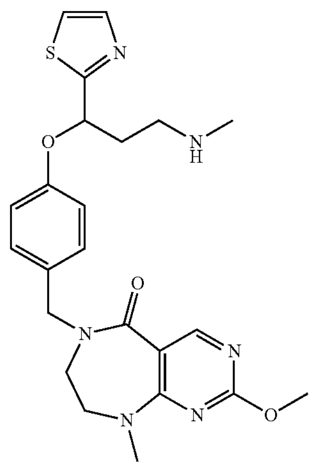 [SMILES: CNCCC(Oc1ccc(CN2CCN(C)c3nc(OC)ncc3C2=O)cc1)c1nccs1] | 2-methoxy-9-methyl-6-(4-(3-(methylamino)-1-(thiazol-2-yl)propoxy)benzyl)-6,7,8,9-tetrahydro-5H-pyrimido[4,5-e][1,4]diazepin-5-one | A | 4.36 | 469.2 (M + H) |
| 391 | 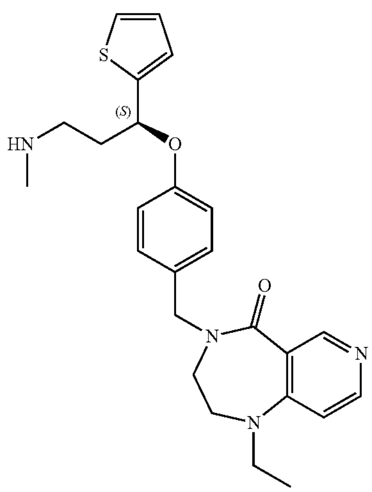 | (S)-1-ethyl-4-(4-(3-(methylamino)-1-(thiophen-2-yl)propoxy)benzyl)-1,2,3,4-tetrahydro-5H-pyrido[4,3-e][1,4]diazepin-5-one | A | 4.58 | 451.2 (M + H) |
| 392 | 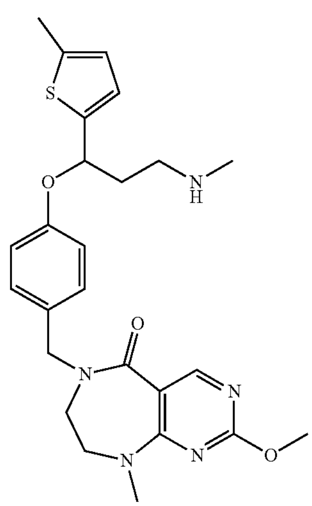 [SMILES: CNCCC(Oc1ccc(CN2CCN(C)c3nc(OC)ncc3C2=O)cc1)c1ccc(C)s1] | 2-methoxy-9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one | A | 4.89 | 482.2 (M + H) |

| EX | Structure | Chemical name | Method | Ret (min) | MS |
|---|---|---|---|---|---|
| 393 | 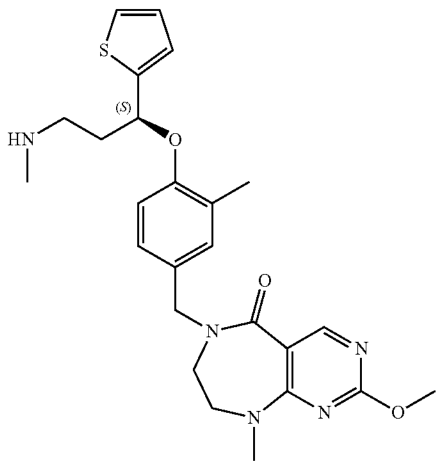 | (S)-2-methoxy-9-methyl-6-(3-methyl-4-(3-(methylamino)-1-(thiophen-2-yl)propoxy)benzyl)-6,7,8,9-tetrahydro-5H-pyrimido[4,5-e][1,4]diazepin-5-one | A | 4.83 | 482.2 (M + H) |
| 394 | 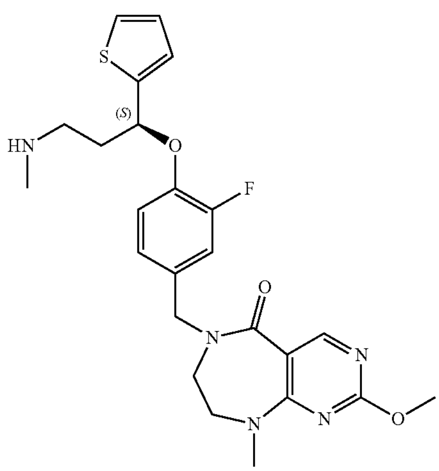 | (S)-6-(3-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | A | 4.71 | 486.2 (M + H) |
| 395 | 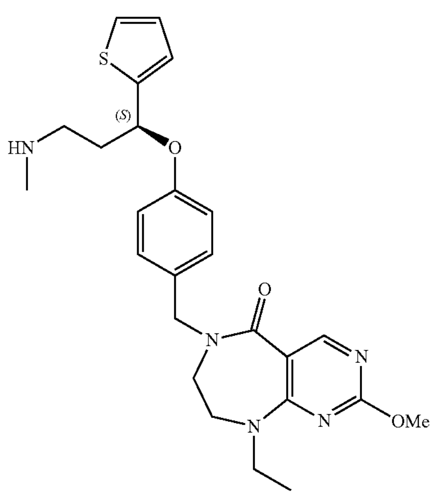 | (S)-9-ethyl-2-methoxy-6-(4-(3-(methylamino)-1-(thiophen-2-yl)propoxy)benzyl)-6,7,8,9-tetrahydro-5H-pyrimido[4,5-e][1,4]diazepin-5-one | A | 4.81 | 482.2 (M + H) |

-continued

| EX | Structure | Chemical name | Method | Ret (min) | MS |
|---|---|---|---|---|---|
| 396 | 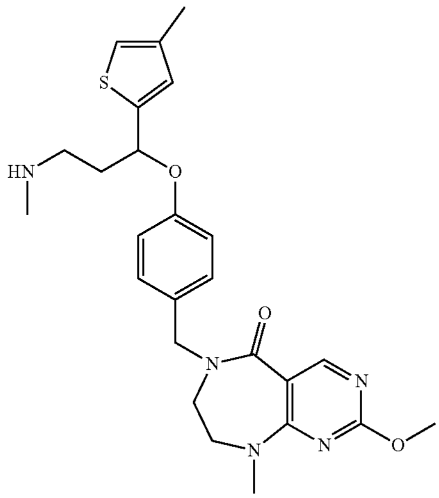 [SMILES: CNCCC(Oc1ccc(CN2CCN(C)c3nc(OC)ncc3C2=O)cc1)c1cc(C)cs1] | 2-methoxy-9-methyl-6-(4-(3-(methylamino)-1-(4-methylthiophen-2-yl)propoxy)benzyl)-6,7,8,9-tetrahydro-5H-pyrimido[4,5-e][1,4]diazepin-5-one | A | 4.86 | 482.2 (M + H) |
| 397 | 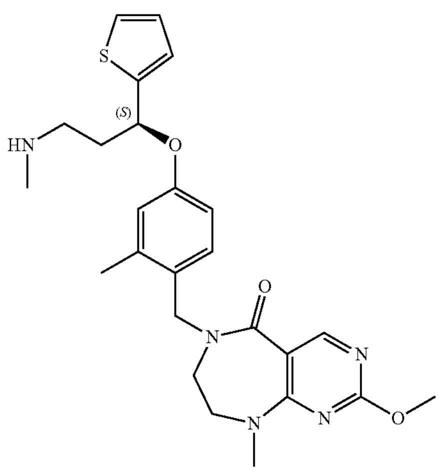 | (S)-2-methoxy-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one | A | 4.77 | 482.2 (M + H) |
| 398 | 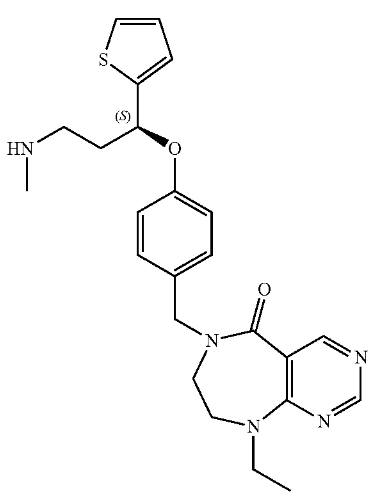 | (S)-9-ethyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.56 | 452.2 (M + H) |

| EX | Structure | Chemical name | Method | Ret (min) | MS |
|---|---|---|---|---|---|
| 399 | 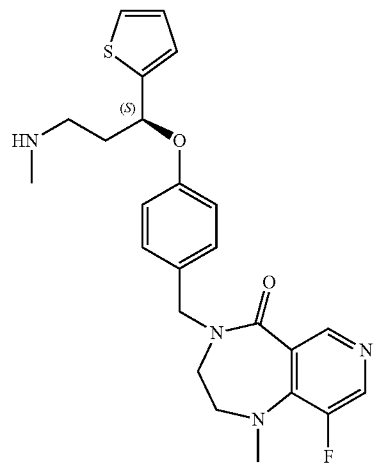 | (S)-9-fluoro-1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.50 | 455.1 (M + H) |
| 400 | 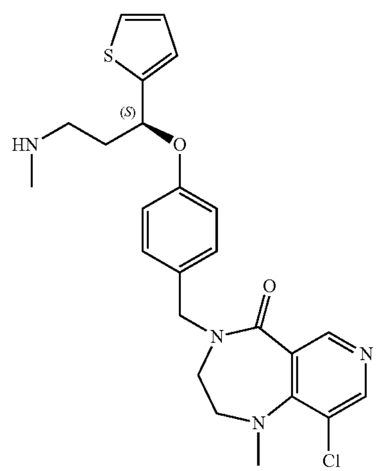 | (S)-9-chloro-1-methyl-4-(4-(3-(methylamino)-1-(thiophen-2-yl)propoxy)benzyl)-1,2,3,4-tetrahydro-5H-pyrido[4,3-e][1,4]diazepin-5-one | A | 4.70 | 471.1 (M + H) |
| 401 | 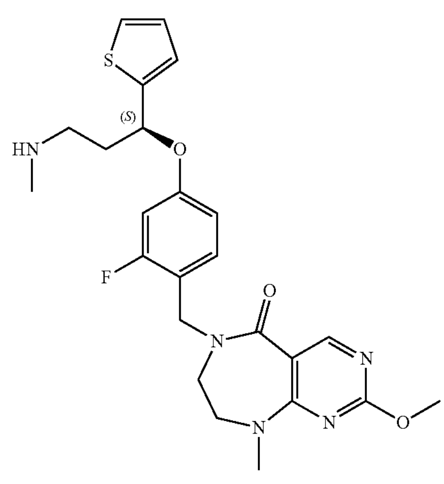 | (S)-6-(2-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | A | 4.75 | 486.2 (M + H) |

| EX | Structure | Chemical name | Method | Ret (min) | MS |
|---|---|---|---|---|---|
| 402 | 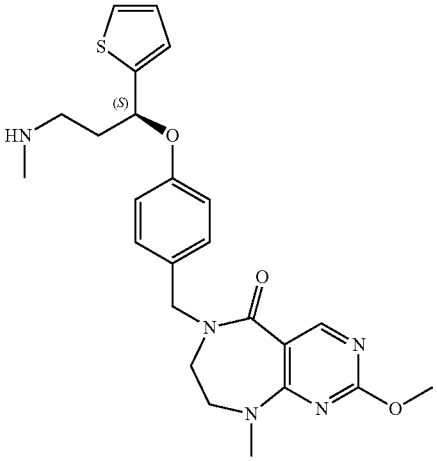 | (S)-2-methoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.59 | 468.2 (M + H) |
| 403 | 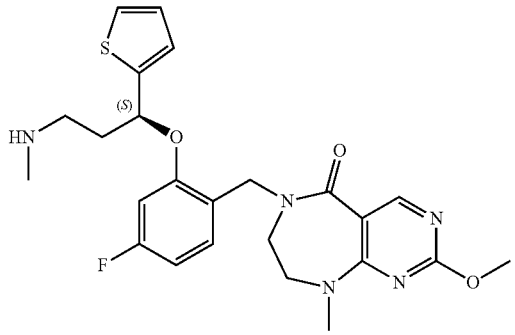 | (S)-6-(4-fluoro-2-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | A | 5.03 | 468.2 (M + H) |

Ex 404-415 were prepared by a sequence of reactions according to the methods described in Ex 62, 69 and 148, and using suitable starting materials:

| EX | Structure | Chemical name | Method | Ret (min) | MS |
|---|---|---|---|---|---|
| 404 | 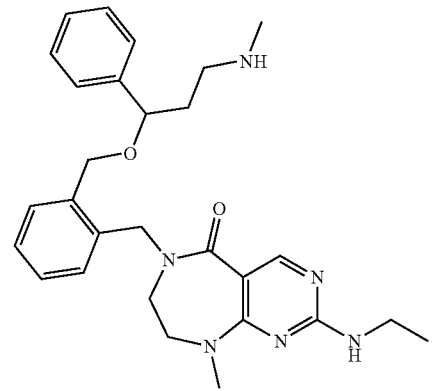 [SMILES: CCNc1ncc2c(n1)N(C)CCN(Cc1ccccc1COC(CCNC)c1ccccc1)C2=O] | 2-(ethylamino)-9-methyl-6-(2-((3-(methylamino)-1-phenylpropoxy)methyl)benzyl)-6,7,8,9-tetrahydro-5H-pyrimido[4,5-e][1,4]diazepin-5-one | A | 5.15 | 489.4 (M + H) |

| EX | Chemical name | Method | Ret (min) | MS |
|---|---|---|---|---|
| 405 | 2-(ethylamino)-9-methyl-6-(4-((3-(methylamino)-1-phenylpropoxy)methyl)benzyl)-6,7,8,9-tetrahydro-5H-pyrimido[4,5-e][1,4]diazepin-5-one | A | 5.16 | 489.3 (M + H) |
| 406 | 2-(ethylamino)-9-methyl-6-(3-((3-(methylamino)-1-phenylpropoxy)methyl)benzyl)-6,7,8,9-tetrahydro-5H-pyrimido[4,5-e][1,4]diazepin-5-one | A | 5.15 | 489.3 (M + H) |
| 407 | 2-(ethylamino)-9-methyl-6-(3-(3-(methylamino)-1-phenylpropoxy)benzyl)-6,7,8,9-tetrahydro-5H-pyrimido[4,5-e][1,4]diazepin-5-one | A | 4.91 | 475.3 (M + H) |

| EX | Structure | Chemical name | Method | Ret (min) | MS |
|---|---|---|---|---|---|
| 408 | 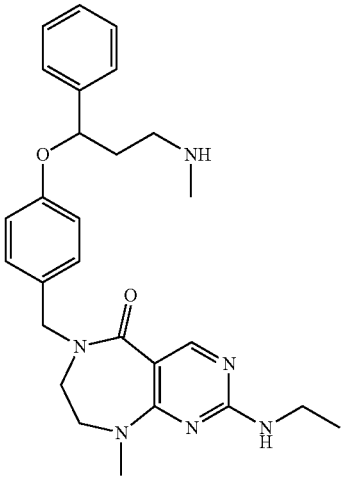 [SMILES: CCNc1ncc2c(n1)N(C)CCN(Cc1ccc(OC(CCNC)c3ccccc3)cc1)C2=O] | 2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | A | 4.94 | 475.3 (M + H) |
| 409 | 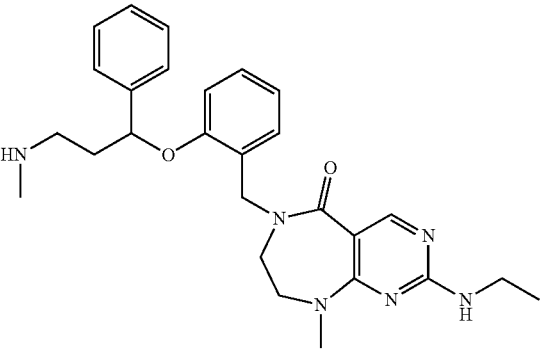 [SMILES: CCNc1ncc2c(n1)N(C)CCN(Cc1ccccc1OC(CCNC)c1ccccc1)C2=O] | 2-(ethylamino)-9-methyl-6-(2-(3-(methylamino)-1-phenylpropoxy)benzyl)-6,7,8,9-tetrahydro-5H-pyrimido[4,5-e][1,4]diazepin-5-one | A | 5.17 | 475.3 (M + H) |
| 410 | 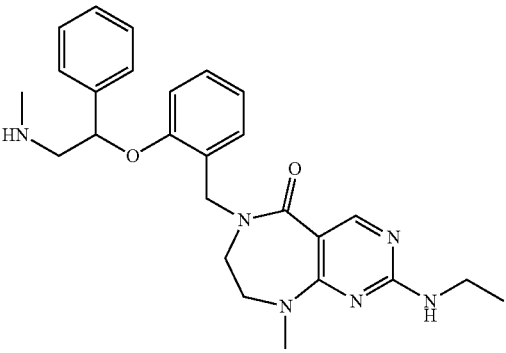 [SMILES: CCNc1ncc2c(n1)N(C)CCN(Cc1ccccc1OC(CNC)c1ccccc1)C2=O] | 2-(ethylamino)-9-methyl-6-(2-(2-(methylamino)-1-phenylethoxy)benzyl)-6,7,8,9-tetrahydro-5H-pyrimido[4,5-e][1,4]diazepin-5-one | A | 5.10 | 461.3 (M + H) |

| EX | Structure | Chemical name | Method | Ret (min) | MS |
|---|---|---|---|---|---|
| 411 | 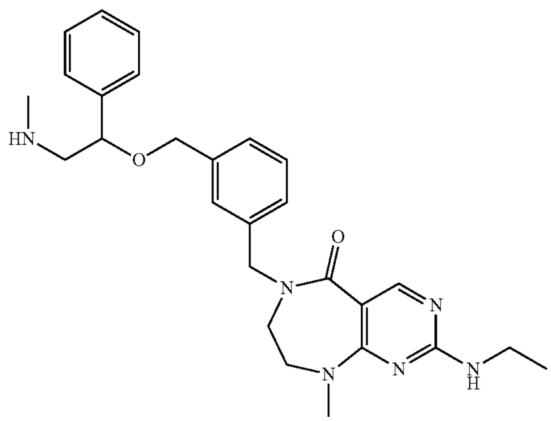 [SMILES: CCNc1ncc2c(n1)N(C)CCN(Cc1cccc(COC(CNC)c3ccccc3)c1)C2=O] | 2-(ethylamino)-9-methyl-6-(3-((2-(methylamino)-1-phenylethoxy)methyl)benzyl)-6,7,8,9-tetrahydro-5H-pyrimido[4,5-e][1,4]diazepin-5-one | A | 5.05 | 475.3 (M + H) |
| 412 | 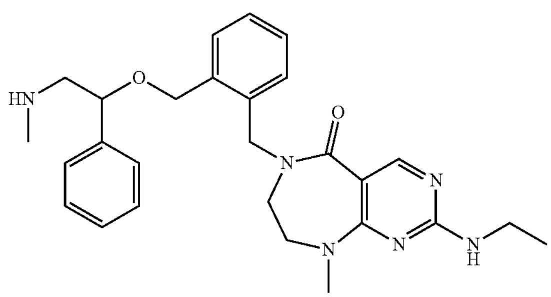 [SMILES: CCNc1ncc2c(n1)N(C)CCN(Cc1ccccc1COC(CNC)c1ccccc1)C2=O] | 2-(ethylamino)-9-methyl-6-(2-((2-(methylamino)-1-phenylethoxy)methyl)benzyl)-6,7,8,9-tetrahydro-5H-pyrimido[4,5-e][1,4]diazepin-5-one | A | 5.05 | 475.3 (M + H) |
| 413 | 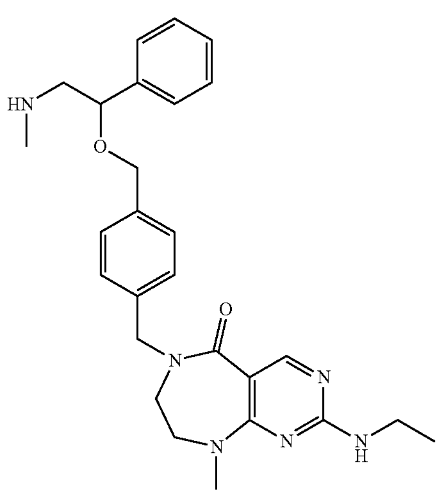 [SMILES: CCNc1ncc2c(n1)N(C)CCN(Cc1ccc(COC(CNC)c3ccccc3)cc1)C2=O] | 2-(ethylamino)-9-methyl-6-(4-((2-(methylamino)-1-phenylethoxy)methyl)benzyl)-6,7,8,9-tetrahydro-5H-pyrimido[4,5-e][1,4]diazepin-5-one | A | 5.03 | 475.3 (M + H) |

| EX | Structure | Chemical name | Method | Ret (min) | MS |
|---|---|---|---|---|---|
| 414 | 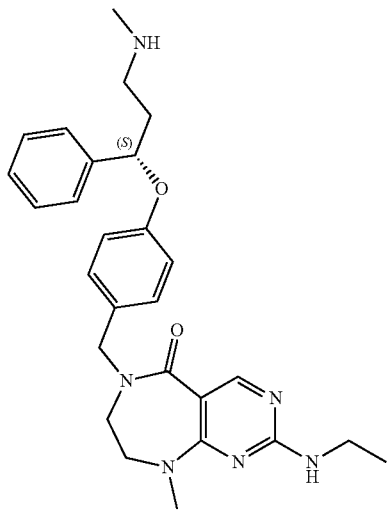 | (S)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | A | 4.94 | 475.3 (M + H) |
| 415 | 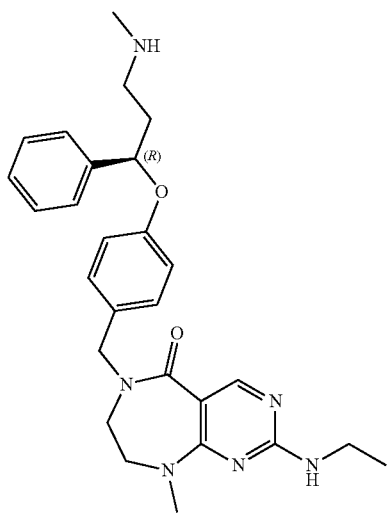 | (R)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | A | 4.93 | 475.3 (M + H) |

Ex 416-420 were prepared by a sequence of reactions according to the methods described in Ex 62, 69 and 225, and using suitable starting materials:

| EX | Structure | Chemical name | Method | Ret (min) | MS |
|---|---|---|---|---|---|
| 416 | 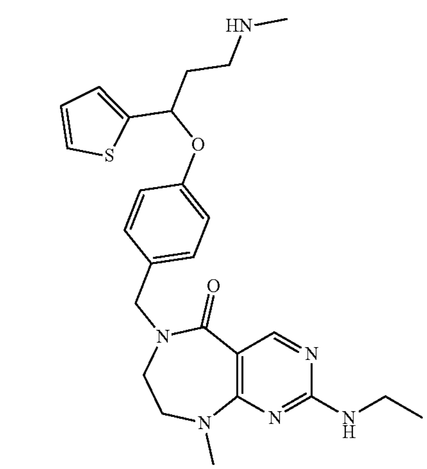 [SMILES: CCNc1ncc2c(n1)N(C)CCN(Cc1ccc(OC(CCNC)c3cccs3)cc1)C2=O] | 2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.86 | 481.2 (M + H) |
| 417 | 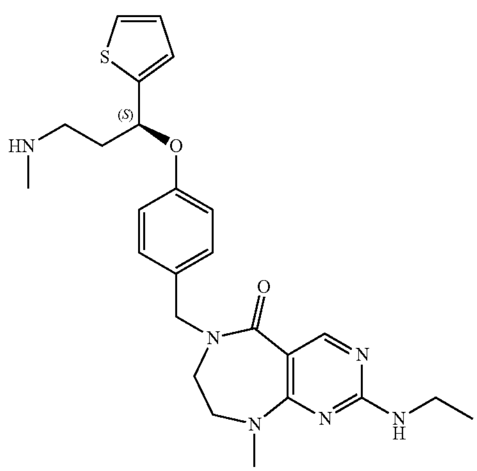 | (S)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.85 | 481.3 (M + H) |
| 418 | 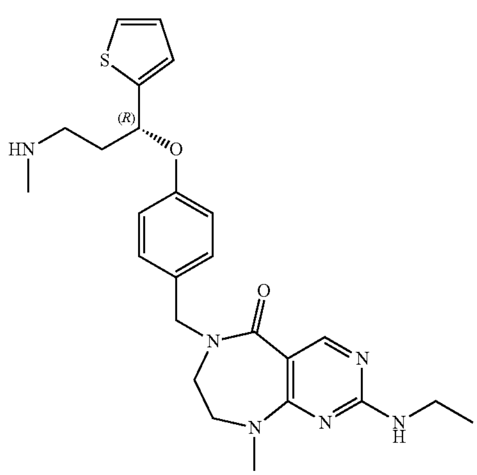 | (R)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.89 | 481.2 (M + H) |

| EX | Structure | Chemical name | Method | Ret (min) | MS |
|---|---|---|---|---|---|
| 419 | 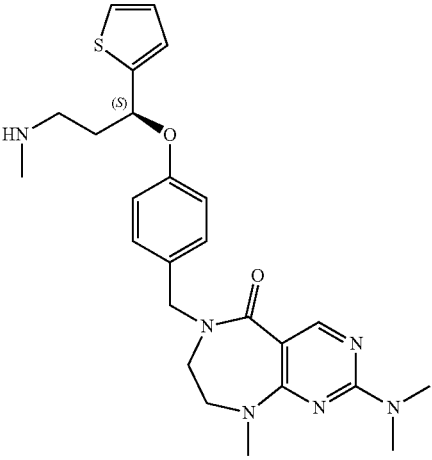 | (S)-2-(dimethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.75 | 481.2 (M + H) |
| 420 | 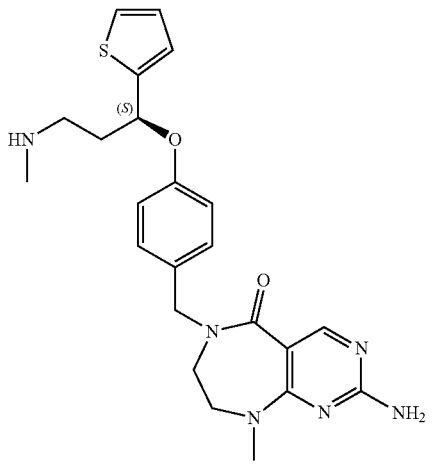 | (S)-2-amino-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.45 | 453.2 (M + H) |

Ex 421-426 were prepared by a sequence of reactions according to the methods described in Ex 62, 142 and 148, and using suitable starting materials:

| EX | Structure | Chemical name | Method | Ret (min) | MS (M + H) |
|---|---|---|---|---|---|
| 421 | 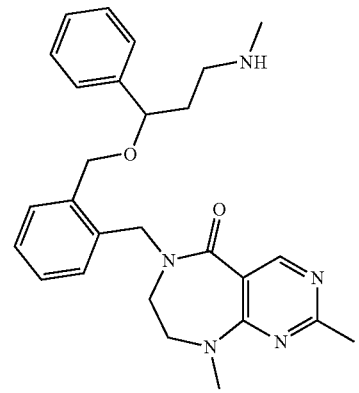 [SMILES: CNCCC(OCc1ccccc1CN1CCN(C)c2nc(C)ncc2C1=O)c1ccccc1] | 2,9-dimethyl-6-(2-((3-(methylamino)-1-phenylpropoxy)methyl)benzyl)-6,7,8,9-tetrahydro-5H-pyrimido[4,5-e][1,4]diazepin-5-one | A | 4.87 | 460.3 (M + H) |

-continued
| EX | Structure | Chemical name | Method | Ret (min) | MS (M + H) |
|---|---|---|---|---|---|
| 422 | 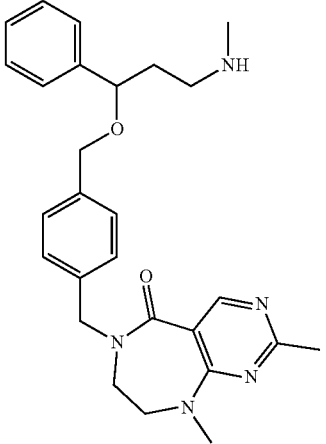 [SMILES: CNCCC(OCc1ccc(CN2CCN(C)c3nc(C)ncc3C2=O)cc1)c1ccccc1] | 2,9-dimethyl-6-(4-((3-(methylamino)-1-phenylpropoxy)methyl)benzyl)-6,7,8,9-tetrahydro-5H-pyrimido[4,5-e][1,4]diazepin-5-one | A | 4.85 | 460.3 (M + H) |
| 423 | 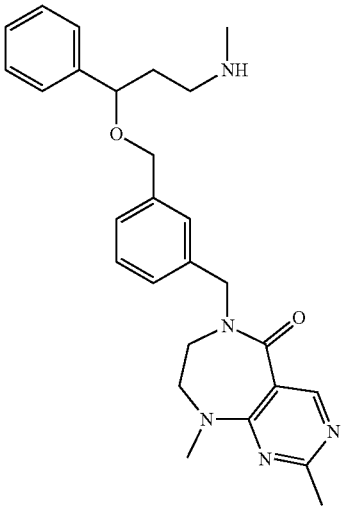 [SMILES: CNCCC(OCc1cccc(CN2CCN(C)c3nc(C)ncc3C2=O)c1)c1ccccc1] | 2,9-dimethyl-6-(3-((3-(methylamino)-1-phenylpropoxy)methyl)benzyl)-6,7,8,9-tetrahydro-5H-pyrimido[4,5-e][1,4]diazepin-5-one | A | 4.85 | 460.3 (M + H) |
| 424 | 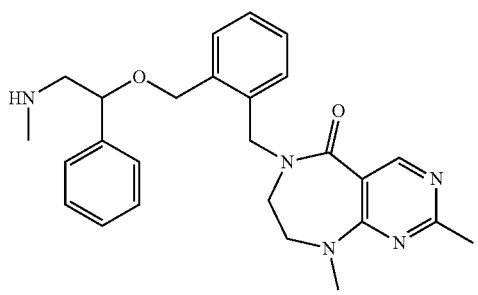 [SMILES: CNCC(OCc1ccccc1CN1CCN(C)c2nc(C)ncc2C1=O)c1ccccc1] | 2,9-dimethyl-6-(2-((2-(methylamino)-1-phenylethoxy)methyl)benzyl)-6,7,8,9-tetrahydro-5H-pyrimido[4,5-e][1,4]diazepin-5-one | A | 4.71 | 446.2 (M + H) |

| EX | Structure | Chemical name | Method | Ret (min) | MS (M + H) |
|---|---|---|---|---|---|
| 425 | 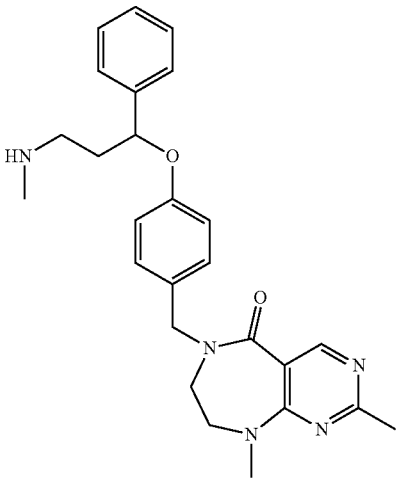 [SMILES: CNCCC(Oc1ccc(CN2CCN(C)c3nc(C)ncc3C2=O)cc1)c1ccccc1] | 2,9-dimethyl-6-(4-(3-(methylamino)-1-phenylpropoxy)benzyl)-6,7,8,9-tetrahydro-5H-pyrimido[4,5-e][1,4]diazepin-5-one | A | 4.61 | 446.3 (M + H) |
| 426 | 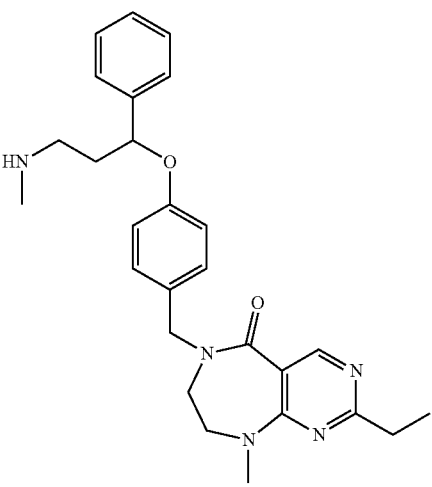 [SMILES: CCc1ncc2c(n1)N(C)CCN(Cc1ccc(OC(CCNC)c3ccccc3)cc1)C2=O] | 2-ethyl-9-methyl-6-(4-(3-(methylamino)-1-phenylpropoxy)benzyl)-6,7,8,9-tetrahydro-5H-pyrimido[4,5-e][1,4]diazepin-5-one | A | 4.79 | 460.3 (M + H) |

Ex 427-428 were prepared by a sequence of reactions according to the methods described in Ex 62, 142 and 225, and using suitable starting materials:

| EX | Structure | Chemical name | Method | Ret (min) | MS |
|---|---|---|---|---|---|
| 427 | 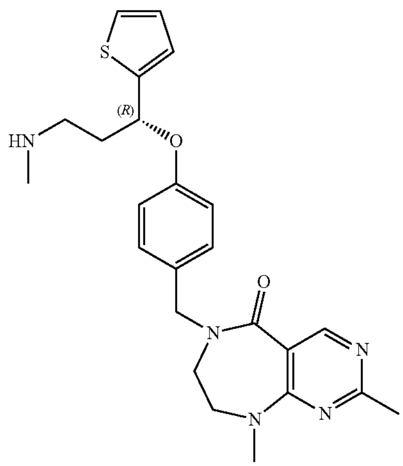 | (R)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.52 | 452.2 (M + H) |
| 428 | 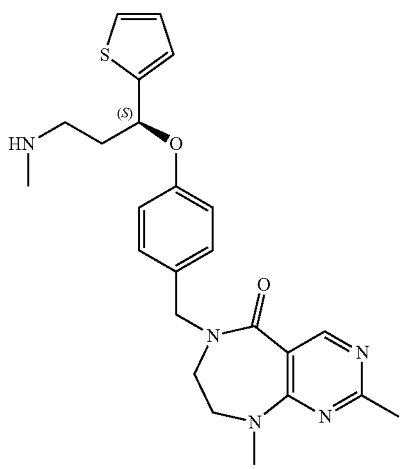 | (S)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.50 | 452.2 (M + H) |

Ex 429-434 were prepared by a sequence of reactions according to the methods described in Ex 62, 145 and 148, and using suitable starting materials:

| EX | Structure | Chemical name | Method | Ret (min) | MS |
|---|---|---|---|---|---|
| 429 | 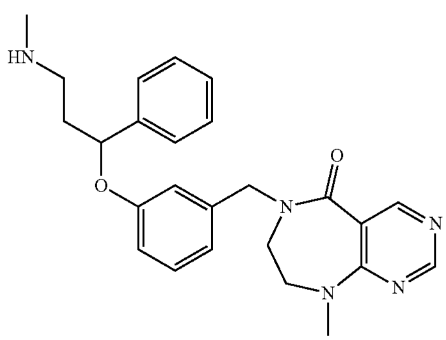 [SMILES: CNCCC(Oc1cccc(CN2CCN(C)c3ncncc3C2=O)c1)c1ccccc1] | 9-methyl-6-(3-(3-(methylamino)-1-phenylpropoxy)benzyl)-6,7,8,9-tetrahydro-5H-pyrimido[4,5-e][1,4]diazepin-5-one | A | 4.46 | 432.3 (M + H) |

-continued
| EX | Structure | Chemical name | Method | Ret (min) | MS |
|---|---|---|---|---|---|
| 430 | 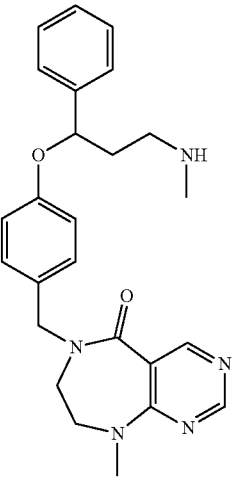 [SMILES: CNCCC(Oc1ccc(CN2CCN(C)c3ncncc3C2=O)cc1)c1ccccc1] | 9-methyl-6-(4-(3-(methylamino)-1-phenylpropoxy)benzyl)-6,7,8,9-tetrahydro-5H-pyrimido[4,5-e][1,4]diazepin-5-one | A | 4.50 | 432.2 (M + H) |
| 431 | 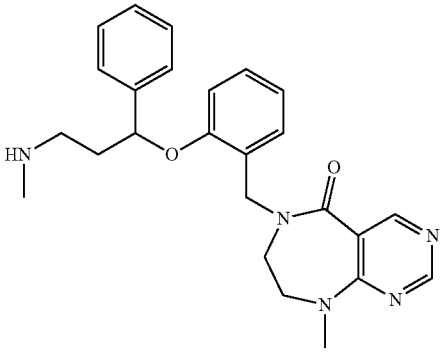 [SMILES: CNCCC(Oc1ccccc1CN1CCN(C)c2ncncc2C1=O)c1ccccc1] | 9-methyl-6-(2-(3-(methylamino)-1-phenylpropoxy)benzyl)-6,7,8,9-tetrahydro-5H-pyrimido[4,5-e][1,4]diazepin-5-one | A | 4.75 | 432.3 (M + H) |
| 432 | 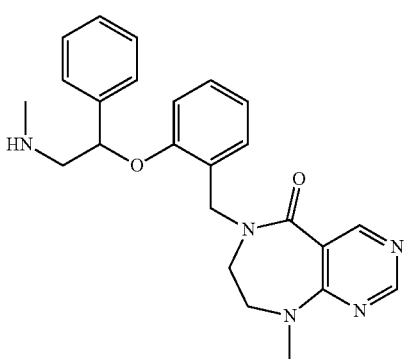 [SMILES: CNCC(Oc1ccccc1CN1CCN(C)c2ncncc2C1=O)c1ccccc1] | 9-methyl-6-(2-(2-(methylamino)-1-phenylethoxy)benzyl)-6,7,8,9-tetrahydro-5H-pyrimido[4,5-e][1,4]diazepin-5-one | A | 4.63 | 418.2 (M + H) |

| EX | Structure | Chemical name | Method | Ret (min) | MS |
|---|---|---|---|---|---|
| 433 | 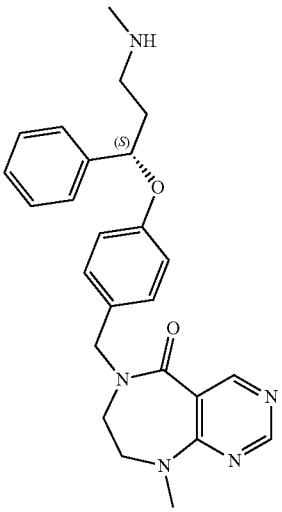 | (S)-9-methyl-6-(4-(3-(methylamino)-1-phenylpropoxy)benzyl)-6,7,8,9-tetrahydro-5H-pyrimido[4,5-e][1,4]diazepin-5-one | A | 4.54 | 432.2 (M + H) |
| 434 | 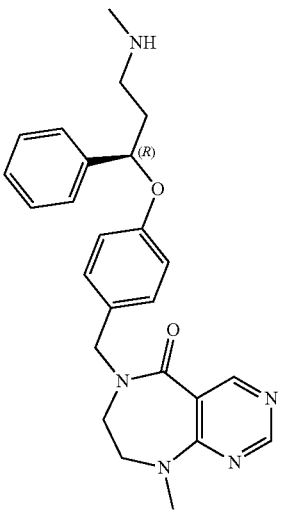 | (R)-9-methyl-6-(4-(3-(methylamino)-1-phenylpropoxy)benzyl)-6,7,8,9-tetrahydro-5H-pyrimido[4,5-e][1,4]diazepin-5-one | A | 4.52 | 432.2 (M + H) |
Ex 435-437 were prepared by a sequence of reactions according to the methods described in Ex 62, 145 and 225, and using suitable starting materials:

| EX | Structure | Chemical name | Method | Ret (min) | MS |
|---|---|---|---|---|---|
| 435 | 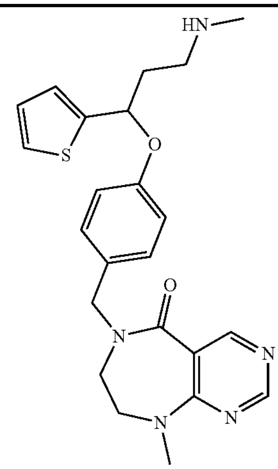 | 9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.42 | 438.2 (M + H) |
| 436 | 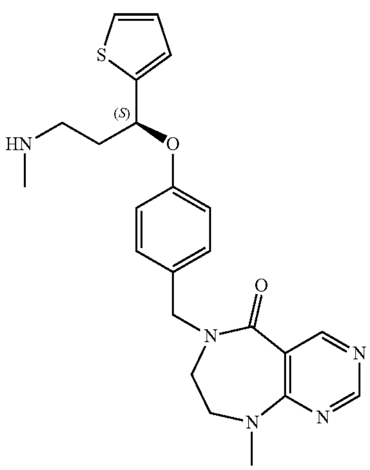 | (S)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.39 | 438.1 (M + H) |
| 437 | 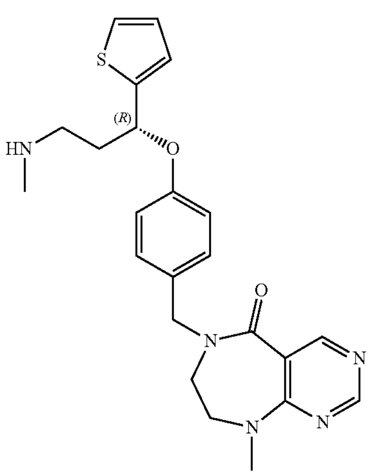 | (R)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | A | 4.43 | 438.2 (M + H) |

Ex 438-442 were prepared by the method described in Ex 275 using suitable starting materials:

| EX | Structure | Chemical name | Method | Ret (min) | MS |
|---|---|---|---|---|---|
| 438 | 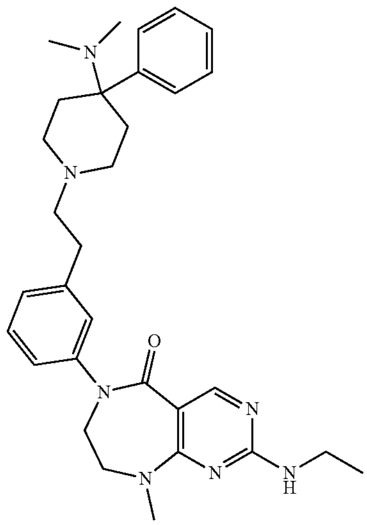 [SMILES: CCNc1ncc2c(n1)N(C)CCN(c1cccc(CCN3CCC(c4ccccc4)(N(C)C)CC3)c1)C2=O] | 6-(3-(2-(4-(dimethylamino)-4-phenylpiperidin-1-yl)ethyl)phenyl)-2-(ethylamino)-9-methyl-6,7,8,9-tetrahydro-5H-pyrimido[4,5-e][1,4]diazepin-5-one | A | 4.28 | 528.3 (M + H) |
| 439 | 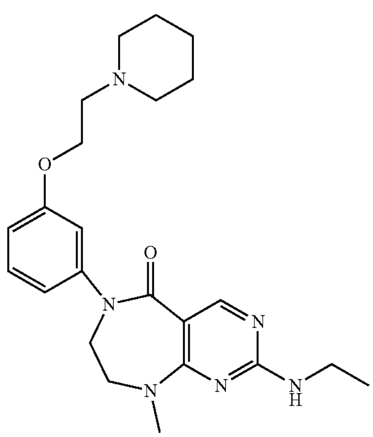 [SMILES: CCNc1ncc2c(n1)N(C)CCN(c1cccc(OCCN3CCCCC3)c1)C2=O] | 2-(ethylamino)-9-methyl-6-(3-(2-(piperidin-1-yl)ethoxy)phenyl)-6,7,8,9-tetrahydro-5H-pyrimido[4,5-e][1,4]diazepin-5-one | A | 4.44 | 425.3 (M + H) |
| 440 | 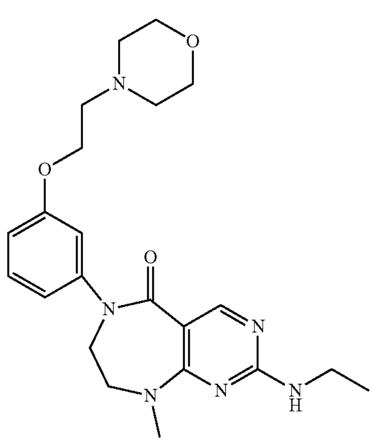 [SMILES: CCNc1ncc2c(n1)N(C)CCN(c1cccc(OCCN3CCOCC3)c1)C2=O] | 2-(ethylamino)-9-methyl-6-(3-(2-morpholinoethoxy)phenyl)-6,7,8,9-tetrahydro-5H-pyrimido[4,5-e][1,4]diazepin-5-one | A | 4.25 | 427.2 (M + H) |

| EX | Structure | Chemical name | Method | Ret (min) | MS |
|---|---|---|---|---|---|
| 441 | 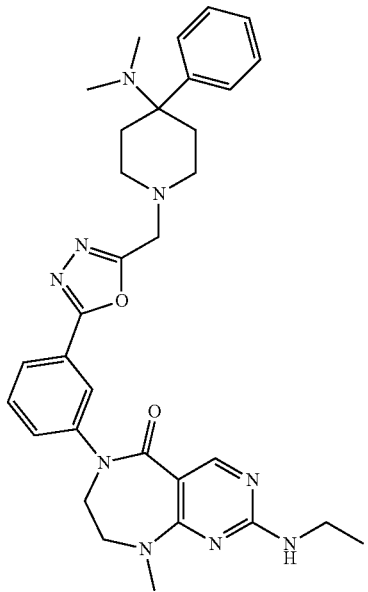 [SMILES: CCNc1ncc2c(n1)N(C)CCN(c1cccc(-c3nnc(CN4CCC(c5ccccc5)(N(C)C)CC4)o3)c1)C2=O] | 6-(3-(5-((4-(dimethylamino)-4-phenylpiperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one | A | 4.59 | 582.3 (M + H) |
| 442 | 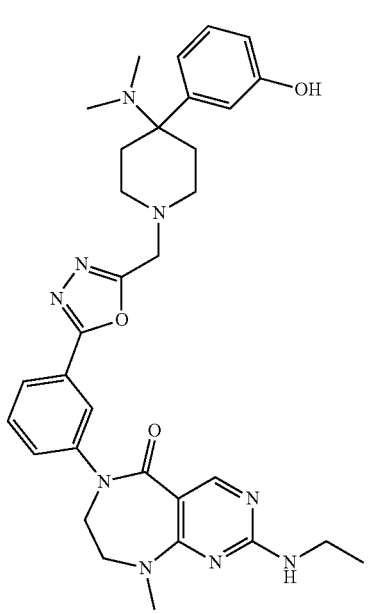 [SMILES: CCNc1ncc2c(n1)N(C)CCN(c1cccc(-c3nnc(CN4CCC(c5cccc(O)c5)(N(C)C)CC4)o3)c1)C2=O] | 6-(3-(5-((4-(dimethylamino)-4-(3-hydroxyphenyl)piperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one | A | 4.42 | 598.3 (M + H) |

Ex 443-463 are prepared by a sequence of reactions according to the methods described in Ex 62 and 148, and using suitable starting materials:

| EX | Structure | Chemical name | MS (M + H) |
|---|---|---|---|
| 443 | 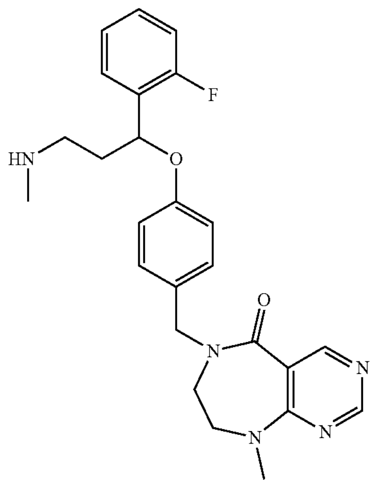 [SMILES: CNCCC(Oc1ccc(CN2CCN(C)c3ncncc3C2=O)cc1)c1ccccc1F] | 6-(4-(1-(2-fluorophenyl)-3-(methylamino)propoxy)benzyl)-9-methyl-6,7,8,9-tetrahydro-5H-pyrimido[4,5-e][1,4]diazepin-5-one | 450.2 |
| 444 | 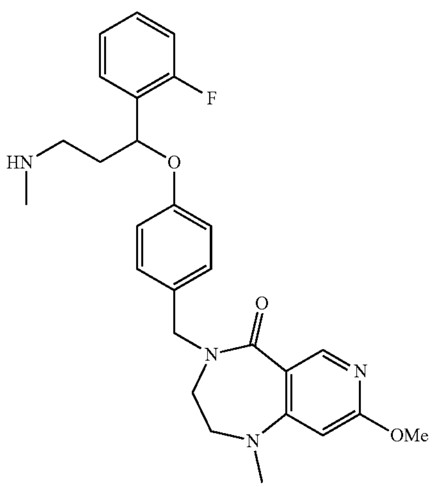 [SMILES: CNCCC(Oc1ccc(CN2CCN(C)c3cc(OC)ncc3C2=O)cc1)c1ccccc1F] | 4-(4-(1-(2-fluorophenyl)-3-(methylamino)propoxy)benzyl)-8-methoxy-1-methyl-1,2,3,4-tetrahydro-5H-pyrido[4,3-e][1,4]diazepin-5-one | 479.2 |
| 445 | 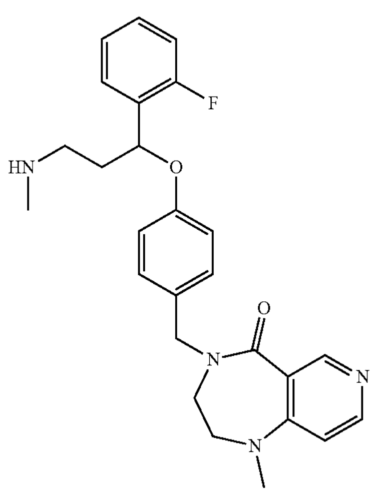 [SMILES: CNCCC(Oc1ccc(CN2CCN(C)c3ccncc3C2=O)cc1)c1ccccc1F] | 4-(4-(1-(2-fluorophenyl)-3-(methylamino)propoxy)benzyl)-1-methyl-1,2,3,4-tetrahydro-5H-pyrido[4,3-e][1,4]diazepin-5-one | 449.2 |

-continued

| EX | Structure | Chemical name | MS (M + H) |
|---|---|---|---|
| 446 | 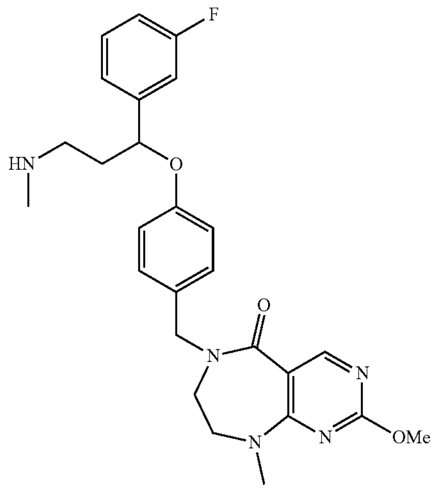 [SMILES: CNCCC(Oc1ccc(CN2CCN(C)c3nc(OC)ncc3C2=O)cc1)c1cccc(F)c1] | 6-(4-(1-(3-fluorophenyl)-3-(methylamino)propoxy)benzyl)-2-methoxy-9-methyl-6,7,8,9-tetrahydro-5H-pyrimido[4,5-e][1,4]diazepin-5-one | 480.2 |
| 447 | 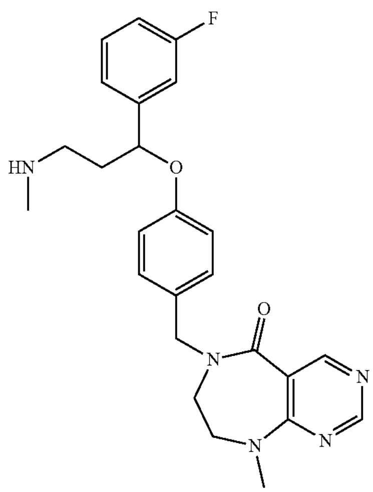 [SMILES: CNCCC(Oc1ccc(CN2CCN(C)c3ncncc3C2=O)cc1)c1cccc(F)c1] | (6-(4-(1-(3-fluorophenyl)-3-(methylamino)propoxy)benzyl)-9-methyl-6,7,8,9-tetrahydro-5H-pyrimido[4,5-e][1,4]diazepin-5-one | 450.2 |
| 448 | 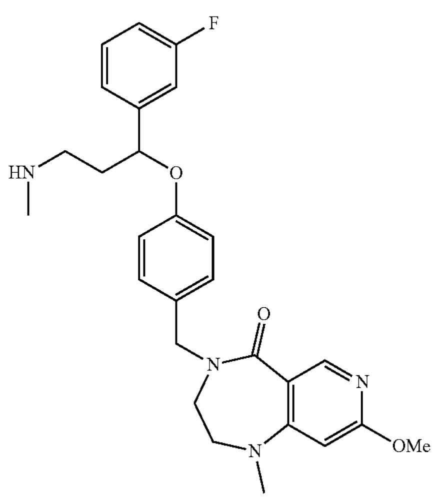 [SMILES: CNCCC(Oc1ccc(CN2CCN(C)c3cc(OC)ncc3C2=O)cc1)c1cccc(F)c1] | 4-(4-(1-(3-fluorophenyl)-3-(methylamino)propoxy)benzyl)-8-methoxy-1-methyl-1,2,3,4-tetrahydro-5H-pyrido[4,3-e][1,4]diazepin-5-one | 479.2 |

-continued

| EX | Structure | Chemical name | MS (M + H) |
|---|---|---|---|
| 449 | 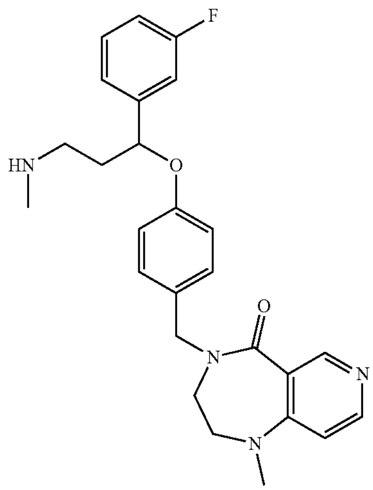 [SMILES: CNCCC(Oc1ccc(CN2CCN(C)c3ccncc3C2=O)cc1)c1cccc(F)c1] | 4-(4-(1-(3-fluorophenyl)-3-(methylamino)propoxy)benzyl)-1-methyl-1,2,3,4-tetrahydro-5H-pyrido[4,3-e][1,4]diazepin-5-one | 449.2 |
| 450 | 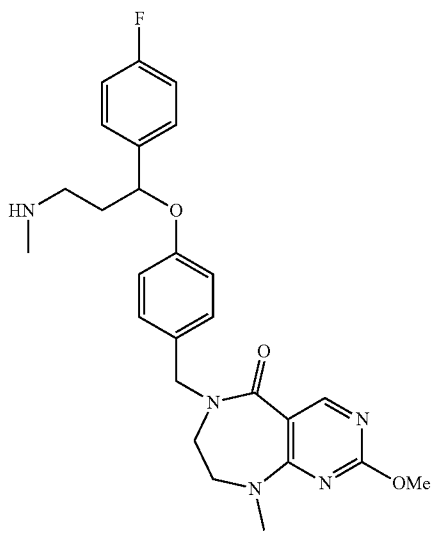 [SMILES: CNCCC(Oc1ccc(CN2CCN(C)c3nc(OC)ncc3C2=O)cc1)c1ccc(F)cc1] | 6-(4-(1-(4-fluorophenyl)-3-(methylamino)propoxy)benzyl)-2-methoxy-9-methyl-6,7,8,9-tetrahydro-5H-pyrimido[4,5-e][1,4]diazepin-5-one | 480.2 |
| 451 | 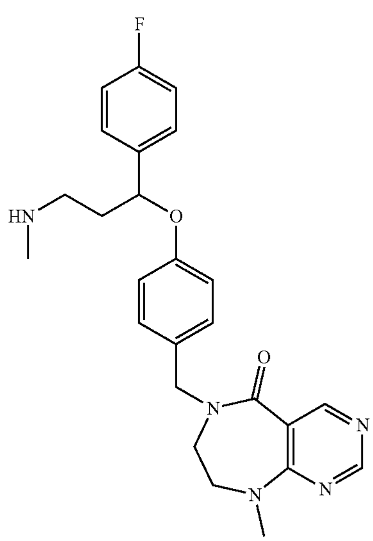 [SMILES: CNCCC(Oc1ccc(CN2CCN(C)c3ncncc3C2=O)cc1)c1ccc(F)cc1] | 6-(4-(1-(4-fluorophenyl)-3-(methylamino)propoxy)benzyl)-9-methyl-6,7,8,9-tetrahydro-5H-pyrimido[4,5-e][1,4]diazepin-5-one | 450.2 |

-continued

| EX | Structure | Chemical name | MS (M + H) |
|---|---|---|---|
| 452 | 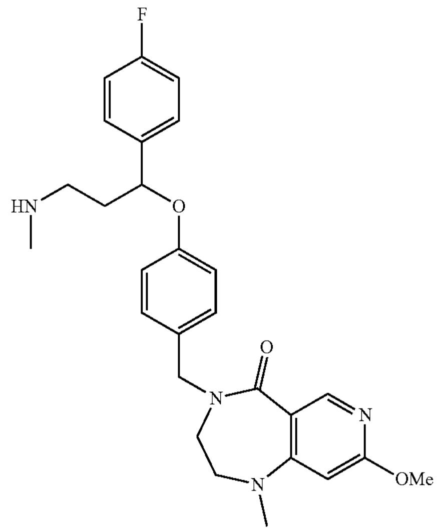 [SMILES: CNCCC(Oc1ccc(CN2CCN(C)c3cc(OC)ncc3C2=O)cc1)c1ccc(F)cc1] | 4-(4-(1-(4-fluorophenyl)-3-(methylamino)propoxy)benzyl)-8-methoxy-1-methyl-1,2,3,4-tetrahydro-5H-pyrido[4,3-e][1,4]diazepin-5-one | 479.2 |
| 453 | 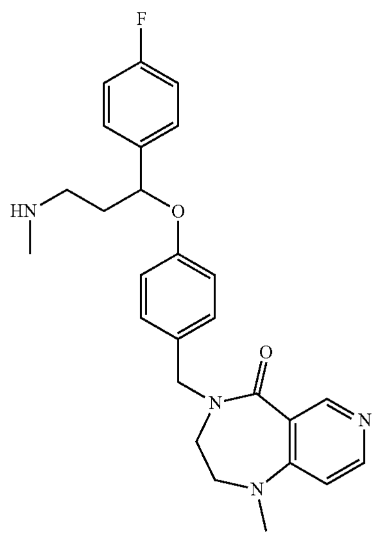 [SMILES: CNCCC(Oc1ccc(CN2CCN(C)c3ccncc3C2=O)cc1)c1ccc(F)cc1] | 4-(4-(1-(4-fluorophenyl)-3-(methylamino)propoxy)benzyl)-1-methyl-1,2,3,4-tetrahydro-5H-pyrido[4,3-e][1,4]diazepin-5-one | 449.2 |
| 454 | 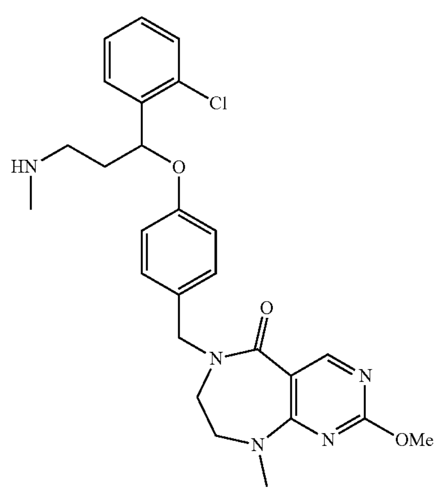 [SMILES: CNCCC(Oc1ccc(CN2CCN(C)c3nc(OC)ncc3C2=O)cc1)c1ccccc1Cl] | 6-(4-(1-(2-chlorophenyl)-3-(methylamino)propoxy)benzyl)-2-methoxy-9-methyl-6,7,8,9-tetrahydro-5H-pyrimido[4,5-e][1,4]diazepin-5-one | 497.2 |

| EX | Structure | Chemical name | MS (M + H) |
|---|---|---|---|
| 455 | 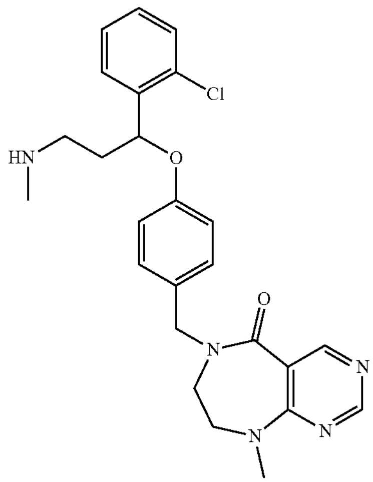 [SMILES: CNCCC(Oc1ccc(CN2CCN(C)c3ncncc3C2=O)cc1)c1ccccc1Cl] | 6-(4-(1-(2-chlorophenyl)-3-(methylamino)propoxy)benzyl)-9-methyl-6,7,8,9-tetrahydro-5H-pyrimido[4,5-e][1,4]diazepin-5-one | 467.2 |
| 456 | 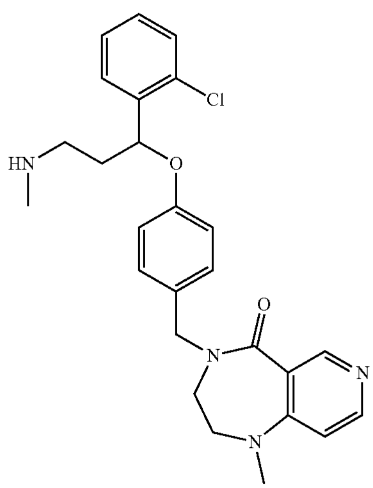 [SMILES: CNCCC(Oc1ccc(CN2CCN(C)c3ccncc3C2=O)cc1)c1ccccc1Cl] | 4-(4-(1-(2-chlorophenyl)-3-(methylamino)propoxy)benzyl)-1-methyl-1,2,3,4-tetrahydro-5H-pyrido[4,3-e][1,4]diazepin-5-one | 466.2 |
| 457 | 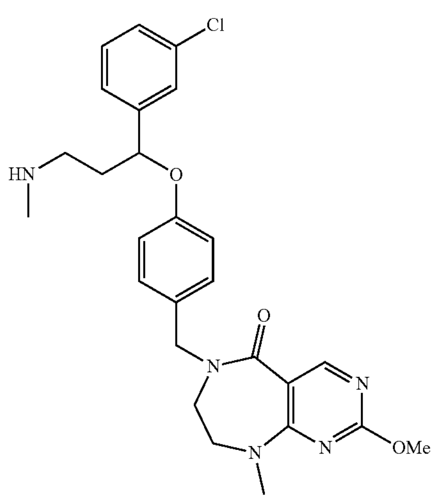 [SMILES: CNCCC(Oc1ccc(CN2CCN(C)c3nc(OC)ncc3C2=O)cc1)c1cccc(Cl)c1] | 6-(4-(1-(3-chlorophenyl)-3-(methylamino)propoxy)benzyl)-2-methoxy-9-methyl-6,7,8,9-tetrahydro-5H-pyrimido[4,5-e][1,4]diazepin-5-one | 497.2 |

-continued

| EX | Structure | Chemical name | MS (M + H) |
|---|---|---|---|
| 458 | 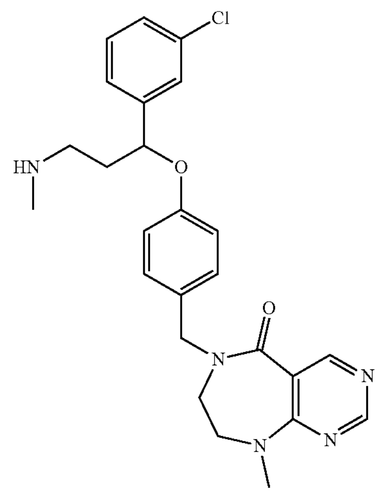 [SMILES: CNCCC(Oc1ccc(CN2CCN(C)c3ncncc3C2=O)cc1)c1cccc(Cl)c1] | 6-(4-(1-(3-chlorophenyl)-3-(methylamino)propoxy)benzyl)-9-methyl-6,7,8,9-tetrahydro-5H-pyrimido[4,5-e][1,4]diazepin-5-one | 467.2 |
| 459 | 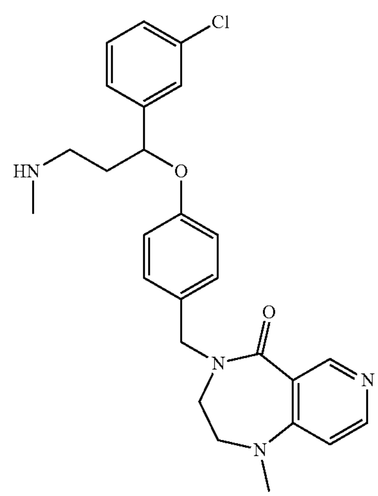 [SMILES: CNCCC(Oc1ccc(CN2CCN(C)c3ccncc3C2=O)cc1)c1cccc(Cl)c1] | 4-(4-(1-(3-chlorophenyl)-3-(methylamino)propoxy)benzyl)-1-methyl-1,2,3,4-tetrahydro-5H-pyrido[4,3-e][1,4]diazepin-5-one | 466.2 |
| 460 | 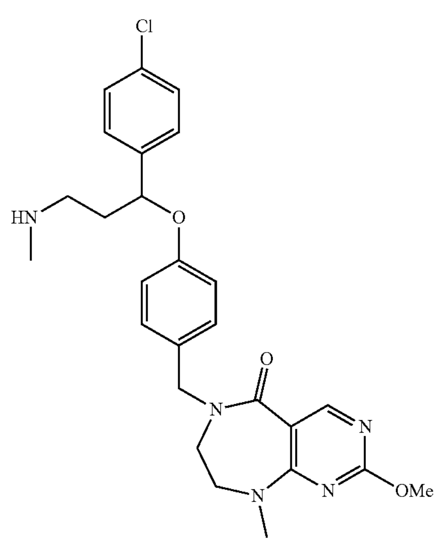 | 6-(4-(1-(4-chlorophenyl)-3-(methylamino)propoxy)benzyl)-2-methoxy-9-methyl-6,7,8,9-tetrahydro-5H-pyrimido[4,5-e][1,4]diazepin-5-one | 497.2 |

-continued

| EX | Structure | Chemical name | MS (M + H) |
|---|---|---|---|
| 461 | 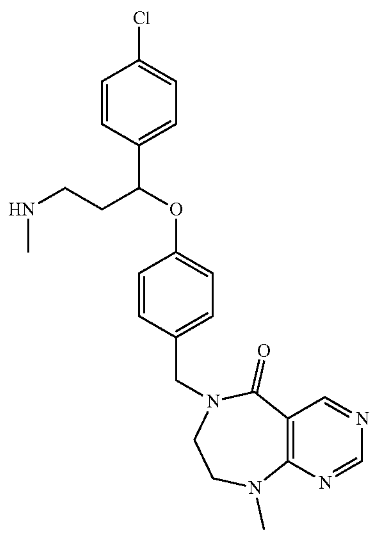 [SMILES: CNCCC(Oc1ccc(CN2CCN(C)c3ncncc3C2=O)cc1)c1ccc(Cl)cc1] | 6-(4-(1-(4-chlorophenyl)-3-(methylamino)propoxy)benzyl)-9-methyl-6,7,8,9-tetrahydro-5H-pyrimido[4,5-e][1,4]diazepin-5-one | 467.2 |
| 462 | 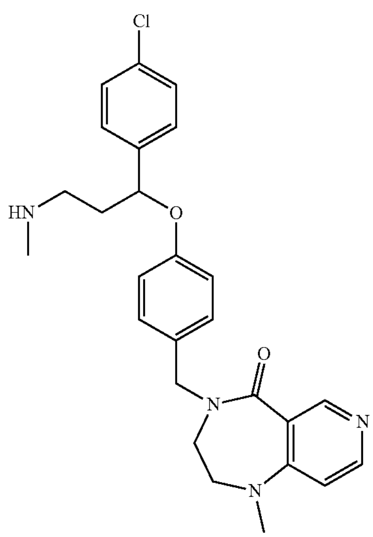 [SMILES: CNCCC(Oc1ccc(CN2CCN(C)c3ccncc3C2=O)cc1)c1ccc(Cl)cc1] | 4-(4-(1-(4-chlorophenyl)-3-(methylamino)propoxy)benzyl)-1-methyl-1,2,3,4-tetrahydro-5H-pyrido[4,3-e][1,4]diazepin-5-one | 466.2 |
| 463 | 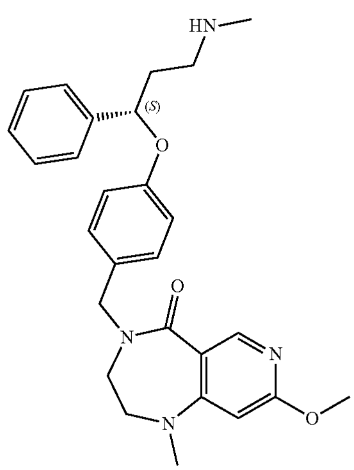 | (S)-8-methoxy-1-methyl-4-(4-(3-(methylamino)-1-phenylpropoxy)benzyl)-1,2,3,4-tetrahydro-5H-pyrido[4,3-e][1,4]diazepin-5-one | 461.2 |

Ex 464-488 are prepared by a sequence of reactions according to the methods described in Ex 62 and 225, and using suitable starting materials:

| EX | Structure | Chemical name | MS (M + H) |
|----|-----------|---------------|------------|
| 464 | 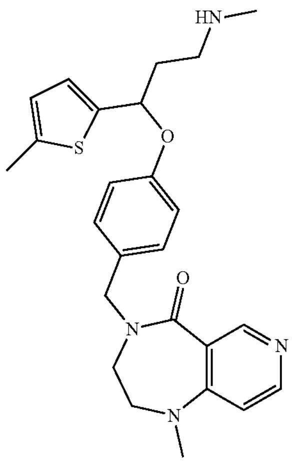 [SMILES: CNCCC(Oc1ccc(CN2CCN(C)c3ccncc3C2=O)cc1)c1ccc(C)s1] | 1-methyl-4-(4-(3-(methylamino)-1-(5-methylthiophen-2-yl)propoxy)benzyl)-1,2,3,4-tetrahydro-5H-pyrido[4,3-e][1,4]diazepin-5-one | 451.2 |
| 465 | 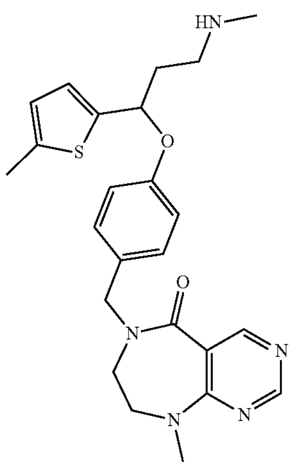 [SMILES: CNCCC(Oc1ccc(CN2CCN(C)c3ncncc3C2=O)cc1)c1ccc(C)s1] | 9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one | 452.2 |
| 466 | 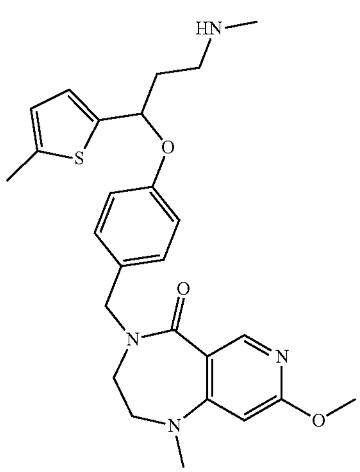 | 8-methoxy-1-methyl-4-(4-(3-(methylamino)-1-(5-methylthiophen-2-yl)propoxy)benzyl)-1,2,3,4-tetrahydro-5H-pyrido[4,3-e][1,4]diazepin-5-one | 481.2 |

| EX | Structure | Chemical name | MS (M + H) |
|---|---|---|---|
| 467 | 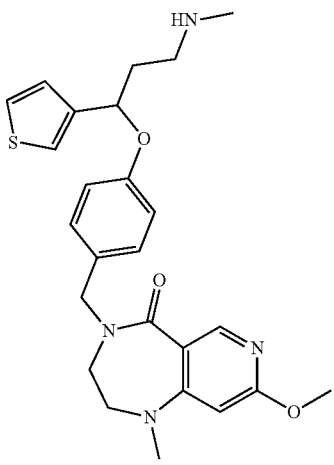 [SMILES: CNCCC(Oc1ccc(CN2CCN(C)c3cc(OC)ncc3C2=O)cc1)c1ccsc1] | 8-methoxy-1-methyl-4-(4-(3-(methylamino)-1-(thiophen-3-yl)propoxy)benzyl)-1,2,3,4-tetrahydro-5H-pyrido[4,3-e][1,4]diazepin-5-one | 467.2 |
| 468 | 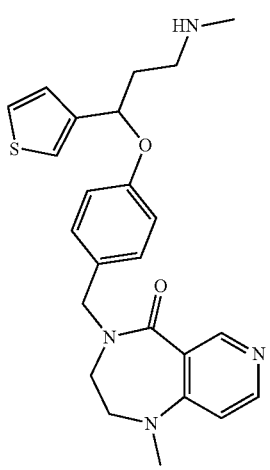 [SMILES: CNCCC(Oc1ccc(CN2CCN(C)c3ccncc3C2=O)cc1)c1ccsc1] | 1-methyl-4-(4-(3-(methylamino)-1-(thiophen-3-yl)propoxy)benzyl)-1,2,3,4-tetrahydro-5H-pyrido[4,3-e][1,4]diazepin-5-one | 437.2 |
| 469 | 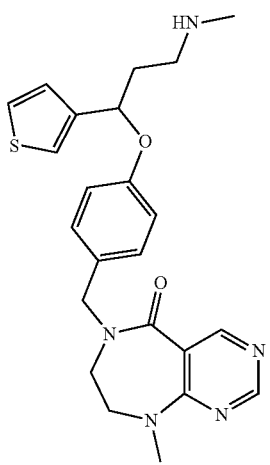 [SMILES: CNCCC(Oc1ccc(CN2CCN(C)c3ncncc3C2=O)cc1)c1ccsc1] | 9-methyl-6-(4-(3-(methylamino)-1-(thiophen-3-yl)propoxy)benzyl)-6,7,8,9-tetrahydro-5H-pyrimido[4,5-e][1,4]diazepin-5-one | 438.2 |

-continued

| EX | Structure | Chemical name | MS (M + H) |
|---|---|---|---|
| 470 | 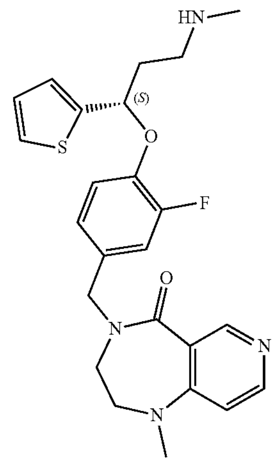 | (S)-4-(3-fluoro-4-(3-(methylamino)-1-(thiophen-2-yl)propoxy)benzyl)-1-methyl-1,2,3,4-tetrahydro-5H-pyrido[4,3-e][1,4]diazepin-5-one | 455.2 |
| 471 | 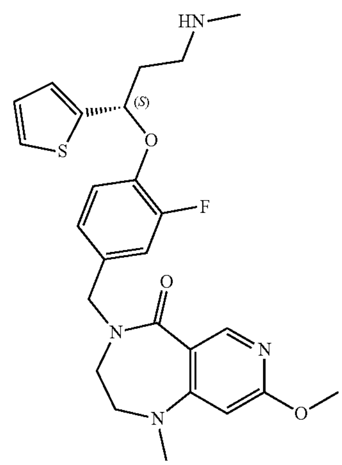 | (S)-4-(3-fluoro-4-(3-(methylamino)-1-(thiophen-2-yl)propoxy)benzyl)-8-methoxy-1-methyl-1,2,3,4-tetrahydro-5H-pyrido[4,3-e][1,4]diazepin-5-one | 485.2 |
| 472 | 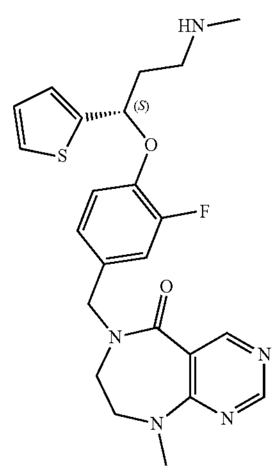 | (S)-6-(3-fluoro-4-(3-(methylamino)-1-(thiophen-2-yl)propoxy)benzyl)-9-methyl-6,7,8,9-tetrahydro-5H-pyrimido[4,5-e][1,4]diazepin-5-one | 456.2 |

-continued
| EX | Structure | Chemical name | MS (M + H) |
|---|---|---|---|
| 473 | 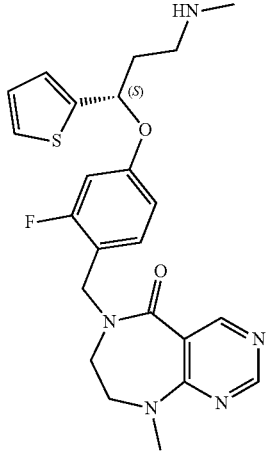 | (S)-6-(2-fluoro-4-(3-(methylamino)-1-(thiophen-2-yl)propoxy)benzyl)-9-methyl-6,7,8,9-tetrahydro-5H-pyrimido[4,5-e][1,4]diazepin-5-one | 456.2 |
| 474 | 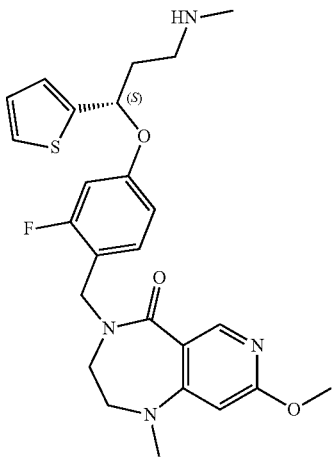 | (S)-4-(2-fluoro-4-(3-(methylamino)-1-(thiophen-2-yl)propoxy)benzyl)-8-methoxy-1-methyl-1,2,3,4-tetrahydro-5H-pyrido[4,3-e][1,4]diazepin-5-one | 485.2 |
| 475 | 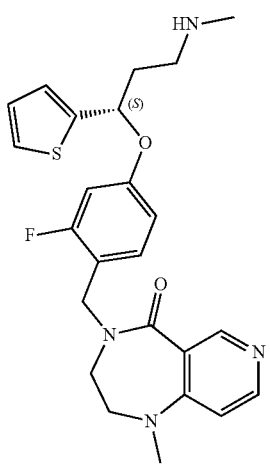 | (S)-4-(2-fluoro-4-(3-(methylamino)-1-(thiophen-2-yl)propoxy)benzyl)-1-methyl-1,2,3,4-tetrahydro-5H-pyrido[4,3-e][1,4]diazepin-5-one | 455.2 |

-continued

| EX | Structure | Chemical name | MS (M + H) |
|---|---|---|---|
| 476 | 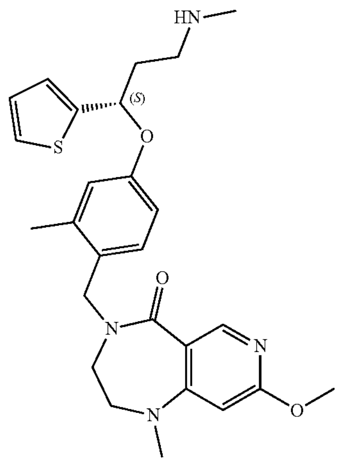 | (S)-8-methoxy-1-methyl-4-(2-methyl-4-(3-(methylamino)-1-(thiophen-2-yl)propoxy)benzyl)-1,2,3,4-tetrahydro-5H-pyrido[4,3-e][1,4]diazepin-5-one | 481.2 |
| 477 | 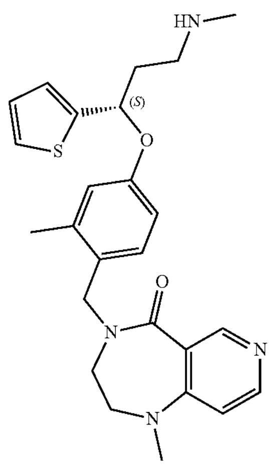 | (S)-1-methyl-4-(2-methyl-4-(3-(methylamino)-1-(thiophen-2-yl)propoxy)benzyl)-1,2,3,4-tetrahydro-5H-pyrido[4,3-e][1,4]diazepin-5-one | 451.2 |
| 478 | 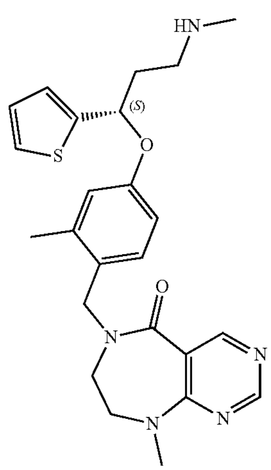 | (S)-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one | 452.2 |

-continued

| EX | Structure | Chemical name | MS (M + H) |
|---|---|---|---|
| 479 | 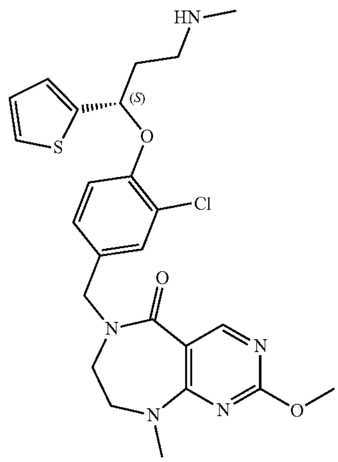 | (S)-6-(3-chloro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | 503.2 |
| 480 | 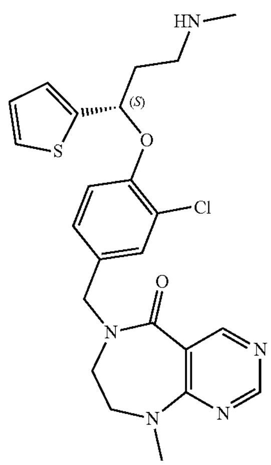 | (S)-6-(3-chloro-4-(3-(methylamino)-1-(thiophen-2-yl)propoxy)benzyl)-9-methyl-6,7,8,9-tetrahydro-5H-pyrimido[4,5-e][1,4]diazepin-5-one | 473.2 |
| 481 | 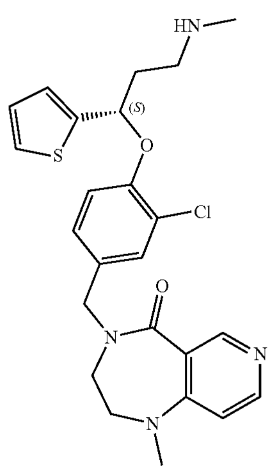 | (S)-4-(3-chloro-4-(3-(methylamino)-1-(thiophen-2-yl)propoxy)benzyl)-1-methyl-1,2,3,4-tetrahydro-5H-pyrido[4,3-e][1,4]diazepin-5-one | 472.2 |

| EX | Structure | Chemical name | MS (M + H) |
|---|---|---|---|
| 482 | 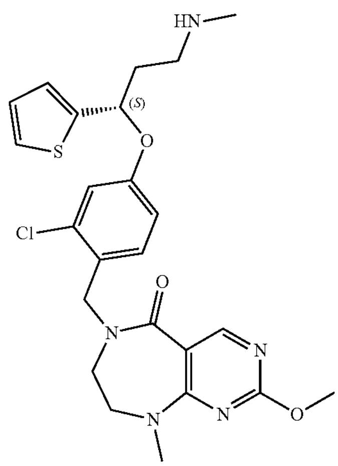 | (S)-6-(2-chloro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | 503.2 |
| 483 | 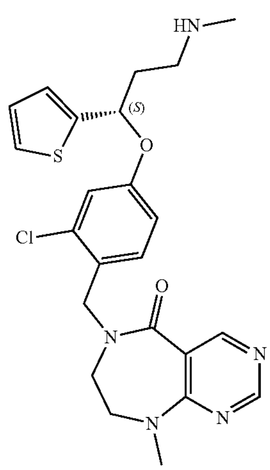 | (S)-6-(2-chloro-4-(3-(methylamino)-1-(thiophen-2-yl)propoxy)benzyl)-9-methyl-6,7,8,9-tetrahydro-5H-pyrimido[4,5-e][1,4]diazepin-5-one | 473.2 |
| 484 | 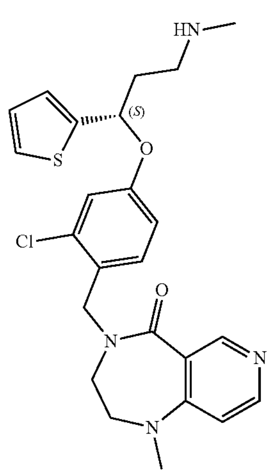 | (S)-4-(2-chloro-4-(3-(methylamino)-1-(thiophen-2-yl)propoxy)benzyl)-1-methyl-1,2,3,4-tetrahydro-5H-pyrido[4,3-e][1,4]diazepin-5-one | 472.2 |

-continued

| EX | Structure | Chemical name | MS (M + H) |
|---|---|---|---|
| 485 | 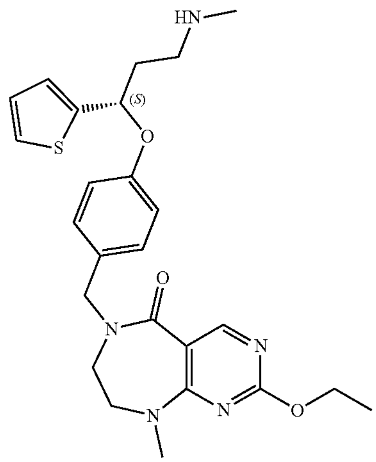 | (S)-2-ethoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one | 482.2 |
| 486 | 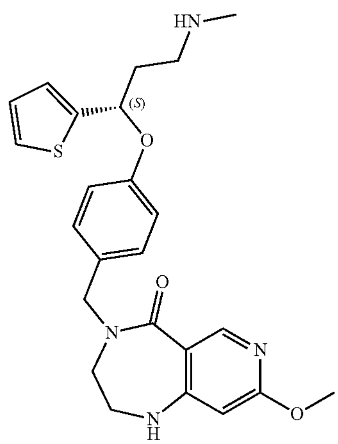 | (S)-8-methoxy-4-(4-(3-(methylamino)-1-(thiophen-2-yl)propoxy)benzyl)-1,2,3,4-tetrahydro-5H-pyrido[4,3-e][1,4]diazepin-5-one | 453.2 |
| 487 | 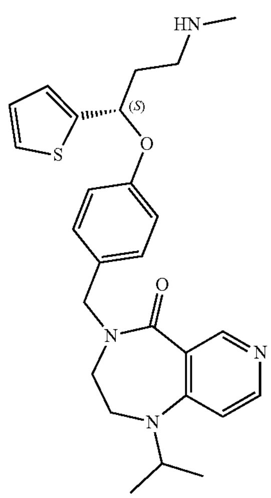 | (S)-1-isopropyl-4-(4-(3-(methylamino)-1-(thiophen-2-yl)propoxy)benzyl)-1,2,3,4-tetrahydro-5H-pyrido[4,3-e][1,4]diazepin-5-one | 465.2 |

| EX | Structure | Chemical name | MS (M + H) |
|---|---|---|---|
| 488 | 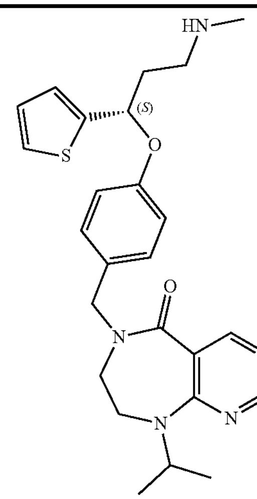 | (S)-9-isopropyl-6-(4-(3-(methylamino)-1-(thiophen-2-yl)propoxy)benzyl)-6,7,8,9-tetrahydro-5H-pyrimido[4,5-e][1,4]diazepin-5-one | 466.2 |

Examples of Biological Activity

Binding Assay to Human α2δ-1 Subunit of Cav2.2 Calcium Channel.

Human α2δ-1 enriched membranes (2.5 µg) were incubated with 15 nM of radiolabeled [3H]-Gabapentin in assay buffer containing Hepes-KOH 10 mM, pH 7.4.

NSB (non specific binding) was measured by adding 10 µM pregabalin. After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4.

Filter plates were dried at 60° C. for 1 hour and 30 µl of scintillation cocktail were added to each well before radioactivity reading.

Readings were performed in a Trilux 1450 Microbeta radioactive counter (Perkin Elmer).

Binding Assay to Human Norepinephrine Transporter (NET).

Human norepinephrine transporter (NET) enriched membranes (5 µg) were incubated with 5 nM of radiolabeled [3H]-Nisoxetin in assay buffer containing 50 mM Tris-HCl, 120 mM NaCl, 5 mM KCl, pH 7.4.

NSB (non specific binding) was measured by adding 1 µM. After 60 min incubation at 4° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, 0.9% NaCl, pH 7.4.

Filter plates were dried at 60° C. for 1 hour and 30 µl of scintillation cocktail were added to each well before radioactivity reading.

Readings were performed in a Trilux 1450 Microbeta radioactive counter (Perkin Elmer).

The following scale has been adopted for representing the binding to the α2δ-1 receptor expressed as Ki:

+ Ki-α2δ-1>=3000 nM

++ 500 nM<Ki-α2δ-1<3000 nM

+++ 100 nM<Ki-α2δ-1<500 nM

++++ Ki-α2δ-1<100 nM

For the dual compounds and regarding the NET receptor, the following scale has been adopted for representing the binding expressed as Ki:

+ Ki-NET>=1000 nM

++ 500 nM<Ki-NET<1000 nM

+++ 100 nM<Ki-NET<500 nM

++++ Ki-NET<100 nM

The results of the binding for α2δ-1 receptor are shown in Table 1:

TABLE 1

| Ex | Structure | Name | Ki (nM) α2δ-1 |
|---|---|---|---|
| 1 | 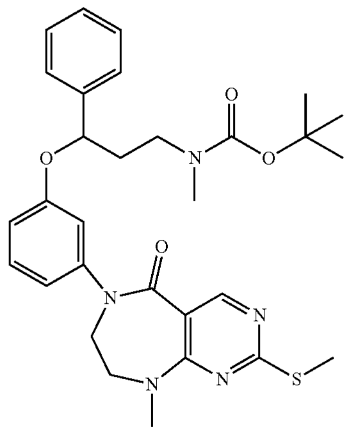 | tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate | + |
| 2 | 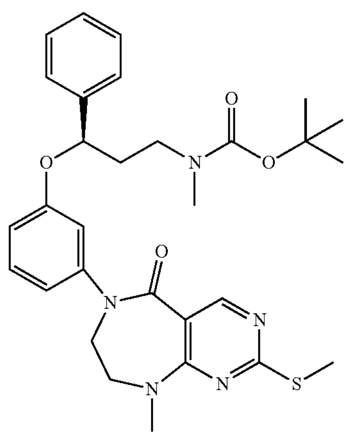 [SMILES: CSc1ncc2c(n1)N(C)CCN(c1cccc(O[C@H](CCN(C)C(=O)OC(C)(C)C)c3ccccc3)c1)C2=O] | tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate | + |
| 3 | 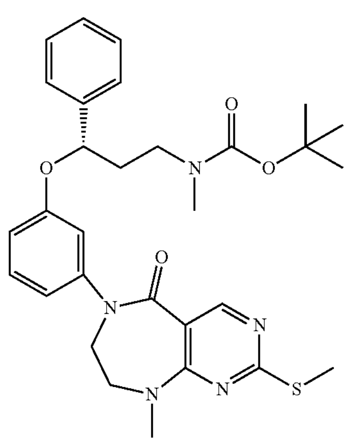 [SMILES: CSc1ncc2c(n1)N(C)CCN(c1cccc(O[C@@H](CCN(C)C(=O)OC(C)(C)C)c3ccccc3)c1)C2=O] | tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate | + |

TABLE 1-continued

| Ex | Structure | Name | Ki (nM) α2δ-1 |
|---|---|---|---|
| 4 | 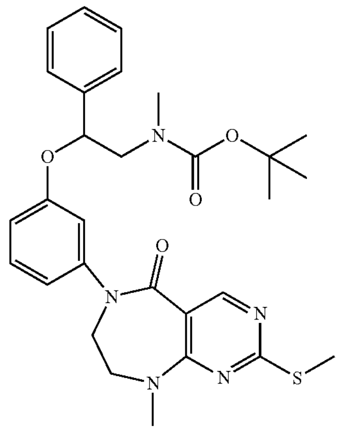 [SMILES: CSc1ncc2c(n1)N(C)CCN(c1cccc(OC(CN(C)C(=O)OC(C)(C)C)c3ccccc3)c1)C2=O] | tert-butyl methyl(2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate | + |
| 5 | 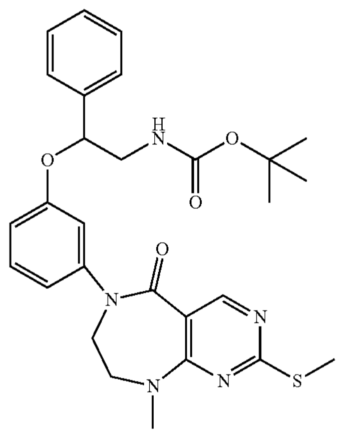 [SMILES: CSc1ncc2c(n1)N(C)CCN(c1cccc(OC(CNC(=O)OC(C)(C)C)c3ccccc3)c1)C2=O] | tert-butyl (2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate | + |
| 6 | 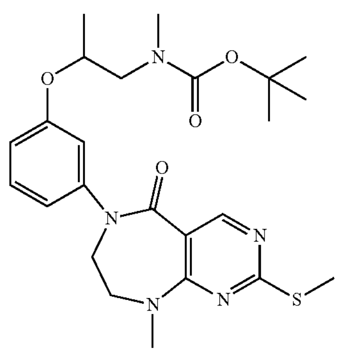 [SMILES: CSc1ncc2c(n1)N(C)CCN(c1cccc(OC(C)CN(C)C(=O)OC(C)(C)C)c1)C2=O] | tert-butyl methyl(2-(3-(9-methyl-2-(methylthio)-5-oxo-5,7,8,9-tetrahydro-6H-pyrimido[4,5-e][1,4]diazepin-6-yl)phenoxy)propyl)carbamate | + |
| 7 | 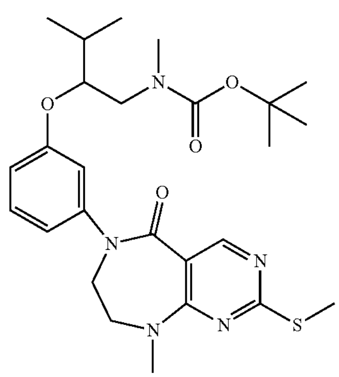 [SMILES: CSc1ncc2c(n1)N(C)CCN(c1cccc(OC(CN(C)C(=O)OC(C)(C)C)C(C)C)c1)C2=O] | tert-butyl methyl(3-methyl-2-(3-(9-methyl-2-(methylthio)-5-oxo-5,7,8,9-tetrahydro-6H-pyrimido[4,5-e][1,4]diazepin-6-yl)phenoxy)butyl)carbamate | + |

TABLE 1-continued

| Ex | Structure | Name | Ki (nM) α2δ-1 |
|---|---|---|---|
| 8 | 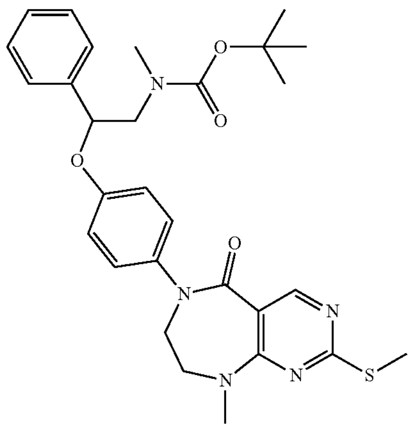 [SMILES: CSc1ncc2c(n1)N(C)CCN(c1ccc(OC(CN(C)C(=O)OC(C)(C)C)c3ccccc3)cc1)C2=O] | tert-butyl methyl(2-(4-(9-methyl-2-(methylthio)-5-oxo-5,7,8,9-tetrahydro-6H-pyrimido[4,5-e][1,4]diazepin-6-yl)phenoxy)-2-phenylethyl)carbamate | + |
| 9 | 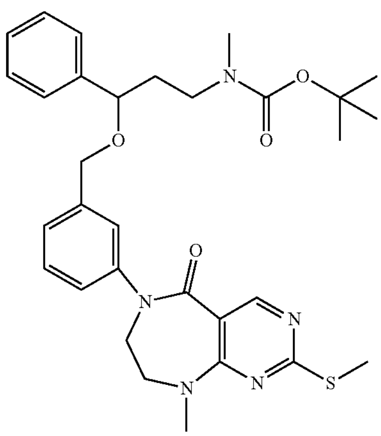 [SMILES: CSc1ncc2c(n1)N(C)CCN(c1cccc(COC(CCN(C)C(=O)OC(C)(C)C)c3ccccc3)c1)C2=O] | tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate | + |
| 10 | 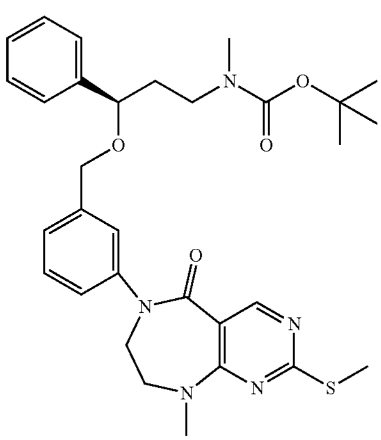 | tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate | + |

TABLE 1-continued

| Ex | Structure | Name | Ki (nM) α2δ-1 |
|---|---|---|---|
| 11 | 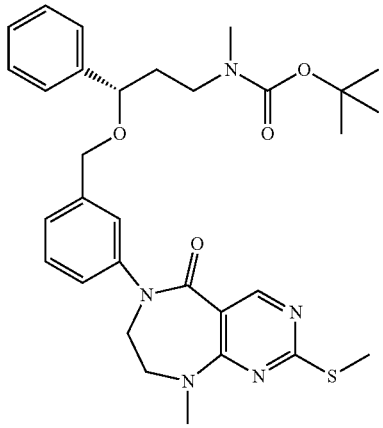 [SMILES: CSc1ncc2c(n1)N(C)CCN(c1cccc(CO[C@@H](CCN(C)C(=O)OC(C)(C)C)c3ccccc3)c1)C2=O] | tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate | + |
| 12 | 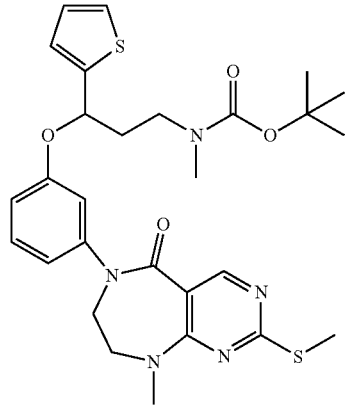 [SMILES: CSc1ncc2c(n1)N(C)CCN(c1cccc(OC(CCN(C)C(=O)OC(C)(C)C)c3cccs3)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate | + |
| 13 | 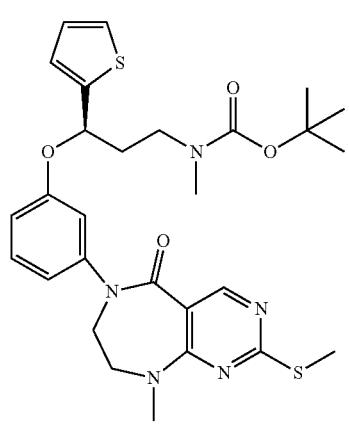 [SMILES: CSc1ncc2c(n1)N(C)CCN(c1cccc(O[C@H](CCN(C)C(=O)OC(C)(C)C)c3cccs3)c1)C2=O] | tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate | + |

TABLE 1-continued

| Ex | Structure | Name | Ki (nM) α2δ-1 |
|---|---|---|---|
| 14 | 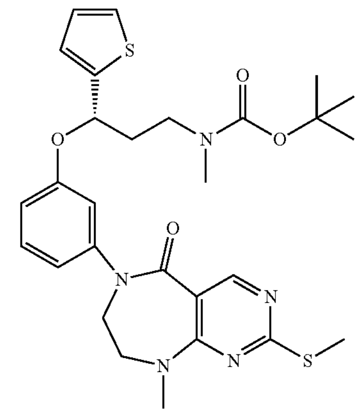 [SMILES: CSc1ncc2c(n1)N(C)CCN(c1cccc(O[C@@H](CCN(C)C(=O)OC(C)(C)C)c3cccs3)c1)C2=O] | tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate | + |
| 15 | 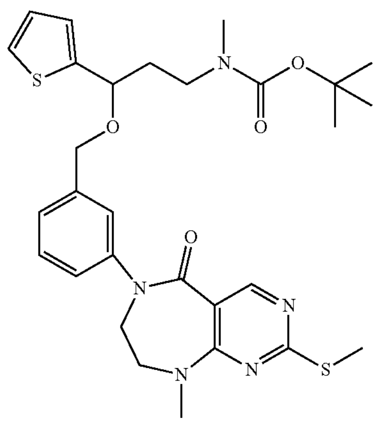 [SMILES: CSc1ncc2c(n1)N(C)CCN(c1cccc(COC(CCN(C)C(=O)OC(C)(C)C)c3cccs3)c1)C2=O] | tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate | + |
| 16 | 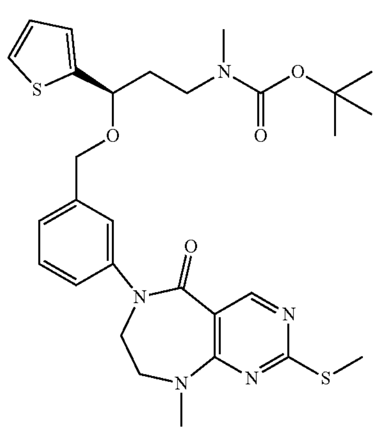 [SMILES: CSc1ncc2c(n1)N(C)CCN(c1cccc(CO[C@H](CCN(C)C(=O)OC(C)(C)C)c3cccs3)c1)C2=O] | tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate | + |

TABLE 1-continued

| Ex | Structure | Name | Ki (nM) α2δ-1 |
|---|---|---|---|
| 17 | 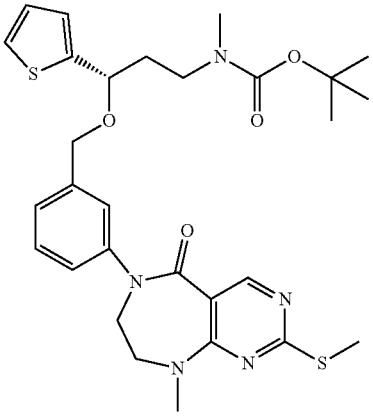 [SMILES: CSc1ncc2c(n1)N(C)CCN(c1cccc(CO[C@@H](CCN(C)C(=O)OC(C)(C)C)c3cccs3)c1)C2=O] | tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate | + |
| 18 | 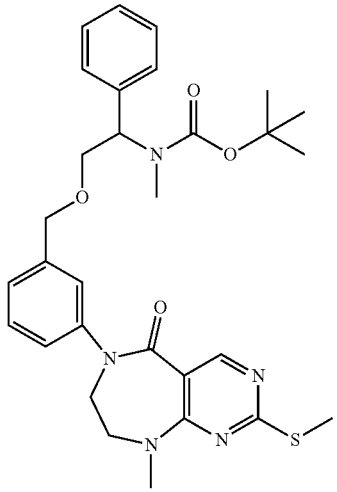 [SMILES: CSc1ncc2c(n1)N(C)CCN(c1cccc(COCC(c3ccccc3)N(C)C(=O)OC(C)(C)C)c1)C2=O] | tert-butyl methyl(2-((3-(9-methyl-2-(methylthio)-5-oxo-5,7,8,9-tetrahydro-6H-pyrimido[4,5-e][1,4]diazepin-6-yl)benzyl)oxy)-1-phenylethyl)carbamate | + |
| 19 | 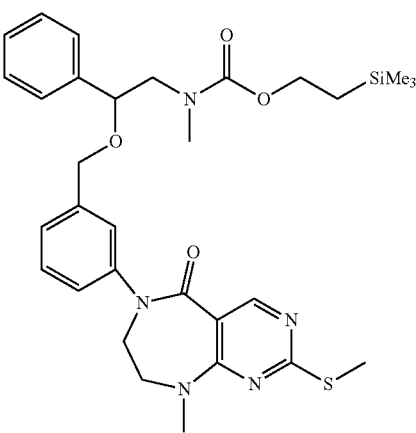 [SMILES: CSc1ncc2c(n1)N(C)CCN(c1cccc(COC(CN(C)C(=O)OCC[Si](C)(C)C)c3ccccc3)c1)C2=O] | 2-(trimethylsilyl)ethyl methyl(2-((3-(9-methyl-2-(methylthio)-5-oxo-5,7,8,9-tetrahydro-6H-pyrimido[4,5-e][1,4]diazepin-6-yl)benzyl)oxy)-2-phenylethyl)carbamate | + |

TABLE 1-continued

| Ex | Structure | Name | Ki (nM) α2δ-1 |
|----|-----------|------|---------------|
| 20 | 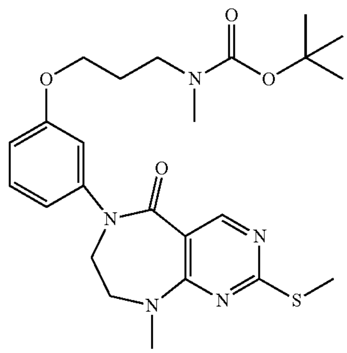 [SMILES: CSc1ncc2c(n1)N(C)CCN(c1cccc(OCCCN(C)C(=O)OC(C)(C)C)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)propyl)carbamate | + |
| 21 | 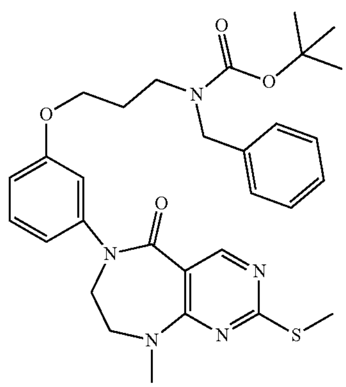 [SMILES: CSc1ncc2c(n1)N(C)CCN(c1cccc(OCCCN(Cc3ccccc3)C(=O)OC(C)(C)C)c1)C2=O] | tert-butyl benzyl(3-(3-(9-methyl-2-(methylthio)-5-oxo-5,7,8,9-tetrahydro-6H-pyrimido[4,5-e][1,4]diazepin-6-yl)phenoxy)propyl)carbamate | + |
| 22 | 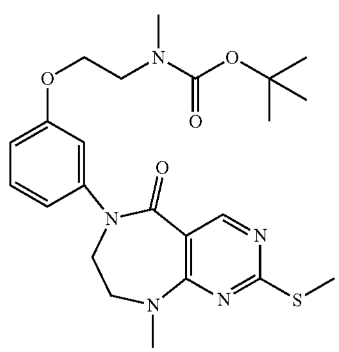 [SMILES: CSc1ncc2c(n1)N(C)CCN(c1cccc(OCCN(C)C(=O)OC(C)(C)C)c1)C2=O] | tert-butyl methyl(2-(3-(9-methyl-2-(methylthio)-5-oxo-5,7,8,9-tetrahydro-6H-pyrimido[4,5-e][1,4]diazepin-6-yl)phenoxy)ethyl)carbamate | + |
| 23 | 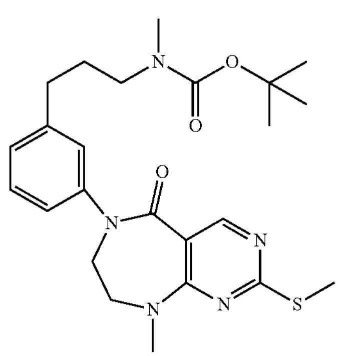 [SMILES: CSc1ncc2c(n1)N(C)CCN(c1cccc(CCCN(C)C(=O)OC(C)(C)C)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenyl)propyl)carbamate | + |

TABLE 1-continued

| Ex | Structure | Name | Ki (nM) α2δ-1 |
|---|---|---|---|
| 24 | 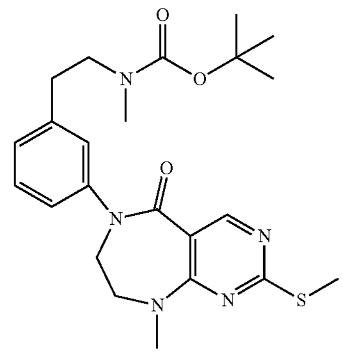 [SMILES: CSc1ncc2c(n1)N(C)CCN(c1cccc(CCN(C)C(=O)OC(C)(C)C)c1)C2=O] | tert-butyl methyl(3-(9-methyl-2-(methylthio)-5-oxo-5,7,8,9-tetrahydro-6H-pyrimido[4,5-e][1,4]diazepin-6-yl)phenethyl)carbamate | + |
| 25 | 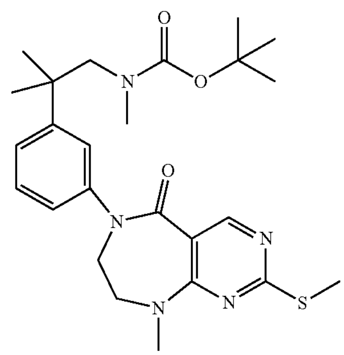 [SMILES: CSc1ncc2c(n1)N(C)CCN(c1cccc(C(C)(C)CN(C)C(=O)OC(C)(C)C)c1)C2=O] | tert-butyl methyl(2-methyl-2-(3-(9-methyl-2-(methylthio)-5-oxo-5,7,8,9-tetrahydro-6H-pyrimido[4,5-e][1,4]diazepin-6-yl)phenyl)propyl)carbamate | + |
| 26 | 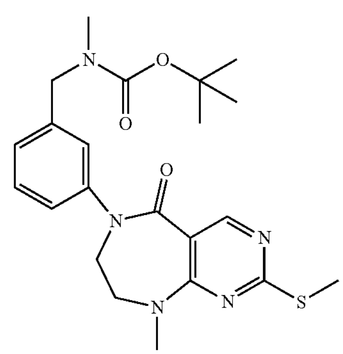 [SMILES: CSc1ncc2c(n1)N(C)CCN(c1cccc(CN(C)C(=O)OC(C)(C)C)c1)C2=O] | tert-butyl methyl(3-(9-methyl-2-(methylthio)-5-oxo-5,7,8,9-tetrahydro-6H-pyrimido[4,5-e][1,4]diazepin-6-yl)benzyl)carbamate | + |
| 27 | 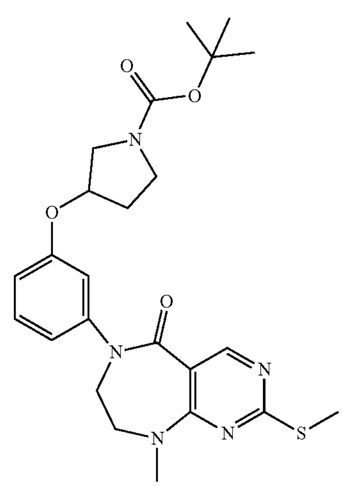 [SMILES: CSc1ncc2c(n1)N(C)CCN(c1cccc(OC3CCN(C(=O)OC(C)(C)C)C3)c1)C2=O] | tert-butyl 3-(3-(9-methyl-2-(methylthio)-5-oxo-5,7,8,9-tetrahydro-6H-pyrimido[4,5-e][1,4]diazepin-6-yl)phenoxy)pyrrolidine-1-carboxylate | + |

TABLE 1-continued

| Ex | Structure | Name | Ki (nM) α2δ-1 |
|---|---|---|---|
| 28 | 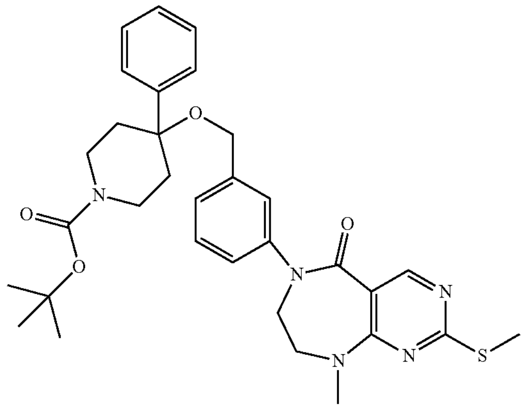 [SMILES: CSc1ncc2c(n1)N(C)CCN(c1cccc(COC3(c4ccccc4)CCN(C(=O)OC(C)(C)C)CC3)c1)C2=O] | tert-butyl 4-((3-(9-methyl-2-(methylthio)-5-oxo-5,7,8,9-tetrahydro-6H-pyrimido[4,5-e][1,4]diazepin-6-yl)benzyl)oxy)-4-phenylpiperidine-1-carboxylate | + |
| 29 | 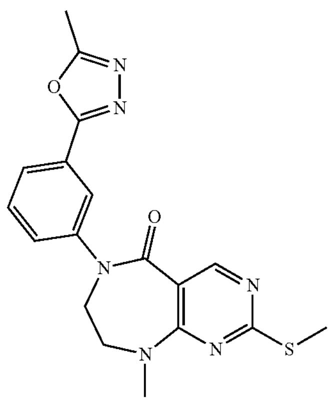 [SMILES: CSc1ncc2c(n1)N(C)CCN(c1cccc(-c3nnc(C)o3)c1)C2=O] | 9-methyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one | + |
| 30 | 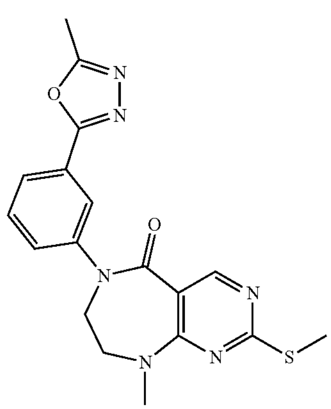 [SMILES: CSc1ncc2c(n1)N(C)CCN(c1cccc(-c3nnc(C)o3)c1)C2=O] | 9-ethyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 31 | 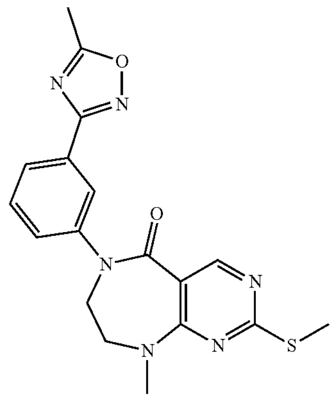 [SMILES: CSc1ncc2c(n1)N(C)CCN(c1cccc(-c3noc(C)n3)c1)C2=O] | 9-methyl-6-(3-(5-methyl-1,2,4-oxadiazol-3-yl)phenyl)-2-(methylthio)-6,7,8,9-tetrahydro-5H-pyrimido[4,5-e][1,4]diazepin-5-one | + |
| 32 | 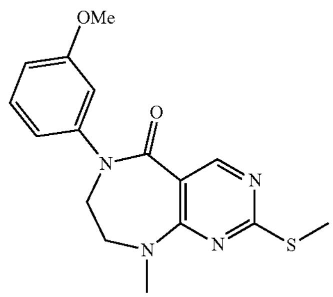 [SMILES: COc1cccc(N2CCN(C)c3nc(SC)ncc3C2=O)c1] | 6-(3-methoxyphenyl)-9-methyl-2-(methylthio)-6,7,8,9-tetrahydro-5H-pyrimido[4,5-e][1,4]diazepin-5-one | + |
| 33 | 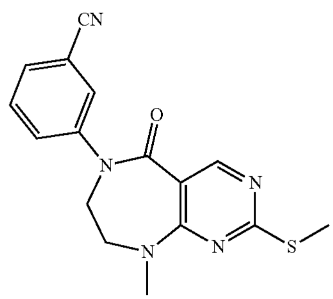 [SMILES: CSc1ncc2c(n1)N(C)CCN(c1cccc(C#N)c1)C2=O] | 3-(9-methyl-2-(methylthio)-5-oxo-5,7,8,9-tetrahydro-6H-pyrimido[4,5-e][1,4]diazepin-6-yl)benzonitrile | + |
| 34 | 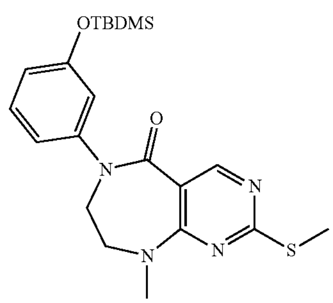 [SMILES: CSc1ncc2c(n1)N(C)CCN(c1cccc(O[Si](C)(C)C(C)(C)C)c1)C2=O] | 6-(3-((tert-butyldimethylsilyl)oxy)phenyl)-9-methyl-2-(methylthio)-6,7,8,9-tetrahydro-5H-pyrimido[4,5-e][1,4]diazepin-5-one | + |
| 35 | 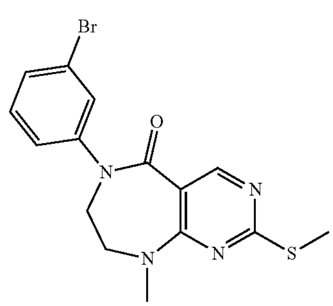 [SMILES: CSc1ncc2c(n1)N(C)CCN(c1cccc(Br)c1)C2=O] | 6-(3-bromophenyl)-9-methyl-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 36 | 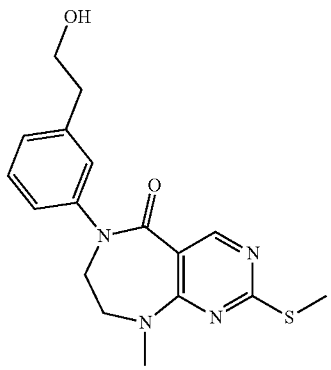 [SMILES: CSc1ncc2c(n1)N(C)CCN(c1cccc(CCO)c1)C2=O] | 6-(3-(2-hydroxyethyl)phenyl)-9-methyl-2-(methylthio)-6,7,8,9-tetrahydro-5H-pyrimido[4,5-e][1,4]diazepin-5-one | + |
| 37 | 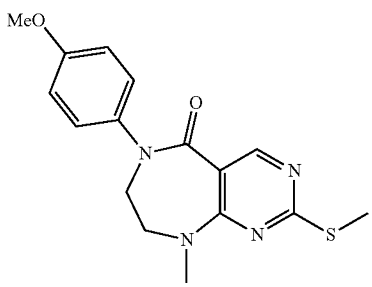 [SMILES: COc1ccc(N2CCN(C)c3nc(SC)ncc3C2=O)cc1] | 6-(4-methoxyphenyl)-9-methyl-2-(methylthio)-6,7,8,9-tetrahydro-5H-pyrimido[4,5-e][1,4]diazepin-5-one | + |
| 38 | 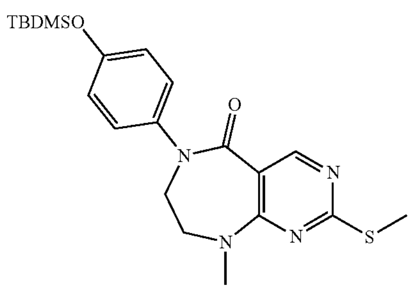 [SMILES: CSc1ncc2c(n1)N(C)CCN(c1ccc(O[Si](C)(C)C(C)(C)C)cc1)C2=O] | 6-(4-((tert-butyldimethylsilyl)oxy)phenyl)-9-methyl-2-(methylthio)-6,7,8,9-tetrahydro-5H-pyrimido[4,5-e][1,4]diazepin-5-one | + |
| 39 | 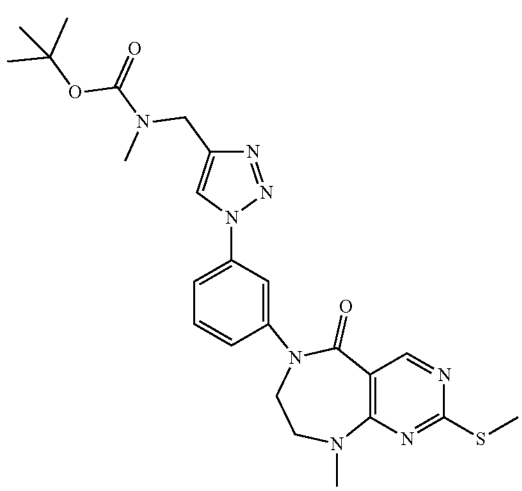 [SMILES: CSc1ncc2c(n1)N(C)CCN(c1cccc(-n3cc(CN(C)C(=O)OC(C)(C)C)nn3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate | + |

TABLE 1-continued

| Ex | Structure | Name | Ki (nM) α2δ-1 |
|---|---|---|---|
| 40 | 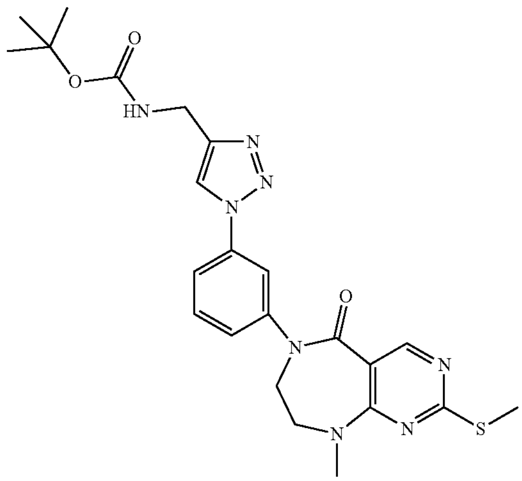 [SMILES: CSc1ncc2c(n1)N(C)CCN(c1cccc(-n3cc(CNC(=O)OC(C)(C)C)nn3)c1)C2=O] | tert-butyl ((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate | + |
| 41 | 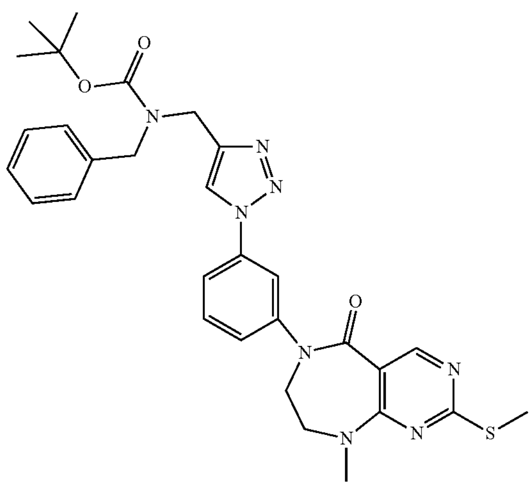 [SMILES: CSc1ncc2c(n1)N(C)CCN(c1cccc(-n3cc(CN(Cc4ccccc4)C(=O)OC(C)(C)C)nn3)c1)C2=O] | tert-butyl benzyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate | + |
| 42 | 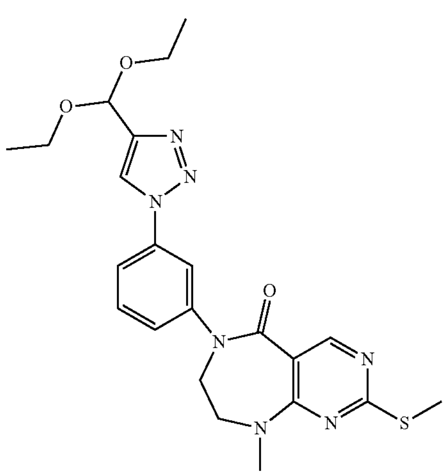 [SMILES: CCOC(OCC)c1cn(-c2cccc(N3CCN(C)c4nc(SC)ncc4C3=O)c2)nn1] | 6-(3-(4-(diethoxymethyl)-1H-1,2,3-triazol-1-yl)phenyl)-9-methyl-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 43 | 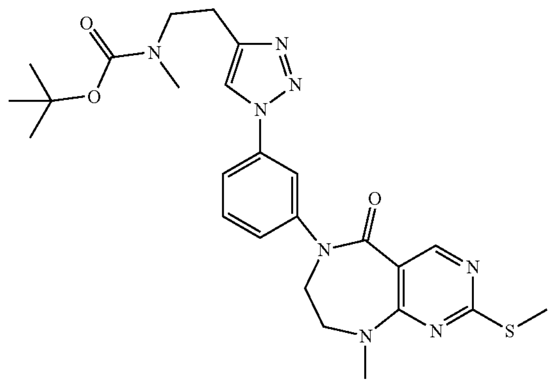 [SMILES: CSc1ncc2c(n1)N(C)CCN(c1cccc(-n3cc(CCN(C)C(=O)OC(C)(C)C)nn3)c1)C2=O] | tert-butyl methyl(2-(1-(3-(9-methyl-2-(methylthio)-5-oxo-5,7,8,9-tetahydro-6H-pyrimido[4,5-e][1,4]diazepin-6-yl)phenyl)-1H-1,2,3-triazol-4-yl)ethyl)carbamate | + |
| 44 | 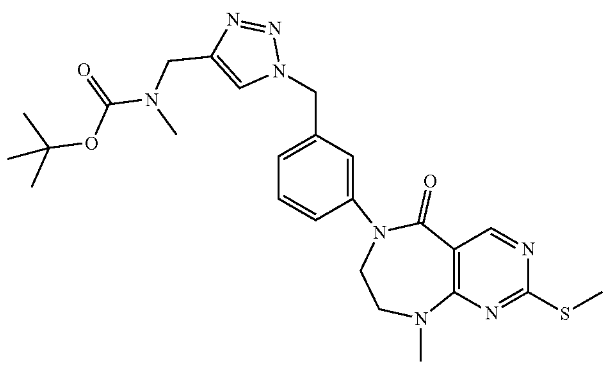 [SMILES: CSc1ncc2c(n1)N(C)CCN(c1cccc(Cn3cc(CN(C)C(=O)OC(C)(C)C)nn3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)benzyl)-1H-1,2,3-triazol-4-yl)methyl)carbamate | + |
| 45 | 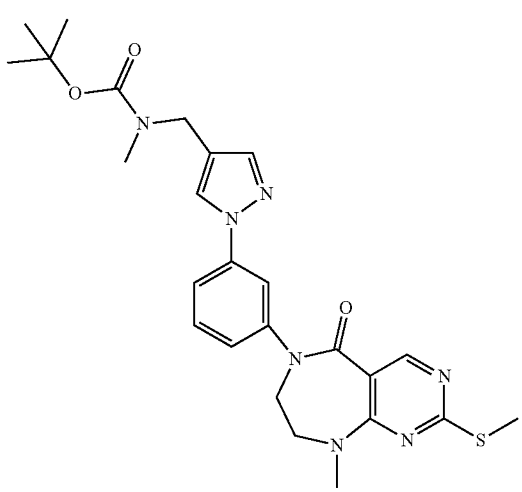 [SMILES: CSc1ncc2c(n1)N(C)CCN(c1cccc(-n3cc(CN(C)C(=O)OC(C)(C)C)cn3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-pyrazol-4-yl)methyl)carbamate | + |

TABLE 1-continued

| Ex | Structure | Name | Ki (nM) α2δ-1 |
|---|---|---|---|
| 46 | 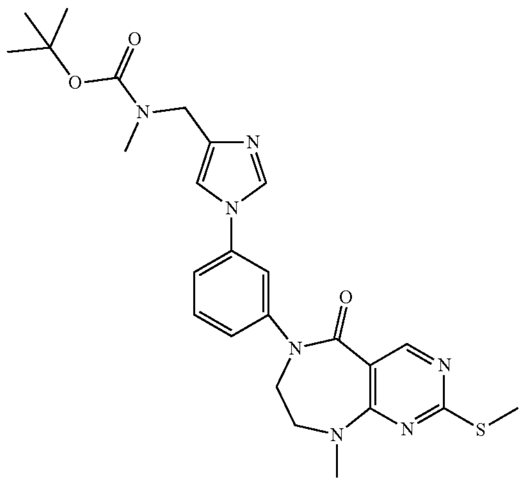 [SMILES: CSc1ncc2c(n1)N(C)CCN(c1cccc(-n3cnc(CN(C)C(=O)OC(C)(C)C)c3)c1)C2=O] | tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-imidazol-4-yl)methyl)carbamate | + |
| 47 | 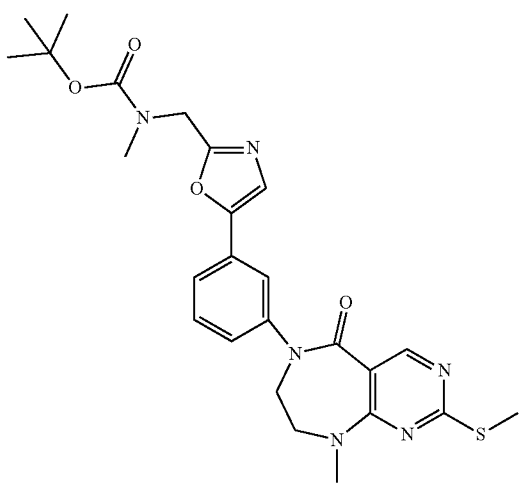 [SMILES: CSc1ncc2c(n1)N(C)CCN(c1cccc(-c3cnc(CN(C)C(=O)OC(C)(C)C)o3)c1)C2=O] | tert-butyl methyl((5-(3-(9-methyl-2-(methylthio)-5-oxo-5,7,8,9-tetrahydro-6H-pyrimido[4,5-e][1,4]diazepin-6-yl)phenyl)-1,3,4-oxadiazol-2-yl)methyl)carbamate | + |
| 48 | 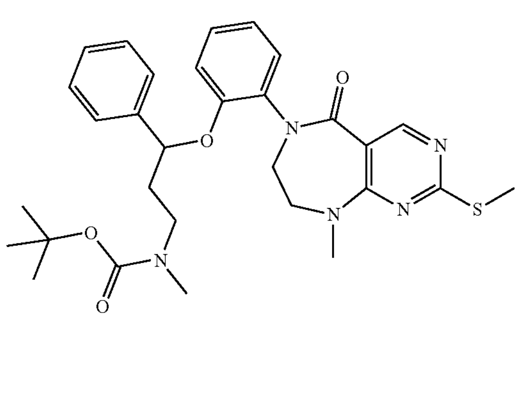 [SMILES: CSc1ncc2c(n1)N(C)CCN(c1ccccc1OC(CCN(C)C(=O)OC(C)(C)C)c1ccccc1)C2=O] | tert-butyl methyl(3-(2-(9-methyl-2-(methylthio)-5-oxo-5,7,8,9-tetrahydro-6H-pyrimido[4,5-e][1,4]diazepin-6-yl)phenoxy)-3-phenylpropyl)carbamate | + |

TABLE 1-continued

| Ex | Structure | Name | Ki (nM) α2δ-1 |
|---|---|---|---|
| 49 | 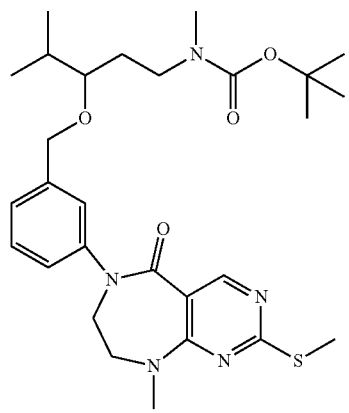 [SMILES: CSc1ncc2c(n1)N(C)CCN(c1cccc(COC(CCN(C)C(=O)OC(C)(C)C)C(C)C)c1)C2=O] | tert-butyl methyl(4-methyl-3-((3-(9-methyl-2-(methylthio)-5-oxo-5,7,8,9-tetrahydro-6H-pyrimido[4,5-e][1,4]diazepin-6-yl)benzyl)oxy)pentyl)carbamate | + |
| 50 | 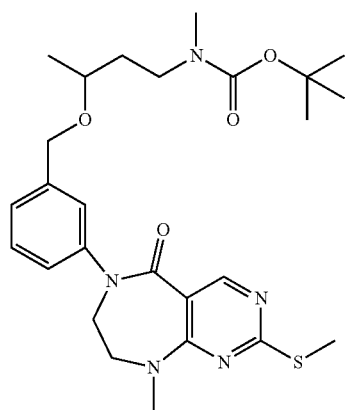 [SMILES: CSc1ncc2c(n1)N(C)CCN(c1cccc(COC(C)CCN(C)C(=O)OC(C)(C)C)c1)C2=O] | tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)butyl)carbamate | + |
| 51 | 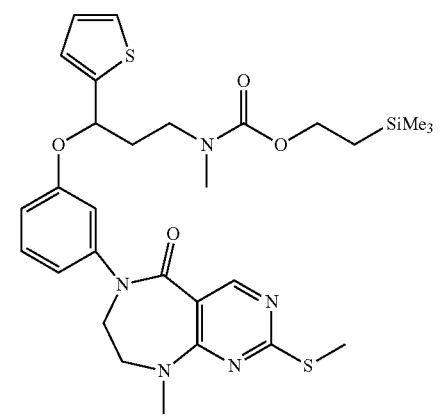 [SMILES: CSc1ncc2c(n1)N(C)CCN(c1cccc(OC(CCN(C)C(=O)OCC[Si](C)(C)C)c3cccs3)c1)C2=O] | 2-(trimethylsilyl)ethyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate | + |

TABLE 1-continued

| Ex | Structure | Name | Ki (nM) α2δ-1 |
|---|---|---|---|
| 52 | 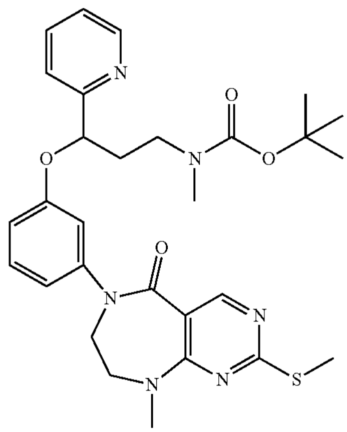 [SMILES: CSc1ncc2c(n1)N(C)CCN(c1cccc(OC(CCN(C)C(=O)OC(C)(C)C)c3ccccn3)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-2-yl)propyl)carbamate | + |
| 53 | 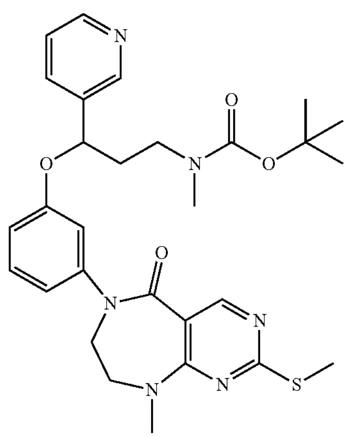 [SMILES: CSc1ncc2c(n1)N(C)CCN(c1cccc(OC(CCN(C)C(=O)OC(C)(C)C)c3cccnc3)c1)C2=O] | tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-3-yl)propyl)carbamate | + |
| 54 | 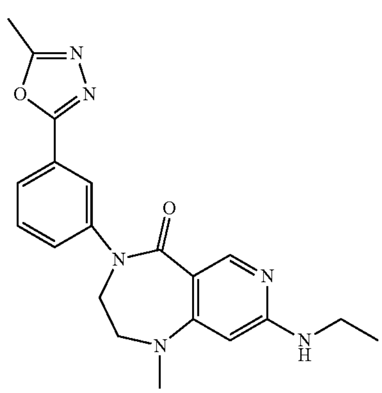 [SMILES: CCNc1cc2c(cn1)C(=O)N(c1cccc(-c3nnc(C)o3)c1)CCN2C] | 8-(ethylamino)-1-methyl-4-(3-(5-methyl-1,3,4-oxadiazol-2-yl)phenyl)-1,2,3,4-tetrahydro-5H-pyrido[4,3-e][1,4]diazepin-5-one | +++ |

TABLE 1-continued

| Ex | Structure | Name | Ki (nM) α2δ-1 |
|---|---|---|---|
| 55 | 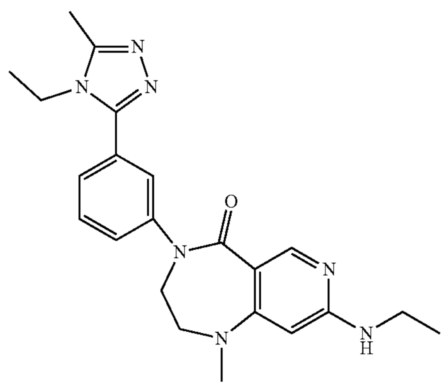 [SMILES: CCNc1cc2c(cn1)C(=O)N(c1cccc(-c3nnc(C)n3CC)c1)CCN2C] | 4-(3-(4-ethyl-5-methyl-4H-1,2,4-triazol-3-yl)phenyl)-8-(ethylamino)-1-methyl-1,2,3,4-tetrahydro-5H-pyrido[4,3-e][1,4]diazepin-5-one | ++ |
| 56 | 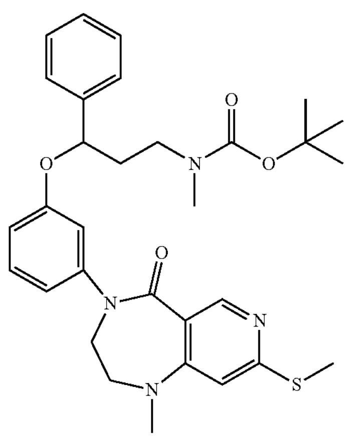 [SMILES: CSc1cc2c(cn1)C(=O)N(c1cccc(OC(CCN(C)C(=O)OC(C)(C)C)c3ccccc3)c1)CCN2C] | tert-butyl (3-(3-(8-(ethylamino)-1-methyl-5-oxo-1,2,3,5-tetrahydro-4H-pyrido[4,3-e][1,4]diazepin-4-yl)phenoxy)-3-phenylpropyl)(methyl)carbamate | + |
| 57 | 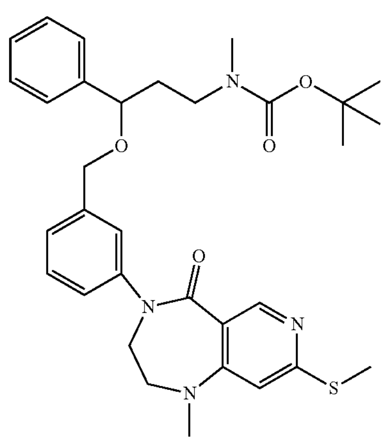 [SMILES: CSc1cc2c(cn1)C(=O)N(c1cccc(COC(CCN(C)C(=O)OC(C)(C)C)c3ccccc3)c1)CCN2C] | tert-butyl (3-((3-(8-(ethylamino)-1-methyl-5-oxo-1,2,3,5-tetrahydro-4H-pyrido[4,3-e][1,4]diazepin-4-yl)benzyl)oxy)-3-phenylpropyl)(methyl)carbamate | + |

TABLE 1-continued

| Ex | Structure | Name | Ki (nM) α2δ-1 |
|---|---|---|---|
| 58 | 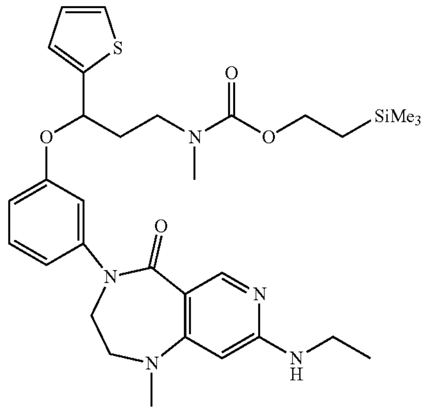 [SMILES: CCNc1cc2c(cn1)C(=O)N(c1cccc(OC(CCN(C)C(=O)OCC[Si](C)(C)C)c3cccs3)c1)CCN2C] | 2-(trimethylsilyl)ethyl (3-(3-(8-(ethylamino)-1-methyl-5-oxo-1,2,3,5-tetrahydro-4H-pyrido[4,3-e][1,4]diazepin-4-yl)phenoxy)-3-(thiophen-2-yl)propyl)(methyl) carbamate | + |
| 59 | 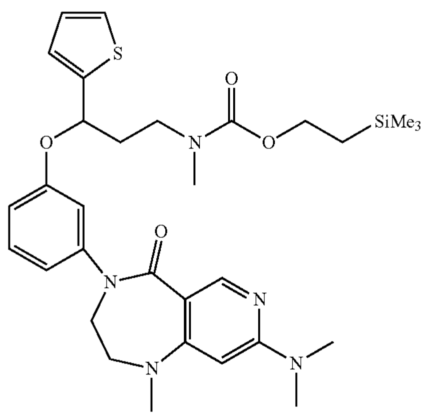 [SMILES: CN(CCC(Oc1cccc(N2CCN(C)c3cc(N(C)C)ncc3C2=O)c1)c1cccs1)C(=O)OCC[Si](C)(C)C] | 2-(trimethylsilyl)ethyl (3-(3-(8-(dimethylamino)-1-methyl-5-oxo-1,2,3,5-tetrahydro-4H-pyrido[4,3-e][1,4]diazepin-4-yl)phenoxy)-3-(thiophen-2-yl)propyl)(methyl) carbamate | + |
| 60 | 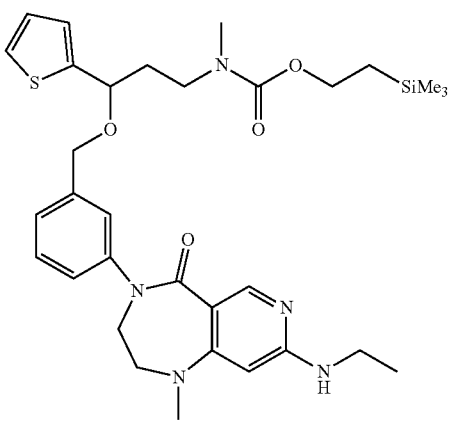 [SMILES: CCNc1cc2c(cn1)C(=O)N(c1cccc(COC(CCN(C)C(=O)OCC[Si](C)(C)C)c3cccs3)c1)CCN2C] | 2-(trimethylsilyl)ethyl (3-((3-(8-(ethylamino)-1-methyl-5-oxo-1,2,3,5-tetrahydro-4H-pyrido[4,3-e][1,4]diazepin-4-yl)benzyl)oxy)-3-(thiophen-2-yl)propyl)(methyl) carbamate | + |

TABLE 1-continued

| Ex | Structure | Name | Ki (nM) α2δ-1 |
|---|---|---|---|
| 61 | 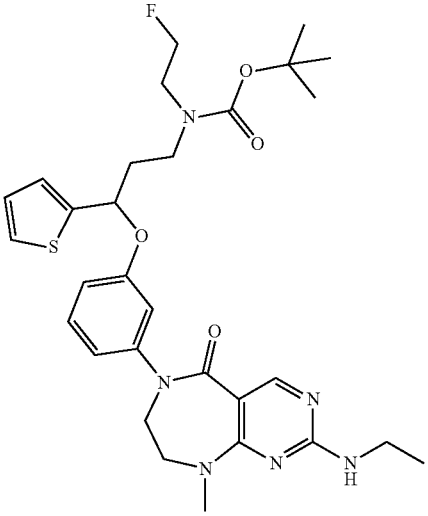 [SMILES: CCNc1ncc2c(n1)N(C)CCN(c1cccc(OC(CCN(CCF)C(=O)OC(C)(C)C)c3cccs3)c1)C2=O] | tert-butyl (2-fluoroethyl)(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate | + |
| 62 | 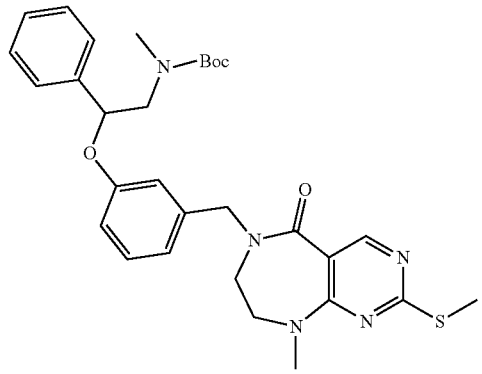 [SMILES: CSc1ncc2c(n1)N(C)CCN(Cc1cccc(OC(CN(C)C(=O)OC(C)(C)C)c3ccccc3)c1)C2=O] | tert-butyl methyl(2-(3-((9-methyl-2-(methylthio)-5-oxo-5,7,8,9-tetahydro-6H-pyrimido[4,5-e][1,4]diazepin-6-yl)methyl)phenoxy)-2-phenylethyl)carbamate | + |
| 63 | 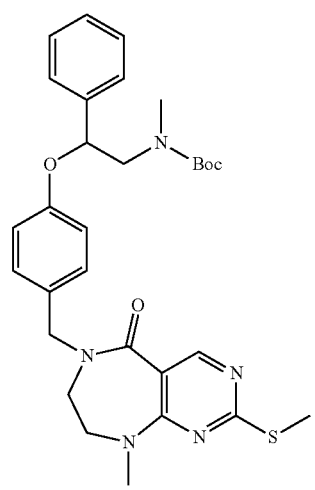 [SMILES: CSc1ncc2c(n1)N(C)CCN(Cc1ccc(OC(CN(C)C(=O)OC(C)(C)C)c3ccccc3)cc1)C2=O] | tert-butyl methyl(2-(4-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate | + |

TABLE 1-continued

| Ex | Structure | Name | Ki (nM) α2δ-1 |
|---|---|---|---|
| 64 | 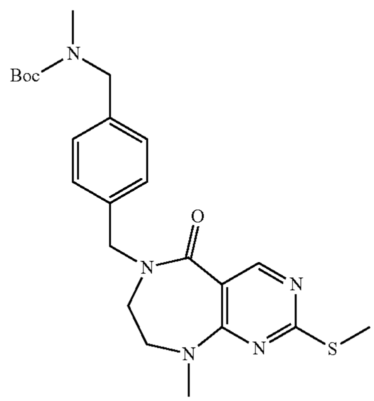 [SMILES: CSc1ncc2c(n1)N(C)CCN(Cc1ccc(CN(C)C(=O)OC(C)(C)C)cc1)C2=O] | tert-butyl methyl(4-((9-methyl-2-(methylthio)-5-oxo-5,7,8,9-tetrahydro-6H-pyrimido[4,5-e][1,4]diazepin-6-yl)methyl)benzyl) carbamate | + |
| 65 | 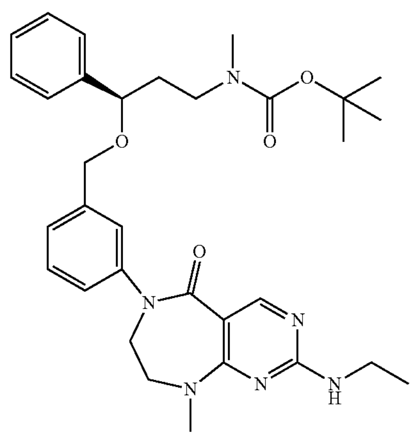 [SMILES: CCNc1ncc2c(n1)N(C)CCN(c1cccc(CO[C@H](CCN(C)C(=O)OC(C)(C)C)c3ccccc3)c1)C2=O] | tert-butyl (R)-(3-((3-(2-(ethylamino)-9-methyl-5,7,8,9-tetrahydro-6H-pyrimido[4,5-e][1,4]diazepin-6-yl)benzyl)oxy)-3-phenylpropyl)(methyl) carbamate | + |
| 66 | 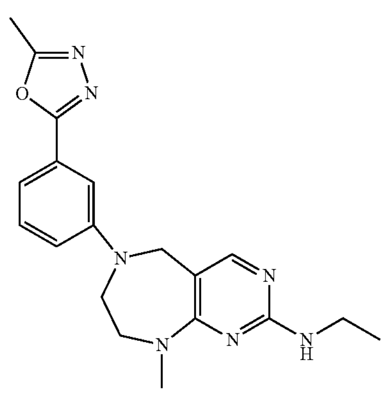 [SMILES: CCNc1ncc2c(n1)N(C)CCN(c1cccc(-c3nnc(C)o3)c1)C2] | N-ethyl-9-methyl-6-(3-(5-methyl-1,3,4-oxadiazol-2-yl)phenyl)-6,7,8,9-tetrahydro-5H-pyrimido[4,5-e][1,4]diazepin-2-amine | ++ |
| 67 | 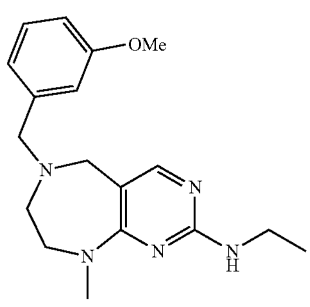 [SMILES: CCNc1ncc2c(n1)N(C)CCN(Cc1cccc(OC)c1)C2] | N-ethyl-6-(3-methoxybenzyl)-9-methyl-6,7,8,9-tetrahydro-5H-pyrimido[4,5-e][1,4]diazepin-2-amine | + |

TABLE 1-continued
| Ex | Structure | Name | Ki (nM) α2δ-1 |
|---|---|---|---|
| 68 | 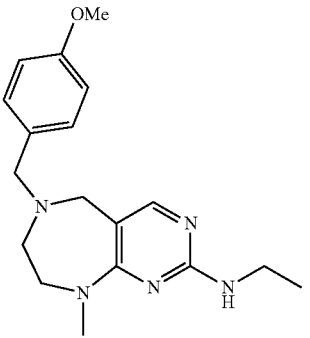 [SMILES: CCNc1ncc2c(n1)N(C)CCN(Cc1ccc(OC)cc1)C2] | N-ethyl-6-(4-methoxybenzyl)-9-methyl-6,7,8,9-tetrahydro-5H-pyrimido[4,5-e][1,4]diazepin-2-amine | + |
| 69 | 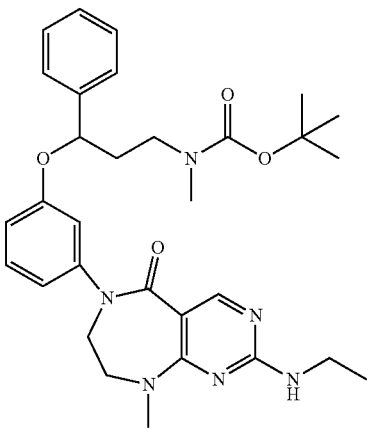 [SMILES: CCNc1ncc2c(n1)N(C)CCN(c1cccc(OC(CCN(C)C(=O)OC(C)(C)C)c3ccccc3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate | + |
| 70 | 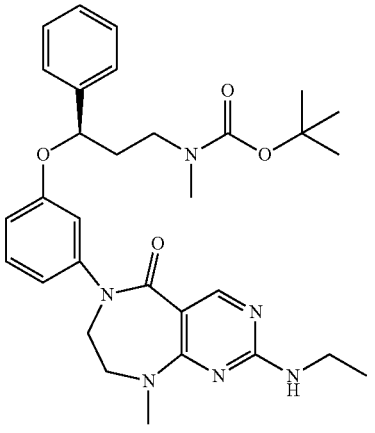 [SMILES: CCNc1ncc2c(n1)N(C)CCN(c1cccc(O[C@H](CCN(C)C(=O)OC(C)(C)C)c3ccccc3)c1)C2=O] | tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate | + |

TABLE 1-continued

| Ex | Structure | Name | Ki (nM) α2δ-1 |
|---|---|---|---|
| 71 | 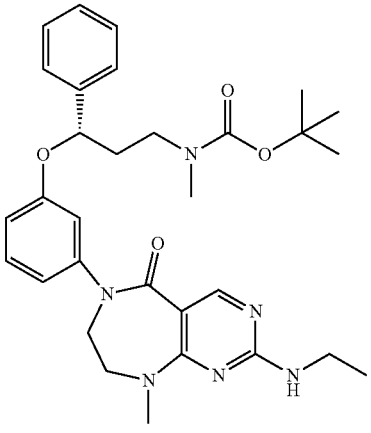 [SMILES: CCNc1ncc2c(n1)N(C)CCN(c1cccc(O[C@@H](CCN(C)C(=O)OC(C)(C)C)c3ccccc3)c1)C2=O] | tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl) carbamate | + |
| 72 | 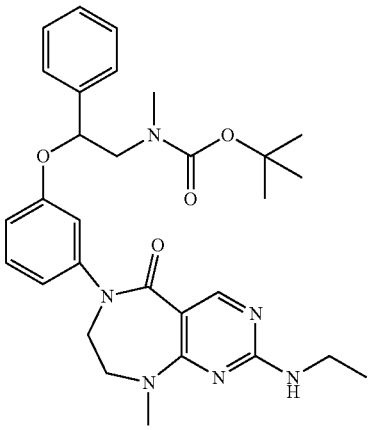 [SMILES: CCNc1ncc2c(n1)N(C)CCN(c1cccc(OC(CN(C)C(=O)OC(C)(C)C)c3ccccc3)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)(methyl) carbamate | + |
| 73 | 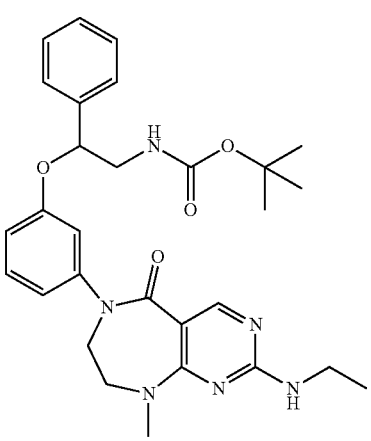 [SMILES: CCNc1ncc2c(n1)N(C)CCN(c1cccc(OC(CNC(=O)OC(C)(C)C)c3ccccc3)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)carbamate | + |

TABLE 1-continued

| Ex | Structure | Name | Ki (nM) α2δ-1 |
|---|---|---|---|
| 74 | 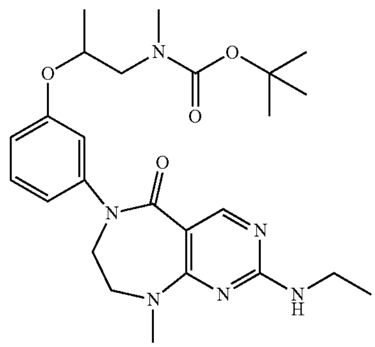 [SMILES: CCNc1ncc2c(n1)N(C)CCN(c1cccc(OC(C)CN(C)C(=O)OC(C)(C)C)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate | + |
| 75 | 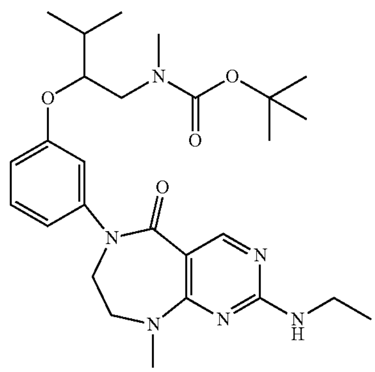 [SMILES: CCNc1ncc2c(n1)N(C)CCN(c1cccc(OC(CN(C)C(=O)OC(C)(C)C)C(C)C)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)-3-methylbutyl)(methyl)carbamate | + |
| 76 | 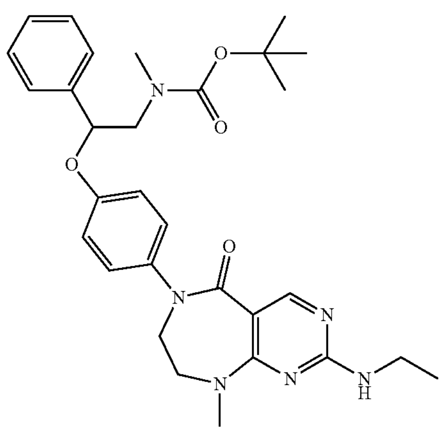 [SMILES: CCNc1ncc2c(n1)N(C)CCN(c1ccc(OC(CN(C)C(=O)OC(C)(C)C)c3ccccc3)cc1)C2=O] | tert-butyl (2-(4-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate | + |
| 77 | 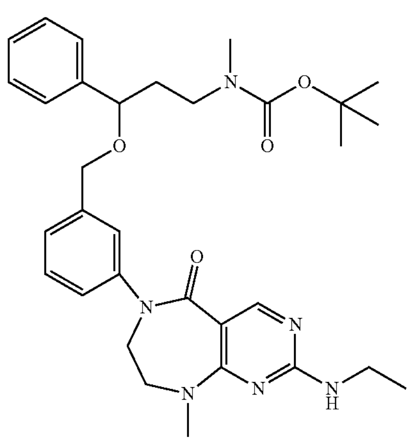 [SMILES: CCNc1ncc2c(n1)N(C)CCN(c1cccc(COC(CCN(C)C(=O)OC(C)(C)C)c3ccccc3)c1)C2=O] | tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate | + |

TABLE 1-continued

| Ex | Structure | Name | Ki (nM) α2δ-1 |
|----|-----------|------|---------------|
| 78 | 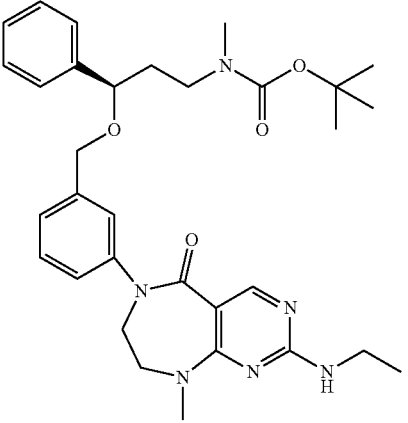 [SMILES: CCNc1ncc2c(n1)N(C)CCN(c1cccc(CO[C@H](CCN(C)C(=O)OC(C)(C)C)c3ccccc3)c1)C2=O] | tert-butyl (R)-3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl) carbamate | + |
| 79 | 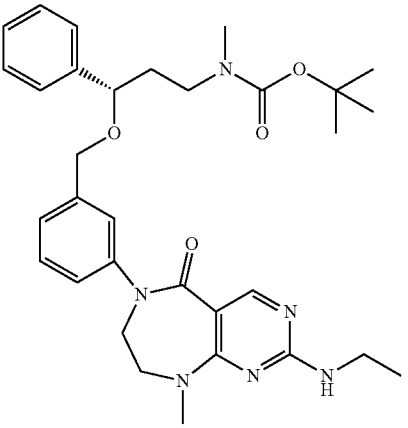 [SMILES: CCNc1ncc2c(n1)N(C)CCN(c1cccc(CO[C@@H](CCN(C)C(=O)OC(C)(C)C)c3ccccc3)c1)C2=O] | tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl) carbamate | + |
| 80 | 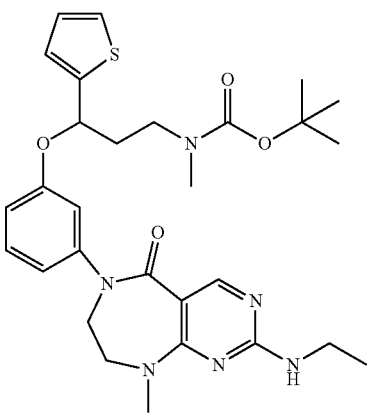 [SMILES: CCNc1ncc2c(n1)N(C)CCN(c1cccc(OC(CCN(C)C(=O)OC(C)(C)C)c3cccs3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl) carbamate | + |

TABLE 1-continued

| Ex | Structure | Name | Ki (nM) α2δ-1 |
|---|---|---|---|
| 81 | 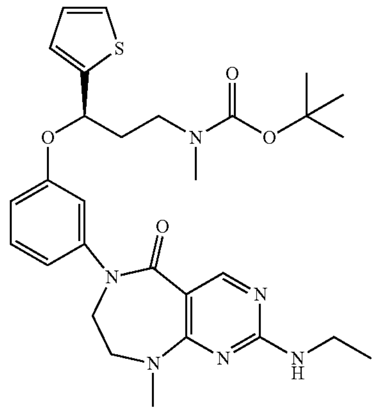 [SMILES: CCNc1ncc2c(n1)N(C)CCN(c1cccc(O[C@H](CCN(C)C(=O)OC(C)(C)C)c3cccs3)c1)C2=O] | tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl) carbamate | + |
| 82 | 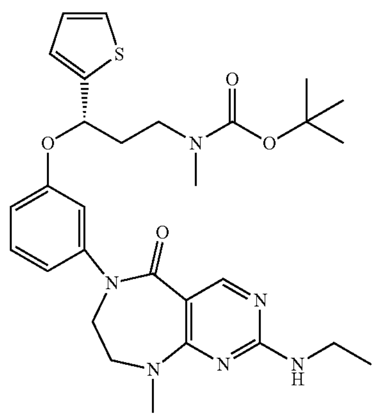 [SMILES: CCNc1ncc2c(n1)N(C)CCN(c1cccc(O[C@@H](CCN(C)C(=O)OC(C)(C)C)c3cccs3)c1)C2=O] | tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl) carbamate | + |
| 83 | 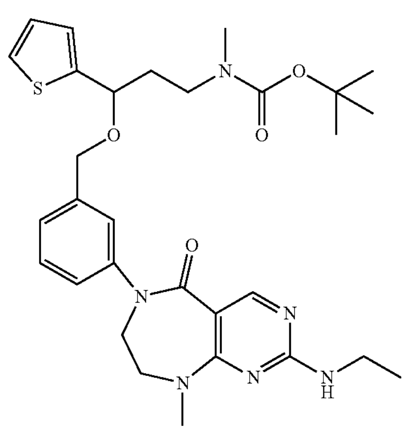 [SMILES: CCNc1ncc2c(n1)N(C)CCN(c1cccc(COC(CCN(C)C(=O)OC(C)(C)C)c3cccs3)c1)C2=O] | tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | + |

TABLE 1-continued

| Ex | Structure | Name | Ki (nM) α2δ-1 |
|---|---|---|---|
| 84 | 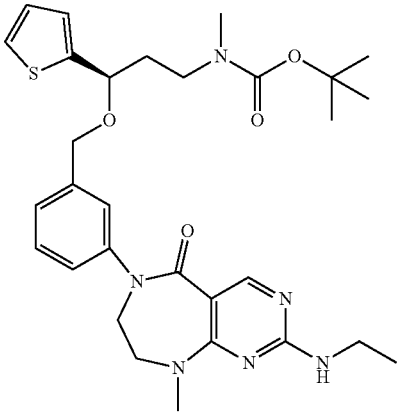 [SMILES: CCNc1ncc2c(n1)N(C)CCN(c1cccc(CO[C@H](CCN(C)C(=O)OC(C)(C)C)c3cccs3)c1)C2=O] | tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | + |
| 85 | 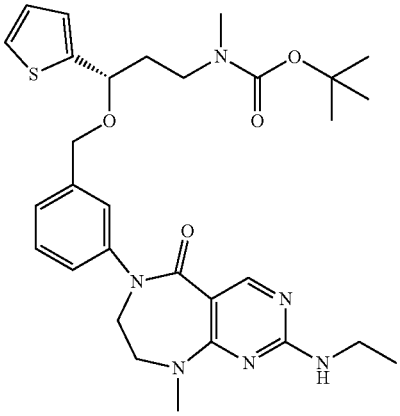 [SMILES: CCNc1ncc2c(n1)N(C)CCN(c1cccc(CO[C@@H](CCN(C)C(=O)OC(C)(C)C)c3cccs3)c1)C2=O] | tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl) carbamate | + |
| 86 | 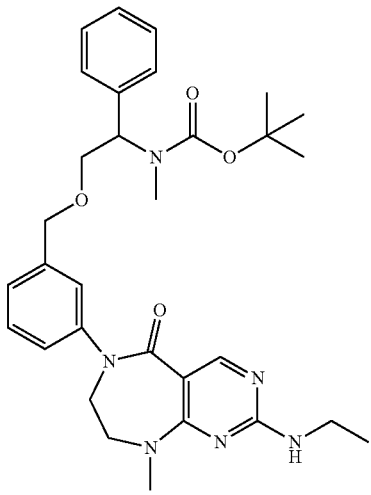 [SMILES: CCNc1ncc2c(n1)N(C)CCN(c1cccc(COCC(c3ccccc3)N(C)C(=O)OC(C)(C)C)c1)C2=O] | tert-butyl (2-((3-(2-(ethyamino)-9-methyl-5-oxo-5,7,8,9-tetrahydro-6H-pyrimido[4,5-e][1,4]diazepin-6-yl)benzyl)oxy)-1-phenylethyl)(methyl) carbamate | + |

TABLE 1-continued

| Ex | Structure | Name | Ki (nM) α2δ-1 |
|---|---|---|---|
| 87 | 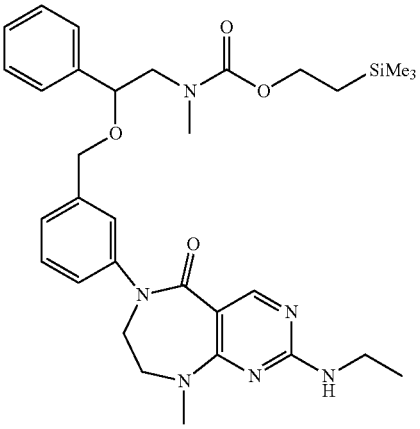 [SMILES: CCNc1ncc2c(n1)N(C)CCN(c1cccc(COC(CN(C)C(=O)OCC[Si](C)(C)C)c3ccccc3)c1)C2=O] | 2-(trimethylsilyl)ethyl (2-((3-(2-(ethylamino)-9-methyl-5-oxo-5,7,8,9-tetrahydro-6H-pyrimido[4,5-e][1,4]diazepin-6-yl)benzyl)oxy)-2-phenylethyl)(methyl)carbamate | + |
| 88 | 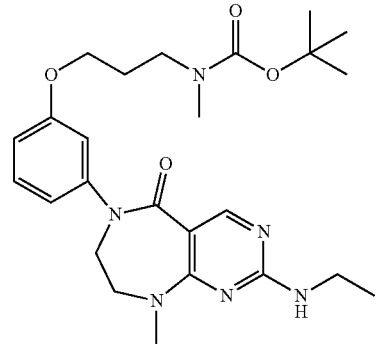 [SMILES: CCNc1ncc2c(n1)N(C)CCN(c1cccc(OCCCN(C)C(=O)OC(C)(C)C)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate | + |
| 89 | 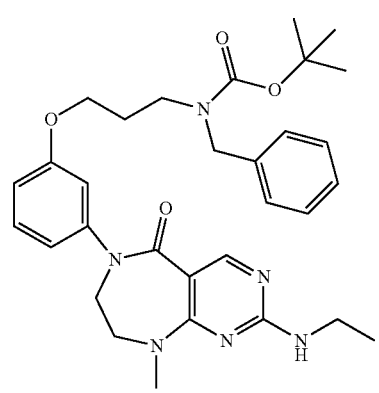 [SMILES: CCNc1ncc2c(n1)N(C)CCN(c1cccc(OCCCN(Cc3ccccc3)C(=O)OC(C)(C)C)c1)C2=O] | tert-butyl benzyl(3-(3-(2-(ethylamino)-9-methyl-5-oxo-5,7,8,9-tetrahydro-6H-pyrimido[4,5-e][1,4]diazepin-6-yl)phenoxy)propyl)carbamate | + |
| 90 | 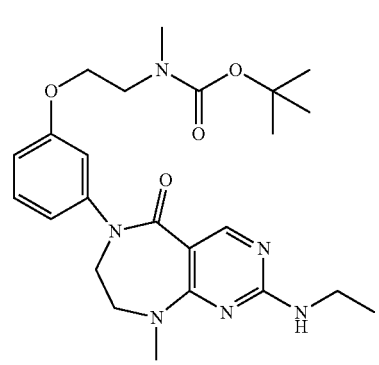 [SMILES: CCNc1ncc2c(n1)N(C)CCN(c1cccc(OCCN(C)C(=O)OC(C)(C)C)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenoxy)ethyl)(methyl)carbamate | + |

TABLE 1-continued

| Ex | Structure | Name | Ki (nM) α2δ-1 |
|---|---|---|---|
| 91 | 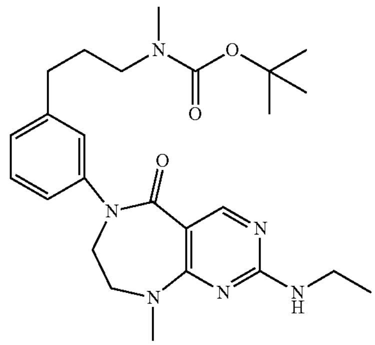 [SMILES: CCNc1ncc2c(n1)N(C)CCN(c1cccc(CCCN(C)C(=O)OC(C)(C)C)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenyl)propyl)(methyl)carbamate | + |
| 92 | 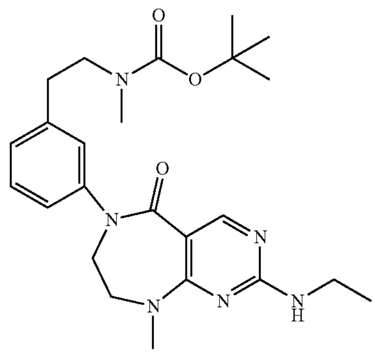 [SMILES: CCNc1ncc2c(n1)N(C)CCN(c1cccc(CCN(C)C(=O)OC(C)(C)C)c1)C2=O] | tert-butyl (3-(2-(ethylamino)-9-methyl-5-oxo-5,7,8,9-tetrahydro-6H-pyrimido[4,5-e][1,4]diazepin-6-yl)phenethyl)(methyl)carbamate | + |
| 93 | 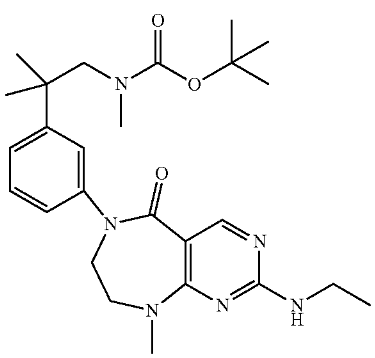 [SMILES: CCNc1ncc2c(n1)N(C)CCN(c1cccc(C(C)(C)CN(C)C(=O)OC(C)(C)C)c1)C2=O] | tert-butyl (2-(3-(2-(ethylamino)-9-methyl-5-oxo-5,7,8,9-tetrahydro-6H-pyrimido[4,5-e][1,4]diazepin-6-yl)phenyl)-2-methylpropyl)(methyl)carbamate | + |
| 94 | 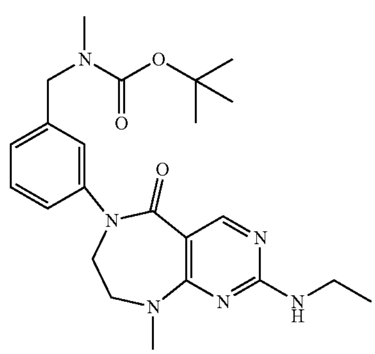 [SMILES: CCNc1ncc2c(n1)N(C)CCN(c1cccc(CN(C)C(=O)OC(C)(C)C)c1)C2=O] | tert-butyl (3-(2-(ethylamino)-9-methyl-5-oxo-5,7,8,9-tetrahydro-6H-pyrimido[4,5-e][1,4]diazepin-6-yl)benzyl)(methyl)carbamate | + |

TABLE 1-continued

| Ex | Structure | Name | Ki (nM) α2δ-1 |
|---|---|---|---|
| 95 | 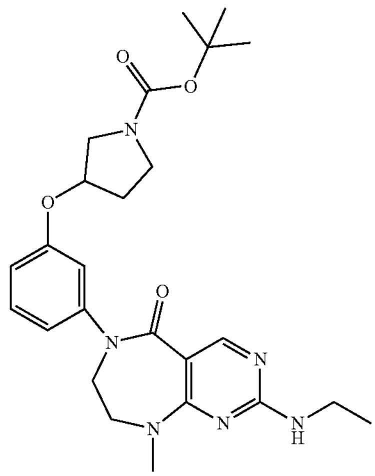 [SMILES: CCNc1ncc2c(n1)N(C)CCN(c1cccc(OC3CCN(C(=O)OC(C)(C)C)C3)c1)C2=O] | tert-butyl 3-(3-(2-(ethylamino)-9-methyl-5-oxo-5,7,8,9-tetrahydro-6H-pyrimido[4,5-e][1,4]diazepin-6-yl)phenoxy)pyrrolidine-1-carboxylate | + |
| 96 | 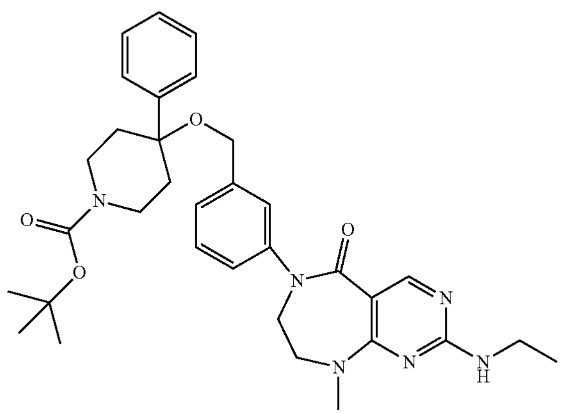 [SMILES: CCNc1ncc2c(n1)N(C)CCN(c1cccc(COC3(c4ccccc4)CCN(C(=O)OC(C)(C)C)CC3)c1)C2=O] | tert-butyl 4-((3-(2-(ethylamino)-9-methyl-5-oxo-5,7,8,9-tetrahydro-6H-pyrimido[4,5-e][1,4]diazepin-6-yl)benzyl)oxy)-4-phenylpiperidine-1-carboxylate | + |
| 97 | 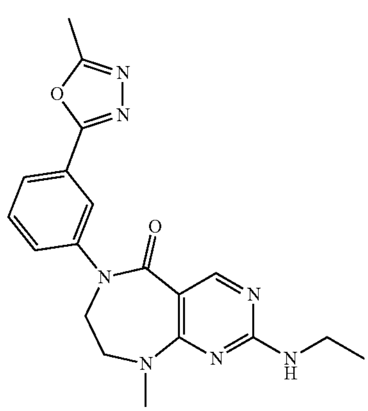 [SMILES: CCNc1ncc2c(n1)N(C)CCN(c1cccc(-c3nnc(C)o3)c1)C2=O] | 2-(ethylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | ++++ |

TABLE 1-continued

| Ex | Structure | Name | Ki (nM) α2δ-1 |
|---|---|---|---|
| 98 | 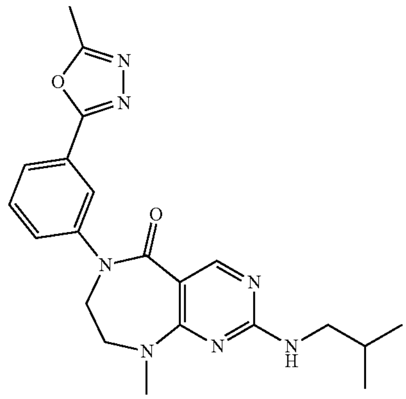 [SMILES: Cc1nnc(-c2cccc(N3CCN(C)c4nc(NCC(C)C)ncc4C3=O)c2)o1] | 2-(isobutylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | + |
| 99 | 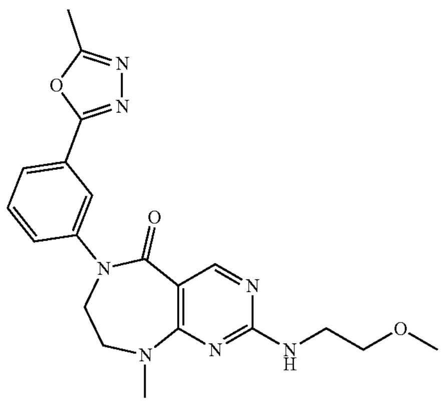 [SMILES: COCCNc1ncc2c(n1)N(C)CCN(c1cccc(-c3nnc(C)o3)c1)C2=O] | 2-((2-methoxyethyl)amino)-9-methyl-6-(3-(5-methyl-1,3,4-oxadiazol-2-yl)phenyl)-6,7,8,9-tetrahydro-5H-pyrimido[4,5-e][1,4]diazepin-5-one | + |
| 100 | 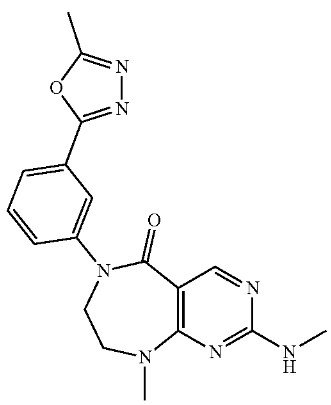 [SMILES: CNc1ncc2c(n1)N(C)CCN(c1cccc(-c3nnc(C)o3)c1)C2=O] | 9-methyl-6-(3-(5-methyl-1,3,4-oxadiazol-2-yl)phenyl)-2-(methylamino)-6,7,8,9-tetrahydro-5H-pyrimido[4,5-e][1,4]diazepin-5-one | +++ |
| 101 | 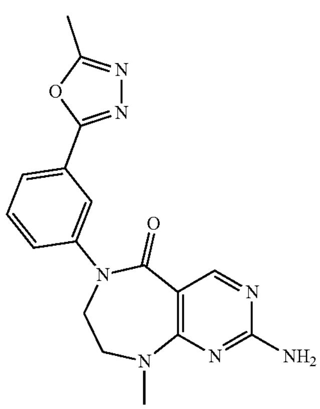 [SMILES: Cc1nnc(-c2cccc(N3CCN(C)c4nc(N)ncc4C3=O)c2)o1] | 2-amino-9-methyl-6-(3-(5-methyl-1,3,4-oxadiazol-2-yl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 102 | 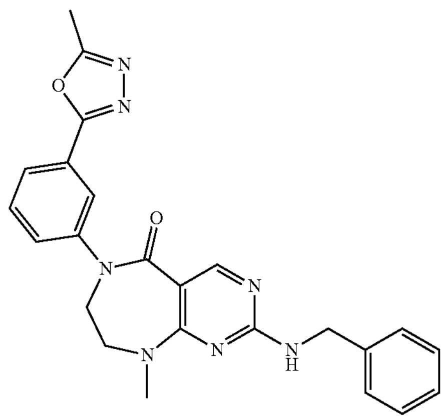 [SMILES: Cc1nnc(-c2cccc(N3CCN(C)c4nc(NCc5ccccc5)ncc4C3=O)c2)o1] | 2-(benzylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | + |
| 103 | 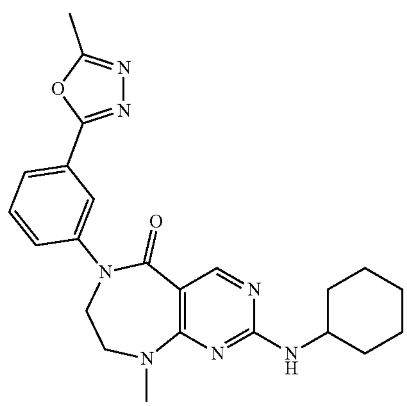 [SMILES: Cc1nnc(-c2cccc(N3CCN(C)c4nc(NC5CCCCC5)ncc4C3=O)c2)o1] | 2-(cyclohexylamino)-9-methyl-6-(3-(5-methyl-1,3,4-oxadiazol-2-yl)phenyl)-6,7,8,9-tetrahydro-5H-pyrimido[4,5-e][1,4]diazepin-5-one | + |
| 104 | 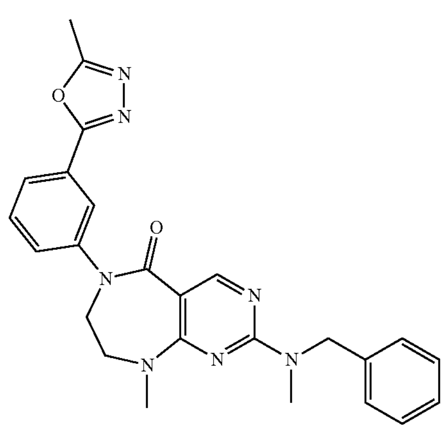 [SMILES: Cc1nnc(-c2cccc(N3CCN(C)c4nc(N(C)Cc5ccccc5)ncc4C3=O)c2)o1] | 2-(benzyl(methyl)amino)-9-methyl-6-(3-(5-methyl-1,3,4-oxadiazol-2-yl)phenyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 105 | 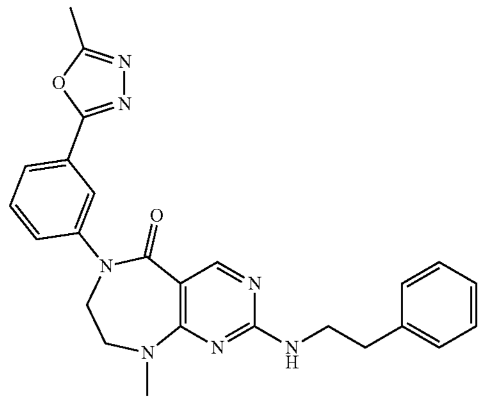 [SMILES: Cc1nnc(-c2cccc(N3CCN(C)c4nc(NCCc5ccccc5)ncc4C3=O)c2)o1] | 9-methyl-6-(3-(5-methyl-1,3,4-oxadiazol-2-yl)phenyl)-2-(phenethylamino)-6,7,8,9-tetrahydro-5H-pyrimido[4,5-e][1,4]diazepin-5-one | + |
| 106 | 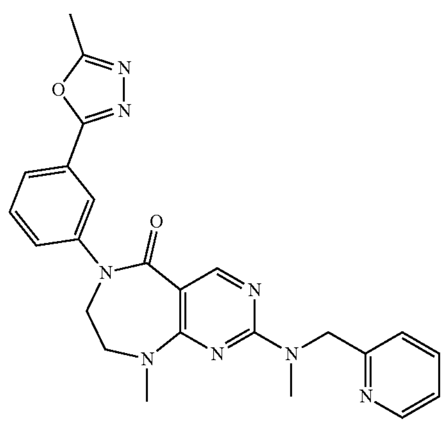 [SMILES: Cc1nnc(-c2cccc(N3CCN(C)c4nc(N(C)Cc5ccccn5)ncc4C3=O)c2)o1] | 9-methyl-2-(methyl(pyridin-2-ylmethyl)amino)-6-(3-(5-methyl-1,3,4-oxadiazol-2-yl)phenyl)-6,7,8,9-tetrahydro-5H-pyrimido[4,5-e][1,4]diazepin-5-one | + |
| 107 | 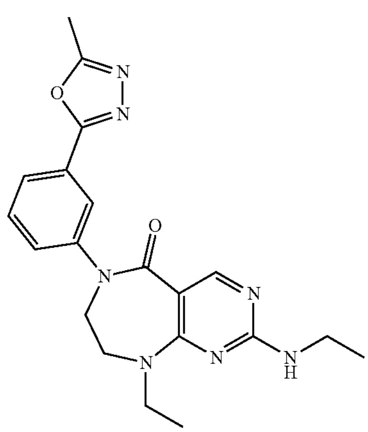 [SMILES: CCNc1ncc2c(n1)N(CC)CCN(c1cccc(-c3nnc(C)o3)c1)C2=O] | 9-ethyl-2-(ethylamino)-6-(3-(5-methyl-1,3,4-oxadiazol-2-yl)phenyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 108 | 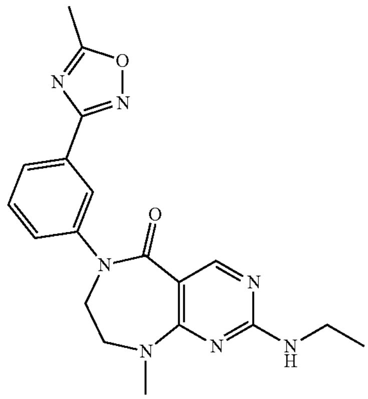 [SMILES: CCNc1ncc2c(n1)N(C)CCN(c1cccc(-c3noc(C)n3)c1)C2=O] | 2-(ethylamino)-9-methyl-6-(3-(5-methyl-1,2,4-oxadiazol-3-yl)phenyl)-6,7,8,9-tetrahydro-5H-pyrimido[4,5-e][1,4]diazepin-5-one | +++ |
| 109 | 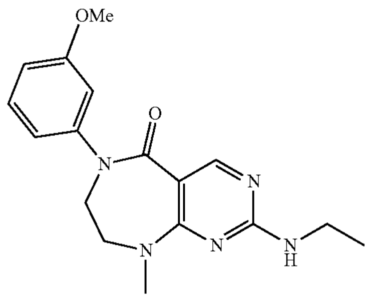 [SMILES: CCNc1ncc2c(n1)N(C)CCN(c1cccc(OC)c1)C2=O] | 2-(ethylamino)-6-(3-methoxyphenyl)-9-methyl-6,7,8,9-tetrahydro-5H-pyrimido[4,5-e][1,4]diazepin-5-one | ++ |
| 110 | 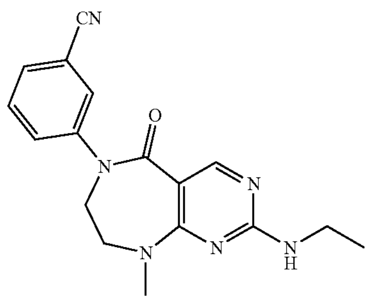 [SMILES: CCNc1ncc2c(n1)N(C)CCN(c1cccc(C#N)c1)C2=O] | 3-(2-(ethylamino)-9-methyl-5-oxo-5,7,8,9-tetrahydro-6H-pyrimido[4,5-e][1,4]diazepin-6-yl)benzonitrile | + |
| 111 | 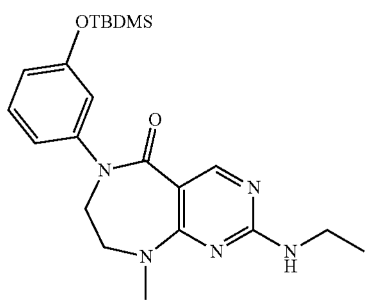 [SMILES: CCNc1ncc2c(n1)N(C)CCN(c1cccc(O[Si](C)(C)C(C)(C)C)c1)C2=O] | 6-(3-((tert-butyldimethylsilyl)oxy)phenyl)-2-(ethylamino)-9-methyl-6,7,8,9-tetrahydro-5H-pyrimido[4,5-e][1,4]diazepin-5-one | + |
| 112 | 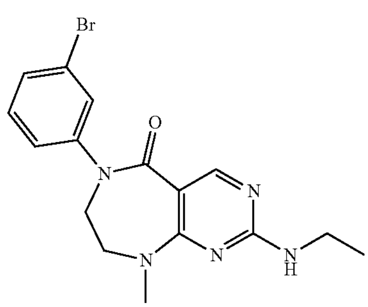 [SMILES: CCNc1ncc2c(n1)N(C)CCN(c1cccc(Br)c1)C2=O] | 6-(3-bromophenyl)-2-(ethylamino)-9-methyl-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 113 | 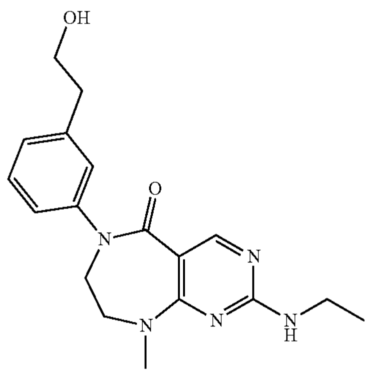 [SMILES: CCNc1ncc2c(n1)N(C)CCN(c1cccc(CCO)c1)C2=O] | 2-(ethylamino)-6-(3-(2-hydroxyethyl)phenyl)-9-methyl-6,7,8,9-tetrahydro-5H-pyrimido[4,5-e][1,4]diazepin-5-one | + |
| 114 | 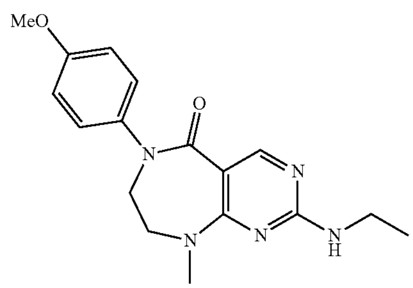 [SMILES: CCNc1ncc2c(n1)N(C)CCN(c1ccc(OC)cc1)C2=O] | 2-(ethylamino)-6-(4-methoxyphenyl)-9-methyl-6,7,8,9-tetrahydro-5H-pyrimido[4,5-e][1,4]diazepin-5-one | + |
| 115 | 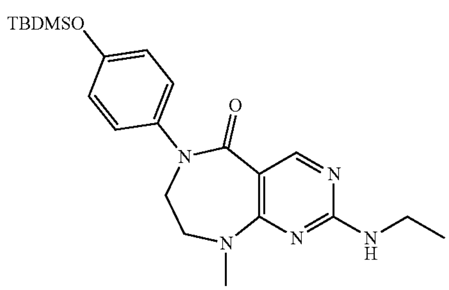 [SMILES: CCNc1ncc2c(n1)N(C)CCN(c1ccc(O[Si](C)(C)C(C)(C)C)cc1)C2=O] | 6-(4-((tert-butyldimethylsilyl)oxy)phenyl)-2-(ethylamino)-9-methyl-6,7,8,9-tetrahydro-5H-pyrimido[4,5-e][1,4]diazepin-5-one | + |
| 116 | 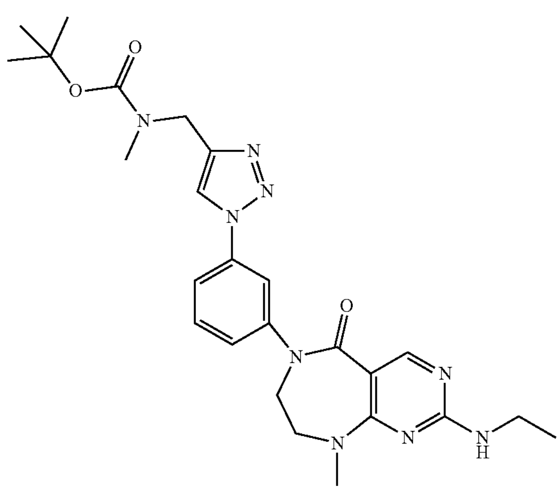 [SMILES: CCNc1ncc2c(n1)N(C)CCN(c1cccc(-n3cc(CN(C)C(=O)OC(C)(C)C)nn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)(methyl)carbamate | + |

TABLE 1-continued

| Ex | Structure | Name | Ki (nM) α2δ-1 |
|---|---|---|---|
| 117 | 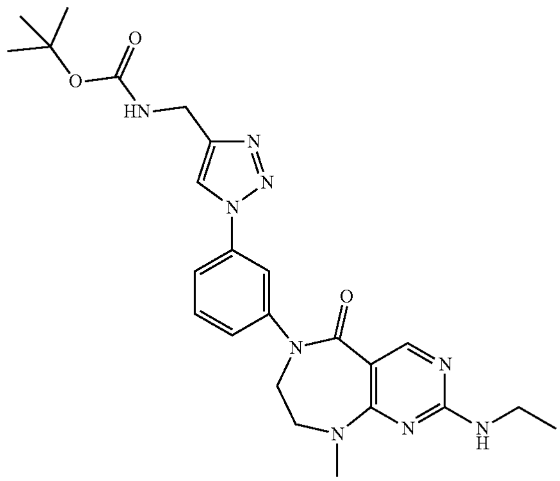 [SMILES: CCNc1ncc2c(n1)N(C)CCN(c1cccc(-n3cc(CNC(=O)OC(C)(C)C)nn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate | + |
| 118 | 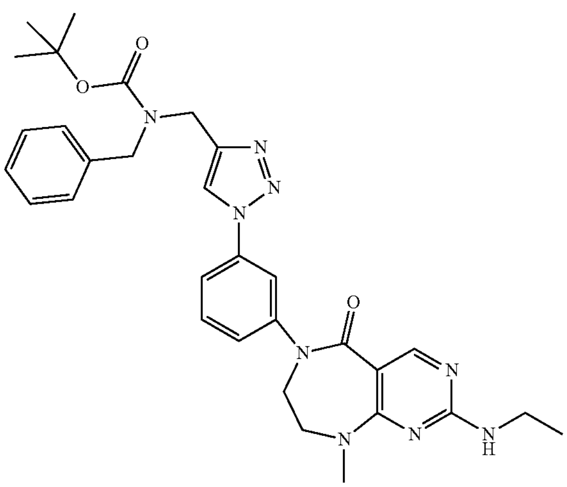 [SMILES: CCNc1ncc2c(n1)N(C)CCN(c1cccc(-n3cc(CN(Cc4ccccc4)C(=O)OC(C)(C)C)nn3)c1)C2=O] | tert-butyl benzyl((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate | + |
| 119 | 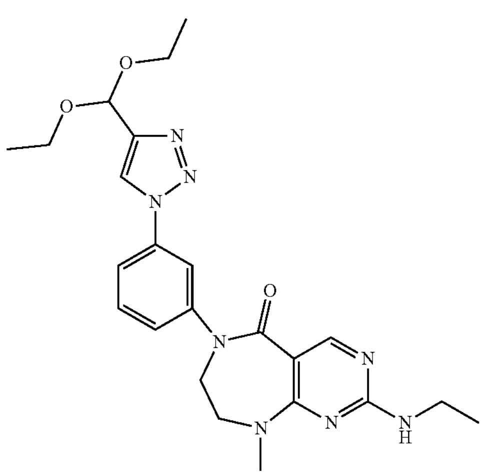 [SMILES: CCNc1ncc2c(n1)N(C)CCN(c1cccc(-n3cc(C(OCC)OCC)nn3)c1)C2=O] | 6-(3-(4-(diethoxymethyl)-1H-1,2,3-triazol-1-yl)phenyl)-2-(ethylamino)-9-methyl-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 120 | 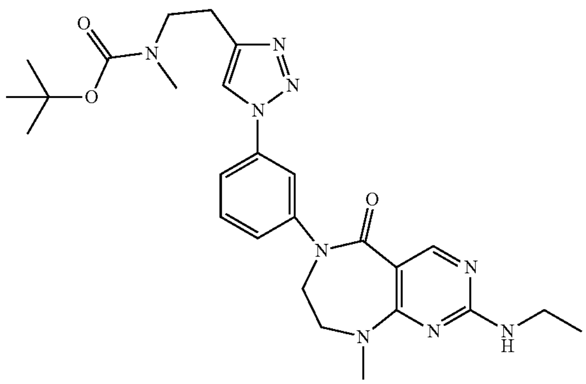 [SMILES: CCNc1ncc2c(n1)N(C)CCN(c1cccc(-n3cc(CCN(C)C(=O)OC(C)(C)C)nn3)c1)C2=O] | tert-butyl (2-(1-(3-(2-(ethylamino)-9-methyl-6-oxo-5,7,8,9-tetrahydro-6H-pyrimido[4,5-e][1,4]diazepin-6-yl)phenyl)-1H-1,2,3-triazol-4-yl)ethyl)(methyl)carbamate | + |
| 121 | 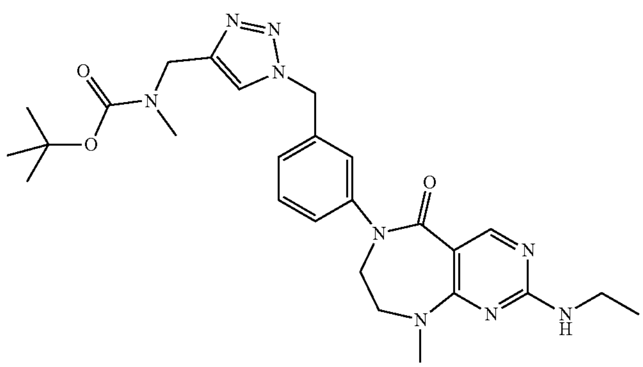 [SMILES: CCNc1ncc2c(n1)N(C)CCN(c1cccc(Cn3cc(CN(C)C(=O)OC(C)(C)C)nn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)benzyl)-1H-1,2,3-triazol-4-yl)methyl)(methyl)carbamate | + |
| 122 | 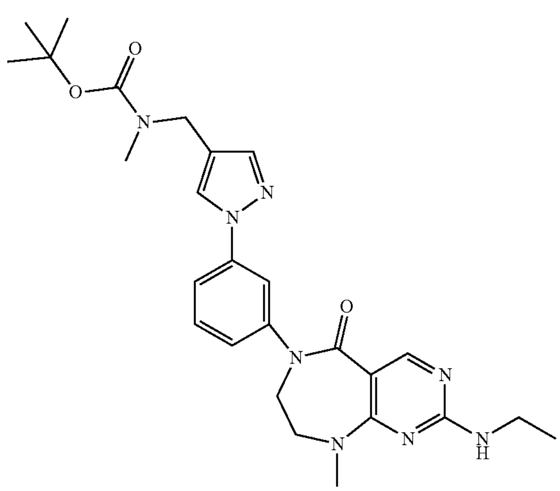 [SMILES: CCNc1ncc2c(n1)N(C)CCN(c1cccc(-n3cc(CN(C)C(=O)OC(C)(C)C)cn3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-pyrazol-4-yl)methyl)(methyl)carbamate | + |

TABLE 1-continued

| Ex | Structure | Name | Ki (nM) α2δ-1 |
|---|---|---|---|
| 123 | 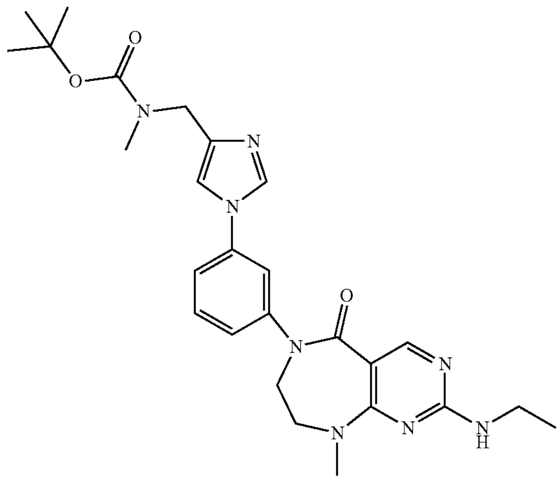 [SMILES: CCNc1ncc2c(n1)N(C)CCN(c1cccc(-n3cnc(CN(C)C(=O)OC(C)(C)C)c3)c1)C2=O] | tert-butyl ((1-(3-(2-(ethylamino)-9-methyl-5-oxo-5,7,8,9-tetrahydro-6H-pyrimido[4,5-e][1,4]diazepin-6-yl)phenyl)-1H-imidazol-4-yl)methyl)(methyl) carbamate | + |
| 124 | 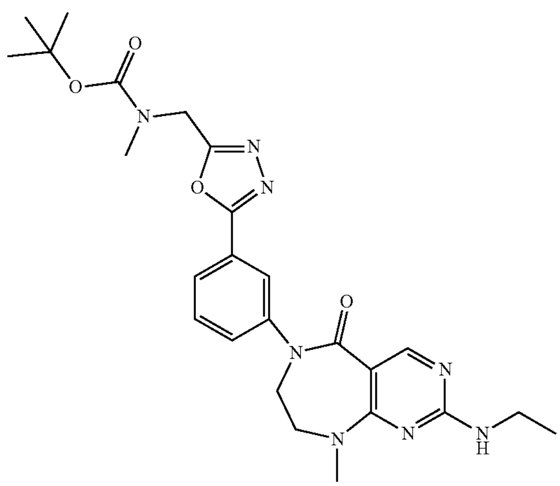 [SMILES: CCNc1ncc2c(n1)N(C)CCN(c1cccc(-c3nnc(CN(C)C(=O)OC(C)(C)C)o3)c1)C2=O] | tert-butyl ((5-(3-(2-(ethylamino)-9-methyl-5-oxo-5,7,8,9-tetrahydro-6H-pyrimido[4,5-e][1,4]diazepin-6-yl)phenyl)-1,3,4-oxadiazol-2-yl)methyl)(methyl) carbamate | + |
| 125 | 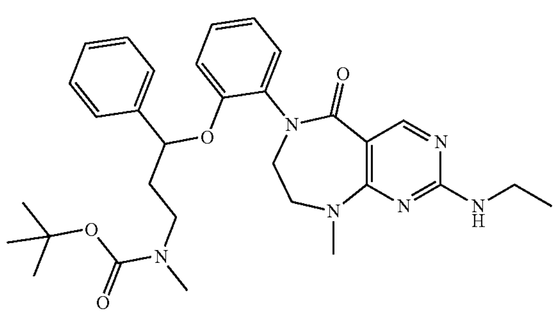 [SMILES: CCNc1ncc2c(n1)N(C)CCN(c1ccccc1OC(CCN(C)C(=O)OC(C)(C)C)c1ccccc1)C2=O] | tert-butyl (3-(2-(2-(ethylamino)-9-methyl-5-oxo-5,7,8,9-tetrahydro-6H-pyrimido[4,5-e][1,4]diazepin-6-yl)phenoxy)-3-phenylpropyl)(methyl) carbamate | + |

TABLE 1-continued

| Ex | Structure | Name | Ki (nM) α2δ-1 |
|---|---|---|---|
| 126 | 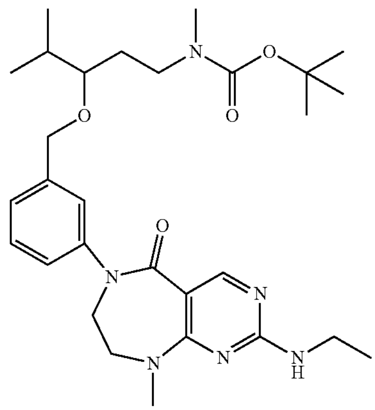 [SMILES: CCNc1ncc2c(n1)N(C)CCN(c1cccc(COC(CCN(C)C(=O)OC(C)(C)C)C(C)C)c1)C2=O] | tert-butyl (3-((3-(2-(ethylamino)-9-methyl-5-oxo-5,7,8,9-tetrahydro-6H-pyrimido[4,5-e][1,4]diazepin-6-yl)benzyl)oxy)-4-methylpentyl)(methyl)carbamate | + |
| 127 | 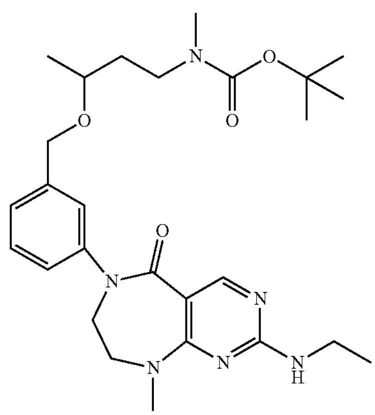 [SMILES: CCNc1ncc2c(n1)N(C)CCN(c1cccc(COC(C)CCN(C)C(=O)OC(C)(C)C)c1)C2=O] | tert-butyl (3-((3-(2-(ethylamino)-9-methyl-5-oxo-5,7,8,9-tetrahydro-6H-pyrimido[4,5-e][1,4]diazepin-6-yl)benzyl)oxy)butyl)(methyl)carbamate | + |
| 128 | 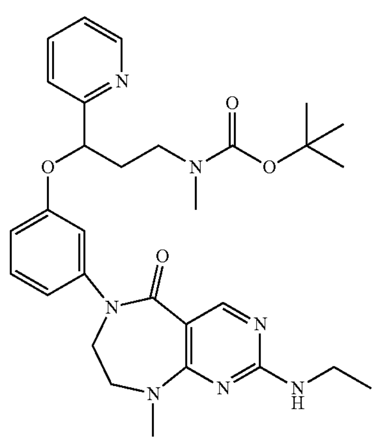 [SMILES: CCNc1ncc2c(n1)N(C)CCN(c1cccc(OC(CCN(C)C(=O)OC(C)(C)C)c3ccccn3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-2-yl)propyl)(methyl)carbamate | + |

TABLE 1-continued

| Ex | Structure | Name | Ki (nM) α2δ-1 |
|---|---|---|---|
| 129 | 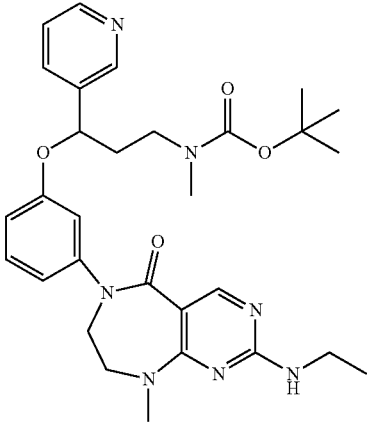 [SMILES: CCNc1ncc2c(n1)N(C)CCN(c1cccc(OC(CCN(C)C(=O)OC(C)(C)C)c3cccnc3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-3-yl)propyl)(methyl)carbamate | + |
| 130 | 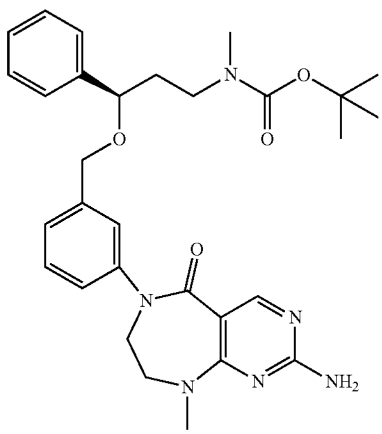 [SMILES: CN(CC[C@@H](OCc1cccc(N2CCN(C)c3nc(N)ncc3C2=O)c1)c1ccccc1)C(=O)OC(C)(C)C] | tert-butyl (R)-(3-((3-(2-amino-9-methyl-5-oxo-5,7,8,9-tetrahydro-6H-pyrimido[4,5-e][1,4]diazepin-6-yl)benzyl)oxy)-3-phenylpropyl)(methyl)carbamate | + |
| 131 | 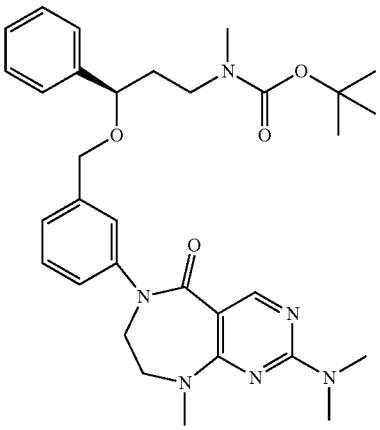 [SMILES: CN(CC[C@@H](OCc1cccc(N2CCN(C)c3nc(N(C)C)ncc3C2=O)c1)c1ccccc1)C(=O)OC(C)(C)C] | tert-butyl (R)-(3-((3-(2-(dimethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate | + |

| Ex | Structure | Name | Ki (nM) α2δ-1 |
|---|---|---|---|
| 132 | 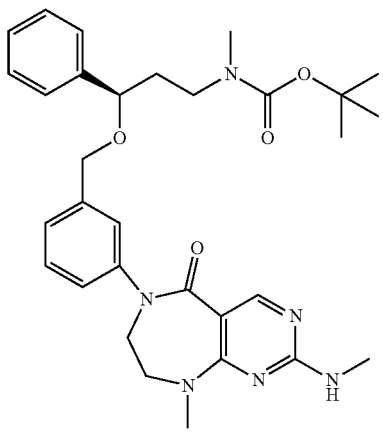 [SMILES: CNc1ncc2c(n1)N(C)CCN(c1cccc(CO[C@H](CCN(C)C(=O)OC(C)(C)C)c3ccccc3)c1)C2=O] | tert-butyl (R)-methyl(3-((3-(9-methyl-2-(methylamino)-5-oxo-5,7,8,9-tetrahydro-6H-pyrimido[4,5-e][1,4]diazepin-6-yl)benzyl)oxy)-3-phenylpropyl)carbamate | + |
| 133 | 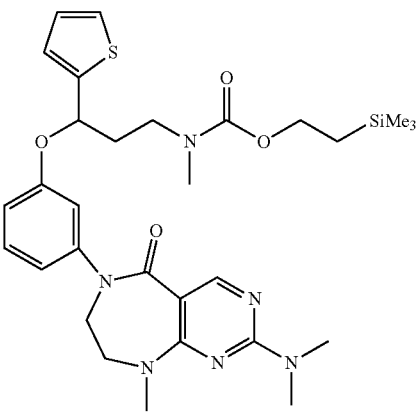 [SMILES: CN(CCC(Oc1cccc(N2CCN(C)c3nc(N(C)C)ncc3C2=O)c1)c1cccs1)C(=O)OCC[Si](C)(C)C] | 2-(trimethylsilyl)ethyl (3-(3-(2-(dimethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate | + |
| 134 | 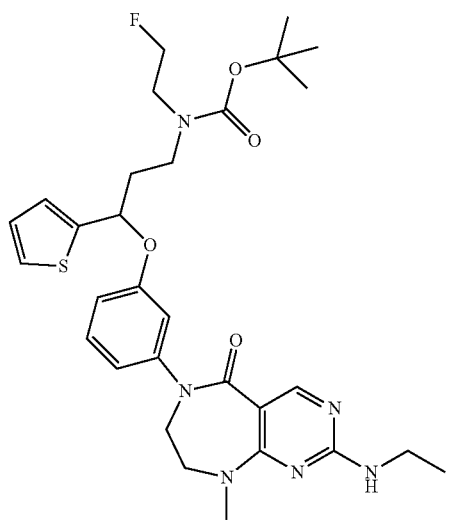 [SMILES: CCNc1ncc2c(n1)N(C)CCN(c1cccc(OC(CCN(CCF)C(=O)OC(C)(C)C)c3cccs3)c1)C2=O] | tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(2-fluoroethyl)carbamate | + |

TABLE 1-continued

| Ex | Structure | Name | Ki (nM) α2δ-1 |
|---|---|---|---|
| 135 | 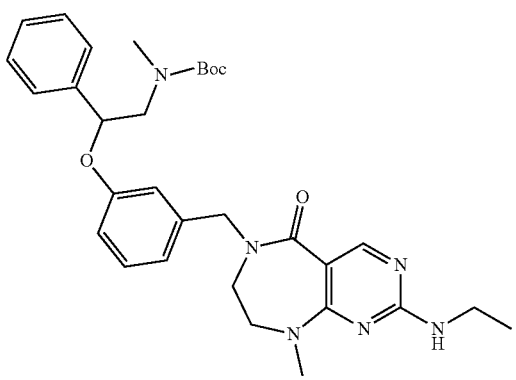 [SMILES: CCNc1ncc2c(n1)N(C)CCN(Cc1cccc(OC(CN(C)C(=O)OC(C)(C)C)c3ccccc3)c1)C2=O] | tert-butyl (2-(3-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate | + |
| 136 | 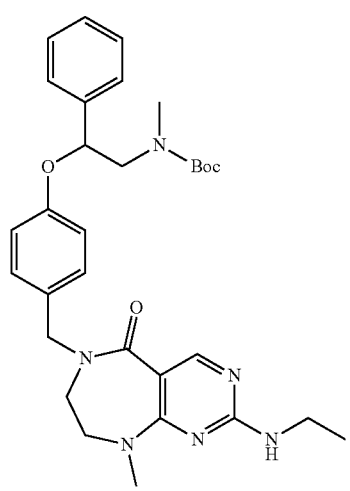 [SMILES: CCNc1ncc2c(n1)N(C)CCN(Cc1ccc(OC(CN(C)C(=O)OC(C)(C)C)c3ccccc3)cc1)C2=O] | tert-butyl (2-(4-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate | + |
| 137 | 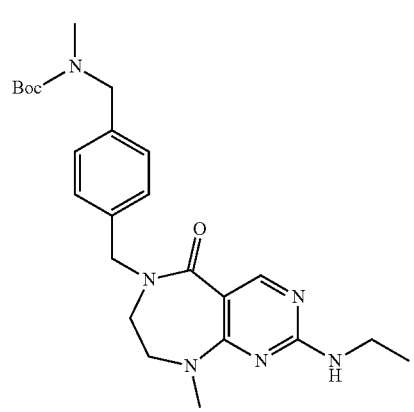 [SMILES: CCNc1ncc2c(n1)N(C)CCN(Cc1ccc(CN(C)C(=O)OC(C)(C)C)cc1)C2=O] | tert-butyl (4-((2-(ethylamino)-9-methyl-5-oxo-5,7,8,9-tetrahydro-6H-pyrimido[4,5-e][1,4]diazepin-6-yl)methyl)benzyl)(methyl)carbamate | + |

TABLE 1-continued

| Ex | Structure | Name | Ki (nM) α2δ-1 |
|---|---|---|---|
| 138 | 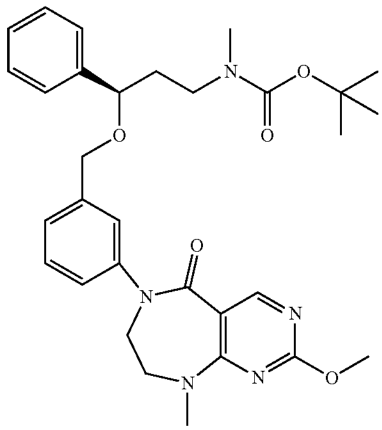 [SMILES: COc1ncc2c(n1)N(C)CCN(c1cccc(CO[C@H](CCN(C)C(=O)OC(C)(C)C)c3ccccc3)c1)C2=O] | tert-butyl (R)-(3-((3-(2-methoxy-9-methyl-5-oxo-5,7,8,9-tetrahydro-6H-pyrimido[4,5-e][1,4]diazepin-6-yl)benzyl)oxy)-3-phenylpropyl)(methyl)carbamate | + |
| 139 | 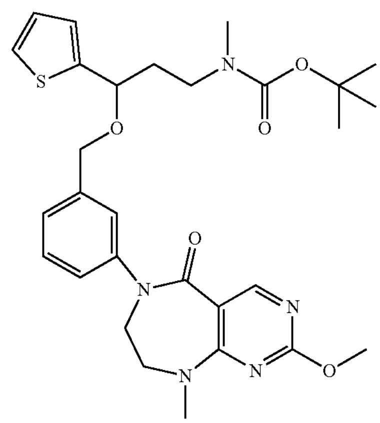 [SMILES: COc1ncc2c(n1)N(C)CCN(c1cccc(COC(CCN(C)C(=O)OC(C)(C)C)c3cccs3)c1)C2=O] | tert-butyl (3-((3-(2-methoxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate | + |
| 140 | 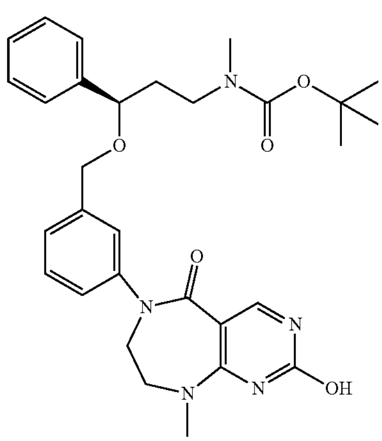 [SMILES: CN(CC[C@@H](OCc1cccc(N2CCN(C)c3nc(O)ncc3C2=O)c1)c1ccccc1)C(=O)OC(C)(C)C] | tert-butyl (R)-(3-((3-(2-hydroxy-9-methyl-5-oxo-5,7,8,9-tetrahydro-6H-pyrimido[4,5-e][1,4]diazepin-6-yl)benzyl)oxy)-3-phenylpropyl)(methyl)carbamate | + |

| Ex | Structure | Name | Ki (nM) α2δ-1 |
|---|---|---|---|
| 141 | 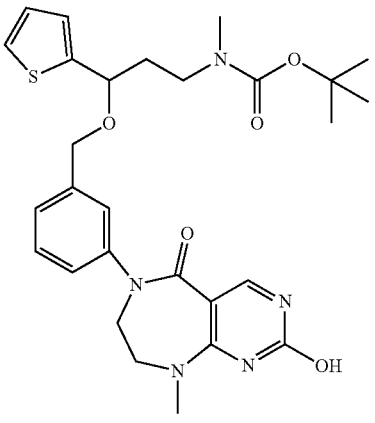 [SMILES: CN(CCC(OCc1cccc(N2CCN(C)c3nc(O)ncc3C2=O)c1)c1cccs1)C(=O)OC(C)(C)C] | tert-butyl (3-((3-(2-hydroxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate | + |
| 142 | 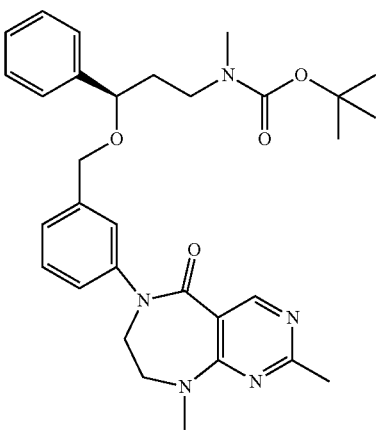 [SMILES: Cc1ncc2c(n1)N(C)CCN(c1cccc(CO[C@H](CCN(C)C(=O)OC(C)(C)C)c3ccccc3)c1)C2=O] | tert-butyl (R)-(3-((3-(2,9-dimethyl-5-oxo-5,7,8,9-tetrahydro-6H-pyrimido[4,5-e][1,4]diazepin-6-yl)benzyl)oxy)-3-phenylpropyl)(methyl)carbamate | + |
| 143 | 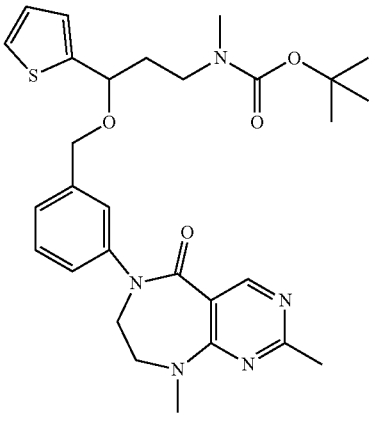 [SMILES: Cc1ncc2c(n1)N(C)CCN(c1cccc(COC(CCN(C)C(=O)OC(C)(C)C)c3cccs3)c1)C2=O] | tert-butyl (3-((3-(2,9-dimethyl-5-oxo-5,7,8,9-tetrahydro-6H-pyrimido[4,5-e][1,4]diazepin-6-yl)benzyl)oxy)-3-(thiophen-2-yl)propyl)(methyl)carbamate | + |

TABLE 1-continued

| Ex | Structure | Name | Ki (nM) α2δ-1 |
|---|---|---|---|
| 144 | 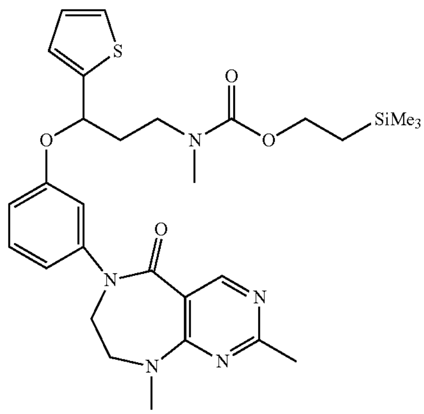 [SMILES: Cc1ncc2c(n1)N(C)CCN(c1cccc(OC(CCN(C)C(=O)OCC[Si](C)(C)C)c3cccs3)c1)C2=O] | 2-(trimethylsilyl)ethyl (3-(3-(2,9-dimethyl-5-oxo-5,7,8,9-tetrahydro-6H-pyrimido[4,5-e][1,4]diazepin-6-yl)phenoxy)-3-(thiophen-2-yl)propyl)(methyl)carbamate | + |
| 145 | 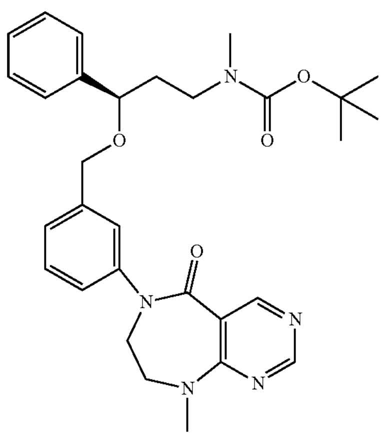 | tert-butyl (R)-methyl(3-((3-(9-methyl-5-oxo-5,7,8,9-tetrahydro-6H-pyrimido[4,5-e][1,4]diazepin-6-yl)benzyl)oxy)-3-phenylpropyl)carbamate | + |
| 146 | 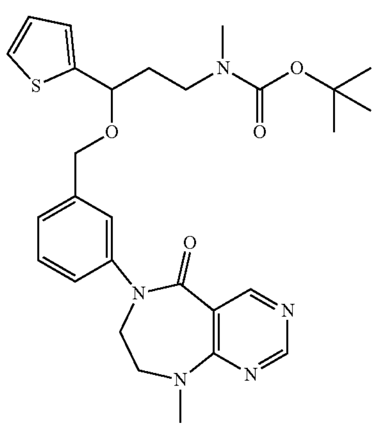 [SMILES: CN(CCC(OCc1cccc(N2CCN(C)c3ncncc3C2=O)c1)c1cccs1)C(=O)OC(C)(C)C] | tert-butyl methyl(3-((3-(9-methyl-5-oxo-5,7,8,9-tetrahydro-6H-pyrimido[4,5-e][1,4]diazepin-6-yl)benzyl)oxy)-3-(thiophen-2-yl)propyl)carbamate | + |

| Ex | Structure | Name | Ki (nM) α2δ-1 |
|---|---|---|---|
| 147 | 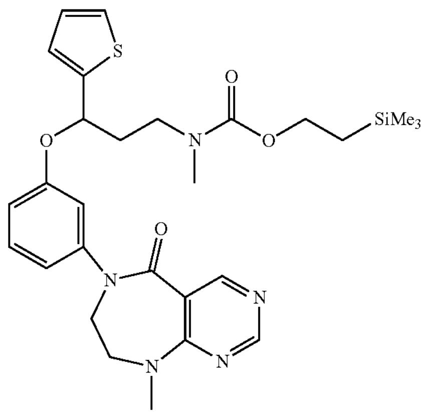 [SMILES: CN(CCC(Oc1cccc(N2CCN(C)c3ncncc3C2=O)c1)c1cccs1)C(=O)OCC[Si](C)(C)C] | 2-(trimethylsilyl)ethyl methyl(3-(3-(9-methyl-5-oxo-5,7,8,9-tetrahydro-6H-pyrimido[4,5-e][1,4]diazepin-6-yl)phenoxy)-3-(thiophen-2-yl)propyl)carbamate | + |
| 148 | 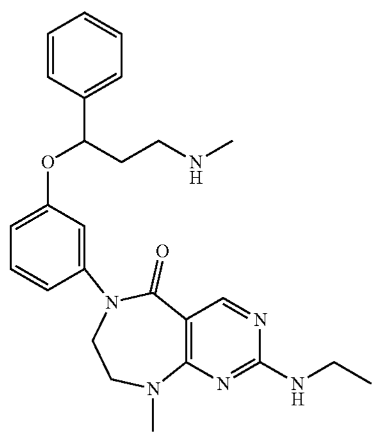 [SMILES: CCNc1ncc2c(n1)N(C)CCN(c1cccc(OC(CCNC)c3ccccc3)c1)C2=O] | 2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | ++ |
| 149 | 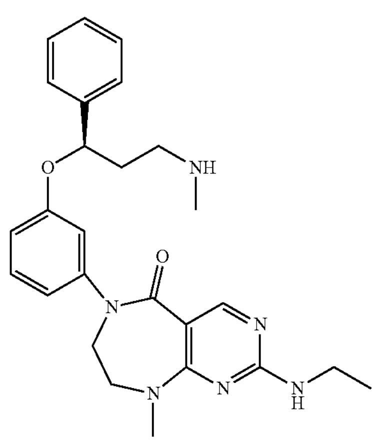 [SMILES: CCNc1ncc2c(n1)N(C)CCN(c1cccc(O[C@H](CCNC)c3ccccc3)c1)C2=O] | (R)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 150 | 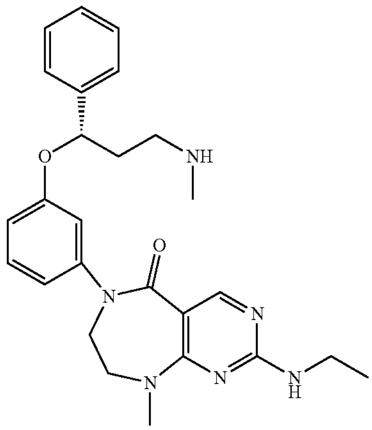 [SMILES: CCNc1ncc2c(n1)N(C)CCN(c1cccc(O[C@@H](CCNC)c3ccccc3)c1)C2=O] | (S)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | ++ |
| 151 | 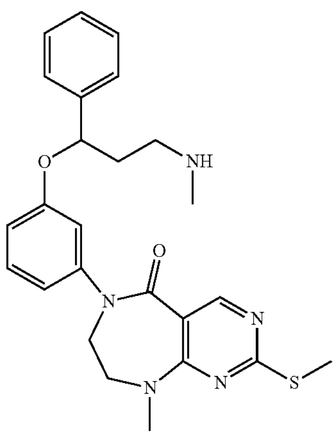 [SMILES: CNCCC(Oc1cccc(N2CCN(C)c3nc(SC)ncc3C2=O)c1)c1ccccc1] | 9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | ++ |
| 152 | 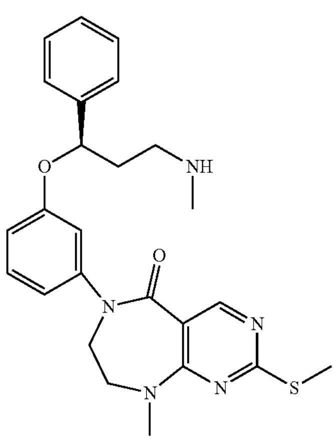 [SMILES: CNCC[C@@H](Oc1cccc(N2CCN(C)c3nc(SC)ncc3C2=O)c1)c1ccccc1] | (R)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 153 | 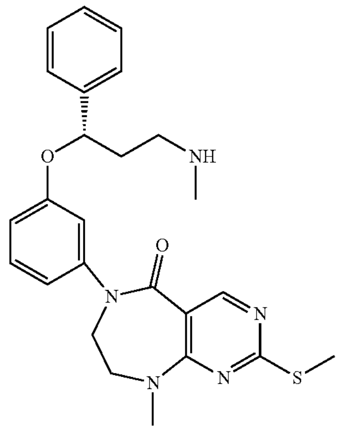 [SMILES: CNCC[C@H](Oc1cccc(N2CCN(C)c3nc(SC)ncc3C2=O)c1)c1ccccc1] | (S)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | + |
| 154 | 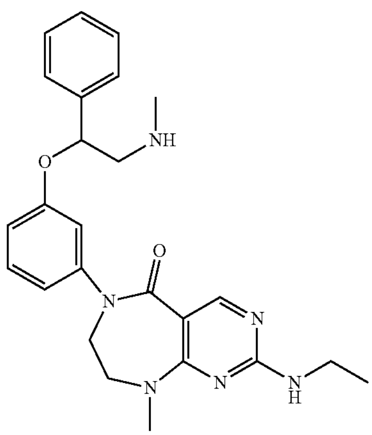 [SMILES: CCNc1ncc2c(n1)N(C)CCN(c1cccc(OC(CNC)c3ccccc3)c1)C2=O] | 2-(ethylamino)-9-methyl-6-(3-(2-(methylamino)-1-phenylethoxy)phenyl)-6,7,8,9-tetrahydro-5H-pyrimido[4,5-e][1,4]diazepin-5-one | ++ |
| 155 | 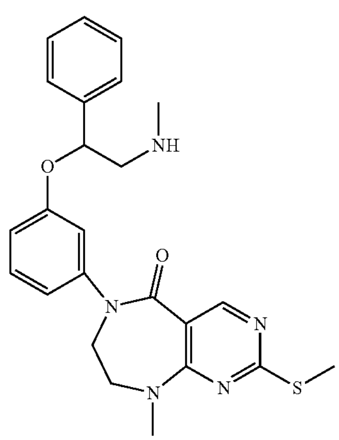 [SMILES: CNCC(Oc1cccc(N2CCN(C)c3nc(SC)ncc3C2=O)c1)c1ccccc1] | 9-methyl-6-(3-(2-(methylamino)-1-phenylethoxy)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 156 | 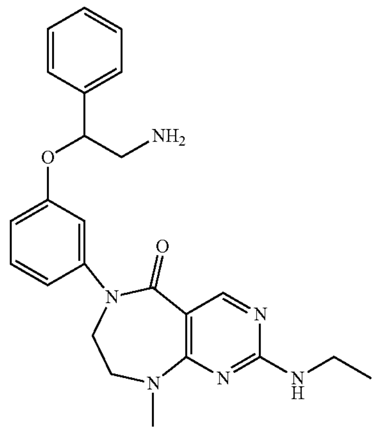 [SMILES: CCNc1ncc2c(n1)N(C)CCN(c1cccc(OC(CN)c3ccccc3)c1)C2=O] | 6-(3-(2-amino-1-phenylethoxy)phenyl)-2-(ethylamino)-9-methyl-6,7,8,9-tetrahydro-5H-pyrimido[4,5-e][1,4]diazepin-5-one | + |
| 157 | 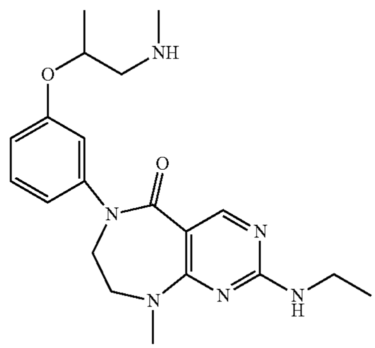 [SMILES: CCNc1ncc2c(n1)N(C)CCN(c1cccc(OC(C)CNC)c1)C2=O] | 2-(ethylamino)-9-methyl-6-(3-((1-(methylamino)propan-2-yl)oxy)phenyl)-6,7,8,9-tetrahydro-5H-pyrimido[4,5-e][1,4]diazepin-5-one | ++ |
| 158 | 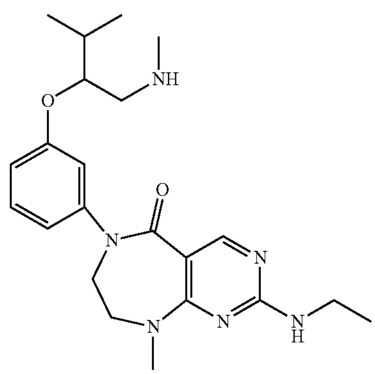 [SMILES: CCNc1ncc2c(n1)N(C)CCN(c1cccc(OC(CNC)C(C)C)c1)C2=O] | 2-(ethylamino)-9-methyl-6-(3-((3-methyl-1-(methylamino)butan-2-yl)oxy)phenyl)-6,7,8,9-tetrahydro-5H-pyrimido[4,5-e][1,4]diazepin-5-one | ++ |
| 159 | 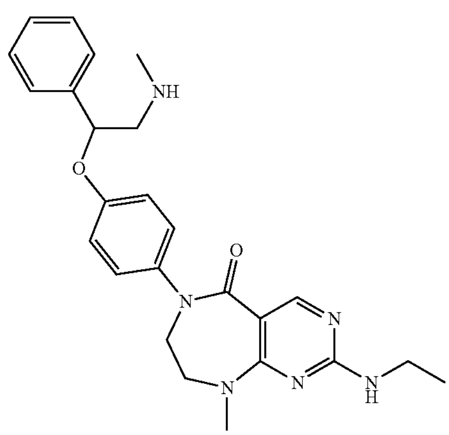 [SMILES: CCNc1ncc2c(n1)N(C)CCN(c1ccc(OC(CNC)c3ccccc3)cc1)C2=O] | 2-(ethylamino)-9-methyl-6-(4-(2-(methylamino)-1-phenylethoxy)phenyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 160 | 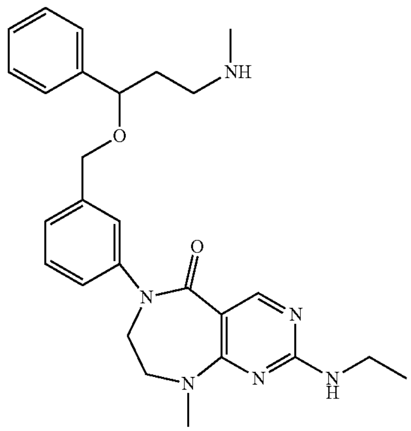 | 2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |
| 161 | 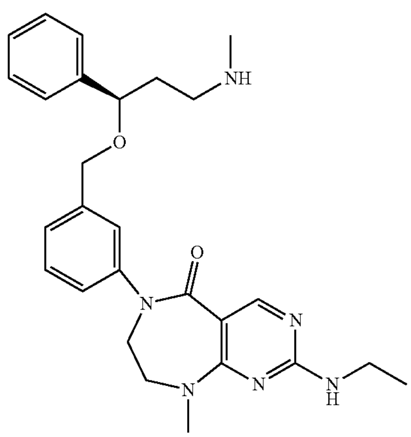 [SMILES: CCNc1ncc2c(n1)N(C)CCN(c1cccc(CO[C@H](CCNC)c3ccccc3)c1)C2=O] | (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |
| 162 | 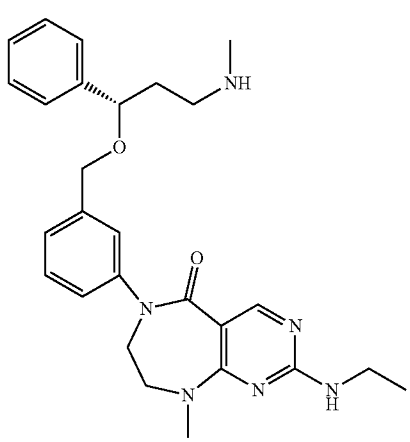 | (S)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 163 | 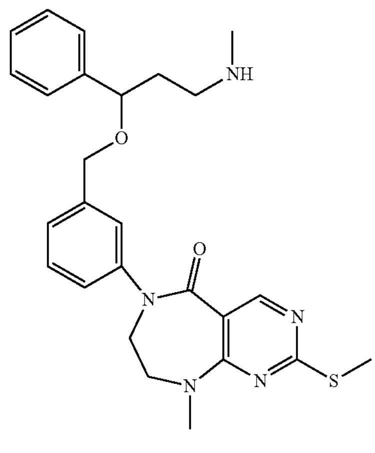 [SMILES: CNCCC(OCc1cccc(N2CCN(C)c3nc(SC)ncc3C2=O)c1)c1ccccc1] | 9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | ++ |
| 164 | 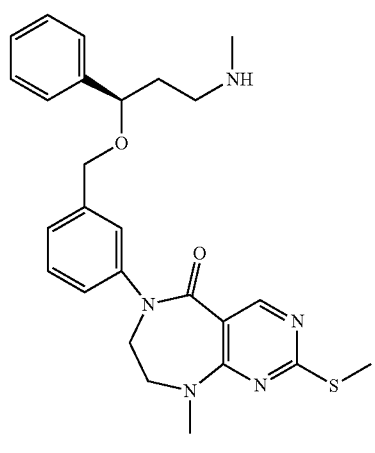 [SMILES: CNCC[C@@H](OCc1cccc(N2CCN(C)c3nc(SC)ncc3C2=O)c1)c1ccccc1] | (R)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | +++ |
| 165 | 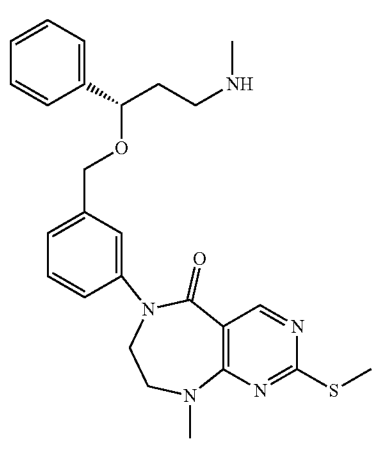 [SMILES: CNCC[C@H](OCc1cccc(N2CCN(C)c3nc(SC)ncc3C2=O)c1)c1ccccc1] | (S)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 166 | 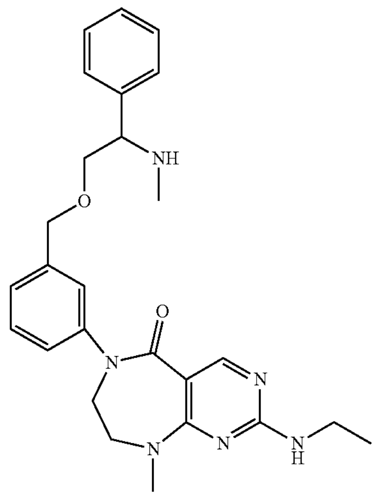 [SMILES: CCNc1ncc2c(n1)N(C)CCN(c1cccc(COCC(NC)c3ccccc3)c1)C2=O] | 2-(ethylamino)-9-methyl-6-(3-((2-(methylamino)-2-phenylethoxy)methyl)phenyl)-6,7,8,9-tetrahydro-5H-pyrimido[4,5-e][1,4]diazepin-5-one | + |
| 167 | 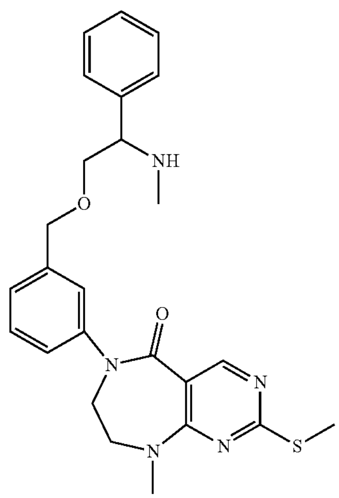 [SMILES: CNC(COCc1cccc(N2CCN(C)c3nc(SC)ncc3C2=O)c1)c1ccccc1] | 9-methyl-6-(3-((2-(methylamino)-2-phenylethoxy)methyl)phenyl)-2-(methylthio)-6,7,8,9-tetrahydro-5H-pyrimido[4,5-e][1,4]diazepin-5-one | + |
| 168 | 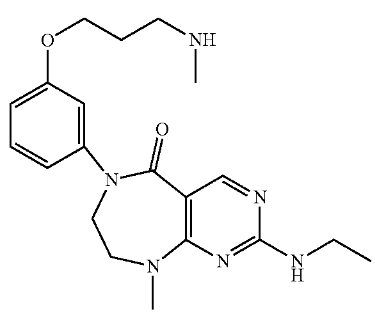 [SMILES: CCNc1ncc2c(n1)N(C)CCN(c1cccc(OCCCNC)c1)C2=O] | 2-(ethylamino)-9-methyl-6-(3-(3-(methylamino)propoxy)phenyl)-6,7,8,9-tetrahydro-5H-pyrimido[4,5-e][1,4]diazepin-5-one | +++ |
| 169 | 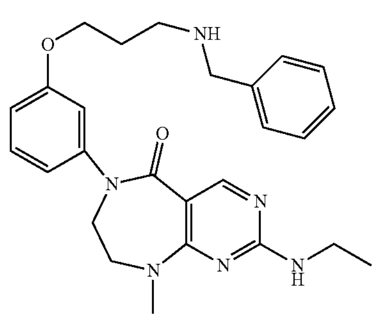 [SMILES: CCNc1ncc2c(n1)N(C)CCN(c1cccc(OCCCNCc3ccccc3)c1)C2=O] | 6-(3-(3-(benzylamino)propoxy)phenyl)-2-(ethylamino)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 170 | 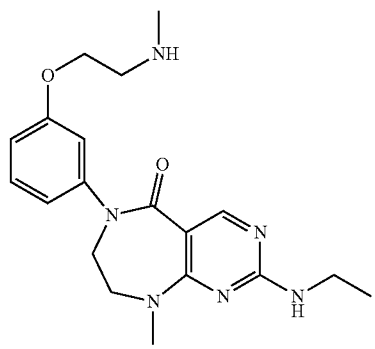 [SMILES: CCNc1ncc2c(n1)N(C)CCN(c1cccc(OCCNC)c1)C2=O] | 2-(ethylamino)-9-methyl-6-(3-(2-(methylamino)ethoxy)phenyl)-6,7,8,9-tetrahydro-5H-pyrimido[4,5-e][1,4]diazepin-5-one | +++ |
| 171 | 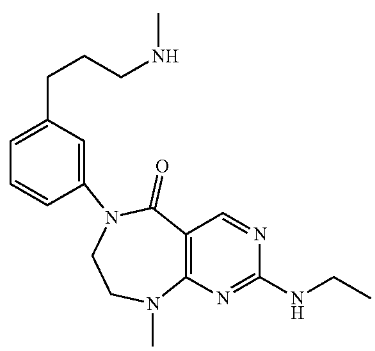 [SMILES: CCNc1ncc2c(n1)N(C)CCN(c1cccc(CCCNC)c1)C2=O] | 2-(ethylamino)-9-methyl-6-(3-(3-(methylamino)propyl)phenyl)-6,7,8,9-tetrahydro-5H-pyrimido[4,5-e][1,4]diazepin-5-one | +++ |
| 172 | 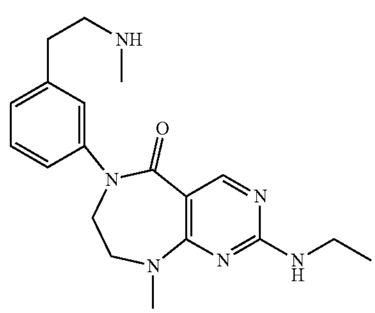 [SMILES: CCNc1ncc2c(n1)N(C)CCN(c1cccc(CCNC)c1)C2=O] | 2-(ethylamino)-9-methyl-6-(3-(2-(methylamino)ethyl)phenyl)-6,7,8,9-tetrahydro-5H-pyrimido[4,5-e][1,4]diazepin-5-one | +++ |
| 173 | 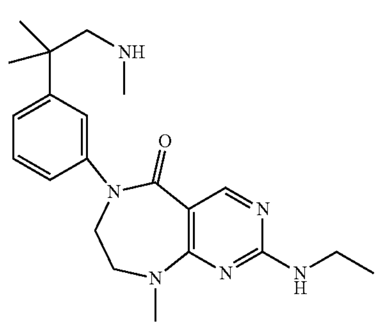 [SMILES: CCNc1ncc2c(n1)N(C)CCN(c1cccc(C(C)(C)CNC)c1)C2=O] | 2-(ethylamino)-9-methyl-6-(3-(2-methyl-1-(methylamino)propan-2-yl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 174 | 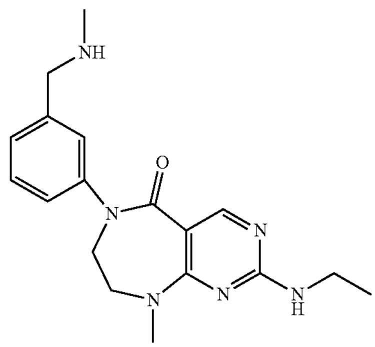 [SMILES: CCNc1ncc2c(n1)N(C)CCN(c1cccc(CNC)c1)C2=O] | 2-(ethylamino)-9-methyl-6-(3-((methylamino)methyl)phenyl)-6,7,8,9-tetrahydro-5H-pyrimido[4,5-e][1,4]diazepin-5-one | ++ |
| 175 | 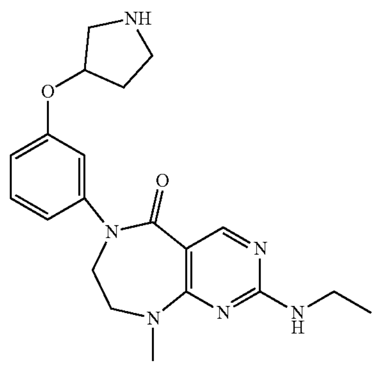 [SMILES: CCNc1ncc2c(n1)N(C)CCN(c1cccc(OC3CCNC3)c1)C2=O] | 2-(ethylamino)-9-methyl-6-(3-(pyrrolidin-3-yloxy)phenyl)-6,7,8,9-tetrahydro-5H-pyrimido[4,5-e][1,4]diazepin-5-one | +++ |
| 176 | 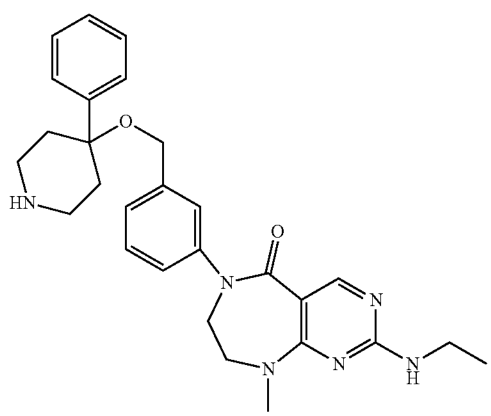 [SMILES: CCNc1ncc2c(n1)N(C)CCN(c1cccc(COC3(c4ccccc4)CCNCC3)c1)C2=O] | 2-(ethylamino)-9-methyl-6-(3-(((4-phenylpiperidin-4-yl)oxy)methyl)phenyl)-6,7,8,9-tetrahydro-5H-pyrimido[4,5-e][1,4]diazepin-5-one | ++ |
| 177 | 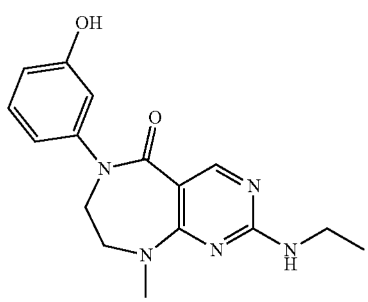 [SMILES: CCNc1ncc2c(n1)N(C)CCN(c1cccc(O)c1)C2=O] | 2-(ethylamino)-6-(3-hydroxyphenyl)-9-methyl-6,7,8,9-tetrahydro-5H-pyrimido[4,5-e][1,4]diazepin-5-one | + |

TABLE 1-continued

| Ex | Structure | Name | Ki (nM) α2δ-1 |
|----|-----------|------|---------------|
| 178 | 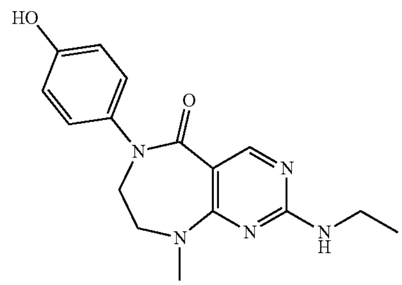 [SMILES: CCNc1ncc2c(n1)N(C)CCN(c1ccc(O)cc1)C2=O] | 2-(ethylamino)-6-(4-hydroxyphenyl)-9-methyl-6,7,8,9-tetrahydro-5H-pyrimido[4,5-e][1,4]diazepin-5-one | + |
| 179 | 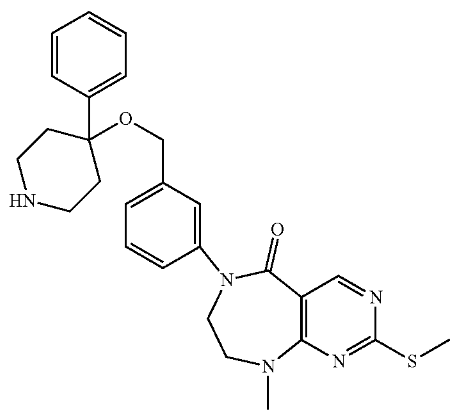 [SMILES: CSc1ncc2c(n1)N(C)CCN(c1cccc(COC3(c4ccccc4)CCNCC3)c1)C2=O] | 9-methyl-2-(methylthio)-6-(3-(((4-phenylpiperidin-4-yl)oxy)methyl)phenyl)-6,7,8,9-tetrahydro-5H-pyrimido[4,5-e][1,4]diazepin-5-one | + |
| 180 | 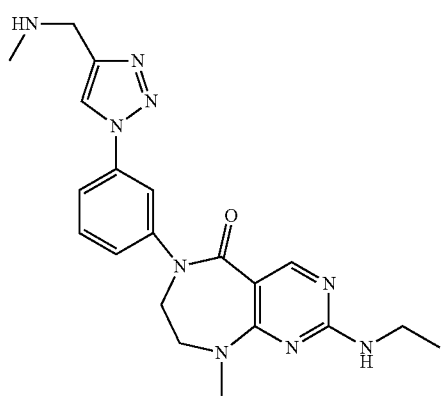 [SMILES: CCNc1ncc2c(n1)N(C)CCN(c1cccc(-n3cc(CNC)nn3)c1)C2=O] | 2-(ethylamino)-9-methyl-6-(3-(4-((methylamino)methyl)-1H-1,2,3-triazol-1-yl)phenyl)-6,7,8,9-tetrahydro-5H-pyrimido[4,5-e][1,4]diazepin-5-one | +++ |
| 181 | 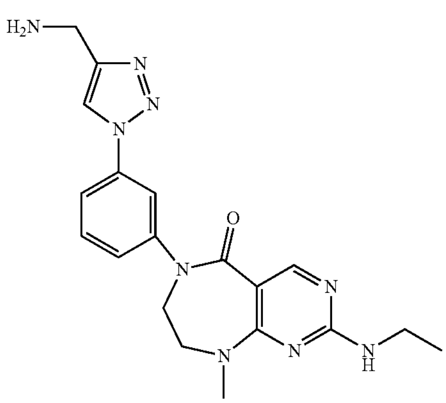 [SMILES: CCNc1ncc2c(n1)N(C)CCN(c1cccc(-n3cc(CN)nn3)c1)C2=O] | 6-(3-(4-(aminomethyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 182 | 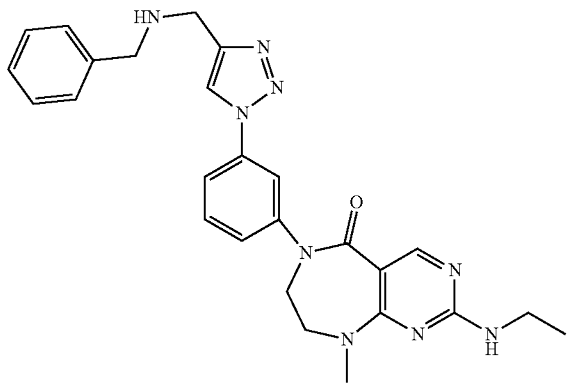 [SMILES: CCNc1ncc2c(n1)N(C)CCN(c1cccc(-n3cc(CNCc4ccccc4)nn3)c1)C2=O] | 6-(3-(4-((benzylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |
| 183 | 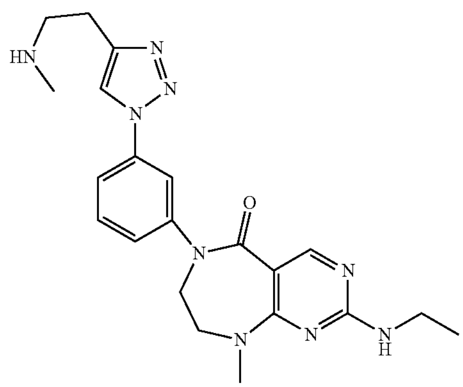 | 2-(ethylamino)-9-methyl-6-(3-(4-(2-(methylamino)ethyl)-1H-1,2,3-triazol-1-yl)phenyl)-6,7,8,9-tetrahydro-5H-pyrimido[4,5-e][1,4]diazepin-5-one | +++ |
| 184 | 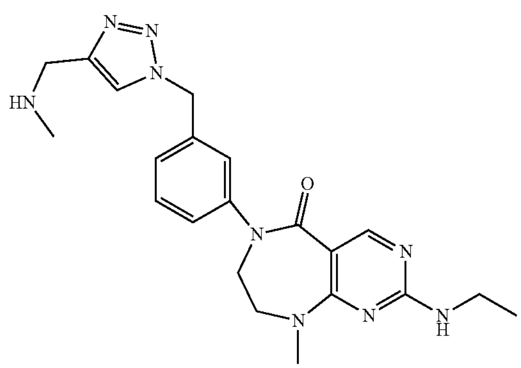 [SMILES: CCNc1ncc2c(n1)N(C)CCN(c1cccc(Cn3cc(CNC)nn3)c1)C2=O] | 2-(ethylamino)-9-methyl-6-(3-((4-((methylamino)methyl)-1H-1,2,3-triazol-1-yl)methyl)phenyl)-6,7,8,9-tetrahydro-5H-pyrimido[4,5-e][1,4]diazepin-5-one | ++ |
| 185 | 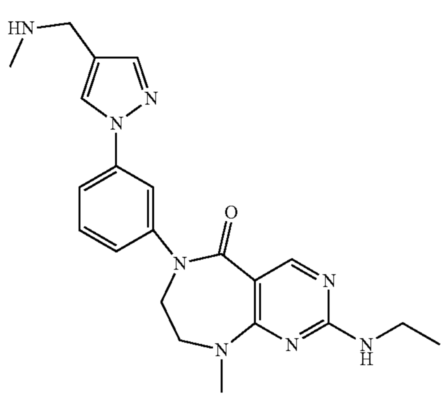 [SMILES: CCNc1ncc2c(n1)N(C)CCN(c1cccc(-n3cc(CNC)cn3)c1)C2=O] | 2-(ethylamino)-9-methyl-6-(3-(4-((methylamino)methyl)-1H-pyrazol-1-yl)phenyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 186 | 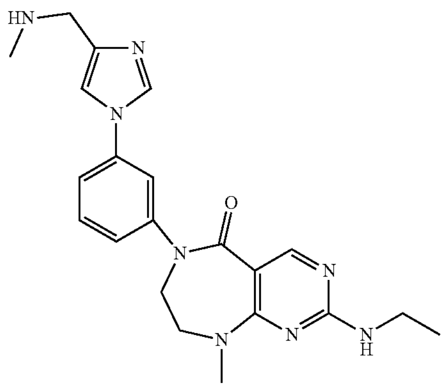 [SMILES: CCNc1ncc2c(n1)N(C)CCN(c1cccc(-n3cnc(CNC)c3)c1)C2=O] | 2-(ethylamino)-9-methyl-6-(3-(4-((methylamino)methyl)-1H-imidazol-1-yl)phenyl)-6,7,8,9-tetrahydro-5H-pyrimido[4,5-e][1,4]diazepin-5-one | +++ |
| 187 | 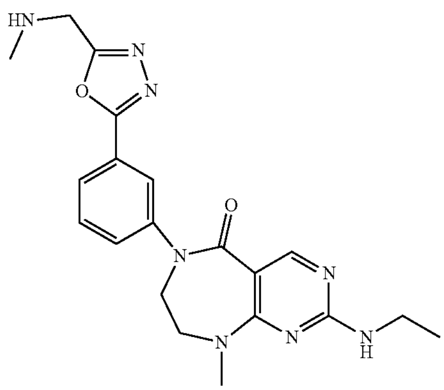 [SMILES: CCNc1ncc2c(n1)N(C)CCN(c1cccc(-c3nnc(CNC)o3)c1)C2=O] | 2-(ethylamino)-9-methyl-6-(3-(5-((methylamino)methyl)-1,3,4-oxadiazol-2-yl)phenyl)-6,7,8,9-tetrahydro-5H-pyrimido[4,5-e][1,4]diazepin-5-one | + |
| 188 | 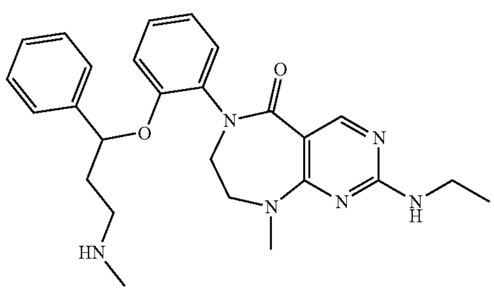 [SMILES: CCNc1ncc2c(n1)N(C)CCN(c1ccccc1OC(CCNC)c1ccccc1)C2=O] | 2-(ethylamino)-9-methyl-6-(2-(3-(methylamino)-1-phenylpropoxy)phenyl)-6,7,8,9-tetrahydro-5H-pyrimido[4,5-e][1,4]diazepin-5-one | + |
| 189 | 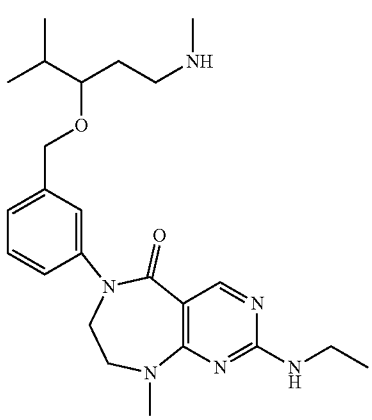 [SMILES: CCNc1ncc2c(n1)N(C)CCN(c1cccc(COC(CCNC)C(C)C)c1)C2=O] | 2-(ethylamino)-9-methyl-6-(3-(((4-methyl-1-(methylamino)pentan-3-yl)oxy)methyl)phenyl)-6,7,8,9-tetrahydro-5H-pyrimido[4,5-e][1,4]diazepin-5-one | ++ |

| Ex | Structure | Name | Ki (nM) α2δ-1 |
|---|---|---|---|
| 190 | 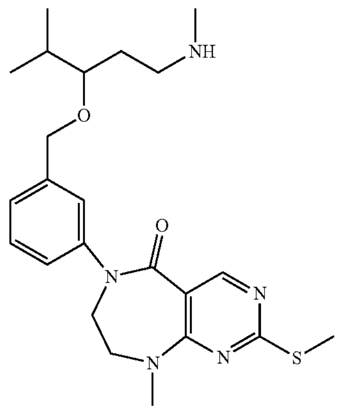 [SMILES: CNCCC(OCc1cccc(N2CCN(C)c3nc(SC)ncc3C2=O)c1)C(C)C] | 9-methyl-6-(3-(((4-methyl-1-(methylamino)pentan-3-yl)oxy)methyl)phenyl)-2-(methylthio)-6,7,8,9-tetrahydro-5H-pyrimido[4,5-e][1,4]diazepin-5-one | + |
| 191 | 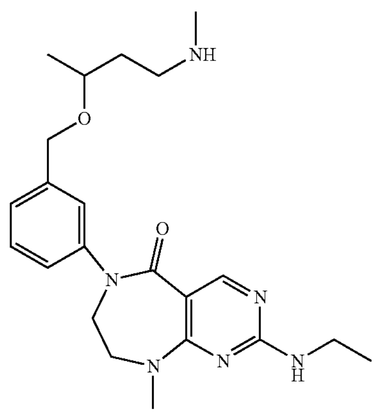 [SMILES: CCNc1ncc2c(n1)N(C)CCN(c1cccc(COC(C)CCNC)c1)C2=O] | 2-(ethylamino)-9-methyl-6-(3-(((4-(methylamino)butan-2-yl)oxy)methyl)phenyl)-6,7,8,9-tetrahydro-5H-pyrimido[4,5-e][1,4]diazepin-5-one | ++ |
| 192 | 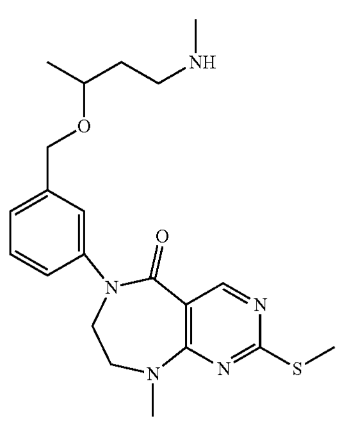 [SMILES: CNCCC(C)OCc1cccc(N2CCN(C)c3nc(SC)ncc3C2=O)c1] | 9-methyl-6-(3-(((4-(methylamino)butan-2-yl)oxy)methyl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 193 | 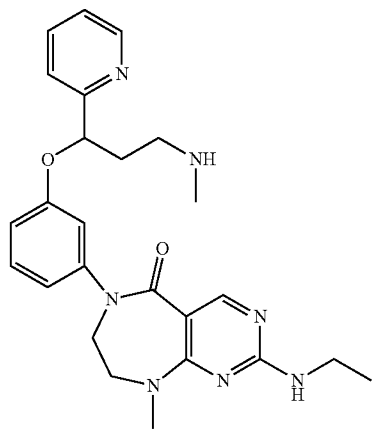 [SMILES: CCNc1ncc2c(n1)N(C)CCN(c1cccc(OC(CCNC)c3ccccn3)c1)C2=O] | 2-(ethylamino)-9-methyl-6-(3-(3-(methylamino)-1-(pyridin-2-yl)propoxy)phenyl)-6,7,8,9-tetrahydro-5H-pyrimido[4,5-e][1,4]diazepin-5-one | ++ |
| 194 | 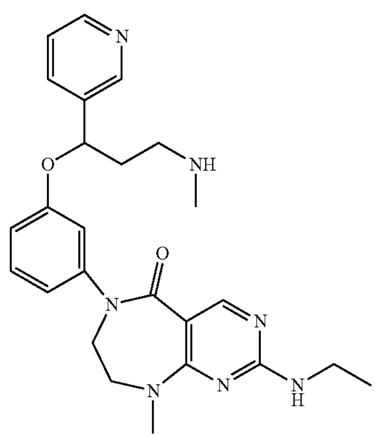 [SMILES: CCNc1ncc2c(n1)N(C)CCN(c1cccc(OC(CCNC)c3cccnc3)c1)C2=O] | 2-(ethylamino)-9-methyl-6-(3-(3-(methylamino)-1-(pyridin-3-yl)propoxy)phenyl)-6,7,8,9-tetrahydro-5H-pyrimido[4,5-e][1,4]diazepin-5-one | ++ |
| 195 | 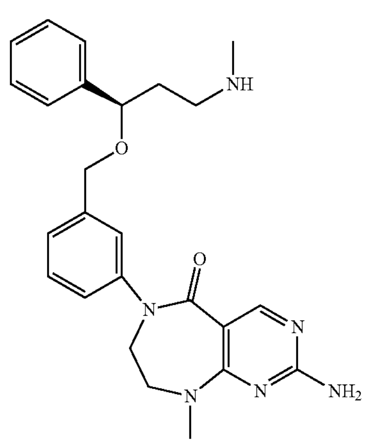 [SMILES: CNCC[C@@H](OCc1cccc(N2CCN(C)c3nc(N)ncc3C2=O)c1)c1ccccc1] | (R)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one | +++ |

TABLE 1-continued
| Ex | Structure | Name | Ki (nM) α2δ-1 |
|---|---|---|---|
| 196 | 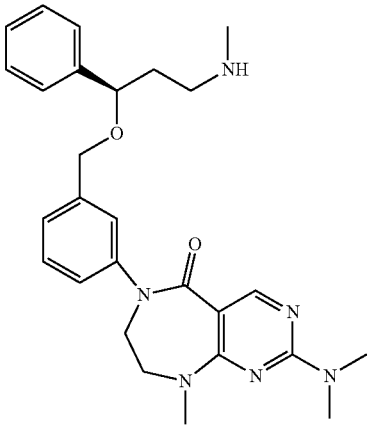 [SMILES: CNCC[C@@H](OCc1cccc(N2CCN(C)c3nc(N(C)C)ncc3C2=O)c1)c1ccccc1] | (R)-2-(dimethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |
| 197 | 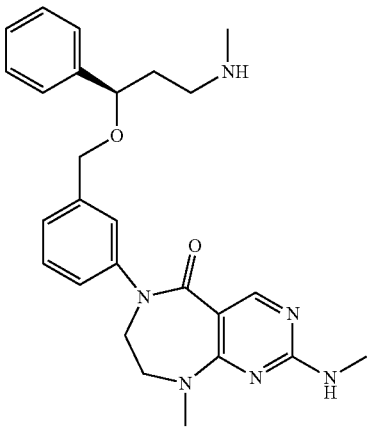 [SMILES: CNCC[C@@H](OCc1cccc(N2CCN(C)c3nc(NC)ncc3C2=O)c1)c1ccccc1] | (R)-9-methyl-2-(methylamino)-6-(3-((3-(methylamino)-1-phenylpropoxy)methyl)phenyl)-6,7,8,9-tetrahydro-5H-pyrimido[4,5-e][1,4]diazepin-5-one | ++ |
| 198 | 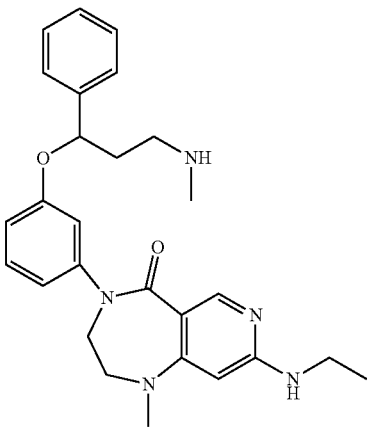 [SMILES: CCNc1cc2c(cn1)C(=O)N(c1cccc(OC(CCNC)c3ccccc3)c1)CCN2C] | 8-(ethylamino)-1-methyl-4-(3-(3-(methylamino)-1-phenylpropoxy)phenyl)-1,2,3,4-tetrahydro-5H-pyrido[4,3-e][1,4]diazepin-5-one | ++ |

TABLE 1-continued

| Ex | Structure | Name | Ki (nM) α2δ-1 |
|---|---|---|---|
| 199 | 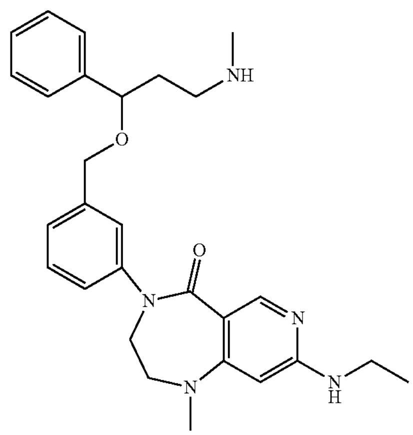 [SMILES: CCNc1cc2c(cn1)C(=O)N(c1cccc(COC(CCNC)c3ccccc3)c1)CCN2C] | 8-(ethylamino)-1-methyl-4-(3-((3-(methylamino)-1-phenylpropoxy)methyl)phenyl)-1,2,3,4-tetrahydro-5H-pyrido[4,3-e][1,4]diazepin-5-one | ++ |
| 200 | 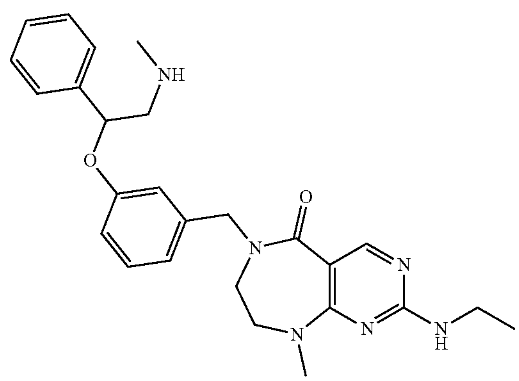 [SMILES: CCNc1ncc2c(n1)N(C)CCN(Cc1cccc(OC(CNC)c3ccccc3)c1)C2=O] | 2-(ethylamino)-9-methyl-6-(3-(2-(methylamino)-1-phenylethoxy)benzyl)-6,7,8,9-tetrahydro-5H-pyrimido[4,5-e][1,4]diazepin-5-one | + |
| 201 | 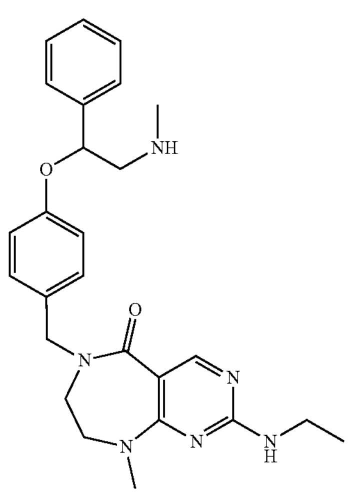 [SMILES: CCNc1ncc2c(n1)N(C)CCN(Cc1ccc(OC(CNC)c3ccccc3)cc1)C2=O] | 2-(ethylamino)-9-methyl-6-(4-(2-(methylamino)-1-phenylethoxy)benzyl)-6,7,8,9-tetrahydro-5H-pyrimido[4,5-e][1,4]diazepin-5-one | + |

TABLE 1-continued
| Ex | Structure | Name | Ki (nM) α2δ-1 |
|---|---|---|---|
| 202 | 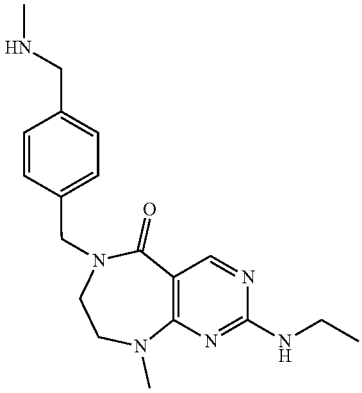 [SMILES: CCNc1ncc2c(n1)N(C)CCN(Cc1ccc(CNC)cc1)C2=O] | 2-(ethylamino)-9-methyl-6-(4-((methylamino)methyl)benzyl)-6,7,8,9-tetrahydro-5H-pyrimido[4,5-e][1,4]diazepin-5-one | ++ |
| 203 | 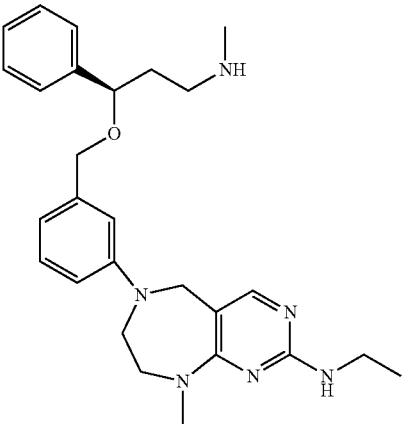 [SMILES: CCNc1ncc2c(n1)N(C)CCN(c1cccc(CO[C@H](CCNC)c3ccccc3)c1)C2] | (R)-N-ethyl-9-methyl-6-(3-((3-(methylamino)-1-phenylpropoxy)methyl)phenyl)-6,7,8,9-tetrahydro-5H-pyrimido[4,5-e][1,4]diazepin-2-amine | ++ |
| 204 | 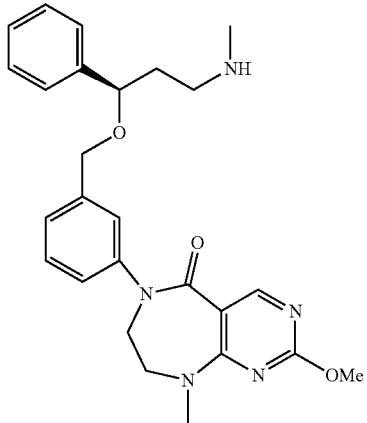 [SMILES: CNCC[C@@H](OCc1cccc(N2CCN(C)c3nc(OC)ncc3C2=O)c1)c1ccccc1] | (R)-2-methoxy-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |

| Ex | Structure | Name | Ki (nM) α2δ-1 |
|---|---|---|---|
| 205 | 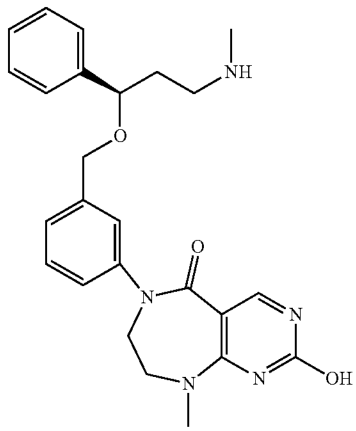 [SMILES: CNCC[C@@H](OCc1cccc(N2CCN(C)c3nc(O)ncc3C2=O)c1)c1ccccc1] | (R)-2-hydroxy-9-methyl-6-(3-((3-(methylamino)-1-phenylpropoxy)methyl)phenyl)-6,7,8,9-tetrahydro-5H-pyrimido[4,5-e][1,4]diazepin-5-one | +++ |
| 206 | 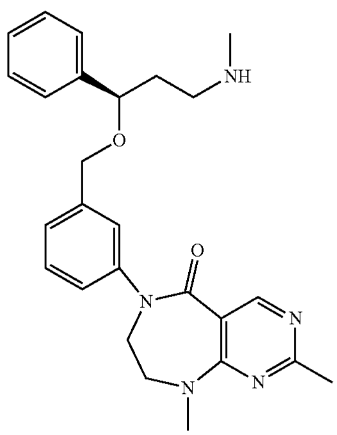 [SMILES: CNCC[C@@H](OCc1cccc(N2CCN(C)c3nc(C)ncc3C2=O)c1)c1ccccc1] | (R)-2,9-dimethyl-6-(3-((3-(methylamino)-1-phenylpropoxy)methyl)phenyl)-6,7,8,9-tetrahydro-5H-pyrimido[4,5-e][1,4]diazepin-5-one | ++ |
| 207 | 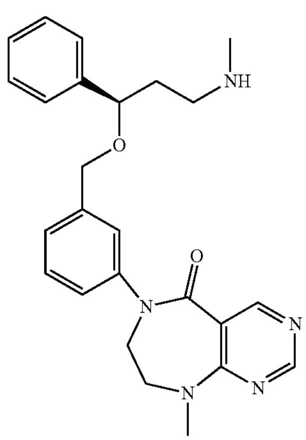 [SMILES: CNCC[C@@H](OCc1cccc(N2CCN(C)c3ncncc3C2=O)c1)c1ccccc1] | (R)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 208 | 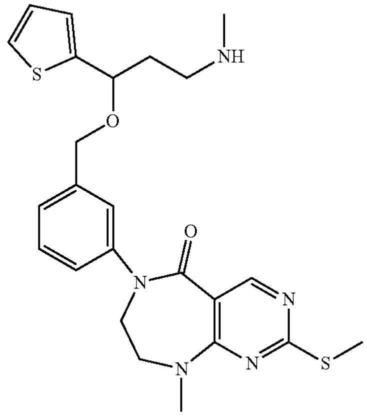 | 9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | ++ |
| 209 | 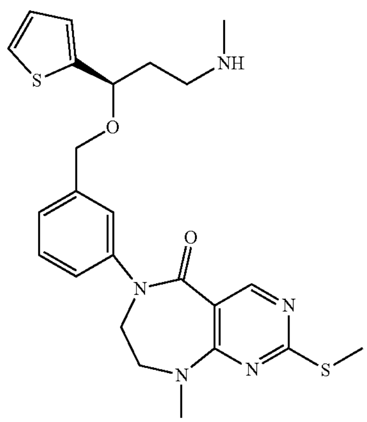 [SMILES: CNCC[C@@H](OCc1cccc(N2CCN(C)c3nc(SC)ncc3C2=O)c1)c1cccs1] | (R)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | +++ |
| 210 | 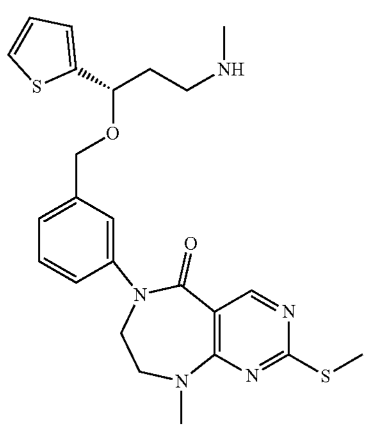 [SMILES: CNCC[C@H](OCc1cccc(N2CCN(C)c3nc(SC)ncc3C2=O)c1)c1cccs1] | (S)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 211 | 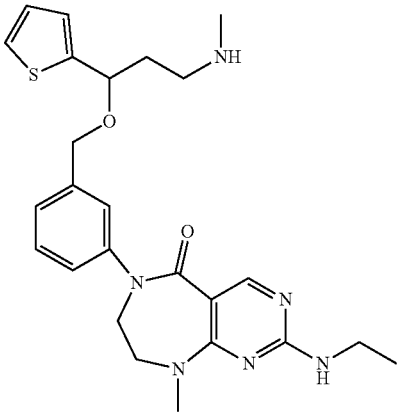 | 2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ |
| 212 | 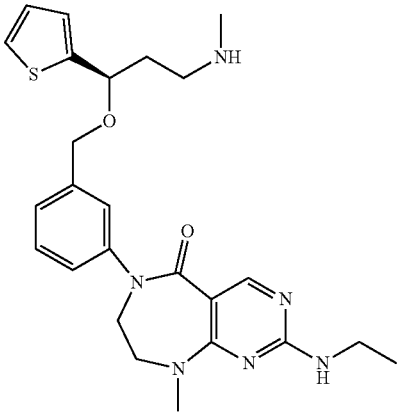 [SMILES: CCNc1ncc2c(n1)N(C)CCN(c1cccc(CO[C@H](CCNC)c3cccs3)c1)C2=O] | (R)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ |
| 213 | 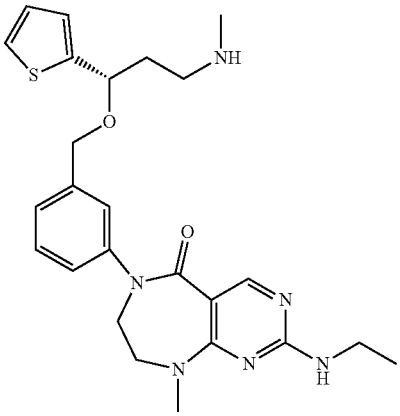 [SMILES: CCNc1ncc2c(n1)N(C)CCN(c1cccc(CO[C@@H](CCNC)c3cccs3)c1)C2=O] | (S)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 214 | 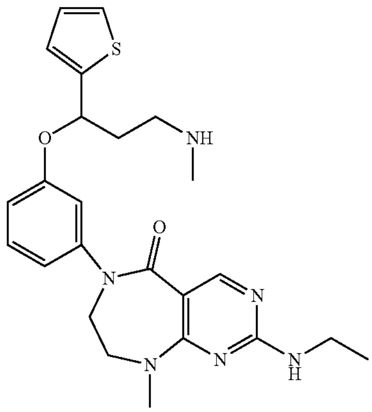 [SMILES: CCNc1ncc2c(n1)N(C)CCN(c1cccc(OC(CCNC)c3cccs3)c1)C2=O] | 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | ++ |
| 215 | 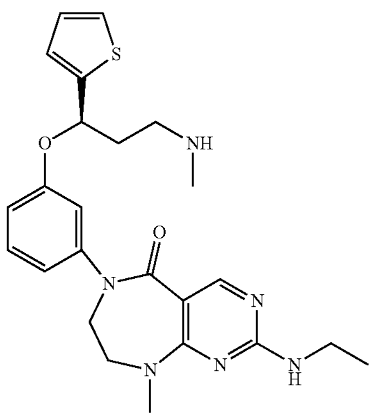 [SMILES: CCNc1ncc2c(n1)N(C)CCN(c1cccc(O[C@H](CCNC)c3cccs3)c1)C2=O] | (R)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ |
| 216 | 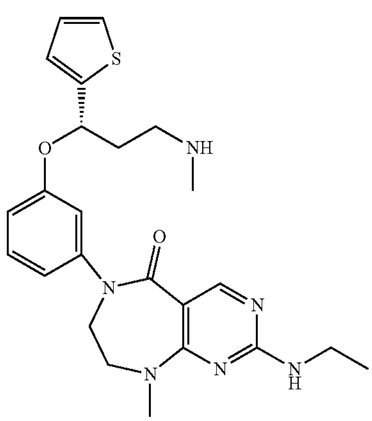 [SMILES: CCNc1ncc2c(n1)N(C)CCN(c1cccc(O[C@@H](CCNC)c3cccs3)c1)C2=O] | (S)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 217 | 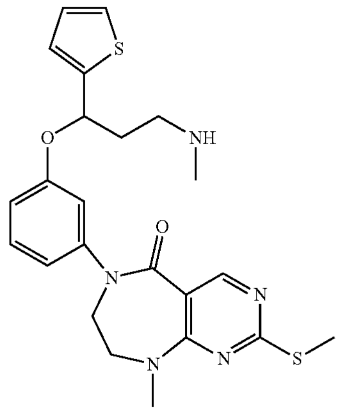 [SMILES: CNCCC(Oc1cccc(N2CCN(C)c3nc(SC)ncc3C2=O)c1)c1cccs1] | 9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | ++ |
| 218 | 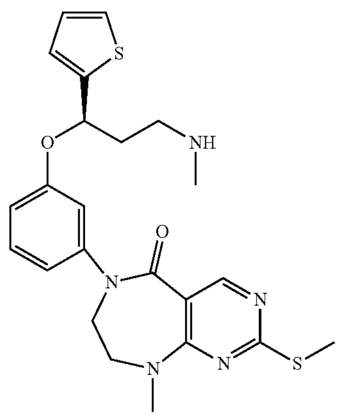 [SMILES: CNCC[C@@H](Oc1cccc(N2CCN(C)c3nc(SC)ncc3C2=O)c1)c1cccs1] | (R)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | ++ |
| 219 | 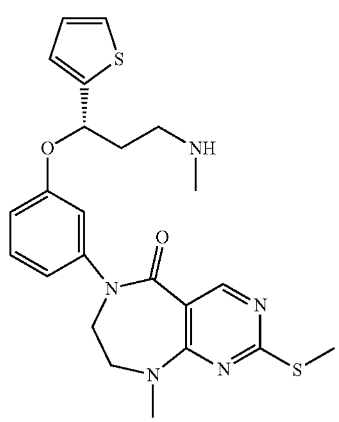 [SMILES: CNCC[C@H](Oc1cccc(N2CCN(C)c3nc(SC)ncc3C2=O)c1)c1cccs1] | (S)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 220 | 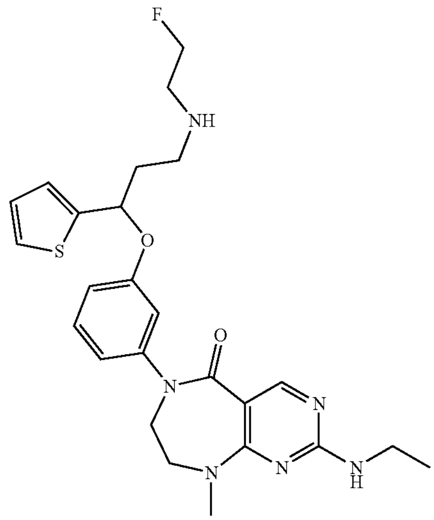 [SMILES: CCNc1ncc2c(n1)N(C)CCN(c1cccc(OC(CCNCCF)c3cccs3)c1)C2=O] | 2-(ethylamino)-6-(3-(3-((2-fluoroethyl)amino)-1-(thiophen-2-yl)propoxy)phenyl)-9-methyl-6,7,8,9-tetrahydro-5H-pyrimido[4,5-e][1,4]diazepin-5-one | ++ |
| 221 | 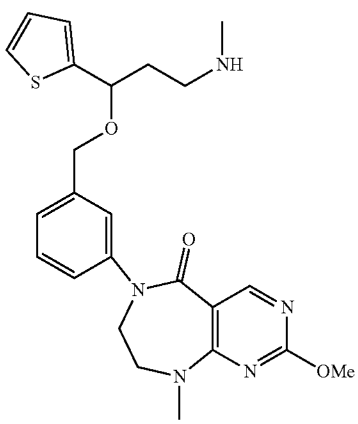 [SMILES: CNCCC(OCc1cccc(N2CCN(C)c3nc(OC)ncc3C2=O)c1)c1cccs1] | 2-methoxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | ++ |
| 222 | 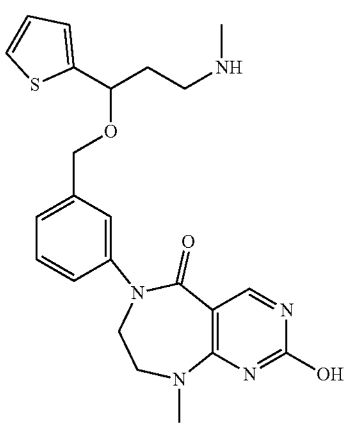 [SMILES: CNCCC(OCc1cccc(N2CCN(C)c3nc(O)ncc3C2=O)c1)c1cccs1] | 2-hydroxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 223 | 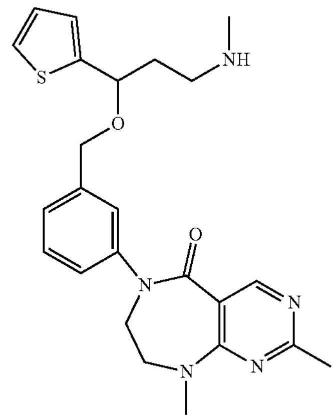 [SMILES: CNCCC(OCc1cccc(N2CCN(C)c3nc(C)ncc3C2=O)c1)c1cccs1] | 2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ |
| 224 | 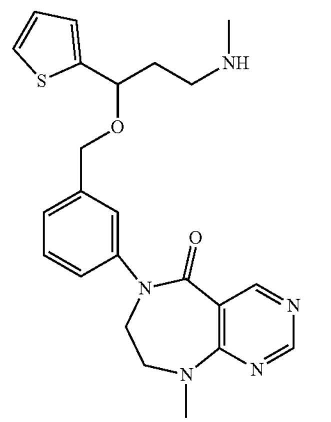 [SMILES: CNCCC(OCc1cccc(N2CCN(C)c3ncncc3C2=O)c1)c1cccs1] | 9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ |
| 225 | 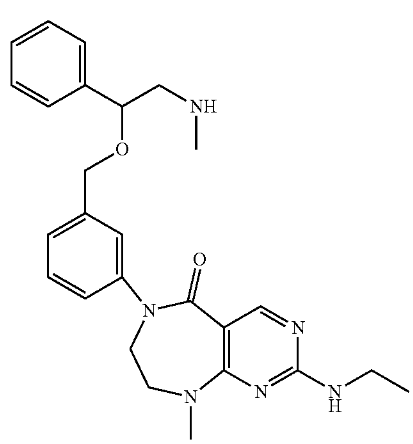 [SMILES: CCNc1ncc2c(n1)N(C)CCN(c1cccc(COC(CNC)c3ccccc3)c1)C2=O] | 2-(ethylamino)-9-methyl-6-(3-((2-(methylamino)-1-phenylethoxy)methyl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 226 | 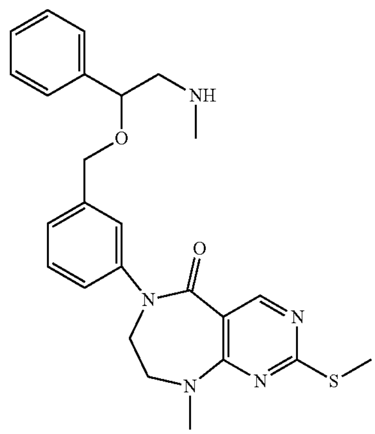 [SMILES: CNCC(OCc1cccc(N2CCN(C)c3nc(SC)ncc3C2=O)c1)c1ccccc1] | 9-methyl-6-(3-((2-(methylamino)-1-phenylethoxy)methyl)phenyl)-2-(methylthio)-6,7,8,9-tetrahydro-5H-pyrimido[4,5-e][1,4]diazepin-5-one | + |
| 227 | 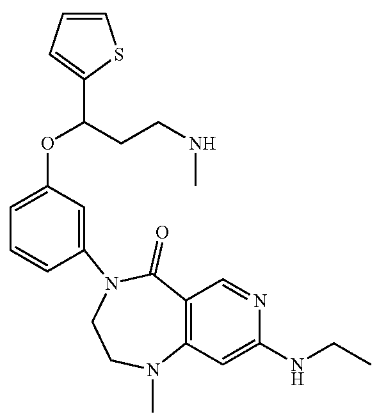 [SMILES: CCNc1cc2c(cn1)C(=O)N(c1cccc(OC(CCNC)c3cccs3)c1)CCN2C] | 8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 228 | 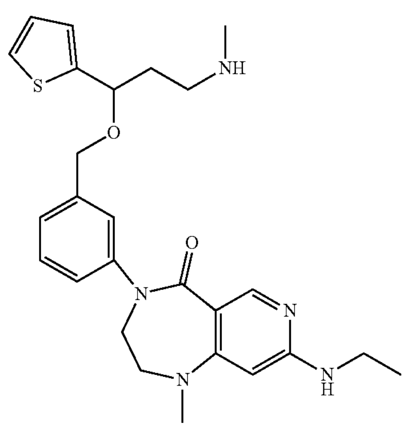 [SMILES: CCNc1cc2c(cn1)C(=O)N(c1cccc(COC(CCNC)c3cccs3)c1)CCN2C] | 8-(ethylamino)-1-methyl-4-(3-((3-(methylamino)-1-(thiophen-2-yl)propoxy)methyl)phenyl)-1,2,3,4-tetrahydro-5H-pyrido[4,3-e][1,4]diazepin-5-one | +++ |

TABLE 1-continued

| Ex | Structure | Name | Ki (nM) α2δ-1 |
|---|---|---|---|
| 229 | 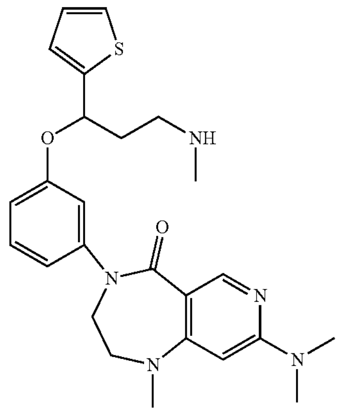 [SMILES: CNCCC(Oc1cccc(N2CCN(C)c3cc(N(C)C)ncc3C2=O)c1)c1cccs1] | 8-(dimethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 230 | 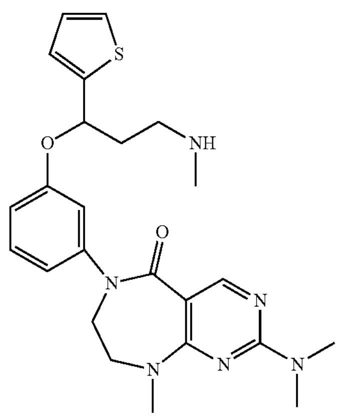 [SMILES: CNCCC(Oc1cccc(N2CCN(C)c3nc(N(C)C)ncc3C2=O)c1)c1cccs1] | 2-(dimethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | ++ |
| 231 | 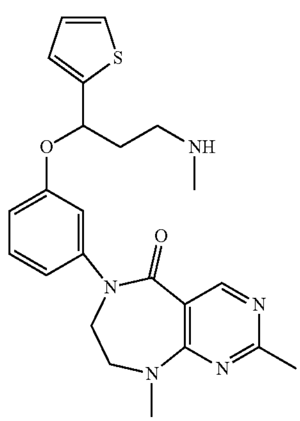 [SMILES: CNCCC(Oc1cccc(N2CCN(C)c3nc(C)ncc3C2=O)c1)c1cccs1] | 2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 232 | 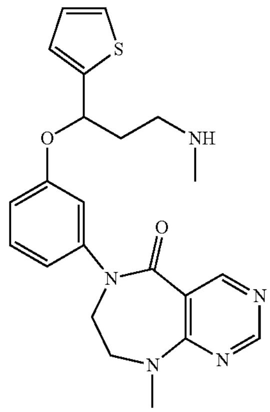 [SMILES: CNCCC(Oc1cccc(N2CCN(C)c3ncncc3C2=O)c1)c1cccs1] | 9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ |
| 233 | 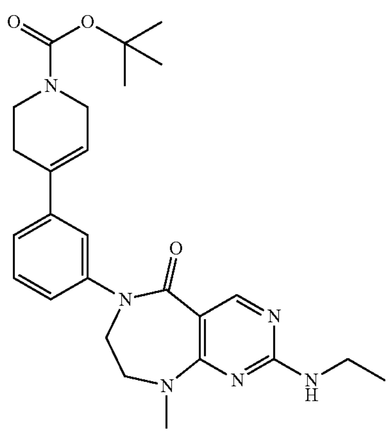 [SMILES: CCNc1ncc2c(n1)N(C)CCN(c1cccc(C3=CCN(C(=O)OC(C)(C)C)CC3)c1)C2=O] | tert-butyl 4-(3-(2-(ethylamino)-9-methyl-5-oxo-5,7,8,9-tetrahydro-6H-pyrimido[4,5-e][1,4]diazepin-6-yl)phenyl)-3,6-dihydropyridine-1(2H)-carboxylate | + |
| 234 | 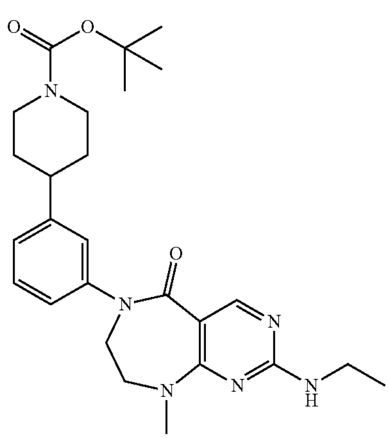 [SMILES: CCNc1ncc2c(n1)N(C)CCN(c1cccc(C3CCN(C(=O)OC(C)(C)C)CC3)c1)C2=O] | tert-butyl 4-(3-(2-(ethylamino)-9-methyl-5-oxo-5,7,8,9-tetrahydro-6H-pyrimido[4,5-e][1,4]diazepin-6-yl)phenyl)piperidine-1-carboxylate | + |

// TABLE 1-continued

| Ex | Structure | Name | Ki (nM) α2δ-1 |
|---|---|---|---|
| 235 | 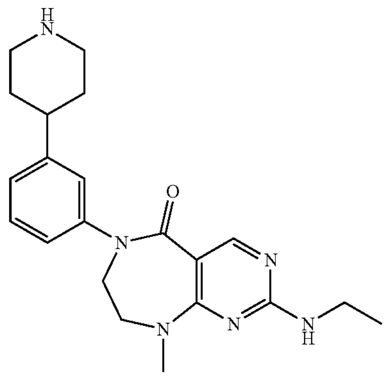 [SMILES: CCNc1ncc2c(n1)N(C)CCN(c1cccc(C3CCNCC3)c1)C2=O] | 2-(ethylamino)-9-methyl-6-(3-(piperidin-4-yl)phenyl)-6,7,8,9-tetrahydro-5H-pyrimido[4,5-e][1,4]diazepin-5-one | +++ |
| 236 | 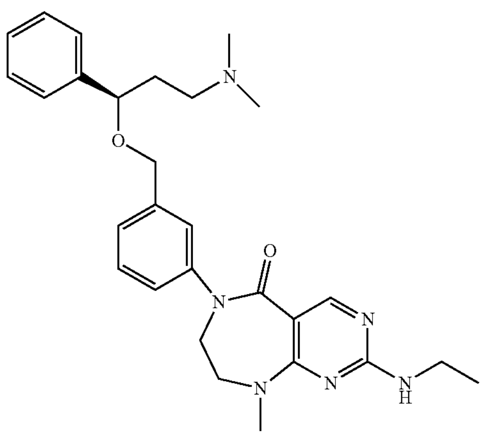 [SMILES: CCNc1ncc2c(n1)N(C)CCN(c1cccc(CO[C@H](CCN(C)C)c3ccccc3)c1)C2=O] | (R)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one | ++ |
| 237 | 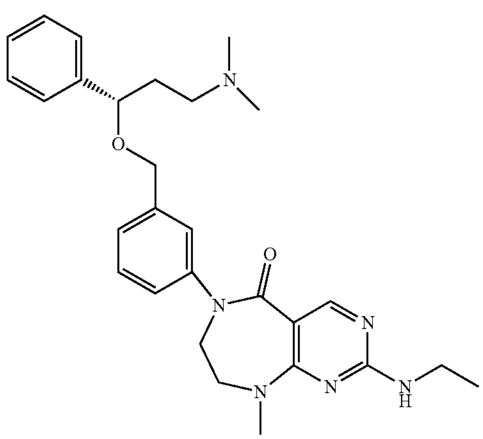 [SMILES: CCNc1ncc2c(n1)N(C)CCN(c1cccc(CO[C@@H](CCN(C)C)c3ccccc3)c1)C2=O] | (S)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 238 | 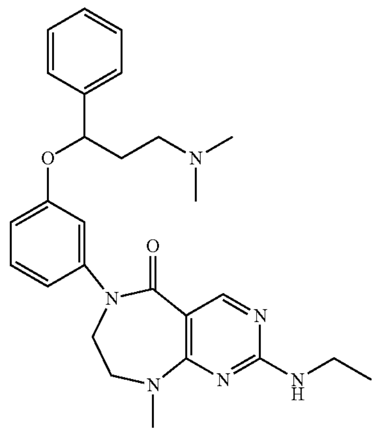 [SMILES: CCNc1ncc2c(n1)N(C)CCN(c1cccc(OC(CCN(C)C)c3ccccc3)c1)C2=O] | 6-(3-(3-(dimethylamino)-1-phenylpropoxy)phenyl)-2-(ethylamino)-9-methyl-6,7,8,9-tetrahydro-5H-pyrimido[4,5-e][1,4]diazepin-5-one | ++ |
| 239 | 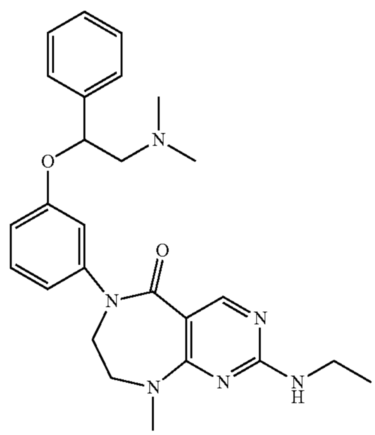 [SMILES: CCNc1ncc2c(n1)N(C)CCN(c1cccc(OC(CN(C)C)c3ccccc3)c1)C2=O] | 6-(3-(2-(dimethylamino)-1-phenylethoxy)phenyl)-2-(ethylamino)-9-methyl-6,7,8,9-tetrahydro-5H-pyrimido[4,5-e][1,4]diazepin-5-one | + |
| 240 | 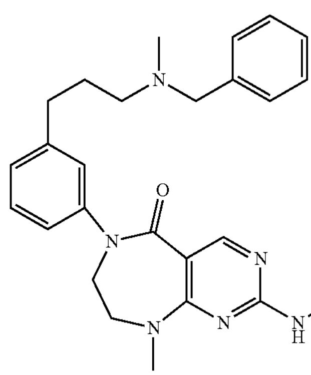 | 6-(3-(3-(benzyl(methyl)amino)propyl)phenyl)-2-(ethylamino)-9-methyl-6,7,8,9-tetrahydro-5H-pyrimido[4,5-e][1,4]diazepin-5-one | +++ |
| 241 | 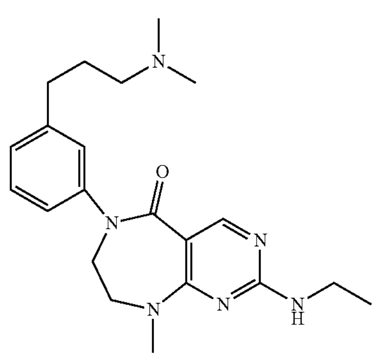 [SMILES: CCNc1ncc2c(n1)N(C)CCN(c1cccc(CCCN(C)C)c1)C2=O] | 6-(3-(3-(dimethylamino)propyl)phenyl)-2-(ethylamino)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 242 | 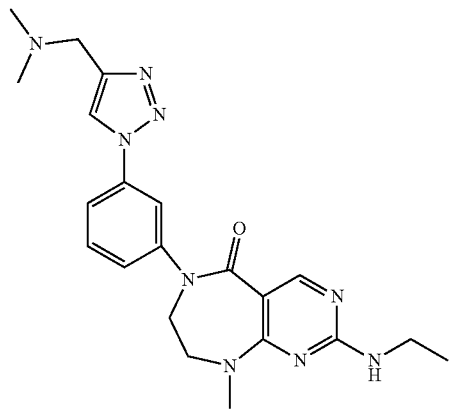 [SMILES: CCNc1ncc2c(n1)N(C)CCN(c1cccc(-n3cc(CN(C)C)nn3)c1)C2=O] | 6-(3-(4-((dimethylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |
| 243 | 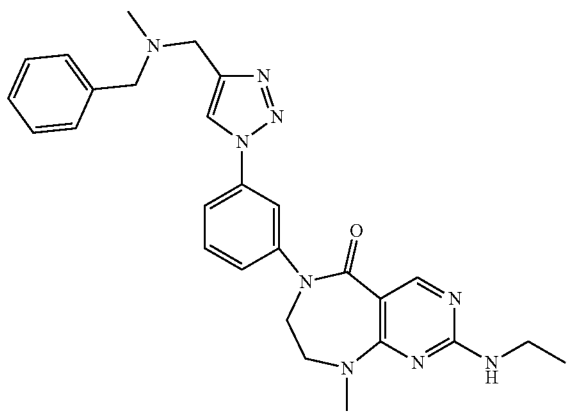 [SMILES: CCNc1ncc2c(n1)N(C)CCN(c1cccc(-n3cc(CN(C)Cc4ccccc4)nn3)c1)C2=O] | 6-(3-(4-((benzyl(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | ++ |
| 244 | 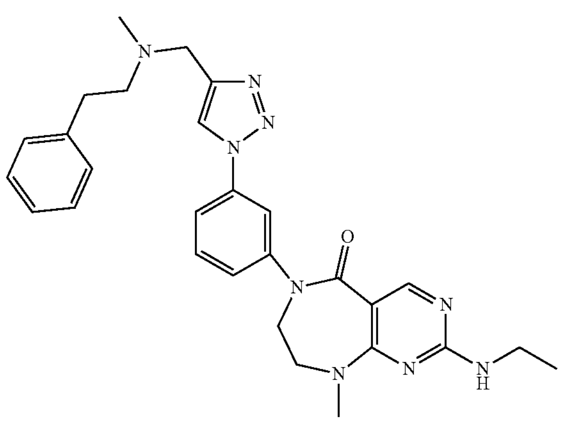 | 2-(ethylamino)-9-methyl-6-(3-(4-((methyl(phenethyl)amino)methyl)-1H-1,2,3-triazol-1-yl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 245 | 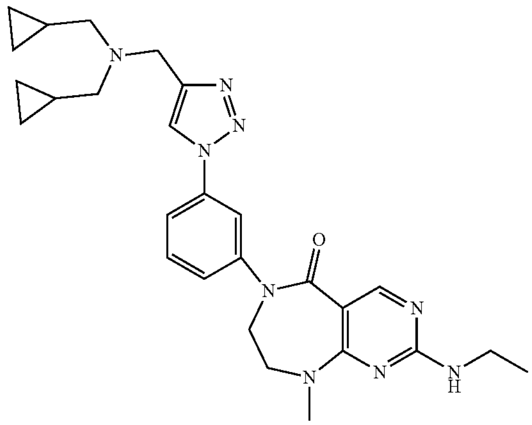 [SMILES: CCNc1ncc2c(n1)N(C)CCN(c1cccc(-n3cc(CN(CC4CC4)CC4CC4)nn3)c1)C2=O] | 6-(3-(4-((bis(cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | ++ |
| 246 | 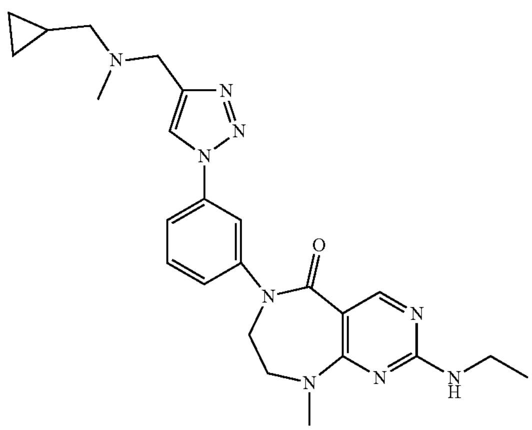 [SMILES: CCNc1ncc2c(n1)N(C)CCN(c1cccc(-n3cc(CN(C)CC4CC4)nn3)c1)C2=O] | 6-(3-(4-(((cyclopropylmethyl)(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |
| 247 | 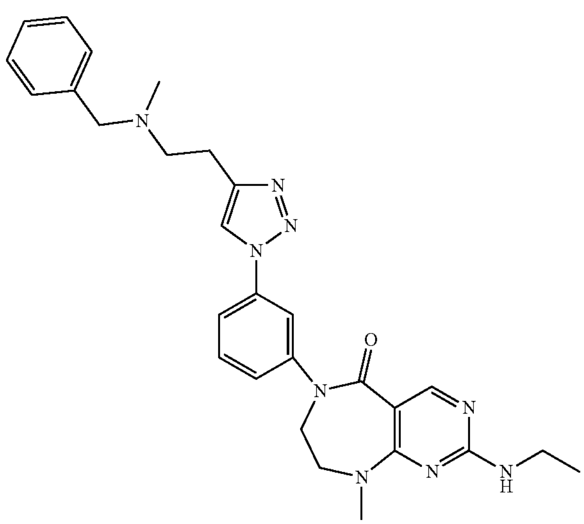 [SMILES: CCNc1ncc2c(n1)N(C)CCN(c1cccc(-n3cc(CCN(C)Cc4ccccc4)nn3)c1)C2=O] | 6-(3-(4-(2-(benzyl(methyl)amino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 248 | 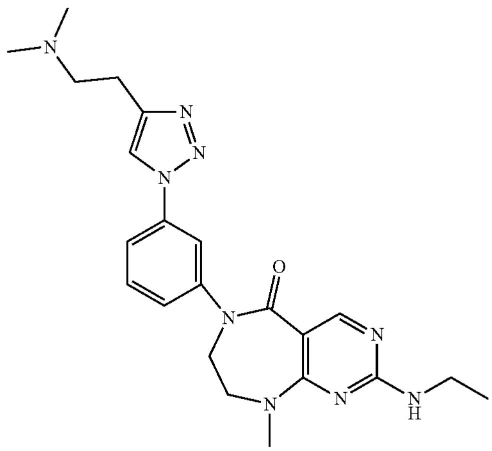 [SMILES: CCNc1ncc2c(n1)N(C)CCN(c1cccc(-n3cc(CCN(C)C)nn3)c1)C2=O] | 6-(3-(4-(2-(dimethylamino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |
| 249 | 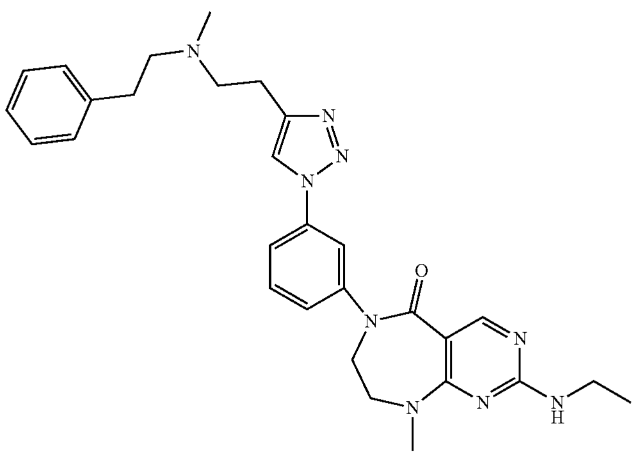 [SMILES: CCNc1ncc2c(n1)N(C)CCN(c1cccc(-n3cc(CCN(C)CCc4ccccc4)nn3)c1)C2=O] | 2-(ethylamino)-9-methyl-6-(3-(4-(2-(methyl(phenethyl)amino)ethyl)-1H-1,2,3-triazol-1-yl)phenyl)-6,7,8,9-tetrahydro-5H-pyrimido[4,5-e][1,4]diazepin-5-one | +++ |
| 250 | 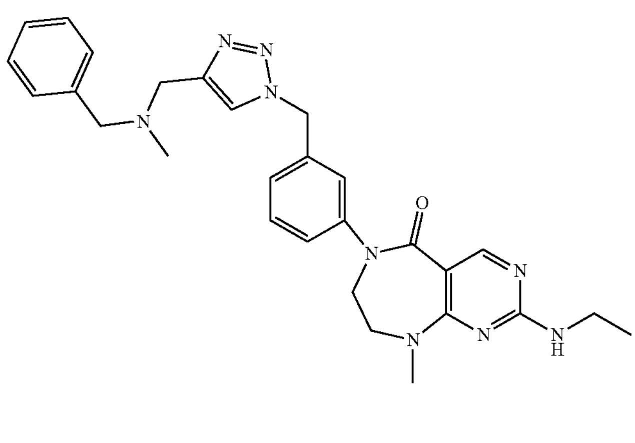 [SMILES: CCNc1ncc2c(n1)N(C)CCN(c1cccc(Cn3cc(CN(C)Cc4ccccc4)nn3)c1)C2=O] | 6-(3-((4-((benzyl(methyl)amino)methyl)-1H-1,2,3-triazol-1-yl)methyl)phenyl)-2-(ethylamino)-9-methyl-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 251 | 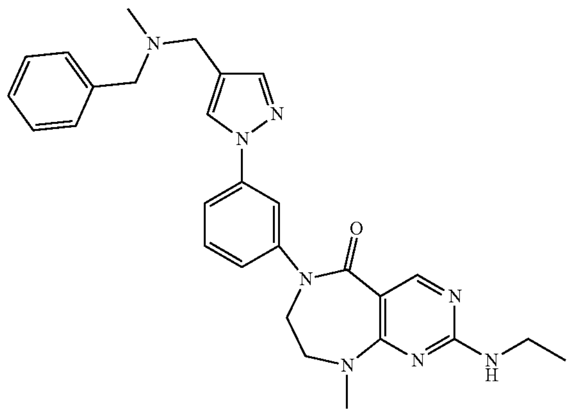 [SMILES: CCNc1ncc2c(n1)N(C)CCN(c1cccc(-n3cc(CN(C)Cc4ccccc4)cn3)c1)C2=O] | 6-(3-(4-((benzyl(methyl)amino)methyl)-1H-pyrazol-1-yl)phenyl)-2-(ethylamino)-9-methyl-6,7,8,9-tetrahydro-5H-pyrimido[4,5-e][1,4]diazepin-5-one | +++ |
| 252 | 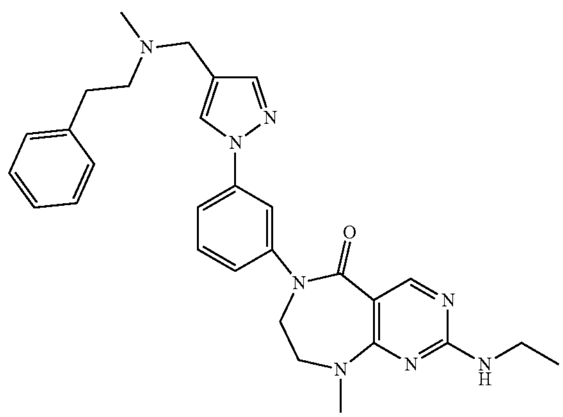 [SMILES: CCNc1ncc2c(n1)N(C)CCN(c1cccc(-n3cc(CN(C)CCc4ccccc4)cn3)c1)C2=O] | 2-(ethylamino)-9-methyl-6-(3-(4-((methyl(phenethyl)amino)methyl)-1H-pyrazol-1-yl)phenyl)-6,7,8,9-tetrahydro-5H-pyrimido[4,5-e][1,4]diazepin-5-one | ++ |
| 253 | 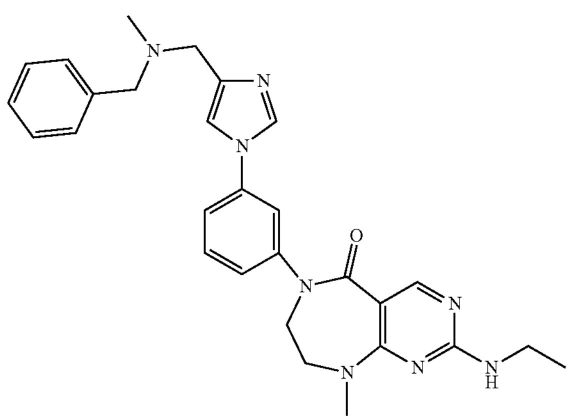 | 6-(3-(4-((benzyl(methyl)amino)methyl)-1H-imidazol-1-yl)phenyl)-2-(ethylamino)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 254 | 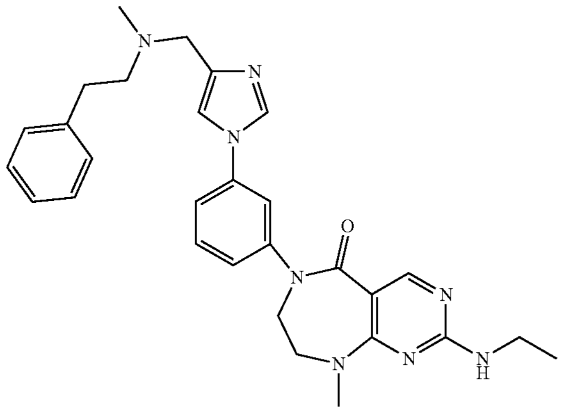 [SMILES: CCNc1ncc2c(n1)N(C)CCN(c1cccc(-n3cnc(CN(C)CCc4ccccc4)c3)c1)C2=O] | 2-(ethylamino)-9-methyl-6-(3-(4-((methyl(phenethyl)amino)methyl)-1H-imidazol-1-yl)phenyl)-6,7,8,9-tetrahydro-5H-pyrimido[4,5-e][1,4]diazepin-5-one | ++ |
| 255 | 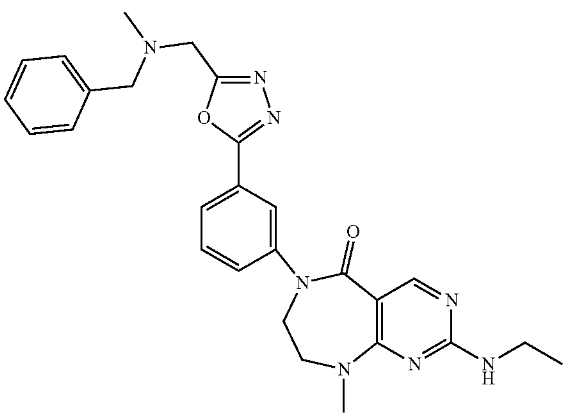 [SMILES: CCNc1ncc2c(n1)N(C)CCN(c1cccc(-c3nnc(CN(C)Cc4ccccc4)o3)c1)C2=O] | 6-(3-(5-((benzyl(methyl)amino)methyl)-1,3,4-oxadiazol-2-yl)phenyl)-2-(ethylamino)-9-methyl-6,7,8,9-tetrahydro-5H-pyrimido[4,5-e][1,4]diazepin-5-one | +++ |
| 256 | 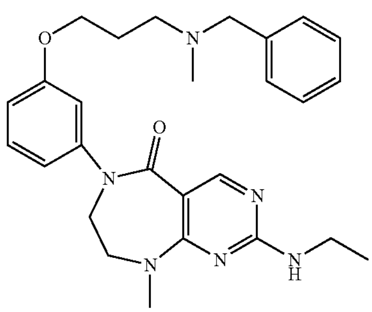 [SMILES: CCNc1ncc2c(n1)N(C)CCN(c1cccc(OCCCN(C)Cc3ccccc3)c1)C2=O] | 6-(3-(3-(benzyl(methyl)amino)propoxy)phenyl)-2-(ethylamino)-9-methyl-6,7,8,9-tetrahydro-5H-pyrimido[4,5-e][1,4]diazepin-5-one | +++ |
| 257 | 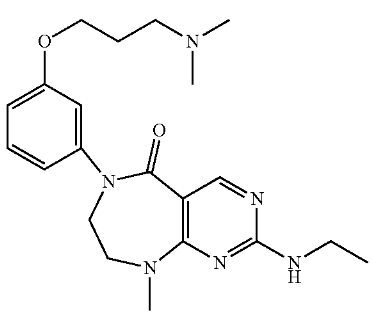 [SMILES: CCNc1ncc2c(n1)N(C)CCN(c1cccc(OCCCN(C)C)c1)C2=O] | 6-(3-(3-(dimethylamino)propoxy)phenyl)-2-(ethylamino)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 258 | 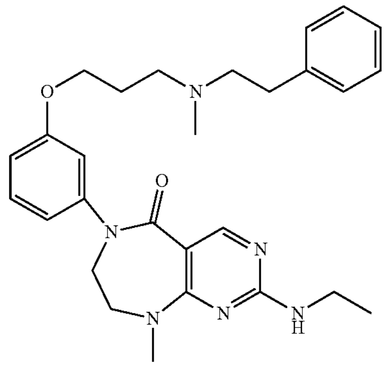 [SMILES: CCNc1ncc2c(n1)N(C)CCN(c1cccc(OCCCN(C)CCc3ccccc3)c1)C2=O] | 2-(ethylamino)-9-methyl-6-(3-(3-(methyl(phenethyl)amino)propoxy)phenyl)-6,7,8,9-tetrahydro-5H-pyrimido[4,5-e][1,4]diazepin-5-one | ++ |
| 259 | 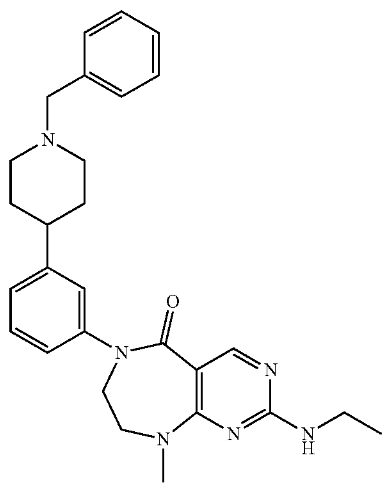 [SMILES: CCNc1ncc2c(n1)N(C)CCN(c1cccc(C3CCN(Cc4ccccc4)CC3)c1)C2=O] | 6-(3-(1-benzylpiperidin-4-yl)phenyl)-2-(ethylamino)-9-methyl-6,7,8,9-tetrahydro-5H-pyrimido[4,5-e][1,4]diazepin-5-one | +++ |
| 260 | 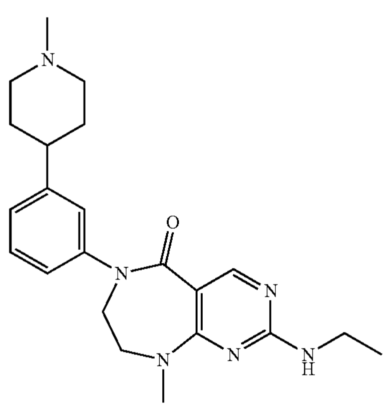 [SMILES: CCNc1ncc2c(n1)N(C)CCN(c1cccc(C3CCN(C)CC3)c1)C2=O] | 2-(ethylamino)-9-methyl-6-(3-(1-methylpiperidin-4-yl)phenyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 261 | 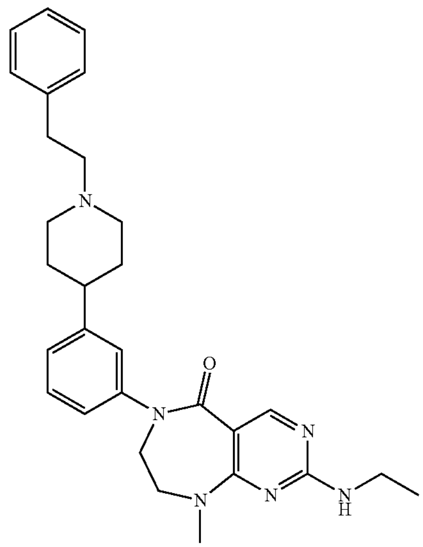 [SMILES: CCNc1ncc2c(n1)N(C)CCN(c1cccc(C3CCN(CCc4ccccc4)CC3)c1)C2=O] | 2-(ethylamino)-9-methyl-6-(3-(1-phenethylpiperidin-4-yl)phenyl)-6,7,8,9-tetrahydro-5H-pyrimido[4,5-e][1,4]diazepin-5-one | +++ |
| 262 | 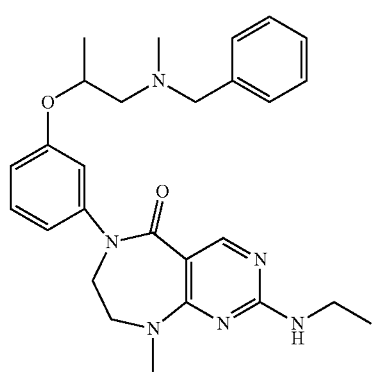 [SMILES: CCNc1ncc2c(n1)N(C)CCN(c1cccc(OC(C)CN(C)Cc3ccccc3)c1)C2=O] | 6-(3-((1-(benzyl(methyl)amino)propan-2-yl)oxy)phenyl)-2-(ethylamino)-9-methyl-6,7,8,9-tetrahydro-5H-pyrimido[4,5-e][1,4]diazepin-5-one | ++ |
| 263 | 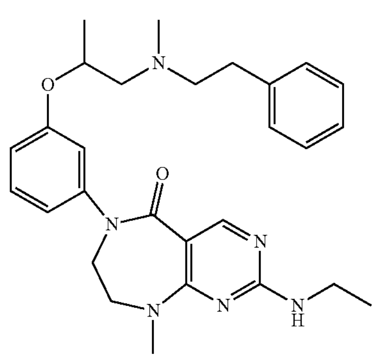 [SMILES: CCNc1ncc2c(n1)N(C)CCN(c1cccc(OC(C)CN(C)CCc3ccccc3)c1)C2=O] | 2-(ethylamino)-9-methyl-6-(3-((1-(methyl(phenethyl)amino)propan-2-yl)oxy)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 264 | 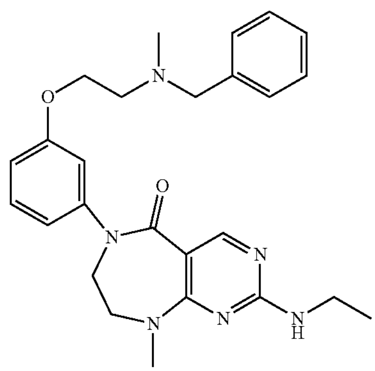 | 6-(3-(2-(benzyl(methyl)amino)ethoxy)phenyl)-2-(ethylamino)-9-methyl-6,7,8,9-tetrahydro-5H-pyrimido[4,5-e][1,4]diazepin-5-one | +++ |
| 265 | 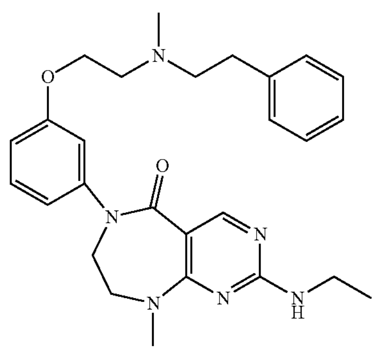 [SMILES: CCNc1ncc2c(n1)N(C)CCN(c1cccc(OCCN(C)CCc3ccccc3)c1)C2=O] | 2-(ethylamino)-9-methyl-6-(3-(2-(methyl(phenethyl)amino)ethoxy)phenyl)-6,7,8,9-tetrahydro-5H-pyrimido[4,5-e][1,4]diazepin-5-one | +++ |
| 266 | 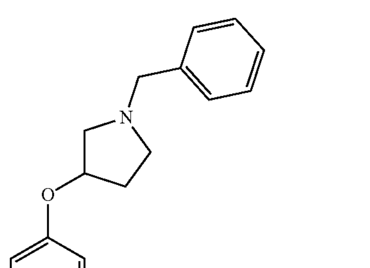 | 6-(3-((1-benzylpyrrolidin-3-yl)oxy)phenyl)-2-(ethylamino)-9-methyl-6,7,8,9-tetrahydro-5H-pyrimido[4,5-e][1,4]diazepin-5-one | +++ |
| 267 | 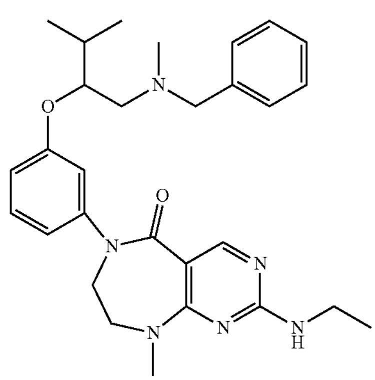 [SMILES: CCNc1ncc2c(n1)N(C)CCN(c1cccc(OC(CN(C)Cc3ccccc3)C(C)C)c1)C2=O] | 6-(3-((1-(benzyl(methyl)amino)-3-methylbutan-2-yl)oxy)phenyl)-2-(ethylamino)-9-methyl-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 268 | 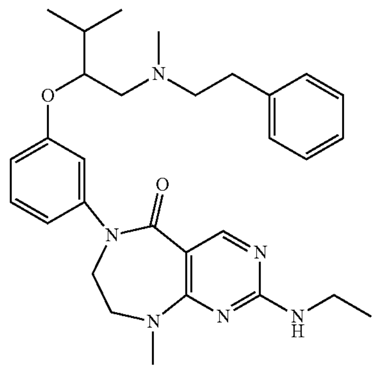 [SMILES: CCNc1ncc2c(n1)N(C)CCN(c1cccc(OC(CN(C)CCc3ccccc3)C(C)C)c1)C2=O] | 2-(ethylamino)-9-methyl-6-(3-((3-methyl-1-(methyl(phenethyl)amino)butan-2-yl)oxy)phenyl)-6,7,8,9-tetrahydro-5H-pyrimido[4,5-e][1,4]diazepin-5-one | ++ |
| 269 | 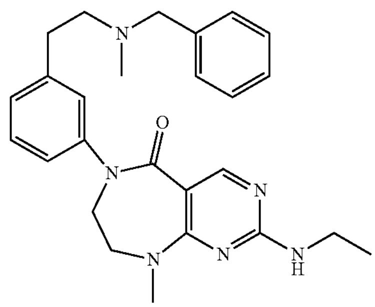 [SMILES: CCNc1ncc2c(n1)N(C)CCN(c1cccc(CCN(C)Cc3ccccc3)c1)C2=O] | 6-(3-(2-(benzyl(methyl)amino)ethyl)phenyl)-2-(ethylamino)-9-methyl-6,7,8,9-tetrahydro-5H-pyrimido[4,5-e][1,4]diazepin-5-one | +++ |
| 270 | 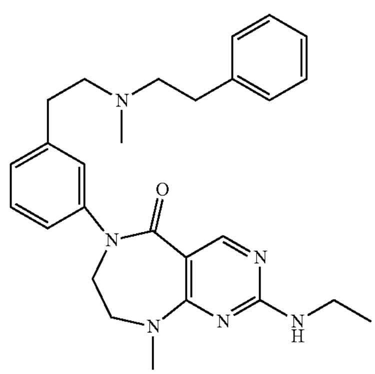 [SMILES: CCNc1ncc2c(n1)N(C)CCN(c1cccc(CCN(C)CCc3ccccc3)c1)C2=O] | 2-(ethylamino)-9-methyl-6-(3-(2-(methyl(phenethyl)amino)ethyl)phenyl)-6,7,8,9-tetrahydro-5H-pyrimido[4,5-e][1,4]diazepin-5-one | +++ |
| 271 | 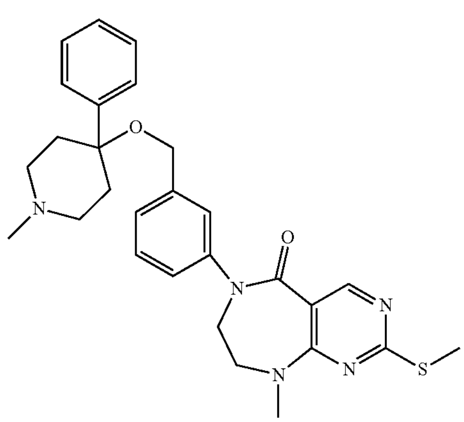 | 9-methyl-6-(3-(((1-methyl-4-phenylpiperidin-4-yl)oxy)methyl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 272 | 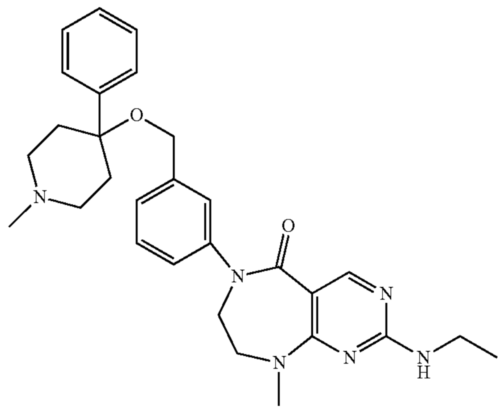 [SMILES: CCNc1ncc2c(n1)N(C)CCN(c1cccc(COC3(c4ccccc4)CCN(C)CC3)c1)C2=O] | 2-(ethylamino)-9-methyl-6-(3-(((1-methyl-4-phenylpiperidin-4-yl)oxy)methyl)phenyl)-6,7,8,9-tetrahydro-5H-pyrimido[4,5-e][1,4]diazepin-5-one | ++ |
| 273 | 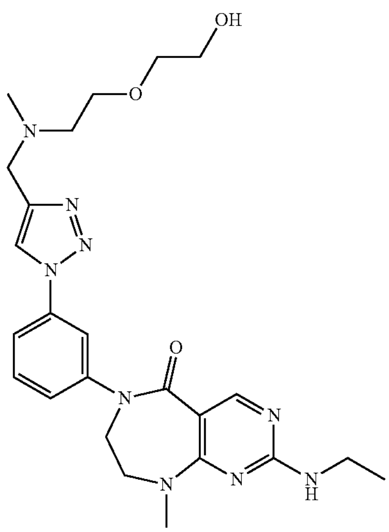 [SMILES: CCNc1ncc2c(n1)N(C)CCN(c1cccc(-n3cc(CN(C)CCOCCO)nn3)c1)C2=O] | 2-(ethylamino)-6-(3-(4-(((2-(2-hydroxyethoxy)ethyl)(methyl)amino)methyl)-1H-1,2,3-triazol-1-yl)phenyl)-9-methyl-6,7,8,9-tetrahydro-5H-pyrimido[4,5-e][1,4]diazepin-5-one | ++ |
| 274 | 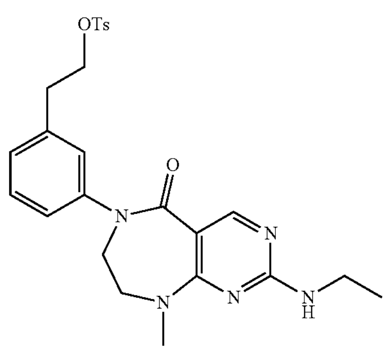 [SMILES: CCNc1ncc2c(n1)N(C)CCN(c1cccc(CCOS(=O)(=O)c3ccc(C)cc3)c1)C2=O] | 3-(2-(ethylamino)-9-methyl-5-oxo-5,7,8,9-tetrahydro-6H-pyrimido[4,5-e][1,4]diazepin-6-yl)phenethyl 4-methylbenzenesulfonate | + |

TABLE 1-continued

| Ex | Structure | Name | Ki (nM) α2δ-1 |
|---|---|---|---|
| 275 | 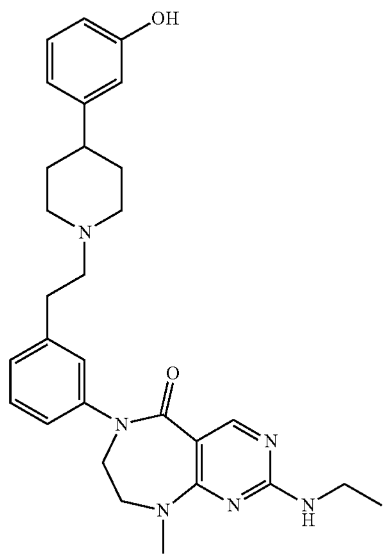 [SMILES: CCNc1ncc2c(n1)N(C)CCN(c1cccc(CCN3CCC(c4cccc(O)c4)CC3)c1)C2=O] | 2-(ethylamino)-6-(3-(2-(4-(3-hydroxyphenyl)piperidin-1-yl)ethyl)phenyl)-9-methyl-6,7,8,9-tetrahydro-5H-pyrimido[4,5-e][1,4]diazepin-5-one | +++ |
| 276 | 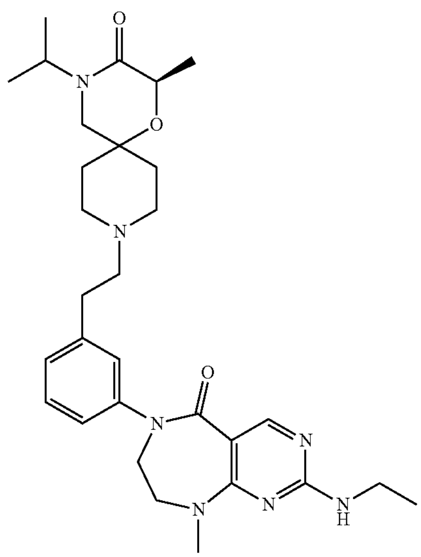 [SMILES: CCNc1ncc2c(n1)N(C)CCN(c1cccc(CCN3CCC4(CC3)CN(C(C)C)C(=O)[C@@H](C)O4)c1)C2=O] | (R)-9-(3-(2-(ethylamino)-9-methyl-5-oxo-5,7,8,9-tetrahydro-6H-pyrimido[4,5-e][1,4]diazepin-6-yl)phenethyl)-4-isopropyl-2-methyl-1-oxa-4,9-diazaspiro[5.5]undecan-3-one | +++ |
| 277 | 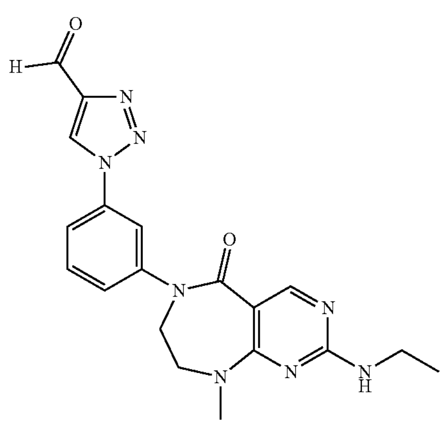 [SMILES: CCNc1ncc2c(n1)N(C)CCN(c1cccc(-n3cc(C=O)nn3)c1)C2=O] | 1-(3-(2-(ethylamino)-9-methyl-5-oxo-5,7,8,9-tetrahydro-6H-pyrimido[4,5-e][1,4]diazepin-6-yl)phenyl)-1H-1,2,3-triazole-4-carbaldehyde | |

TABLE 1-continued

| Ex | Structure | Name | Ki (nM) α2δ-1 |
|---|---|---|---|
| 278 | 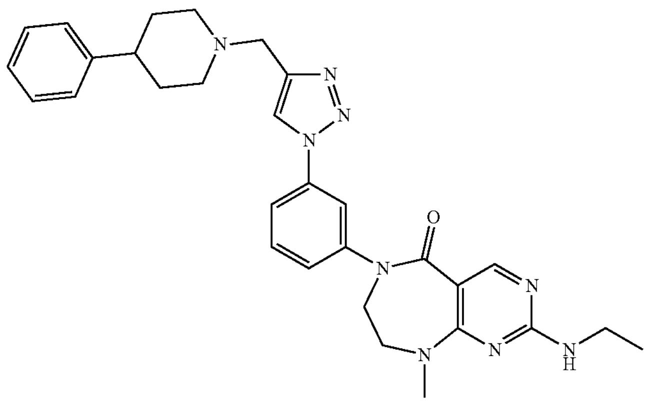 [SMILES: CCNc1ncc2c(n1)N(C)CCN(c1cccc(-n3cc(CN4CCC(c5ccccc5)CC4)nn3)c1)C2=O] | 2-(ethylamino)-9-methyl-6-(3-(4-((4-phenylpiperidin-1-yl)methyl)-1H-1,2,3-triazol-1-yl)phenyl)-6,7,8,9-tetrahydro-5H-pyrimido[4,5-e][1,4]diazepin-5-one | ++ |
| 279 | 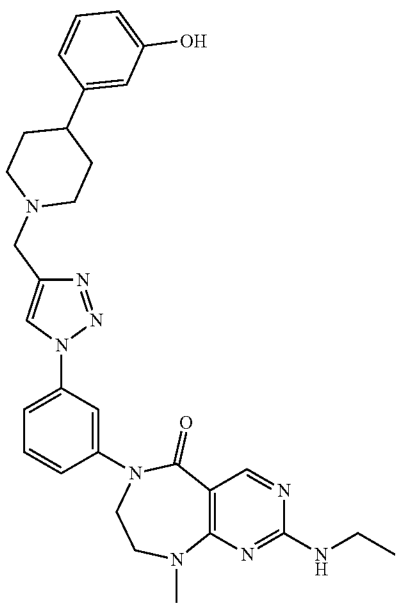 [SMILES: CCNc1ncc2c(n1)N(C)CCN(c1cccc(-n3cc(CN4CCC(c5cccc(O)c5)CC4)nn3)c1)C2=O] | 2-(ethylamino)-6-(3-(4-((4-(3-hydroxyphenyl)piperidin-1-yl)methyl)-1H-1,2,3-triazol-1-yl)phenyl)-9-methyl-6,7,8,9-tetrahydro-5H-pyrimido[4,5-e][1,4]diazepin-5-one | +++ |
| 280 | 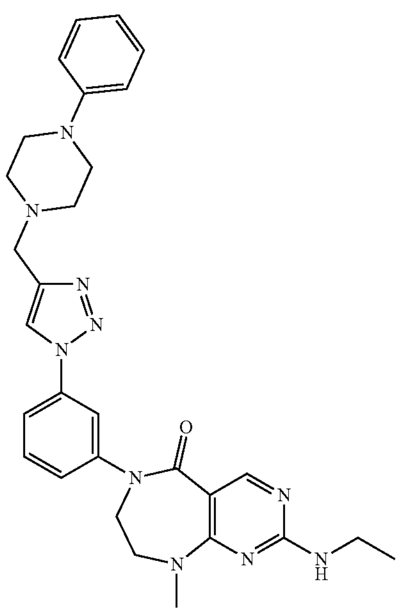 [SMILES: CCNc1ncc2c(n1)N(C)CCN(c1cccc(-n3cc(CN4CCN(c5ccccc5)CC4)nn3)c1)C2=O] | 2-(ethylamino)-9-methyl-6-(3-(4-((4-phenylpiperazin-1-yl)methyl)-1H-1,2,3-triazol-1-yl)phenyl)-6,7,8,9-tetrahydro-5H-pyrimido[4,5-e][1,4]diazepin-5-one | +++ |

TABLE 1-continued

| Ex | Name | Ki (nM) α2δ-1 |
|---|---|---|
| 281 | 2-(ethylamino)-9-methyl-6-(3-(4-(piperidin-1-ylmethyl)-1H-1,2,3-triazol-1-yl)phenyl)-6,7,8,9-tetrahydro-5H-pyrimido[4,5-e][1,4]diazepin-5-one | +++ |
| 282 | 6-(3-(4-((3,4-dihydroisoquinolin-2(1H)-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | ++ |
| 283 | 6-(3-(4-((3,4-dihydro-2H-spiro[isoquinoline-1,4'-piperidin]-1'-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |

| Ex | Structure | Name | Ki (nM) α2δ-1 |
|---|---|---|---|
| 284 | 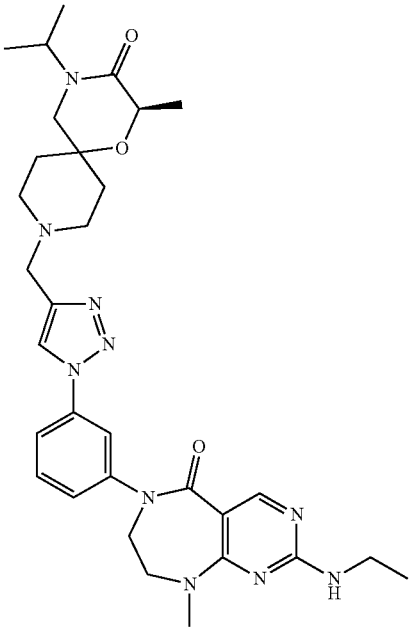 [SMILES: CCNc1ncc2c(n1)N(C)CCN(c1cccc(-n3cc(CN4CCC5(CC4)CN(C(C)C)C(=O)[C@@H](C)O5)nn3)c1)C2=O] | (R)-9-((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)-4-isopropyl-2-methyl-1-oxa-4,9-diazaspiro[5.5]undecan-3-one | +++ |
| 285 | 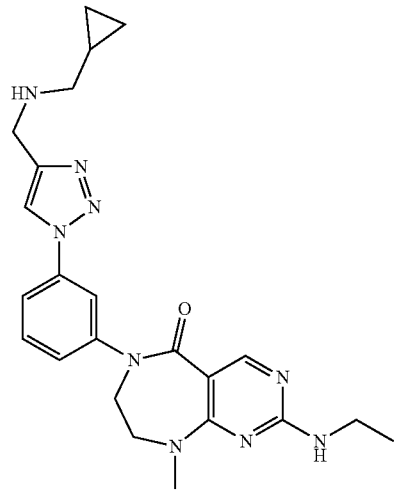 [SMILES: CCNc1ncc2c(n1)N(C)CCN(c1cccc(-n3cc(CNCC4CC4)nn3)c1)C2=O] | 6-(3-(4-(((cyclopropylmethyl)amino)methyl-1H-1,2,3-triazol-1-yl)phenyl)-2-(ethylamino)-9-methyl-6,7,8,9-tetrahydro-5H-pyrimido[4,5-e][1,4]diazepin-5-one | +++ |
| 286 | 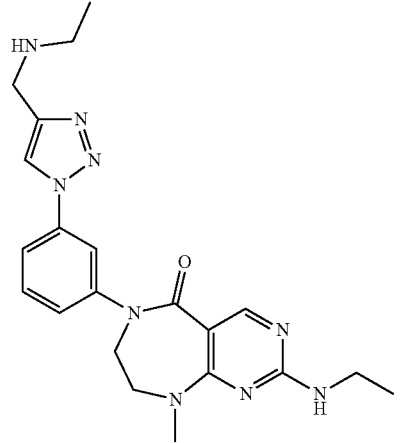 [SMILES: CCNCc1cn(-c2cccc(N3CCN(C)c4nc(NCC)ncc4C3=O)c2)nn1] | 2-(ethylamino)-6-(3-(4-((ethylamino)methyl)-1H-1,2,3-triazol-1-yl)phenyl)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 287 | 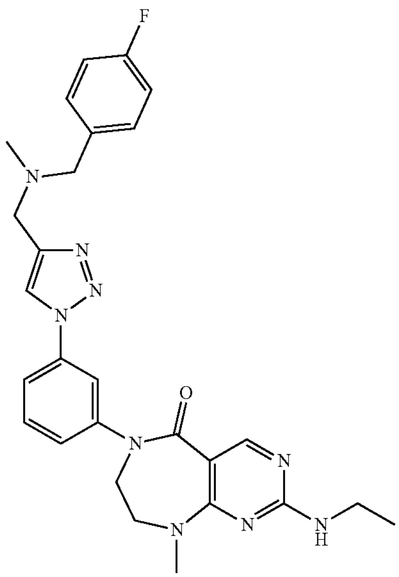 [SMILES: CCNc1ncc2c(n1)N(C)CCN(c1cccc(-n3cc(CN(C)Cc4ccc(F)cc4)nn3)c1)C2=O] | 2-(ethylamino)-6-(3-(4-((((4-fluorobenzyl)(methyl)amino)methyl)-1H-1,2,3-triazol-1-yl)phenyl)-9-methyl-6,7,8,9-tetrahydro-5H-pyrimido[4,5-e][1,4]diazepin-5-one | ++ |
| 288 | 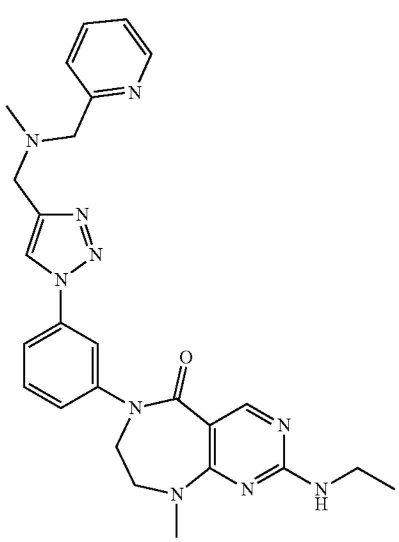 [SMILES: CCNc1ncc2c(n1)N(C)CCN(c1cccc(-n3cc(CN(C)Cc4ccccn4)nn3)c1)C2=O] | 2-(ethylamino)-9-methyl-6-(3-(4-((methyl(pyridin-2-ylmethyl)amino)methyl)-1H-1,2,3-triazol-1-yl)phenyl)-6,7,8,9-tetrahydro-5H-pyrimido[4,5-e][1,4]diazepin-5-one | ++ |

TABLE 1-continued
| Ex | Structure | Name | Ki (nM) α2δ-1 |
|---|---|---|---|
| 289 | 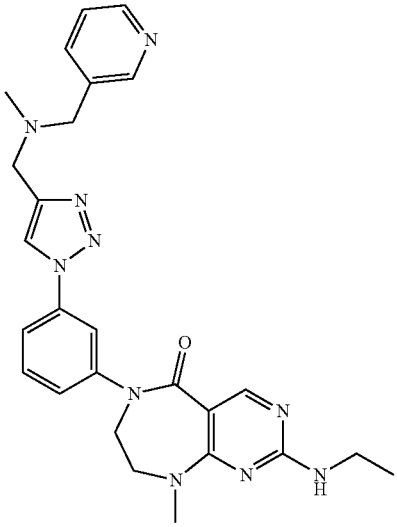 [SMILES: CCNc1ncc2c(n1)N(C)CCN(c1cccc(-n3cc(CN(C)Cc4cccnc4)nn3)c1)C2=O] | 2-(ethylamino)-9-methyl-6-(3-(4-((methyl(pyridin-3-ylmethyl)amino)methyl)-1H-1,2,3-triazol-1-yl)phenyl)-6,7,8,9-tetrahydro-5H-pyrimido[4,5-e][1,4]diazepin-5-one | +++ |
| 290 | 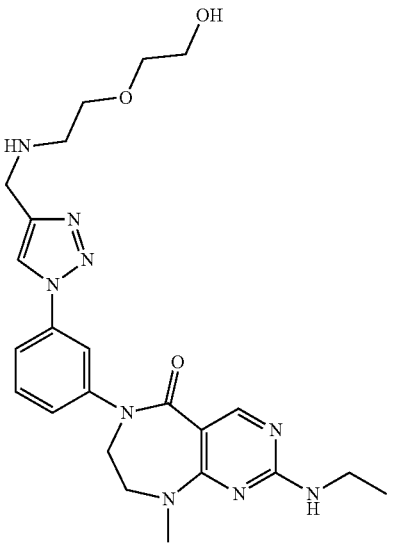 [SMILES: CCNc1ncc2c(n1)N(C)CCN(c1cccc(-n3cc(CNCCOCCO)nn3)c1)C2=O] | 2-(ethylamino)-6-(3-(4-(((2-(2-hydroxyethoxy)ethyl)amino)methyl)-1H-1,2,3-triazol-1-yl)phenyl)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 291 | 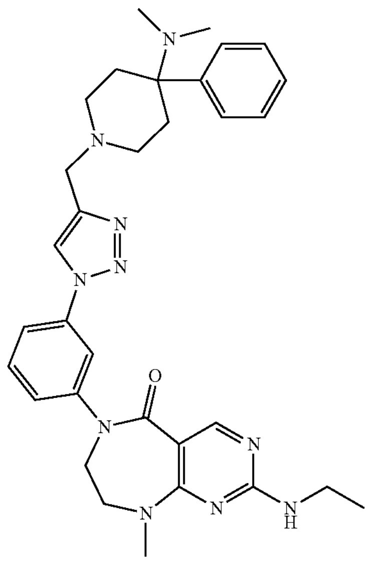 [SMILES: CCNc1ncc2c(n1)N(C)CCN(c1cccc(-n3cc(CN4CCC(c5ccccc5)(N(C)C)CC4)nn3)c1)C2=O] | 6-(3-(4-((4-(dimethylamino)-4-phenylpiperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |
| 292 | 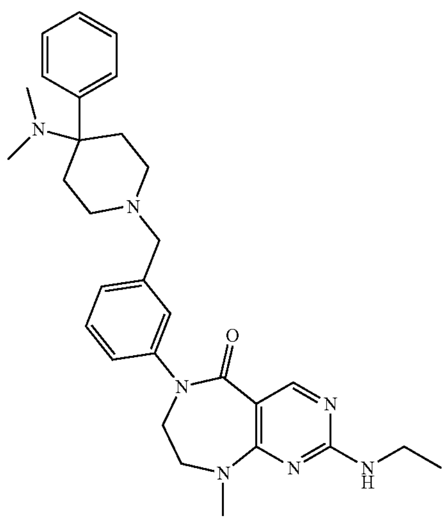 [SMILES: CCNc1ncc2c(n1)N(C)CCN(c1cccc(CN3CCC(c4ccccc4)(N(C)C)CC3)c1)C2=O] | 6-(3-((4-(dimethylamino)-4-phenylpiperidin-1-yl)methyl)phenyl)-2-(ethylamino)-9-methyl-6,7,8,9-tetrahydro-5H-pyrimido[4,5-e][1,4]diazepin-5-one | ++ |
| 293 | 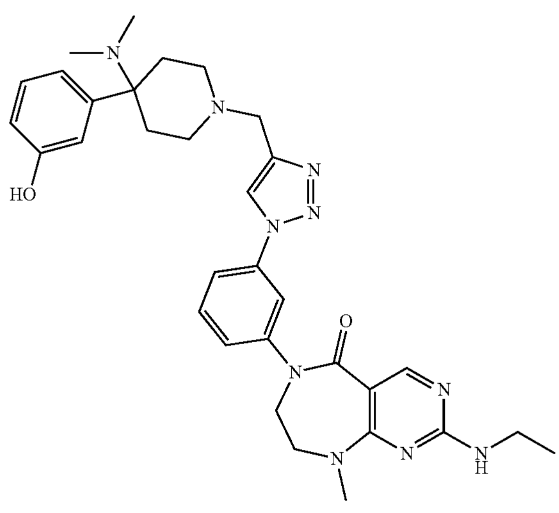 [SMILES: CCNc1ncc2c(n1)N(C)CCN(c1cccc(-n3cc(CN4CCC(c5cccc(O)c5)(N(C)C)CC4)nn3)c1)C2=O] | 6-(3-(4-((4-(dimethylamino)-4-(3-hydroxyphenyl)piperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ |

| Ex | Structure | Name | Ki (nM) α2δ-1 |
|---|---|---|---|
| 294 | 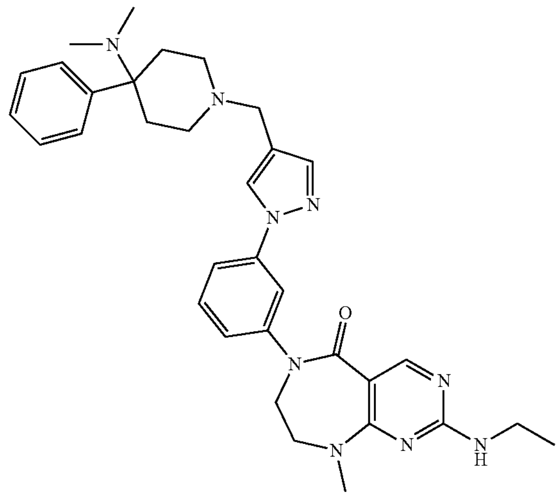 [SMILES: CCNc1ncc2c(n1)N(C)CCN(c1cccc(-n3cc(CN4CCC(c5ccccc5)(N(C)C)CC4)cn3)c1)C2=O] | 6-(3-(4-((4-(dimethylamino)-4-phenylpiperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one | ++ |
| 295 | 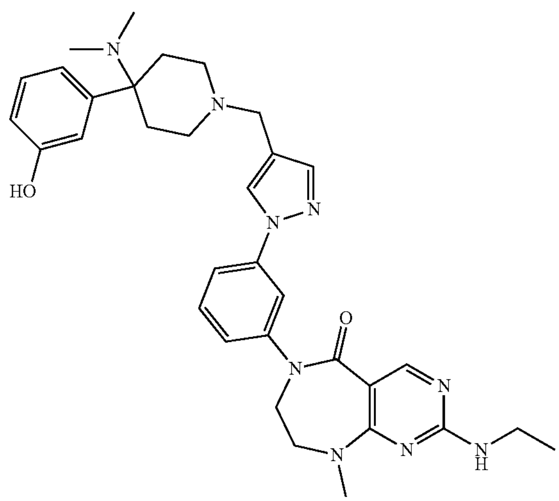 [SMILES: CCNc1ncc2c(n1)N(C)CCN(c1cccc(-n3cc(CN4CCC(c5cccc(O)c5)(N(C)C)CC4)cn3)c1)C2=O] | 6-(3-(4-((4-(dimethylamino)-4-(3-hydroxyphenyl)piperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one | +++ |
| 296 | 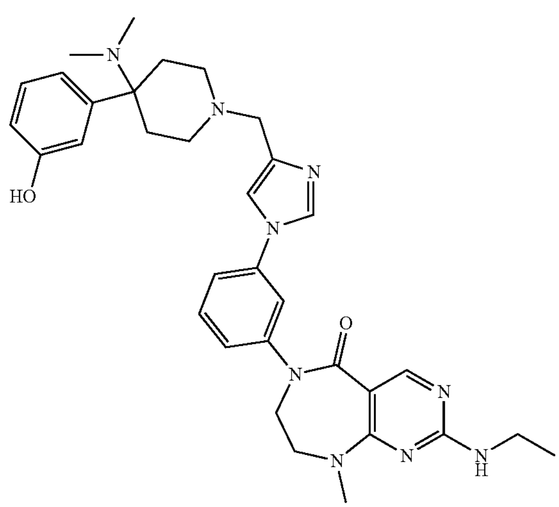 [SMILES: CCNc1ncc2c(n1)N(C)CCN(c1cccc(-n3cnc(CN4CCC(c5cccc(O)c5)(N(C)C)CC4)c3)c1)C2=O] | 6-(3-(4-((4-(dimethylamino)-4-(3-hydroxyphenyl)piperidin-1-yl)methyl)-1H-imidazol-1-yl)phenyl)-2-(ethylamino)-9-methyl-6,7,8,9-tetrahydro-5H-pyrimido[4,5-e][1,4]diazepin-5-one | ++ |

| Ex | Structure | Name | Ki (nM) α2δ-1 |
|---|---|---|---|
| 297 | 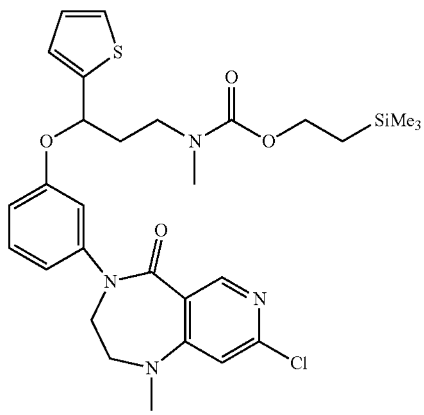 [SMILES: CN(CCC(Oc1cccc(N2CCN(C)c3cc(Cl)ncc3C2=O)c1)c1cccs1)C(=O)OCC[Si](C)(C)C] | 2-(trimethylsilyl)ethyl (3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate | + |
| 298 | 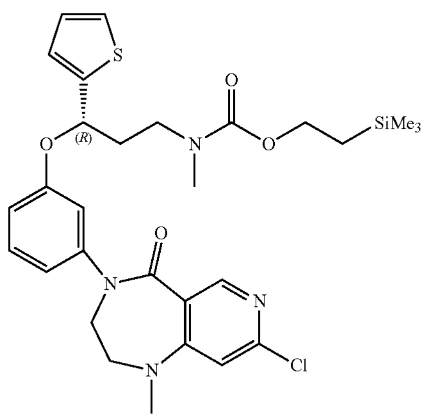 | 2-(trimethylsilyl)ethyl (S)-(3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate | + |
| 299 | 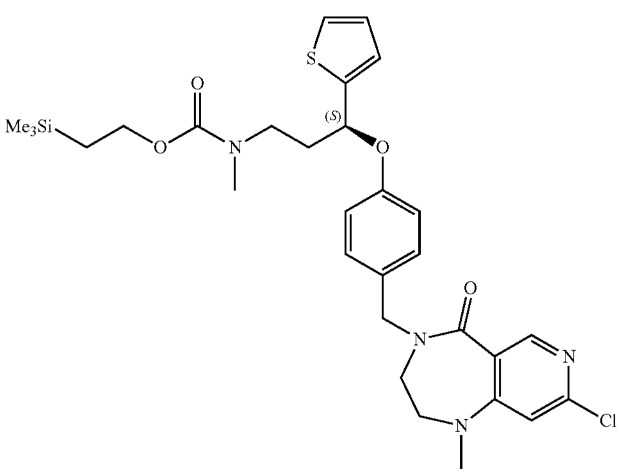 | 2-(trimethylsilyl)ethyl (S)-(3-(4-((8-chloro-1-methyl-5-oxo-1,2,3,5-tetrahydro-4H-pyrido[4,3-e][1,4]diazepin-4-yl)methyl)phenoxy)-3-(thiophen-2-yl)propyl)(methyl)carbamate | + |

TABLE 1-continued

| Ex | Structure | Name | Ki (nM) α2δ-1 |
|---|---|---|---|
| 300 | 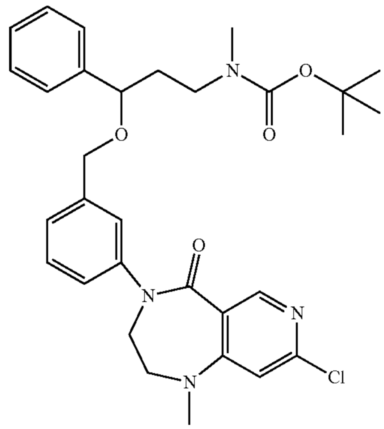 | tert-butyl (3-((3-(8-chloro-1-methyl-5-oxo-1,2,3,5-tetrahydro-4H-pyrido[4,3-e][1,4]diazepin-4-yl)benzyl)oxy)-3-phenylpropyl)(methyl) carbamate | + |
| 301 | 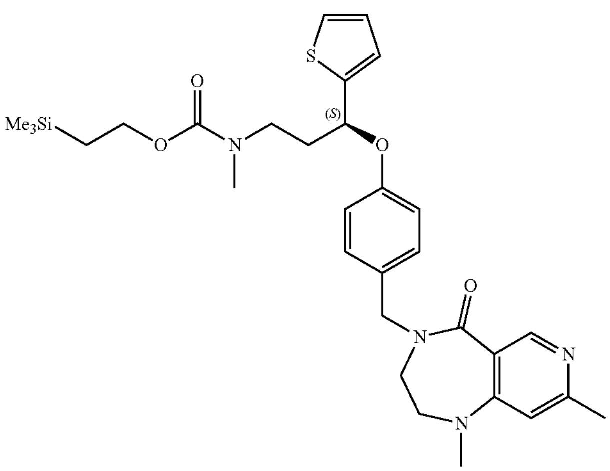 | 2-(trimethylsilyl)ethyl (S)-(3-(4-((1,8-dimethyl-5-oxo-1,2,3,5-tetrahydro-4H-pyrido[4,3-e][1,4]diazepin-4-yl)methyl)phenoxy)-3-(thiophen-2-yl)propyl)(methyl) carbamate | + |
| 302 | 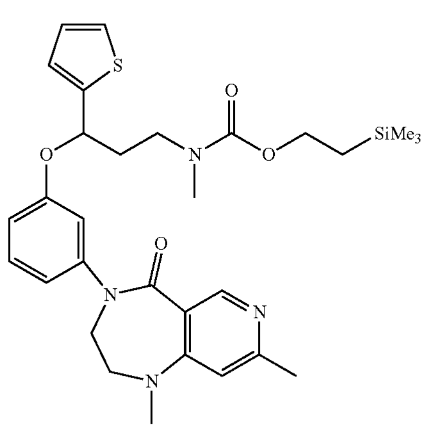 [SMILES: Cc1cc2c(cn1)C(=O)N(c1cccc(OC(CCN(C)C(=O)OCC[Si](C)(C)C)c3cccs3)c1)CCN2C] | 2-(trimethylsilyl)ethyl (3-(3-(1,8-dimethyl-5-oxo-1,2,3,5-tetrahydro-4H-pyrido[4,3-e][1,4]diazepin-4-yl)phenoxy)-3-(thiophen-2-yl)propyl)(methyl)carbamate | + |

TABLE 1-continued

| Ex | Structure | Name | Ki (nM) α2δ-1 |
|---|---|---|---|
| 303 | 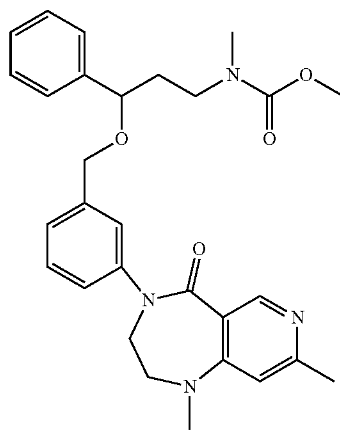 | tert-butyl (3-((3-(1,8-dimethyl-5-oxo-1,2,3,5-tetrahydro-4H-pyrido[4,3-e][1,4]diazepin-4-yl)benzyl)oxy)-3-phenylpropyl)(methyl) carbamate | + |
| 304 | 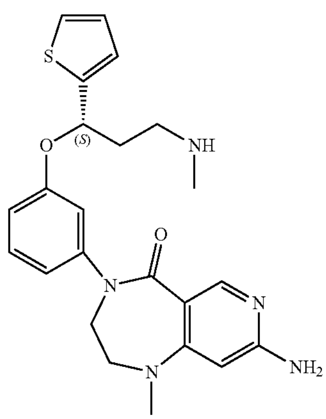 | (S)-8-amino-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 305 | 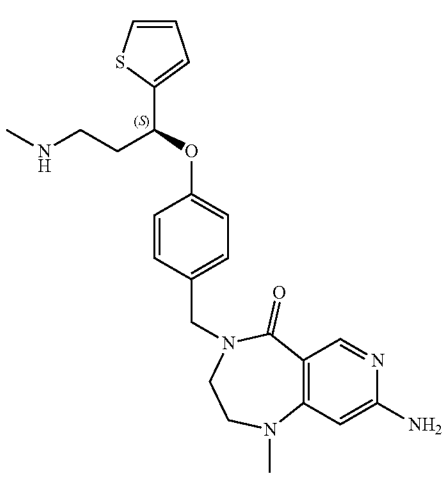 | (S)-8-amino-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ |

TABLE 1-continued

| Ex | Structure | Name | Ki (nM) α2δ-1 |
|---|---|---|---|
| 306 | 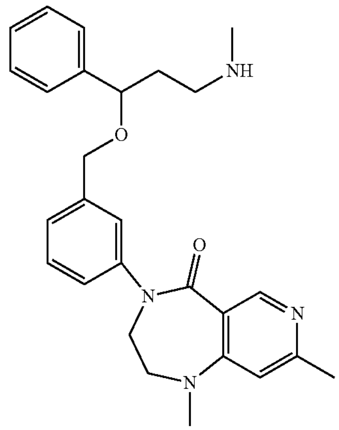 [SMILES: CNCCC(OCc1cccc(N2CCN(C)c3cc(C)ncc3C2=O)c1)c1ccccc1] | 1,8-dimethyl-4-(3-((3-(methylamino)-1-phenylpropoxy)methyl)phenyl)-1,2,3,4-tetrahydro-5H-pyrido[4,3-e][1,4]diazepin-5-one | ++ |
| 307 | 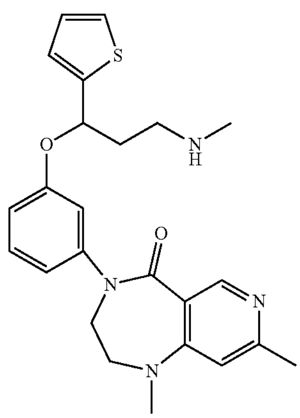 [SMILES: CNCCC(Oc1cccc(N2CCN(C)c3cc(C)ncc3C2=O)c1)c1cccs1] | 1,8-dimethyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 308 | 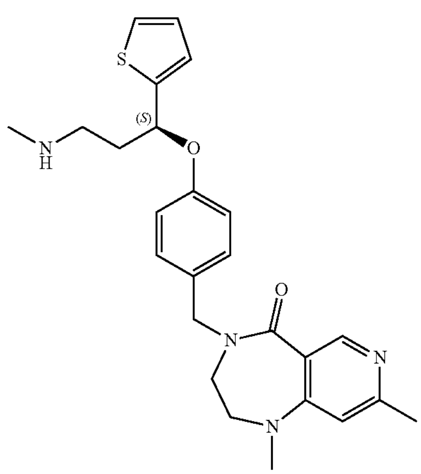 | (S)-1,8-dimethyl-4-(4-(3-(methylamino)-1-(thiophen-2-yl)propoxy)benzyl)-1,2,3,4-tetrahydro-5H-pyrido[4,3-e][1,4]diazepin-5-one | +++ |

TABLE 1-continued

| Ex | Structure | Name | Ki (nM) α2δ-1 |
|---|---|---|---|
| 309 | 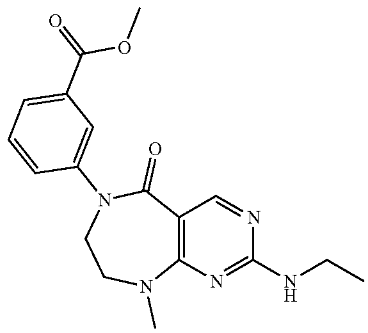 [SMILES: CCNc1ncc2c(n1)N(C)CCN(c1cccc(C(=O)OC)c1)C2=O] | methyl 3-(2-(ethylamino)-9-methyl-5-oxo-5,7,8,9-tetrahydro-6H-pyrimido[4,5-e][1,4]diazepin-6-yl)benzoate | +++ |
| 310 | 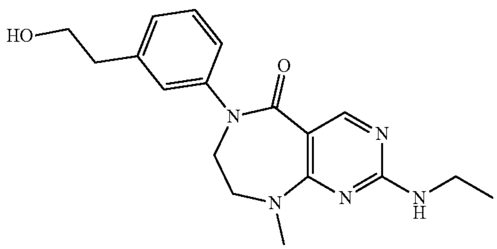 [SMILES: CCNc1ncc2c(n1)N(C)CCN(c1cccc(CCO)c1)C2=O] | 2-(ethylamino)-6-(3-(2-hydroxyethyl)phenyl)-9-methyl-6,7,8,9-tetrahydro-5H-pyrimido[4,5-e][1,4]diazepin-5-one | + |
| 311 | 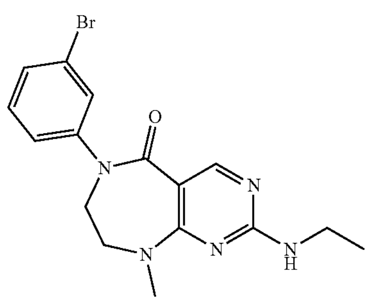 [SMILES: CCNc1ncc2c(n1)N(C)CCN(c1cccc(Br)c1)C2=O] | 6-(3-bromophenyl)-2-(ethylamino)-9-methyl-6,7,8,9-tetrahydro-5H-pyrimido[4,5-e][1,4]diazepin-5-one | ++ |
| 312 | 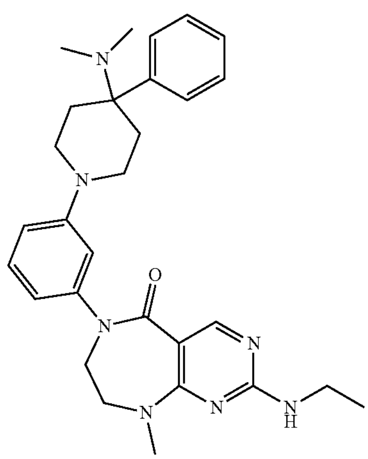 [SMILES: CCNc1ncc2c(n1)N(C)CCN(c1cccc(N3CCC(c4ccccc4)(N(C)C)CC3)c1)C2=O] | 6-(3-(4-(dimethylamino)-4-phenylpiperidin-1-yl)phenyl)-2-(ethylamino)-9-methyl-6,7,8,9-tetrahydro-5H-pyrimido[4,5-e][1,4]diazepin-5-one | ++ |

| Ex | Structure | Name | Ki (nM) α2δ-1 |
|---|---|---|---|
| 313 | 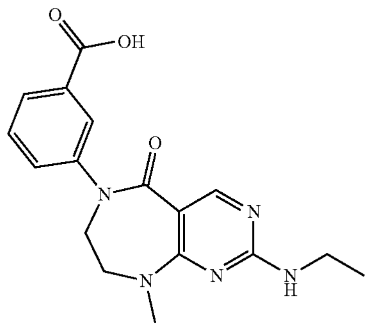 [SMILES: CCNc1ncc2c(n1)N(C)CCN(c1cccc(C(=O)O)c1)C2=O] | 3-(2-(ethylamino)-9-methyl-5-oxo-5,7,8,9-tetrahydro-6H-pyrimido[4,5-e][1,4]diazepin-6-yl)benzoic acid | + |
| 314 | 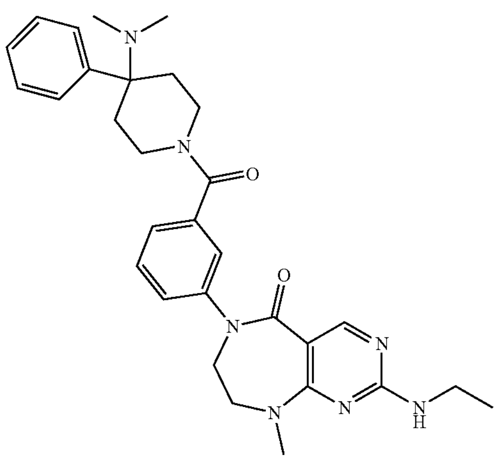 [SMILES: CCNc1ncc2c(n1)N(C)CCN(c1cccc(C(=O)N3CCC(c4ccccc4)(N(C)C)CC3)c1)C2=O] | 6-(3-(4-(dimethylamino)-4-phenylpiperidine-1-carbonyl)phenyl)-2-(ethylamino)-9-methyl-6,7,8,9-tetrahydro-5H-pyrimido[4,5-e][1,4]diazepin-5-one | + |
| 315 | 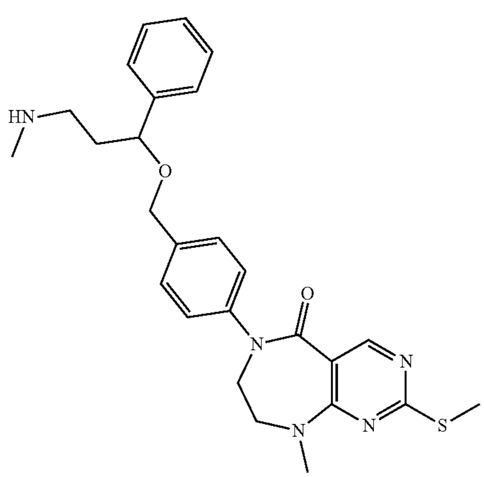 | 9-methyl-6-(4-((3-(methylamino)-1-phenylpropoxy)methyl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 316 | 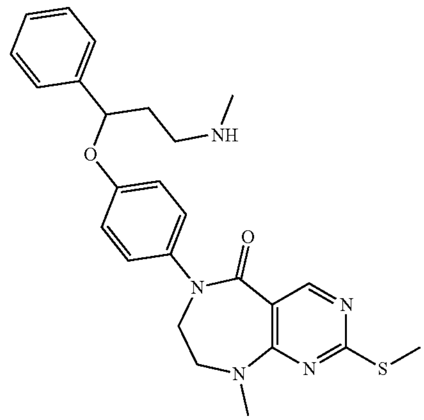 [SMILES: CNCCC(Oc1ccc(N2CCN(C)c3nc(SC)ncc3C2=O)cc1)c1ccccc1] | 9-methyl-6-(4-(3-(methylamino)-1-phenylpropoxy)phenyl)-2-(methylthio)-6,7,8,9-tetrahydro-5H-pyrimido[4,5-e][1,4]diazepin-5-one | + |
| 317 | 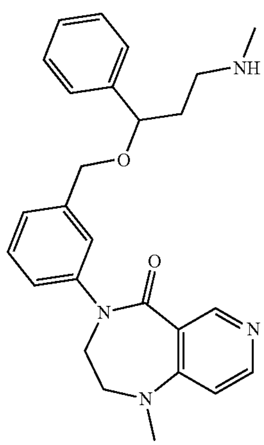 [SMILES: CNCCC(OCc1cccc(N2CCN(C)c3ccncc3C2=O)c1)c1ccccc1] | 1-methyl-4-(3-((3-(methylamino)-1-phenylpropoxy)methyl)phenyl)-1,2,3,4-tetrahydro-5H-pyrido[4,3-e][1,4]diazepin-5-one | ++ |
| 318 | 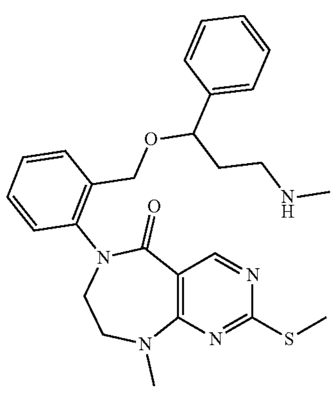 [SMILES: CNCCC(OCc1ccccc1N1CCN(C)c2nc(SC)ncc2C1=O)c1ccccc1] | 9-methyl-6-(2-((3-(methylamino)-1-phenylpropoxy)methyl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 319 | 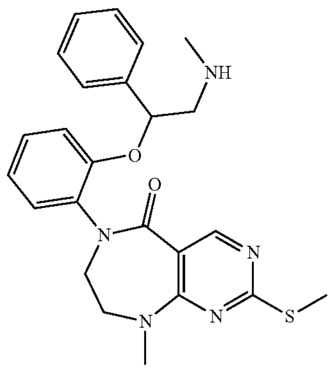 [SMILES: CNCC(Oc1ccccc1N1CCN(C)c2nc(SC)ncc2C1=O)c1ccccc1] | 9-methyl-6-(2-(2-(methylamino)-1-phenylethoxy)phenyl)-2-(methylthio)-6,7,8,9-tetrahydro-5H-pyrimido[4,5-e][1,4]diazepin-5-one | + |
| 320 | 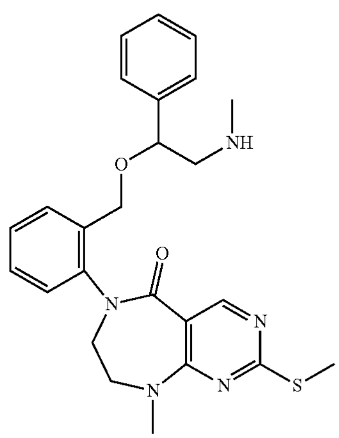 [SMILES: CNCC(OCc1ccccc1N1CCN(C)c2nc(SC)ncc2C1=O)c1ccccc1] | 9-methyl-6-(2-((2-(methylamino)-1-phenylethoxy)methyl)phenyl)-2-(methylthio)-6,7,8,9-tetrahydro-5H-pyrimido[4,5-e][1,4]diazepin-5-one | + |
| 321 | 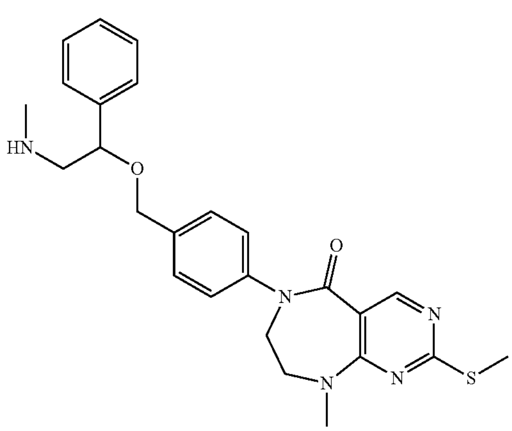 [SMILES: CNCC(OCc1ccc(N2CCN(C)c3nc(SC)ncc3C2=O)cc1)c1ccccc1] | 9-methyl-6-(4-((2-(methylamino)-1-phenylethoxy)methyl)phenyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 322 | 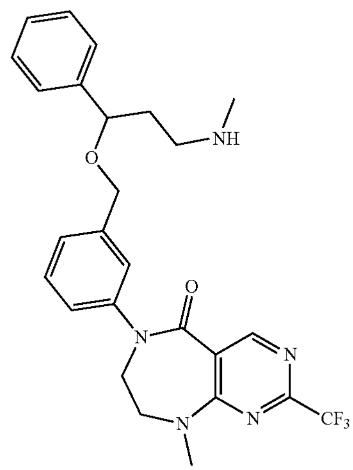 [SMILES: CNCCC(OCc1cccc(N2CCN(C)c3nc(C(F)(F)F)ncc3C2=O)c1)c1ccccc1] | 9-methyl-6-(3-((3-(methylamino)-1-phenylpropoxy)methyl)phenyl)-2-(trifluoromethyl)-6,7,8,9-tetrahydro-5H-pyrimido[4,5-e][1,4]diazepin-5-one | + |
| 323 | 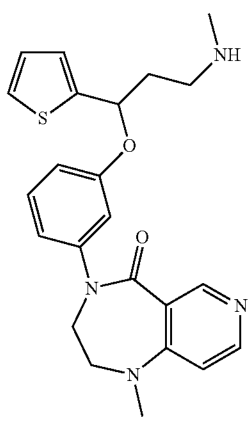 [SMILES: CNCCC(Oc1cccc(N2CCN(C)c3ccncc3C2=O)c1)c1cccs1] | 1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 324 | 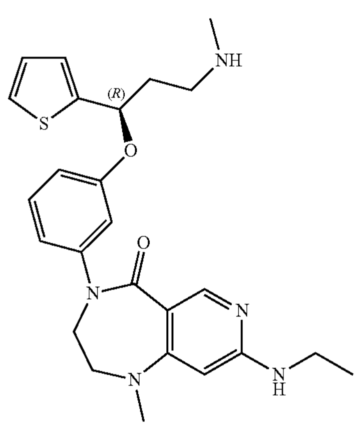 | (R)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | ++ |

TABLE 1-continued

| Ex | Structure | Name | Ki (nM) α2δ-1 |
|---|---|---|---|
| 325 | 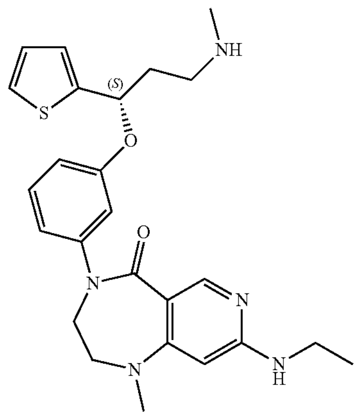 | (S)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 326 | 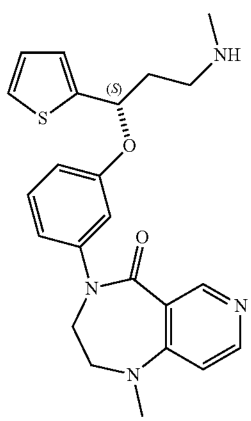 | (S)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 327 | 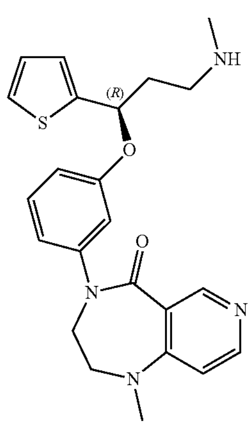 | (R)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |

TABLE 1-continued

| Ex | Structure | Name | Ki (nM) α2δ-1 |
|----|-----------|------|---------------|
| 328 | 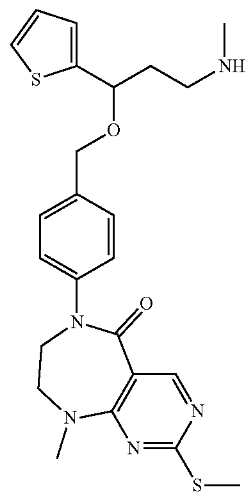 [SMILES: CNCCC(OCc1ccc(N2CCN(C)c3nc(SC)ncc3C2=O)cc1)c1cccs1] | 9-methyl-6-(4-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | + |
| 329 | 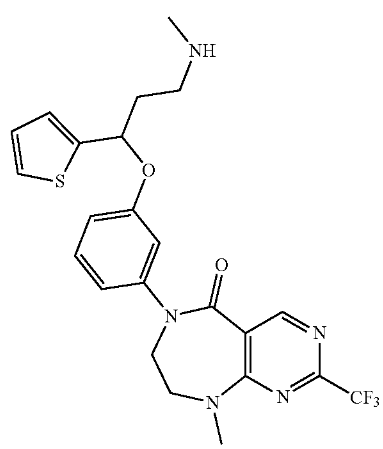 [SMILES: CNCCC(Oc1cccc(N2CCN(C)c3nc(C(F)(F)F)ncc3C2=O)c1)c1cccs1] | 9-methyl-6-(3-(3-(methylamino)-1-(thiophen-2-yl)propoxy)phenyl)-2-(trifluoromethyl)-6,7,8,9-tetrahydro-5H-pyrimido[4,5-e][1,4]diazepin-5-one | + |
| 330 | 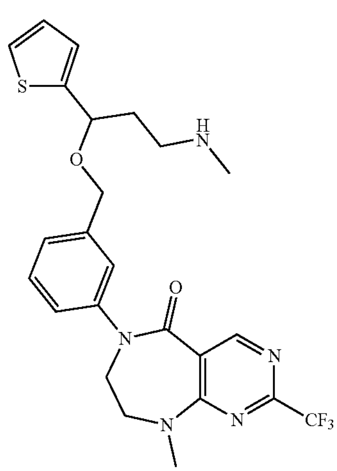 [SMILES: CNCCC(OCc1cccc(N2CCN(C)c3nc(C(F)(F)F)ncc3C2=O)c1)c1cccs1] | 9-methyl-6-(3-((3-(methylamino)-1-(thiophen-2-yl)propoxy)methyl)phenyl)-2-(trifluoromethyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 331 | 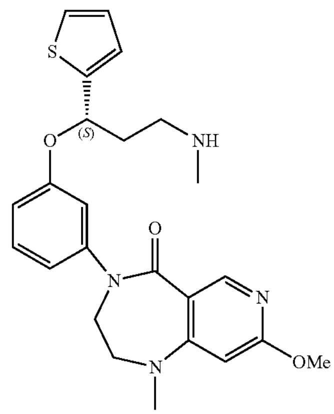 | (S)-8-methoxy-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ |
| 332 | 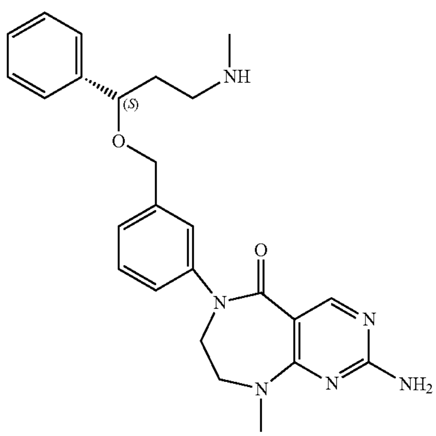 | (S)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one | + |
| 333 | 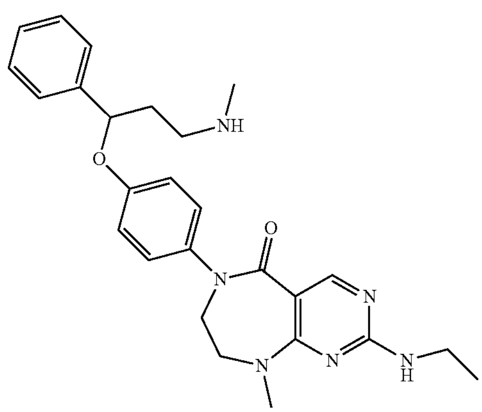 [SMILES: CCNc1ncc2c(n1)N(C)CCN(c1ccc(OC(CCNC)c3ccccc3)cc1)C2=O] | 2-(ethylamino)-9-methyl-6-(4-(3-(methylamino)-1-phenylpropoxy)phenyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 334 | 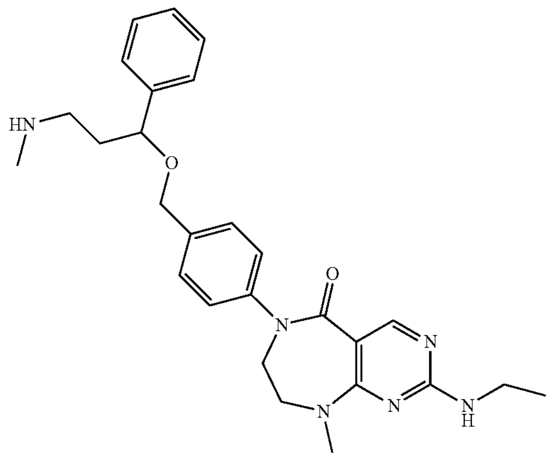 [SMILES: CCNc1ncc2c(n1)N(C)CCN(c1ccc(COC(CCNC)c3ccccc3)cc1)C2=O] | 2-(ethylamino)-9-methyl-6-(4-((3-(methylamino)-1-phenylpropoxy)methyl)phenyl)-6,7,8,9-tetrahydro-5H-pyrimido[4,5-e][1,4]diazepin-5-one | + |
| 335 | 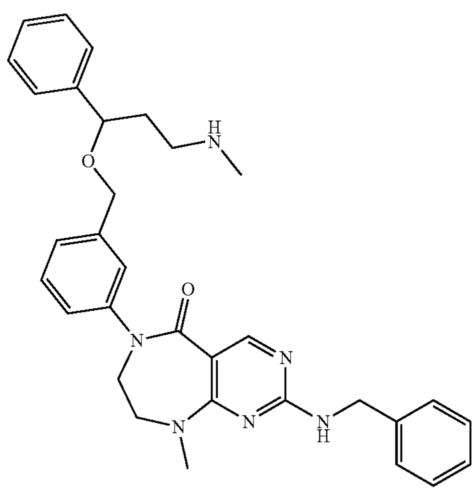 [SMILES: CNCCC(OCc1cccc(N2CCN(C)c3nc(NCc4ccccc4)ncc3C2=O)c1)c1ccccc1] | 2-(benzylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |
| 336 | 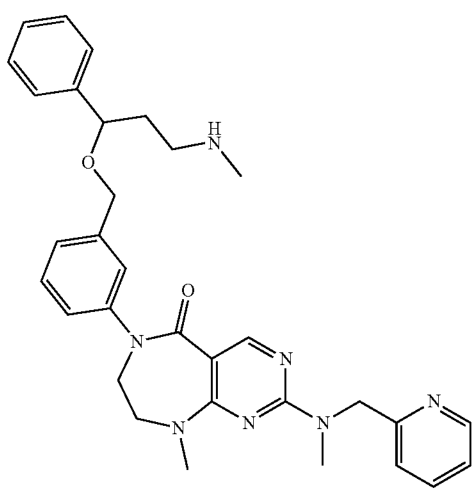 [SMILES: CNCCC(OCc1cccc(N2CCN(C)c3nc(N(C)Cc4ccccn4)ncc3C2=O)c1)c1ccccc1] | 9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 337 | 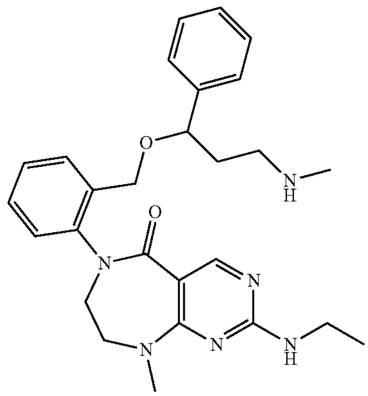 [SMILES: CCNc1ncc2c(n1)N(C)CCN(c1ccccc1COC(CCNC)c1ccccc1)C2=O] | 2-(ethylamino)-9-methyl-6-(2-((3-(methylamino)-1-phenylpropoxy)methyl)phenyl)-6,7,8,9-tetrahydro-5H-pyrimido[4,5-e][1,4]diazepin-5-one | + |
| 338 | 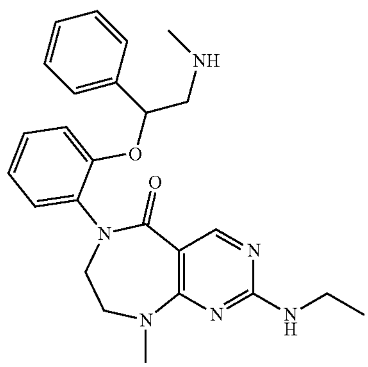 [SMILES: CCNc1ncc2c(n1)N(C)CCN(c1ccccc1OC(CNC)c1ccccc1)C2=O] | 2-(ethylamino)-9-methyl-6-(2-(2-(methylamino)-1-phenylethoxy)phenyl)-6,7,8,9-tetrahydro-5H-pyrimido[4,5-e][1,4]diazepin-5-one | + |
| 339 | 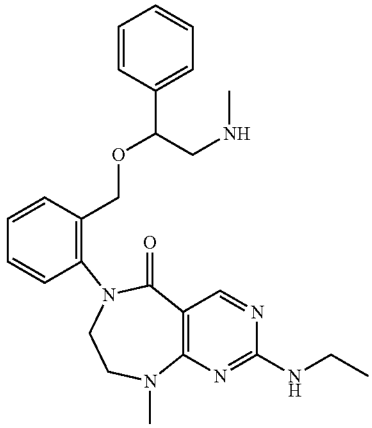 [SMILES: CCNc1ncc2c(n1)N(C)CCN(c1ccccc1COC(CNC)c1ccccc1)C2=O] | 2-(ethylamino)-9-methyl-6-(2-((2-(methylamino)-1-phenylethoxy)methyl)phenyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 340 | 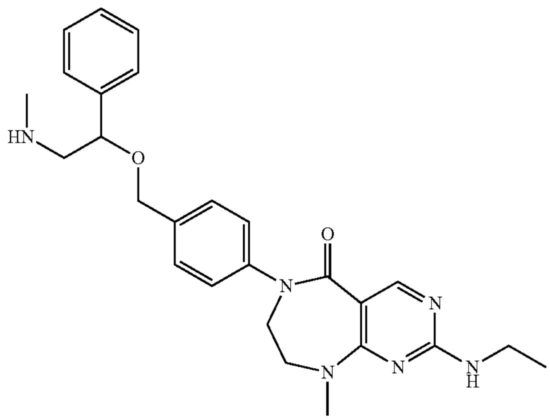 [SMILES: CCNc1ncc2c(n1)N(C)CCN(c1ccc(COC(CNC)c3ccccc3)cc1)C2=O] | 2-(ethylamino)-9-methyl-6-(4-((2-(methylamino)-1-phenylethoxy)methyl)phenyl)-6,7,8,9-tetrahydro-5H-pyrimido[4,5-e][1,4]diazepin-5-one | + |
| 341 | 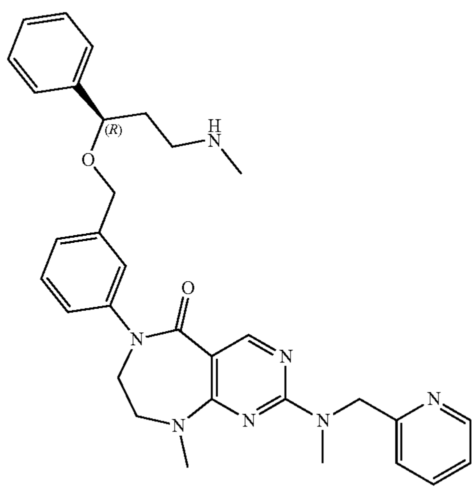 | (R)-9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | +++ |
| 342 | 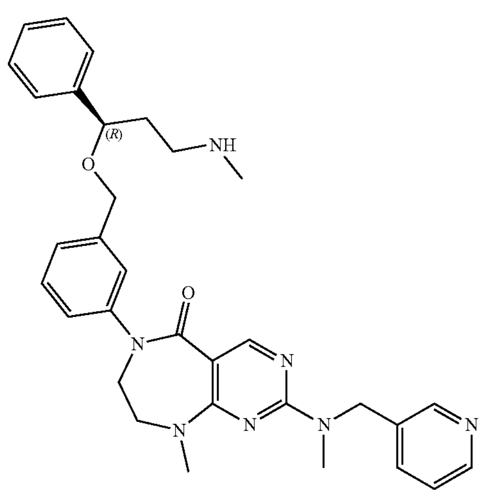 | (R)-9-methyl-2-(methyl(pyridin-3-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 343 | 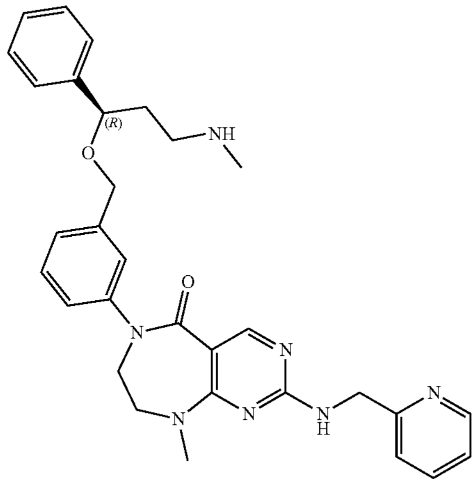 | (R)-9-methyl-6-(3-((3-(methylamino)-1-phenylpropoxy)methyl)phenyl)-2-((pyridin-2-ylmethyl)amino)-6,7,8,9-tetrahydro-5H-pyrimido[4,5-e][1,4]diazepin-5-one | +++ |
| 344 | 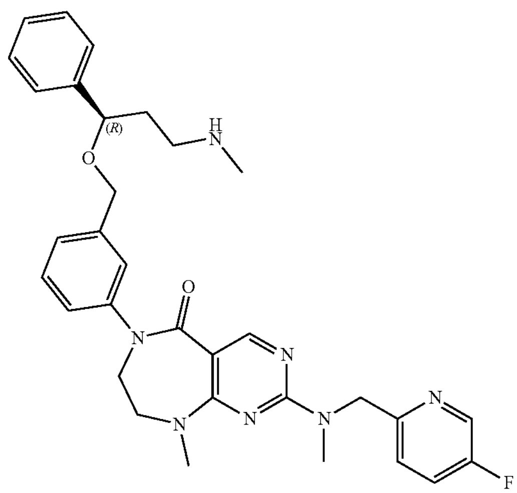 | (R)-2-(((5-fluoropyridin-2-yl)methyl)(methyl)amino)-9-methyl-6-(3-((3-(methylamino)-1-phenylpropoxy)methyl)phenyl)-6,7,8,9-tetrahydro-5H-pyrimido[4,5-e][1,4]diazepin-5-one | +++ |
| 345 | 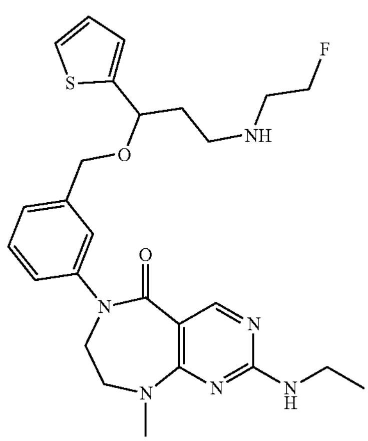 [SMILES: CCNc1ncc2c(n1)N(C)CCN(c1cccc(COC(CCNCCF)c3cccs3)c1)C2=O] | 2-(ethylamino)-6-(3-((3-((2-fluoroethyl)amino)-1-(thiophen-2-yl)propoxy)methyl)phenyl)-9-methyl-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 346 | 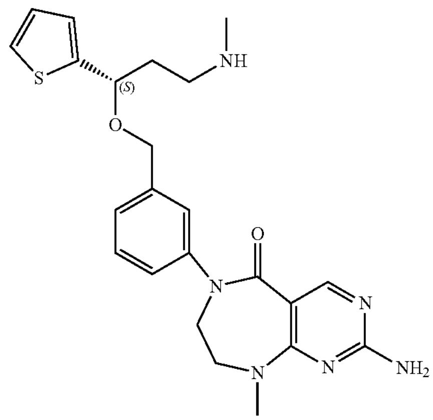 | (S)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | + |
| 347 | 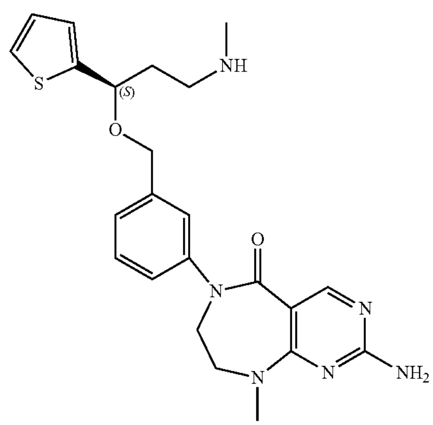 | (R)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ |
| 348 | 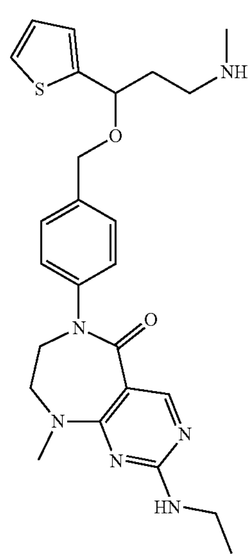 [SMILES: CCNc1ncc2c(n1)N(C)CCN(c1ccc(COC(CCNC)c3cccs3)cc1)C2=O] | 2-(ethylamino)-9-methyl-6-(4-((3-(methylamino)-1-(thiophen-2-yl)propoxy)methyl)phenyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 349 | 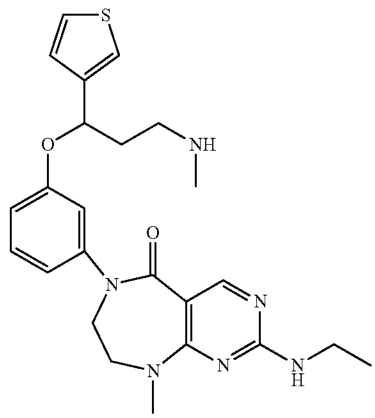 [SMILES: CCNc1ncc2c(n1)N(C)CCN(c1cccc(OC(CCNC)c3ccsc3)c1)C2=O] | 2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | +++ |
| 350 | 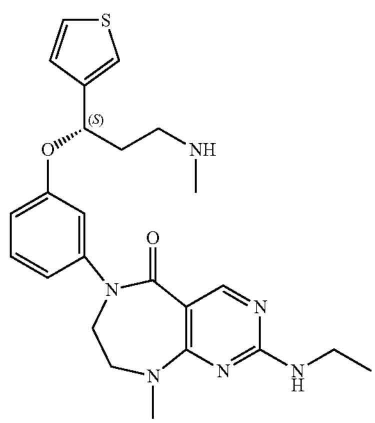 | (S)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | +++ |
| 351 | 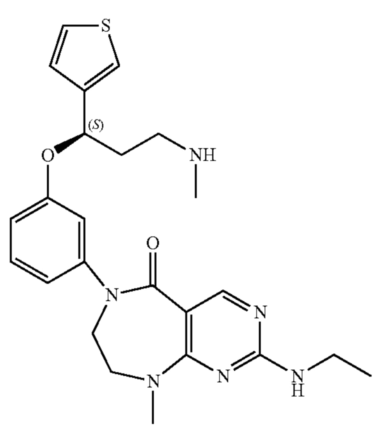 | (R)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 352 | 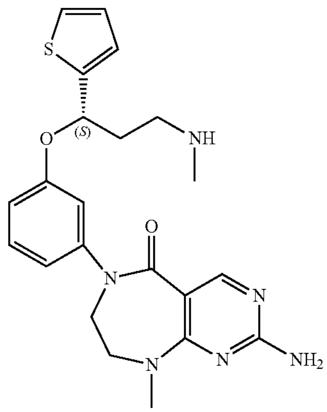 | (S)-2-amino-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ |
| 353 | 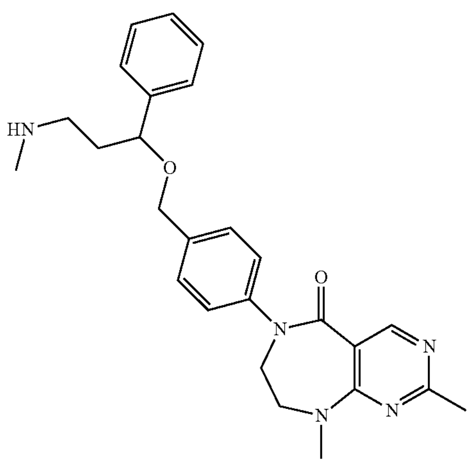 | 2,9-dimethyl-6-(4-((3-(methylamino)-1-phenylpropoxy)methyl)phenyl)-6,7,8,9-tetrahydro-5H-pyrimido[4,5-e][1,4]diazepin-5-one | + |
| 354 | 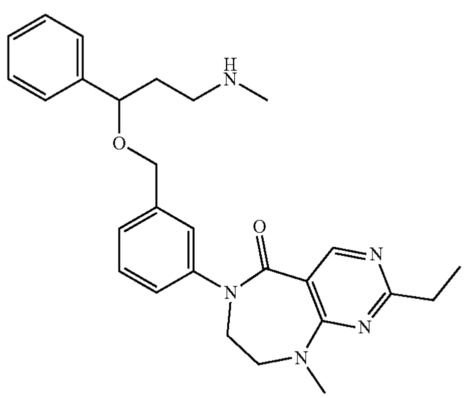 [SMILES: CCc1ncc2c(n1)N(C)CCN(c1cccc(COC(CCNC)c3ccccc3)c1)C2=O] | 2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 355 | 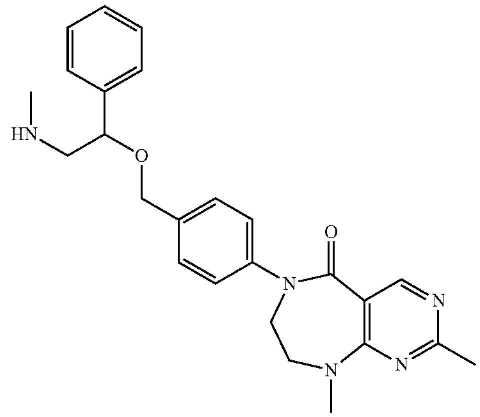 [SMILES: CNCC(OCc1ccc(N2CCN(C)c3nc(C)ncc3C2=O)cc1)c1ccccc1] | 2,9-dimethyl-6-(4-((2-(methylamino)-1-phenylethoxy)methyl)phenyl)-6,7,8,9-tetrahydro-5H-pyrimido[4,5-e][1,4]diazepin-5-one | + |
| 356 | 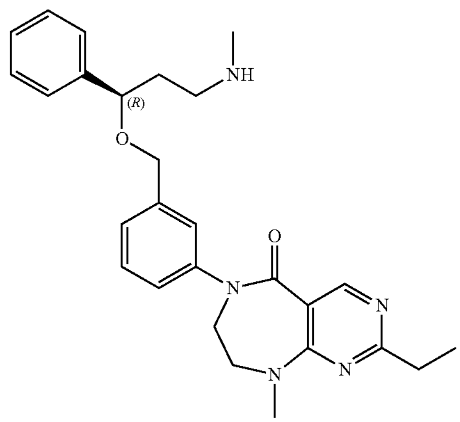 | (R)-2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one | ++ |
| 357 | 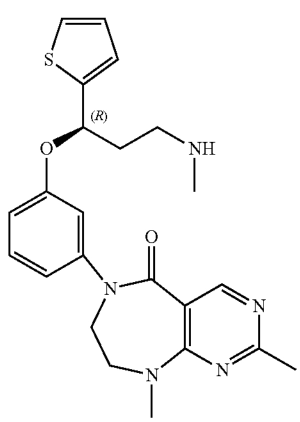 | (R)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 358 | 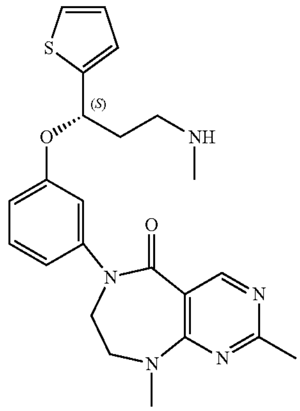 | (S)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | ++ |
| 359 | 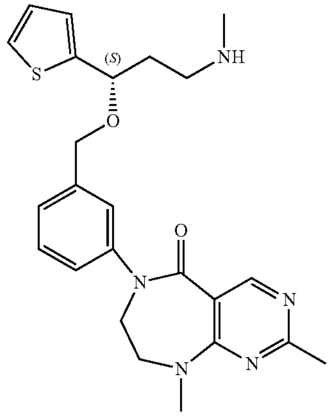 | (S)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | + |
| 360 | 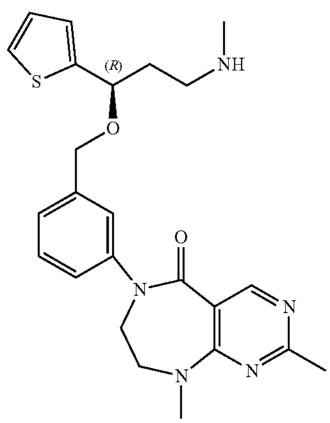 | (R)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ |
| 361 | 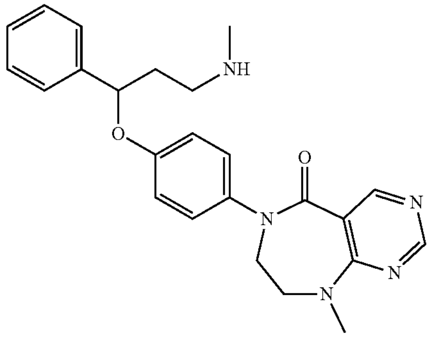 [SMILES: CNCCC(Oc1ccc(N2CCN(C)c3ncncc3C2=O)cc1)c1ccccc1] | 9-methyl-6-(4-(3-(methylamino)-1-phenylpropoxy)phenyl)-6,7,8,9-tetrahydro-5H-pyrimido[4,5-e][1,4]diazepin-5-one | + |

TABLE 1-continued
| Ex | Structure | Name | Ki (nM) α2δ-1 |
|---|---|---|---|
| 362 | 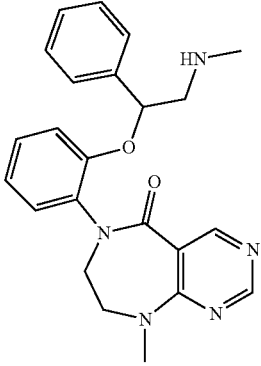 [SMILES: CNCC(Oc1ccccc1N1CCN(C)c2ncncc2C1=O)c1ccccc1] | 9-methyl-6-(2-(2-(methylamino)-1-phenylethoxy)phenyl)-6,7,8,9-tetrahydro-5H-pyrimido[4,5-e][1,4]diazepin-5-one | + |
| 363 | 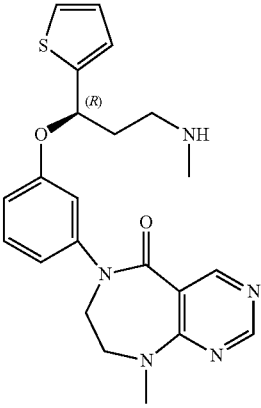 | (R)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | ++ |
| 364 | 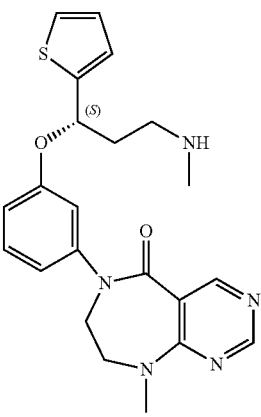 | (S)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|----|-----------|------|----------------|
| 365 | 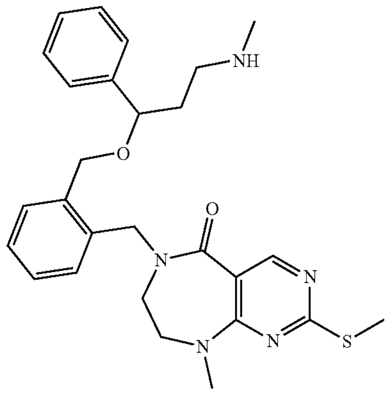 [SMILES: CNCCC(OCc1ccccc1CN1CCN(C)c2nc(SC)ncc2C1=O)c1ccccc1] | 9-methyl-6-(2-((3-(methylamino)-1-phenylpropoxy)methyl)benzyl)-2-(methylthio)-6,7,8,9-tetrahydro-5H-pyrimido[4,5-e][1,4]diazepin-5-one | + |
| 366 | 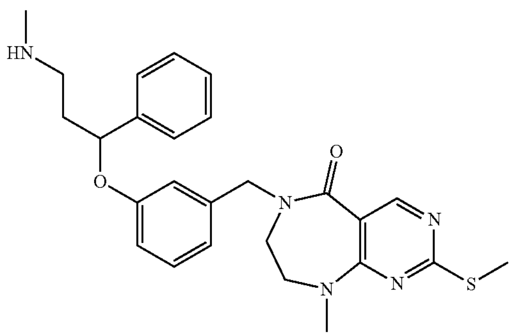 [SMILES: CNCCC(Oc1cccc(CN2CCN(C)c3nc(SC)ncc3C2=O)c1)c1ccccc1] | 9-methyl-6-(3-(3-(methylamino)-1-phenylpropoxy)benzyl)-2-(methylthio)-6,7,8,9-tetrahydro-5H-pyrimido[4,5-e][1,4]diazepin-5-one | + |
| 367 | 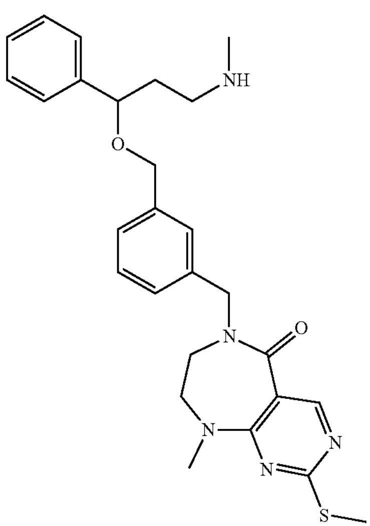 [SMILES: CNCCC(OCc1cccc(CN2CCN(C)c3nc(SC)ncc3C2=O)c1)c1ccccc1] | 9-methyl-6-(3-((3-(methylamino)-1-phenylpropoxy)methyl)benzyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 368 | 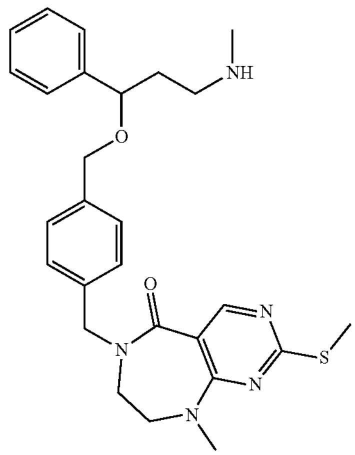 | 9-methyl-6-(4-((3-(methylamino)-1-phenylpropoxy)methyl)benzyl)-2-(methylthio)-6,7,8,9-tetrahydro-5H-pyrimido[4,5-e][1,4]diazepin-5-one | + |
| 369 | 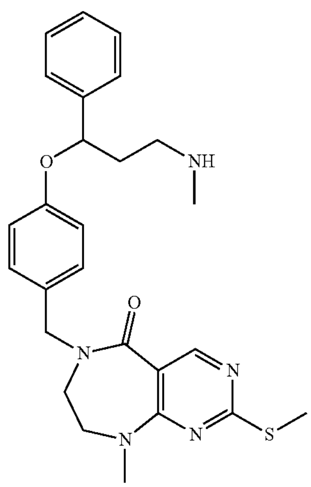 [SMILES: CNCCC(Oc1ccc(CN2CCN(C)c3nc(SC)ncc3C2=O)cc1)c1ccccc1] | 9-methyl-6-(4-(3-(methylamino)-1-phenylpropoxy)benzyl)-2-(methylthio)-6,7,8,9-tetrahydro-5H-pyrimido[4,5-e][1,4]diazepin-5-one | ++ |
| 370 | 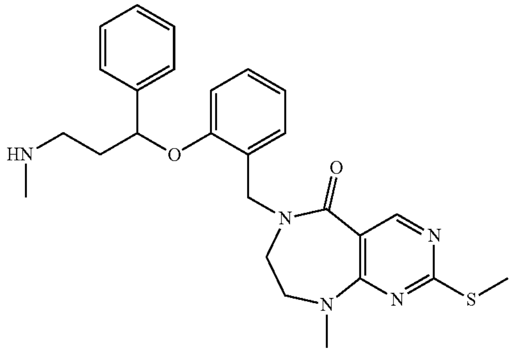 [SMILES: CNCCC(Oc1ccccc1CN1CCN(C)c2nc(SC)ncc2C1=O)c1ccccc1] | 9-methyl-6-(2-(3-(methylamino)-1-phenylpropoxy)benzyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 371 | 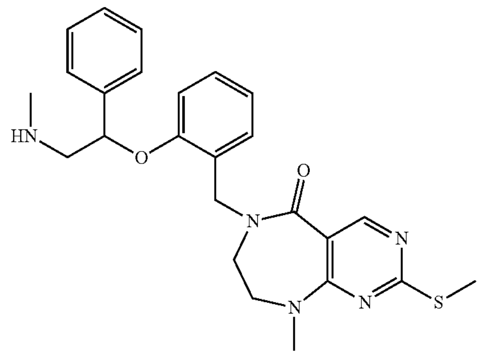 [SMILES: CNCC(Oc1ccccc1CN1CCN(C)c2nc(SC)ncc2C1=O)c1ccccc1] | 9-methyl-6-(2-(2-(methylamino)-1-phenylethoxy)benzyl)-2-(methylthio)-6,7,8,9-tetrahydro-5H-pyrimido[4,5-e][1,4]diazepin-5-one | + |
| 372 | 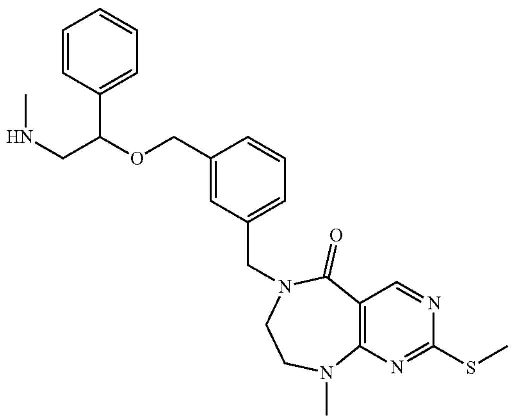 [SMILES: CNCC(OCc1cccc(CN2CCN(C)c3nc(SC)ncc3C2=O)c1)c1ccccc1] | 9-methyl-6-(3-((2-(methylamino)-1-phenylethoxy)methyl)benzyl)-2-(methylthio)-6,7,8,9-tetrahydro-5H-pyrimido[4,5-e][1,4]diazepin-5-one | + |
| 373 | 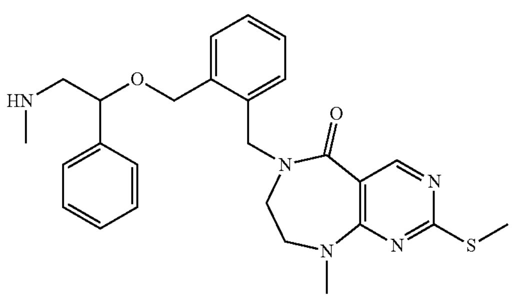 [SMILES: CNCC(OCc1ccccc1CN1CCN(C)c2nc(SC)ncc2C1=O)c1ccccc1] | 9-methyl-6-(2-((2-(methylamino)-1-phenylethoxy)methyl)benzyl)-2-(methylthio)-6,7,8,9-tetrahydro-5H-pyrimido[4,5-e][1,4]diazepin-5-one | + |
| 374 | 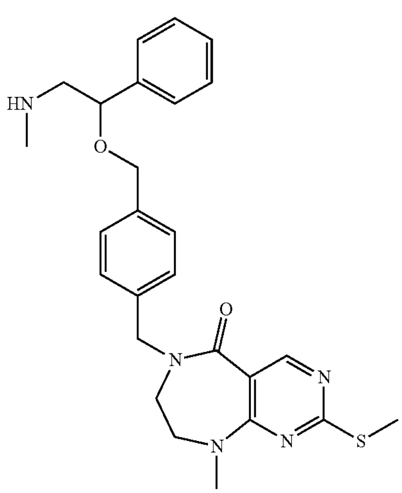 [SMILES: CNCC(OCc1ccc(CN2CCN(C)c3nc(SC)ncc3C2=O)cc1)c1ccccc1] | 9-methyl-6-(4-((2-(methylamino)-1-phenylethoxy)methyl)benzyl)-2-(methylthio)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 375 | 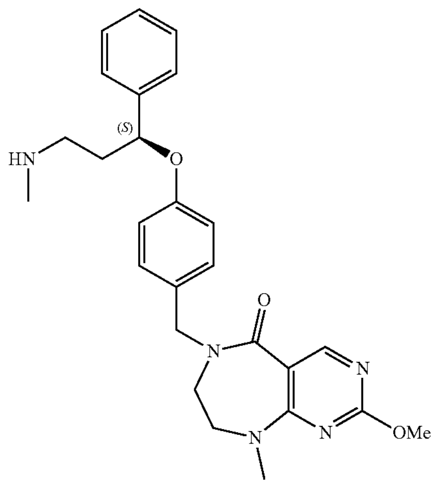 | (S)-2-methoxy-9-methyl-6-(4-(3-(methylamino)-1-phenylpropoxy)benzyl)-6,7,8,9-tetrahydro-5H-pyrimido[4,5-e][1,4]diazepin-5-one | +++ |
| 376 | 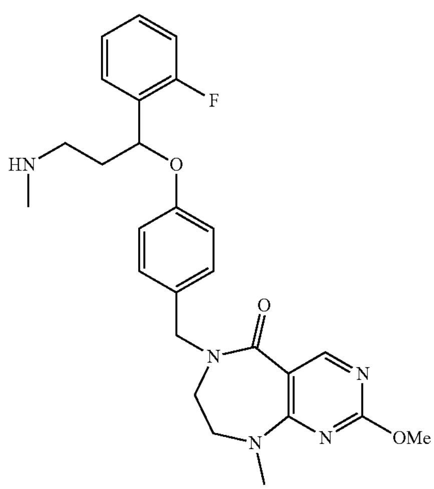 [SMILES: CNCCC(Oc1ccc(CN2CCN(C)c3nc(OC)ncc3C2=O)cc1)c1ccccc1F] | 6-(4-(1-(2-fluorophenyl)-3-(methylamino)propoxy)benzyl)-2-methoxy-9-methyl-6,7,8,9-tetrahydro-5H-pyrimido[4,5-e][1,4]diazepin-5-one | ++ |
| 377 | 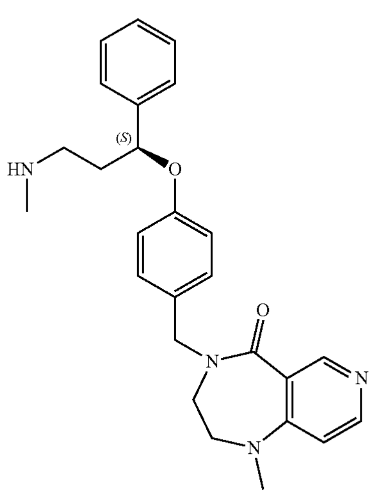 | (S)-1-methyl-4-(4-(3-(methylamino)-1-phenylpropoxy)benzyl)-1,2,3,4-tetrahydro-5H-pyrido[4,3-e][1,4]diazepin-5-one | ++ |

| Ex | Structure | Name | Ki (nM) α2δ-1 |
|---|---|---|---|
| 378 | 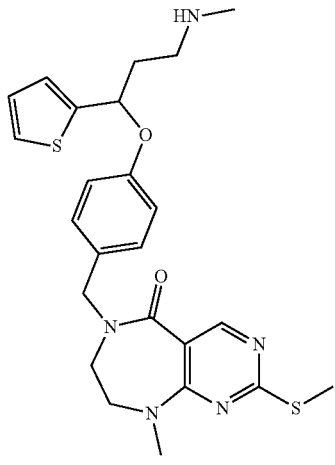 [SMILES: CNCCC(Oc1ccc(CN2CCN(C)c3nc(SC)ncc3C2=O)cc1)c1cccs1] | 9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | ++ |
| 379 | 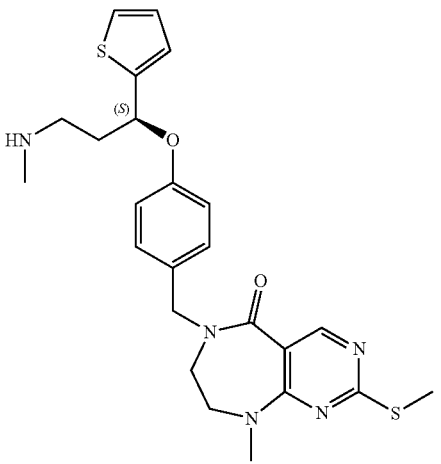 | (S)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | +++ |
| 380 | 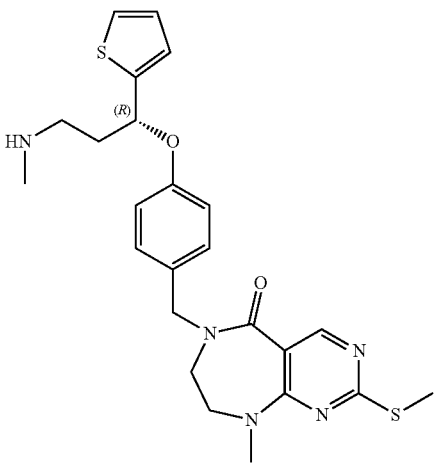 | (R)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | ++ |

TABLE 1-continued
| Ex | Structure | Name | Ki (nM) α2δ-1 |
|---|---|---|---|
| 381 | 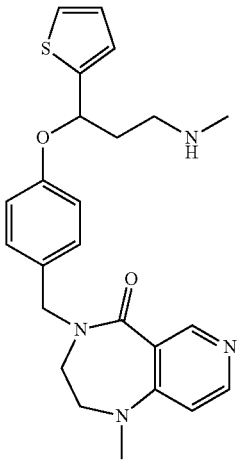 [SMILES: CNCCC(Oc1ccc(CN2CCN(C)c3ccncc3C2=O)cc1)c1cccs1] | 1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ |
| 382 | 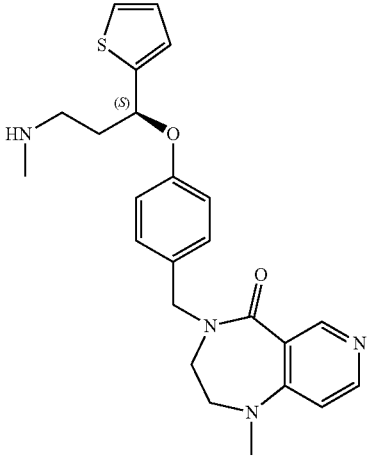 | (S)-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ |
| 383 | 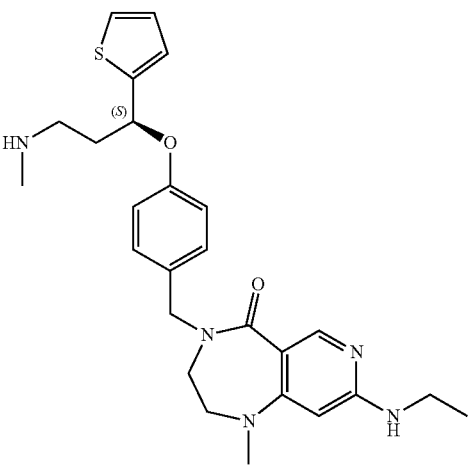 | (S)-8-(ethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ |

| Ex | Structure | Name | Ki (nM) α2δ-1 |
|---|---|---|---|
| 384 | 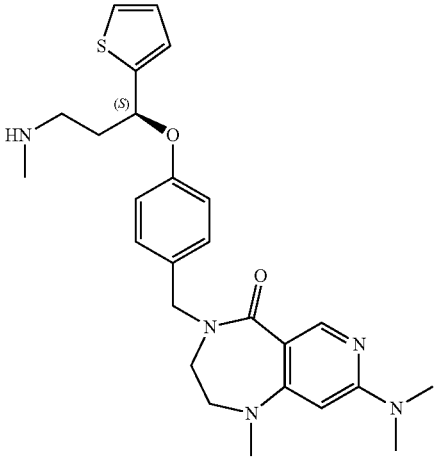 | (S)-8-(dimethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ |
| 385 | 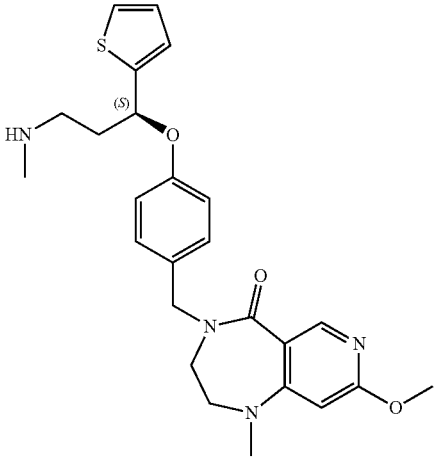 | (S)-8-methoxy-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ |
| 386 | 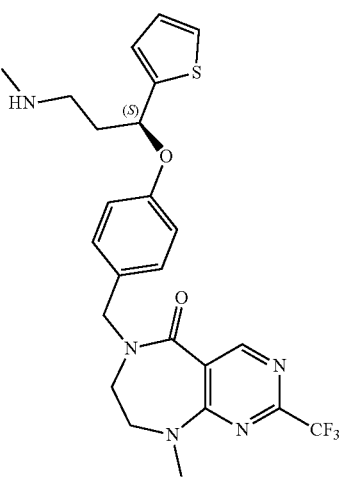 | (S)-9-methyl-6-(4-(3-(methylamino)-1-(thiophen-2-yl)propoxy)benzyl)-2-(trifluoromethyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 387 | 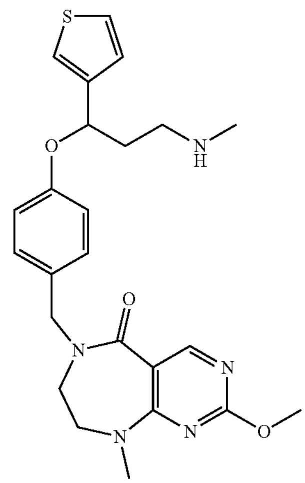 [SMILES: CNCCC(Oc1ccc(CN2CCN(C)c3nc(OC)ncc3C2=O)cc1)c1ccsc1] | 2-methoxy-9-methyl-6-(4-(3-(methylamino)-1-(thiophen-3-yl)propoxy)benzyl)-6,7,8,9-tetrahydro-5H-pyrimido[4,5-e][1,4]diazepin-5-one | +++ |
| 388 | 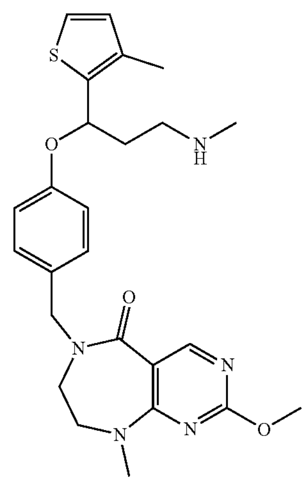 [SMILES: CNCCC(Oc1ccc(CN2CCN(C)c3nc(OC)ncc3C2=O)cc1)c1sccc1C] | 2-methoxy-9-methyl-6-(4-(3-(methylamino)-1-(3-methylthiophen-2-yl)propoxy)benzyl)-6,7,8,9-tetrahydro-5H-pyrimido[4,5-e][1,4]diazepin-5-one | + |
| 389 | 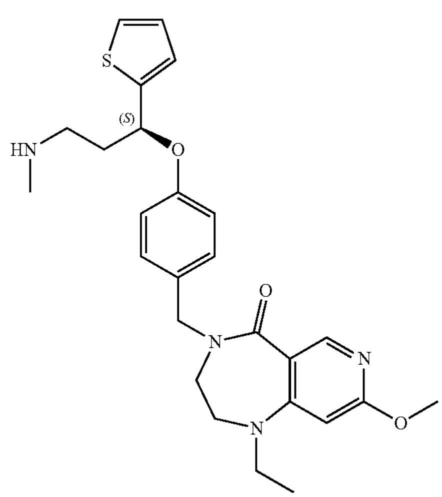 | (S)-1-ethyl-8-methoxy-4-(4-(3-(methylamino)-1-(thiophen-2-yl)propoxy)benzyl)-1,2,3,4-tetrahydro-5H-pyrido[4,3-e][1,4]diazepin-5-one | +++ |

TABLE 1-continued

| Ex | Structure | Name | Ki (nM) α2δ-1 |
|---|---|---|---|
| 390 | 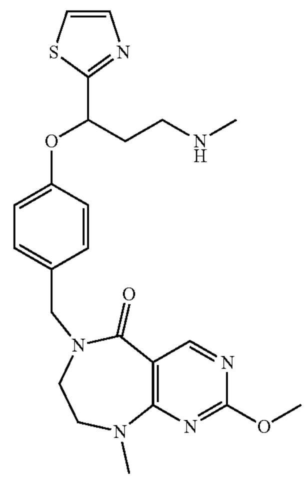 [SMILES: CNCCC(Oc1ccc(CN2CCN(C)c3nc(OC)ncc3C2=O)cc1)c1nccs1] | 2-methoxy-9-methyl-6-(4-(3-(methylamino)-1-(thiazol-2-yl)propoxy)benzyl)-6,7,8,9-tetrahydro-5H-pyrimido[4,5-e][1,4]diazepin-5-one | +++ |
| 391 | 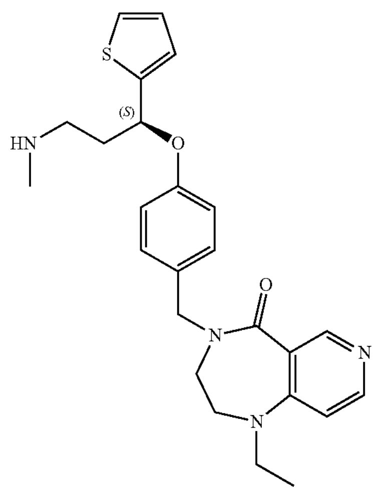 | (S)-1-ethyl-4-(4-(3-(methylamino)-1-(thiophen-2-yl)propoxy)benzyl)-1,2,3,4-tetrahydro-5H-pyrido[4,3-e][1,4]diazepin-5-one | +++ |
| 392 | 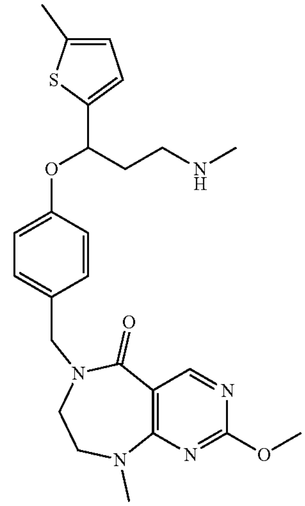 [SMILES: CNCCC(Oc1ccc(CN2CCN(C)c3nc(OC)ncc3C2=O)cc1)c1ccc(C)s1] | 2-methoxy-9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 393 | 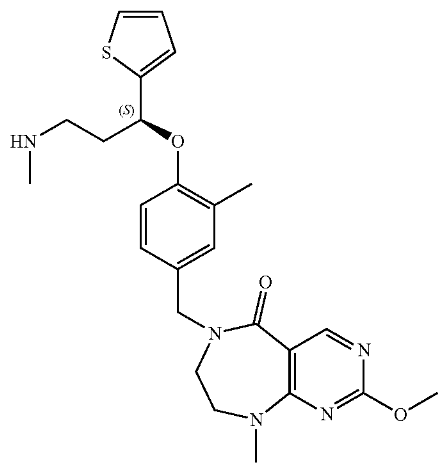 | (S)-2-methoxy-9-methyl-6-(3-methyl-4-(3-(methylamino)-1-(thiophen-2-yl)propoxy)benzyl)-6,7,8,9-tetrahydro-5H-pyrimido[4,5-e][1,4]diazepin-5-one | +++ |
| 394 | 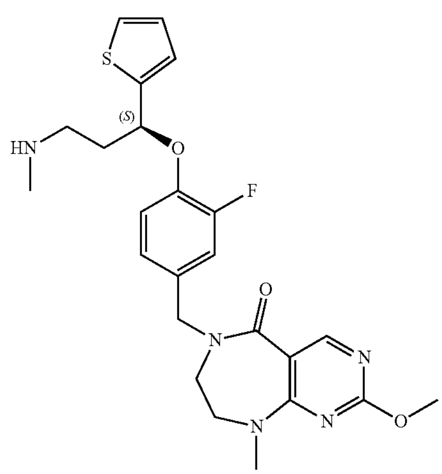 | (S)-6-(3-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | +++ |
| 395 | 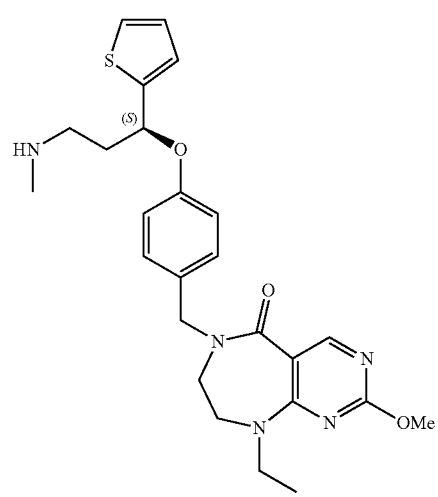 | S)-9-ethyl-2-methoxy-6-(4-(3-(methylamino)-1-(thiophen-2-yl)propoxy)benzyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 396 | 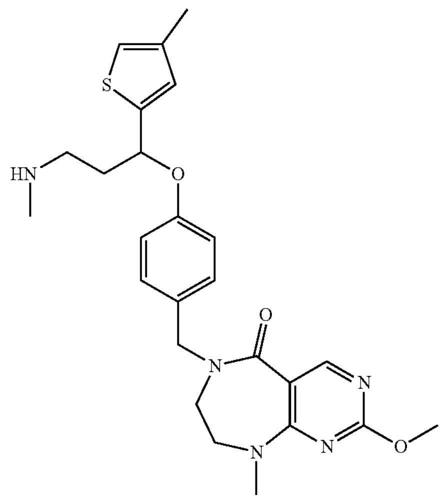 [SMILES: CNCCC(Oc1ccc(CN2CCN(C)c3nc(OC)ncc3C2=O)cc1)c1cc(C)cs1] | 2-methoxy-9-methyl-6-(4-(3-(methylamino)-1-(4-methylthiophen-2-yl)propoxy)benzyl)-6,7,8,9-tetrahydro-5H-pyrimido[4,5-e][1,4]diazepin-5-one | +++ |
| 397 | 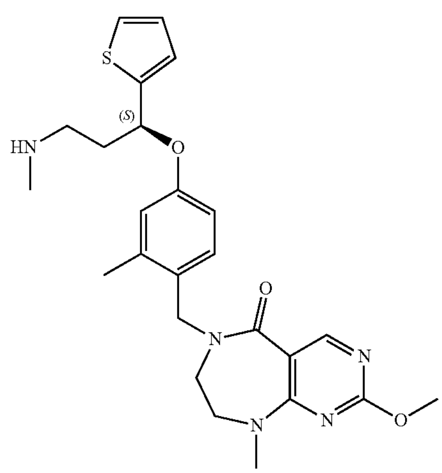 | (S)-2-methoxy-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one | ++++ |
| 398 | 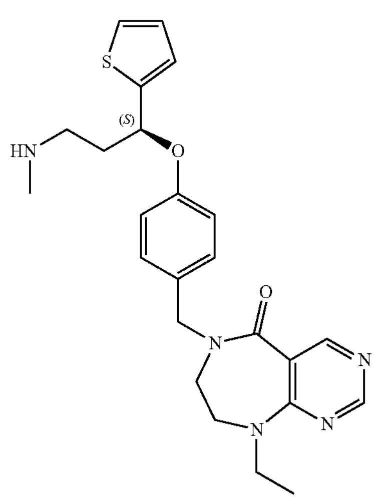 | (S)-9-ethyl-6-(4-(3-(methylamino)-1-(thiophen-2-yl)propoxy)benzyl)-6,7,8,9-tetrahydro-5H-pyrimido[4,5-e][1,4]diazepin-5-one | +++ |

| Ex | Structure | Name | Ki (nM) α2δ-1 |
|---|---|---|---|
| 399 | 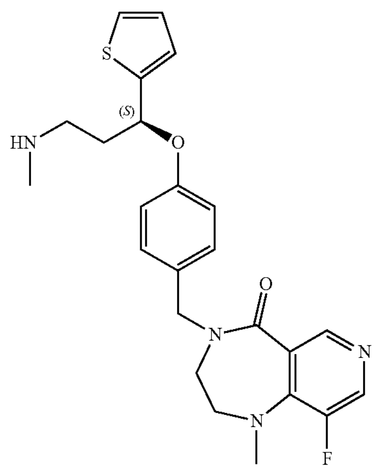 | (S)-9-fluoro-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ |
| 400 | 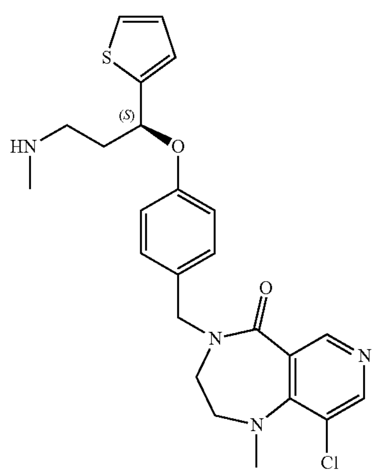 | (S)-9-chloro-1-methyl-4-(4-(3-(methylamino)-1-(thiophen-2-yl)propoxy)benzyl)-1,2,3,4-tetrahydro-5H-pyrido[4,3-e][1,4]diazepin-5-one | ++ |
| 401 | 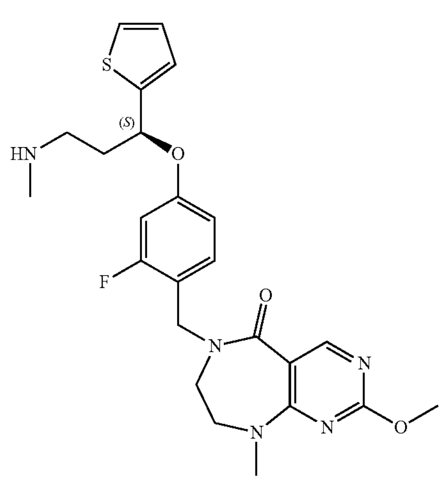 | (S)-6-(2-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | ++++ |

TABLE 1-continued

| Ex | Structure | Name | Ki (nM) α2δ-1 |
|----|-----------|------|---------------|
| 402 | 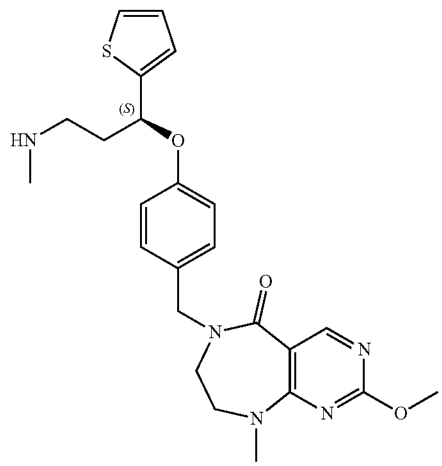 | (S)-2-methoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ |
| 403 | 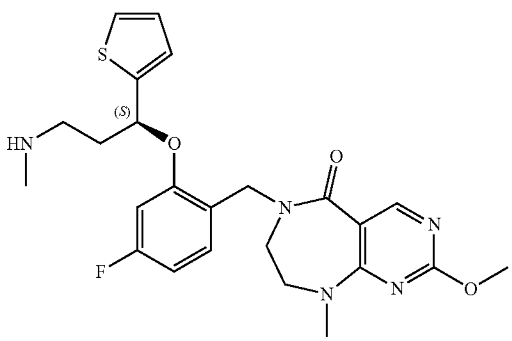 | (S)-6-(4-fluoro-2-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | + |
| 404 | 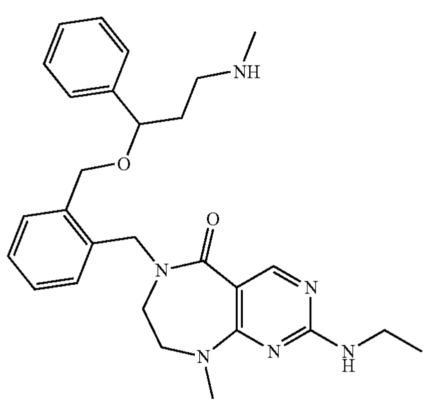 [SMILES: CCNc1ncc2c(n1)N(C)CCN(Cc1ccccc1COC(CCNC)c1ccccc1)C2=O] | 2-(ethylamino)-9-methyl-6-(2-((3-(methylamino)-1-phenylpropoxy)methyl)benzyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 405 | 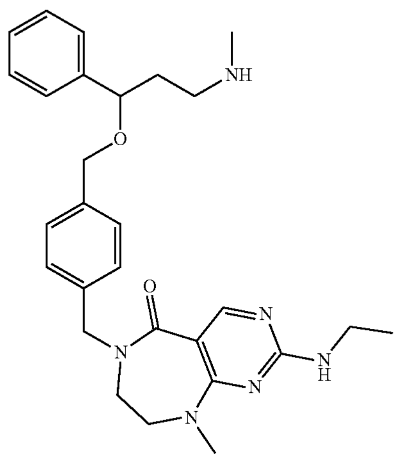 [SMILES: CCNc1ncc2c(n1)N(C)CCN(Cc1ccc(COC(CCNC)c3ccccc3)cc1)C2=O] | 2-(ethylamino)-9-methyl-6-(4-((3-(methylamino)-1-phenylpropoxy)methyl)benzyl)-6,7,8,9-tetrahydro-5H-pyrimido[4,5-e][1,4]diazepin-5-one | + |
| 406 | 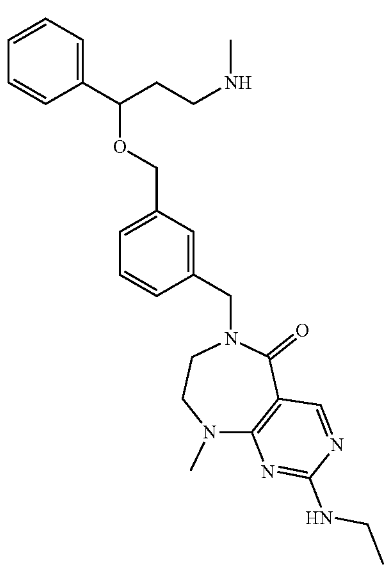 [SMILES: CCNc1ncc2c(n1)N(C)CCN(Cc1cccc(COC(CCNC)c3ccccc3)c1)C2=O] | 2-(ethylamino)-9-methyl-6-(3-((3-(methylamino)-1-phenylpropoxy)methyl)benzyl)-6,7,8,9-tetrahydro-5H-pyrimido[4,5-e][1,4]diazepin-5-one | + |
| 407 | 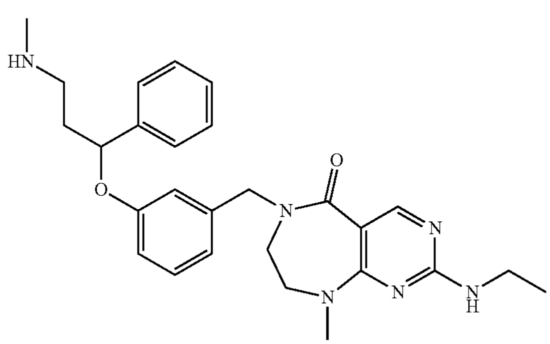 [SMILES: CCNc1ncc2c(n1)N(C)CCN(Cc1cccc(OC(CCNC)c3ccccc3)c1)C2=O] | 2-(ethylamino)-9-methyl-6-(3-(3-(methylamino)-1-phenylpropoxy)benzyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 408 | 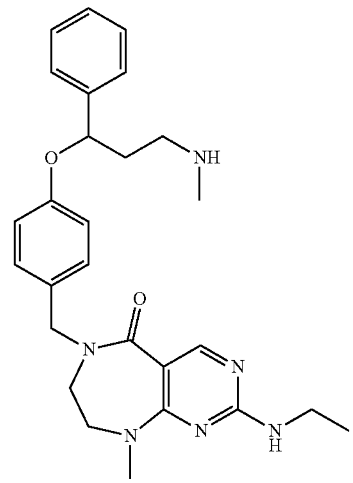 [SMILES: CCNc1ncc2c(n1)N(C)CCN(Cc1ccc(OC(CCNC)c3ccccc3)cc1)C2=O] | 2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | ++ |
| 409 | 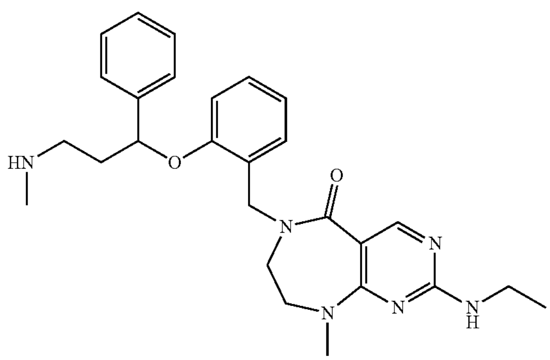 [SMILES: CCNc1ncc2c(n1)N(C)CCN(Cc1ccccc1OC(CCNC)c1ccccc1)C2=O] | 2-(ethylamino)-9-methyl-6-(2-(3-(methylamino)-1-phenylpropoxy)benzyl)-6,7,8,9-tetrahydro-5H-pyrimido[4,5-e][1,4]diazepin-5-one | + |
| 410 | 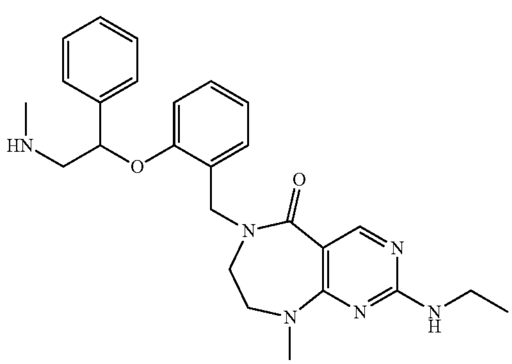 [SMILES: CCNc1ncc2c(n1)N(C)CCN(Cc1ccccc1OC(CNC)c1ccccc1)C2=O] | 2-(ethylamino)-9-methyl-6-(2-(2-(methylamino)-1-phenylethoxy)benzyl)-6,7,8,9-tetrahydro-5H-pyrimido[4,5-e][1,4]diazepin-5-one | + |

TABLE 1-continued
| Ex | Structure | Name | Ki (nM) α2δ-1 |
|---|---|---|---|
| 411 | 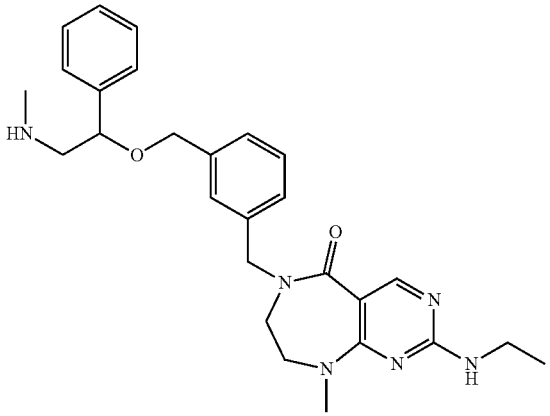 [SMILES: CCNc1ncc2c(n1)N(C)CCN(Cc1cccc(COC(CNC)c3ccccc3)c1)C2=O] | 2-(ethylamino)-9-methyl-6-(3-((2-(methylamino)-1-phenylethoxy)methyl)benzyl)-6,7,8,9-tetrahydro-5H-pyrimido[4,5-e][1,4]diazepin-5-one | + |
| 412 | 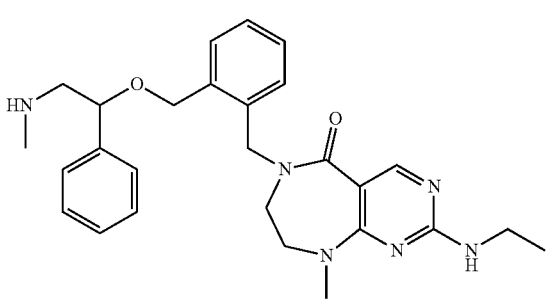 [SMILES: CCNc1ncc2c(n1)N(C)CCN(Cc1ccccc1COC(CNC)c1ccccc1)C2=O] | 2-(ethylamino)-9-methyl-6-(2-((2-(methylamino)-1-phenylethoxy)methyl)benzyl)-6,7,8,9-tetrahydro-5H-pyrimido[4,5-e][1,4]diazepin-5-one | + |
| 413 | 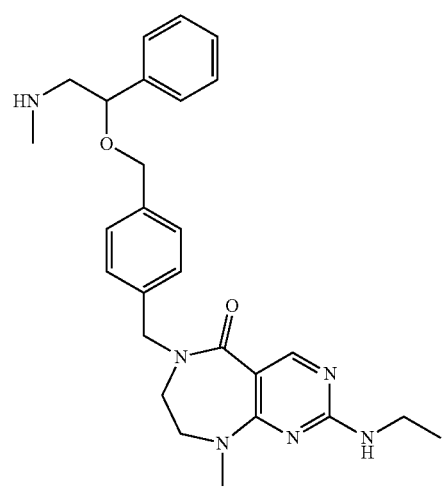 [SMILES: CCNc1ncc2c(n1)N(C)CCN(Cc1ccc(COC(CNC)c3ccccc3)cc1)C2=O] | 2-(ethylamino)-9-methyl-6-(4-((2-(methylamino)-1-phenylethoxy)methyl)benzyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|---|---|---|---|
| 414 | 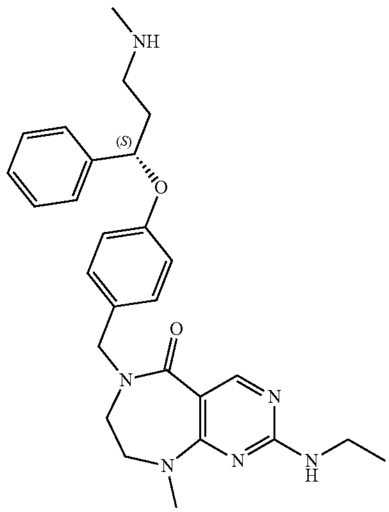 | (S)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | ++ |
| 415 | 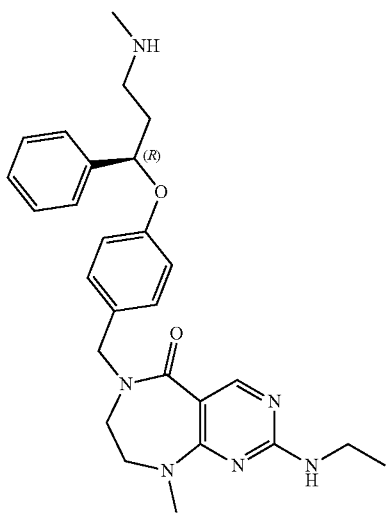 | (R)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | ++ |
| 416 | 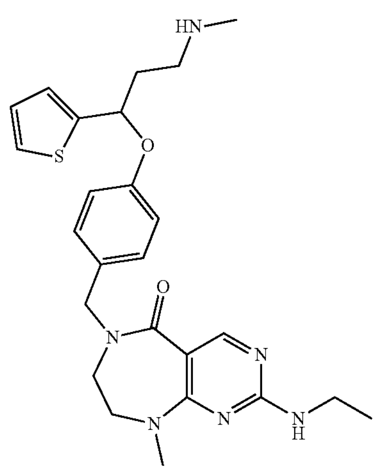 [SMILES: CCNc1ncc2c(n1)N(C)CCN(Cc1ccc(OC(CCNC)c3cccs3)cc1)C2=O] | 2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | ++ |

TABLE 1-continued

| Ex | Structure | Name | Ki (nM) α2δ-1 |
|----|-----------|------|----------------|
| 417 | 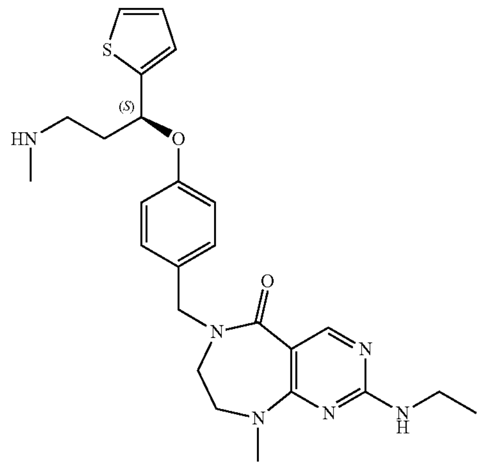 | (S)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ |
| 418 | 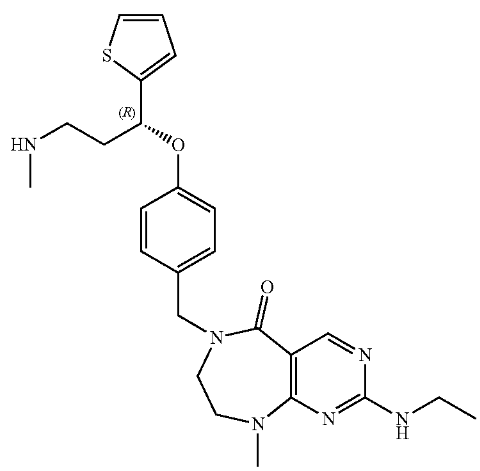 | (R)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | ++ |
| 419 | 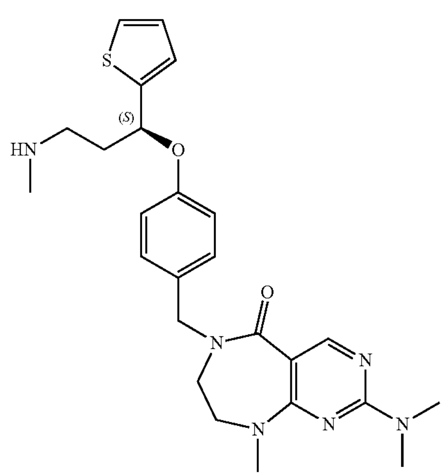 | (S)-2-(dimethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ |

TABLE 1-continued

| Ex | Structure | Name | Ki (nM) α2δ-1 |
|---|---|---|---|
| 420 | 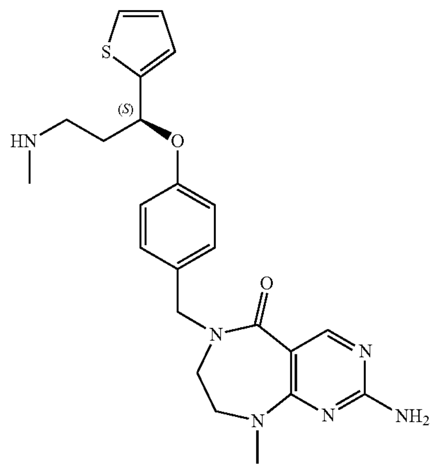 | (S)-2-amino-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ |
| 421 | 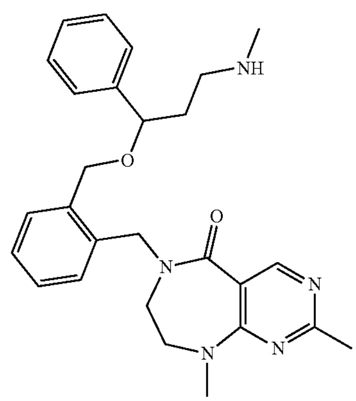 [SMILES: CNCCC(OCc1ccccc1CN1CCN(C)c2nc(C)ncc2C1=O)c1ccccc1] | 2,9-dimethyl-6-(2-((3-(methylamino)-1-phenylpropoxy)methyl)benzyl)-6,7,8,9-tetrahydro-5H-pyrimido[4,5-e][1,4]diazepin-5-one | + |
| 422 | 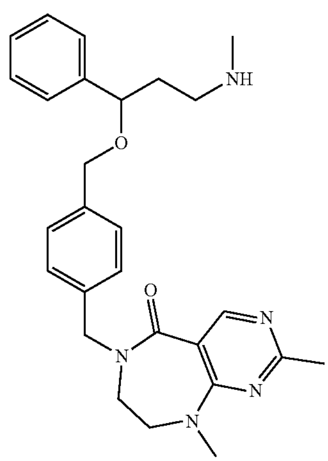 [SMILES: CNCCC(OCc1ccc(CN2CCN(C)c3nc(C)ncc3C2=O)cc1)c1ccccc1] | 2,9-dimethyl-6-(4-((3-(methylamino)-1-phenylpropoxy)methyl)benzyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 423 | 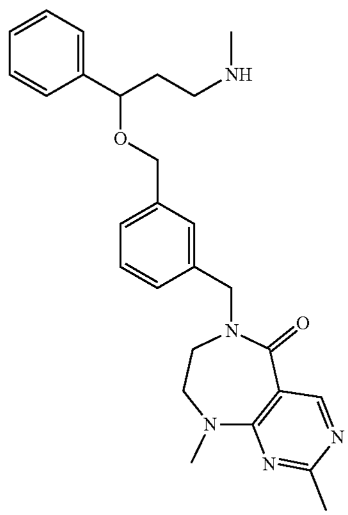 [SMILES: CNCCC(OCc1cccc(CN2CCN(C)c3nc(C)ncc3C2=O)c1)c1ccccc1] | 2,9-dimethyl-6-(3-((3-(methylamino)-1-phenylpropoxy)methyl)benzyl)-6,7,8,9-tetrahydro-5H-pyrimido[4,5-e][1,4]diazepin-5-one | + |
| 424 | 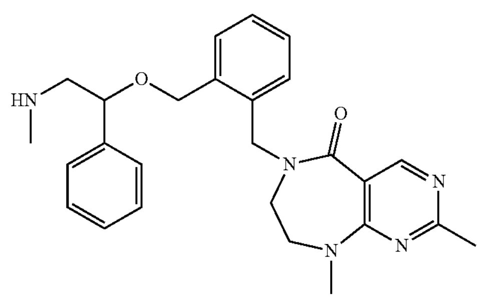 [SMILES: CNCC(OCc1ccccc1CN1CCN(C)c2nc(C)ncc2C1=O)c1ccccc1] | 2,9-dimethyl-6-(2-((2-(methylamino)-1-phenylethoxy)methyl)benzyl)-6,7,8,9-tetrahydro-5H-pyrimido[4,5-e][1,4]diazepin-5-one | + |
| 425 | 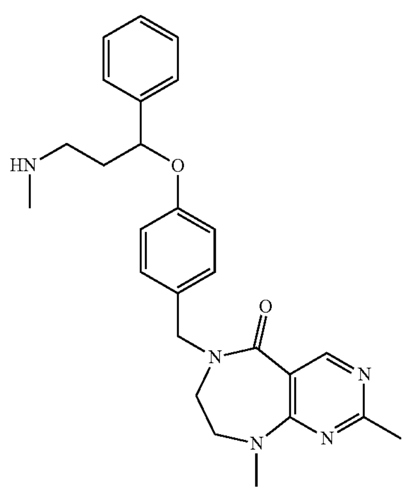 [SMILES: CNCCC(Oc1ccc(CN2CCN(C)c3nc(C)ncc3C2=O)cc1)c1ccccc1] | 2,9-dimethyl-6-(4-(3-(methylamino)-1-phenylpropoxy)benzyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 426 | 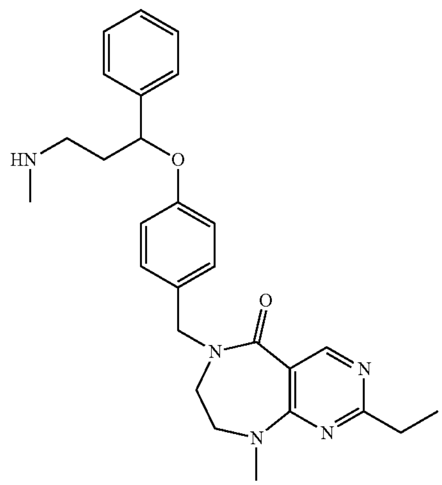 [SMILES: CCc1ncc2c(n1)N(C)CCN(Cc1ccc(OC(CCNC)c3ccccc3)cc1)C2=O] | 2-ethyl-9-methyl-6-(4-(3-(methylamino)-1-phenylpropoxy)benzyl)-6,7,8,9-tetrahydro-5H-pyrimido[4,5-e][1,4]diazepin-5-one | ++ |
| 427 | 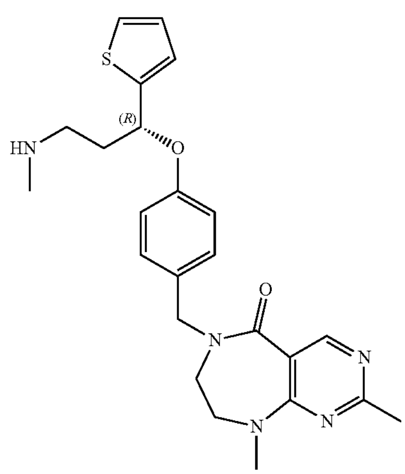 | (R)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one | + |
| 428 | 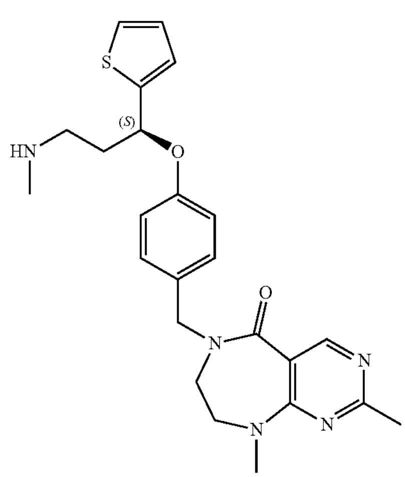 | (S)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one | +++ |

TABLE 1-continued
| Ex | Structure | Name | Ki (nM) α2δ-1 |
|---|---|---|---|
| 429 | 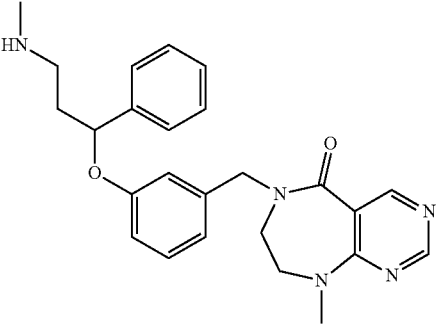 [SMILES: CNCCC(Oc1cccc(CN2CCN(C)c3ncncc3C2=O)c1)c1ccccc1] | 9-methyl-6-(3-(3-(methylamino)-1-phenylpropoxy)benzyl)-6,7,8,9-tetrahydro-5H-pyrimido[4,5-e][1,4]diazepin-5-one | + |
| 430 | 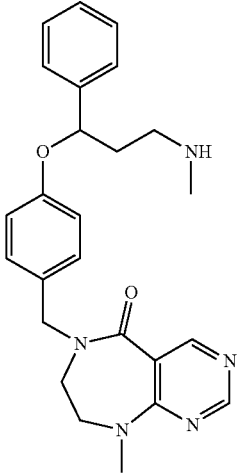 [SMILES: CNCCC(Oc1ccc(CN2CCN(C)c3ncncc3C2=O)cc1)c1ccccc1] | 9-methyl-6-(4-(3-(methylamino)-1-phenylpropoxy)benzyl)-6,7,8,9-tetrahydro-5H-pyrimido[4,5-e][1,4]diazepin-5-one | ++ |
| 431 | 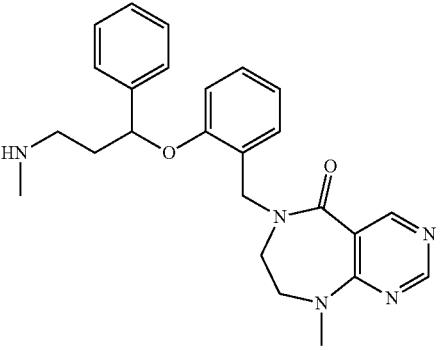 [SMILES: CNCCC(Oc1ccccc1CN1CCN(C)c2ncncc2C1=O)c1ccccc1] | 9-methyl-6-(2-(3-(methylamino)-1-phenylpropoxy)benzyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 432 | 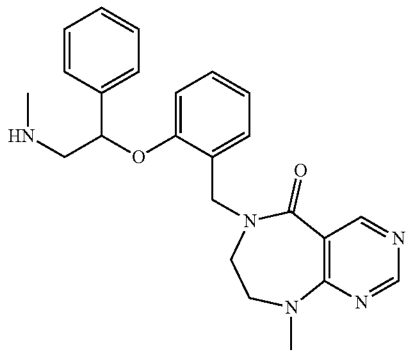 [SMILES: CNCC(Oc1ccccc1CN1CCN(C)c2ncncc2C1=O)c1ccccc1] | 9-methyl-6-(2-(2-(methylamino)-1-phenylethoxy)benzyl)-6,7,8,9-tetrahydro-5H-pyrimido[4,5-e][1,4]diazepin-5-one | + |
| 433 | 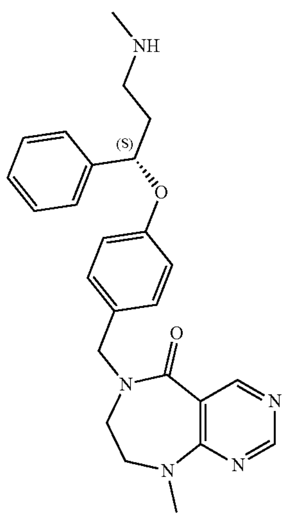 | (S)-9-methyl-6-(4-(3-(methylamino)-1-phenylpropoxy)benzyl)-6,7,8,9-tetrahydro-5H-pyrimido[4,5-e][1,4]diazepin-5-one | ++ |
| 434 | 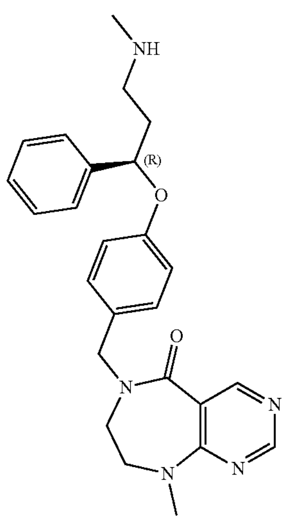 | (R)-9-methyl-6-(4-(3-(methylamino)-1-phenylpropoxy)benzyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 435 | 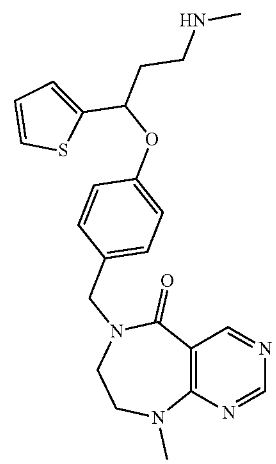 [SMILES: CNCCC(Oc1ccc(CN2CCN(C)c3ncncc3C2=O)cc1)c1cccs1] | 9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ |
| 436 | 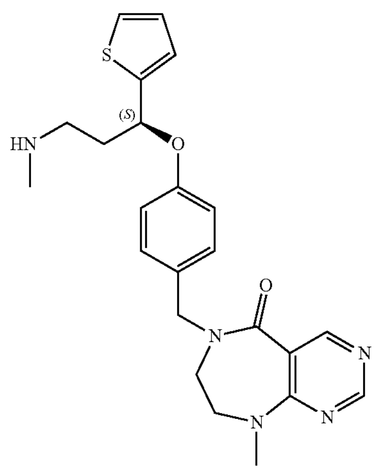 | (S)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ |
| 437 | 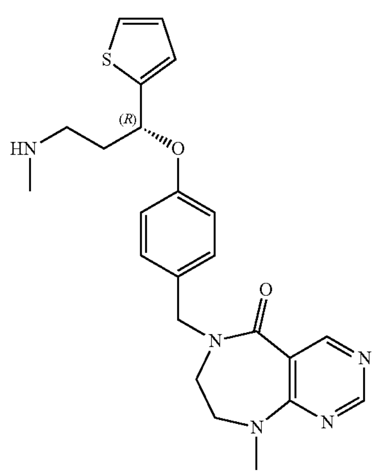 | (R)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | + |

TABLE 1-continued

| Ex | Structure | Name | Ki (nM) α2δ-1 |
|---|---|---|---|
| 438 | 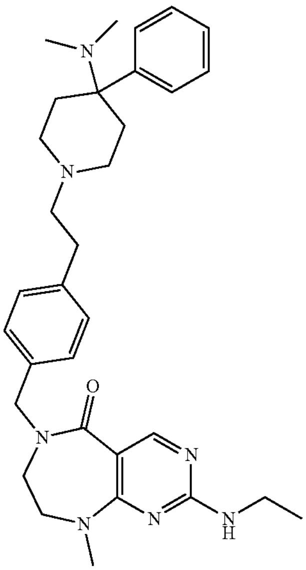 [SMILES: CCNc1ncc2c(n1)N(C)CCN(Cc1ccc(CCN3CCC(c4ccccc4)(N(C)C)CC3)cc1)C2=O] | 6-(3-(2-(4-(dimethylamino)-4-phenylpiperidin-1-yl)ethyl)phenyl)-2-(ethylamino)-9-methyl-6,7,8,9-tetrahydro-5H-pyrimido[4,5-e][1,4]diazepin-5-one | ++ |
| 439 | 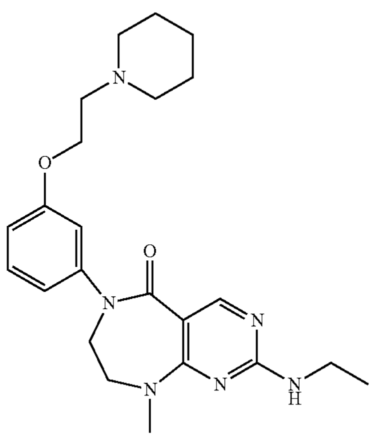 [SMILES: CCNc1ncc2c(n1)N(C)CCN(c1cccc(OCCN3CCCCC3)c1)C2=O] | 2-(ethylamino)-9-methyl-6-(3-(2-(piperidin-1-yl)ethoxy)phenyl)-6,7,8,9-tetrahydro-5H-pyrimido[4,5-e][1,4]diazepin-5-one | ++ |
| 440 | 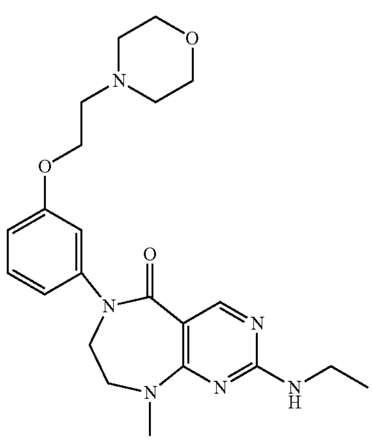 [SMILES: CCNc1ncc2c(n1)N(C)CCN(c1cccc(OCCN3CCOCC3)c1)C2=O] | 2-(ethylamino)-9-methyl-6-(3-(2-morpholinoethoxy)phenyl)-6,7,8,9-tetrahydro-5H-pyrimido[4,5-e][1,4]diazepin-5-one | ++ |

TABLE 1-continued
| Ex | Structure | Name | Ki (nM) α2δ-1 |
|----|-----------|------|---------------|
| 441 | 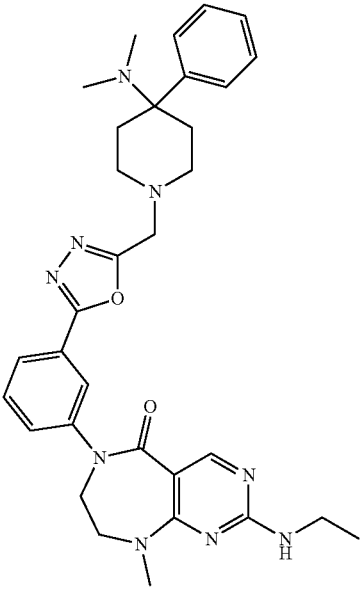 [SMILES: CCNc1ncc2c(n1)N(C)CCN(c1cccc(-c3nnc(CN4CCC(c5ccccc5)(N(C)C)CC4)o3)c1)C2=O] | 6-(3-(5-((4-(dimethylamino)-4-phenylpiperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one | +++ |
| 442 | 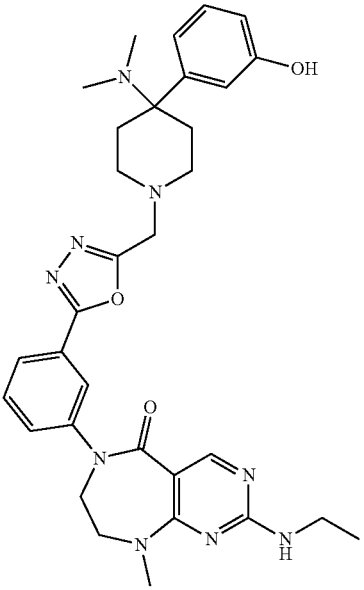 [SMILES: CCNc1ncc2c(n1)N(C)CCN(c1cccc(-c3nnc(CN4CCC(c5cccc(O)c5)(N(C)C)CC4)o3)c1)C2=O] | 6-(3-(5-((4-(dimethylamino)-4-(3-hydroxyphenyl)piperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one | ++++ |

The binding results for the α2δ-1 and the NET receptor for the dual compounds are shown in Table 2:

| Ex | Structure | Name | Ki (nM) α2δ-1 | Ki (nM) NET |
|---|---|---|---|---|
| 148 | 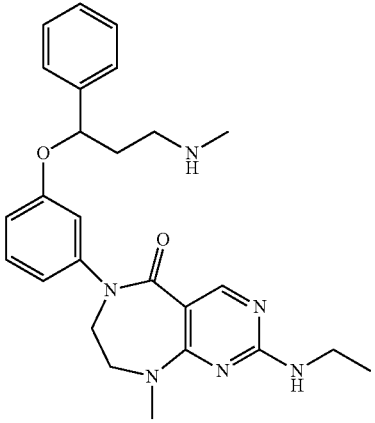 [SMILES: CCNc1ncc2c(n1)N(C)CCN(c1cccc(OC(CCNC)c3ccccc3)c1)C2=O] | 2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | ++ | +++ |
| 149 | 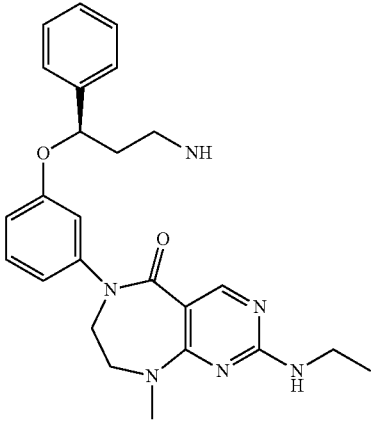 [SMILES: CCNc1ncc2c(n1)N(C)CCN(c1cccc(O[C@H](CCN)c3ccccc3)c1)C2=O] | (R)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | ++ | ++ |
| 150 | 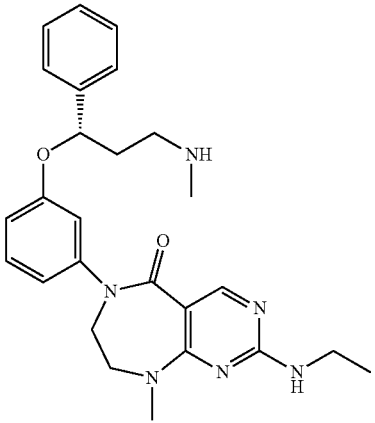 [SMILES: CCNc1ncc2c(n1)N(C)CCN(c1cccc(O[C@@H](CCNC)c3ccccc3)c1)C2=O] | (S)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one | ++ | ++++ |

-continued

| Ex | Structure | Name | Ki (nM) α2δ-1 | Ki (nM) NET |
|---|---|---|---|---|
| 151 | 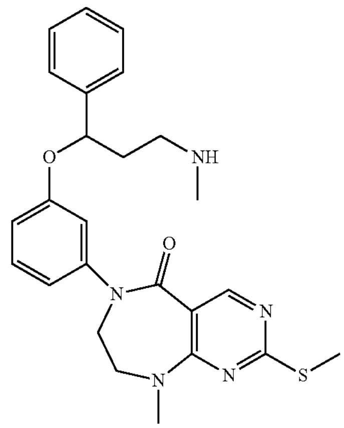 | 9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | ++ | ++++ |
| 152 | 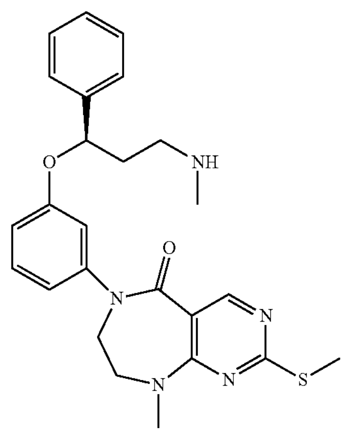 [SMILES: CNCC[C@@H](Oc1cccc(N2CCN(C)c3nc(SC)ncc3C2=O)c1)c1ccccc1] | (R)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | ++ | +++ |
| 153 | 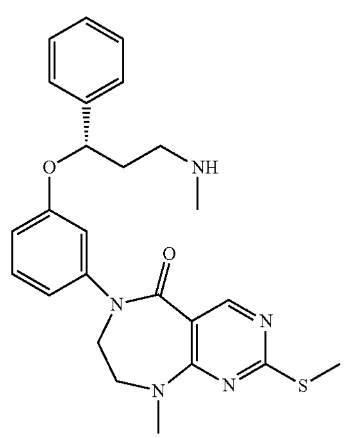 [SMILES: CNCC[C@H](Oc1cccc(N2CCN(C)c3nc(SC)ncc3C2=O)c1)c1ccccc1] | (S)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one | + | ++++ |

-continued

| Ex | Structure | Name | Ki (nM) α2δ-1 | Ki (nM) NET |
|---|---|---|---|---|
| 154 | 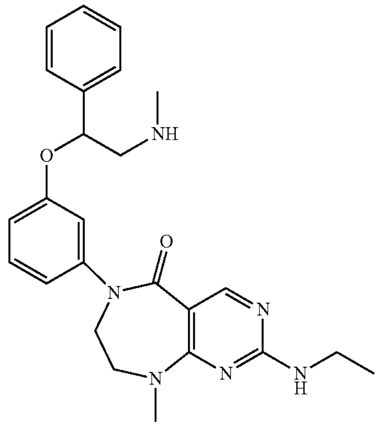 [SMILES: CCNc1ncc2c(n1)N(C)CCN(c1cccc(OC(CNC)c3ccccc3)c1)C2=O] | 2-(ethylamino)-9-methyl-6-(3-(2-(methylamino)-1-phenylethoxy)phenyl)-6,7,8,9-tetrahydro-5H-pyrimido[4,5-e][1,4]diazepin-5-one | ++ | +++ |
| 159 | 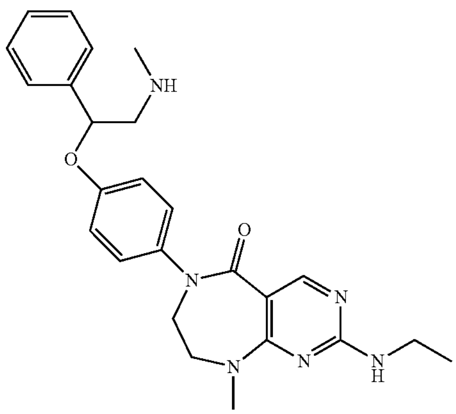 [SMILES: CCNc1ncc2c(n1)N(C)CCN(c1ccc(OC(CNC)c3ccccc3)cc1)C2=O] | 2-(ethylamino)-9-methyl-6-(4-(2-(methylamino)-1-phenylethoxy)phenyl)-6,7,8,9-tetrahydro-5H-pyrimido[4,5-e][1,4]diazepin-5-one | + | + |
| 160 | 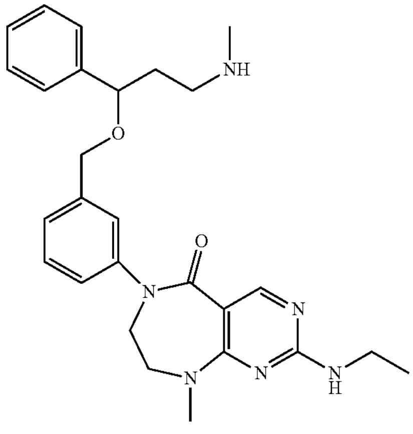 | 2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | ++ |

| Ex | Structure | Name | Ki (nM) α2δ-1 | Ki (nM) NET |
|---|---|---|---|---|
| 161 | 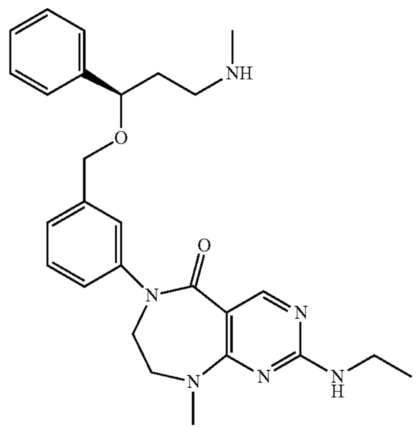 [SMILES: CCNc1ncc2c(n1)N(C)CCN(c1cccc(CO[C@H](CCNC)c3ccccc3)c1)C2=O] | (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | ++ |
| 162 | 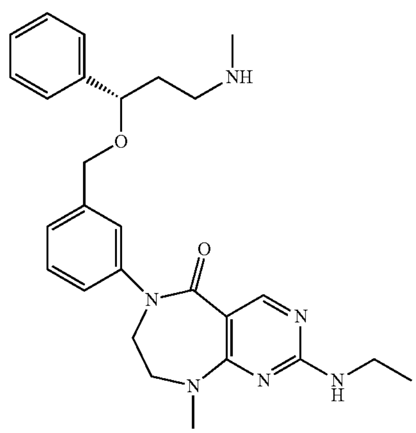 [SMILES: CCNc1ncc2c(n1)N(C)CCN(c1cccc(CO[C@@H](CCNC)c3ccccc3)c1)C2=O] | (S)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | ++ |
| 163 | 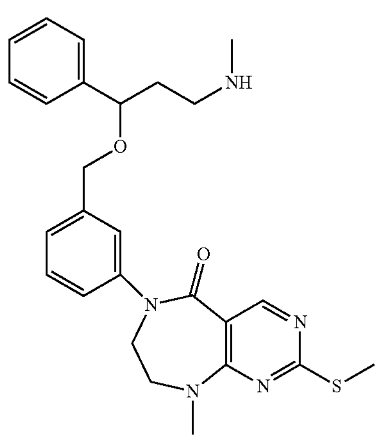 [SMILES: CNCCC(OCc1cccc(N2CCN(C)c3nc(SC)ncc3C2=O)c1)c1ccccc1] | 9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | ++ | +++ |

| Ex | Structure | Name | Ki (nM) α2δ-1 | Ki (nM) NET |
|---|---|---|---|---|
| 164 | 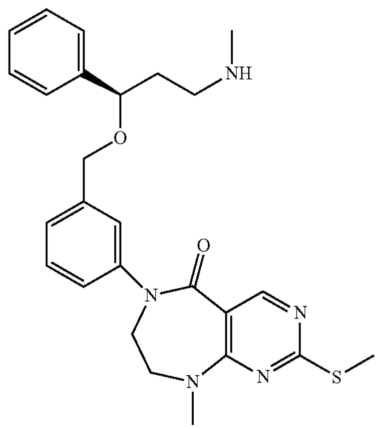 [SMILES: CNCC[C@@H](OCc1cccc(N2CCN(C)c3nc(SC)ncc3C2=O)c1)c1ccccc1] | (R)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | +++ | +++ |
| 165 | 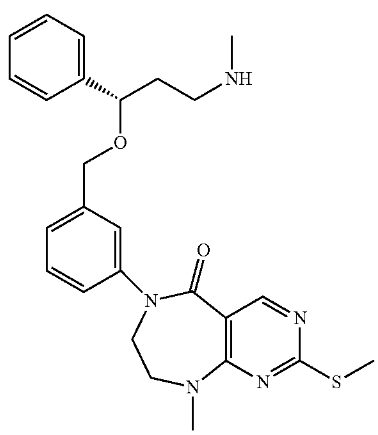 | (S)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one | + | +++ |
| 166 | 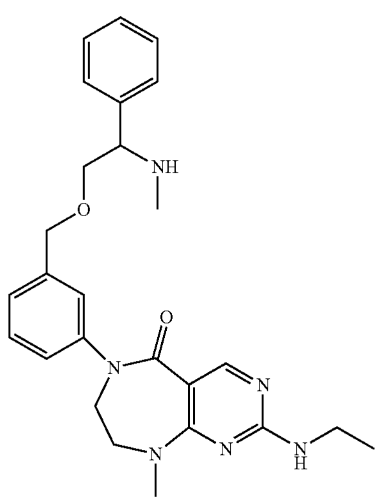 [SMILES: CCNc1ncc2c(n1)N(C)CCN(c1cccc(COCC(NC)c3ccccc3)c1)C2=O] | 2-(ethylamino)-9-methyl-6-(3-((2-(methylamino)-2-phenylethoxy)methyl)phenyl)-6,7,8,9-tetrahydro-5H-pyrimido[4,5-e][1,4]diazepin-5-one | ++ | ++ |

-continued

| Ex | Structure | Name | Ki (nM) α2δ-1 | Ki (nM) NET |
|---|---|---|---|---|
| 167 | 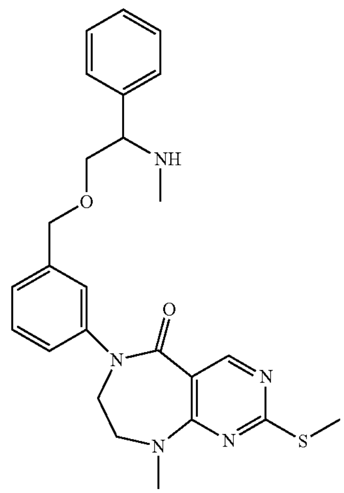 [SMILES: CNC(COCc1cccc(N2CCN(C)c3nc(SC)ncc3C2=O)c1)c1ccccc1] | 9-methyl-6-(3-((2-(methylamino)-2-phenylethoxy)methyl)phenyl)-2-(methylthio)-6,7,8,9-tetrahydro-5H-pyrimido[4,5-e][1,4]diazepin-5-one | + | + |
| 169 | 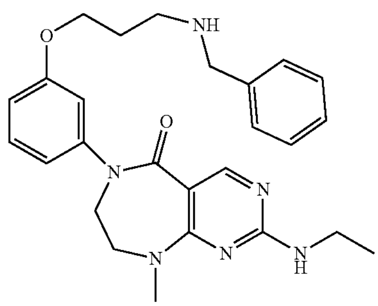 [SMILES: CCNc1ncc2c(n1)N(C)CCN(c1cccc(OCCCNCc3ccccc3)c1)C2=O] | 6-(3-(3-(benzylamino)propoxy)phenyl)-2-(ethylamino)-9-methyl-6,7,8,9-tetrahydro-5H-pyrimido[4,5-e][1,4]diazepin-5-one | +++ | ++ |
| 173 | 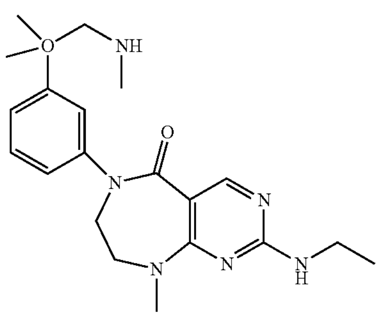 | 2-(ethylamino)-9-methyl-6-(3-(2-methyl-1-(methylamino)propan-2-yl)phenyl)-6,7,8,9-tetrahydro-5H-pyrimido[4,5-e][1,4]diazepin-5-one | ++ | + |
| 176 | 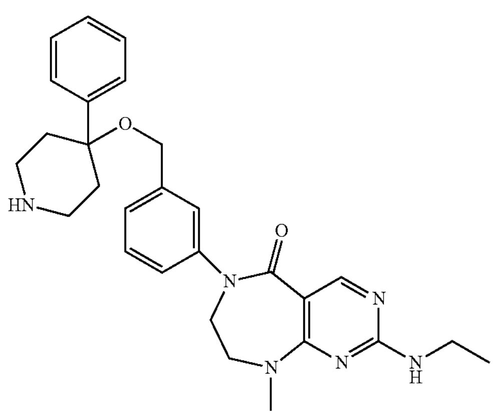 [SMILES: CCNc1ncc2c(n1)N(C)CCN(c1cccc(COC3(c4ccccc4)CCNCC3)c1)C2=O] | 2-(ethylamino)-9-methyl-6-(3-(((4-phenylpiperidin-4-yl)oxy)methyl)phenyl)-6,7,8,9-tetrahydro-5H-pyrimido[4,5-e][1,4]diazepin-5-one | ++ | + |

| Ex | Structure | Name | Ki (nM) α2δ-1 | Ki (nM) NET |
|---|---|---|---|---|
| 179 | 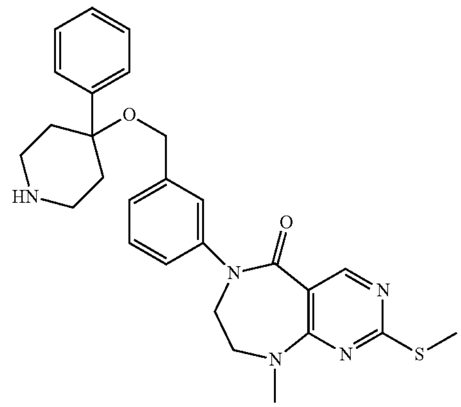 [SMILES: CSc1ncc2c(n1)N(C)CCN(c1cccc(COC3(c4ccccc4)CCNCC3)c1)C2=O] | 9-methyl-2-(methylthio)-6-(3-(((4-phenylpiperidin-4-yl)oxy)methyl)phenyl)-6,7,8,9-tetrahydro-5H-pyrimido[4,5-e][1,4]diazepin-5-one | + | + |
| 182 | 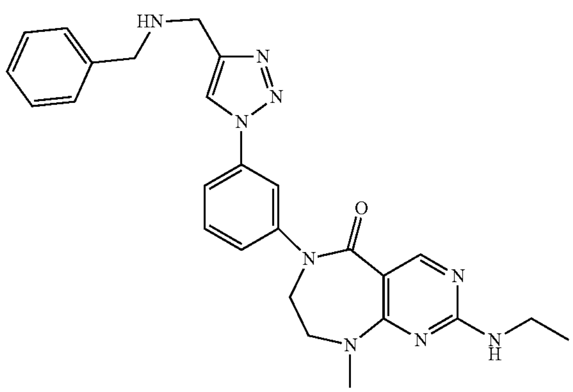 [SMILES: CCNc1ncc2c(n1)N(C)CCN(c1cccc(-n3cc(CNCc4ccccc4)nn3)c1)C2=O] | 6-(3-(4-((benzylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ | ++++ |
| 183 | 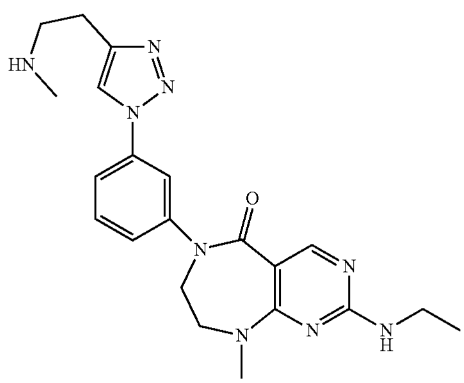 [SMILES: CCNc1ncc2c(n1)N(C)CCN(c1cccc(-n3cc(CCNC)nn3)c1)C2=O] | 2-(ethylamino)-9-methyl-6-(3-(4-(2-(methylamino)ethyl)-1H-1,2,3-triazol-1-yl)phenyl)-6,7,8,9-tetrahydro-5H-pyrimido[4,5-e][1,4]diazepin-5-one | +++ | + |

| Ex | Structure | Name | Ki (nM) α2δ-1 | Ki (nM) NET |
|---|---|---|---|---|
| 193 | 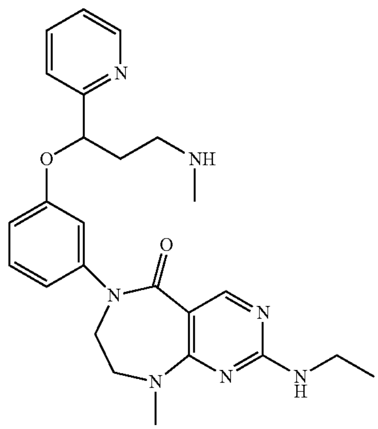 [SMILES: CCNc1ncc2c(n1)N(C)CCN(c1cccc(OC(CCNC)c3ccccn3)c1)C2=O] | 2-(ethylamino)-9-methyl-6-(3-(3-(methylamino)-1-(pyridin-2-yl)propoxy)phenyl)-6,7,8,9-tetrahydro-5H-pyrimido[4,5-e][1,4]diazepin-5-one | ++ | + |
| 194 | 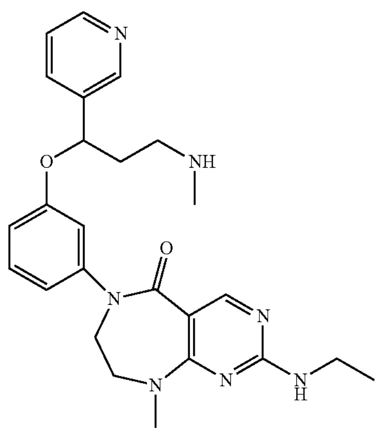 [SMILES: CCNc1ncc2c(n1)N(C)CCN(c1cccc(OC(CCNC)c3cccnc3)c1)C2=O] | 2-(ethylamino)-9-methyl-6-(3-(3-(methylamino)-1-(pyridin-3-yl)propoxy)phenyl)-6,7,8,9-tetrahydro-5H-pyrimido[4,5-e][1,4]diazepin-5-one | ++ | + |
| 195 | 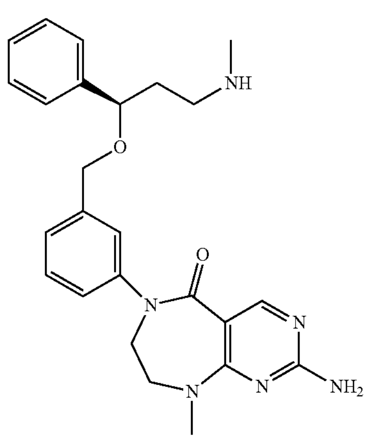 [SMILES: CNCC[C@@H](OCc1cccc(N2CCN(C)c3nc(N)ncc3C2=O)c1)c1ccccc1] | (R)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | ++ |

-continued

| Ex | Structure | Name | Ki (nM) α2δ-1 | Ki (nM) NET |
|---|---|---|---|---|
| 196 | 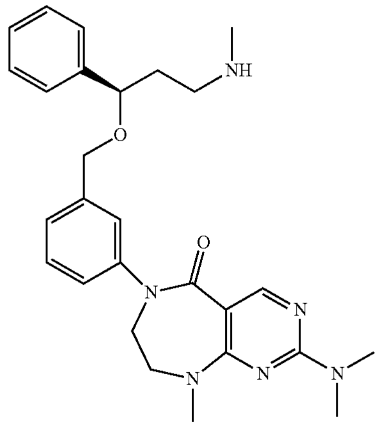 [SMILES: CNCC[C@@H](OCc1cccc(N2CCN(C)c3nc(N(C)C)ncc3C2=O)c1)c1ccccc1] | (R)-2-(dimethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | ++ |
| 197 | 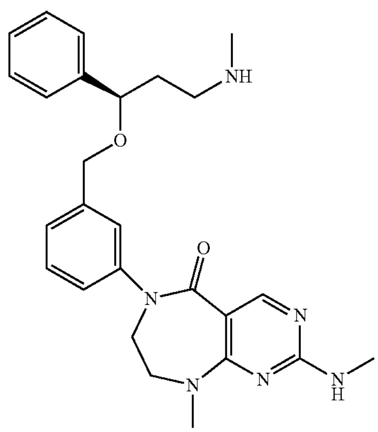 [SMILES: CNCC[C@@H](OCc1cccc(N2CCN(C)c3nc(NC)ncc3C2=O)c1)c1ccccc1] | (R)-9-methyl-2-(methylamino)-6-(3-((3-(methylamino)-1-phenylpropoxy)methyl)phenyl)-6,7,8,9-tetrahydro-5H-pyrimido[4,5-e][1,4]diazepin-5-one | ++ | ++ |
| 198 | 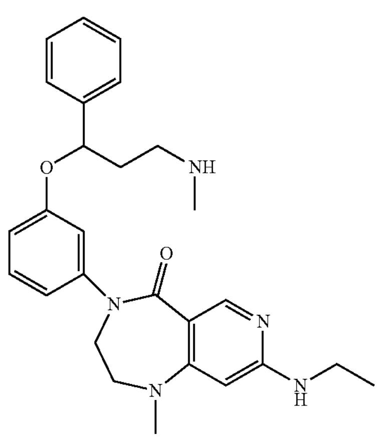 [SMILES: CCNc1cc2c(cn1)C(=O)N(c1cccc(OC(CCNC)c3ccccc3)c1)CCN2C] | 8-(ethylamino)-1-methyl-4-(3-(3-(methylamino)-1-phenylpropoxy)phenyl)-1,2,3,4-tetrahydro-5H-pyrido[4,3-e][1,4]diazepin-5-one | ++ | +++ |

| Ex | Structure | Name | Ki (nM) α2δ-1 | Ki (nM) NET |
|---|---|---|---|---|
| 199 | 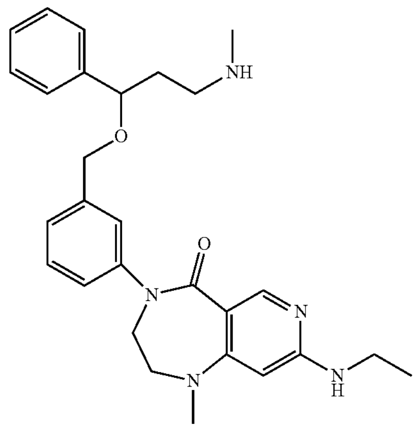 [SMILES: CCNc1cc2c(cn1)C(=O)N(c1cccc(COC(CCNC)c3ccccc3)c1)CCN2C] | 8-(ethylamino)-1-methyl-4-(3-((3-(methylamino)-1-phenylpropoxy)methyl)phenyl)-1,2,3,4-tetrahydro-5H-pyrido[4,3-e][1,4]diazepin-5-one | ++ | + |
| 201 | 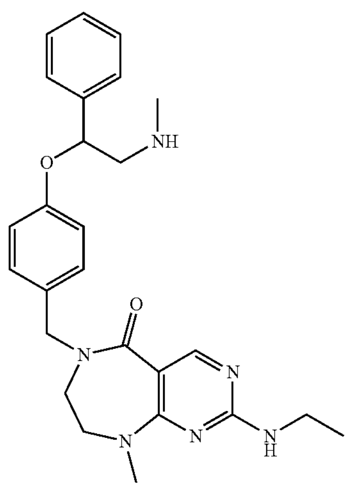 [SMILES: CCNc1ncc2c(n1)N(C)CCN(Cc1ccc(OC(CNC)c3ccccc3)cc1)C2=O] | 2-(ethylamino)-9-methyl-6-(4-(2-(methylamino)-1-phenylethoxy)benzyl)-6,7,8,9-tetrahydro-5H-pyrimido[4,5-e][1,4]diazepin-5-one | + | ++++ |
| 203 | 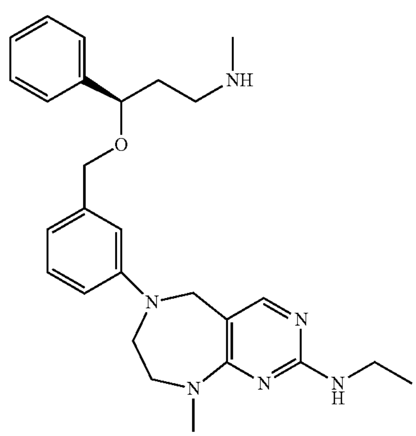 [SMILES: CCNc1ncc2c(n1)N(C)CCN(c1cccc(CO[C@H](CCNC)c3ccccc3)c1)C2] | (R)-N-ethyl-9-methyl-6-(3-((3-(methylamino)-1-phenylpropoxy)methyl)phenyl)-6,7,8,9-tetrahydro-5H-pyrimido[4,5-e][1,4]diazepin-2-amine | ++ | ++ |

| Ex | Structure | Name | Ki (nM) α2δ-1 | Ki (nM) NET |
|---|---|---|---|---|
| 204 | 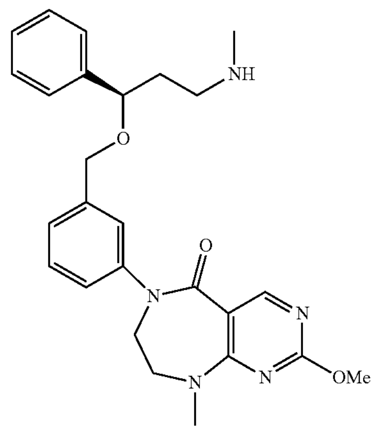 [SMILES: CNCC[C@@H](OCc1cccc(N2CCN(C)c3nc(OC)ncc3C2=O)c1)c1ccccc1] | (R)-2-methoxy-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | +++ |
| 205 | 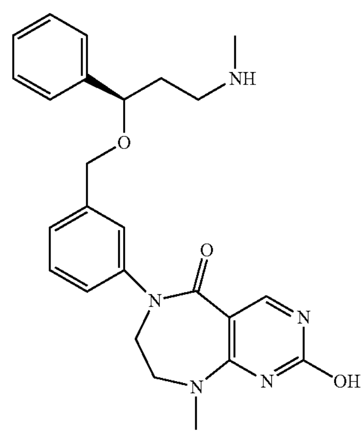 [SMILES: CNCC[C@@H](OCc1cccc(N2CCN(C)c3nc(O)ncc3C2=O)c1)c1ccccc1] | (R)-2-hydroxy-9-methyl-6-(3-((3-(methylamino)-1-phenylpropoxy)methyl)phenyl)-6,7,8,9-tetrahydro-5H-pyrimido[4,5-e][1,4]diazepin-5-one | +++ | + |
| 206 | 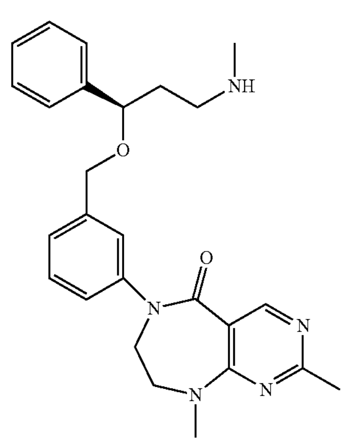 [SMILES: CNCC[C@@H](OCc1cccc(N2CCN(C)c3nc(C)ncc3C2=O)c1)c1ccccc1] | (R)-2,9-dimethyl-6-(3-((3-(methylamino)-1-phenylpropoxy)methyl)phenyl)-6,7,8,9-tetrahydro-5H-pyrimido[4,5-e][1,4]diazepin-5-one | +++ | +++ |

| Ex | Structure | Name | Ki (nM) α2δ-1 | Ki (nM) NET |
|---|---|---|---|---|
| 207 | 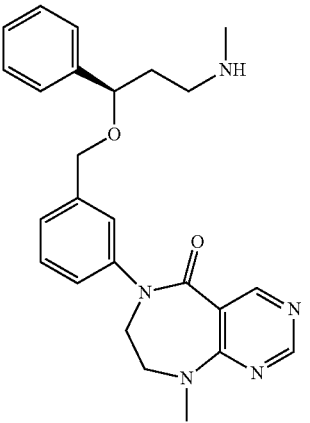 [SMILES: CNCC[C@@H](OCc1cccc(N2CCN(C)c3ncncc3C2=O)c1)c1ccccc1] | (R)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | ++ |
| 208 | 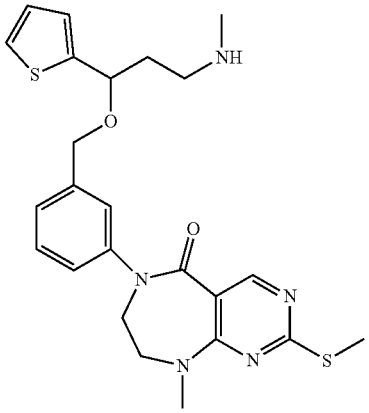 [SMILES: CNCCC(OCc1cccc(N2CCN(C)c3nc(SC)ncc3C2=O)c1)c1cccs1] | 9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | ++ | ++ |
| 209 | 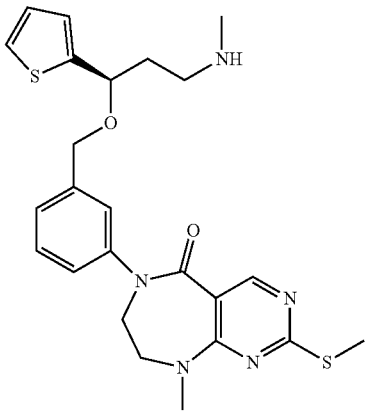 [SMILES: CNCC[C@@H](OCc1cccc(N2CCN(C)c3nc(SC)ncc3C2=O)c1)c1cccs1] | (R)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | +++ | +++ |

-continued

| Ex | Structure | Name | Ki (nM) α2δ-1 | Ki (nM) NET |
|---|---|---|---|---|
| 210 | 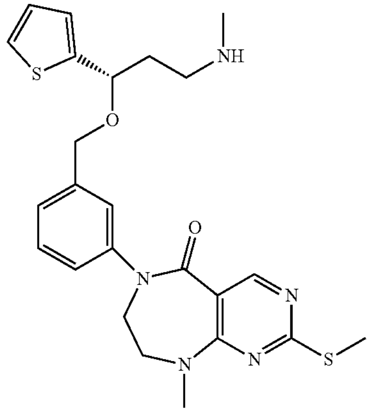 [SMILES: CNCC[C@H](OCc1cccc(N2CCN(C)c3nc(SC)ncc3C2=O)c1)c1cccs1] | (S)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | + | +++ |
| 211 | 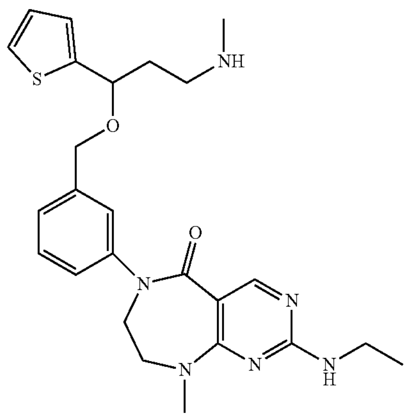 [SMILES: CCNc1ncc2c(n1)N(C)CCN(c1cccc(COC(CCNC)c3cccs3)c1)C2=O] | 2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | + |
| 212 | 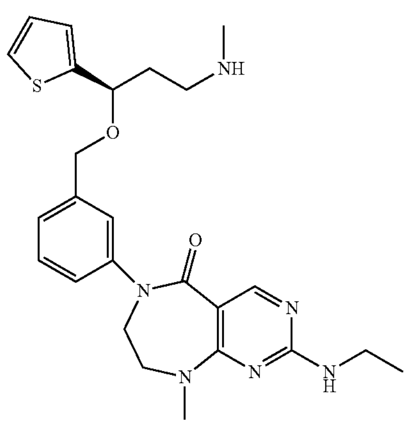 [SMILES: CCNc1ncc2c(n1)N(C)CCN(c1cccc(CO[C@H](CCNC)c3cccs3)c1)C2=O] | (R)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | + |

-continued

| Ex | Structure | Name | Ki (nM) α2δ-1 | Ki (nM) NET |
|---|---|---|---|---|
| 213 | 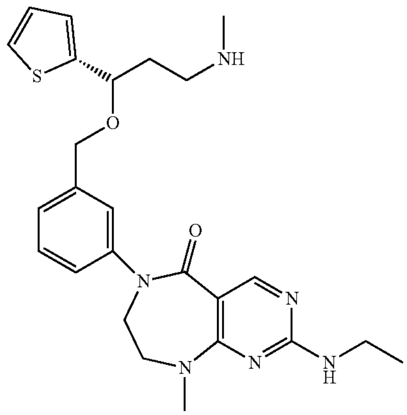 | (S)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | ++ | + |
| 214 | 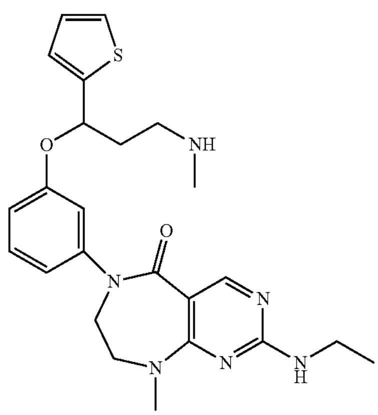 [SMILES: CCNc1ncc2c(n1)N(C)CCN(c1cccc(OC(CCNC)c3cccs3)c1)C2=O] | 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | ++ | ++ |
| 215 | 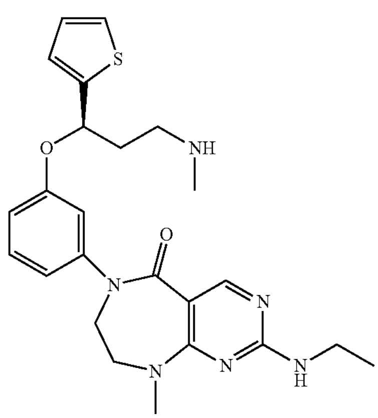 [SMILES: CCNc1ncc2c(n1)N(C)CCN(c1cccc(O[C@H](CCNC)c3cccs3)c1)C2=O] | (R)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ | + |

| Ex | Structure | Name | Ki (nM) α2δ-1 | Ki (nM) NET |
|---|---|---|---|---|
| 216 | 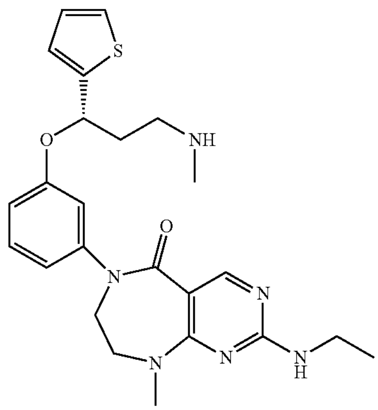 [SMILES: CCNc1ncc2c(n1)N(C)CCN(c1cccc(O[C@@H](CCNC)c3cccs3)c1)C2=O] | (S)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ | +++ |
| 217 | 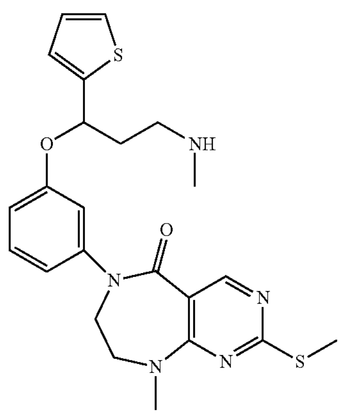 | 9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | ++ | ++++ |
| 218 | 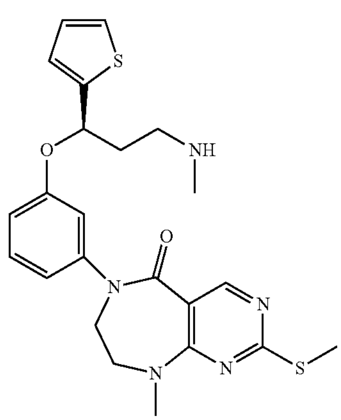 [SMILES: CNCC[C@@H](Oc1cccc(N2CCN(C)c3nc(SC)ncc3C2=O)c1)c1cccs1] | (R)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | ++ | ++ |

-continued

| Ex | Structure | Name | Ki (nM) α2δ-1 | Ki (nM) NET |
|---|---|---|---|---|
| 219 | 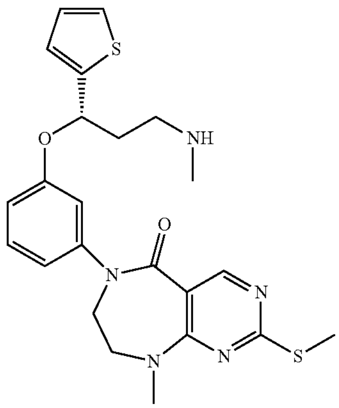 [SMILES: CNCC[C@H](Oc1cccc(N2CCN(C)c3nc(SC)ncc3C2=O)c1)c1cccs1] | (S)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one | ++ | ++++ |
| 221 | 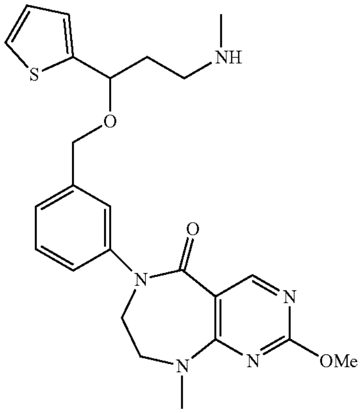 [SMILES: CNCCC(OCc1cccc(N2CCN(C)c3nc(OC)ncc3C2=O)c1)c1cccs1] | 2-methoxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | ++ |
| 222 | 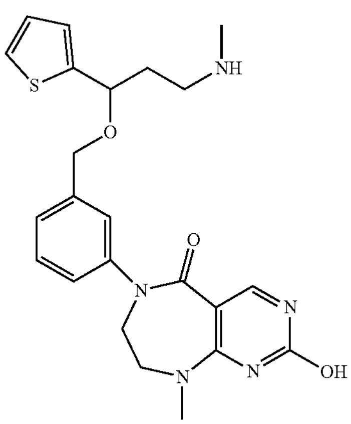 [SMILES: CNCCC(OCc1cccc(N2CCN(C)c3nc(O)ncc3C2=O)c1)c1cccs1] | 2-hydroxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | + |

| Ex | Structure | Name | Ki (nM) α2δ-1 | Ki (nM) NET |
|---|---|---|---|---|
| 223 | 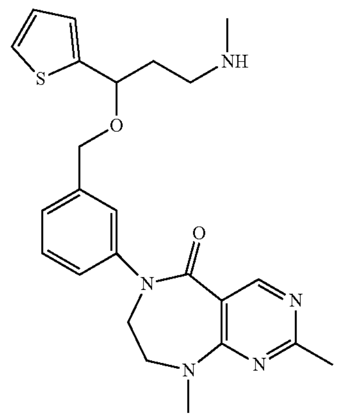 [SMILES: CNCCC(OCc1cccc(N2CCN(C)c3nc(C)ncc3C2=O)c1)c1cccs1] | 2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | ++ |
| 224 | 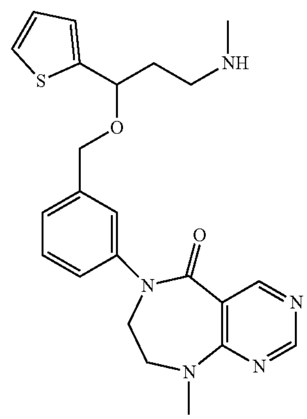 [SMILES: CNCCC(OCc1cccc(N2CCN(C)c3ncncc3C2=O)c1)c1cccs1] | 9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | + |
| 225 | 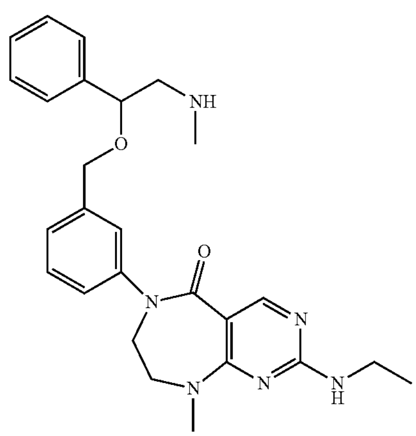 [SMILES: CCNc1ncc2c(n1)N(C)CCN(c1cccc(COC(CNC)c3ccccc3)c1)C2=O] | 2-(ethylamino)-9-methyl-6-(3-((2-(methylamino)-1-phenylethoxy)methyl)phenyl)-6,7,8,9-tetrahydro-5H-pyrimido[4,5-e][1,4]diazepin-5-one | ++ | + |

| Ex | Structure | Name | Ki (nM) α2δ-1 | Ki (nM) NET |
|---|---|---|---|---|
| 226 | 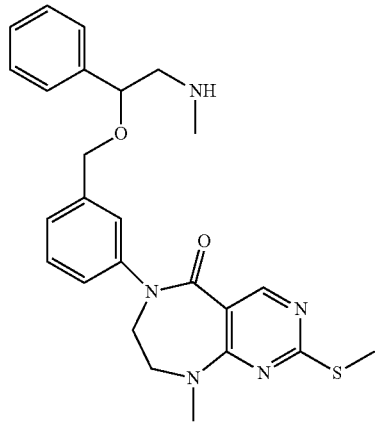 [SMILES: CNCC(OCc1cccc(N2CCN(C)c3nc(SC)ncc3C2=O)c1)c1ccccc1] | 9-methyl-6-(3-((2-(methylamino)-1-phenylethoxy)methyl)phenyl)-2-(methylthio)-6,7,8,9-tetrahydro-5H-pyrimido[4,5-e][1,4]diazepin-5-one | + | ++ |
| 227 | 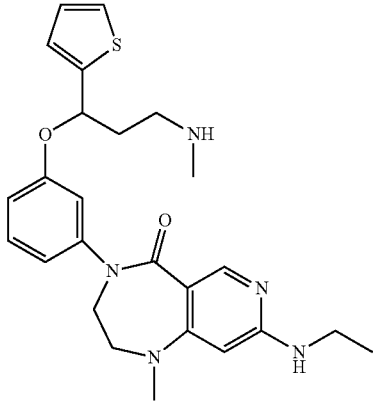 | 8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | +++ |
| 229 | 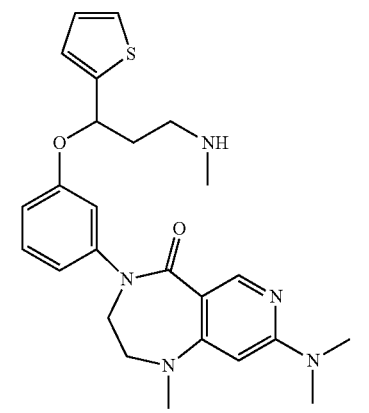 [SMILES: CNCCC(Oc1cccc(N2CCN(C)c3cc(N(C)C)ncc3C2=O)c1)c1cccs1] | 8-(dimethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | + |

-continued

| Ex | Structure | Name | Ki (nM) α2δ-1 | Ki (nM) NET |
|---|---|---|---|---|
| 230 | 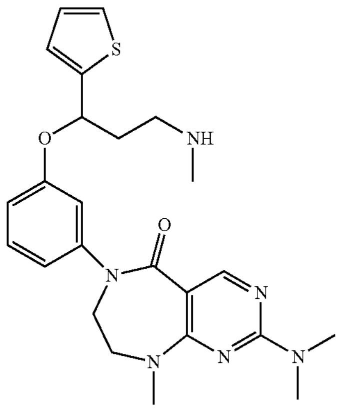 [SMILES: CNCCC(Oc1cccc(N2CCN(C)c3nc(N(C)C)ncc3C2=O)c1)c1cccs1] | 2-(dimethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | ++ | +++ |
| 231 | 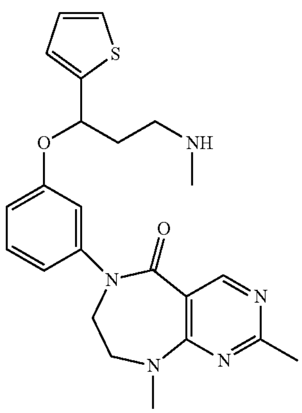 [SMILES: CNCCC(Oc1cccc(N2CCN(C)c3nc(C)ncc3C2=O)c1)c1cccs1] | 2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | ++ | ++++ |
| 232 | 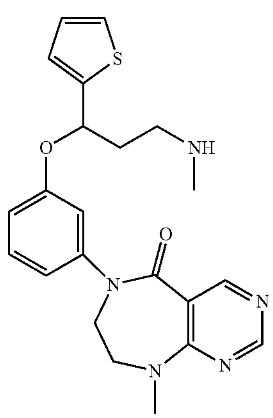 [SMILES: CNCCC(Oc1cccc(N2CCN(C)c3ncncc3C2=O)c1)c1cccs1] | 9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ | ++++ |

-continued

| Ex | Structure | Name | Ki (nM) α2δ-1 | Ki (nM) NET |
|---|---|---|---|---|
| 236 | 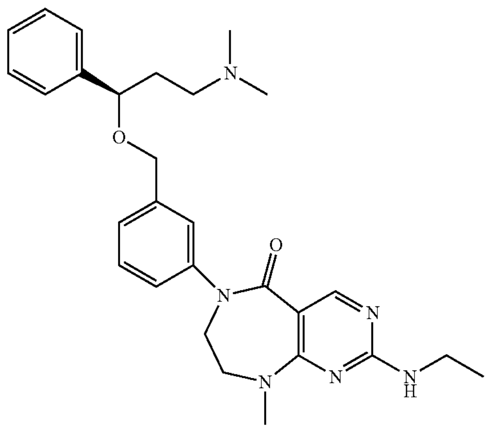 [SMILES: CCNc1ncc2c(n1)N(C)CCN(c1cccc(CO[C@H](CCN(C)C)c3ccccc3)c1)C2=O] | (R)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one | ++ | ++ |
| 237 | 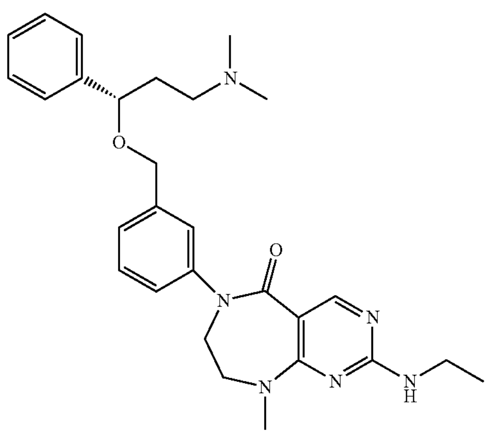 [SMILES: CCNc1ncc2c(n1)N(C)CCN(c1cccc(CO[C@@H](CCN(C)C)c3ccccc3)c1)C2=O] | (S)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one | ++ | + |
| 238 | 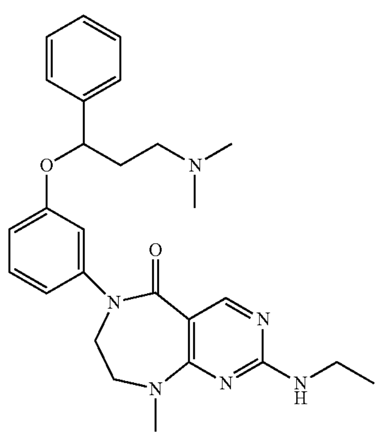 [SMILES: CCNc1ncc2c(n1)N(C)CCN(c1cccc(OC(CCN(C)C)c3ccccc3)c1)C2=O] | 6-(3-(3-(dimethylamino)-1-phenylpropoxy)phenyl)-2-(ethylamino)-9-methyl-6,7,8,9-tetrahydro-5H-pyrimido[4,5-e][1,4]diazepin-5-one | ++ | + |

-continued

| Ex | Structure | Name | Ki (nM) α2δ-1 | Ki (nM) NET |
|---|---|---|---|---|
| 239 | 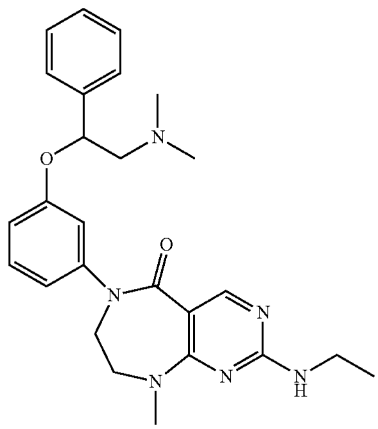 [SMILES: CCNc1ncc2c(n1)N(C)CCN(c1cccc(OC(CN(C)C)c3ccccc3)c1)C2=O] | 6-(3-(2-(dimethylamino)-1-phenylethoxy)phenyl)-2-(ethylamino)-9-methyl-6,7,8,9-tetrahydro-5H-pyrimido[4,5-e][1,4]diazepin-5-one | + | ++ |
| 240 | 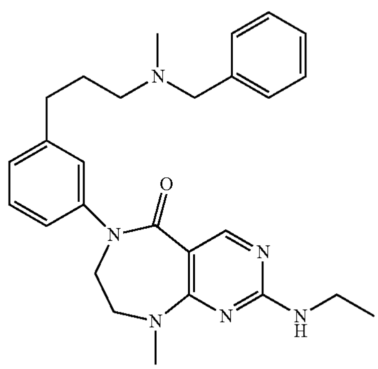 [SMILES: CCNc1ncc2c(n1)N(C)CCN(c1cccc(CCCN(C)Cc3ccccc3)c1)C2=O] | 6-(3-(3-(benzyl(methyl)amino)propyl)phenyl)-2-(ethylamino)-9-methyl-6,7,8,9-tetrahydro-5H-pyrimido[4,5-e][1,4]diazepin-5-one | +++ | + |
| 241 | 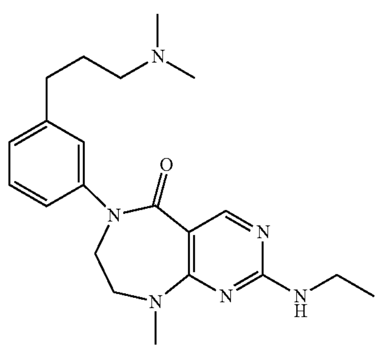 [SMILES: CCNc1ncc2c(n1)N(C)CCN(c1cccc(CCCN(C)C)c1)C2=O] | 6-(3-(3-(dimethylamino)propyl)phenyl)-2-(ethylamino)-9-methyl-6,7,8,9-tetrahydro-5H-pyrimido[4,5-e][1,4]diazepin-5-one | +++ | + |
| 242 | 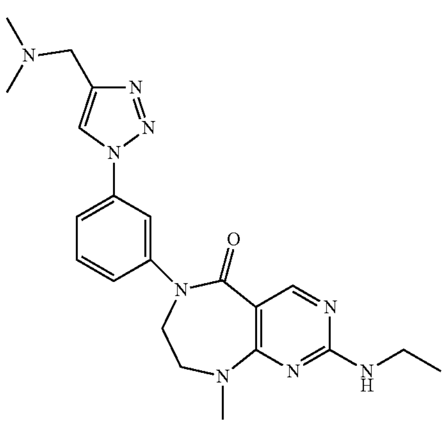 [SMILES: CCNc1ncc2c(n1)N(C)CCN(c1cccc(-n3cc(CN(C)C)nn3)c1)C2=O] | 6-(3-(4-((dimethylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ | + |

| Ex | Structure | Name | Ki (nM) α2δ-1 | Ki (nM) NET |
|---|---|---|---|---|
| 243 | 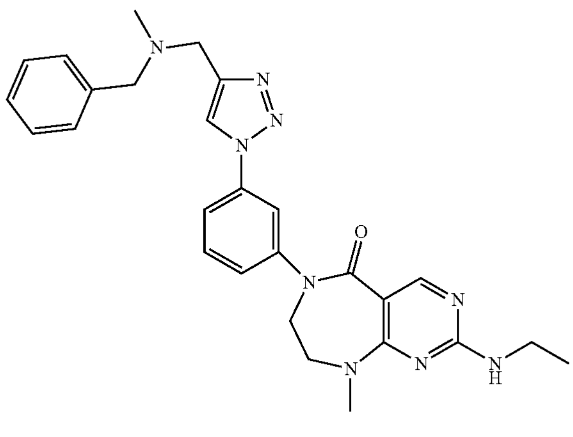 [SMILES: CCNc1ncc2c(n1)N(C)CCN(c1cccc(-n3cc(CN(C)Cc4ccccc4)nn3)c1)C2=O] | 6-(3-(4-((benzyl(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | ++ | ++++ |
| 244 | 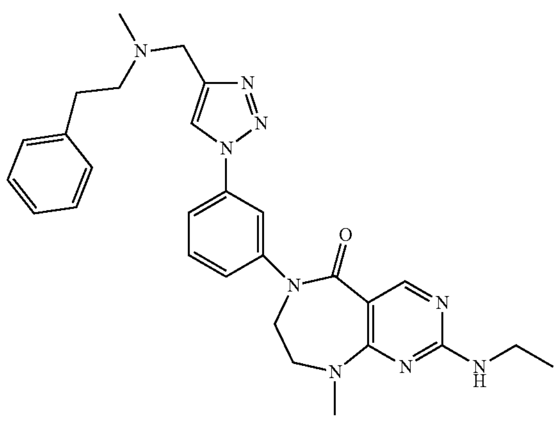 [SMILES: CCNc1ncc2c(n1)N(C)CCN(c1cccc(-n3cc(CN(C)CCc4ccccc4)nn3)c1)C2=O] | 2-(ethylamino)-9-methyl-6-(3-(4-((methyl(phenethyl)amino)methyl)-1H-1,2,3-triazol-1-yl)phenyl)-6,7,8,9-tetrahydro-5H-pyrimido[4,5-e][1,4]diazepin-5-one | ++ | ++++ |
| 246 | 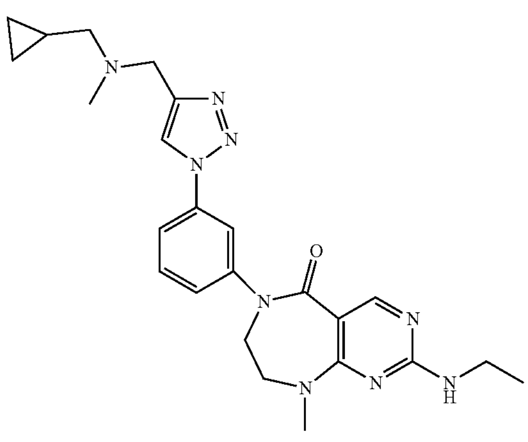 [SMILES: CCNc1ncc2c(n1)N(C)CCN(c1cccc(-n3cc(CN(C)CC4CC4)nn3)c1)C2=O] | 6-(3-(4-(((cyclopropylmethyl)(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ | +++ |

| Ex | Structure | Name | Ki (nM) α2δ-1 | Ki (nM) NET |
|---|---|---|---|---|
| 251 | 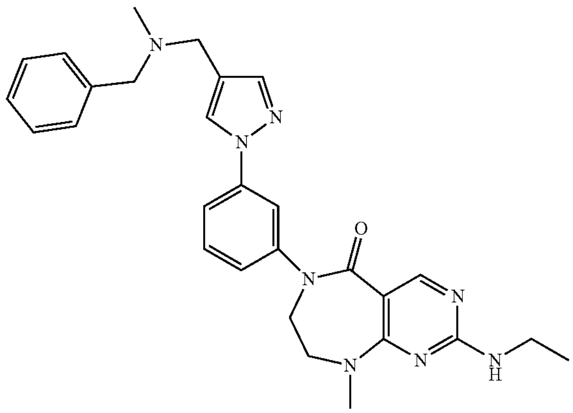 [SMILES: CCNc1ncc2c(n1)N(C)CCN(c1cccc(-n3cc(CN(C)Cc4ccccc4)cn3)c1)C2=O] | 6-(3-(4-((benzyl(methyl)amino)methyl)-1H-pyrazol-1-yl)phenyl)-2-(ethylamino)-9-methyl-6,7,8,9-tetrahydro-5H-pyrimido[4,5-e][1,4]diazepin-5-one | +++ | ++++ |
| 252 | 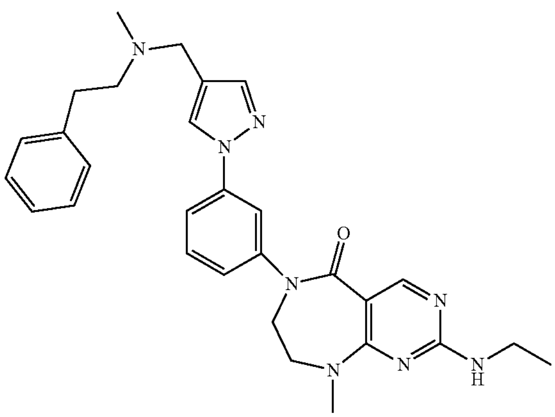 [SMILES: CCNc1ncc2c(n1)N(C)CCN(c1cccc(-n3cc(CN(C)CCc4ccccc4)cn3)c1)C2=O] | 2-(ethylamino)-9-methyl-6-(3-(4-((methyl(phenethyl)amino)methyl)-1H-pyrazol-1-yl)phenyl)-6,7,8,9-tetrahydro-5H-pyrimido[4,5-e][1,4]diazepin-5-one | ++ | +++ |
| 253 | 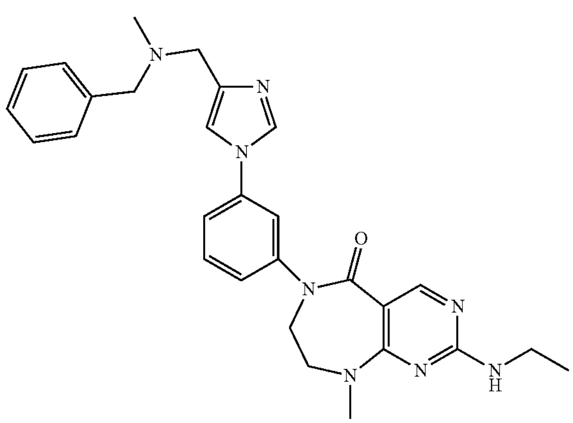 [SMILES: CCNc1ncc2c(n1)N(C)CCN(c1cccc(-n3cnc(CN(C)Cc4ccccc4)c3)c1)C2=O] | 6-(3-(4-((benzyl(methyl)amino)methyl)-1H-imidazol-1-yl)phenyl)-2-(ethylamino)-9-methyl-6,7,8,9-tetrahydro-5H-pyrimido[4,5-e][1,4]diazepin-5-one | +++ | +++ |

-continued
| Ex | Structure | Name | Ki (nM) α2δ-1 | Ki (nM) NET |
|---|---|---|---|---|
| 254 | 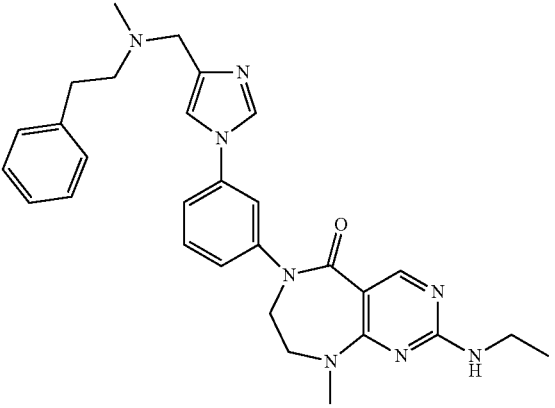 [SMILES: CCNc1ncc2c(n1)N(C)CCN(c1cccc(-n3cnc(CN(C)CCc4ccccc4)c3)c1)C2=O] | 2-(ethylamino)-9-methyl-6-(3-(4-((methyl(phenethyl)amino)methyl)-1H-imidazol-1-yl)phenyl)-6,7,8,9-tetrahydro-5H-pyrimido[4,5-e][1,4]diazepin-5-one | ++ | ++ |
| 256 | 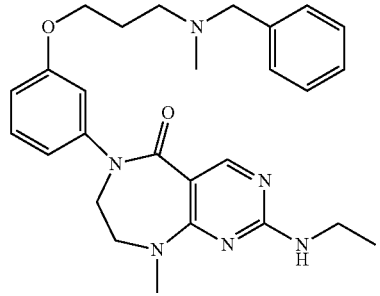 [SMILES: CCNc1ncc2c(n1)N(C)CCN(c1cccc(OCCCN(C)Cc3ccccc3)c1)C2=O] | 6-(3-(3-(benzyl(methyl)amino)propoxy)phenyl)-2-(ethylamino)-9-methyl-6,7,8,9-tetrahydro-5H-pyrimido[4,5-e][1,4]diazepin-5-one | +++ | ++ |
| 261 | 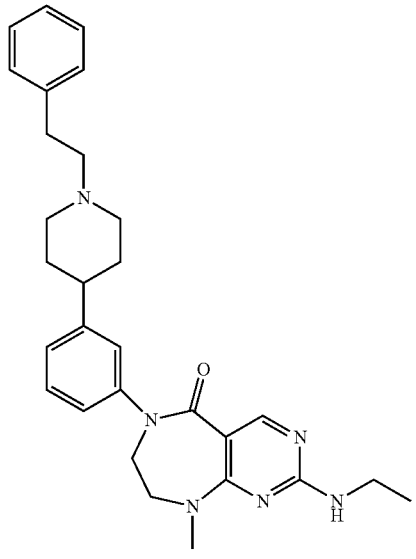 [SMILES: CCNc1ncc2c(n1)N(C)CCN(c1cccc(C3CCN(CCc4ccccc4)CC3)c1)C2=O] | 2-(ethylamino)-9-methyl-6-(3-(1-phenethylpiperidin-4-yl)phenyl)-6,7,8,9-tetrahydro-5H-pyrimido[4,5-e][1,4]diazepin-5-one | +++ | +++ |

-continued

| Ex | Structure | Name | Ki (nM) α2δ-1 | Ki (nM) NET |
|---|---|---|---|---|
| 264 | 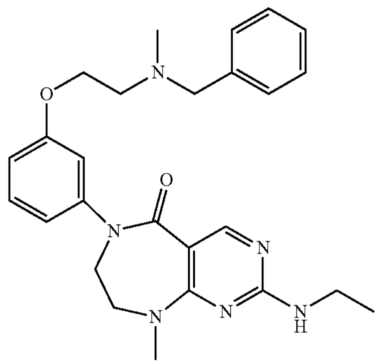 [SMILES: CCNc1ncc2c(n1)N(C)CCN(c1cccc(OCCN(C)Cc3ccccc3)c1)C2=O] | 6-(3-(2-(benzyl(methyl)amino)ethoxy)phenyl)-2-(ethylamino)-9-methyl-6,7,8,9-tetrahydro-5H-pyrimido[4,5-e][1,4]diazepin-5-one | +++ | +++ |
| 265 | 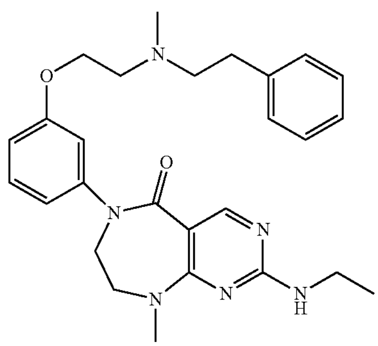 [SMILES: CCNc1ncc2c(n1)N(C)CCN(c1cccc(OCCN(C)CCc3ccccc3)c1)C2=O] | 2-(ethylamino)-9-methyl-6-(3-(2-(methyl(phenethyl)amino)ethoxy)phenyl)-6,7,8,9-tetrahydro-5H-pyrimido[4,5-e][1,4]diazepin-5-one | +++ | +++ |
| 271 | 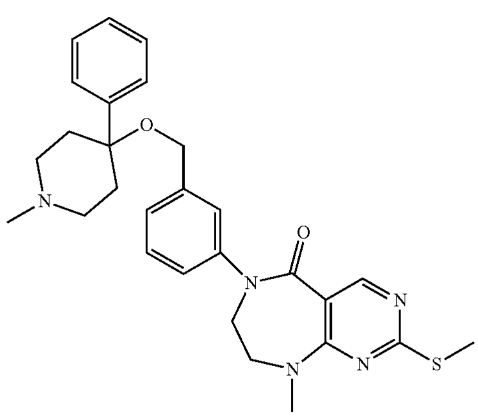 | 9-methyl-6-(3-(((1-methyl-4-phenylpiperidin-4-yl)oxy)methyl)phenyl)-2-(methylthio)-6,7,8,9-tetrahydro-5H-pyrimido[4,5-e][1,4]diazepin-5-one | + | + |

-continued

| Ex | Structure | Name | Ki (nM) α2δ-1 | Ki (nM) NET |
|---|---|---|---|---|
| 275 | 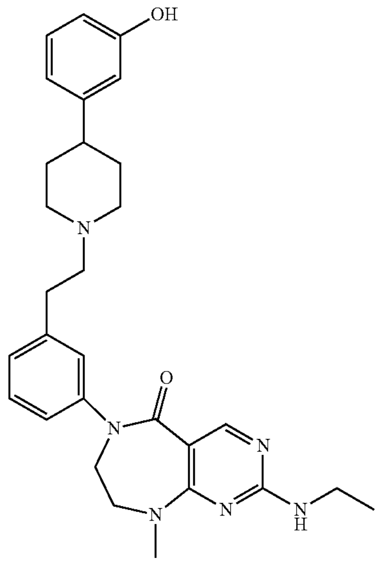 [SMILES: CCNc1ncc2c(n1)N(C)CCN(c1cccc(CCN3CCC(c4cccc(O)c4)CC3)c1)C2=O] | 2-(ethylamino)-6-(3-(2-(4-(3-hydroxyphenyl)piperidin-1-yl)ethyl)phenyl)-9-methyl-6,7,8,9-tetrahydro-5H-pyrimido[4,5-e][1,4]diazepin-5-one | +++ | ++ |
| 278 | 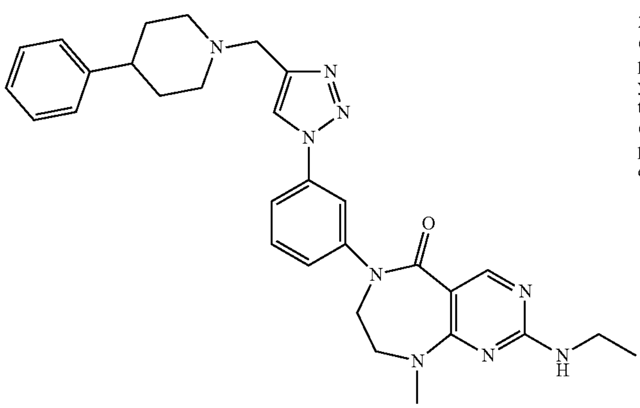 [SMILES: CCNc1ncc2c(n1)N(C)CCN(c1cccc(-n3cc(CN4CCC(c5ccccc5)CC4)nn3)c1)C2=O] | 2-(ethylamino)-9-methyl-6-(3-(4-((4-phenylpiperidin-1-yl)methyl)-1H-1,2,3-triazol-1-yl)phenyl)-6,7,8,9-tetrahydro-5H-pyrimido[4,5-e][1,4]diazepin-5-one | ++ | ++++ |
| 279 | 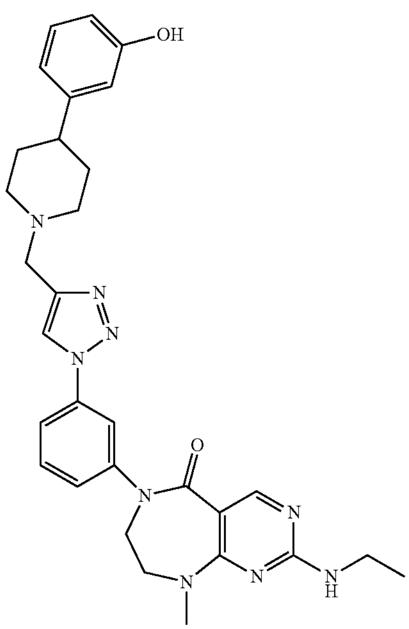 [SMILES: CCNc1ncc2c(n1)N(C)CCN(c1cccc(-n3cc(CN4CCC(c5cccc(O)c5)CC4)nn3)c1)C2=O] | 2-(ethylamino)-6-(3-(4-((4-(3-hydroxyphenyl)piperidin-1-yl)methyl)-1H-1,2,3-triazol-1-yl)phenyl)-9-methyl-6,7,8,9-tetrahydro-5H-pyrimido[4,5-e][1,4]diazepin-5-one | +++ | ++++ |

-continued

| Ex | Structure | Name | Ki (nM) α2δ-1 | Ki (nM) NET |
|---|---|---|---|---|
| 281 | 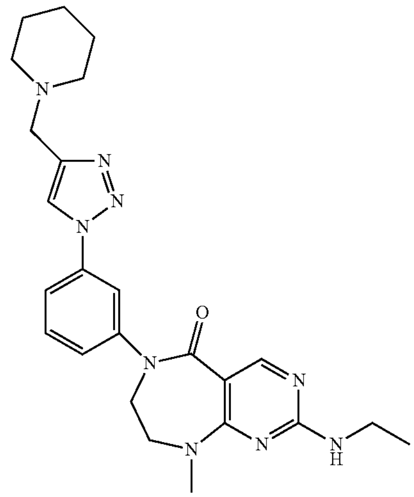 [SMILES: CCNc1ncc2c(n1)N(C)CCN(c1cccc(-n3cc(CN4CCCCC4)nn3)c1)C2=O] | 2-(ethylamino)-9-methyl-6-(3-(4-(piperidin-1-ylmethyl)-1H-1,2,3-triazol-1-yl)phenyl)-6,7,8,9-tetrahydro-5H-pyrimido[4,5-e][1,4]diazepin-5-one | +++ | +++ |
| 285 | 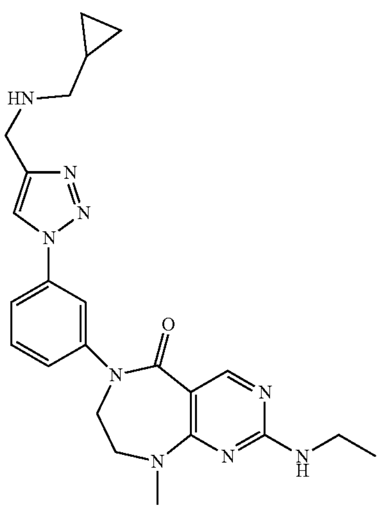 [SMILES: CCNc1ncc2c(n1)N(C)CCN(c1cccc(-n3cc(CNCC4CC4)nn3)c1)C2=O] | 6-(3-(4-(((cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one | +++ | +++ |
| 287 | 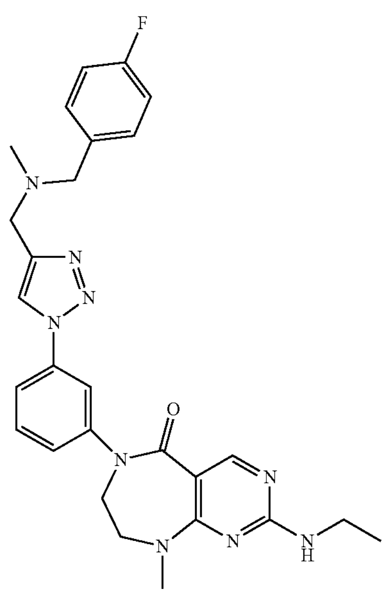 [SMILES: CCNc1ncc2c(n1)N(C)CCN(c1cccc(-n3cc(CN(C)Cc4ccc(F)cc4)nn3)c1)C2=O] | 2-(ethylamino)-6-(3-(4-(((4-fluorobenzyl)(methyl)amino)methyl)-1H-1,2,3-triazol-1-yhphenyl)-9-methyl-6,7,8,9-tetrahydro-5H-pyrimido[4,5-e][1,4]diazepin-5-one | ++ | ++++ |

| Ex | Structure | Name | Ki (nM) α2δ-1 | Ki (nM) NET |
|---|---|---|---|---|
| 288 | 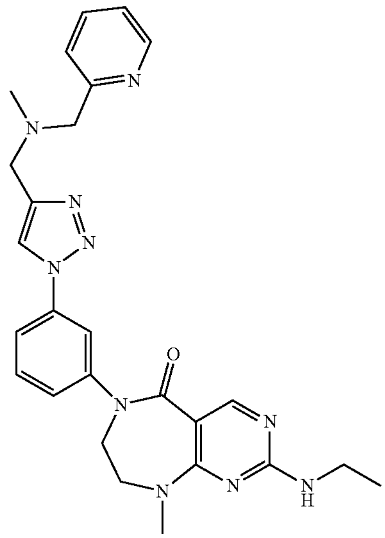 [SMILES: CCNc1ncc2c(n1)N(C)CCN(c1cccc(-n3cc(CN(C)Cc4ccccn4)nn3)c1)C2=O] | 2-(ethylamino)-9-methyl-6-(3-(4-((methyl(pyridin-2-ylmethyl)amino)methyl)-1H-1,2,3-triazol-1-yl)phenyl)-6,7,8,9-tetrahydro-5H-pyrimido[4,5-e][1,4]diazepin-5-one | ++ | +++ |
| 289 | 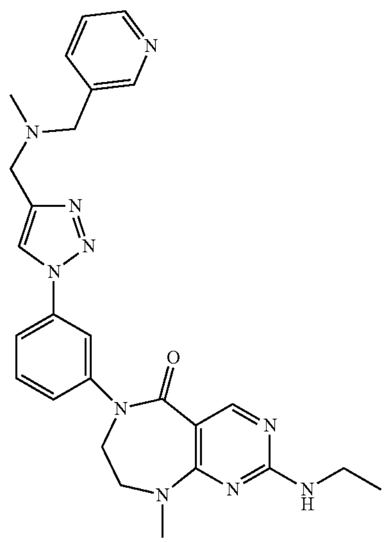 [SMILES: CCNc1ncc2c(n1)N(C)CCN(c1cccc(-n3cc(CN(C)Cc4cccnc4)nn3)c1)C2=O] | 2-(ethylamino)-9-methyl-6-(3-(4-((methyl(pyridin-3-ylmethyl)amino)methyl)-1H-1,2,3-triazol-1-yl)phenyl)-6,7,8,9-tetrahydro-5H-pyrimido[4,5-e][1,4]diazepin-5-one | +++ | ++ |
| 304 | 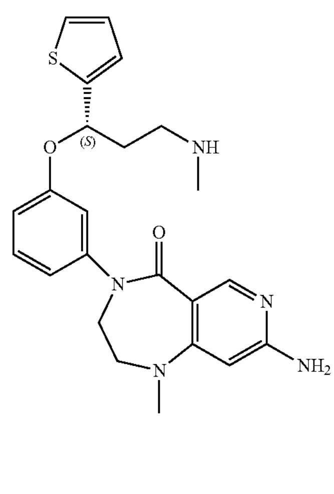 | (S)-8-amino-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | +++ |

-continued

| Ex | Structure | Name | Ki (nM) α2δ-1 | Ki (nM) NET |
|---|---|---|---|---|
| 305 | 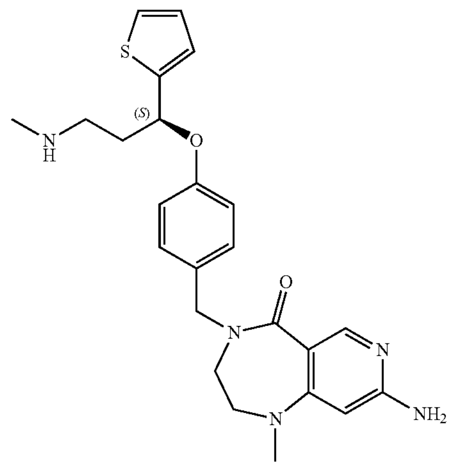 | (S)-8-amino-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ | +++ |
| 307 | 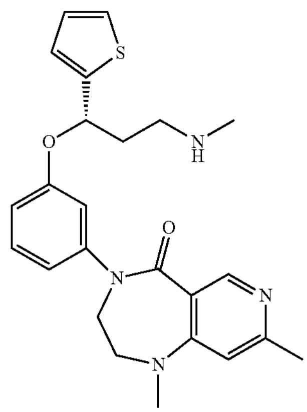 [SMILES: CNCC[C@H](Oc1cccc(N2CCN(C)c3cc(C)ncc3C2=O)c1)c1cccs1] | 1,8-dimethyl-4-(3-(3-(methylamino)-1-(thiophen-2-yl)propoxy)phenyl)-1,2,3,4-tetrahydro-5H-pyrido[4,3-e][1,4]diazepin-5-one | +++ | +++ |
| 308 | 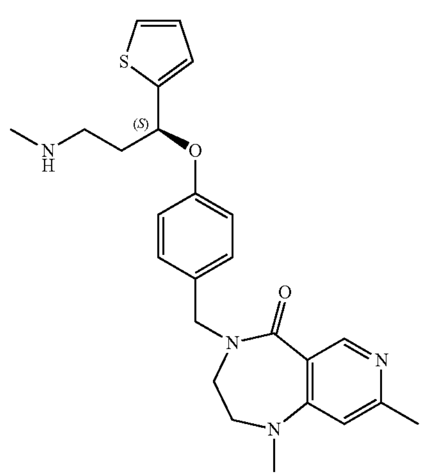 | (S)-1,8-dimethyl-4-(4-(3-(methylamino)-1-(thiophen-2-yl)propoxy)benzyl)-1,2,3,4-tetrahydro-5H-pyrido[4,3-e][1,4]diazepin-5-one | +++ | +++ |

| Ex | Structure | Name | Ki (nM) α2δ-1 | Ki (nM) NET |
|---|---|---|---|---|
| 315 | 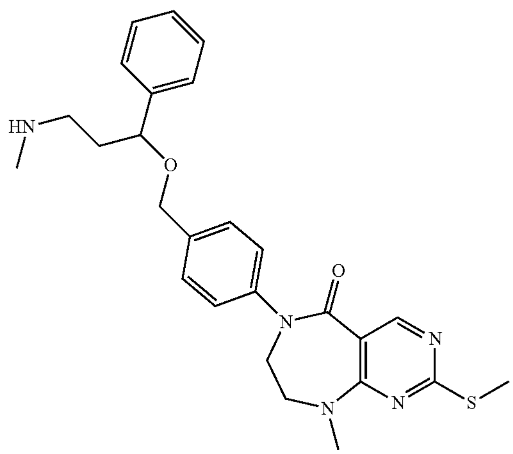 | 9-methyl-6-(4-((3-(methylamino)-1-phenylpropoxy)methyl)phenyl)-2-(methylthio)-6,7,8,9-tetrahydro-5H-pyrimido[4,5-e][1,4]diazepin-5-one | + | ++++ |
| 316 | 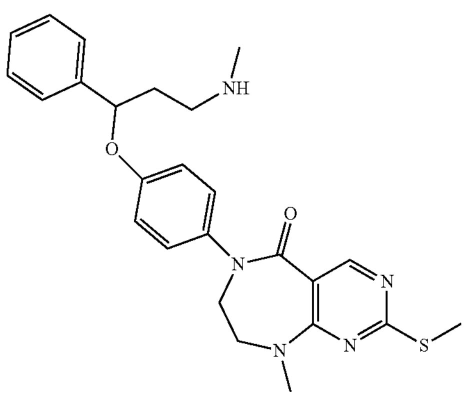 [SMILES: CNCCC(Oc1ccc(N2CCN(C)c3nc(SC)ncc3C2=O)cc1)c1ccccc1] | 9-methyl-6-(4-(3-(methylamino)-1-phenylpropoxy)phenyl)-2-(methylthio)-6,7,8,9-tetrahydro-5H-pyrimido[4,5-e][1,4]diazepin-5-one | + | ++ |
| 321 | 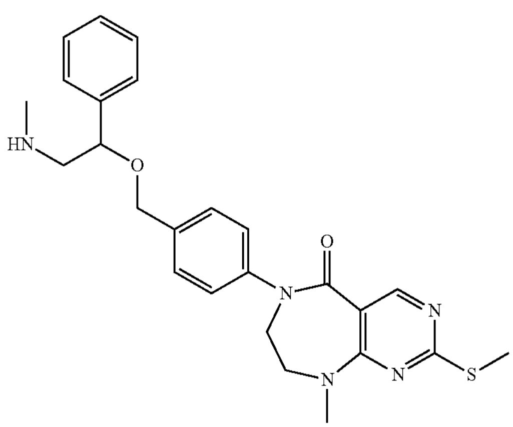 | 9-methyl-6-(4-((2-(methylamino)-1-phenylethoxy)methyl)phenyl)-2-(methylthio)-6,7,8,9-tetrahydro-5H-pyrimido[4,5-e][1,4]diazepin-5-one | + | ++++ |

| Ex | Structure | Name | Ki (nM) α2δ-1 | Ki (nM) NET |
|---|---|---|---|---|
| 322 | 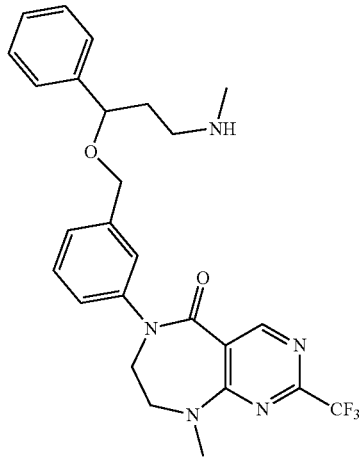 [SMILES: CNCCC(OCc1cccc(N2CCN(C)c3nc(C(F)(F)F)ncc3C2=O)c1)c1ccccc1] | 9-methyl-6-(3-((3-(methylamino)-1-phenylpropoxy)methyl)phenyl)-2-(trifluoromethyl)-6,7,8,9-tetrahydro-5H-pyrimido[4,5-e][1,4]diazepin-5-one | + | +++ |
| 323 | 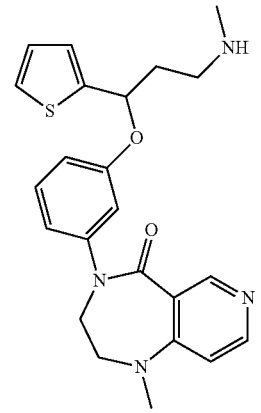 [SMILES: CNCCC(Oc1cccc(N2CCN(C)c3ccncc3C2=O)c1)c1cccs1] | 1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | +++ |
| 325 | 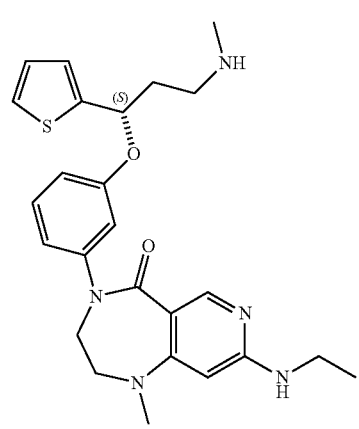 | (S)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | ++++ |

-continued

| Ex | Structure | Name | Ki (nM) α2δ-1 | Ki (nM) NET |
|---|---|---|---|---|
| 326 | 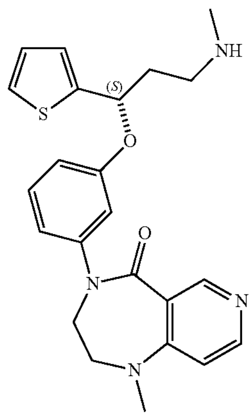 | (S)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | +++ |
| 327 | 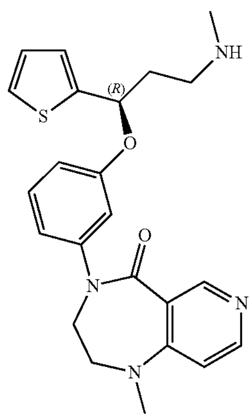 | (R)-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | + |
| 328 | 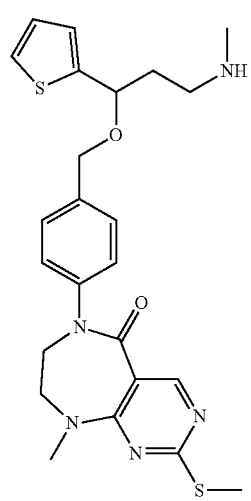 [SMILES: CNCCC(OCc1ccc(N2CCN(C)c3nc(SC)ncc3C2=O)cc1)c1cccs1] | 9-methyl-6-(4-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one | + | ++++ |

-continued

| Ex | Structure | Name | Ki (nM) α2δ-1 | Ki (nM) NET |
|---|---|---|---|---|
| 329 | 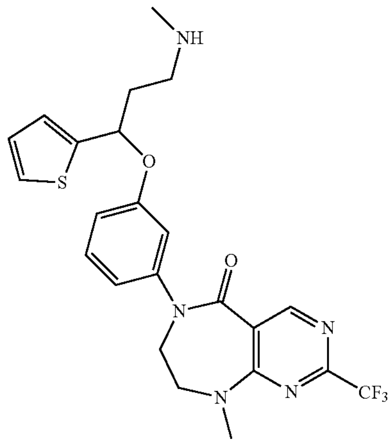 [SMILES: CNCCC(Oc1cccc(N2CCN(C)c3nc(C(F)(F)F)ncc3C2=O)c1)c1cccs1] | 9-methyl-6-(3-(3-(methylamino)-1-(thiophen-2-yl)propoxy)phenyl)-2-(trifluoromethyl)-6,7,8,9-tetrahydro-5H-pyrimido[4,5-e][1,4]diazepin-5-one | + | ++++ |
| 330 | 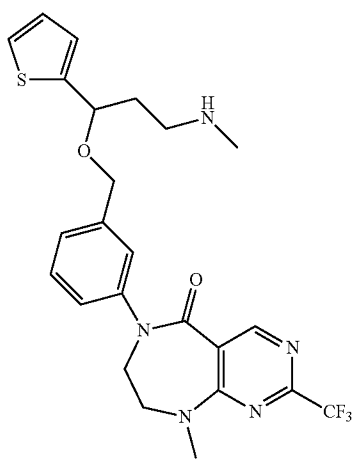 [SMILES: CNCCC(OCc1cccc(N2CCN(C)c3nc(C(F)(F)F)ncc3C2=O)c1)c1cccs1] | 9-methyl-6-(3-((3-(methylamino)-1-(thiophen-2-yl)propoxy)methyl)phenyl)-2-(trifluoromethyl)-6,7,8,9-tetrahydro-5H-pyrimido[4,5-e][1,4]diazepin-5-one | ++ | +++ |
| 331 | 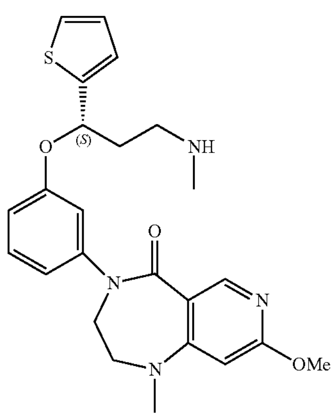 | (S)-8-methoxy-1-methyl-4-(3-(3-(methylamino)-1-(thiophen-2-yl)propoxy)phenyl)-1,2,3,4-tetrahydro-5H-pyrido[4,3-e][1,4]diazepin-5-one | +++ | ++++ |

-continued

| Ex | Structure | Name | Ki (nM) α2δ-1 | Ki (nM) NET |
|---|---|---|---|---|
| 333 | 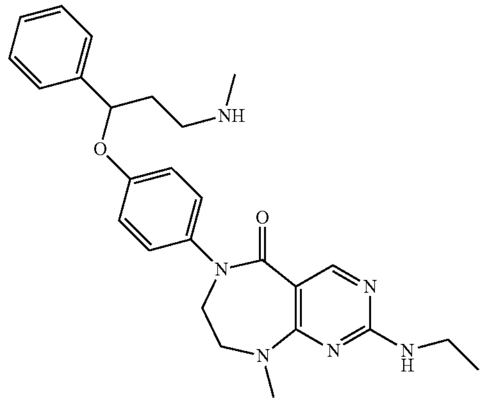 [SMILES: CCNc1ncc2c(n1)N(C)CCN(c1ccc(OC(CCNC)c3ccccc3)cc1)C2=O] | 2-(ethylamino)-9-methyl-6-(4-(3-(methylamino)-1-phenylpropoxy)phenyl)-6,7,8,9-tetrahydro-5H-pyrimido[4,5-e][1,4]diazepin-5-one | + | ++ |
| 334 | 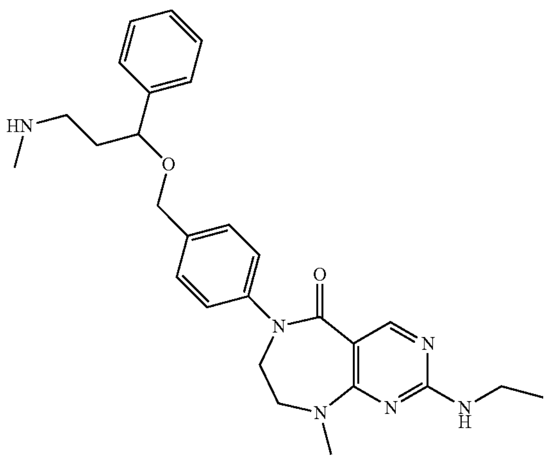 [SMILES: CCNc1ncc2c(n1)N(C)CCN(c1ccc(COC(CCNC)c3ccccc3)cc1)C2=O] | 2-(ethylamino)-9-methyl-6-(4-((3-(methylamino)-1-phenylpropoxy)methyl)phenyl)-6,7,8,9-tetrahydro-5H-pyrimido[4,5-e][1,4]diazepin-5-one | + | ++++ |
| 335 | 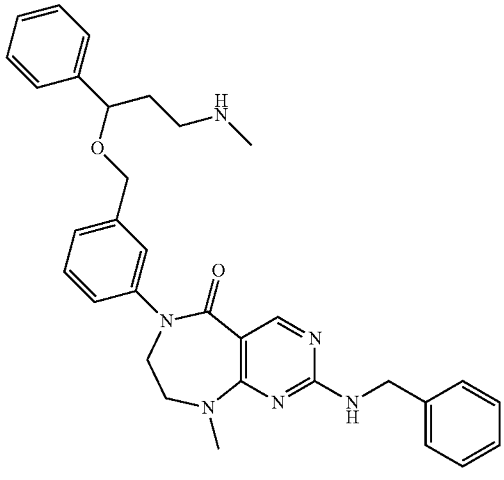 [SMILES: CNCCC(OCc1cccc(N2CCN(C)c3nc(NCc4ccccc4)ncc3C2=O)c1)c1ccccc1] | 2-(benzylamino)-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | ++++ |

| Ex | Structure | Name | Ki (nM) α2δ-1 | Ki (nM) NET |
|----|-----------|------|---------------|-------------|
| 336 | 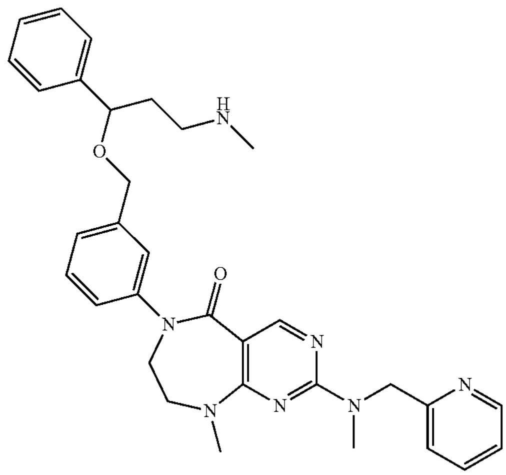 [SMILES: CNCCC(OCc1cccc(N2CCN(C)c3nc(N(C)Cc4ccccn4)ncc3C2=O)c1)c1ccccc1] | 9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | ++ | +++ |
| 340 | 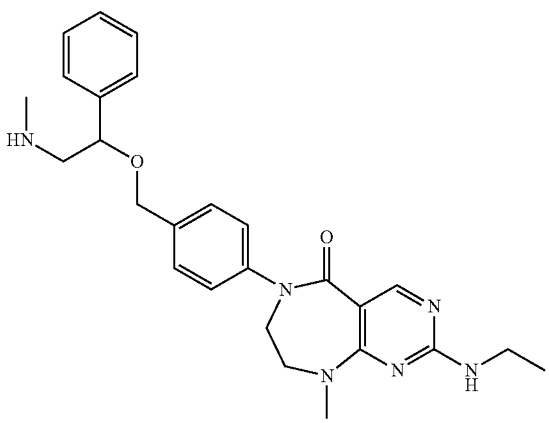 [SMILES: CCNc1ncc2c(n1)N(C)CCN(c1ccc(COC(CNC)c3ccccc3)cc1)C2=O] | 2-(ethylamino)-9-methyl-6-(4-((2-(methylamino)-1-phenylethoxy)methyl)phenyl)-6,7,8,9-tetrahydro-5H-pyrimido[4,5-e][1,4]diazepin-5-one | + | ++++ |
| 341 | 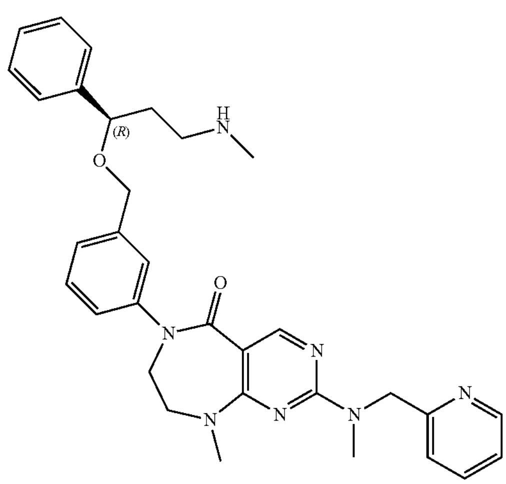 | (R)-9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | +++ | +++ |

-continued

| Ex | Structure | Name | Ki (nM) α2δ-1 | Ki (nM) NET |
|---|---|---|---|---|
| 342 | 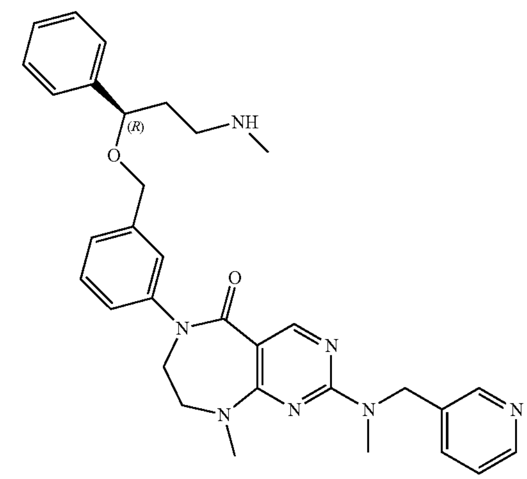 | (R)-9-methyl-2-(methyl(pyridin-3-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one | +++ | +++ |
| 343 | 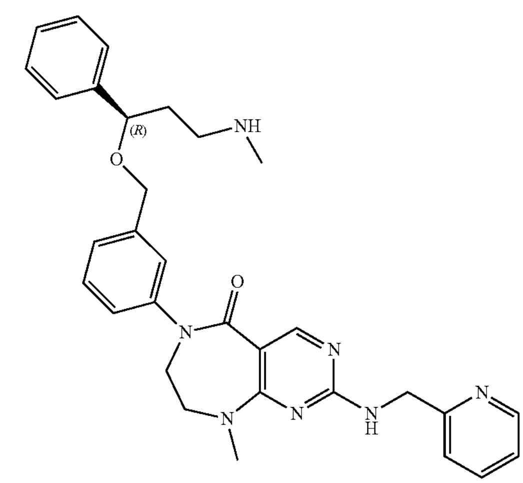 | (R)-9-methyl-6-(3-((3-(methylamino)-1-phenylpropoxy)methyl)phenyl)-2-((pyridin-2-ylmethyl)amino)-6,7,8,9-tetrahydro-5H-pyrimido[4,5-e][1,4]diazepin-5-one | +++ | +++ |
| 344 | 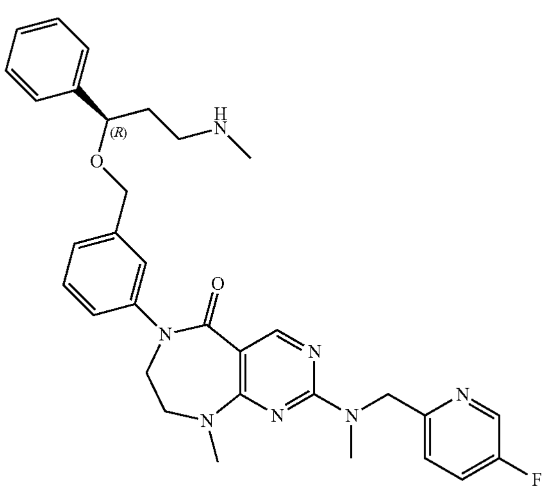 | (R)-2-(((5-fluoropyridin-2-yl)methyl)(methyl)amino)-9-methyl-6-(3-((3-(methylamino)-1-phenylpropoxy)methyl)phenyl)-6,7,8,9-tetrahydro-5H-pyrimido[4,5-e][1,4]diazepin-5-one | +++ | ++ |

-continued

| Ex | Structure | Name | Ki (nM) α2δ-1 | Ki (nM) NET |
|---|---|---|---|---|
| 347 | 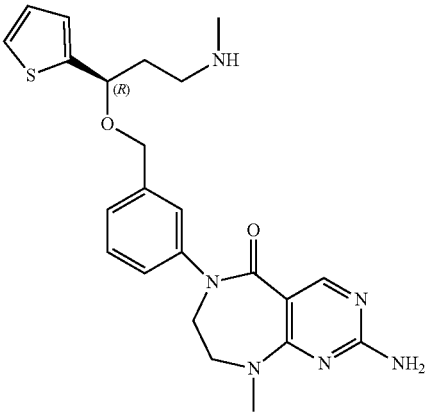 | (R)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | ++ |
| 348 | 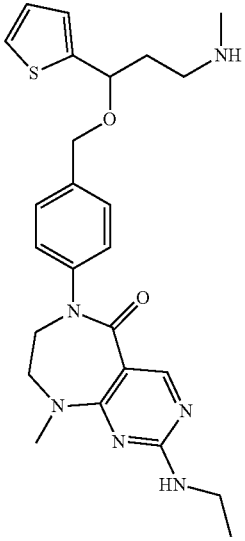 [SMILES: CCNc1ncc2c(n1)N(C)CCN(c1ccc(COC(CCNC)c3cccs3)cc1)C2=O] | 2-(ethylamino)-9-methyl-6-(4-((3-(methylamino)-1-(thiophen-2-yl)propoxy)methyl)phenyl)-6,7,8,9-tetrahydro-5H-pyrimido[4,5-e][1,4]diazepin-5-one | + | +++ |
| 349 | 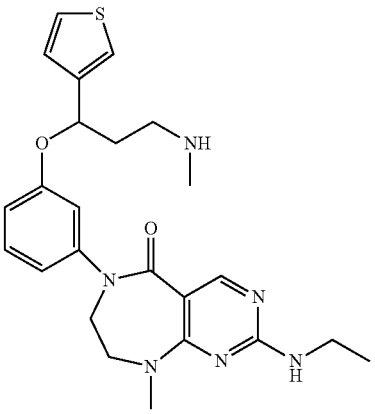 [SMILES: CCNc1ncc2c(n1)N(C)CCN(c1cccc(OC(CCNC)c3ccsc3)c1)C2=O] | 2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | +++ | +++ |

| Ex | Structure | Name | Ki (nM) α2δ-1 | Ki (nM) NET |
|---|---|---|---|---|
| 350 | 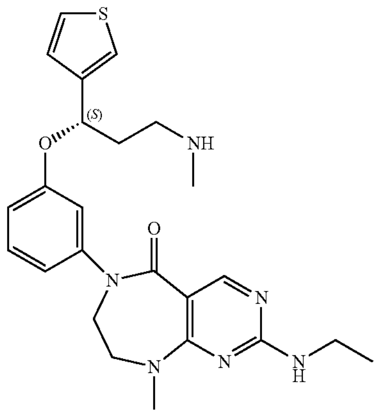 | (S)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | +++ | ++++ |
| 351 | 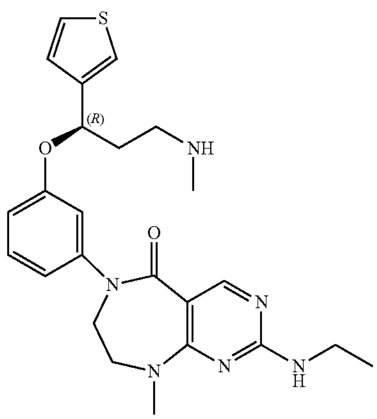 | (R)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one | ++ | + |
| 352 | 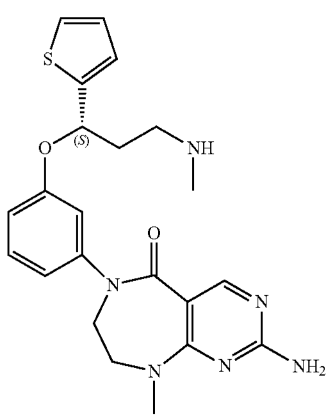 | (S)-2-amino-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ | ++++ |

-continued

| Ex | Structure | Name | Ki (nM) α2δ-1 | Ki (nM) NET |
|---|---|---|---|---|
| 353 | 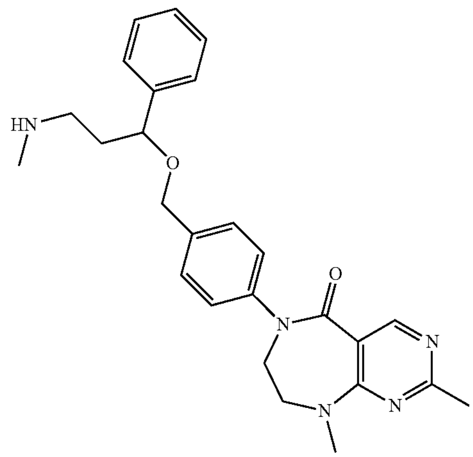 | 2,9-dimethyl-6-(4-((3-(methylamino)-1-phenylpropoxy)methyl)phenyl)-6,7,8,9-tetrahydro-5H-pyrimido[4,5-e][1,4]diazepin-5-one | + | ++++ |
| 354 | 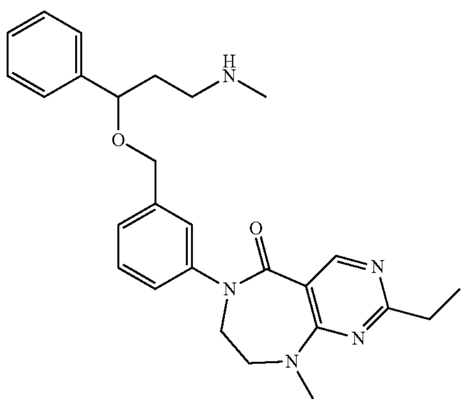 [SMILES: CCc1ncc2c(n1)N(C)CCN(c1cccc(COC(CCNC)c3ccccc3)c1)C2=O] | 2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | +++ |
| 355 | 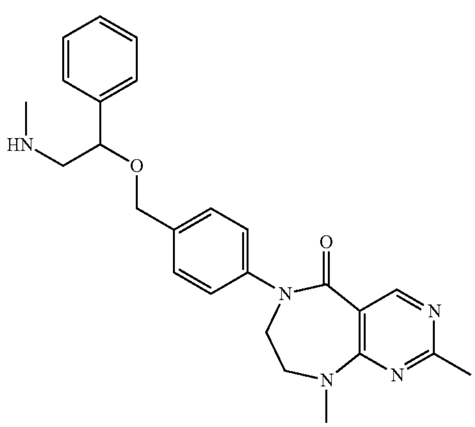 [SMILES: CNCC(OCc1ccc(N2CCN(C)c3nc(C)ncc3C2=O)cc1)c1ccccc1] | 2,9-dimethyl-6-(4-((2-(methylamino)-1-phenylethoxy)methyl)phenyl)-6,7,8,9-tetrahydro-5H-pyrimido[4,5-e][1,4]diazepin-5-one | + | ++++ |

| Ex | Structure | Name | Ki (nM) α2δ-1 | Ki (nM) NET |
|---|---|---|---|---|
| 356 | 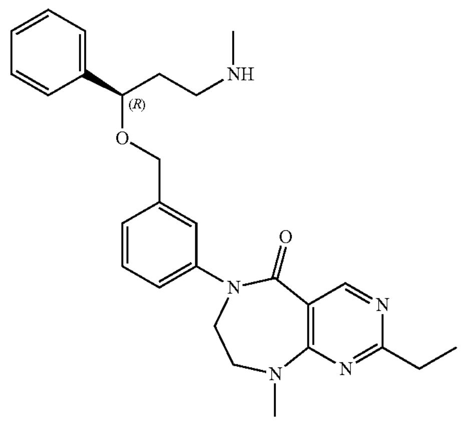 | (R)-2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one | ++ | +++ |
| 357 | 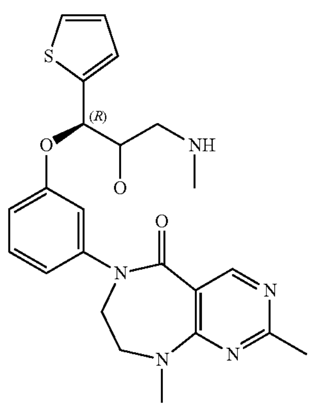 | (R)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | ++ | + |
| 358 | 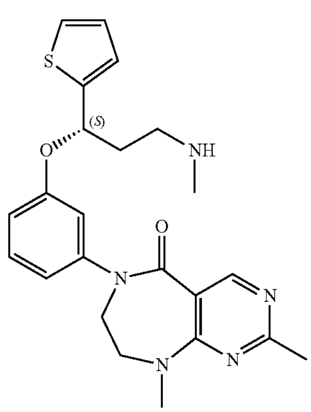 | (S)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one | ++ | +++ |

-continued

| Ex | Structure | Name | Ki (nM) α2δ-1 | Ki (nM) NET |
|---|---|---|---|---|
| 360 | 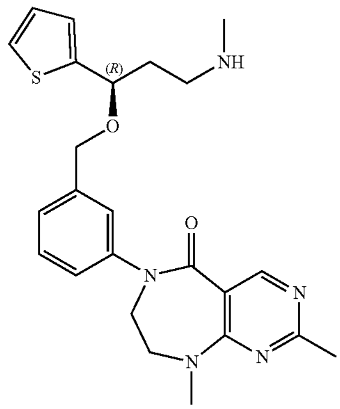 | (R)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one | +++ | ++ |
| 364 | 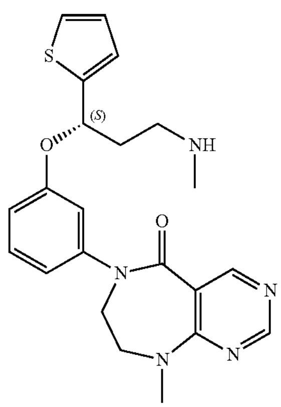 | (S)-9-methyl-6-(3-(3-(methylamino)-1-(thiophen-2-yl)propoxy)phenyl)-6,7,8,9-tetrahydro-5H-pyrimido[4,5-e][1,4]diazepin-5-one | +++ | ++++ |
| 366 | 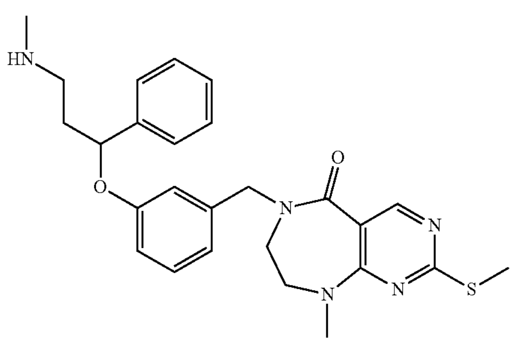 | 9-methyl-6-(3-(3-(methylamino)-1-phenylpropoxy)benzyl)-2-(methylthio)-6,7,8,9-tetrahydro-5H-pyrimido[4,5-e][1,4]diazepin-5-one | + | ++ |

| Ex | Structure | Name | Ki (nM) α2δ-1 | Ki (nM) NET |
|---|---|---|---|---|
| 367 | 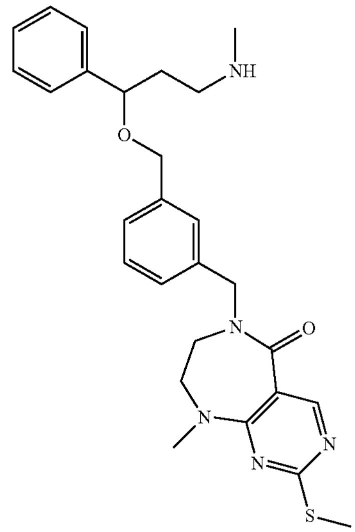 [SMILES: CNCCC(OCc1cccc(CN2CCN(C)c3nc(SC)ncc3C2=O)c1)c1ccccc1] | 9-methyl-6-(3-((3-(methylamino)-1-phenylpropoxy)methyl)benzyl)-2-(methylthio)-6,7,8,9-tetrahydro-5H-pyrimido[4,5-e][1,4]diazepin-5-one | + | +++ |
| 368 | 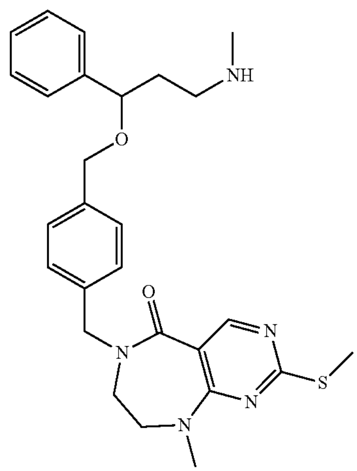 [SMILES: CNCCC(OCc1ccc(CN2CCN(C)c3nc(SC)ncc3C2=O)cc1)c1ccccc1] | 9-methyl-6-(4-((3-(methylamino)-1-phenylpropoxy)methyl)benzyl)-2-(methylthio)-6,7,8,9-tetrahydro-5H-pyrimido[4,5-e][1,4]diazepin-5-one | + | +++ |
| 369 | 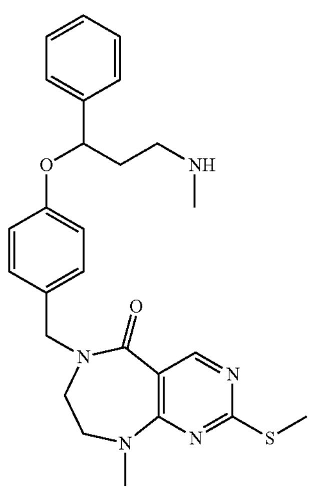 [SMILES: CNCCC(Oc1ccc(CN2CCN(C)c3nc(SC)ncc3C2=O)cc1)c1ccccc1] | 9-methyl-6-(4-(3-(methylamino)-1-phenylpropoxy)benzyl)-2-(methylthio)-6,7,8,9-tetrahydro-5H-pyrimido[4,5-e][1,4]diazepin-5-one | ++ | ++++ |

| Ex | Structure | Name | Ki (nM) α2δ-1 | Ki (nM) NET |
|---|---|---|---|---|
| 372 | 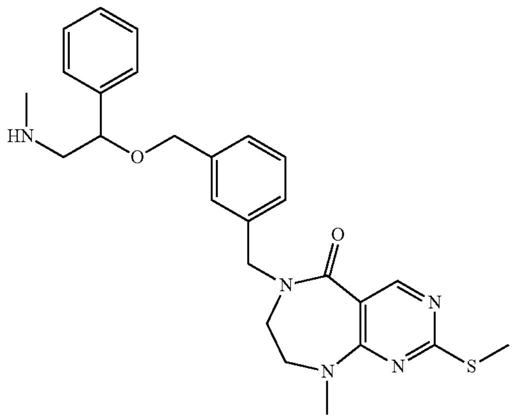 [SMILES: CNCC(OCc1cccc(CN2CCN(C)c3nc(SC)ncc3C2=O)c1)c1ccccc1] | 9-methyl-6-(3-((2-(methylamino)-1-phenylethoxy)methyl)benzyl)-2-(methylthio)-6,7,8,9-tetrahydro-5H-pyrimido[4,5-e][1,4]diazepin-5-one | + | +++ |
| 374 | 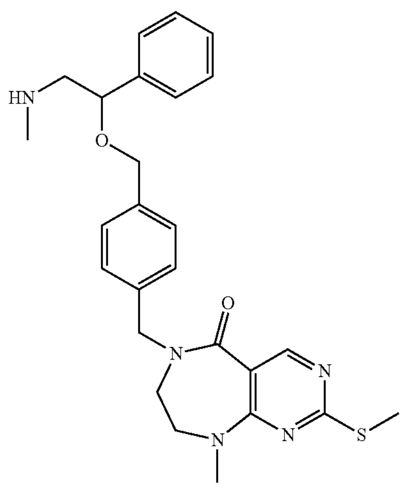 | 9-methyl-6-(4-((2-(methylamino)-1-phenylethoxy)methyl)benzyl)-2-(methylthio)-6,7,8,9-tetrahydro-5H-pyrimido[4,5-e][1,4]diazepin-5-one | + | +++ |
| 375 | 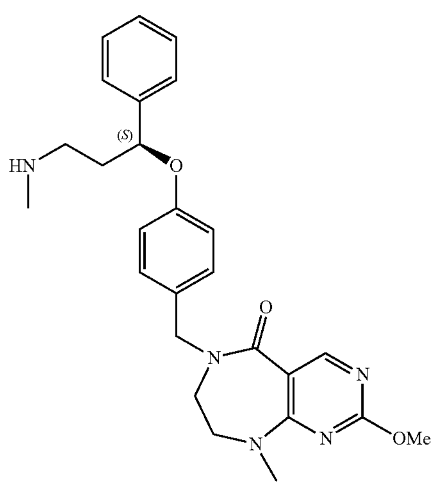 | (S)-2-methoxy-9-methyl-6-(4-(3-(methylamino)-1-phenylpropoxy)benzyl)-6,7,8,9-tetrahydro-5H-pyrimido[4,5-e][1,4]diazepin-5-one | +++ | ++++ |

| Ex | Structure | Name | Ki (nM) α2δ-1 | Ki (nM) NET |
|---|---|---|---|---|
| 378 | 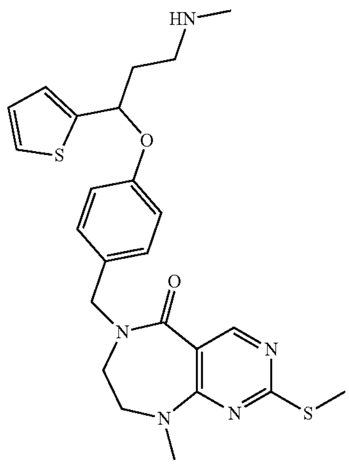 [SMILES: CNCCC(Oc1ccc(CN2CCN(C)c3nc(SC)ncc3C2=O)cc1)c1cccs1] | 9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | ++ | ++++ |
| 379 | 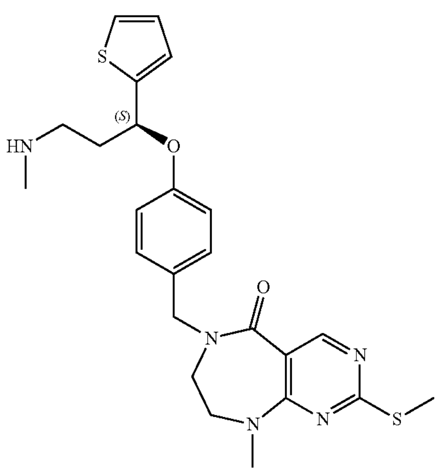 | (S)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | +++ | ++++ |
| 380 | 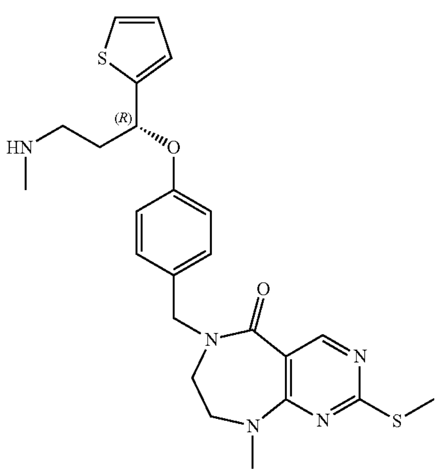 | (R)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one | ++ | +++ |

-continued

| Ex | Structure | Name | Ki (nM) α2δ-1 | Ki (nM) NET |
|---|---|---|---|---|
| 381 | 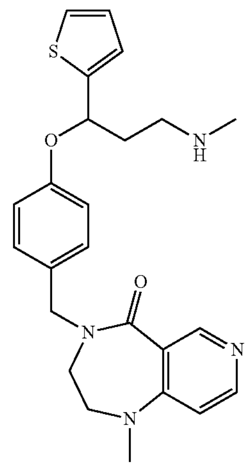 [SMILES: CNCCC(Oc1ccc(CN2CCN(C)c3ccncc3C2=O)cc1)c1cccs1] | 1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ | +++ |
| 382 | 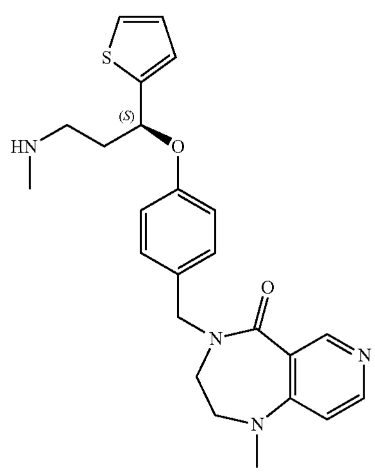 | (S)-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ | +++ |
| 383 | 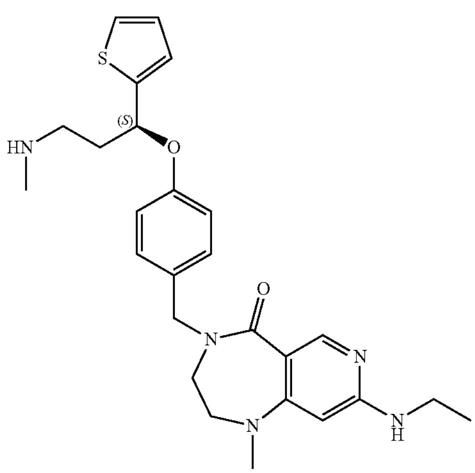 | (S)-8-(ethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ | +++ |

-continued

| Ex | Structure | Name | Ki (nM) α2δ-1 | Ki (nM) NET |
|---|---|---|---|---|
| 384 | 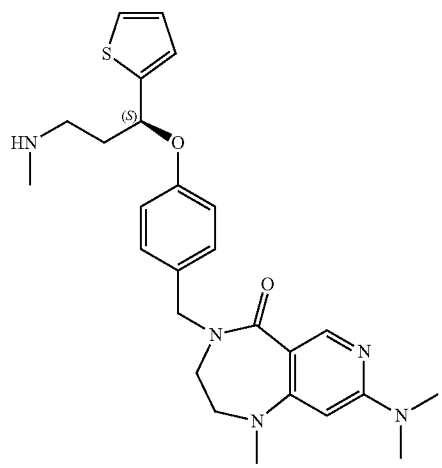 | (S)-8-(dimethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ | ++ |
| 385 | 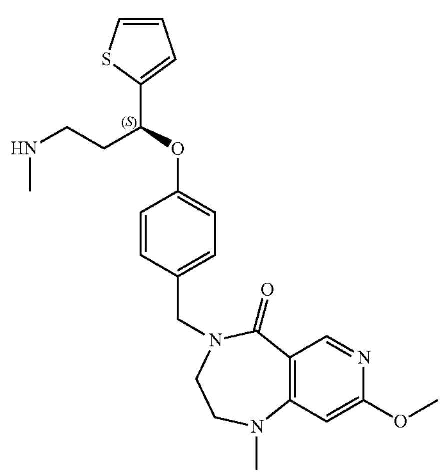 | (S)-8-methoxy-1-methyl-4-(4-(3-(methylamino)-1-(thiophen-2-yl)propoxy)benzyl)-1,2,3,4-tetrahydro-5H-pyrido[4,3-e][1,4]diazepin-5-one | +++ | +++ |
| 386 | 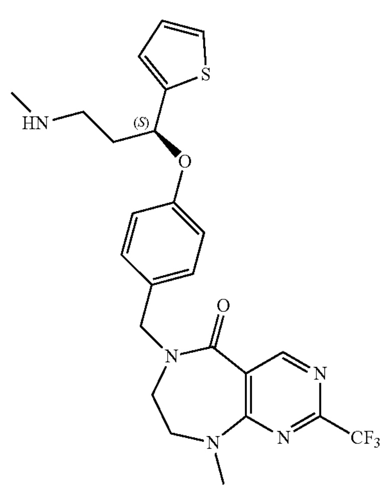 | (S)-9-methyl-6-(4-(3-(methylamino)-1-(thiophen-2-yl)propoxy)benzyl)-2-(trifluoromethyl)-6,7,8,9-tetrahydro-5H-pyrimido[4,5-e][1,4]diazepin-5-one | +++ | ++++ |

| Ex | Structure | Name | Ki (nM) α2δ-1 | Ki (nM) NET |
|---|---|---|---|---|
| 387 | 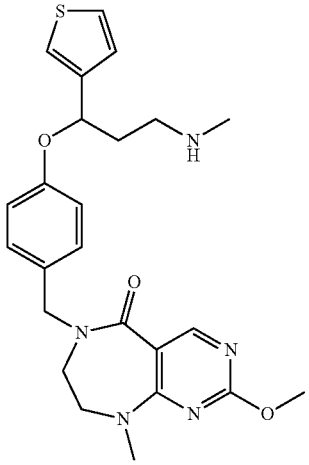 [SMILES: CNCCC(Oc1ccc(CN2CCN(C)c3nc(OC)ncc3C2=O)cc1)c1ccsc1] | 2-methoxy-9-methyl-6-(4-(3-(methylamino)-1-(thiophen-3-yl)propoxy)benzyl)-6,7,8,9-tetrahydro-5H-pyrimido[4,5-e][1,4]diazepin-5-one | +++ | ++++ |
| 388 | 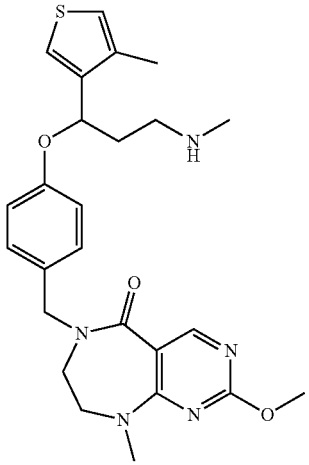 [SMILES: CNCCC(Oc1ccc(CN2CCN(C)c3nc(OC)ncc3C2=O)cc1)c1cscc1C] | 2-methoxy-9-methyl-6-(4-(3-(methylamino)-1-(3-methylthiophen-2-yl)propoxy)benzyl)-6,7,8,9-tetrahydro-5H-pyrimido[4,5-e][1,4]diazepin-5-one | + | ++++ |
| 389 | 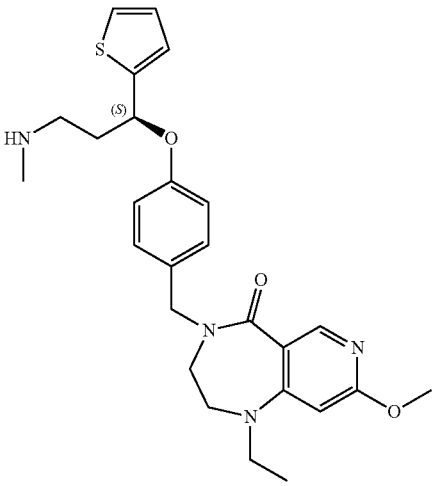 | (S)-1-ethyl-8-methoxy-4-(4-(3-(methylamino)-1-(thiophen-2-yl)propoxy)benzyl)-1,2,3,4-tetrahydro-5H-pyrido[4,3-e][1,4]diazepin-5-one | +++ | ++++ |

| Ex | Structure | Name | Ki (nM) α2δ-1 | Ki (nM) NET |
|---|---|---|---|---|
| 391 | 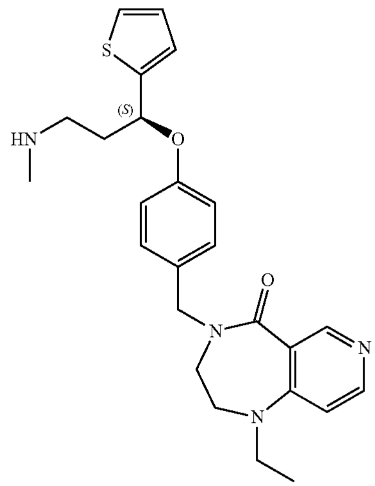 | (S)-1-ethyl-4-(4-(3-(methylamino)-1-(thiophen-2-yl)propoxy)benzyl)-1,2,3,4-tetrahydro-5H-pyrido[4,3-e][1,4]diazepin-5-one | +++ | ++++ |
| 392 | 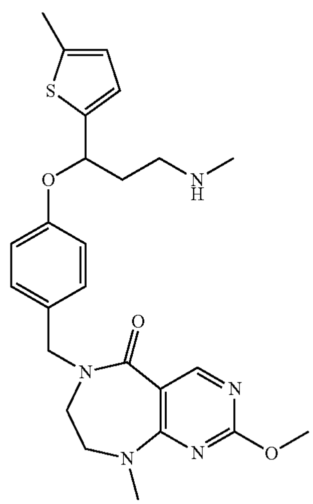 [SMILES: CNCCC(Oc1ccc(CN2CCN(C)c3nc(OC)ncc3C2=O)cc1)c1ccc(C)s1] | 2-methoxy-9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one | +++ | ++++ |
| 394 | 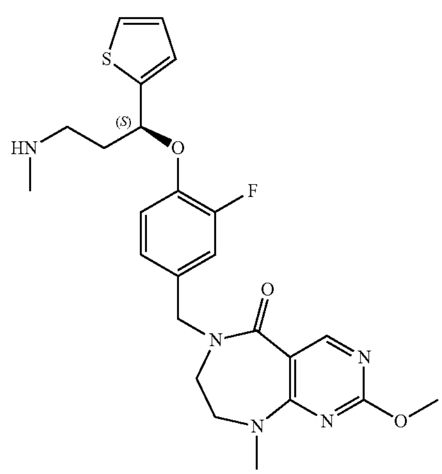 | (S)-6-(3-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one | +++ | ++++ |

-continued

| Ex | Structure | Name | Ki (nM) α2δ-1 | Ki (nM) NET |
|---|---|---|---|---|
| 402 | 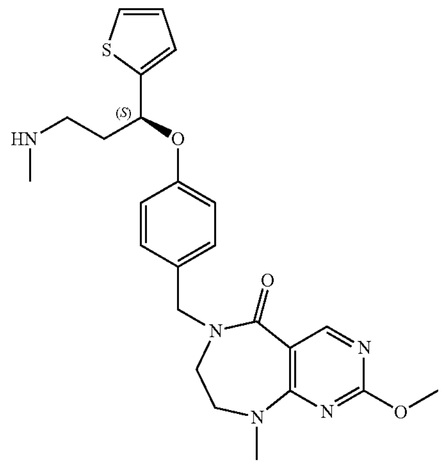 | (S)-2-methoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ | ++++ |
| 405 | 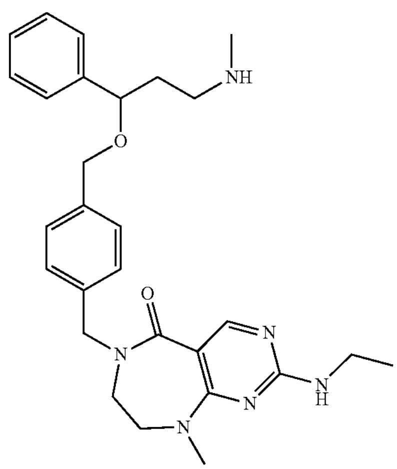 [SMILES: CCNc1ncc2c(n1)N(C)CCN(Cc1ccc(COC(CCNC)c3ccccc3)cc1)C2=O] | 2-(ethylamino)-9-methyl-6-(4-((3-(methylamino)-1-phenylpropoxy)methyl)benzyl)-6,7,8,9-tetrahydro-5H-pyrimido[4,5-e][1,4]diazepin-5-one | + | +++ |
| 406 | 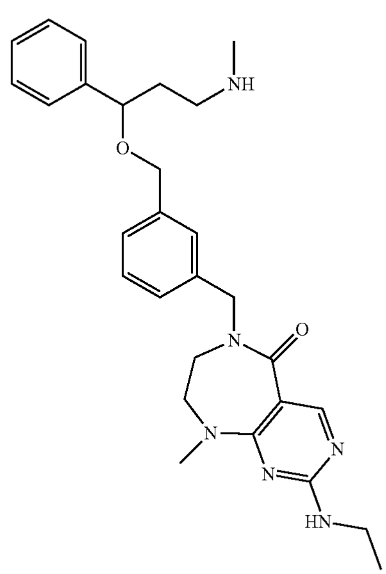 [SMILES: CCNc1ncc2c(n1)N(C)CCN(Cc1cccc(COC(CCNC)c3ccccc3)c1)C2=O] | 2-(ethylamino)-9-methyl-6-(3-((3-(methylamino)-1-phenylpropoxy)methyl)benzyl)-6,7,8,9-tetrahydro-5H-pyrimido[4,5-e][1,4]diazepin-5-one | + | +++ |

| Ex | Structure | Name | Ki (nM) α2δ-1 | Ki (nM) NET |
|---|---|---|---|---|
| 408 | 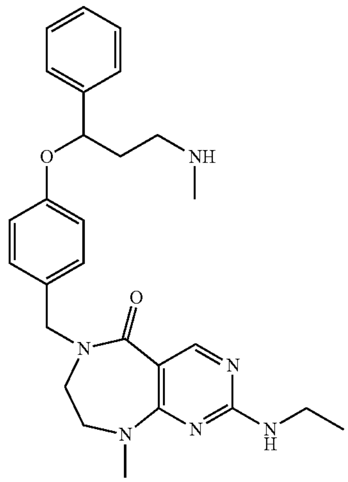 [SMILES: CCNc1ncc2c(n1)N(C)CCN(Cc1ccc(OC(CCNC)c3ccccc3)cc1)C2=O] | 2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | ++ | ++++ |
| 411 | 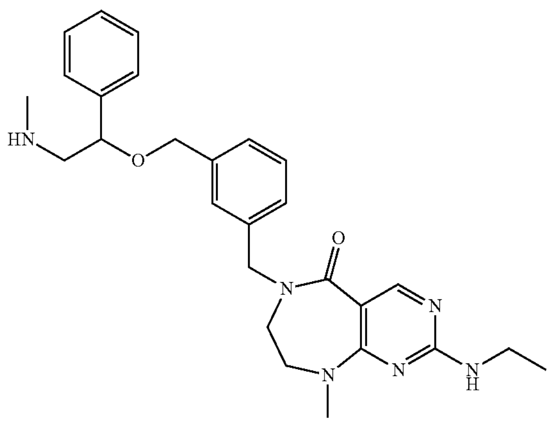 [SMILES: CCNc1ncc2c(n1)N(C)CCN(Cc1cccc(COC(CNC)c3ccccc3)c1)C2=O] | 2-(ethylamino)-9-methyl-6-(3-((2-(methylamino)-1-phenylethoxy)methyl)benzyl)-6,7,8,9-tetrahydro-5H-pyrimido[4,5-e][1,4]diazepin-5-one | + | ++ |
| 413 | 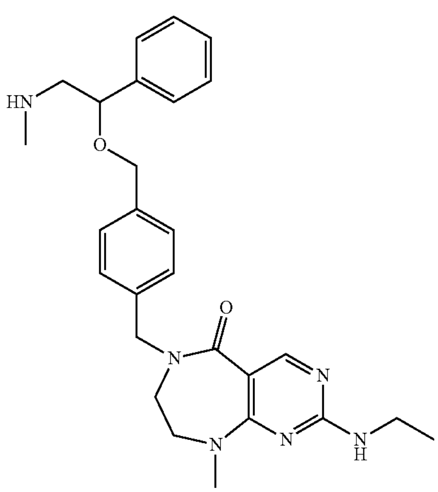 [SMILES: CCNc1ncc2c(n1)N(C)CCN(Cc1ccc(COC(CNC)c3ccccc3)cc1)C2=O] | 2-(ethylamino)-9-methyl-6-(4-((2-(methylamino)-1-phenylethoxy)methyl)benzyl)-6,7,8,9-tetrahydro-5H-pyrimido[4,5-e][1,4]diazepin-5-one | ++ | +++ |

-continued

| Ex | Structure | Name | Ki (nM) α2δ-1 | Ki (nM) NET |
|---|---|---|---|---|
| 414 | 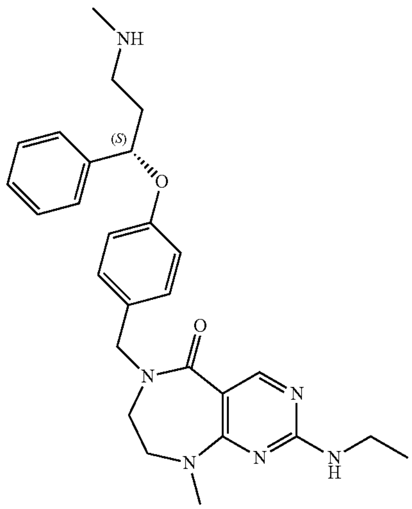 | (S)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | ++ | ++++ |
| 415 | 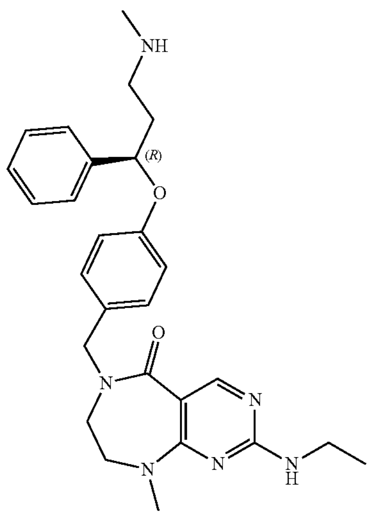 | (R)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one | ++ | +++ |
| 416 | 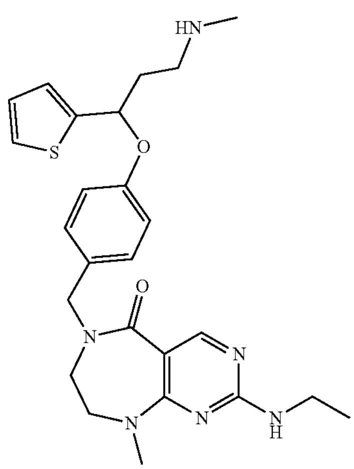 [SMILES: CCNc1ncc2c(n1)N(C)CCN(Cc1ccc(OC(CCNC)c3cccs3)cc1)C2=O] | 2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | ++ | ++++ |

| Ex | Structure | Name | Ki (nM) α2δ-1 | Ki (nM) NET |
|---|---|---|---|---|
| 417 | 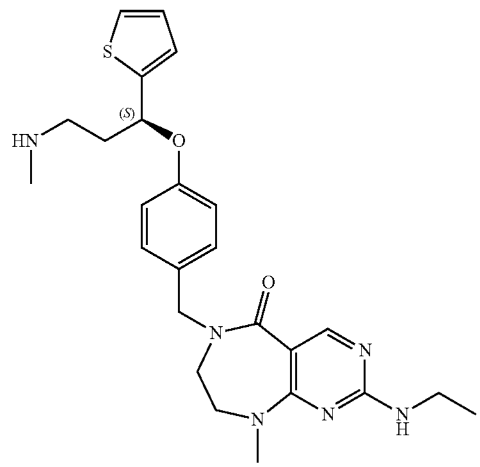 | (S)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ | ++++ |
| 418 | 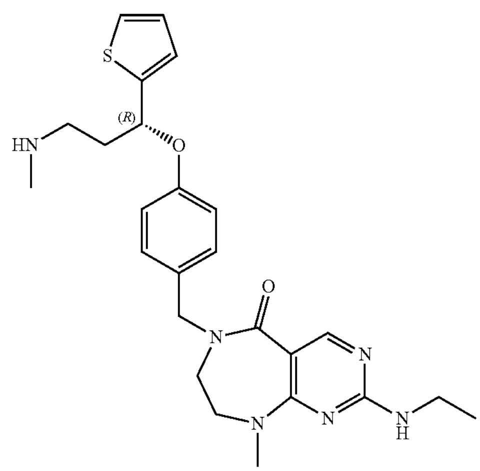 | (R)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | ++ | ++ |
| 419 | 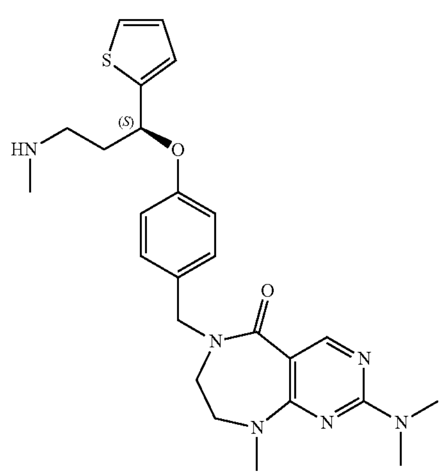 | (S)-2-(dimethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ | +++ |

-continued

| Ex | Structure | Name | Ki (nM) α2δ-1 | Ki (nM) NET |
|---|---|---|---|---|
| 420 | 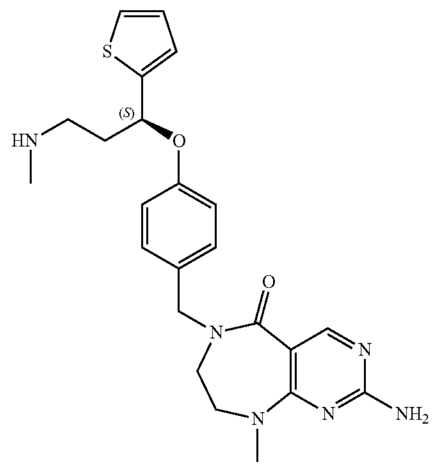 | (S)-2-amino-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ | ++++ |
| 422 | 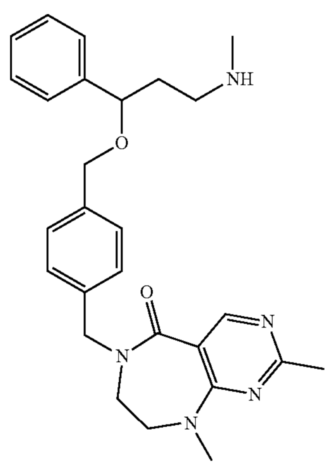 [SMILES: CNCCC(OCc1ccc(CN2CCN(C)c3nc(C)ncc3C2=O)cc1)c1ccccc1] | 2,9-dimethyl-6-(4-((3-(methylamino)-1-phenylpropoxy)methyl)benzyl)-6,7,8,9-tetrahydro-5H-pyrimido[4,5-e][1,4]diazepin-5-one | + | ++ |
| 423 | 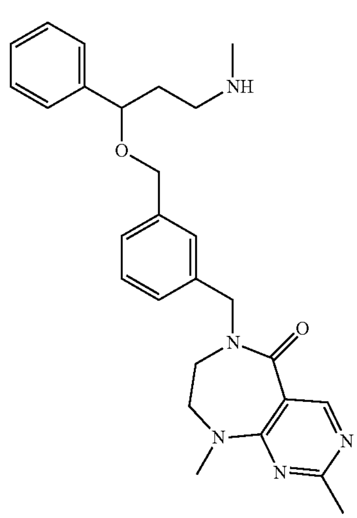 [SMILES: CNCCC(OCc1cccc(CN2CCN(C)c3nc(C)ncc3C2=O)c1)c1ccccc1] | 2,9-dimethyl-6-(3-((3-(methylamino)-1-phenylpropoxy)methyl)benzyl)-6,7,8,9-tetrahydro-5H-pyrimido[4,5-e][1,4]diazepin-5-one | + | +++ |

| Ex | Structure | Name | Ki (nM) α2δ-1 | Ki (nM) NET |
|---|---|---|---|---|
| 425 | 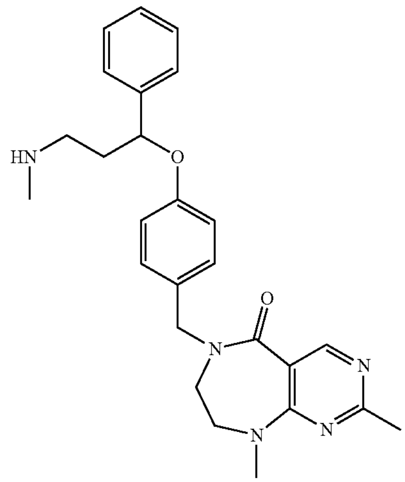 | 2,9-dimethyl-6-(4-(3-(methylamino)-1-phenylpropoxy)benzyl)-6,7,8,9-tetrahydro-5H-pyrimido[4,5-e][1,4]diazepin-5-one | + | ++++ |
| 426 | 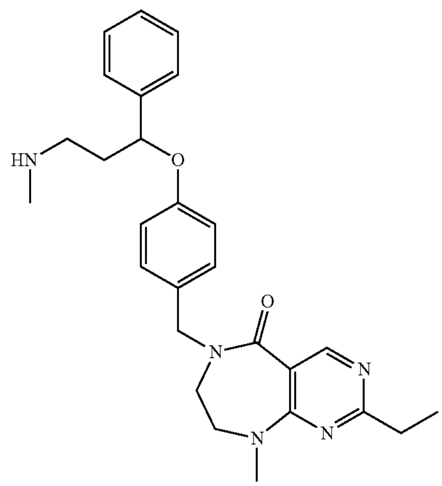 [SMILES: CCc1ncc2c(n1)N(C)CCN(Cc1ccc(OC(CCNC)c3ccccc3)cc1)C2=O] | 2-ethyl-9-methyl-6-(4-(3-(methylamino)-1-phenylpropoxy)benzyl)-6,7,8,9-tetrahydro-5H-pyrimido[4,5-e][1,4]diazepin-5-one | ++ | ++++ |
| 427 | 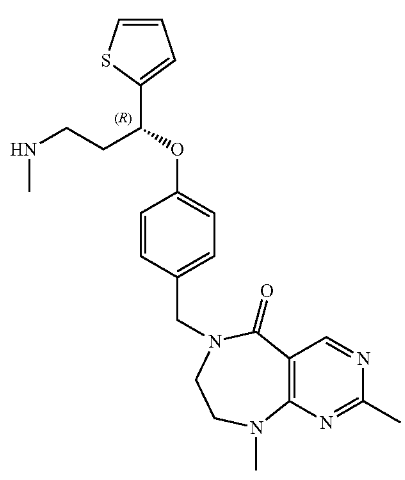 | (R)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one | + | ++ |

| Ex | Structure | Name | Ki (nM) α2δ-1 | Ki (nM) NET |
|---|---|---|---|---|
| 428 | 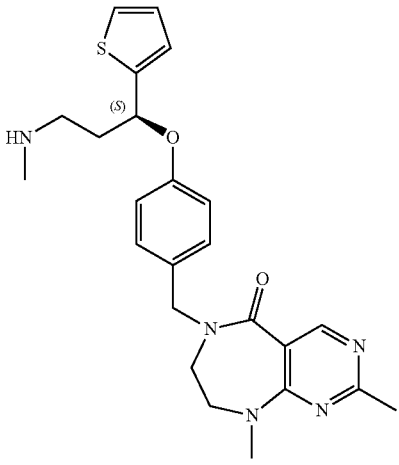 | (S)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one | +++ | ++++ |
| 430 | 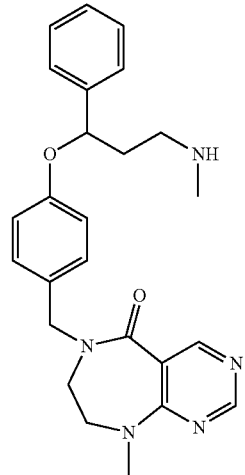 [SMILES: CNCCC(Oc1ccc(CN2CCN(C)c3ncncc3C2=O)cc1)c1ccccc1] | 9-methyl-6-(4-(3-(methylamino)-1-phenylpropoxy)benzyl)-6,7,8,9-tetrahydro-5H-pyrimido[4,5-e][1,4]diazepin-5-one | ++ | ++++ |
| 433 | 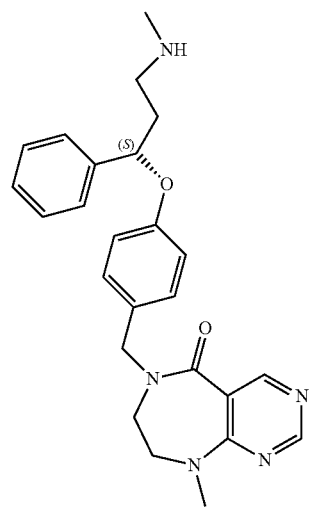 | (S)-9-methyl-6-(4-(3-(methylamino)-1-phenylpropoxy)benzyl)-6,7,8,9-tetrahydro-5H-pyrimido[4,5-e][1,4]diazepin-5-one | ++ | ++++ |

| Ex | Structure | Name | Ki (nM) α2δ-1 | Ki (nM) NET |
|---|---|---|---|---|
| 434 | 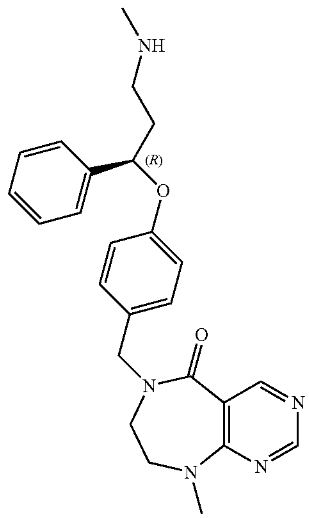 | (R)-9-methyl-6-(4-(3-(methylamino)-1-phenylpropoxy)benzyl)-6,7,8,9-tetrahydro-5H-pyrimido[4,5-e][1,4]diazepin-5-one | + | +++ |
| 435 | 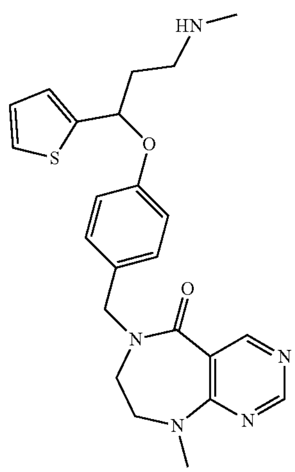 [SMILES: CNCCC(Oc1ccc(CN2CCN(C)c3ncncc3C2=O)cc1)c1cccs1] | 9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ | ++++ |
| 436 | 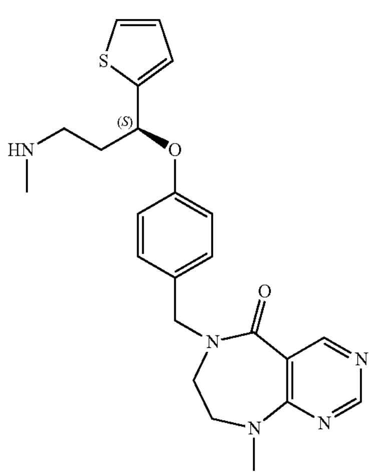 | (S)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | +++ | ++++ |

| Ex | Structure | Name | Ki (nM) α2δ-1 | Ki (nM) NET |
|---|---|---|---|---|
| 437 | 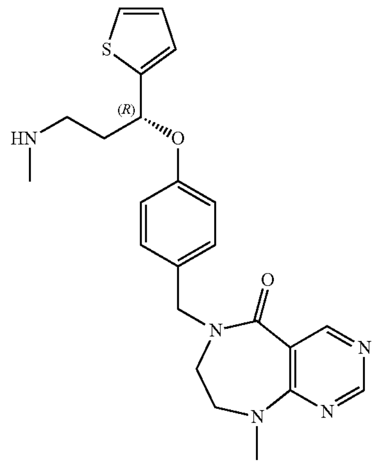 | (R)-9-methyl-6-(4-(3-(methylamino)-1-(thiophen-2-yl)propoxy)benzyl)-6,7,8,9-tetrahydro-5H-pyrimido[4,5-e][1,4]diazepin-5-one | + | ++ |
| 442 | 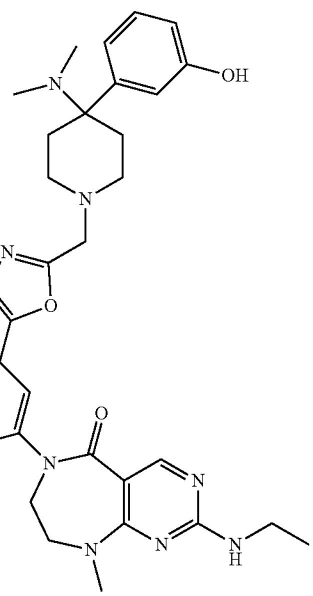 | 6-(3-(5-((4-(dimethylamino)-4-(3-hydroxyphenyl)piperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one | ++++ | ++++ |

The invention claimed is:
1. A compound of general formula (I):

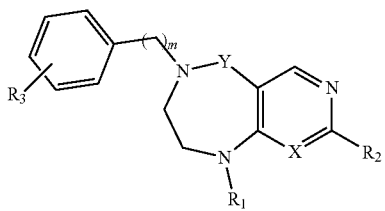

wherein:
X is CRx or N;
Rx is a hydrogen atom; a branched or unbranched $C_{1-6}$ alkyl radical; or a halogen atom;
Y is $CH_2$ or C=O;
m is 0, 1 or 2;

$R_1$ is a hydrogen atom; or a linear or branched $C_{1-6}$ alkyl radical;

$R_2$ is a hydrogen atom; a branched or unbranched $C_{1-6}$ alkyl radical; a halogen atom; haloalkyl; —$SR_{2a}$; —$NR_{2a}R_{2b}$; or —$OR_{2a}$;

$R_{2a}$ and $R_{2b}$ independently represent a hydrogen atom; a branched or unbranched $C_{1-4}$ alkyl radical; a $C_{3-6}$ cycloalkyl radical; —$(CH_2)_r$-aryl, wherein the aryl group is a 6-membered ring and r is 0, 1 or 2; —$(CH_2)_s$-heteroaryl, wherein the heteroaryl group is a 5 or 6-membered aromatic ring having at least one nitrogen atom and optionally having one or more additional heteroatoms selected from nitrogen, oxygen and sulfur, optionally substituted by at least one halogen atom and s is 0, 1 or 2; or —$(CH_2)_2$—O—$CH_3$;

$R_3$ is a hydrogen atom; —CN; —OH; halogen; branched or unbranched $C_{1-6}$ alkyl radical; —$(CH_2)_p$—O—$R_4$, wherein p is 0, 1 or 2; —$(CH_2)_q$—$NR_5R_6$, wherein q is 0, 1, 2 or 3; —$C(CH_3)_2$—$CH_2$—$NR_5R_6$; —C(=O) $NR_5R_6$; a 5 or 6 membered heteroaryl group having at least one heteroatom selected from N, O and S, and being substituted by one or two $R_7$ substituents and which may be attached to the phenyl ring by a $C_{1-3}$ alkylene group; a 5 or 6 membered heterocycloalkyl radical having one or two nitrogen atoms and being unsubstituted or optionally substituted by one or two $R_8$ substituents and which may be attached to the phenyl ring by a $C_{1-3}$ alkylene group; or —C(=O)$OR_9$;

$R_4$ is a hydrogen atom; a branched or unbranched $C_{1-6}$ alkyl radical; a tert-butyldimethylsilyl radical; a methylbenzenesulfonate radical; a —$CHR_{4a}R_{4b}$; a —$CH_2$—$CHR_{4a}R_{4b}$; or a 5 or 6-membered heterocycloalkyl radical having at least one N atom and being optionally substituted by one or two $R_{4c}$ radical;

$R_{4a}$ is a hydrogen atom; a branched or unbranched $C_{1-6}$ alkyl radical; a 5 or 6-membered aryl group optionally substituted by a at least one halogen atom; or a 5 or 6-membered heteroaryl group, having at least one heteroatom selected from N, O or S, and being optionally substituted by at least a branched or unbranched $C_{1-6}$ alkyl radical;

$R_{4b}$ is a —$(CH_2)_j$—$NR_{4b'}R_{4b''}$, wherein j is 0, 1, 2 or 3;

$R_{4b'}$ and $R_{4b''}$ independently represent a hydrogen atom; a branched or unbranched $C_{1-6}$ alkyl radical; a $C_{1-6}$ haloalkyl radical; a benzyl group; a phenethyl group; a tert-butyloxycarbonyl group; or a (trimethylsilyl)ethyloxycarbonyl group; or $R_{4b'}$ and $R_{4b''}$, together with the nitrogen to which they are attached, form a 5 or 6-membered heterocycloalkyl radical optionally containing an additional heteroatom selected from N, O and S;

$R_{4c}$ is a hydrogen atom; a branched or unbranched $C_{1-6}$ alkyl radical; a phenyl group; a benzyl group; or a tert-butyloxycarbonyl group;

$R_5$ and $R_6$ independently represent a hydrogen atom; a branched or unbranched $C_{1-6}$ alkyl radical; a tert-butyloxycarbonyl group; a benzyl group; a phenethyl group; or $R_5$ and $R_6$, together with the nitrogen to which they are attached, form a 5 or 6-membered heterocycloalkyl radical which may be mono or bisubstituted by a phenyl group, which may be optionally substituted by a branched or unbranched $C_{1-6}$ alkyl radical, a halogen atom, —OH or —CN; or by an —NRR', wherein R and R' independently represent a hydrogen atom or a branched or unbranched $C_{1-6}$ alkyl radical; or $R_5$ and $R_6$, together with the nitrogen atom to which they are attached, form 5 or 6-membered heterocycloalkyl radical which may be spirofused to another 5 or 6-membered heterocycloalkyl radical having at least one heteroatom selected from N, O and S, optionally containing an additional heteroatom selected from N, O and S, which may be substituted by one or more substituents selected from a branched or unbranched $C_{1-6}$ alkyl radical; a halogen atom, an —OH, a —CN and an =O;

$R_7$ is a hydrogen atom; a branched or unbranched $C_{1-6}$ alkyl radical; a —C(=O)H group; a —$(CH_2)_p$—$NR_{7a}R_{7b}$, wherein p is 0, 1, 2 or 3; or a —(CH)$R_{7c}R_{7d}$;

$R_{7a}$ and $R_{7b}$ independently represent a hydrogen atom; a branched or unbranched $C_{1-6}$ alkyl radical; a tert-butyloxycarbonyl group; a benzyl group optionally substituted by a halogen; a phenethyl group; a —$(CH_2)$-cyclopropyl; a hydroxyethoxyethyl group; an —OH; a —C(=O)H group; a pyridinylmethyl group; or $R_{7a}$ and $R_{7b}$, together with the nitrogen to which they are attached, form a 5 or 6-membered heterocycloalkyl radical which may additionally contain a second N atom, which radical may be substituted by a —$NR_{7a'}R_{7b'}$, wherein $R_{7a'}$ and $R_{7b'}$ independently represent a hydrogen atom or a branched or unbranched $C_{1-6}$ alkyl radical; or by a phenyl group, which may be optionally substituted by a branched or unbranched $C_{1-6}$ alkyl radical, a halogen atom, an —OH or a —CN; or $R_{7a}$ and $R_{7b}$, together with the nitrogen atom to which they are attached, form 5 or 6-membered heterocycloalkyl radical which may be fused to a 5 or 6 membered aromatic ring or may be spirofused to either a single 5 or 6-membered heterocycloalkyl ring having at least one heteroatom selected from N, O and S, optionally containing an additional heteroatom selected from N, O and S, which may be substituted by one or more substituents selected from a branched or unbranched $C_{1-6}$ alkyl radical, a halogen atom, an —OH, a —CN or an =O; or may be spirofused to a bicyclic ring system formed by a 5 or 6-membered heterocycloalkyl ring having at least one heteroatom selected from N, O and S, optionally containing an additional heteroatom selected from N, O and S, fused to 5 or 6-membered aromatic ring;

$R_{7c}$ and $R_{7d}$ independently represent a hydrogen atom; a branched or unbranched $C_{1-6}$ alkyl radical; or $C_{1-6}$alkoxy radical; and $R_8$ is a hydrogen atom; a branched or unbranched $C_{1-6}$ alkyl radical; a tert-butyloxycarbonyl group; a phenyl group; a benzyl group; a phenethyl group; or a —$NR8_aR_{8b'}$, wherein $R_{8a'}$ and $R_{8b'}$ represent a hydrogen atom or a branched or unbranched $C_{1-6}$ alkyl radical; and $R_9$ is a hydrogen atom; or a linear or branched $C_{1-6}$ alkyl radical;

or a pharmaceutically acceptable salt, stereoisomer, or solvate thereof.

2. The compound according to claim 1, wherein $R_2$ is a hydrogen atom; a branched or unbranched $C_{1-6}$ alkyl radical; a halogen atom; haloalkyl; —$SR_{2a}$; —$NR_{2a}R_{2b}$; or —$OR_{2a}$; wherein $R_{2a}$ and $R_{2b}$ are independently selected from a hydrogen atom and a branched or unbranched $C_{1-4}$ alkyl radical; —$(CH_2)_2$—O—$CH_3$; or a group selected from:

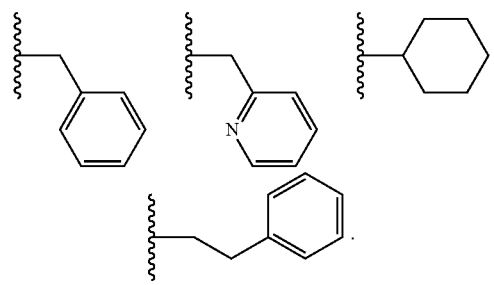

3. The compound according to claim 1, wherein $R_3$ represents a —$(CH_2)_p$—O—$R_4$ wherein p is 0, 1 or 2 and wherein $R_4$ is:
a hydrogen atom;
a branched or unbranched $C_{1-6}$ alkyl radical;
a tert-butyldimethylsilyl radical;
a methylbenzenesulfonate radical;

a —CHR$_{4a}$R$_{4b}$ or a —CH$_2$—CHR$_{4a}$R$_{4b}$ a wherein R$_{4a}$ is a hydrogen atom; a branched or unbranched C$_{1-6}$ alkyl radical; or a group selected from:

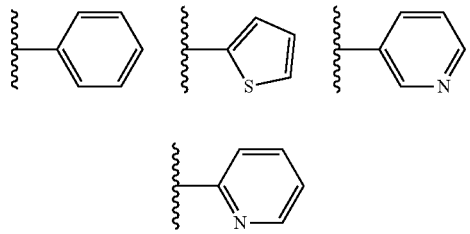

and wherein R$_{4b}$ is a —(CH$_2$)$_j$—NR$_{4b'}$R$_{4b''}$ being j 0, 1, 2 or 3 and R$_{4b'}$ and R$_{4b''}$ are independently from one another a hydrogen atom; a branched or unbranched C$_{1-6}$ alkyl radical; a C$_{1-6}$ haloalkyl radical; a benzyl group; a phenethyl group; a tert-butyloxycarbonyl group; a (trimethylsilyl)ethyloxycarbonyl group; or R$_{4b'}$ and R$_{4b''}$ together with the bridging nitrogen form a group selected from:

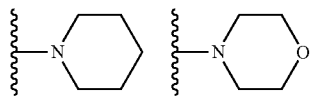

a group selected from:

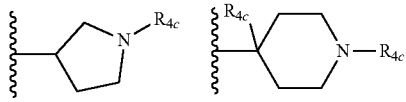

wherein R$_{4c}$ is a hydrogen atom; a branched or unbranched C$_{1-6}$ alkyl radical; a phenyl group; a benzyl group; or a tert-butyloxycarbonyl group.

4. The compound according to claim 1, wherein R$_3$ represents a —(CH$_2$)$_q$—NR$_5$R$_6$; —C(CH$_3$)$_2$—CH$_2$—NR$_5$R$_6$; or —C(=O)NR$_5$R$_6$ wherein q is 0, 1, 2 or 3 and wherein R$_5$ and R$_6$ independently represent:

a hydrogen atom;
a branched or unbranched C$_{1-6}$ alkyl radical;
a tert-butyloxycarbonyl group;
a group selected from:

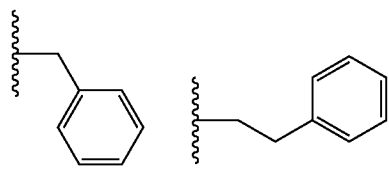

or wherein R$_5$ and R$_6$, together with the nitrogen atom to which they are attached, form one of the following structures:

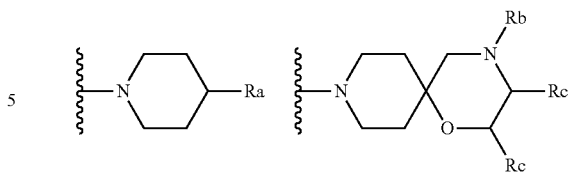

wherein R$_a$ is a phenyl group which may be optionally substituted by a branched or unbranched C$_{1-6}$ alkyl radical, a halogen atom, an —OH or a —CN; or a —NRR', wherein R and R' independently represent a hydrogen atom or a branched or unbranched C$_{1-6}$ alkyl radical;

R$_b$ is a branched or unbranched C$_{1-6}$ alkyl radical; a halogen atom; —OH; or —CN; and R$_c$ is a branched or unbranched C$_{1-6}$ alkyl radical; a halogen atom; —OH; —CN; or =O.

5. The compound according to claim 1, wherein R$_3$ represents a group selected from:

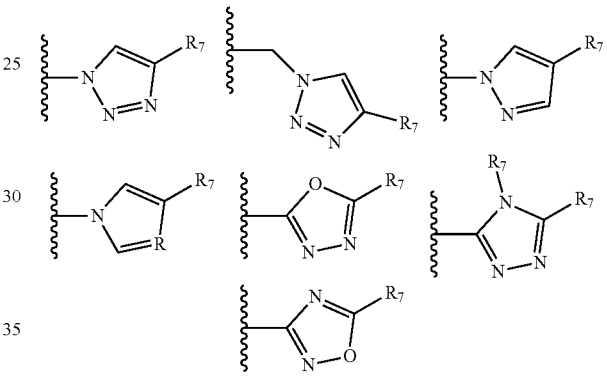

wherein R$_7$ is:
a hydrogen atom;
a branched or unbranched C$_{1-6}$ alkyl radical;
a —C(=O)H group;
—(CH$_2$)$_p$—NR$_{7a}$R$_{7b}$, wherein p is 0, 1, 2 or 3 or —(CH)R$_{7c}$R$_{7d}$;
wherein R$_{7a}$ and R$_{7b}$ independently represent a hydrogen atom; a branched or unbranched C$_{1-6}$ alkyl radical; a tert-butyloxycarbonyl group; a benzyl group optionally substituted by a halogen; a phenethyl group; a —(CH$_2$)-cyclopropyl group; a hydroxyethoxyethyl group; an —OH; a —C(=O)H group; a pyridinylmethyl group; or R$_{7a}$ and R$_{7b}$, together with the nitrogen atom to which they are attached, represent one of the following structures:

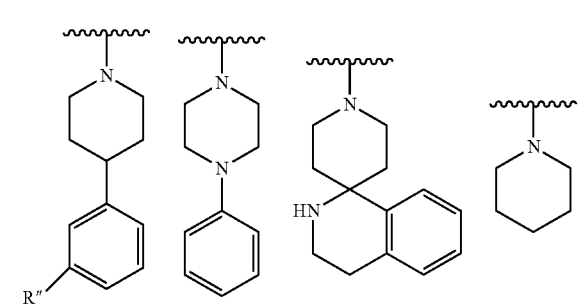

-continued

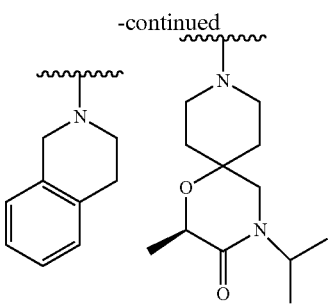

wherein R" is a hydrogen or an —OH group;
and wherein $R_{7c}$ and $R_{7d}$ independently represent a hydrogen atom; a branched or unbranched $C_{1-6}$ alkyl radical; or $C_{1-6}$ alkoxy radical.

6. The compound according to claim 1, wherein $R_3$ represents a group selected from:

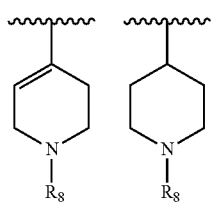

wherein $R_8$ is a hydrogen atom; a branched or unbranched $C_{1-6}$ alkyl radical; a tert-butyloxycarbonyl group; a benzyl group or a phenethyl group.

7. The compound according to claim 1, wherein $R_3$ is —C(=O)OR$_9$, wherein is $R_9$ a hydrogen atom or a linear or branched $C_{1-6}$ alkyl radical.

8. The compound according to claim 1, which is selected from the following list:

[1] tert-Butyl methyl(3-(3-(9-methyl-2-(methylthio)-5-oxo-5,7,8,9-tetrahydro-6H-pyrimido [4,5-e][1,4]diazepin-6-yl)phenoxy)-3-phenylpropyl)carbamate;

[2] tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

[3] tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-phenylpropyl)carbamate;

[4] tert-butyl methyl(2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate;

[5] tert-butyl (2-(3-(9-methyl-2-(methylthio)-5-oxo-5,7,8,9-tetrahydro-6H-pyrimido[4,5-e][1,4]diazepin-6-yl)phenoxy)-2-phenylethyl)carbamate;

[6] tert-butyl methyl(2-(3-(9-methyl-2-(methylthio)-5-oxo-5,7,8,9-tetrahydro-6H-pyrimido[4,5-e][1,4]diazepin-6-yl)phenoxy)propyl)carbamate;

[7] tert-butyl methyl(3-methyl-2-(3-(9-methyl-2-(methylthio)-5-oxo-5,7,8,9-tetrahydro-6H-pyrimido[4,5-e][1,4]diazepin-6-yl)phenoxy)butyl)carbamate;

[8] tert-butyl methyl(2-(4-(9-methyl-2-(methylthio)-5-oxo-5,7,8,9-tetrahydro-6H-pyrimido[4,5-e][1,4]diazepin-6-yl)phenoxy)-2-phenylethyl)carbamate;

[9] tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

[10] tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

[11] tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-phenylpropyl)carbamate;

[12] tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[13] tert-butyl (R)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[14] tert-butyl (S)-methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[15] tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

[16] tert-butyl (R)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

[17] tert-butyl (S)-methyl(3-((3-(9-methyl-2-(methylthio)-5-oxo-5,7,8,9-tetrahydro-6H-pyrimido[4,5-e][1,4]diazepin-6-yl)benzyl)oxy)-3-(thiophen-2-yl)propyl)carbamate;

[18] tert-butyl methyl(2-((3-(9-methyl-2-(methylthio)-5-oxo-5,7,8,9-tetrahydro-6H-pyrimido[4,5-e][1,4]diazepin-6-yl)benzyl)oxy)-1-phenylethyl)carbamate;

[19] 2-(trimethylsilyl)ethyl methyl(2-((3-(9-methyl-2-(methylthio)-5-oxo-5,7,8,9-tetrahydro-6H-pyrimido[4,5-e][1,4]diazepin-6-yl)benzyl)oxy)-2-phenylethyl)carbamate;

[20] tert-butyl methyl(3-(3-(9-methyl-2-(methylthio)-5-oxo-5,7,8,9-tetrahydro-6H-pyrimido[4,5-e][1,4]diazepin-6-yl)phenoxy)propyl)carbamate;

[21] tert-butyl benzyl(3-(3-(9-methyl-2-(methylthio)-5-oxo-5,7,8,9-tetrahydro-6H-pyrimido[4,5-e][1,4]diazepin-6-yl)phenoxy)propyl)carbamate;

[22] tert-butyl methyl(2-(3-(9-methyl-2-(methylthio)-5-oxo-5,7,8,9-tetrahydro-6H-pyrimido[4,5-e][1,4]diazepin-6-yl)phenoxy)ethyl)carbamate;

[23] tert-butyl methyl(3-(3-(9-methyl-2-(methylthio)-5-oxo-5,7,8,9-tetrahydro-6H-pyrimido[4,5-e][1,4]diazepin-6-yl)phenyl)propyl)carbamate;

[24] tert-butyl methyl(3-(9-methyl-2-(methylthio)-5-oxo-5,7,8,9-tetrahydro-6H-pyrimido[4,5-e][1,4]diazepin-6-yl)phenethyl)carbamate;

[25] tert-butyl methyl(2-methyl-2-(3-(9-methyl-2-(methylthio)-5-oxo-5,7,8,9-tetrahydro-6H-pyrimido[4,5-e][1,4]diazepin-6-yl)phenyl)propyl)carbamate;

[26] tert-butyl methyl(3-(9-methyl-2-(methylthio)-5-oxo-5,7,8,9-tetrahydro-6H-pyrimido[4,5-e][1,4]diazepin-6-yl)benzyl)carbamate;

[27] tert-butyl 3-(3-(9-methyl-2-(methylthio)-5-oxo-5,7,8,9-tetrahydro-6H-pyrimido[4,5-e][1,4]diazepin-6-yl)phenoxy)pyrrolidine-1-carboxylate;

[28] tert-butyl 4-((3-(9-methyl-2-(methylthio)-5-oxo-5,7,8,9-tetrahydro-6H-pyrimido[4,5-e][1,4]diazepin-6-yl)benzyl)oxy)-4-phenylpiperidine-1-carboxylate;

[29] 9-methyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one;

[30] 9-ethyl-6-(3-(5-methyl-1,3,4-oxadiazol-2-yl)phenyl)-2-(methylthio)-6,7,8,9-tetrahydro-5H-pyrimido[4,5-e][1,4]diazepin-5-one;

[31] 9-methyl-6-(3-(5-methyl-1,2,4-oxadiazol-3-yl)phenyl)-2-(methylthio)-6,7,8,9-tetrahydro-5H-pyrimido[4,5-e][1,4]diazepin-5-one;

[32] 6-(3-methoxyphenyl)-9-methyl-2-(methylthio)-6,7,8,9-tetrahydro-5H-pyrimido[4,5-e][1,4]diazepin-5-one;

[33] 3-(9-methyl-2-(methylthio)-5-oxo-5,7,8,9-tetrahydro-6H-pyrimido[4,5-e][1,4]diazepin-6-yl)benzonitrile;

[34] 6-(3-((tert-butyldimethylsilyl)oxy)phenyl)-9-methyl-2-(methylthio)-6,7,8,9-tetrahydro-5H-pyrimido[4,5-e][1,4]diazepin-5-one;

[35] 6-(3-bromophenyl)-9-methyl-2-(methylthio)-6,7,8,9-tetrahydro-5H-pyrimido[4,5-e][1,4]diazepin-5-one;

[36] 6-(3-(2-hydroxyethyl) phenyl)-9-methyl-2-(methylthio)-6,7,8,9-tetrahydro-5H-pyrimido[4,5-e][1,4]diazepin-5-one;

[37] 6-(4-methoxyphenyl)-9-methyl-2-(methylthio)-6,7,8,9-tetrahydro-5H-pyrimido[4,5-e][1,4]diazepin-5-one;

[38] 6-(4-((tert-butyldimethylsilyl)oxy)phenyl)-9-methyl-2-(methylthio)-6,7,8,9-tetrahydro-5H-pyrimido[4,5-e][1,4]diazepin-5-one;

[39] tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

[40] tert-butyl ((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

[41] tert-butyl benzyl((1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)methyl)carbamate;

[42] 6-(3-(4-(diethoxymethyl)-1H-1,2,3-triazol-1-yl)phenyl)-9-methyl-2-(methylthio)-6,7,8,9-tetrahydro-5H-pyrimido[4,5-e][1,4]diazepin-5-one;

[43] tert-butyl methyl(2-(1-(3-(9-methyl-2-(methylthio)-5-oxo-5,7,8,9-tetrahydro-6H-pyrimido[4,5-e][1,4]diazepin-6-yl)phenyl)-1H-1,2,3-triazol-4-yl)ethyl)carbamate;

[44] tert-butyl methyl((1-(3-(9-methyl-2-(methylthio)-5-oxo-5,7,8,9-tetrahydro-6H-pyrimido[4,5-e][1,4]diazepin-6-yl)benzyl)-1H-1,2,3-triazol-4-yl)methyl)carbamate;

[45] tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-pyrazol-4-yl)methyl)carbamate;

[46] tert-butyl methyl((1-(3-(9-methyl-2-(methylthio)-5-oxo-5,7,8,9-tetrahydro-6H-pyrimido[4,5-e][1,4]diazepin-6-yl)phenyl)-1H-imidazol-4-yl)methyl)carbamate;

[47] tert-butyl methyl((5-(3-(9-methyl-2-(methylthio)-5-oxo-5,7,8,9-tetrahydro-6H-pyrimido[4,5-e][1,4]diazepin-6-yl)phenyl)-1,3,4-oxadiazol-2-yl)methyl)carbamate;

[48] tert-butyl methyl(3-(2-(9-methyl-2-(methylthio)-5-oxo-5,7,8,9-tetrahydro-6H-pyrimido[4,5-e][1,4] diazepin-6-yl) phenoxy)-3-phenylpropyl)carbamate;

[49] tert-butyl methyl(4-methyl-3-((3-(9-methyl-2-(methylthio)-5-oxo-5,7,8,9-tetrahydro-6H-pyrimido[4,5-e][1,4]diazepin-6-yl)benzyl)oxy)pentyl)carbamate;

[50] tert-butyl methyl(3-((3-(9-methyl-2-(methylthio)-5-oxo-5,7,8,9-tetrahydro-6H-pyrimido[4,5-e][1,4]diazepin-6-yl)benzyl)oxy)butyl)carbamate;

[51] 2-(trimethylsilyl)ethyl methyl(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl)carbamate;

[52] tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-2-yl)propyl)carbamate;

[53] tert-butyl methyl(3-(3-(9-methyl-2-(methylthio)-5-oxo-5,7,8,9-tetrahydro-6H-pyrimido[4,5-e][1,4]diazepin-6-yl)phenoxy)-3-(pyridin-3-yl)propyl)carbamate;

[54] 8-(ethylamino)-1-methyl-4-(3-(5-methyl-1,3,4-oxadiazol-2-yl)phenyl)-1,2,3,4-tetrahydro-5H-pyrido[4,3-e][1,4]diazepin-5-one;

[55] 4-(3-(4-ethyl-5-methyl-4H-1,2,4-triazol-3-yl)phenyl)-8-(ethylamino)-1-methyl-1,2,3,4-tetrahydro-5H-pyrido[4,3-e][1,4]diazepin-5-one;

[56] tert-butyl (3-(3-(8-(ethylamino)-1-methyl-5-oxo-1,2,3,5-tetrahydro-4H-pyrido[4,3-e][1,4]diazepin-4-yl)phenoxy)-3-phenylpropyl)(methyl)carbamate;

[57] tert-butyl (3-((3-(8-(ethylamino)-1-methyl-5-oxo-1,2,3,5-tetrahydro-4H-pyrido[4,3-e][1,4]diazepin-4-yl)benzyl)oxy)-3-phenylpropyl)(methyl)carbamate;

[58] 2-(trimethylsilyl)ethyl (3-(3-(8-(ethylamino)-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[59] 2-(trimethylsilyl)ethyl (3-(3-(8-(dimethylamino)-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[60] 2-(trimethylsilyl)ethyl (3-((3-(8-(ethylamino)-1-methyl-5-oxo-1,2,3,5-tetrahydro-4H-pyrido[4,3-e][1,4]diazepin-4-yl)benzyl)oxy)-3-(thiophen-2-yl)propyl)(methyl)carbamate;

[61] tert-butyl (2-fluoroethyl)(3-(3-(9-methyl-2-(methylthio)-5-oxo-5,7,8,9-tetrahydro-6H-pyrimido[4,5-e][1,4]diazepin-6-yl)phenoxy)-3-(thiophen-2-yl)propyl) carbamate;

[62] tert-Butyl methyl(2-(3-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate;

[63] tert-butyl methyl(2-(4-((9-methyl-2-(methylthio)-5-oxo-5,7,8,9-tetrahydro-6H-pyrimido[4,5-e][1,4]diazepin-6-yl)methyl)phenoxy)-2-phenylethyl)carbamate;

[64] tert-butyl methyl(4-((9-methyl-2-(methylthio)-5-oxo-5,7,8,9-tetrahydro-6H-pyrimido[4,5-e][1,4]diazepin-6-yl)methyl)benzyl)carbamate;

[65] tert-Butyl (R)-(3-((3-(2-(ethylamino)-9-methyl-5,7,8,9-tetrahydro-6H-pyrimido [4,5-e][1,4]diazepin-6-yl)benzyl)oxy)-3-phenylpropyl)(methyl)carbamate;

[66] N-ethyl-9-methyl-6-(3-(5-methyl-1,3,4-oxadiazol-2-yl)phenyl)-6,7,8,9-tetrahydro-5H-pyrimido[4,5-e][1,4]diazepin-2-amine;

[67] N-ethyl-6-(3-methoxybenzyl)-9-methyl-6,7,8,9-tetrahydro-5H-pyrimido [4,5-e][1,4]diazepin-2-amine;

[68] N-ethyl-6-(4-methoxybenzyl)-9-methyl-6,7,8,9-tetrahydro-5H-pyrimido[4,5-e][1,4]diazepin-2-amine;

[69] tert-Butyl (3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[70] tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[71] tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[72] tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate;

[73] tert-butyl (2-(3-(2-(ethylamino)-9-methyl-5-oxo-5,7,8,9-tetrahydro-6H-pyrimido[4,5-e][1,4]diazepin-6-yl)phenoxy)-2-phenylethyl)carbamate;

[74] tert-butyl (2-(3-(2-(ethylamino)-9-methyl-5-oxo-5,7,8,9-tetrahydro-6H-pyrimido[4,5-e][1,4]diazepin-6-yl)phenoxy)propyl)(methyl)carbamate;

[75] tert-butyl (2-(3-(2-(ethylamino)-9-methyl-5-oxo-5,7,8,9-tetrahydro-6H-pyrimido[4,5-e][1,4] diazepin-6-yl)phenoxy)-3-methylbutyl)(methyl)carbamate;

[76] tert-butyl (2-(4-(2-(ethylamino)-9-methyl-5-oxo-5,7,8,9-tetrahydro-6H-pyrimido[4,5-e][1,4]diazepin-6-yl)phenoxy)-2-phenylethyl)(methyl)carbamate;

[77] tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[78] tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[79] tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[80] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[81] tert-butyl (R)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[82] tert-butyl (S)-(3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[83] tert-butyl (3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[84] tert-butyl (R)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[85] tert-butyl (S)-(3-((3-(2-(ethylamino)-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[86] tert-butyl (2-((3-(2-(ethylamino)-9-methyl-5-oxo-5,7,8,9-tetrahydro-6H-pyrimido[4,5-e][1,4]diazepin-6-yl)benzyl)oxy)-1-phenylethyl)(methyl)carbamate;

[87] 2-(trimethylsilyl)ethyl (2-((3-(2-(ethylamino)-9-methyl-5-oxo-5,7,8,9-tetrahydro-6H-pyrimido[4,5-e][1,4]diazepin-6-yl)benzyl)oxy)-2-phenylethyl)(methyl)carbamate;

[88] tert-butyl (3-3-(2-(ethylamino)-9-methyl-5-oxo-5,7,8,9-tetrahydro-6H-pyrimido[4,5-e][1,4]diazepin-6-yl)phenoxy)propyl)(methyl)carbamate;

[89] tert-butyl benzyl(3-(3-(2-(ethylamino)-9-methyl-5-oxo-5,7,8,9-tetrahydro-6H-pyrimido[4,5-e][1,4]diazepin-6-yl)phenoxy)propyl)carbamate;

[90] tert-butyl (2-(3-(2-(ethylamino)-9-methyl-5-oxo-5,7,8,9-tetrahydro-6H-pyrimido[4,5-e][1,4]diazepin-6-yl)phenoxy)ethyl)(methyl)carbamate;

[91] tert-butyl (3-(3-(2-(ethylamino)-9-methyl-5-oxo-5,7,8,9-tetrahydro-6H-pyrimido[4,5-e][1,4]diazepin-6-yl)phenyl)propyl)(methyl)carbamate;

[92] tert-butyl (3-(2-(ethylamino)-9-methyl-5-oxo-5,7,8,9-tetrahydro-6H-pyrimido[4,5-e][1,4]diazepin-6-yl)phenethyl)(methyl)carbamate;

[93] tert-butyl (2-(3-(2-(ethylamino)-9-methyl-5-oxo-5,7,8,9-tetrahydro-6H-pyrimido[4,5-e][1,4]diazepin-6-yl)phenyl)-2-methylpropyl)(methyl)carbamate;

[94] tert-butyl (3-(2-(ethylamino)-9-methyl-5-oxo-5,7,8,9-tetrahydro-6H-pyrimido[4,5-e][1,4]diazepin-6-yl)benzyl)(methyl)carbamate;

[95] tert-butyl 3-(3-(2-(ethylamino)-9-methyl-5-oxo-5,7,8,9-tetrahydro-6H-pyrimido[4,5-e][1,4]diazepin-6-yl)phenoxy)pyrrolidine-1-carboxylate;

[96] tert-butyl 4-((3-(2-(ethylamino)-9-methyl-5-oxo-5,7,8,9-tetrahydro-6H-pyrimido[4,5-e][1,4]diazepin-6-yl)benzyl)oxy)-4-phenylpiperidine-1-carboxylate;

[97] 2-(ethylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[98] 2-(isobutylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[99] 2-((2-methoxyethyl)amino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[100] 9-methyl-6-(3-(5-methyl-1,3,4-oxadiazol-2-yl)phenyl)-2-(methylamino)-6,7,8,9-tetrahydro-5H-pyrimido[4,5-e][1,4]diazepin-5-one;

[101] 2-amino-9-methyl-6-(3-(5-methyl-1,3,4-oxadiazol-2-yl)phenyl)-6,7,8,9-tetrahydro-5H-pyrimido[4,5-e][1,4]di2-(benzylamino)-9-methyl-6-(3-(5-methyl-1,3,4-oxadiazol-2-yl)phenyl)-6,7,8,9-tetrahydro-5H-pyrimido[4,5-e][1,4]diazepin-5-one azepin-5-one;

[102] 2-(benzylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[103] 2-(cyclohexylamino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[104] 2-(benzyl(methyl) amino)-9-methyl-6-(3-(5-methyl-1,3,4-oxadiazol-2-yl)phenyl)-6,7,8,9-tetrahydro-5H-pyrimido[4,5-e][1,4]diazepin-5-one;

[105] 9-methyl-6-(3-(5-methyl-1,3,4-oxadiazol-2-yl)phenyl)-2-(phenethylamino)-6,7,8,9-tetrahydro-5H-pyrimido[4,5-e][1,4]diazepin-5-one;

[106] 9-methyl-2-(methyl (pyridin-2-ylmethyl) amino)-6-(3-(5-methyl-1,3,4-oxadiazol-2-yl)phenyl)-6,7,8,9-tetrahydro-5H-pyrimido[4,5-e][1,4]diazepin-5-one;

[107] 9-ethyl-2-(ethylamino)-6-(3-(5-methyl-1,3,4-oxadiazol-2-yl)phenyl)-6,7,8,9-tetrahydro-5H-pyrimido[4,5-e][1,4]diazepin-5-one;

[108] 2-(ethylamino)-9-methyl-6-(3-(5-methyl-1,2,4-oxadiazol-3-yl)phenyl)-6,7,8,9-tetrahydro-5H-pyrimido[4,5-e][1,4]diazepin-5-one;

[109] 2-(ethylamino)-6-(3-methoxyphenyl)-9-methyl-6,7,8,9-tetrahydro-5H-pyrimido[4,5-e][1,4]diazepin-5-one;

[110] 3-(2-(ethylamino)-9-methyl-5-oxo-5,7,8,9-tetrahydro-6H-pyrimido[4,5-e][1,4]diazepin-6-yl)benzonitrile;

[111] 6-(3-((tert-butyldimethylsilyl)oxy)phenyl)-2-(ethylamino)-9-methyl-6,7,8,9-tetrahydro-5H-pyrimido[4,5-e][1,4]diazepin-5-one;

[112] 2-(ethylamino)-6-(3-(2-hydroxyethyl)phenyl)-9-methyl-6,7,8,9-tetrahydro-5H-pyrimido[4,5-e][1,4]diazepin-5-one;

[113] 2-(ethylamino)-6-(3-(2-hydroxyethyl)phenyl)-9-methyl-6,7,8,9-tetrahydro-5H-pyrimido[4,5-e][1,4]diazepin-5-one;

[114] 2-(ethylamino)-6-(4-methoxyphenyl)-9-methyl-6,7,8,9-tetrahydro-5H-pyrimido[4,5-e][1,4]diazepin-5-one;

[115] 6-(4-((tert-butyldimethylsilyl)oxy)phenyl)-2-(ethylamino)-9-methyl-6,7,8,9-tetrahydro-5H-pyrimido[4,5-e][1,4]diazepin-5-one;

[116] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)(methyl)carbamate;

[117] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate;

[118] tert-butyl benzyl((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)carbamate;

[119] 6-(3-(4-(diethoxymethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[120] tert-butyl (2-(1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)ethyl)(methyl)carbamate;

[121] tert-butyl ((1-(3-(2-(ethylamino)-9-methyl-5-oxo-5,7,8,9-tetrahydro-6H-pyrimido[4,5-e][1,4]diazepin-6-yl)benzyl)-1H-1,2,3-triazol-4-yl)methyl)carbamate;

[122] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-pyrazol-4-yl)methyl)(methyl)carbamate;

[123] tert-butyl ((1-(3-(2-(ethylamino)-9-methyl-5-oxo-5,7,8,9-tetrahydro-6H-pyrimido[4,5-e][1,4]diazepin-6-yl)phenyl)-1H-imidazol-4-yl)methyl)(methyl)carbamate;

[124] tert-butyl ((5-(3-(2-(ethylamino)-9-methyl-5-oxo-5,7,8,9-tetrahydro-6H-pyrimido[4,5-e][1,4]diazepin-6-yl)phenyl)-1,3,4-oxadiazol-2-yl)methyl)(methyl)carbamate;

[125] tert-butyl (3-(2-(2-(ethylamino)-9-methyl-5-oxo-5,7,8,9-tetrahydro-6H-pyrimido[4,5-e][1,4]diazepin-6-yl)phenoxy)-3-phenylpropyl)(methyl)carbamate;

[126] tert-butyl (3-((3-(2-(ethylamino)-9-methyl-5-oxo-5,7,8,9-tetrahydro-6H-pyrimido[4,5-e][1,4]diazepin-6-yl)benzyl)oxy)-4-methylpentyl)(methyl)carbamate;

[127] tert-butyl (3-((3-(2-(ethylamino)-9-methyl-5-oxo-5,7,8,9-tetrahydro-6H-pyrimido[4,5-e][1,4]diazepin-6-yl)benzyl)oxy)butyl)(methyl)carbamate;

[128] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-2-yl)propyl)(methyl)carbamate;

[129] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(pyridin-3-yl)propyl)(methyl)carbamate;

[130] tert-butyl (R)-(3-((3-(2-amino-9-methyl-5-oxo-5,7,8,9-tetrahydro-6H-pyrimido[4,5-e][1,4]diazepin-6-yl)benzyl)oxy)-3-phenylpropyl)(methyl)carbamate;

[131] tert-butyl (R)-(3-((3-(2-(dimethylamino)-9-methyl-5-oxo-5,7,8,9-tetrahydro-6H-pyrimido[4,5-e][1,4]diazepin-6-yl)benzyl)oxy)-3-phenylpropyl)(methyl)carbamate;

[132] tert-butyl (R)-methyl(3-((3-(9-methyl-2-(methylamino)-5-oxo-5,7,8,9-tetrahydro-6H-pyrimido[4,5-e][1,4]diazepin-6-yl)benzyl)oxy)-3-phenylpropyl)carbamate;

[133] 2-(trimethylsilyl)ethyl (3-(3-(2-(dimethylamino)-9-methyl-5-oxo-5,7,8,9-tetrahydro-6H-pyrimido[4,5-e][1,4]diazepin-6-yl)phenoxy)-3-(thiophen-2-yl)propyl)(methyl)carbamate;

[134] tert-butyl (3-(3-(2-(ethylamino)-9-methyl-5-oxo-5,7,8,9-tetrahydro-6H-pyrimido[4,5-e][1,4]diazepin-6-yl)phenoxy)-3-(thiophen-2-yl)propyl)(2-fluoroethyl)carbamate;

[135] tert-butyl (2-(3-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate;

[136] tert-butyl (2-(4-((2-(ethylamino)-9-methyl-5-oxo-5,7,8,9-tetrahydro-6H-pyrimido[4,5-e][1,4]diazepin-6-yl)methyl)phenoxy)-2-phenylethyl)(methyl)carbamate;

[137] tert-butyl (4-((2-(ethylamino)-9-methyl-5-oxo-5,7,8,9-tetrahydro-6H-pyrimido[4,5-e][1,4]diazepin-6-yl)methyl)benzyl)(methyl)carbamate;

[138] tert-Butyl (R)-(3-((3-(2-methoxy-9-methyl-5-oxo-5,7,8,9-tetrahydro-6H-pyrimido[4,5-e][1,4]diazepin-6-yl)benzyl)oxy)-3-phenylpropyl)(methyl)carbamate;

[139] tert-butyl (3-((3-(2-methoxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[140] tert-Butyl (R)-(3-((3-(2-hydroxy-9-methyl-5-oxo-5,7,8,9-tetrahydro-6H-pyrimido[4,5-e][1,4]diazepin-6-yl)benzyl)oxy)-3-phenylpropyl)(methyl)carbamate;

[141] tert-butyl (3-((3-(2-hydroxy-9-methyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[142] tert-Butyl (R)-(3-((3-(2,9-dimethyl-5-oxo-5,7,8,9-tetrahydro-6H-pyrimido[4,5-e][1,4]diazepin-6-yl)benzyl)oxy)-3-phenylpropyl)(methyl)carbamate;

[143] tert-butyl (3-((3-(2,9-dimethyl-5-oxo-5,7,8,9-tetrahydro-6H-pyrimido[4,5-e][1,4]diazepin-6-yl)benzyl)oxy)-3-(thiophen-2-yl)propyl)(methyl)carbamate;

[144] 2-(trimethylsilyl)ethyl (3-(3-(2,9-dimethyl-5-oxo-5,7,8,9-tetrahydro-6H-pyrimido[4,5-e][1,4]diazepin-6-yl)phenoxy)-3-(thiophen-2-yl)propyl)(methyl)carbamate;

[145] tert-Butyl (R)-methyl(3-((3-(9-methyl-5-oxo-5,7,8,9-tetrahydro-6H-pyrimido[4,5-e][1,4]diazepin-6-yl)benzyl)oxy)-3-phenylpropyl)carbamate;

[146] tert-butyl methyl(3-((3-(9-methyl-5-oxo-5,7,8,9-tetrahydro-6H-pyrimido[4,5-e][1,4]diazepin-6-yl)benzyl)oxy)-3-(thiophen-2-yl)propyl)carbamate;

[147] 2-(trimethylsilyl)ethyl methyl(3-(3-(9-methyl-5-oxo-5,7,8,9-tetrahydro-6H-pyrimido[4,5-e][1,4]diazepin-6-yl)phenoxy)-3-(thiophen-2-yl)propyl)carbamate;

[148] 2-(Ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[149] (R)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[150] (S)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[151] 9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[152] (R)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[153] (S)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[154] 2-(ethylamino)-9-methyl-6-(3-(2-(methylamino)-1-phenylethoxy)phenyl)-6,7,8,9-tetrahydro-5H-pyrimido[4,5-e][1,4]diazepin-5-one;

[155] 9-methyl-6-(3-(2-(methylamino)-1-phenylethoxy)phenyl)-2-(methylthio)-6,7,8,9-tetrahydro-5H-pyrimido[4,5-e][1,4]diazepin-5-one;

[156] 6-(3-(2-amino-1-phenylethoxy)phenyl)-2-(ethylamino)-9-methyl-6,7,8,9-tetrahydro-5H-pyrimido[4,5-e][1,4]diazepin-5-one;

[157] 2-(ethylamino)-9-methyl-6-(3-((1-(methylamino)propan-2-yl)oxy)phenyl)-6,7,8,9-tetrahydro-5H-pyrimido[4,5-e][1,4]diazepin-5-one;

[158] 2-(ethylamino)-9-methyl-6-(3-((3-methyl-1-(methylamino)butan-2-yl)oxy)phenyl)-6,7,8,9-tetrahydro-5H-pyrimido[4,5-e][1,4]diazepin-5-one;

[159] 2-(ethylamino)-9-methyl-6-(4-(2-(methylamino)-1-phenylethoxy)phenyl)-6,7,8,9-tetrahydro-5H-pyrimido[4,5-e][1,4]diazepin-5-one;

[160] 2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[161] (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[162] (S)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[163] 9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[164] (R)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[165] (S)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[166] 2-(ethylamino)-9-methyl-6-(3-((2-(methylamino)-2-phenylethoxy)methyl)phenyl)-6,7,8,9-tetrahydro-5H-pyrimido[4,5-e][1,4]diazepin-5-one;

[167] 9-methyl-6-(3-((2-(methylamino)-2-phenylethoxy)methyl)phenyl)-2-(methylthio)-6,7,8,9-tetrahydro-5H-pyrimido[4,5-e][1,4]diazepin-5-one;

[168] 2-(ethylamino)-9-methyl-6-(3-(3-(methylamino)propoxy)phenyl)-6,7,8,9-tetrahydro-5H-pyrimido[4,5-e][1,4]diazepin-5-one;

[169] 6-(3-(3-(benzylamino)propoxy)phenyl)-2-(ethylamino)-9-methyl-6,7,8,9-tetrahydro-5H-pyrimido[4,5-e][1,4]diazepin-5-one;

[170] 2-(ethylamino)-9-methyl-6-(3-(2-(methylamino)ethoxy)phenyl)-6,7,8,9-tetrahydro-5H-pyrimido[4,5-e][1,4]diazepin-5-one;

[171] 2-(ethylamino)-9-methyl-6-(3-(3-(methylamino)propyl)phenyl)-6,7,8,9-tetrahydro-5H-pyrimido[4,5-e][1,4]diazepin-5-one;

[172] 2-(ethylamino)-9-methyl-6-(3-(2-(methylamino)ethyl)phenyl)-6,7,8,9-tetrahydro-5H-pyrimido[4,5-e][1,4]diazepin-5-one;

[173] 2-(ethylamino)-9-methyl-6-(3-(2-methyl-1-(methylamino)propan-2-yl)phenyl)-6,7,8,9-tetrahydro-5H-pyrimido[4,5-e][1,4]diazepin-5-one;

[174] 2-(ethylamino)-9-methyl-6-(3-((methylamino)methyl)phenyl)-6,7,8,9-tetrahydro-5H-pyrimido[4,5-e][1,4]diazepin-5-one;

[175] 2-(ethylamino)-9-methyl-6-(3-(pyrrolidin-3-yloxy)phenyl)-6,7,8,9-tetrahydro-5H-pyrimido[4,5-e][1,4]diazepin-5-one;

[176] 2-(ethylamino)-9-methyl-6-(3-(((4-phenylpiperidin-4-yl)oxy)methyl)phenyl)-6,7,8,9-tetrahydro-5H-pyrimido[4,5-e][1,4]diazepin-5-one;

[177] 2-(ethylamino)-6-(3-hydroxyphenyl)-9-methyl-6,7,8,9-tetrahydro-5H-pyrimido[4,5-e][1,4]diazepin-5-one;

[178] 2-(ethylamino)-6-(4-hydroxyphenyl)-9-methyl-6,7,8,9-tetrahydro-5H-pyrimido[4,5-e][1,4]diazepin-5-one;

[179] 9-methyl-2-(methylthio)-6-(3-(((4-phenylpiperidin-4-yl)oxy)methyl)phenyl)-6,7,8,9-tetrahydro-5H-pyrimido[4,5-e][1,4]diazepin-5-one;

[180] 2-(ethylamino)-9-methyl-6-(3-(4-((methylamino)methyl)-1H-1,2,3-triazol-1-yl)phenyl)-6,7,8,9-tetrahydro-5H-pyrimido[4,5-e][1,4]diazepin-5-one;

[181] 6-(3-(4-(aminomethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[182] 6-(3-(4-((benzylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[183] 2-(ethylamino)-9-methyl-6-(3-(4-(2-(methylamino)ethyl)-1H-1,2,3-triazol-1-yl)phenyl)-6,7,8,9-tetrahydro-5H-pyrimido[4,5-e][1,4]diazepin-5-one;

[184] 2-(ethylamino)-9-methyl-6-((4-((methylamino)methyl)-1H-1,2,3-triazol-1-yl)methyl)phenyl)-6,7,8,9-tetrahydro-5H-pyrimido[4,5-e][1,4]diazepin-5-one;

[185] 2-(ethylamino)-9-methyl-6-(3-(4-((methylamino)methyl)-1H-pyrazol-1-yl)phenyl)-6,7,8,9-tetrahydro-5H-pyrimido[4,5-e][1,4]diazepin-5-one;

[186] 2-(ethylamino)-9-methyl-6-(3-(4-((methylamino)methyl)-1H-imidazol-1-yl)phenyl)-6,7,8,9-tetrahydro-5H-pyrimido[4,5-e][1,4]diazepin-5-one;

[187] 2-(ethylamino)-9-methyl-6-(3-(5-((methylamino)methyl)-1,3,4-oxadiazol-2-yl)phenyl)-6,7,8,9-tetrahydro-5H-pyrimido[4,5-e][1,4]diazepin-5-one;

[188] 2-(ethylamino)-9-methyl-6-(2-(3-(methylamino)-1-phenylpropoxy)phenyl)-6,7,8,9-tetrahydro-5H-pyrimido[4,5-e][1,4]diazepin-5-one;

[189] 2-(ethylamino)-9-methyl-6-(3-(((4-methyl-1-(methylamino)pentan-3-yl)oxy)methyl)phenyl)-6,7,8,9-tetrahydro-5H-pyrimido[4,5-e][1,4]diazepin-5-one;

[190] 9-methyl-6-(3-(((4-methyl-1-(methylamino)pentan-3-yl)oxy)methyl) phenyl)-2-(methylthio)-6,7,8,9-tetrahydro-5H-pyrimido[4,5-e][1,4]diazepin-5-one;

[191] 2-(ethylamino)-9-methyl-6-(3-(((4-(methylamino)butan-2-yl)oxy)methyl)phenyl)-6,7,8,9-tetrahydro-5H-pyrimido[4,5-e][1,4]diazepin-5-one;

[192] 9-methyl-6-(3-(((4-(methylamino)butan-2-yl)oxy)methyl)phenyl)-2-(methylthio)-6,7,8,9-tetrahydro-5H-pyrimido[4,5-e][1,4]diazepin-5-one;

[193] 2-(ethylamino)-9-methyl-6-(3-(3-(methylamino)-1-(pyridin-2-yl)propoxy)phenyl)-6,7,8,9-tetrahydro-5H-pyrimido[4,5-e][1,4]diazepin-5-one;

[194] 2-(ethylamino)-9-methyl-6-(3-(3-(methylamino)-1-(pyridin-3-yl)propoxy)phenyl)-6,7,8,9-tetrahydro-5H-pyrimido[4,5-e][1,4]diazepin-5-one;

[195] (R)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one;

[196] (R)-2-(dimethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[197] (R)-9-methyl-2-(methylamino)-6-(3-((3-(methylamino)-1-phenylpropoxy)methyl)phenyl)-6,7,8,9-tetrahydro-5H-pyrimido[4,5-e][1,4]diazepin-5-one;

[198] 8-(ethylamino)-1-methyl-4-(3-(3-(methylamino)-1-phenylpropoxy)phenyl)-1,2,3,4-tetrahydro-5H-pyrido[4,3-e][1,4]diazepin-5-one;

[199] 8-(ethylamino)-1-methyl-4-(3-((3-(methylamino)-1-phenylpropoxy)methyl)phenyl)-1,2,3,4-tetrahydro-5H-pyrido[4,3-e][1,4]diazepin-5-one;

[200] 2-(ethylamino)-9-methyl-6-(3-(2-(methylamino)-1-phenylethoxy)benzyl)-6,7,8,9-tetrahydro-5H-pyrimido[4,5-e][1,4]diazepin-5-one;

[201] 2-(ethylamino)-9-methyl-6-(4-(2-(methylamino)-1-phenylethoxy)benzyl)-6,7,8,9-tetrahydro-5H-pyrimido[4,5-e][1,4]diazepin-5-one;

[202] 2-(ethylamino)-9-methyl-6-(4-((methylamino)methyl)benzyl)-6,7,8,9-tetrahydro-5H-pyrimido[4,5-e][1,4]diazepin-5-one;

[203] (R)—N-ethyl-9-methyl-6-(3-((3-(methylamino)-1-phenylpropoxy)methyl)phenyl)-6,7,8,9-tetrahydro-5H-pyrimido[4,5-e][1,4]diazepin-2-amine;

[204] (R)-2-methoxy-9-methyl-6-(3-((3-(methylamino)-1-phenylpropoxy)methyl)phenyl)-6,7,8,9-tetrahydro-5H-pyrimido[4,5-e][1,4]diazepin-5-one;

[205] (R)-2-hydroxy-9-methyl-6-(3-((3-(methylamino)-1-phenylpropoxy)methyl)phenyl)-6,7,8,9-tetrahydro-5H-pyrimido[4,5-e][1,4]diazepin-5-one;

[206] (R)-2,9-dimethyl-6-(3-((3-(methylamino)-1-phenylpropoxy)methyl)phenyl)-6,7,8,9-tetrahydro-5H-pyrimido[4,5-e][1,4]diazepin-5-one;

[207] (R)-9-methyl-6-(3-((3-(methylamino)-1-phenylpropoxy)methyl)phenyl)-6,7,8,9-tetrahydro-5H-pyrimido[4,5-e][1,4]diazepin-5-one;

[208] 9-Methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[209] (R)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[210] (S)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[211] 2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[212] (R)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[213] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[214] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[215] (R)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[216] (S)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[217] 9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[218] (R)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[219] (S)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;

[220] 2-(ethylamino)-6-(3-(3-((2-fluoroethyl)amino)-1-(thiophen-2-yl)propoxy)phenyl)-9-methyl-6,7,8,9-tetrahydro-5H-pyrimido[4,5-e][1,4]diazepin-5-one;

[221] 2-methoxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[222] 2-hydroxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[223] 2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[224] 9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[225] 2-(Ethylamino)-9-methyl-6-(3-((2-(methylamino)-1-phenylethoxy) methyl)phenyl)-6,7,8,9-tetrahydro-5H-pyrimido[4,5-e][1,4]diazepin-5-one;

[226] 9-methyl-6-(3-((2-(methylamino)-1-phenylethoxy)methyl)phenyl)-2-(methylthio)-6,7,8,9-tetrahydro-5H-pyrimido[4,5-e][1,4]diazepin-5-one;

[227] 8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[228] 8-(ethylamino)-1-methyl-4-(3-((3-(methylamino)-1-(thiophen-2-yl)propoxy)methyl)phenyl)-1,2,3,4-tetrahydro-5H-pyrido[4,3-e][1,4]diazepin-5-one;

[229] 8-(dimethylamino)-1-methyl-4-(3-((3-(methylamino)-1-(thiophen-2-yl)propoxy)methyl)phenyl)-1,2,3,4-tetrahydro-5H-pyrido[4,3-e][1,4]diazepin-5-one;

[230] 2-(dimethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[231] 2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[232] 9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[233] tert-Butyl 4-(3-(2-(ethylamino)-9-methyl-5-oxo-5,7,8,9-tetrahydro-6H-pyrimido[4,5-e][1,4]diazepin-6-yl)phenyl)-3,6-dihydropyridine-1(2H)-carboxylate;

[234] tert-Butyl 4-(3-(2-(ethylamino)-9-methyl-5-oxo-5,7,8,9-tetrahydro-6H-pyrimido[4,5-e][1,4]diazepin-6-yl)phenyl)piperidine-1-carboxylate;

[235] 2-(Ethylamino)-9-methyl-6-(3-(piperidin-4-yl)phenyl)-6,7,8,9-tetrahydro-5H-pyrimido[4,5-e][1,4]diazepin-5-one;

[236] (R)-6-(3-((3-(Dimethylamino)-1-phenylpropoxy)methyl)phenyl)-2-(ethylamino)-9-methyl-6,7,8,9-tetrahydro-5H-pyrimido[4,5-e][1,4]diazepin-5-one;

[237] (S)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one;

[238] 6-(3-(3-(dimethylamino)-1-phenylpropoxy)phenyl)-2-(ethylamino)-9-methyl-6,7,8,9-tetrahydro-5H-pyrimido[4,5-e][1,4]diazepin-5-one;

[239] 6-(3-(2-(dimethylamino)-1-phenylethoxy)phenyl)-2-(ethylamino)-9-methyl-6,7,8,9-tetrahydro-5H-pyrimido[4,5-e][1,4]diazepin-5-one;

[240] 6-(3-(3-(benzyl(methyl)amino)propyl)phenyl)-2-(ethylamino)-9-methyl-6,7,8,9-tetrahydro-5H-pyrimido[4,5-e][1,4]diazepin-5-one;

[241] 6-(3-(3-(dimethylamino)propyl)phenyl)-2-(ethylamino)-9-methyl-6,7,8,9-tetrahydro-5H-pyrimido[4,5-e][1,4]diazepin-5-one;

[242] 6-(3-(4-((dimethylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[243] 6-(3-(4-((benzyl(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[244] 2-(ethylamino)-9-methyl-6-(3-(4-((methyl(phenethyl)amino)methyl)-1H-1,2,3-triazol-1-yl)phenyl)-6,7,8,9-tetrahydro-5H-pyrimido[4,5-e][1,4]diazepin-5-one;

[245] 6-(3-(4-((bis(cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[246] 6-(3-(4-(((cyclopropylmethyl)(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[247] 6-(3-(4-(2-(benzyl(methyl)amino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[248] 6-(3-(4-(2-(dimethylamino)ethyl)-1H-1,2,3-triazol-1-yl)phenyl)-2-(ethylamino)-9-methyl-6,7,8,9-tetrahydro-5H-pyrimido[4,5-e][1,4]diazepin-5-one;

[249] 2-(ethylamino)-9-methyl-6-(3-(4-(2-(methyl(phenethyl)amino)ethyl)-1H-1,2,3-triazol-1-yl)phenyl)-6,7,8,9-tetrahydro-5H-pyrimido[4,5-e][1,4]diazepin-5-one;

[250] 6-(3-((4-((benzyl (methyl)amino)methyl)-1H-1,2,3-triazol-1-yl)methyl)phenyl)-2-(ethylamino)-9-methyl-6,7,8,9-tetrahydro-5H-pyrimido[4,5-e][1,4]diazepin-5-one;

[251] 6-(3-(4-((benzyl(methyl)amino)methyl)-1H-pyrazol-1-yl)phenyl)-2-(ethylamino)-9-methyl-6,7,8,9-tetrahydro-5H-pyrimido[4,5-e][1,4]diazepin-5-one;

[252] 2-(ethylamino)-9-methyl-6-(3-(4-((methyl(phenethyl)amino)methyl)-1H-pyrazol-1-yl)phenyl)-6,7,8,9-tetrahydro-5H-pyrimido[4,5-e][1,4]diazepin-5-one;

[253] 6-(3-(4-((benzyl(methyl)amino)methyl)-1H-imidazol-1-yl)phenyl)-2-(ethylamino)-9-methyl-6,7,8,9-tetrahydro-5H-pyrimido[4,5-e][1,4]diazepin-5-one;

[254] 2-(ethylamino)-9-methyl-6-(3-(4-((methyl(phenethyl)amino)methyl)-1H-imidazol-1-yl)phenyl)-6,7,8,9-tetrahydro-5H-pyrimido[4,5-e][1,4]diazepin-5-one;

[255] 6-(3-(5-((benzyl(methyl)amino)methyl)-1,3,4-oxadiazol-2-yl)phenyl)-2-(ethylamino)-9-methyl-6,7,8,9-tetrahydro-5H-pyrimido[4,5-e][1,4]diazepin-5-one;

[256] 6-(3-(3-(benzyl(methyl)amino)propoxy)phenyl)-2-(ethylamino)-9-methyl-6,7,8,9-tetrahydro-5H-pyrimido[4,5-e][1,4]diazepin-5-one;

[257] 6-(3-(3-(dimethylamino)propoxy)phenyl)-2-(ethylamino)-9-methyl-6,7,8,9-tetrahydro-5H-pyrimido[4,5-e][1,4]diazepin-5-one;

[258] 2-(ethylamino)-9-methyl-6-(3-(3-(methyl(phenethyl)amino)propoxy)phenyl)-6,7,8,9-tetrahydro-5H-pyrimido[4,5-e][1,4]diazepin-5-one;

[259] 6-(3-(1-benzylpiperidin-4-yl)phenyl)-2-(ethylamino)-9-methyl-6,7,8,9-tetrahydro-5H-pyrimido[4,5-e][1,4]diazepin-5-one;

[260] 2-(ethylamino)-9-methyl-6-(3-(1-methylpiperidin-4-yl)phenyl)-6,7,8,9-tetrahydro-5H-pyrimido[4,5-e][1,4]diazepin-5-one;

[261] 2-(ethylamino)-9-methyl-6-(3-(1-phenethylpiperidin-4-yl)phenyl)-6,7,8,9-tetrahydro-5H-pyrimido[4,5-e][1,4]diazepin-5-one;

[262] 6-(3-((1-(benzyl(methyl)amino)propan-2-yl)oxy)phenyl)-2-(ethylamino)-9-methyl-6,7,8,9-tetrahydro-5H-pyrimido[4,5-e][1,4]diazepin-5-one;

[263] 2-(ethylamino)-9-methyl-6-(3-((1-(methyl(phenethyl)amino)propan-2-yl)oxy)phenyl)-6,7,8,9-tetrahydro-5H-pyrimido[4,5-e][1,4]diazepin-5-one;

[264] 6-(3-(2-(benzyl(methyl)amino)ethoxy)phenyl)-2-(ethylamino)-9-methyl-6,7,8,9-tetrahydro-5H-pyrimido[4,5-e][1,4]diazepin-5-one;

[265] 2-(ethylamino)-9-methyl-6-(3-(2-(methyl(phenethyl)amino)ethoxy)phenyl)-6,7,8,9-tetrahydro-5H-pyrimido[4,5-e][1,4]diazepin-5-one;

[266] 6-(3-((1-benzylpyrrolidin-3-yl)oxy)phenyl)-2-(ethylamino)-9-methyl-6,7,8,9-tetrahydro-5H-pyrimido[4,5-e][1,4]diazepin-5-one;

[267] 6-(3-((1-(benzyl(methyl)amino)-3-methylbutan-2-yl)oxy)phenyl)-2-(ethylamino)-9-methyl-6,7,8,9-tetrahydro-5H-pyrimido[4,5-e][1,4]diazepin-5-one;

[268] 2-(ethylamino)-9-methyl-6-(3-((3-methyl-1-(methyl(phenethyl)amino)butan-2-yl)oxy)phenyl)-6,7,8,9-tetrahydro-5H-pyrimido[4,5-e][1,4]diazepin-5-one;

[269] 6-(3-(2-(benzyl(methyl)amino)ethyl)phenyl)-2-(ethylamino)-9-methyl-6,7,8,9-tetrahydro-5H-pyrimido[4,5-e][1,4]diazepin-5-one;

[270] 2-(ethylamino)-9-methyl-6-(3-(2-(methyl(phenethyl)amino)ethyl)phenyl)-6,7,8,9-tetrahydro-5H-pyrimido[4,5-e][1,4]diazepin-5-one;

[271] 9-methyl-6-(3-(((1-methyl-4-phenylpiperidin-4-yl)oxy)methyl)phenyl)-2-(methylthio)-6,7,8,9-tetrahydro-5H-pyrimido[4,5-e][1,4]diazepin-5-one;

[272] 2-(ethylamino)-9-methyl-6-(3-(((1-methyl-4-phenylpiperidin-4-yl)oxy)methyl)phenyl)-6,7,8,9-tetrahydro-5H-pyrimido[4,5-e][1,4]diazepin-5-one;

[273] 2-(ethylamino)-6-(3-(4-(((2-(2-hydroxyethoxy)ethyl)(methyl)amino)methyl)-1H-1,2,3-triazol-1-yl)phenyl)-9-methyl-6,7,8,9-tetrahydro-5H-pyrimido[4,5-e][1,4]diazepin-5-one;

[274] 3-(2-(Ethylamino)-9-methyl-5-oxo-5,7,8,9-tetrahydro-6H-pyrimido[4,5-e][1,4] diazepin-6-yl)phenethyl 4-methylbenzenesulfonate;

[275] 2-(Ethylamino)-6-(3-(2-(4-(3-hydroxyphenyl)piperidin-1-yl)ethyl)phenyl)-9-methyl-6,7,8,9-tetrahydro-5H-pyrimido[4,5-e][1,4]diazepin-5-one;

[276] (R)-9-(3-(2-(ethylamino)-9-methyl-5-oxo-5,7,8,9-tetrahydro-6H-pyrimido[4,5-e][1,4]diazepin-6-yl)phenethyl)-4-isopropyl-2-methyl-1-oxa-4,9-diazaspiro[5.5]undecan-3-one;

[277] 1-(3-(2-(Ethylamino)-9-methyl-5-oxo-5,7,8,9-tetrahydro-6H-pyrimido[4,5-e][1,4]diazepin-6-yl)phenyl)-1H-1,2,3-triazole-4-carbaldehyde;

[278] 2-(Ethylamino)-9-methyl-6-(3-(4-((4-phenylpiperidin-1-yl)methyl)-1H-1,2,3-triazol-1-yl)phenyl)-6,7,8,9-tetrahydro-5H-pyrimido[4,5-e][1,4]diazepin-5-one;

[279] 2-(ethylamino)-6-(3-(4-((4-(3-hydroxyphenyl)piperidin-1-yl)methyl)-1H-1,2,3-triazol-1-yl)phenyl)-9-methyl-6,7,8,9-tetrahydro-5H-pyrimido[4,5-e][1,4]diazepin-5-one;

[280] 2-(ethylamino)-9-methyl-6-(3-(4-((4-phenylpiperazin-1-yl)methyl)-1H-1,2,3-triazol-1-yl)phenyl)-6,7,8,9-tetrahydro-5H-pyrimido[4,5-e][1,4]diazepin-5-one;

[281] 2-(ethylamino)-9-methyl-6-(3-(4-(piperidin-1-ylmethyl)-1H-1,2,3-triazol-1-yl)phenyl)-6,7,8,9-tetrahydro-5H-pyrimido[4,5-e][1,4]diazepin-5-one;

[282] 6-(3-(4-((3,4-dihydroisoquinolin-2(1H)-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[283] 6-(3-(4-((3,4-dihydro-2H-spiro[isoquinoline-1,4'-piperidin]-1'-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[284] (R)-9-((1-(3-(2-(ethylamino)-9-methyl-5-oxo-5,7,8,9-tetrahydro-6H-pyrimido[4,5-e][1,4]diazepin-6-yl)phenyl)-1H-1,2,3-triazol-4-yl)methyl)-4-isopropyl-2-methyl-1-oxa-4,9-diazaspiro[5.5]undecan-3-one;

[285] 6-(3-(4-(((cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[286] 2-(ethylamino)-6-(3-(4-((ethylamino)methyl)-1H-1,2,3-triazol-1-yl)phenyl)-9-methyl-6,7,8,9-tetrahydro-5H-pyrimido[4,5-e][1,4]diazepin-5-one;

[287] 2-(ethylamino)-6-(3-(4-(((4-fluorobenzyl)(methyl)amino)methyl)-1H-1,2,3-triazol-1-yl)phenyl)-9-methyl-6,7,8,9-tetrahydro-5H-pyrimido[4,5-e][1,4]diazepin-5-one;

[288] 2-(ethylamino)-9-methyl-6-(3-(4-((methyl(pyridin-2-ylmethyl)amino)methyl)-1H-1,2,3-triazol-1-yl)phenyl)-6,7,8,9-tetrahydro-5H-pyrimido[4,5-e][1,4]diazepin-5-one;

[289] 2-(ethylamino)-9-methyl-6-(3-(4-((methyl(pyridin-3-ylmethyl)amino)methyl)-1H-1,2,3-triazol-1-yl)phenyl)-6,7,8,9-tetrahydro-5H-pyrimido[4,5-e][1,4]diazepin-5-one;

[290] 2-(ethylamino)-6-(3-(4-(((2-(2-hydroxyethoxy)ethyl)amino)methyl)-1H-1,2,3-triazol-1-yl)phenyl)-9-methyl-6,7,8,9-tetrahydro-5H-pyrimido[4,5-e][1,4]diazepin-5-one;

[291] 6-(3-(4-((4-(dimethylamino)-4-phenylpiperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[292] 6-(3-((4-(dimethylamino)-4-phenylpiperidin-1-yl)methyl)phenyl)-2-(ethylamino)-9-methyl-6,7,8,9-tetrahydro-5H-pyrimido[4,5-e][1,4]diazepin-5-one;

[293] 6-(3-(4-((4-(dimethylamino)-4-(3-hydroxyphenyl)piperidin-1-yl)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[294] 6-(3-(4-((4-(dimethylamino)-4-phenylpiperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one;

[295] 6-(3-(4-((4-(dimethylamino)-4-(3-hydroxyphenyl)piperidin-1-yl)methyl)-1H-pyrazol-1-yl)phenyl)-2-(ethylamino)-9-methyl-6,7,8,9-tetrahydro-5H-pyrimido[4,5-e][1,4]diazepin-5-one;

[296] 6-(3-(4-((4-(dimethylamino)-4-(3-hydroxyphenyl)piperidin-1-yl)methyl)-1H-imidazol-1-yl)phenyl)-2-(ethylamino)-9-methyl-6,7,8,9-tetrahydro-5H-pyrimido[4,5-e][1,4]diazepin-5-one;

[297] 2-(trimethylsilyl)ethyl (3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[298] 2-(trimethylsilyl)ethyl (S)-(3-(3-(8-chloro-1-methyl-5-oxo-1,2,3,5-tetrahydro-4H-pyrido[4,3-e][1,4]diazepin-4-yl)phenoxy)-3-(thiophen-2-yl)propyl)(methyl)carbamate;

[299] 2-(trimethylsilyl)ethyl (S)-(3-(4-((8-chloro-1-methyl-5-oxo-1,2,3,5-tetrahydro-4H-pyrido[4,3-e][1,4]diazepin-4-yl)methyl)phenoxy)-3-(thiophen-2-yl)propyl)(methyl)carbamate;

[300] tert-butyl (3-((3-(8-chloro-1-methyl-5-oxo-1,2,3,5-tetrahydro-4H-pyrido[4,3-e][1,4]diazepin-4-yl)benzyl)oxy)-3-phenylpropyl)(methyl)carbamate;

[301] 2-(Trimethylsilyl)ethyl (S)-(3-(4-((1,8-dimethyl-5-oxo-1,2,3,5-tetrahydro-4H-pyrido[4,3-e][1,4]diazepin-4-yl)methyl)phenoxy)-3-(thiophen-2-yl)propyl)(methyl)carbamate;

[302] 2-(trimethylsilyl)ethyl (3-(3-(1,8-dimethyl-5-oxo-1,2,3,5-tetrahydro-4H-pyrido[4,3-e][1,4]diazepin-4-yl)phenoxy)-3-(thiophen-2-yl)propyl)(methyl)carbamate;

[303] tert-butyl (3-((3-(1,8-dimethyl-5-oxo-1,2,3,5-tetrahydro-4H-pyrido[4,3-e][1,4]diazepin-4-yl)benzyl)oxy)-3-phenylpropyl)(methyl)carbamate;

[304] (S)-8-Amino-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[305] (S)-8-amino-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[306] 1,8-dimethyl-4-(3-((3-(methylamino)-1-phenylpropoxy)methyl)phenyl)-1,2,3,4-tetrahydro-5H-pyrido[4,3-e][1,4]diazepin-5-one;

[307] 1,8-dimethyl-4-(3-(3-(methylamino)-1-(thiophen-2-yl)propoxy)phenyl)-1,2,3,4-tetrahydro-5H-pyrido[4,3-e][1,4]diazepin-5-one;

[308] (S)-1,8-dimethyl-4-(4-(3-(methylamino)-1-(thiophen-2-yl)propoxy)benzyl)-1,2,3,4-tetrahydro-5H-pyrido[4,3-e][1,4]diazepin-5-one;

[309] methyl 3-(2-(ethylamino)-9-methyl-5-oxo-5,7,8,9-tetrahydro-6H-pyrimido[4,5-e][1,4]diazepin-6-yl)benzoate;

[310] 2-(ethylamino)-6-(3-(2-hydroxyethyl)phenyl)-9-methyl-6,7,8,9-tetrahydro-5H-pyrimido[4,5-e][1,4]diazepin-5-one;

[311] 6-(3-bromophenyl)-2-(ethylamino)-9-methyl-6,7,8,9-tetrahydro-5H-pyrimido[4,5-e][1,4]diazepin-5-one;

[312] 6-(3-(4-(Dimethylamino)-4-phenylpiperidin-1-yl)phenyl)-2-(ethylamino)-9-methyl-6,7,8,9-tetrahydro-5H-pyrimido[4,5-e][1,4]diazepin-5-one;

[313] 3-(2-(Ethylamino)-9-methyl-5-oxo-5,7,8,9-tetrahydro-6H-pyrimido[4,5-e][1,4]diazepin-6-yl)benzoic acid;

[314] 6-(3-(4-(Dimethylamino)-4-phenylpiperidine-1-carbonyl)-phenyl)-2-(ethylamino)-9-methyl-6,7,8,9-tetrahydro-5H-pyrimido[4,5-e][1,4]-diazepin-5-one;

[315] 9-methyl-6-(4-((3-(methylamino)-1-phenylpropoxy)methyl)phenyl)-2-(methylthio)-6,7,8,9-tetrahydro-5H-pyrimido[4,5-e][1,4]diazepin-5-one;

[316] 9-methyl-6-(4-(3-(methylamino)-1-phenylpropoxy)phenyl)-2-(methylthio)-6,7,8,9-tetrahydro-5H-pyrimido[4,5-e][1,4]diazepin-5-one;

[317] 1-methyl-4-(3-((3-(methylamino)-1-phenylpropoxy)methyl)phenyl)-1,2,3,4-tetrahydro-5H-pyrido[4,3-e][1,4]diazepin-5-one;
[318] 9-methyl-6-(2-((3-(methylamino)-1-phenylpropoxy)methyl)phenyl)-2-(methylthio)-6,7,8,9-tetrahydro-5H-pyrimido[4,5-e][1,4]diazepin-5-one;
[319] 9-methyl-6-(2-(2-(methylamino)-1-phenylethoxy)phenyl)-2-(methylthio)-6,7,8,9-tetrahydro-5H-pyrimido[4,5-e][1,4]diazepin-5-one;
[320] 9-methyl-6-(2-((2-(methylamino)-1-phenylethoxy)methyl)phenyl)-2-(methylthio)-6,7,8,9-tetrahydro-5H-pyrimido[4,5-e][1,4]diazepin-5-one;
[321] 9-methyl-6-(4-((2-(methylamino)-1-phenylethoxy)methyl)phenyl)-2-(methylthio)-6,7,8,9-tetrahydro-5H-pyrimido[4,5-e][1,4]diazepin-5-one;
[322] 9-methyl-6-(3-((3-(methylamino)-1-phenylpropoxy)methyl)phenyl)-2-(trifluoromethyl)-6,7,8,9-tetrahydro-5H-pyrimido[4,5-e][1,4]diazepin-5-one;
[323] 1-methyl-4-(3-(3-(methylamino)-1-(thiophen-2-yl)propoxy)phenyl)-1,2,3,4-tetrahydro-5H-pyrido[4,3-e][1,4]diazepin-5-one;
[324] (R)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[325] (S)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[326] (S)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[327] (R)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[328] 9-methyl-6-(4-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;
[329] 9-methyl-6-(3-(3-(methylamino)-1-(thiophen-2-yl)propoxy)phenyl)-2-(trifluoromethyl)-6,7,8,9-tetrahydro-5H-pyrimido[4,5-e][1,4]diazepin-5-one;
[330] 9-methyl-6-(3-((3-(methylamino)-1-(thiophen-2-yl)propoxy)methyl)phenyl)-2-(trifluoromethyl)-6,7,8,9-tetrahydro-5H-pyrimido[4,5-e][1,4]diazepin-5-one;
[331] (S)-8-methoxy-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[332] (S)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one;
[333] 2-(ethylamino)-9-methyl-6-(4-(3-(methylamino)-1-phenylpropoxy)phenyl)-6,7,8,9-tetrahydro-5H-pyrimido[4,5-e][1,4]diazepin-5-one;
[334] 2-(ethylamino)-9-methyl-6-(4-((3-(methylamino)-1-phenylpropoxy)methyl)phenyl)-6,7,8,9-tetrahydro-5H-pyrimido[4,5-e][1,4]diazepin-5-one;
[335] 2-(benzylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;
[336] 9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;
[337] 2-(ethylamino)-9-methyl-6-(2-((3-(methylamino)-1-phenylpropoxy)methyl)phenyl)-6,7,8,9-tetrahydro-5H-pyrimido[4,5-e][1,4]diazepin-5-one;
[338] 2-(ethylamino)-9-methyl-6-(2-(2-(methylamino)-1-phenylethoxy)phenyl)-6,7,8,9-tetrahydro-5H-pyrimido[4,5-e][1,4]diazepin-5-one;
[339] 2-(ethylamino)-9-methyl-6-(2-((2-(methylamino)-1-phenylethoxy)methyl)phenyl)-6,7,8,9-tetrahydro-5H-pyrimido[4,5-e][1,4]diazepin-5-one;
[340] 2-(ethylamino)-9-methyl-6-(4-((2-(methylamino)-1-phenylethoxy)methyl)phenyl)-6,7,8,9-tetrahydro-5H-pyrimido[4,5-e][1,4]diazepin-5-one;
[341] (R)-9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;
[342] (R)-9-methyl-2-(methyl(pyridin-3-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;
[343] (R)-9-methyl-6-(3-((3-(methylamino)-1-phenylpropoxy)methyl)phenyl)-2-((pyridin-2-ylmethyl)amino)-6,7,8,9-tetrahydro-5H-pyrimido[4,5-e][1,4]diazepin-5-one;
[344] (R)-2-(((5-fluoropyridin-2-yl)methyl)(methyl)amino)-9-methyl-6-(3-((3-(methylamino)-1-phenylpropoxy)methyl)phenyl)-6,7,8,9-tetrahydro-5H-pyrimido[4,5-e][1,4]diazepin-5-one;
[345] 2-(ethylamino)-6-(3-((3-((2-fluoroethyl)amino)-1-(thiophen-2-yl)propoxy)methyl)phenyl)-9-methyl-6,7,8,9-tetrahydro-5H-pyrimido[4,5-e][1,4]diazepin-5-one;
[346] (S)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[347] (R)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[348] 2-(ethylamino)-9-methyl-6-(4-((3-(methylamino)-1-(thiophen-2-yl)propoxy)methyl)phenyl)-6,7,8,9-tetrahydro-5H-pyrimido[4,5-e][1,4]diazepin-5-one;
[349] 2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;
[350] (S)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one
[351] (R)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;
[352] (S)-2-amino-9-methyl-6-(3-(3-(methylamino)-1-(thiophen-2-yl)propoxy)phenyl)-6,7,8,9-tetrahydro-5H-pyrimido[4,5-e][1,4]diazepin-5-one;
[353] 2,9-dimethyl-6-(4-((3-(methylamino)-1-phenylpropoxy)methyl)phenyl)-6,7,8,9-tetrahydro-5H-pyrimido[4,5-e][1,4]diazepin-5-one;
[354] 2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;
[355] 2,9-dimethyl-6-(4-((2-(methylamino)-1-phenylethoxy)methyl)phenyl)-6,7,8,9-tetrahydro-5H-pyrimido[4,5-e][1,4]diazepin-5-one;
[356] (R)-2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;
[357] (R)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;
[358] (S)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[359] (S)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[360] (R)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[361] 9-methyl-6-(4-(3-(methylamino)-1-phenylpropoxy)phenyl)-6,7,8,9-tetrahydro-5H-pyrimido[4,5-e][1,4]diazepin-5-one;

[362] 9-methyl-6-(2-(2-(methylamino)-1-phenylethoxy)phenyl)-6,7,8,9-tetrahydro-5H-pyrimido[4,5-e][1,4]diazepin-5-one;

[363] (R)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[364] (S)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[365] 9-methyl-6-(2-((3-(methylamino)-1-phenylpropoxy)methyl)benzyl)-2-(methylthio)-6,7,8,9-tetrahydro-5H-pyrimido[4,5-e][1,4]diazepin-5-one;

[366] 9-methyl-6-(3-(3-(methylamino)-1-phenylpropoxy)benzyl)-2-(methylthio)-6,7,8,9-tetrahydro-5H-pyrimido[4,5-e][1,4]diazepin-5-one;

[367] 9-methyl-6-(3-((3-(methylamino)-1-phenylpropoxy)methyl)benzyl)-2-(methylthio)-6,7,8,9-tetrahydro-5H-pyrimido[4,5-e][1,4]diazepin-5-one;

[368] 9-methyl-6-(4-((3-(methylamino)-1-phenylpropoxy)methyl)benzyl)-2-(methylthio)-6,7,8,9-tetrahydro-5H-pyrimido[4,5-e][1,4]diazepin-5-one;

[369] 9-methyl-6-(4-(3-(methylamino)-1-phenylpropoxy)benzyl)-2-(methylthio)-6,7,8,9-tetrahydro-5H-pyrimido[4,5-e][1,4]diazepin-5-one;

[370] 9-methyl-6-(2-(3-(methylamino)-1-phenylpropoxy)benzyl)-2-(methylthio)-6,7,8,9-tetrahydro-5H-pyrimido[4,5-e][1,4]diazepin-5-one;

[371] 9-methyl-6-(2-(2-(methylamino)-1-phenylethoxy)benzyl)-2-(methylthio)-6,7,8,9-tetrahydro-5H-pyrimido[4,5-e][1,4]diazepin-5-one;

[372] 9-methyl-6-(3-((2-(methylamino)-1-phenylethoxy)methyl)benzyl)-2-(methylthio)-6,7,8,9-tetrahydro-5H-pyrimido[4,5-e][1,4]diazepin-5-one;

[373] 9-methyl-6-(2-((2-(methylamino)-1-phenylethoxy)methyl)benzyl)-2-(methylthio)-6,7,8,9-tetrahydro-5H-pyrimido[4,5-e][1,4]diazepin-5-one;

[374] 9-methyl-6-(4-((2-(methylamino)-1-phenylethoxy)methyl)benzyl)-2-(methylthio)-6,7,8,9-tetrahydro-5H-pyrimido[4,5-e][1,4]diazepin-5-one;

[375] (S)-2-methoxy-9-methyl-6-(4-(3-(methylamino)-1-phenylpropoxy)benzyl)-6,7,8,9-tetrahydro-5H-pyrimido[4,5-e][1,4]diazepin-5-one;

[376] 6-(4-(1-(2-fluorophenyl)-3-(methylamino)propoxy)benzyl)-2-methoxy-9-methyl-6,7,8,9-tetrahydro-5H-pyrimido[4,5-e][1,4]diazepin-5-one;

[377] (S)-1-methyl-4-(4-(3-(methylamino)-1-phenylpropoxy)benzyl)-1,2,3,4-tetrahydro-5H-pyrido[4,3-e][1,4]diazepin-5-one;

[378] 9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[379] (S)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[380] (R)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[381] 1-methyl-4-(4-(3-(methylamino)-1-(thiophen-2-yl)propoxy)benzyl)-1,2,3,4-tetrahydro-5H-pyrido[4,3-e][1,4]diazepin-5-one;

[382] (S)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[383] (S)-8-(ethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[384] (S)-8-(dimethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[385] (S)-8-methoxy-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[386] (S)-9-methyl-6-(4-(3-(methylamino)-1-(thiophen-2-yl)propoxy)benzyl)-2-(trifluoromethyl)-6,7,8,9-tetrahydro-5H-pyrimido[4,5-e][1,4]diazepin-5-one;

[387] 2-methoxy-9-methyl-6-(4-(3-(methylamino)-1-(thiophen-3-yl)propoxy)benzyl)-6,7,8,9-tetrahydro-5H-pyrimido[4,5-e][1,4]diazepin-5-one;

[388] 2-methoxy-9-methyl-6-(4-(3-(methylamino)-1-(3-methylthiophen-2-yl)propoxy)benzyl)-6,7,8,9-tetrahydro-5H-pyrimido[4,5-e][1,4]diazepin-5-one;

[389] (S)-1-ethyl-8-methoxy-4-(4-(3-(methylamino)-1-(thiophen-2-yl)propoxy)benzyl)-1,2,3,4-tetrahydro-5H-pyrido[4,3-e][1,4]diazepin-5-one;

[390] 2-methoxy-9-methyl-6-(4-(3-(methylamino)-1-(thiazol-2-yl)propoxy)benzyl)-6,7,8,9-tetrahydro-5H-pyrimido[4,5-e][1,4]diazepin-5-one;

[391] (S)-1-ethyl-4-(4-(3-(methylamino)-1-(thiophen-2-yl)propoxy)benzyl)-1,2,3,4-tetrahydro-5H-pyrido[4,3-e][1,4]diazepin-5-one;

[392] 2-methoxy-9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one;

[393] (S)-2-methoxy-9-methyl-6-(3-methyl-4-(3-(methylamino)-1-(thiophen-2-yl)propoxy)benzyl)-6,7,8,9-tetrahydro-5H-pyrimido[4,5-e][1,4]diazepin-5-one;

[394] (S)-6-(3-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[395] (S)-9-ethyl-2-methoxy-6-(4-(3-(methylamino)-1-(thiophen-2-yl)propoxy)benzyl)-6,7,8,9-tetrahydro-5H-pyrimido[4,5-e][1,4]diazepin-5-one;

[396] 2-methoxy-9-methyl-6-(4-(3-(methylamino)-1-(4-methylthiophen-2-yl)propoxy)benzyl)-6,7,8,9-tetrahydro-5H-pyrimido[4,5-e][1,4]diazepin-5-one;

[397] (S)-2-methoxy-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one;

[398] (S)-9-ethyl-6-(4-(3-(methylamino)-1-(thiophen-2-yl)propoxy)benzyl)-6,7,8,9-tetrahydro-5H-pyrimido[4,5-e][1,4]diazepin-5-one;

[399] (S)-9-fluoro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[400] (S)-9-chloro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[401] (S)-6-(2-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[402] (S)-2-methoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[403] (S)-6-(4-fluoro-2-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[404] 2-(ethylamino)-9-methyl-6-(2-((3-(methylamino)-1-phenylpropoxy)methyl)benzyl)-6,7,8,9-tetrahydro-5H-pyrimido[4,5-e][1,4]diazepin-5-one;

[405] 2-(ethylamino)-9-methyl-6-(4-((3-(methylamino)-1-phenylpropoxy)methyl)benzyl)-6,7,8,9-tetrahydro-5H-pyrimido[4,5-e][1,4]diazepin-5-one;

[406] 2-(ethylamino)-9-methyl-6-(3-((3-(methylamino)-1-phenylpropoxy)methyl)benzyl)-6,7,8,9-tetrahydro-5H-pyrimido[4,5-e][1,4]diazepin-5-one;

[407] 2-(ethylamino)-9-methyl-6-(3-(3-(methylamino)-1-phenylpropoxy)benzyl)-6,7,8,9-tetrahydro-5H-pyrimido[4,5-e][1,4]diazepin-5-one;

[408] 2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[409] 2-(ethylamino)-9-methyl-6-(2-(3-(methylamino)-1-phenylpropoxy)benzyl)-6,7,8,9-tetrahydro-5H-pyrimido[4,5-e][1,4]diazepin-5-one;

[410] 2-(ethylamino)-9-methyl-6-(2-(2-(methylamino)-1-phenylethoxy)benzyl)-6,7,8,9-tetrahydro-5H-pyrimido[4,5-e][1,4]diazepin-5-one;

[411] 2-(ethylamino)-9-methyl-6-(3-((2-(methylamino)-1-phenylethoxy)methyl)benzyl)-6,7,8,9-tetrahydro-5H-pyrimido[4,5-e][1,4]diazepin-5-one;

[412] 2-(ethylamino)-9-methyl-6-(2-((2-(methylamino)-1-phenylethoxy)methyl)benzyl)-6,7,8,9-tetrahydro-5H-pyrimido[4,5-e][1,4]diazepin-5-one;

[413] 2-(ethylamino)-9-methyl-6-(4-((2-(methylamino)-1-phenylethoxy)methyl)benzyl)-6,7,8,9-tetrahydro-5H-pyrimido[4,5-e][1,4]diazepin-5-one;

[414] (S)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[415] (R)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[416] 2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[417] (S)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[418] (R)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[419] (S)-2-(dimethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[420] (S)-2-amino-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[421] 2,9-dimethyl-6-(2-((3-(methylamino)-1-phenylpropoxy)methyl)benzyl)-6,7,8,9-tetrahydro-5H-pyrimido[4,5-e][1,4]diazepin-5-one;

[422] 2,9-dimethyl-6-(4-((3-(methylamino)-1-phenylpropoxy)methyl)benzyl)-6,7,8,9-tetrahydro-5H-pyrimido[4,5-e][1,4]diazepin-5-one;

[423] 2,9-dimethyl-6-(3-((3-(methylamino)-1-phenylpropoxy)methyl)benzyl)-6,7,8,9-tetrahydro-5H-pyrimido[4,5-e][1,4]diazepin-5-one;

[424] 2,9-dimethyl-6-(2-((2-(methylamino)-1-phenylethoxy)methyl)benzyl)-6,7,8,9-tetrahydro-5H-pyrimido[4,5-e][1,4]diazepin-5-one;

[425] 2,9-dimethyl-6-(4-(3-(methylamino)-1-phenylpropoxy)benzyl)-6,7,8,9-tetrahydro-5H-pyrimido[4,5-e][1,4]diazepin-5-one;

[426] 2-ethyl-9-methyl-6-(4-(3-(methylamino)-1-phenylpropoxy)benzyl)-6,7,8,9-tetrahydro-5H-pyrimido[4,5-e][1,4]diazepin-5-one;

[427] (R)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[428] (S)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[429] 9-methyl-6-(3-(3-(methylamino)-1-phenylpropoxy)benzyl)-6,7,8,9-tetrahydro-5H-pyrimido[4,5-e][1,4]diazepin-5-one;

[430] 9-methyl-6-(4-(3-(methylamino)-1-phenylpropoxy)benzyl)-6,7,8,9-tetrahydro-5H-pyrimido[4,5-e][1,4]diazepin-5-one;

[431] 9-methyl-6-(2-(3-(methylamino)-1-phenylpropoxy)benzyl)-6,7,8,9-tetrahydro-5H-pyrimido[4,5-e][1,4]diazepin-5-one;

[432] 9-methyl-6-(2-(2-(methylamino)-1-phenylethoxy)benzyl)-6,7,8,9-tetrahydro-5H-pyrimido[4,5-e][1,4]diazepin-5-one;

[433] (S)-9-methyl-6-(4-(3-(methylamino)-1-phenylpropoxy)benzyl)-6,7,8,9-tetrahydro-5H-pyrimido[4,5-e][1,4]diazepin-5-one;

[434] (R)-9-methyl-6-(4-(3-(methylamino)-1-phenylpropoxy)benzyl)-6,7,8,9-tetrahydro-5H-pyrimido[4,5-e][1,4]diazepin-5-one;

[435] 9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[436] (S)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[437] (R)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[438] 6-(3-(2-(4-(dimethylamino)-4-phenylpiperidin-1-yl)ethyl)phenyl)-2-(ethylamino)-9-methyl-6,7,8,9-tetrahydro-5H-pyrimido[4,5-e][1,4]diazepin-5-one;

[439] 2-(ethylamino)-9-methyl-6-(3-(2-(piperidin-1-yl)ethoxy)phenyl)-6,7,8,9-tetrahydro-5H-pyrimido[4,5-e][1,4]diazepin-5-one;

[440] 2-(ethylamino)-9-methyl-6-(3-(2-morpholinoethoxy)phenyl)-6,7,8,9-tetrahydro-5H-pyrimido[4,5-e][1,4]diazepin-5-one;

[441] 6-(3-(5-((4-(dimethylamino)-4-phenylpiperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one;

[442] 6-(3-(5-((4-(dimethylamino)-4-(3-hydroxyphenyl)piperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one;

[443] 6-(4-(1-(2-fluorophenyl)-3-(methylamino)propoxy)benzyl)-9-methyl-6,7,8,9-tetrahydro-5H-pyrimido[4,5-e][1,4]diazepin-5-one;

[444] 4-(4-(1-(2-fluorophenyl)-3-(methylamino)propoxy)benzyl)-8-methoxy-1-methyl-1,2,3,4-tetrahydro-5H-pyrido[4,3-e][1,4]diazepin-5-one;

[445] 4-(4-(1-(2-fluorophenyl)-3-(methylamino)propoxy)benzyl)-1-methyl-1,2,3,4-tetrahydro-5H-pyrido[4,3-e][1,4]diazepin-5-one;

[446] 6-(4-(1-(3-fluorophenyl)-3-(methylamino)propoxy)benzyl)-2-methoxy-9-methyl-6,7,8,9-tetrahydro-5H-pyrimido[4,5-e][1,4]diazepin-5-one;
[447] 6-(4-(1-(3-fluorophenyl)-3-(methylamino)propoxy)benzyl)-9-methyl-6,7,8,9-tetrahydro-5H-pyrimido[4,5-e][1,4]diazepin-5-one;
[448] 4-(4-(1-(3-fluorophenyl)-3-(methylamino)propoxy)benzyl)-8-methoxy-1-methyl-1,2,3,4-tetrahydro-5H-pyrido[4,3-e][1,4]diazepin-5-one;
[449] 4-(4-(1-(3-fluorophenyl)-3-(methylamino)propoxy)benzyl)-1-methyl-1,2,3,4-tetrahydro-5H-pyrido[4,3-e][1,4]diazepin-5-one;
[450] 6-(4-(1-(4-fluorophenyl)-3-(methylamino)propoxy)benzyl)-2-methoxy-9-methyl-6,7,8,9-tetrahydro-5H-pyrimido[4,5-e][1,4]diazepin-5-one;
[451] 6-(4-(1-(4-fluorophenyl)-3-(methylamino)propoxy)benzyl)-9-methyl-6,7,8,9-tetrahydro-5H-pyrimido[4,5-e][1,4]diazepin-5-one;
[452] 4-(4-(1-(4-fluorophenyl)-3-(methylamino)propoxy)benzyl)-8-methoxy-1-methyl-1,2,3,4-tetrahydro-5H-pyrido[4,3-e][1,4]diazepin-5-one;
[453] 4-(4-(1-(4-fluorophenyl)-3-(methylamino)propoxy)benzyl)-1-methyl-1,2,3,4-tetrahydro-5H-pyrido[4,3-e][1,4]diazepin-5-one;
[454] 6-(4-(1-(2-chlorophenyl)-3-(methylamino)propoxy)benzyl)-2-methoxy-9-methyl-6,7,8,9-tetrahydro-5H-pyrimido[4,5-e][1,4]diazepin-5-one;
[455] 6-(4-(1-(2-chlorophenyl)-3-(methylamino)propoxy)benzyl)-9-methyl-6,7,8,9-tetrahydro-5H-pyrimido[4,5-e][1,4]diazepin-5-one;
[456] 4-(4-(1-(2-chlorophenyl)-3-(methylamino)propoxy)benzyl)-1-methyl-1,2,3,4-tetrahydro-5H-pyrido[4,3-e][1,4]diazepin-5-one;
[457] 6-(4-(1-(3-chlorophenyl)-3-(methylamino)propoxy)benzyl)-2-methoxy-9-methyl-6,7,8,9-tetrahydro-5H-pyrimido[4,5-e][1,4]diazepin-5-one;
[458] 6-(4-(1-(3-chlorophenyl)-3-(methylamino)propoxy)benzyl)-9-methyl-6,7,8,9-tetrahydro-5H-pyrimido[4,5-e][1,4]diazepin-5-one;
[459] 4-(4-(1-(3-chlorophenyl)-3-(methylamino)propoxy)benzyl)-1-methyl-1,2,3,4-tetrahydro-5H-pyrido[4,3-e][1,4]diazepin-5-one;
[460] 6-(4-(1-(4-chlorophenyl)-3-(methylamino)propoxy)benzyl)-2-methoxy-9-methyl-6,7,8,9-tetrahydro-5H-pyrimido[4,5-e][1,4]diazepin-5-one;
[461] 6-(4-(1-(4-chlorophenyl)-3-(methylamino)propoxy)benzyl)-9-methyl-6,7,8,9-tetrahydro-5H-pyrimido[4,5-e][1,4]diazepin-5-one;
[462] 4-(4-(1-(4-chlorophenyl)-3-(methylamino)propoxy)benzyl)-1-methyl-1,2,3,4-tetrahydro-5H-pyrido[4,3-e][1,4]diazepin-5-one;
[463] (S)-8-methoxy-1-methyl-4-(4-(3-(methylamino)-1-phenylpropoxy)benzyl)-1,2,3,4-tetrahydro-5H-pyrido[4,3-e][1,4]diazepin-5-one;
[464] 1-methyl-4-(4-(3-(methylamino)-1-(5-methylthiophen-2-yl)propoxy)benzyl)-1,2,3,4-tetrahydro-5H-pyrido[4,3-e][1,4]diazepin-5-one;
[465] 9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one;
[466] 8-methoxy-1-methyl-4-(4-(3-(methylamino)-1-(5-methylthiophen-2-yl)propoxy)benzyl)-1,2,3,4-tetrahydro-5H-pyrido[4,3-e][1,4]diazepin-5-one;
[467] 8-methoxy-1-methyl-4-(4-(3-(methylamino)-1-(thiophen-3-yl)propoxy)benzyl)-1,2,3,4-tetrahydro-5H-pyrido[4,3-e][1,4]diazepin-5-one;
[468] 1-methyl-4-(4-(3-(methylamino)-1-(thiophen-3-yl)propoxy)benzyl)-1,2,3,4-tetrahydro-5H-pyrido[4,3-e][1,4]diazepin-5-one;
[469] 9-methyl-6-(4-(3-(methylamino)-1-(thiophen-3-yl)propoxy)benzyl)-6,7,8,9-tetrahydro-5H-pyrimido[4,5-e][1,4]diazepin-5-one;
[470] (S)-4-(3-fluoro-4-(3-(methylamino)-1-(thiophen-2-yl)propoxy)benzyl)-1-methyl-1,2,3,4-tetrahydro-5H-pyrido[4,3-e][1,4]diazepin-5-one;
[471] (S)-4-(3-fluoro-4-(3-(methylamino)-1-(thiophen-2-yl)propoxy)benzyl)-8-methoxy-1-methyl-1,2,3,4-tetrahydro-5H-pyrido[4,3-e][1,4]diazepin-5-one;
[472] (S)-6-(3-fluoro-4-(3-(methylamino)-1-(thiophen-2-yl)propoxy)benzyl)-9-methyl-6,7,8,9-tetrahydro-5H-pyrimido[4,5-e][1,4]diazepin-5-one;
[473] (S)-6-(2-fluoro-4-(3-(methylamino)-1-(thiophen-2-yl)propoxy)benzyl)-9-methyl-6,7,8,9-tetrahydro-5H-pyrimido[4,5-e][1,4]diazepin-5-one;
[474] (S)-4-(2-fluoro-4-(3-(methylamino)-1-(thiophen-2-yl)propoxy)benzyl)-8-methoxy-1-methyl-1,2,3,4-tetrahydro-5H-pyrido[4,3-e][1,4]diazepin-5-one;
[475] (S)-4-(2-fluoro-4-(3-(methylamino)-1-(thiophen-2-yl)propoxy)benzyl)-1-methyl-1,2,3,4-tetrahydro-5H-pyrido[4,3-e][1,4]diazepin-5-one;
[476] (S)-8-methoxy-1-methyl-4-(2-methyl-4-(3-(methylamino)-1-(thiophen-2-yl)propoxy)benzyl)-1,2,3,4-tetrahydro-5H-pyrido[4,3-e][1,4]diazepin-5-one;
[477] (S)-1-methyl-4-(2-methyl-4-(3-(methylamino)-1-(thiophen-2-yl)propoxy)benzyl)-1,2,3,4-tetrahydro-5H-pyrido[4,3-e][1,4]diazepin-5-one;
[478] (S)-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one;
[479] (S)-6-(3-chloro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;
[480] (S)-6-(3-chloro-4-(3-(methylamino)-1-(thiophen-2-yl)propoxy)benzyl)-9-methyl-6,7,8,9-tetrahydro-5H-pyrimido[4,5-e][1,4]diazepin-5-one;
[481] (S)-4-(3-chloro-4-(3-(methylamino)-1-(thiophen-2-yl)propoxy)benzyl)-1-methyl-1,2,3,4-tetrahydro-5H-pyrido[4,3-e][1,4]diazepin-5-one;
[482] (S)-6-(2-chloro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;
[483] (S)-6-(2-chloro-4-(3-(methylamino)-1-(thiophen-2-yl)propoxy)benzyl)-9-methyl-6,7,8,9-tetrahydro-5H-pyrimido[4,5-e][1,4]diazepin-5-one;
[484] (S)-4-(2-chloro-4-(3-(methylamino)-1-(thiophen-2-yl)propoxy)benzyl)-1-methyl-1,2,3,4-tetrahydro-5H-pyrido[4,3-e][1,4]diazepin-5-one;
[485] (S)-2-ethoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one;
[486] (S)-8-methoxy-4-(4-(3-(methylamino)-1-(thiophen-2-yl)propoxy)benzyl)-1,2,3,4-tetrahydro-5H-pyrido[4,3-e][1,4]diazepin-5-one;
[487] (S)-1-isopropyl-4-(4-(3-(methylamino)-1-(thiophen-2-yl)propoxy)benzyl)-1,2,3,4-tetrahydro-5H-pyrido[4,3-e][1,4]diazepin-5-one; and
[488] (S)-9-isopropyl-6-(4-(3-(methylamino)-1-(thiophen-2-yl)propoxy)benzyl)-6,7,8,9-tetrahydro-5H-pyrimido[4,5-e][1,4]diazepin-5-one.

9. The compound according to claim 1, having one of the following formula (Ia), (Ib), (Ic), (Id), (Ie), (If) or (Ig):

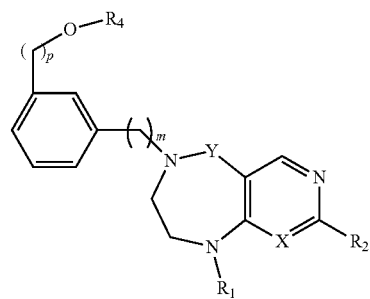
(Ia)
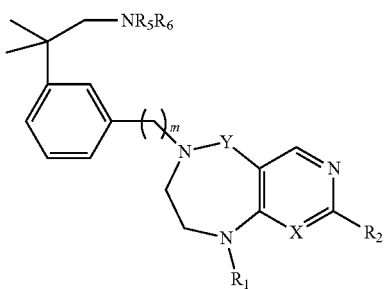
(Ib)
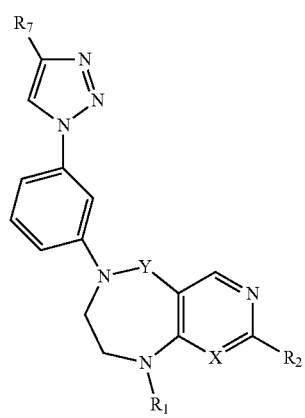
(Ic)
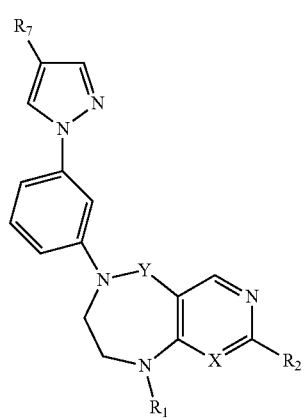
(Id)
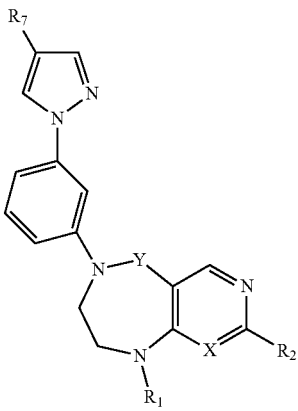
(Ie)
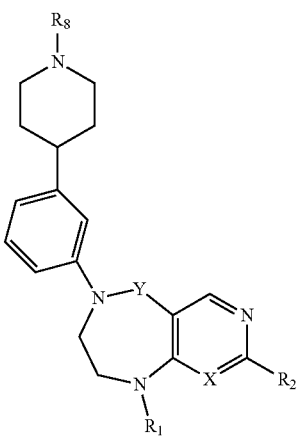
(If)
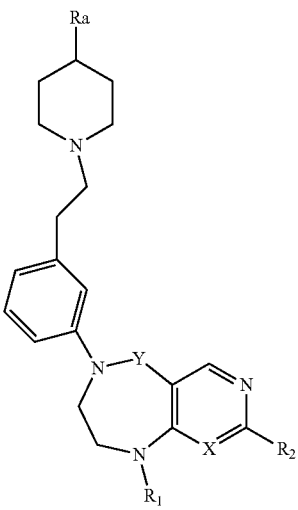
(Ig)
wherein X, Y, $R_1$, $R_2$, m and p are as defined in claim 1;
$R_4$ represents a —$CHR_{4a}R_{4b}$ or a —$CH_2$—$CHR_{4a}R_{4b}$ moiety wherein
  $R_{4a}$ is a group selected from:
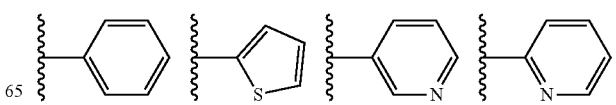

and R$_{4b}$ represents a —(CH$_2$)$_j$—NR$_{4b'}$R$_{4b''}$ moiety, wherein j is 0, 1, 2 or 3 and R$_{4b'}$ and R$_{4b''}$ independently represent a hydrogen atom; a branched or unbranched C$_{1-6}$ alkyl radical; a benzyl group; or a phenethyl group;

R$_5$ and R$_6$ independently represent a hydrogen atom or a branched or unbranched C$_{1-6}$ alkyl radical;

R$_7$ is a —(CH$_2$)$_p$—NR$_{7a}$R$_{7b}$ moiety, wherein p is 0, 1, 2 or 3 and wherein R$_{7a}$ and R$_{7b}$ independently represent a hydrogen atom; a branched or unbranched C$_{1-6}$ alkyl radical; a benzyl group optionally substituted by a halogen; a phenethyl group; a —(CH$_2$)-cyclopropyl; a pyridinylmethyl group; or R$_{7a}$ and R$_{7b}$, together with the nitrogen atom to which they are attached, form one of the following structures:

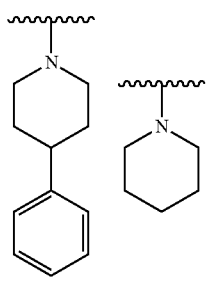

R$_8$ is a phenethyl group; and
R$_a$ is phenyl group optionally substituted with an —OH group.

10. The compound according to claim 1, which is selected from the following group:

[148] 2-(Ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[149] (R)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[150] (S)-2-(ethylamino)-9-methyl-6-(3-(3-(methylamino)-1-phenylpropoxy)phenyl)-6,7,8,9-tetrahydro-5H-pyrimido[4,5-e][1,4]diazepin-5-one;

[151] 9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[152] (R)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[153] (S)-9-methyl-6-(3-(3-(methylamino)-1-phenylpropoxy)phenyl)-2-(methylthio)-6,7,8,9-tetrahydro-5H-pyrimido[4,5-e][1,4]diazepin-5-one;

[154] 2-(ethylamino)-9-methyl-6-(3-(2-(methylamino)-1-phenylethoxy)phenyl)-6,7,8,9-tetrahydro-5H-pyrimido[4,5-e][1,4]diazepin-5-one;

[156] 6-(3-(2-amino-1-phenylethoxy)phenyl)-2-(ethylamino)-9-methyl-6,7,8,9-tetrahydro-5H-pyrimido[4,5-e][1,4]diazepin-5-one;

[159] 2-(ethylamino)-9-methyl-6-(4-(2-(methylamino)-1-phenylethoxy)phenyl)-6,7,8,9-tetrahydro-5H-pyrimido[4,5-e][1,4]diazepin-5-one;

[160] 2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[161] (R)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[162] (S)-2-(ethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[163] 9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[164] (R)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[165] (S)-9-methyl-6-(3-((3-(methylamino)-1-phenylpropoxy)methyl)phenyl)-2-(methylthio)-6,7,8,9-tetrahydro-5H-pyrimido[4,5-e][1,4]diazepin-5-one;

[166] 2-(ethylamino)-9-methyl-6-(3-((2-(methylamino)-2-phenylethoxy)methyl)phenyl)-6,7,8,9-tetrahydro-5H-pyrimido[4,5-e][1,4]diazepin-5-one;

[167] 9-methyl-6-(3-((2-(methylamino)-2-phenylethoxy)methyl)phenyl)-2-(methylthio)-6,7,8,9-tetrahydro-5H-pyrimido[4,5-e][1,4]diazepin-5-one;

[169] 6-(3-(3-(benzylamino)propoxy)phenyl)-2-(ethylamino)-9-methyl-6,7,8,9-tetrahydro-5H-pyrimido[4,5-e][1,4]diazepin-5-one;

[173] 2-(ethylamino)-9-methyl-6-(3-(2-methyl-1-(methylamino)propan-2-yl)phenyl)-6,7,8,9-tetrahydro-5H-pyrimido[4,5-e][1,4]diazepin-5-one;

[176] 2-(ethylamino)-9-methyl-6-(3-(((4-phenylpiperidin-4-yl)oxy)methyl)phenyl)-6,7,8,9-tetrahydro-5H-pyrimido[4,5-e][1,4]diazepin-5-one;

[179] 9-methyl-2-(methylthio)-6-(3-(((4-phenylpiperidin-4-yl)oxy)methyl)phenyl)-6,7,8,9-tetrahydro-5H-pyrimido[4,5-e][1,4]diazepin-5-one;

[182] 6-(3-(4-((benzylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[183] 2-(ethylamino)-9-methyl-6-(3-(4-(2-(methylamino)ethyl)-1H-1,2,3-triazol-1-yl)phenyl)-6,7,8,9-tetrahydro-5H-pyrimido[4,5-e][1,4]diazepin-5-one;

[193] 2-(ethylamino)-9-methyl-6-(3-(3-(methylamino)-1-(pyridin-2-yl)propoxy)phenyl)-6,7,8,9-tetrahydro-5H-pyrimido[4,5-e][1,4]diazepin-5-one;

[194] 2-(ethylamino)-9-methyl-6-(3-(3-(methylamino)-1-(pyridin-3-yl)propoxy)phenyl)-6,7,8,9-tetrahydro-5H-pyrimido[4,5-e][1,4]diazepin-5-one;

[195] (R)-2-amino-9-methyl-6-(3-((3-(methylamino)-1-phenylpropoxy)methyl)phenyl)-6,7,8,9-tetrahydro-5H-pyrimido[4,5-e][1,4]diazepin-5-one;

[196] (R)-2-(dimethylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[197] (R)-9-methyl-2-(methylamino)-6-(3-((3-(methylamino)-1-phenylpropoxy)methyl)phenyl)-6,7,8,9-tetrahydro-5H-pyrimido[4,5-e][1,4]diazepin-5-one;

[198] 8-(ethylamino)-1-methyl-4-(3-(3-(methylamino)-1-phenylpropoxy)phenyl)-1,2,3,4-tetrahydro-5H-pyrido[4,3-e][1,4]diazepin-5-one;

[199] 8-(ethylamino)-1-methyl-4-(3-((3-(methylamino)-1-phenylpropoxy)methyl)phenyl)-1,2,3,4-tetrahydro-5H-pyrido[4,3-e][1,4]diazepin-5-one;

[201] 2-(ethylamino)-9-methyl-6-(4-(2-(methylamino)-1-phenylethoxy)benzyl)-6,7,8,9-tetrahydro-5H-pyrimido[4,5-e][1,4]diazepin-5-one;

[203] (R)—N-ethyl-9-methyl-6-(3-((3-(methylamino)-1-phenylpropoxy)methyl)phenyl)-6,7,8,9-tetrahydro-5H-pyrimido[4,5-e][1,4]diazepin-2-amine;

[204] (R)-2-methoxy-9-methyl-6-(3-((3-(methylamino)-1-phenylpropoxy)methyl)phenyl)-6,7,8,9-tetrahydro-5H-pyrimido[4,5-e][1,4]diazepin-5-one;
[205] (R)-2-hydroxy-9-methyl-6-(3-((3-(methylamino)-1-phenylpropoxy)methyl)phenyl)-6,7,8,9-tetrahydro-5H-pyrimido[4,5-e][1,4]diazepin-5-one;
[206] (R)-2,9-dimethyl-6-(3-((3-(methylamino)-1-phenylpropoxy)methyl)phenyl)-6,7,8,9-tetrahydro-5H-pyrimido[4,5-e][1,4]diazepin-5-one;
[207] (R)-9-methyl-6-(3-((3-(methylamino)-1-phenylpropoxy)methyl)phenyl)-6,7,8,9-tetrahydro-5H-pyrimido[4,5-e][1,4]diazepin-5-one;
[208] 9-Methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;
[209] (R)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;
[210] (S)-9-methyl-6-(3-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;
[211] 2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[212] (R)-2-(ethylamino)-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[213] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;
[214] 2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;
[215] (R)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;
[216] (S)-2-(ethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;
[217] 9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;
[218] (R)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;
[219] (S)-9-methyl-6-(3-(3-(methylamino)-1-(thiophen-2-yl)propoxy)phenyl)-2-(methylthio)-6,7,8,9-tetrahydro-5H-pyrimido[4,5-e][1,4]diazepin-5-one;
[220] 2-(ethylamino)-6-(3-(3-((2-fluoroethyl)amino)-1-(thiophen-2-yl)propoxy)phenyl)-9-methyl-6,7,8,9-tetrahydro-5H-pyrimido[4,5-e][1,4]diazepin-5-one;
[221] 2-methoxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[222] 2-hydroxy-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[223] 2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[224] 9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;
[225] 2-(Ethylamino)-9-methyl-6-(3-((2-(methylamino)-1-phenylethoxy) methyl)phenyl)-6,7,8,9-tetrahydro-5H-pyrimido[4,5-e][1,4]diazepin-5-one;
[226] 9-methyl-6-(3-((2-(methylamino)-1-phenylethoxy)methyl)phenyl)-2-(methylthio)-6,7,8,9-tetrahydro-5H-pyrimido[4,5-e][1,4]diazepin-5-one;
[227] 8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[229] 8-(dimethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;
[230] 2-(dimethylamino)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;
[231] 2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;
[232] 9-methyl-6-(3-(3-(methylamino)-1-(thiophen-2-yl)propoxy)phenyl)-6,7,8,9-tetrahydro-5H-pyrimido[4,5-e][1,4]diazepin-5-one;
[236] (R)-6-(3-((3-(Dimethylamino)-1-phenylpropoxy)methyl)phenyl)-2-(ethylamino)-9-methyl-6,7,8,9-tetrahydro-5H-pyrimido[4,5-e][1,4]diazepin-5-one;
[237] (S)-6-(3-((3-(dimethylamino)-1-phenylpropoxy)methyl)phenyl)-2-(ethylamino)-9-methyl-6,7,8,9-tetrahydro-5H-pyrimido[4,5-e][1,4]diazepin-5-one;
[238] 6-(3-(3-(dimethylamino)-1-phenylpropoxy)phenyl)-2-(ethylamino)-9-methyl-6,7,8,9-tetrahydro-5H-pyrimido[4,5-e][1,4]diazepin-5-one;
[239] 6-(3-(2-(dimethylamino)-1-phenylethoxy)phenyl)-2-(ethylamino)-9-methyl-6,7,8,9-tetrahydro-5H-pyrimido[4,5-e][1,4]diazepin-5-one;
[240] 6-(3-(3-(benzyl(methyl)amino)propyl)phenyl)-2-(ethylamino)-9-methyl-6,7,8,9-tetrahydro-5H-pyrimido[4,5-e][1,4]diazepin-5-one;
[241] 6-(3-(3-(dimethylamino)propyl)phenyl)-2-(ethylamino)-9-methyl-6,7,8,9-tetrahydro-5H-pyrimido[4,5-e][1,4]diazepin-5-one;
[242] 6-(3-(4-((dimethylamino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;
[243] 6-(3-(4-((benzyl(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;
[244] 2-(ethylamino)-9-methyl-6-(3-(4-((methyl(phenethyl)amino)methyl)-1H-1,2,3-triazol-1-yl)phenyl)-6,7,8,9-tetrahydro-5H-pyrimido[4,5-e][1,4]diazepin-5-one;
[246] 6-(3-(4-(((cyclopropylmethyl)(methyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;
[251] 6-(3-(4-((benzyl(methyl)amino)methyl)-1H-pyrazol-1-yl)phenyl)-2-(ethylamino)-9-methyl-6,7,8,9-tetrahydro-5H-pyrimido[4,5-e][1,4]diazepin-5-one;
[252] 2-(ethylamino)-9-methyl-6-(3-(4-((methyl(phenethyl)amino)methyl)-1H-pyrazol-1-yl)phenyl)-6,7,8,9-tetrahydro-5H-pyrimido[4,5-e][1,4]diazepin-5-one;
[253] 6-(3-(4-((benzyl(methyl)amino)methyl)-1H-imidazol-1-yl)phenyl)-2-(ethylamino)-9-methyl-6,7,8,9-tetrahydro-5H-pyrimido[4,5-e][1,4]diazepin-5-one;
[254] 2-(ethylamino)-9-methyl-6-(3-(4-((methyl(phenethyl)amino)methyl)-1H-imidazol-1-yl)phenyl)-6,7,8,9-tetrahydro-5H-pyrimido[4,5-e][1,4]diazepin-5-one;
[256] 6-(3-(3-(benzyl(methyl)amino)propoxy)phenyl)-2-(ethylamino)-9-methyl-6,7,8,9-tetrahydro-5H-pyrimido[4,5-e][1,4]diazepin-5-one;

[261] 2-(ethylamino)-9-methyl-6-(3-(1-phenethylpiperidin-4-yl)phenyl)-6,7,8,9-tetrahydro-5H-pyrimido[4,5-e][1,4]diazepin-5-one;

[264] 6-(3-(2-(benzyl(methyl)amino)ethoxy)phenyl)-2-(ethylamino)-9-methyl-6,7,8,9-tetrahydro-5H-pyrimido[4,5-e][1,4]diazepin-5-one;

[265] 2-(ethylamino)-9-methyl-6-(3-(2-(methyl(phenethyl)amino)ethoxy)phenyl)-6,7,8,9-tetrahydro-5H-pyrimido[4,5-e][1,4]diazepin-5-one;

[271] 9-methyl-6-(3-(((1-methyl-4-phenylpiperidin-4-yl)oxy)methyl)phenyl)-2-(methylthio)-6,7,8,9-tetrahydro-5H-pyrimido[4,5-e][1,4]diazepin-5-one;

[272] 2-(ethylamino)-9-methyl-6-(3-(((1-methyl-4-phenylpiperidin-4-yl)oxy)methyl)phenyl)-6,7,8,9-tetrahydro-5H-pyrimido[4,5-e][1,4]diazepin-5-one;

[275] 2-(Ethylamino)-6-(3-(2-(4-(3-hydroxyphenyl)piperidin-1-yl)ethyl)phenyl)-9-methyl-6,7,8,9-tetrahydro-5H-pyrimido[4,5-e][1,4]diazepin-5-one;

[278] 2-(Ethylamino)-9-methyl-6-(3-(4-((4-phenylpiperidin-1-yl)methyl)-1H-1,2,3-triazol-1-yl)phenyl)-6,7,8,9-tetrahydro-5H-pyrimido[4,5-e][1,4]diazepin-5-one;

[279] 2-(ethylamino)-6-(3-(4-((4-(3-hydroxyphenyl)piperidin-1-yl)methyl)-1H-1,2,3-triazol-1-yl)phenyl)-9-methyl-6,7,8,9-tetrahydro-5H-pyrimido[4,5-e][1,4]diazepin-5-one;

[281] 2-(ethylamino)-9-methyl-6-(3-(4-(piperidin-1-ylmethyl)-1H-1,2,3-triazol-1-yl)phenyl)-6,7,8,9-tetrahydro-5H-pyrimido[4,5-e][1,4]diazepin-5-one;

[285] 6-(3-(4-(((cyclopropylmethyl)amino)methyl)-1H-1,2,3-triazol-1-yl)phenyl)-2-(ethylamino)-9-methyl-6,7,8,9-tetrahydro-5H-pyrimido[4,5-e][1,4]diazepin-5-one;

[287] 2-(ethylamino)-6-(3-(4-(((4-fluorobenzyl)(methyl)amino)methyl)-1H-1,2,3-triazol-1-yl)phenyl)-9-methyl-6,7,8,9-tetrahydro-5H-pyrimido[4,5-e][1,4]diazepin-5-one;

[288] 2-(ethylamino)-9-methyl-6-(3-(4-((methyl(pyridin-2-ylmethyl)amino)methyl)-1H-1,2,3-triazol-1-yl)phenyl)-6,7,8,9-tetrahydro-5H-pyrimido[4,5-e][1,4]diazepin-5-one;

[289] 2-(ethylamino)-9-methyl-6-(3-(4-((methyl(pyridin-3-ylmethyl)amino)methyl)-1H-1,2,3-triazol-1-yl)phenyl)-6,7,8,9-tetrahydro-5H-pyrimido[4,5-e][1,4]diazepin-5-one;

[304] (S)-8-amino-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[305] (S)-8-amino-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[307] 1,8-dimethyl-4-(3-(3-(methylamino)-1-(thiophen-2-yl)propoxy)phenyl)-1,2,3,4-tetrahydro-5H-pyrido[4,3-e][1,4]diazepin-5-one;

[308] (S)-1,8-dimethyl-4-(4-(3-(methylamino)-1-(thiophen-2-yl)propoxy)benzyl)-1,2,3,4-tetrahydro-5H-pyrido[4,3-e][1,4]diazepin-5-one;

[315] 9-methyl-6-(4-((3-(methylamino)-1-phenylpropoxy)methyl)phenyl)-2-(methylthio)-6,7,8,9-tetrahydro-5H-pyrimido[4,5-e][1,4]diazepin-5-one;

[316] 9-methyl-6-(4-(3-(methylamino)-1-phenylpropoxy)phenyl)-2-(methylthio)-6,7,8,9-tetrahydro-5H-pyrimido[4,5-e][1,4]diazepin-5-one;

[321] 9-methyl-6-(4-((2-(methylamino)-1-phenylethoxy)methyl)phenyl)-2-(methylthio)-6,7,8,9-tetrahydro-5H-pyrimido[4,5-e][1,4]diazepin-5-one;

[322] 9-methyl-6-(3-((3-(methylamino)-1-phenylpropoxy)methyl)phenyl)-2-(trifluoromethyl)-6,7,8,9-tetrahydro-5H-pyrimido[4,5-e][1,4]diazepin-5-one;

[323] 1-methyl-4-(3-(3-(methylamino)-1-(thiophen-2-yl)propoxy)phenyl)-1,2,3,4-tetrahydro-5H-pyrido[4,3-e][1,4]diazepin-5-one;

[325] (S)-8-(ethylamino)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[326] (S)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[327] (R)-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[328] 9-methyl-6-(4-((3-(methylamino)-1-(thiophen-2-yl)propoxy)methyl)phenyl)-2-(methylthio)-6,7,8,9-tetrahydro-5H-pyrimido[4,5-e][1,4]diazepin-5-one;

[329] 9-methyl-6-(3-(3-(methylamino)-1-(thiophen-2-yl)propoxy)phenyl)-2-(trifluoromethyl)-6,7,8,9-tetrahydro-5H-pyrimido[4,5-e][1,4]diazepin-5-one;

[330] 9-methyl-6-(3-((3-(methylamino)-1-(thiophen-2-yl)propoxy)methyl)phenyl)-2-(trifluoromethyl)-6,7,8,9-tetrahydro-5H-pyrimido[4,5-e][1,4]diazepin-5-one;

[331] (S)-8-methoxy-1-methyl-4-(3-(3-(methylamino)-1-(thiophen-2-yl)propoxy)phenyl)-1,2,3,4-tetrahydro-5H-pyrido[4,3-e][1,4]diazepin-5-one;

[333] 2-(ethylamino)-9-methyl-6-(4-(3-(methylamino)-1-phenylpropoxy)phenyl)-6,7,8,9-tetrahydro-5H-pyrimido[4,5-e][1,4]diazepin-5-one;

[334] 2-(ethylamino)-9-methyl-6-(4-((3-(methylamino)-1-phenylpropoxy)methyl)phenyl)-6,7,8,9-tetrahydro-5H-pyrimido[4,5-e][1,4]diazepin-5-one;

[335] 2-(benzylamino)-9-methyl-6-(3-((3-(methylamino)-1-phenylpropoxy)methyl)phenyl)-6,7,8,9-tetrahydro-5H-pyrimido[4,5-e][1,4]diazepin-5-one;

[336] 9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;

[340] 2-(ethylamino)-9-methyl-6-(4-((2-(methylamino)-1-phenylethoxy)methyl)phenyl)-6,7,8,9-tetrahydro-5H-pyrimido[4,5-e][1,4]diazepin-5-one;

[341] (R)-9-methyl-2-(methyl(pyridin-2-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;

[342] (R)-9-methyl-2-(methyl(pyridin-3-ylmethyl)amino)-6-(3-((3-(methylamino)-1-phenylpropoxy)methyl)phenyl)-6,7,8,9-tetrahydro-5H-pyrimido[4,5-e][1,4]diazepin-5-one;

[343] (R)-9-methyl-6-(3-((3-(methylamino)-1-phenylpropoxy)methyl)phenyl)-2-((pyridin-2-ylmethyl)amino)-6,7,8,9-tetrahydro-5H-pyrimido[4,5-e][1,4]diazepin-5-one;

[344] (R)-2-(((5-fluoropyridin-2-yl)methyl)(methyl)amino)-9-methyl-6-(3-((3-(methylamino)-1-phenylpropoxy)methyl)phenyl)-6,7,8,9-tetrahydro-5H-pyrimido[4,5-e][1,4]diazepin-5-one

[347] (R)-2-amino-9-methyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[348] 2-(ethylamino)-9-methyl-6-(4-((3-(methylamino)-1-(thiophen-2-yl)propoxy)methyl)phenyl)-6,7,8,9-tetrahydro-5H-pyrimido[4,5-e][1,4]diazepin-5-one;

[349] 2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;

[350] (R)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;

[351] (S)-2-(ethylamino)-9-methyl-6-(3-(3-(methylamino)-1-(thiophen-3-yl)propoxy)phenyl)-6,7,8,9-tetrahydro-5H-pyrimido[4,5-e][1,4]diazepin-5-one;

[352] (S)-2-amino-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[353] 2,9-dimethyl-6-(4-((3-(methylamino)-1-phenylpropoxy)methyl)phenyl)-6,7,8,9-tetrahydro-5H-pyrimido[4,5-e][1,4]diazepin-5-one;

[354] 2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;

[355] 2,9-dimethyl-6-(4-((2-(methylamino)-1-phenylethoxy)methyl)phenyl)-6,7,8,9-tetrahydro-5H-pyrimido[4,5-e][1,4]diazepin-5-one;

[356] (R)-2-ethyl-9-methyl-6-(3-((3-(methylamino)-1-phenylpropoxy)methyl)phenyl)-6,7,8,9-tetrahydro-5H-pyrimido[4,5-e][1,4]diazepin-5-one;

[357] (R)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[358] (S)-2,9-dimethyl-6-(3-(3-(methylamino)-1-(thiophen-2-yl)propoxy)phenyl)-6,7,8,9-tetrahydro-5H-pyrimido[4,5-e][1,4]diazepin-5-one;

[360] (R)-2,9-dimethyl-6-(3-((3-(methylamino)-1-(thiophen-2-yl)propoxy)methyl)phenyl)-6,7,8,9-tetrahydro-5H-pyrimido[4,5-e][1,4]diazepin-5-one;

[364] (S)-9-methyl-6-(3-(3-(methylamino)-1-(thiophen-2-yl)propoxy)phenyl)-6,7,8,9-tetrahydro-5H-pyrimido[4,5-e][1,4]diazepin-5-one;

[366] 9-methyl-6-(3-(3-(methylamino)-1-phenylpropoxy)benzyl)-2-(methylthio)-6,7,8,9-tetrahydro-5H-pyrimido[4,5-e][1,4]diazepin-5-one;

[367] 9-methyl-6-(3-((3-(methylamino)-1-phenylpropoxy)methyl)benzyl)-2-(methylthio)-6,7,8,9-tetrahydro-5H-pyrimido[4,5-e][1,4]diazepin-5-one;

[368] 9-methyl-6-(4-((3-(methylamino)-1-phenylpropoxy)methyl)benzyl)-2-(methylthio)-6,7,8,9-tetrahydro-5H-pyrimido[4,5-e][1,4]diazepin-5-one;

[369] 9-methyl-6-(4-(3-(methylamino)-1-phenylpropoxy)benzyl)-2-(methylthio)-6,7,8,9-tetrahydro-5H-pyrimido[4,5-e][1,4]diazepin-5-one;

[372] 9-methyl-6-(3-((2-(methylamino)-1-phenylethoxy)methyl)benzyl)-2-(methylthio)-6,7,8,9-tetrahydro-5H-pyrimido[4,5-e][1,4]diazepin-5-one;

[374] 9-methyl-6-(4-((2-(methylamino)-1-phenylethoxy)methyl)benzyl)-2-(methylthio)-6,7,8,9-tetrahydro-5H-pyrimido[4,5-e][1,4]diazepin-5-one;

[375] (S)-2-methoxy-9-methyl-6-(4-(3-(methylamino)-1-phenylpropoxy)benzyl)-6,7,8,9-tetrahydro-5H-pyrimido[4,5-e][1,4]diazepin-5-one;

[378] 9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[379] (S)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[380] (R)-9-methyl-6-(4-(3-(methylamino)-1-(thiophen-2-yl)propoxy)benzyl)-2-(methylthio)-6,7,8,9-tetrahydro-5H-pyrimido[4,5-e][1,4]diazepin-5-one;

[381] 1-methyl-4-(4-(3-(methylamino)-1-(thiophen-2-yl)propoxy)benzyl)-1,2,3,4-tetrahydro-5H-pyrido[4,3-e][1,4]diazepin-5-one;

[382] (S)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[383] (S)-8-(ethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[384] (S)-8-(dimethylamino)-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[385] (S)-8-methoxy-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[386] (S)-9-methyl-6-(4-(3-(methylamino)-1-(thiophen-2-yl)propoxy)benzyl)-2-(trifluoromethyl)-6,7,8,9-tetrahydro-5H-pyrimido[4,5-e][1,4]diazepin-5-one;

[387] 2-methoxy-9-methyl-6-(4-(3-(methylamino)-1-(thiophen-3-yl)propoxy)benzyl)-6,7,8,9-tetrahydro-5H-pyrimido[4,5-e][1,4]diazepin-5-one;

[388] 2-methoxy-9-methyl-6-(4-(3-(methylamino)-1-(3-methylthiophen-2-yl)propoxy)benzyl)-6,7,8,9-tetrahydro-5H-pyrimido[4,5-e][1,4]diazepin-5-one;

[389] (S)-1-ethyl-8-methoxy-4-(4-(3-(methylamino)-1-(thiophen-2-yl)propoxy)benzyl)-1,2,3,4-tetrahydro-5H-pyrido[4,3-e][1,4]diazepin-5-one;

[391] (S)-1-ethyl-4-(4-(3-(methylamino)-1-(thiophen-2-yl)propoxy)benzyl)-1,2,3,4-tetrahydro-5H-pyrido[4,3-e][1,4]diazepin-5-one;

[392] 2-methoxy-9-methyl-6-(4-(3-(methylamino)-1-(5-methylthiophen-2-yl)propoxy)benzyl)-6,7,8,9-tetrahydro-5H-pyrimido[4,5-e][1,4]diazepin-5-one;

[394] (S)-6-(3-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[395] S)-9-ethyl-2-methoxy-6-(4-(3-(methylamino)-1-(thiophen-2-yl)propoxy)benzyl)-6,7,8,9-tetrahydro-5H-pyrimido[4,5-e][1,4]diazepin-5-one;

[396] 2-methoxy-9-methyl-6-(4-(3-(methylamino)-1-(4-methylthiophen-2-yl)propoxy)benzyl)-6,7,8,9-tetrahydro-5H-pyrimido[4,5-e][1,4]diazepin-5-one;

[397] (S)-2-methoxy-9-methyl-6-(2-methyl-4-(3-(methylamino)-1-(thiophen-2-yl)propoxy)benzyl)-6,7,8,9-tetrahydro-5H-pyrimido[4,5-e][1,4]diazepin-5-one;

[398] (S)-9-ethyl-6-(4-(3-(methylamino)-1-(thiophen-2-yl)propoxy)benzyl)-6,7,8,9-tetrahydro-5H-pyrimido[4,5-e][1,4]diazepin-5-one;

[399] (S)-9-fluoro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[400] (S)-9-chloro-1-methyl-4-(4-(3-(methylamino)-1-(thiophen-2-yl)propoxy)benzyl)-1,2,3,4-tetrahydro-5H-pyrido[4,3-e][1,4]diazepin-5-one;

[401] (S)-6-(2-fluoro-4-(3-(methylamino)-1-(thiophen-2-yl)propoxy)benzyl)-2-methoxy-9-methyl-6,7,8,9-tetrahydro-5H-pyrimido[4,5-e][1,4]diazepin-5-one;

[402] (S)-2-methoxy-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[405] 2-(ethylamino)-9-methyl-6-(4-((3-(methylamino)-1-phenylpropoxy)methyl)benzyl)-6,7,8,9-tetrahydro-5H-pyrimido[4,5-e][1,4]diazepin-5-one;

[406] 2-(ethylamino)-9-methyl-6-(3-((3-(methylamino)-1-phenylpropoxy)methyl)benzyl)-6,7,8,9-tetrahydro-5H-pyrimido[4,5-e][1,4]diazepin-5-one;

[408] 2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[411] 2-(ethylamino)-9-methyl-6-(3-((2-(methylamino)-1-phenylethoxy)methyl)benzyl)-6,7,8,9-tetrahydro-5H-pyrimido[4,5-e][1,4]diazepin-5-one;

[413] 2-(ethylamino)-9-methyl-6-(4-((2-(methylamino)-1-phenylethoxy)methyl)benzyl)-6,7,8,9-tetrahydro-5H-pyrimido[4,5-e][1,4]diazepin-5-one;

[414] (S)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[415] (R)-2-(ethylamino)-9-methyl-6-(4-(3-(methylamino)-1-phenylpropoxy)benzyl)-6,7,8,9-tetrahydro-5H-pyrimido[4,5-e][1,4]diazepin-5-one;

[416] 2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[417] (S)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[418] (R)-2-(ethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[419] (S)-2-(dimethylamino)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[420] (S)-2-amino-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[422] 2,9-dimethyl-6-(4-((3-(methylamino)-1-phenylpropoxy)methyl)benzyl)-6,7,8,9-tetrahydro-5H-pyrimido[4,5-e][1,4]diazepin-5-one;

[423] 2,9-dimethyl-6-(3-((3-(methylamino)-1-phenylpropoxy)methyl)benzyl)-6,7,8,9-tetrahydro-5H-pyrimido[4,5-e][1,4]diazepin-5-one;

[425] 2,9-dimethyl-6-(4-(3-(methylamino)-1-phenylpropoxy)benzyl)-6,7,8,9-tetrahydro-5H-pyrimido[4,5-e][1,4]diazepin-5-one;

[426] 2-ethyl-9-methyl-6-(4-(3-(methylamino)-1-phenylpropoxy)benzyl)-6,7,8,9-tetrahydro-5H-pyrimido[4,5-e][1,4]diazepin-5-one;

[427] (R)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[428] (S)-2,9-dimethyl-6-(4-(3-(methylamino)-1-(thiophen-2-yl)propoxy)benzyl)-6,7,8,9-tetrahydro-5H-pyrimido[4,5-e][1,4]diazepin-5-one;

[430] 9-methyl-6-(4-(3-(methylamino)-1-phenylpropoxy)benzyl)-6,7,8,9-tetrahydro-5H-pyrimido[4,5-e][1,4]diazepin-5-one;

[433] (S)-9-methyl-6-(4-(3-(methylamino)-1-phenylpropoxy)benzyl)-6,7,8,9-tetrahydro-5H-pyrimido[4,5-e][1,4]diazepin-5-one;

[434] (R)-9-methyl-6-(4-(3-(methylamino)-1-phenylpropoxy)benzyl)-6,7,8,9-tetrahydro-5H-pyrimido[4,5-e][1,4]diazepin-5-one;

[435] 9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[436] (S)-9-methyl-6-(4-(3-(methylamino)-1-(thiophen-2-yl)propoxy)benzyl)-6,7,8,9-tetrahydro-5H-pyrimido[4,5-e][1,4]diazepin-5-one;

[437] (R)-9-methyl-6-(4-(3-(methylamino)-1-(thiophen-2-yl)propoxy)benzyl)-6,7,8,9-tetrahydro-5H-pyrimido[4,5-e][1,4]diazepin-5-one and

[442] 6-(3-(5-((4-(dimethylamino)-4-(3-hydroxyphenyl)piperidin-1-yl)methyl)-1,3,4-oxadiazol-2-yl)phenyl)-2-(ethylamino)-9-methyl-6,7,8,9-tetrahydro-5H-pyrimido[4,5-e][1,4]diazepin-5-one.

11. A process for the preparation of a compound of general formula (I') as defined in claim 1:

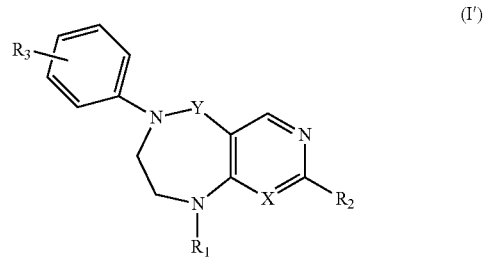

(I')

comprising the reaction between a compound of formula (VII) or formula (IV):

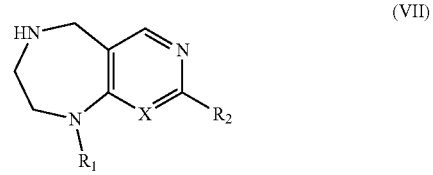

(VII)

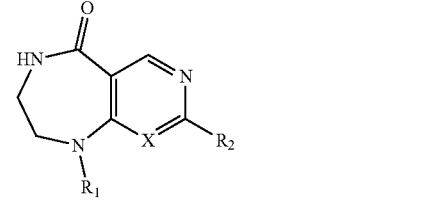

(IV)

and a compound of formula (VIII):

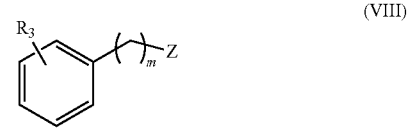

(VIII)

wherein $R_1$, $R_2$, $R_3$, X and Y are as defined in claim 1, m is 0 and Z is a suitable leaving group.

12. A process for the preparation of a compound of general formula (I″) as defined in claim 1:

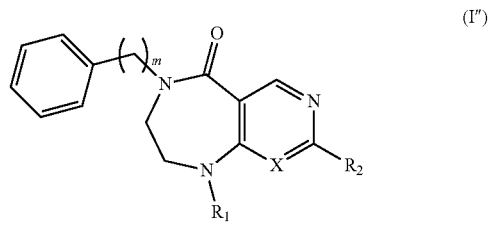

(I″)

comprising the reaction between a compound of formula (IV):

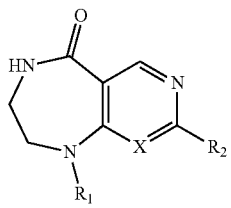

(IV)

and a compound of formula (VIII):

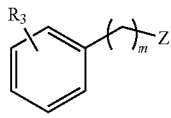

(VIII)

wherein $R_1$, $R_2$, $R_3$ and X are as defined in claim 1, m represents 1 or 2 and Z represents a suitable leaving group.

13. A process for the preparation of a compound of general formula (I''') as defined in claim 1:

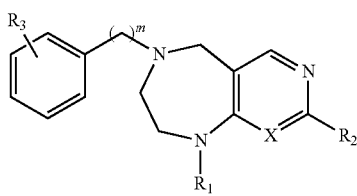

(I''')

comprising the reaction between a compound of formula (VII):

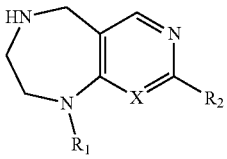

(VII)

and either:

a) a compound of formula (IX):

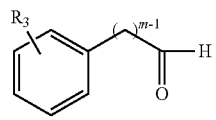

(IX)

or b) a compound of formula (VIII):

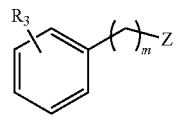

(VIII)

wherein $R_1$, $R_2$, $R_3$ and X are as defined in claim 1, m is 1 or 2 and Z is a suitable leaving group.

14. A method of treating pain, depression, anxiety or attention-deficit-/hyperactivity disorder (ADHD) in a subject in need thereof, comprising administration of an effective amount of the compound according to claim 1.

15. The method according to claim 14, wherein the pain is neuropathic pain, inflammatory pain, chronic pain or other pain conditions involving allodynia and/or hyperalgesia.

16. A pharmaceutical composition comprising the compound according to claim 1, or a pharmaceutically acceptable salt, stereoisomer, or solvate thereof, and at least a pharmaceutically acceptable carrier, additive, adjuvant or vehicle.

17. The compound according to claim 2, wherein
$R_2$ is methyl; the halogen atom is chloro, the haloalkyl is trifluoromethyl; and
the branched or unbranched $C_{1-4}$ alkyl radical in $R_{2a}$ and $R_{2b}$ is methyl, ethyl, isopropyl or isobutyl.

18. The compound according to claim 3, wherein
$R_4$ is methyl or ethyl;
the branched or unbranched $C_{1-6}$ alkyl radical in $R_{4a}$ is methyl or isopropyl;
$R_{4b'}$ and $R_{4b''}$ are methyl; and
$R_{4c}$ is methyl.

19. The compound according to claim 4, wherein
$R_5$ and $R_6$ are methyl;
the branched or unbranched $C_{1-6}$ alkyl radical in $R_b$ is, methyl or isopropyl; and
the branched or unbranched $C_{1-6}$ alkyl radical in $R_c$ is methyl or isopropyl.

20. The compound according to claim 5, wherein
$R_7$ is methyl or ethyl;
$R_{7a}$ and $R_{7b}$ are each independently methyl or ethyl;
the $C_{1-6}$ alkoxy radical in $R_{7c}$ and $R_{7d}$ is ethoxy.

21. The compound according to claim 7, wherein $R_9$ is methyl.

* * * * *